US012758220B2

(12) United States Patent
Lee et al.

(10) Patent No.: US 12,758,220 B2
(45) **Date of Patent: *Oct. 13, 2026**

(54) END TOOL OF SURGICAL INSTRUMENT, AND SURGICAL INSTRUMENT COMPRISING SAME

(71) Applicant: LIVSMED INC., Seongnam-si (KR)

(72) Inventors: Jaeyeong Lee, Seongnam-si (KR); Junghwan Kim, Seongnam-si (KR); Jung Joo Lee, Seongnam-si (KR); Heejin Kim, Seongnam-si (KR); Dongkyu Jang, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 19/210,381

(22) Filed: May 16, 2025

(65) Prior Publication Data

US 2025/0275768 A1 Sep. 4, 2025

Related U.S. Application Data

(63) Continuation of application No. 18/288,002, filed as application No. PCT/KR2022/005795 on Apr. 22, 2022, now Pat. No. 12,349,903.

(30) Foreign Application Priority Data

Apr. 23, 2021 (KR) ........................ 10-2021-0053353
Apr. 28, 2021 (KR) ........................ 10-2021-0055322

(51) Int. Cl.
*A61B 17/072* (2006.01)

(52) U.S. Cl.
CPC .............................. *A61B 17/07207* (2013.01)

(58) Field of Classification Search
CPC ............ A61B 17/07207; A61B 17/068; A61B 17/072; A61B 2017/07278; A61B 2017/07285; A61B 2017/07271; A61B 2017/07214; A61B 2017/07221; A61B 2017/07228; A61B 2017/07257; A61B 2017/07264
See application file for complete search history.

(56) References Cited

U.S. PATENT DOCUMENTS 5,762,256 A * 6/1998 Mastri .................. A61B 17/072 227/176.1
12,089,847 B2 * 9/2024 Lee .................... A61B 17/2909
(Continued)

FOREIGN PATENT DOCUMENTS

CA 2966895 A1 11/2017
JP 2014-508571 A 4/2014
(Continued)

*Primary Examiner* — Linda J. Hodge
(74) *Attorney, Agent, or Firm* — Bridgeway IP Law Group, PLLC; Sang Ho Lee; Hyun Woo Shin

(57) ABSTRACT

The present disclosure relates to an end tool of a surgical instrument and a surgical instrument including the same, and more particularly, to an end tool of a surgical instrument that may be mounted on a robotic arm or operable manually to be used in laparoscopic surgery or other various surgeries, wherein the end tool is rotatable in two or more directions and is moved in a way that intuitively matches a motion of a manipulation part, and a surgical instrument including the same.

19 Claims, 185 Drawing Sheets

(56) References Cited

U.S. PATENT DOCUMENTS

| | | | | |
|---|---|---|---|---|
| 12,329,380 | B2 * | 6/2025 | Lee | A61B 17/07207 |
| 2004/0199147 | A1 * | 10/2004 | Nishizawa | A61B 17/062 606/1 |
| 2011/0132962 | A1 | 6/2011 | Hall et al. | |
| 2012/0018326 | A1 | 1/2012 | Racenet et al. | |
| 2012/0181322 | A1 * | 7/2012 | Whitman | A61B 17/068 227/176.1 |
| 2013/0153623 | A1 | 6/2013 | Felder et al. | |
| 2016/0166129 | A1 * | 6/2016 | Walish | A61B 1/307 600/104 |
| 2016/0166249 | A1 | 6/2016 | Knodel | |
| 2017/0265865 | A1 | 9/2017 | Burbank | |
| 2017/0265954 | A1 * | 9/2017 | Burbank | A61B 34/37 |
| 2020/0038127 | A1 | 2/2020 | Chaplin et al. | |
| 2020/0305989 | A1 | 10/2020 | Schuh et al. | |

FOREIGN PATENT DOCUMENTS

| | | | |
|---|---|---|---|
| JP | 2014-508572 | A | 4/2014 |
| KR | 10-2007-0079046 | A | 8/2007 |
| KR | 10-2012-0081913 | A | 7/2012 |
| KR | 10-1369235 | B1 | 3/2014 |
| KR | 10-2019-0091494 | A | 8/2019 |
| KR | 10-2020-0105791 | A | 9/2020 |
| WO | 2004/112618 | A2 | 12/2004 |
| WO | 2021/037153 | A1 | 3/2021 |

* cited by examiner (a)

(b)

(a)

(b)

(a)

(b)

(c)

10

(a)

(b)

(a)

(b)

(a)

(b)

(a)

(b)

(a)

(b)

(a)

(b)

(b)

(a)

END TOOL OF SURGICAL INSTRUMENT, AND SURGICAL INSTRUMENT COMPRISING SAME

CROSS-REFERENCE TO RELATED APPLICATIONS

This application is a continuation application of the U.S. Utility patent application Ser. No. 18/288,002 filed on Oct. 23, 2023, which is a U.S. national-stage application of PCT/KR2022/005795 filed on Apr. 22, 2022, and claims priority to Korean patent application Nos. 10-2021-0053353 filed on Apr. 23, 2021, and 10-2021-0055322 filed on Apr. 28, 2021, the entire disclosures of which are incorporated herein by reference.

TECHNICAL FIELD

The present disclosure relates to an end tool of a surgical instrument and a surgical instrument including the same, and more particularly, to an end tool of a surgical instrument that may be mounted on a robotic arm or operable manually to be used in laparoscopic surgery or other various surgeries, wherein the end tool is rotatable in two or more directions and is moved in a way that intuitively matches a motion of a manipulation part, and a surgical instrument including the same.

BACKGROUND ART

In recent years, laparoscopic surgery has been actively utilized to reduce postoperative recovery time and complications through small incisions. The laparoscopic surgery is a surgical method in which a plurality of small holes are drilled in the abdomen of a patient and the inside of the abdominal cavity is observed through these holes, and is widely used in general surgery and the like.

In performing the laparoscopic surgery, a suturing instrument inserted into the body is used to suture a surgical site in the abdominal cavity, and a surgical stapler for suturing the surgical site using medical staples is used as the suturing instrument.

In general, a surgical stapler is a medical instrument that is often used for cutting and anastomosis of an organ in abdominal and thoracic surgery. The surgical stapler includes an open stapler used in thoracotomy and laparotomy and an endo stapler used in thoracoscopic surgery and celioscopic surgery.

The surgical stapler has advantages of not only shortening operation time since cutting of a surgical site and anastomosis of an organ are simultaneously performed, but also accurately stapling the surgical site. In addition, the surgical stapler has advantages of a faster recovery and a smaller scar than those when tissue is cut and stapled using a surgical stapling thread, and thus has been widely used in modern surgical operations. In particular, the surgical stapler has been widely used in cancer surgery to cut cancer tissue and suture a cut site.

The aforementioned background technology is technical information possessed by the inventor for derivation of the present disclosure or acquired by the inventor during the derivation of the present disclosure, and is not necessarily prior art disclosed to the public before the application of the present disclosure.

DESCRIPTION OF EMBODIMENTS

Technical Problem

The present disclosure is directed to providing a surgical instrument, which may be mounted on a robotic arm or operable manually to be used in laparoscopic surgery or other various surgeries and includes an end tool rotatable in two or more directions and moved in a way that intuitively matches a motion of a manipulation part, and a surgical instrument including the same.

Technical Solution to Problem

According to an embodiment of the present disclosure, there is provided a surgical instrument including an end tool which includes a first jaw, a second jaw formed to face the first jaw, a first jaw pulley coupled to the first jaw and formed to be rotatable around a first shaft, a second jaw pulley coupled to the second jaw, formed to be rotatable around a shaft substantially the same as or parallel to the first shaft, and formed to be spaced apart from the first jaw pulley by a certain extent, and a staple drive assembly including one or more staple pulleys at least partially formed between the first jaw pulley and the second jaw pulley, and a cartridge which includes a reciprocating assembly that is connected to the staple drive assembly, and linearly moved when the staple pulley is rotationally moved, and an operation member that is brought into contact with the reciprocating assembly, and is moved in one direction by the reciprocating assembly when the reciprocating assembly is moved in the one direction.

Other aspects, features, and advantages other than those described above will become apparent from the following drawings, claims, and detailed description of the disclosure.

Advantageous Effects of Disclosure

According to the present disclosure, a manipulating direction of a manipulation part by a surgical operator and an operating direction of an end tool are intuitively the same direction, so that convenience of the surgical operator can be improved, and accuracy, reliability, and speed of surgery can be improved.

BEST MODE

Figure 1:
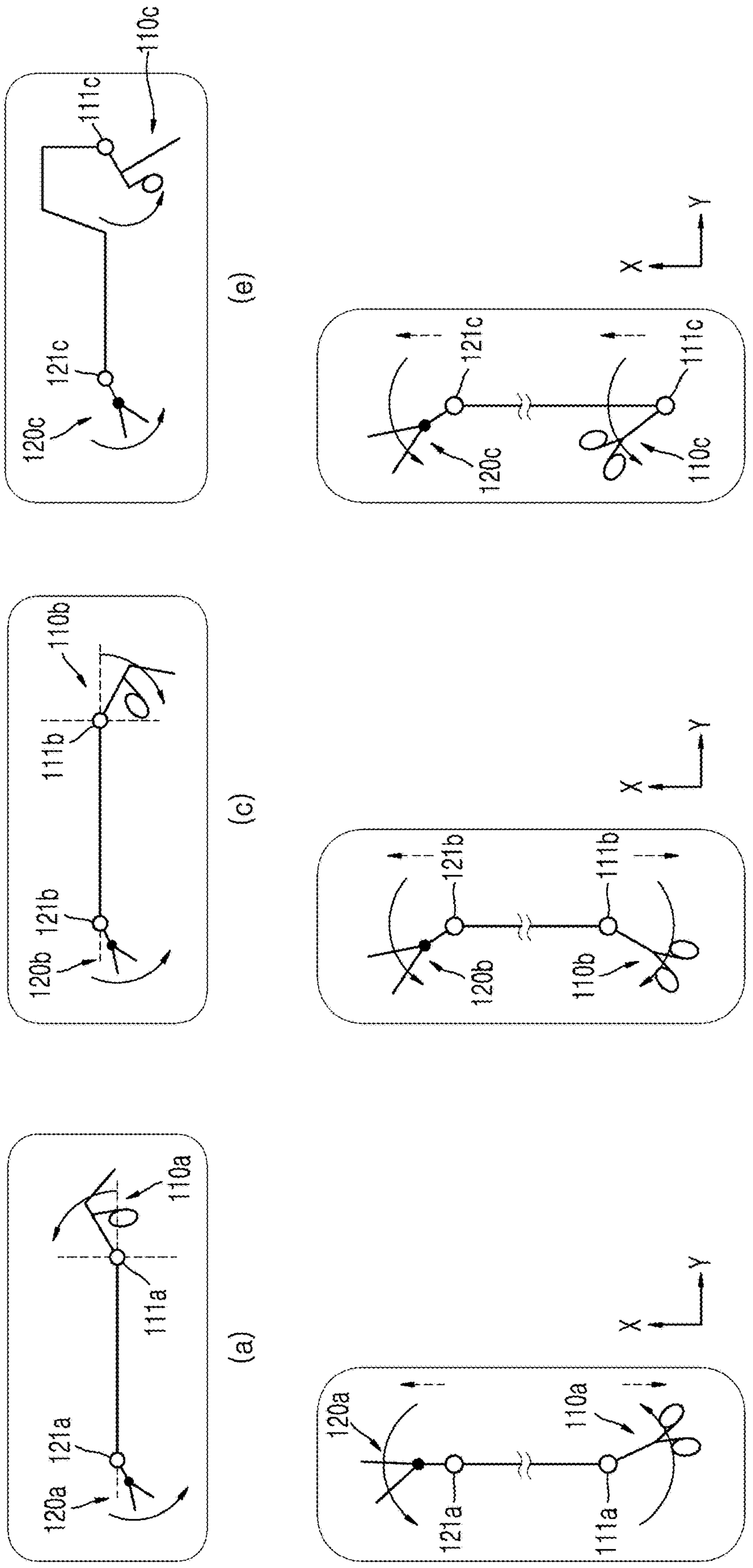
FIG. 1 shows (a) a conceptual diagram of a pitch motion of a conventional surgical instrument, (b) a conceptual diagram of a yaw motion thereof, (c) a conceptual diagram of a pitch motion of another conventional surgical instrument, (d) a conceptual diagram of a yaw motion thereof, (e) a conceptual diagram of a pitch motion of a surgical instrument according to the present disclosure, and (f) a conceptual diagram of a yaw motion thereof.

According to an embodiment of the present disclosure, there is provided a surgical instrument including an end tool which includes a first jaw, a second jaw formed to face the first jaw, a first jaw pulley coupled to the first jaw and formed to be rotatable around a first shaft, a second jaw pulley coupled to the second jaw, formed to be rotatable around a shaft substantially the same as or parallel to the first shaft, and formed to be spaced apart from the first jaw pulley by a certain extent, and a staple drive assembly including one or more staple pulleys at least partially formed between the first jaw pulley and the second jaw pulley, and a cartridge which includes a reciprocating assembly that is connected to the staple drive assembly, and linearly moved when the staple pulley is rotationally moved, and an operation member that is brought into contact with the reciprocating assembly, and is moved in one direction by the reciprocating assembly when the reciprocating assembly is moved in the one direction.

In the present disclosure, when the staple pulley is rotated, the reciprocating assembly connected to the staple drive assembly may be moved toward a distal end or a proximal end of the cartridge.

In the present disclosure, when the staple pulley is alternately rotated in a clockwise direction and a counterclockwise direction, the reciprocating assembly connected to the staple drive assembly may be alternately moved toward the distal end and the proximal end of the cartridge.

In the present disclosure, when the reciprocating assembly is moved toward the distal end of the cartridge, the operation member may be moved toward the distal end of the cartridge by the reciprocating assembly.

In the present disclosure, a bidirectional rotational motion of the staple pulley may be converted into a reciprocating linear motion of the reciprocating assembly, which is connected to the staple drive assembly, by the staple drive assembly.

In the present disclosure, as the operation member is moved in the one direction, a wedge of the operation member may sequentially push and raise a plurality of staples in the cartridge to perform a stapling motion, and simultaneously, a blade formed on one side of the wedge of the operation member may be moved in the one direction to perform a cutting motion.

In the present disclosure, the staple drive assembly may include a link member configured to connect the staple pulley and the reciprocating assembly.

In the present disclosure, the operation member may include a ratchet member having a ratchet formed at least one surface thereon, and the ratchet of the ratchet member may be formed to be in contact with the reciprocating assembly.

in the present disclosure, the operation member may be moved toward a distal end of the cartridge together with the reciprocating assembly only when the reciprocating assembly is moved toward the distal end of the cartridge.

In the present disclosure, when the staple pulley is rotated in a first direction between a clockwise direction and a counterclockwise direction, the link member connected to the staple pulley, the reciprocating assembly connected to the link member, and the operation member in contact with the reciprocating assembly may be moved toward a distal end of the cartridge.

In the present disclosure, when the staple pulley is rotated in a direction opposite to the first direction between the clockwise and counterclockwise directions, the link member connected to the staple pulley and the reciprocating assembly connected to the link member may be moved toward a proximal end of the end tool, and the operation member may remain stationary with respect to the one direction.

In the present disclosure, the staple drive assembly may include a first link member connected to one region of the staple pulley, and a second link member connected to the other region of the staple pulley, and the reciprocating assembly may include a first reciprocating member coupled to the first link member and a second reciprocating member coupled to the second link member.

In the present disclosure, the operation member may include a ratchet member having a first ratchet and a second ratchet formed thereon, wherein the first ratchet may be formed to be in contact with the first reciprocating member, and the second ratchet may be formed to be in contact with the second reciprocating member.

In the present disclosure, when the staple pulley is rotated in one direction, the first ratchet and the first reciprocating member may be in contact with each other, and when the staple pulley is rotated in the other direction, the second ratchet and the second reciprocating member may be in contact with each other.

In the present disclosure, when the staple pulley is rotated in a first direction between a clockwise direction and a counterclockwise direction, the first link member connected to the staple pulley, the first reciprocating member connected to the first link member, and the operation member in contact with the first reciprocating member may be moved toward a distal end of the cartridge.

In the present disclosure, when the staple pulley is rotated in a direction opposite to the first direction between the clockwise and counterclockwise directions, the second link member connected to the staple pulley, the second reciprocating member connected to the second link member, and the operation member in contact with the second reciprocating member may be moved toward the distal end of the cartridge.

In the present disclosure, the surgical instrument may further include a staple wire coupled to the staple pulley and configured to rotate the staple pulley.

In the present disclosure, each of a deactivated state, in which the staple drive assembly and the reciprocating assembly are spaced apart from each other, and an activated state, in which the staple drive assembly and the reciprocating assembly are coupled to each other, may exist.

In the present disclosure, only in the activated state, when the staple pulley is rotationally moved, which may cause the reciprocating assembly to be linearly moved.

In the present disclosure, the surgical instrument may further include a pair of end tool first jaw pitch main pulleys formed on one side of the first jaw pulley, and formed to be rotatable around a second shaft forming a predetermined angle with the first shaft, and a pair of end tool second jaw pitch main pulleys formed on one side of the second jaw pulley, and formed to be rotatable around a shaft that is substantially the same as or parallel to the second shaft.

In the present disclosure, the end tool may be formed to be yaw-rotatable around the first shaft and simultaneously pitch-rotatable around the second shaft.

In the present disclosure, the first jaw pulley, the staple pulley, and the second jaw pulley may be sequentially stacked.

According to another embodiment of the present disclosure, there is provided an end tool of a surgical instrument, the end tool including a first jaw capable of accommodating a cartridge, a second jaw formed to face the first jaw, a first jaw pulley coupled to the first jaw and formed to be rotatable around a first shaft, a second jaw pulley coupled to the second jaw, formed to be rotatable around a shaft substantially the same as or parallel to the first shaft, and formed to be spaced apart from the first jaw pulley by a certain extent, a staple drive assembly including one or more staple pulleys at least partially formed between the first jaw pulley and the second jaw pulley, and a staple wire at least partially in contact with the staple pulley and configured to transmit, to the staple pulley, a driving force necessary for rotating the staple pulley, wherein the staple drive assembly is connected to a reciprocating assembly of the cartridge and configured to convert a rotational motion of the staple pulley into a linear motion of the reciprocating assembly.

In the present disclosure, the end tool may further include an end tool hub including a first jaw pulley coupling part and a second jaw pulley coupling part, which are formed to face each other, and a guide part configured to connect the first jaw pulley coupling part and the second jaw pulley coupling part, wherein the first jaw pulley may be disposed adjacent to the first jaw pulley coupling part of the end tool hub, the second jaw pulley may be disposed adjacent to the second jaw pulley coupling part of the end tool hub, and at least a portion of the staple drive assembly may be formed between the first jaw pulley and the second jaw pulley.

In the present disclosure, the first shaft may be sequentially inserted through the first jaw pulley coupling part, the first jaw pulley, the staple pulley, the second jaw pulley, and the second jaw pulley coupling part.

In the present disclosure, the first jaw pulley, the staple pulley, and the second jaw pulley may be sequentially stacked in the end tool hub.

In the present disclosure, the first jaw pulley, the staple pulley, and the second jaw pulley may be formed to be rotatable independently of each other.

In the present disclosure, the end tool may further include a staple auxiliary pulley disposed between the staple pulley and the guide part.

In the present disclosure, the staple wire may be located on a common internal tangent of the staple pulley and the staple auxiliary pulley, and a rotation angle of the staple pulley may be increased by the staple auxiliary pulley.

In the present disclosure, a region of the guide part adjacent to the first jaw pulley, the staple pulley, and the second jaw pulley may be formed such that a cross section thereof is curved with a predetermined curvature.

In the present disclosure, the staple wire may be located on a common internal tangent of the staple pulley and the guide part, and a rotation angle of the staple pulley may be increased by the guide part.

In the present disclosure, the staple drive assembly may include a staple link assembly configured to connect the staple pulley and the reciprocating assembly.

In the present disclosure, the staple link assembly may include a first link coupled to the staple pulley, and a second link coupled to each of the first link and the reciprocating assembly.

In the present disclosure, when the staple pulley is alternately rotated in a clockwise direction and a counterclockwise direction, the staple link assembly connected to the staple pulley may be alternately moved toward a distal end and a proximal end of the end tool.

In the present disclosure, a bidirectional rotational motion of the staple pulley may be converted into a reciprocating linear motion of the reciprocating assembly, which is connected to the staple link assembly, by the staple link assembly.

In the present disclosure, a guide groove may be formed in a length direction of the first jaw, and the staple link assembly may be moved along the guide groove.

In the present disclosure, the end tool may further include a jaw rotation shaft inserted through the first jaw and the second jaw and being the center of rotation of the first jaw and the second jaw, wherein the first shaft may be a jaw pulley rotation shaft, which is inserted through the first jaw pulley and the second jaw pulley and being the center of rotation of the first jaw pulley and the second jaw pulley, and the jaw rotation shaft may be moved relative to the jaw pulley rotation shaft when the first jaw pulley and the second jaw pulley are rotated around the jaw pulley rotation shaft.

In the present disclosure, when the first jaw and the second jaw are closed, the jaw rotation shaft may be moved toward a distal end of the end tool, and when the first jaw and the second jaw are opened, the jaw rotation shaft may be moved toward a proximal end of the end tool.

In the present disclosure, the surgical instrument may further include a pair of end tool first jaw pitch main pulleys formed on one side of the first jaw pulley, and formed to be rotatable around a second shaft forming a predetermined angle with the first shaft, and a pair of end tool second jaw pitch main pulleys formed on one side of the second jaw pulley, and formed to be rotatable around a shaft that is substantially the same as or parallel to the second shaft.

In the present disclosure, the end tool may be formed to be yaw-rotatable around the first shaft and simultaneously pitch-rotatable around the second shaft.

The end tool may further include a first jaw wire of which at least a part is wound on the first jaw pulley and the pair of end tool first jaw pitch main pulleys, and a second jaw wire of which at least a part is wound on the second jaw pulley and the pair of end tool second jaw pitch main pulleys.

According to another embodiment of the present disclosure, there is provided an end tool of a surgical instrument, the end tool including a first jaw and a second jaw that are rotatable independently of each other, a first jaw pulley coupled to the first jaw and formed to be rotatable around a first shaft, a second jaw pulley coupled to the second jaw and formed to be rotatable around a shaft that is substantially the same as or parallel to the first shaft, a staple pulley formed to be rotatable around a shaft substantially the same as or parallel to the first shaft, and disposed adjacent to the first jaw pulley or the second jaw pulley, and a staple link assembly connected to the staple pulley and reciprocating according to a bidirectional rotation of the staple pulley.

In the present disclosure, the staple link assembly may be coupled to a reciprocating assembly of a cartridge accommodated in the first jaw and may reciprocate the reciprocating assembly.

In the present disclosure, the staple link assembly may be moved toward a distal end or a proximal end of the end tool according to a rotation direction of the staple pulley.

In the present disclosure, a protrusion may be formed on one side of the staple pulley and the staple link assembly, a hole may be formed on the other side of the staple pulley and the staple link assembly, and the protrusion may be axially coupled to the hole.

In the present disclosure, a protruding member may be formed on the staple pulley, a slot is formed in the staple link assembly, and when the staple pulley is rotated, the protruding member may be moved in the slot while coming into contact with the slot.

In the present disclosure, the staple link assembly may include a single link.

In the present disclosure, the staple link assembly may include a link member.

In the present disclosure, the link member may include a first link coupled to the staple pulley, and a second link coupled to the first link.

In the present disclosure, the staple link assembly may include a first link member and a second link member.

In the present disclosure, a cartridge accommodated in the first jaw may include a first reciprocating member and a second reciprocating member, wherein the first link member may be connected to the first reciprocating member, and the second link member may be connected to the second reciprocating member.

In the present disclosure, a guide groove may be formed in a length direction of the first jaw, and the staple link assembly may be moved along the guide groove.

In the present disclosure, the end tool may include a pair of end tool first jaw pitch main pulleys formed on one side of the first jaw pulley, and formed to be rotatable around a second shaft forming a predetermined angle with the first shaft, and a pair of end tool second jaw pitch main pulleys formed on one side of the second jaw pulley, and formed to be rotatable around a shaft that is substantially the same as or parallel to the second shaft.

In the present disclosure, when the first jaw pulley and the second jaw pulley are rotated in the same direction around the second shaft, the staple pulley may be rotated together with the first jaw pulley and the second jaw pulley.

In the present disclosure, when the first jaw pulley and the second jaw pulley are rotated in the same direction around the first shaft, the staple pulley may be rotated together with the first jaw pulley and the second jaw pulley.

In the present disclosure, when the first jaw pulley and the second jaw pulley are rotated in different directions around the first shaft, the staple pulley may be rotated together with either the first jaw pulley or the second jaw pulley.

In the present disclosure, there may be a case in which the first jaw pulley and the second jaw pulley are not rotated while the staple pulley is rotated around the first shaft by a staple wire.

In the present disclosure, a cartridge accommodation part in which a cartridge is accommodated may be formed in the first jaw, and an anvil with which a staple of the cartridge is in contact may be formed in the second jaw.

In the present disclosure, the end tool may further include a first jaw wire of which at least a portion is wound around the first jaw pulley, a second jaw wire of which at least a portion is wound around the second jaw pulley, and a staple wire of which at least a portion is wound around the staple pulley.

According to another embodiment of the present disclosure, there is provided an end tool of a surgical instrument, the end tool including a first jaw and a second jaw that are rotatable independently of each other, a first jaw pulley coupled to the first jaw and formed to be rotatable around a first shaft, a first jaw wire of which at least a portion is wound around the first jaw pulley, a second jaw pulley coupled to the second jaw and formed to be rotatable around the first shaft, a second jaw wire of which at least a portion is wound around the second jaw pulley, a pair of end tool first jaw pitch main pulleys formed on one side of the first jaw pulley, and formed to be rotatable around a second shaft forming a predetermined angle with the first shaft, a pair of end tool second jaw pitch main pulleys formed on one side of the second jaw pulley, and formed to be rotatable around a shaft that is substantially the same as or parallel to the second shaft, a staple pulley formed to be rotatable around the first shaft and disposed between the first jaw pulley and the second jaw pulley, a staple link assembly connected to the staple pulley and reciprocating according to a bidirectional rotation of the staple pulley, and a staple wire at least partially in contact with the staple pulley and configured to transmit, to the staple pulley, a driving force necessary for rotating the staple pulley.

In the present disclosure, a bidirectional rotational motion of the staple pulley may be converted into a reciprocating linear motion of the staple link assembly.

In the present disclosure, the staple link assembly may be coupled to a reciprocating assembly of a cartridge accommodated in the first jaw, and a rotational motion of the staple pulley may be transmitted to an operation member of the cartridge via the staple link assembly and the reciprocating assembly.

In the present disclosure, a bidirectional rotational motion of the staple pulley may be converted into a reciprocating linear motion of the reciprocating assembly, which is connected to the staple link assembly, by the staple link assembly.

In the present disclosure, the end tool may further include a jaw rotation shaft inserted through the first jaw and the second jaw and being the center of rotation of the first jaw and the second jaw, wherein the first shaft may be a jaw pulley rotation shaft, which is inserted through the first jaw pulley and the second jaw pulley and being the center of rotation of the first jaw pulley and the second jaw pulley, and the jaw rotation shaft may be moved relative to the jaw pulley rotation shaft when the first jaw pulley and the second jaw pulley are rotated around the jaw pulley rotation shaft.

In the present disclosure, when the first jaw and the second jaw are closed, the jaw rotation shaft may be moved toward a distal end of the end tool, and when the first jaw and the second jaw are opened, the jaw rotation shaft may be moved toward a proximal end of the end tool.

In the present disclosure, a movable-coupling-allowed hole may be formed in the first jaw or the second jaw, a shaft coupling part may be formed in the first jaw pulley or the second jaw pulley, and the shaft coupling part may be movable to a certain extent in the movable-coupling-allowed hole while being fitted into the movable-coupling-allowed hole.

In the present disclosure, when the staple pulley is alternately rotated in a clockwise direction and a counterclockwise direction, the staple link assembly connected to the staple pulley may be alternately moved toward a distal end and a proximal end of the end tool.

In the present disclosure, a guide groove may be formed in a length direction of the first jaw, and the staple link assembly may be moved along the guide groove.

In the present disclosure, the end tool may further include an end tool hub including a first jaw pulley coupling part and a second jaw pulley coupling part, which are formed to face each other, and a guide part configured to connect the first jaw pulley coupling part and the second jaw pulley coupling part, wherein a region of the guide part adjacent to the first jaw pulley, the staple pulley, and the second jaw pulley may be formed such that a cross section thereof is curved with a predetermined curvature.

In the present disclosure, the staple wire may be located on a common internal tangent of the staple pulley and the guide part, and a rotation angle of the staple pulley may be increased by the guide part.

In the present disclosure, the first jaw, the first jaw pulley, the second jaw, and the second jaw pulley may be formed to rotate around the same shaft of rotation.

In the present disclosure, the first jaw pulley, the staple pulley, and the second jaw pulley may be sequentially stacked.

In the present disclosure, a guide groove may be formed in a length direction of an anvil of the second jaw, and a clamp of a cartridge accommodated in the first jaw may be formed to be movable along the guide groove.

In the present disclosure, coupling grooves through which the clamp is inserted into and withdrawn from the anvil may be formed at both end portions of the guide groove of the anvil.

In the present disclosure, the end tool may further include a pair of end tool first jaw pitch main pulleys formed on one side of the first jaw pulley, and formed to be rotatable around a second shaft forming a predetermined angle with the first shaft, a pair of end tool second jaw pitch main pulleys formed on one side of the second jaw pulley, and formed to be rotatable around a shaft that is substantially the same as or parallel to the second shaft.

In the present disclosure, the end tool may be formed to be yaw-rotatable around the first shaft and simultaneously pitch-rotatable around the second shaft.

In the present disclosure, the end tool may further include a first jaw wire of which at least a portion is wound around the first jaw pulley and the pair of end tool first jaw pitch main pulleys, and a second jaw wire of which at least a portion is wound around the second jaw pulley and the pair of end tool second jaw pitch main pulleys.

In the present disclosure, the end tool may further include a staple second auxiliary pulley disposed between the first jaw pulley and the end tool first jaw pitch main pulley or between the second jaw pulley and the end tool second jaw pitch main pulley, formed to be rotatable around a shaft substantially the same as or parallel to the second shaft, and configured to guide a path of the first jaw wire or the second jaw wire.

According to another embodiment of the present disclosure, there is provided a surgical instrument including a first jaw capable of accommodating a cartridge, a second jaw formed to face the first jaw, a first jaw pulley coupled to the first jaw and formed to be rotatable around a first shaft, a second jaw pulley coupled to the second jaw, formed to be rotatable around a shaft substantially the same as or parallel to the first shaft, and formed to be spaced apart from the first jaw pulley by a certain extent, one or more staple pulleys at least partially formed between the first jaw pulley and the second jaw pulley, a staple link assembly including a first link member coupled to one region of the staple pulley and a second link member coupled to the other region of the staple pulley, and a staple wire of which at least a portion is wound around the staple pulley.

In the present disclosure, the first link member may be coupled to a first reciprocating member of the cartridge accommodated in the first jaw, and the second link member may be coupled to a second reciprocating member of the cartridge accommodated in the first jaw.

In the present disclosure, a first link coupling part and a second link coupling part may be formed in the staple pulley, the first link member may be coupled to the first link coupling part, and the second link member may be coupled to the second link coupling part.

In the present disclosure, the first link coupling part and the second link coupling part may be disposed on opposite sides of a central axis of the staple pulley.

In the present disclosure, when the staple pulley is rotated in one direction, the first link member and the second link member may be moved in opposite directions to each other.

In the present disclosure, when the staple pulley is rotated in one direction, the first link member may be moved toward a distal end of the end tool, and the second link member may be moved toward a proximal end of the end tool.

In the present disclosure, the cartridge accommodated in the first jaw may include a reciprocating assembly including a first reciprocating member and a second reciprocating member formed to face each other, and a ratchet member formed to be movable along the reciprocating assembly and having a first ratchet and a second ratchet formed thereon.

In the present disclosure, the first ratchet may be formed to be in contact with the first reciprocating member, and the second ratchet may be formed to be in contact with the second reciprocating member.

In the present disclosure, when the staple pulley is rotated in one direction, the first ratchet and the first reciprocating member may be in contact with each other, and when the staple pulley is rotated in the other direction, the second ratchet and the second reciprocating member may be in contact with each other.

In the present disclosure, when the staple pulley is rotated in one direction, the ratchet member is moved toward a distal end of the cartridge as the first reciprocating member is brought into close contact with and pushes the first ratchet, and when the staple pulley is rotated in the other direction, the ratchet member may be moved toward the distal end of the cartridge as the second reciprocating member is brought into close contact with and pushes the second ratchet.

In the present disclosure, when the staple pulley is rotated in one direction, the first link member connected to the staple pulley, the first reciprocating member connected to the first link member, and the ratchet member in contact with the first reciprocating member may be moved toward a distal end of the cartridge, and when the staple pulley is rotated in the other direction, the second link member connected to the staple pulley, the second reciprocating member connected to the second link member, and the ratchet member in contact with the second reciprocating member may be moved toward the distal end of the cartridge.

In the present disclosure, the first link member may include a first link and a second link, and the second link member may include a third link and a fourth link.

In the present disclosure, a coupling part, which is formed on the first link member and coupled to the first reciprocating member, and a coupling part, which is formed on the second link member and coupled to the second reciprocating member, may have substantially the same height with respect to the first shaft.

In the present disclosure, the fourth link may be formed in the form of a bar that is bent one or more times.

In the present disclosure, the first ratchet may be formed on one side surface of the ratchet member, and the second ratchet may be formed on the other side surface of the ratchet member.

In the present disclosure, when the first reciprocating member is moved toward a proximal end of the end tool, the first reciprocating member may push the first ratchet toward the second reciprocating member, and when the second reciprocating member is moved toward the proximal end of the end tool, the second reciprocating member may push the second ratchet toward the first reciprocating member.

In the present disclosure, the ratchet member may include a first ratchet member having one surface on which the first ratchet is formed, and a second ratchet member having one surface on which the second ratchet is formed.

In the present disclosure, when the first reciprocating member is moved toward a proximal end of the end tool, the first reciprocating member may push the first ratchet toward the second reciprocating member, and when the second reciprocating member is moved toward the proximal end of the end tool, the second reciprocating member may push the second ratchet toward the first reciprocating member.

In the present disclosure, the surgical instrument may further include a first elastic member interposed between the first ratchet member and the first reciprocating member and configured to apply an elastic force in a direction in which the first ratchet member comes into close contact with the first reciprocating member, and a second elastic member interposed between the first ratchet member and the second reciprocating member and configured to apply an elastic force in a direction in which the second ratchet member comes into close contact with the second reciprocating member.

In the present disclosure, the surgical instrument may further include a pair of end tool first jaw pitch main pulleys formed on one side of the first jaw pulley and formed to be rotatable around a second shaft forming a predetermined angle with the first shaft, and a pair of end tool second jaw pitch main pulleys formed on one side of the second jaw pulley, and formed to be rotatable around a shaft that is substantially the same as or parallel to the second shaft.

In the present disclosure, the end tool may be formed to be yaw-rotatable around the first shaft and simultaneously pitch-rotatable around the second shaft.

In the present disclosure, the surgical instrument may further include a first jaw wire of which at least a portion is wound around the first jaw pulley and the pair of end tool first jaw pitch main pulleys, and a second jaw wire of which at least a portion is wound around the second jaw pulley and the pair of end tool second jaw pitch main pulleys.

According to another embodiment of the present disclosure, there is provided an end tool of a surgical instrument, the end tool including a first jaw capable of accommodating a cartridge, a second jaw formed to face the first jaw, a first jaw pulley coupled to the first jaw and formed to be rotatable around a first shaft, a second jaw pulley coupled to the second jaw, formed to be rotatable around a shaft substantially the same as or parallel to the first shaft, and formed to be spaced apart from the first jaw pulley by a certain extent, a staple pulley disposed between the first jaw pulley and the second jaw pulley and having a protruding member formed in one region thereof, a link having a slot formed on one region thereof, wherein the protruding member of the staple pulley is inserted into the slot, and a staple wire of which at least a portion is wound around the staple pulley.

In the present disclosure, when the staple pulley is rotated, the link may be moved as the protruding member is moved in the slot while coming into contact with the slot.

In the present disclosure, the link may be formed as a single member.

In the present disclosure, when the staple pulley is rotated, the link is moved in one direction, wherein the link may be moved along a width of the slot in the one direction.

In the present disclosure, the protruding member may be formed in the form of a pin, and the link may be moved as the protruding member presses the slot of the link while rotating.

In the present disclosure, the slot may be formed obliquely without being concentric with the staple pulley, and the pin may be moved along the slot.

In the present disclosure, the protruding member may be formed in the form of a cam, and the link may be moved as the protruding member presses the slot of the link while rotating.

In the present disclosure, a center of the protruding member may not coincide with a center of the staple pulley, and the protruding member may be formed to be eccentric to a certain extent with respect to the staple pulley.

In the present disclosure, the cartridge accommodated in the first jaw may include a reciprocating assembly and an operation member, and each of a deactivated state, in which the link and the reciprocating assembly are spaced apart from each other, and an activated state, in which the link and the reciprocating assembly are coupled to each other, may exist.

In the present disclosure, only in the activated state, when the staple pulley is rotationally moved, which may cause the reciprocating assembly to be linearly moved.

In the present disclosure, when the first jaw and the second jaw are opened, the reciprocating assembly may be moved toward a proximal end of the end tool.

In the present disclosure, when the first jaw and the second jaw are closed, the reciprocating assembly and the link may be in contact with each other.

In the present disclosure, when the staple pulley is rotated in a state in which the first jaw and the second jaw are closed, the end tool may be switched to the activated state in which the link and the reciprocating assembly are coupled to each other.

In the present disclosure, a bidirectional rotational motion of the staple pulley may be converted into a reciprocating linear motion of the reciprocating assembly, which is connected to the link, by the link.

In the present disclosure, a bidirectional rotational motion of the staple pulley may be converted into a reciprocating linear motion of the link.

In the present disclosure, the first jaw pulley, the staple pulley, and the second jaw pulley may be sequentially stacked.

In the present disclosure, the end tool may further include a pair of end tool first jaw pitch main pulleys formed on one side of the first jaw pulley and formed to be rotatable around a second shaft forming a predetermined angle with the first shaft, and a pair of end tool second jaw pitch main pulleys formed on one side of the second jaw pulley, and formed to be rotatable around a shaft that is substantially the same as or parallel to the second shaft.

In the present disclosure, the end tool may be formed to be yaw-rotatable around the first shaft and simultaneously pitch-rotatable around the second shaft.

In the present disclosure, the end tool may further include a first jaw wire of which at least a portion is wound around the first jaw pulley and the pair of end tool first jaw pitch main pulleys, and a second jaw wire of which at least a portion is wound around the second jaw pulley and the pair of end tool second jaw pitch main pulleys.

According to another embodiment of the present disclosure, there is provided a cartridge of a surgical instrument having an end tool rotatable in at least one direction, the cartridge including a housing, a cover configured to cover one surface of the housing and having a slit formed in a first direction that is a length direction of the housing, a plurality of staples disposed inside the housing, a reciprocating assembly disposed inside the housing, formed to be movable in the first direction with respect to the housing, and having a plurality of recesses formed on at least one surface thereof, and an operation member formed on one side of the reciprocating assembly to be in contact with the reciprocating assembly and to be movable in the first direction by the reciprocating assembly.

In the present disclosure, the reciprocating assembly may be connected to a staple drive assembly formed on the end tool, and may be moved in the first direction when a staple pulley of the staple drive assembly is rotated.

In the present disclosure, when the staple pulley is alternately rotated in a clockwise direction and a counterclockwise direction, the reciprocating assembly connected to the staple drive assembly may be alternately moved toward a distal end and a proximal end of the cartridge.

In the present disclosure, the reciprocating assembly may move the operation member in contact with the reciprocating assembly in the first direction while moving toward the distal end of the cartridge.

In the present disclosure, the operation member may include a body, one or more wedges formed on one side of the body and each including an inclined surface formed to have a greater height at a proximal end side of the cartridge than a distal end side of the cartridge, a blade formed on one side of the wedge and including a sharp edge, and a ratchet member formed on one side of the body and having one or more ratchets formed thereon to be in contact with the recesses of the reciprocating assembly.

In the present disclosure, the cartridge may further include an elastic member formed between the body or the wedge and the ratchet member and configured to provide an elastic force to press the ratchet toward the reciprocating assembly.

In the present disclosure, when the reciprocating assembly is moved toward the distal end of the cartridge, the reciprocating assembly may be brought into close contact with and pushes the ratchet so that the operation member is moved toward the distal end of the cartridge.

In the present disclosure, when the reciprocating assembly is moved toward the proximal end of the cartridge, the operation member may remain stationary with respect to the one direction.

In the present disclosure, when the reciprocating assembly is moved toward the proximal end of the cartridge, an inclined surface of the reciprocating assembly may press an inclined surface of the ratchet in a direction in which the ratchet member is away from the reciprocating assembly.

In the present disclosure, the reciprocating assembly may include a first reciprocating member and a second reciprocating member formed to face each other, and the ratchet member may include a first ratchet formed to be in contact with the first reciprocating member, and a second ratchet formed to be in contact with the second reciprocating member.

In the present disclosure, when the first reciprocating member is moved toward the distal end of the cartridge, the first reciprocating member may be brought into close contact with and push the first ratchet so that the operation member is moved toward the distal end of the cartridge, and when the second reciprocating member is moved toward the distal end of the cartridge, the second reciprocating member may be brought into close contact with and push the second ratchet so that the operation member is moved toward the distal end of the cartridge.

In the present disclosure, the first reciprocating member and the second reciprocating member may be alternately moved toward the distal end of the cartridge.

In the present disclosure, the first reciprocating member may be connected to a first link member connected to one region of a staple pulley of the end tool, the second reciprocating member may be connected to a second link member connected to the other region of the staple pulley, when the staple pulley is rotated in one direction, the first link member connected to the staple pulley, the first reciprocating member connected to the first link member, and the ratchet member in contact with the first reciprocating member may be moved toward the distal end of the cartridge, and when the staple pulley is rotated in the other direction, the second link member connected to the staple pulley, the second reciprocating member connected to the second link member, and the ratchet member in contact with the second reciprocating member may be moved toward the distal end of the cartridge.

In the present disclosure, the first ratchet may be formed on one side surface of the ratchet member, and the second ratchet may be formed on the other side surface of the ratchet member.

In the present disclosure, when the first reciprocating member is moved toward the proximal end of the cartridge, the first reciprocating member may push the first ratchet toward the second reciprocating member, and when the second reciprocating member is moved toward the proximal end of the cartridge, the second reciprocating member may push the second ratchet toward the first reciprocating member.

In the present disclosure, the ratchet member may include a first ratchet member having one surface on which the first ratchet is formed, and a second ratchet member having one surface on which the second ratchet is formed.

In the present disclosure, when the first reciprocating member is moved toward the proximal end of the cartridge, the first reciprocating member may push the first ratchet toward the second reciprocating member, and when the second reciprocating member is moved toward the proximal end of the cartridge, the second reciprocating member may push the second ratchet toward the first reciprocating member.

In the present disclosure, the cartridge may further include a first elastic member interposed between the first ratchet member and the first reciprocating member and configured to apply an elastic force in a direction in which the first ratchet member comes into close contact with the first reciprocating member, and a second elastic member interposed between the first ratchet member and the second reciprocating member and configured to apply an elastic force in a direction in which the second ratchet member comes into close contact with the second reciprocating member.

In the present disclosure, one or more protrusions may be formed in a region of an inner surface of the housing, which is to be in contact with the operation member, and a snap to be in contact with the protrusion may be formed in the operation member.

In the present disclosure, when the reciprocating assembly is moved toward the proximal end of the cartridge, the snap and the protrusion may be in contact with each other to prevent the operation member from moving toward the proximal end of the cartridge.

In the present disclosure, one end portion of the snap may be coupled to the operation member and is formed to be elastically deformable to a certain extent.

In the present disclosure, each of the one or more protrusions may include an inclined surface formed to have a greater height at the proximal end side of the cartridge than the distal end side of the cartridge.

In the present disclosure, a clamp formed to extend in the first direction may be formed at one side of the blade of the operation member.

In the present disclosure, a guide groove may be formed in an anvil of a second jaw of the end tool in the first direction, and the clamp may be moved along the guide groove.

In the present disclosure, coupling grooves through which the clamp is inserted into and withdrawn from the anvil may be formed at both end portions of the anvil.

According to another embodiment of the present disclosure, there is provided a method of driving a surgical instrument, the method comprising operations (a) in which, when a staple pulley of a staple drive assembly is rotated in a first direction around a first shaft, a staple link assembly connected to the staple pulley and a reciprocating assembly of a cartridge connected to the staple link assembly are moved along a second shaft toward a distal end of the cartridge, (b) in which, when the reciprocating assembly is moved toward the distal end of the cartridge, an operation member in contact with the reciprocating assembly is moved toward the distal end of the cartridge together with the reciprocating assembly, (c) in which, as the operation member is moved toward the distal end of the cartridge, the operation member ejects staples in the cartridge to the outside of the cartridge, and simultaneously, a blade of the operation member is moved toward the distal end of the cartridge, and (d) in which, when the staple pulley is rotated in a second direction opposite to the first direction around the first shaft, the staple link assembly, which is connected to the staple pulley, and the reciprocating assembly of the cartridge, which is connected to the staple link assembly, are moved toward a proximal end of the cartridge.

In the present disclosure, when the staple pulley is rotated in the first direction or the second direction, the reciprocating assembly may be moved toward the distal end of the cartridge or the proximal end of the cartridge.

In the present disclosure, a bidirectional rotational motion of the staple pulley around the first shaft may be converted into a reciprocating linear motion of the reciprocating assembly, which is connected to the staple pulley, with respect to the second shaft.

In the present disclosure, the operation member may be moved toward the distal end of the cartridge by the reciprocating linear motion of the reciprocating assembly.

In the present disclosure, a rack may be formed on one surface of the reciprocating assembly, the operation member may include a ratchet member having a ratchet formed thereon, and as the rack pushes the ratchet member while being in close contact with the ratchet member, the ratchet member may be moved toward the distal end of the cartridge.

In the present disclosure, in operation (d), the operation member may remain stationary with respect to a direction of the second shaft.

in the present disclosure, the operation member may be moved toward the distal end of the cartridge together with the reciprocating assembly only when the reciprocating assembly is moved toward the distal end of the cartridge.

In the present disclosure, the staple drive assembly may include a first link member connected to one region of the staple pulley, and a second link member connected to the other region of the staple pulley, the reciprocating assembly may include a first reciprocating member coupled to the first link member and a second reciprocating member coupled to the second link member, and the operation member may include a ratchet member on which a first ratchet and a second ratchet are formed.

In the present disclosure, in operation (a), the first ratchet and the first reciprocating member may be in contact with each other, and in operation (b), the second ratchet and the second reciprocating member may be in contact with each other.

In the present disclosure, in operation (a), the first link member connected to the staple pulley, the first reciprocating member connected to the first link member, and the operation member in contact with the first reciprocating member may be moved toward the distal end of the cartridge, and the second link member connected to the staple pulley and the second reciprocating member connected to the second link member may be moved toward the proximal end of the cartridge.

In the present disclosure, in operation (d), the first link member connected to the staple pulley and the first reciprocating member connected to the first link member may be moved toward the distal end of the cartridge, and the second link member connected to the staple pulley, the second reciprocating member connected to the second link member, and the operation member in contact with the second reciprocating member may be moved toward the distal end of the cartridge.

In the present disclosure, in operation (d), the operation member may be moved toward the distal end of the cartridge.

In the present disclosure, the surgical instrument may further include a staple wire coupled to the staple pulley to rotate the staple pulley, wherein a bidirectional rotation of the staple pulley may be converted into a reciprocating linear motion of the reciprocating assembly by the staple wire.

In the present disclosure, as the operation member is moved toward the distal end of the cartridge, a wedge of the operation member may sequentially push and raise a plurality of staples in the cartridge to perform a stapling motion, and simultaneously, a blade formed on one side of the wedge of the operation member may be moved toward the distal end of the cartridge to perform a cutting motion.

In the present disclosure, operations (a) to (d) may be repeatedly performed.

MODE OF DISCLOSURE

While the present disclosure is susceptible to various modifications and alternative forms, specific embodiments thereof are shown by way of example in the drawings and will herein be described in detail. However, it should be understood that there is no intent to limit the present disclosure to the particular forms disclosed herein, rather, the present disclosure should be construed to cover various modifications, equivalents, and alternatives of embodiments of the present disclosure. In describing the present disclosure, detailed description of known related arts will be omitted when it is determined that the gist of the present disclosure may be unnecessarily obscured.

Although terms such as "first," "second," and the like may be used to describe various components, such components should not be limited to the above terms. The terms are only used to distinguish one component from another.

The terms used herein are for the purpose of describing particular embodiments only and are not intended to be limiting to the present disclosure. Singular forms are intended to include plural forms as well, unless the context clearly indicates otherwise. In the present application, it will be further understood that the terms "comprise," "comprising," "include," and/or "including", when used in this specification, specify the presence of stated features, integers, steps, operations, elements, components and/or groups thereof but do not preclude the presence or addition of one or more other features, integers, steps, operations, elements, components and/or groups thereof.

Hereinafter, the embodiments of the present disclosure will be described below in detail with reference to the accompanying drawings, and when the embodiments of the present disclosure are described with reference to the drawings, the same or corresponding components are given the same reference numerals, and repetitive descriptions thereof will be omitted.

Further, in describing the various embodiments of the present disclosure, it is to be understood that each embodiment is not intended to be interpreted or implemented independently, and that the technical ideas described in each embodiment may be interpreted or implemented in combination with other embodiments described separately.

In a surgical instrument according to the present disclosure, when a manipulation part is rotated in one direction for at least any one of pitch, yaw, and actuation motions, an end tool is rotated in intuitively the same direction as a direction in which the manipulation part is moved.

FIG. 1A is a conceptual diagram of a pitch motion of a conventional surgical instrument, and FIG. 1B is a conceptual diagram of a yaw motion thereof.

Referring to FIG. 1A, in performing a pitch motion of a conventional surgical instrument, in a state in which an end tool 120*a* is formed in front of a rotation center 121*a* of the end tool, and a manipulation part 110*a* is formed at the rear of a rotation center 111*a* of the manipulation part, when the manipulation part 110*a* is rotated in a clockwise direction, the end tool 120*a* is also rotated in the clockwise direction, and when the manipulation part 120*a* is rotated in a counterclockwise direction, the end tool 120*a* is also rotated in the counterclockwise direction. Referring to FIG. 1B, in performing a yaw motion of the conventional surgical instrument, in a state in which the end tool 120*a* is formed in front of the rotation center 121*a* of the end tool, and the manipulation part 110*a* is formed at the rear of the rotation center 111*a* of the manipulation part, when the manipulation part 110*a* is rotated in the clockwise direction, the end tool 120*a* is also rotated in the clockwise direction, and when the manipulation part 120*a* is rotated in the counterclockwise direction, the end tool 120*a* is also rotated in the counterclockwise direction. In this case, in view of left and right directions of a user, when the user moves the manipulation part 110*a* to the left, the end tool 120*a* is moved to the right, and when the user moves the manipulation part 110*a* to the right, the end tool 120*a* is moved to the left. As a result, a manipulation direction of the user and an operation direction of the end tool are opposite to each other, which may cause the user to make a mistake, and user's manipulation may not be easy.

FIG. 1C is a conceptual diagram of a pitch motion of another conventional surgical instrument, and FIG. 1D is a conceptual diagram of a yaw motion thereof.

Referring to FIG. 1C, in the conventional surgical instrument, which is partially formed in a mirror symmetrical shape, in performing a pitch motion, in a state in which an end tool 120*b* is formed in front of a rotation center 121*b* of the end tool, and a manipulation part 110*b* is formed at the rear of a rotation center 111*b* of the manipulation part, when the manipulation part 110*b* is rotated in the clockwise direction, the end tool 120*b* is rotated in the counterclockwise direction, and when the manipulation part 110*b* is rotated in the counterclockwise direction, the end tool 120*b* is rotated in the clockwise direction. In this case, in view of rotation directions of the manipulation part and the end tool, a rotation direction in which the user rotates the manipulation part 110*b* and a rotation direction of the end tool 120*b* according thereto are opposite to each other. As a result, the user may be confused with the manipulation direction, and as the operation of a joint is not intuitive, the user may make an error. Further, referring to FIG. 1D, in performing a yaw motion, in a state in which the end tool 120*b* is formed in front of the rotation center 121*b* of the end tool, and the manipulation part 110*b* is formed at the rear of the rotation center 111*b* of the manipulation part, when the manipulation part 110*b* is rotated in the clockwise direction, the end tool 120*b* is rotated in the counterclockwise direction, and when the manipulation part 110*b* is rotated in the counterclockwise direction, the end tool 120*b* is rotated in the clockwise direction. In this case, in view of rotation directions of the manipulation part and the end tool, a rotation direction in which the user rotates the manipulation part 110*b* and a rotation direction of the end tool 120*b* according thereto are opposite to each other. As a result, the user may be confused with the manipulation direction, and as the operation of the joint is not intuitive, the user may make an error. In the user's pitch or yaw manipulation of the conventional surgical instrument, the user's manipulation direction and the end tool's operation direction do not match each other in view of one of the rotation direction and the left and right directions. This is because the configurations of the end tool and the manipulation part are different from each other in the joint configuration of the conventional surgical instrument. That is, this is because the manipulation part is formed at the rear of the rotation center of the manipulation part, while the end tool is formed in front of the rotation center of the end tool. In order to address the above problems, in a surgical instrument according to an embodiment of the present disclosure, which is illustrated in FIGS. 1E and 1F, an end tool 120*c* is formed in front of a rotation center 121*c* of the end tool and a manipulation part 110*c* is also formed in front of a rotation center 111*c* of the manipulation part, so that the operations of the manipulation part 110*c* and the end tool 120*c* are intuitively matched with each other. In other words, unlike existing examples such as those shown in FIGS. 1A, 1B, 1C, and 1D, in which the manipulation part is close to a user with respect to the joint thereof (that is, away from the end tool), the surgical instrument according to an embodiment of the present disclosure, which is illustrated in FIGS. 1E and 1F, is formed such that at least a portion of the manipulation part is closer (than a joint thereof) to the end tool with respect to the joint thereof at any one moment or more in a manipulation process.

In other words, in the conventional surgical instrument as illustrated in FIGS. 1A, 1B, 1C, and 1D, the manipulation part is formed at the rear of the rotation center thereof, while the end tool is located in front of the rotation center thereof, and thus the end tool is moved at a front side thereof with a rear side fixed through a motion of the manipulation part that is moved at a rear side thereof with a front side thereof fixed, which is not an intuitively matching structure. Accordingly, a mismatch may occur between the manipulation of the manipulation part and the motion of the end tool in view of the left and right directions or in view of the rotation direction, which may cause confusion to the user, and the manipulation of the manipulation part may be difficult to perform intuitively and quickly and may cause mistakes. In contrast, in the surgical instrument according to an embodiment of the present disclosure, since both the end tool and the manipulation part are moved with respect to the rotation center formed at the rear side thereof, it may be said that the motions are intuitively matched with each other in terms of structure. In other words, moving portions of the manipulation part are moved with respect to the rotation center formed at the rear side thereof just as moving portions of the end tool are moved with respect to the rotation center formed at the rear side thereof, and thus it may be said that the motions are intuitively matched with each other in terms of structure. This allows the user to intuitively and quickly perform a control in a direction toward the end tool, and a possibility of making a mistake may be significantly reduced. Hereinafter, a detailed mechanism enabling the above-described function will be described below.

First Embodiment of Surgical Instrument

Figure 2:
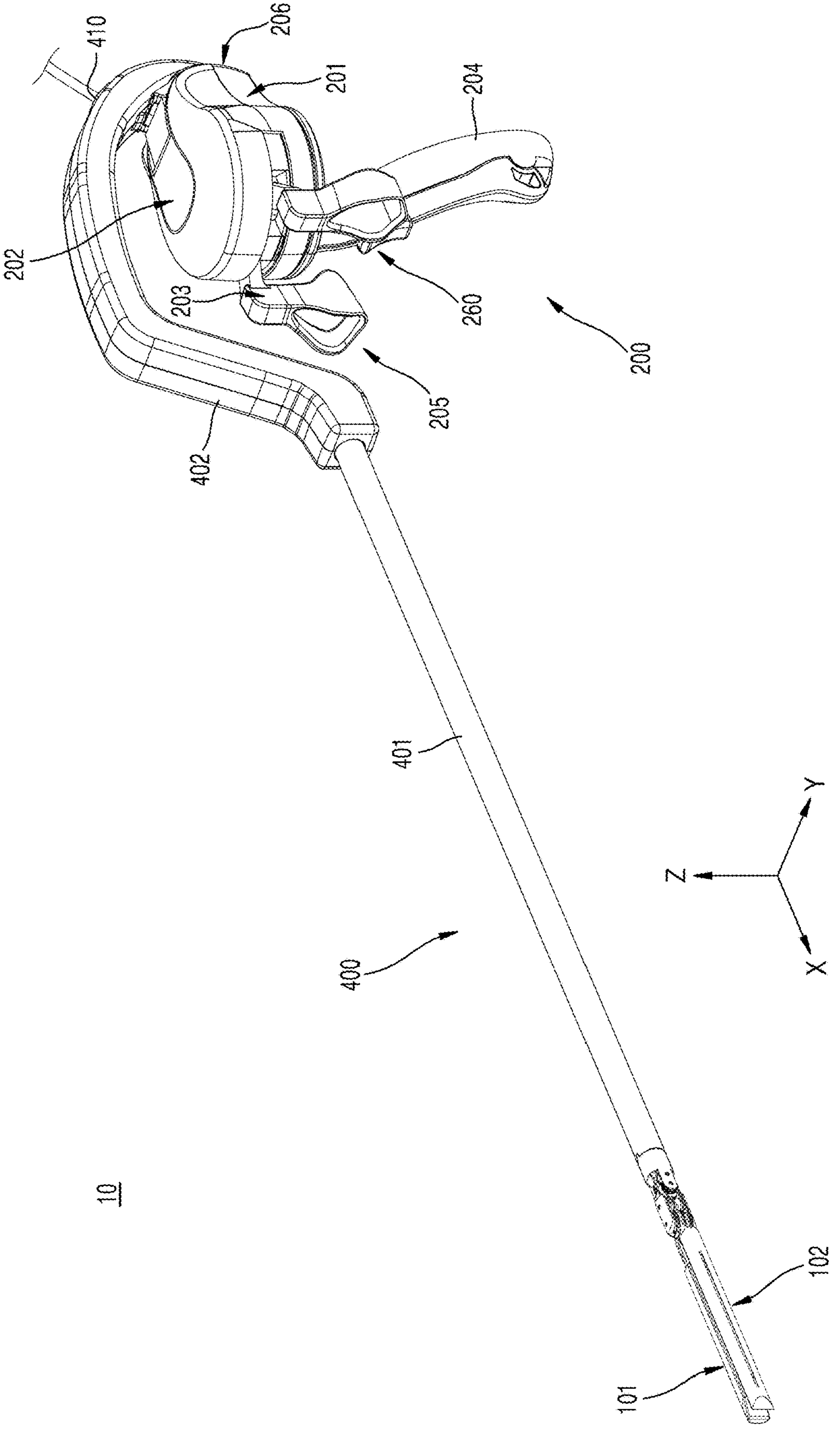
FIG. 2 is a perspective view illustrating a surgical instrument according to a first embodiment of the present disclosure.
Figure 3:
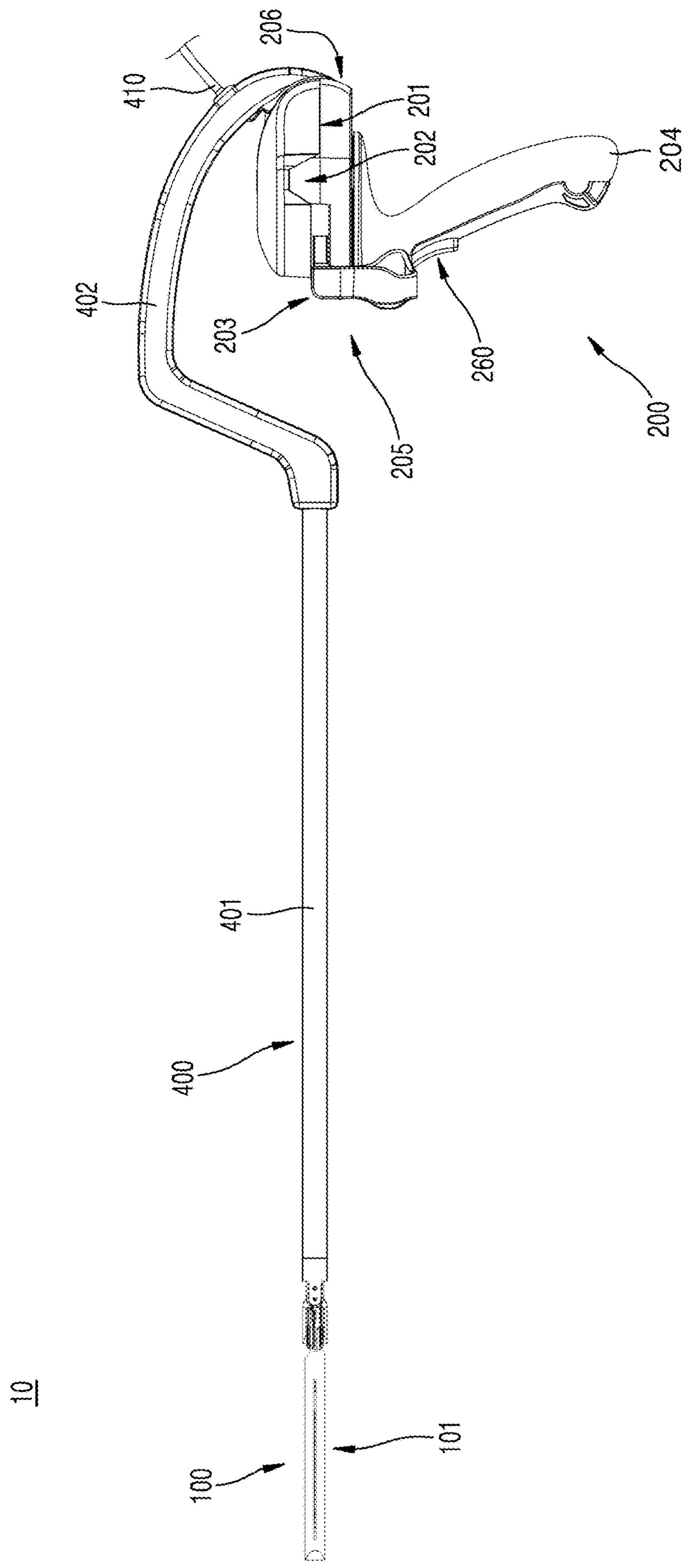
FIG. 3 is a side view of the surgical instrument of FIG. 2.
Figure 4:
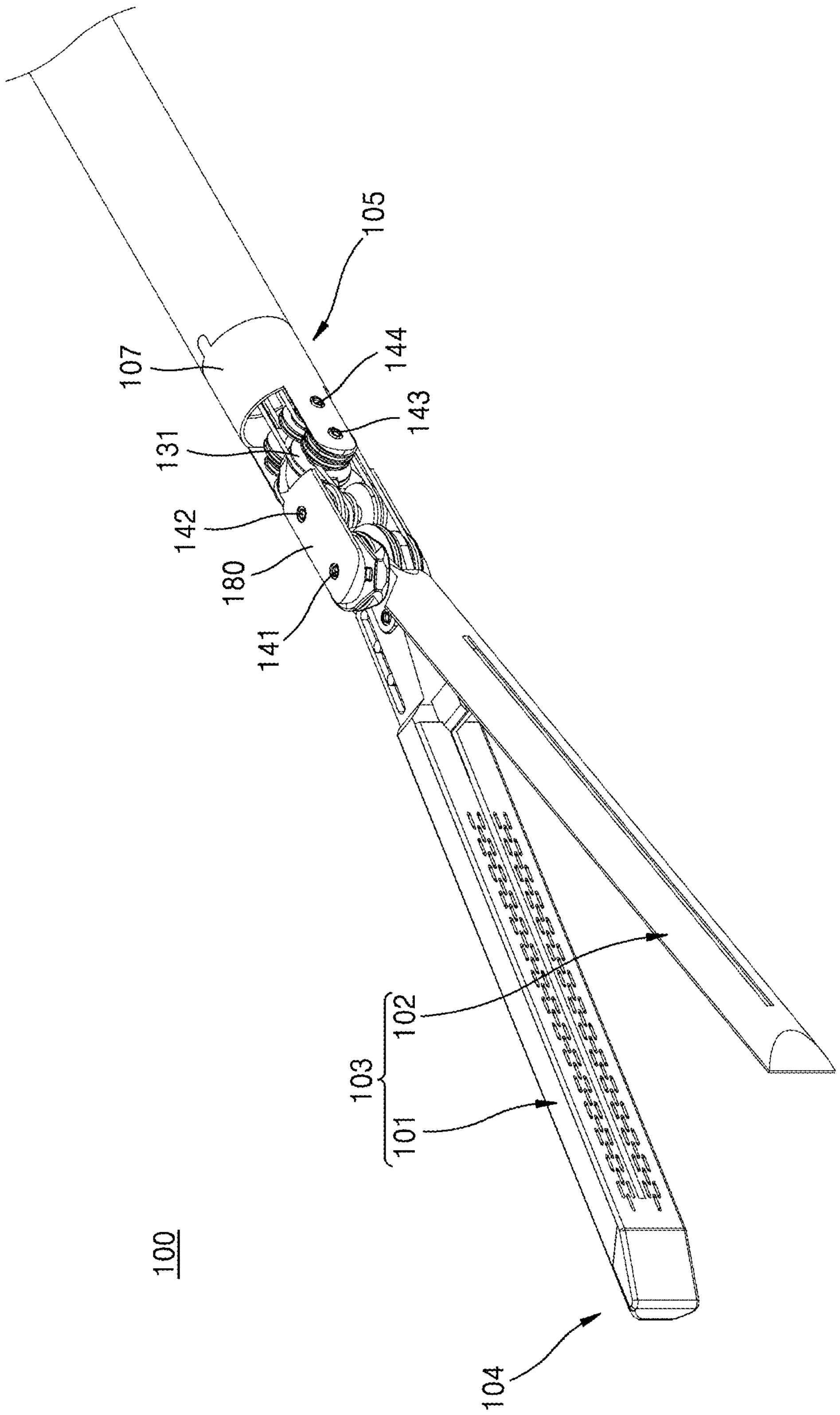
FIGS. 4 and 5 are perspective views illustrating an end tool of the surgical instrument of FIG. 2.
Figure 5:
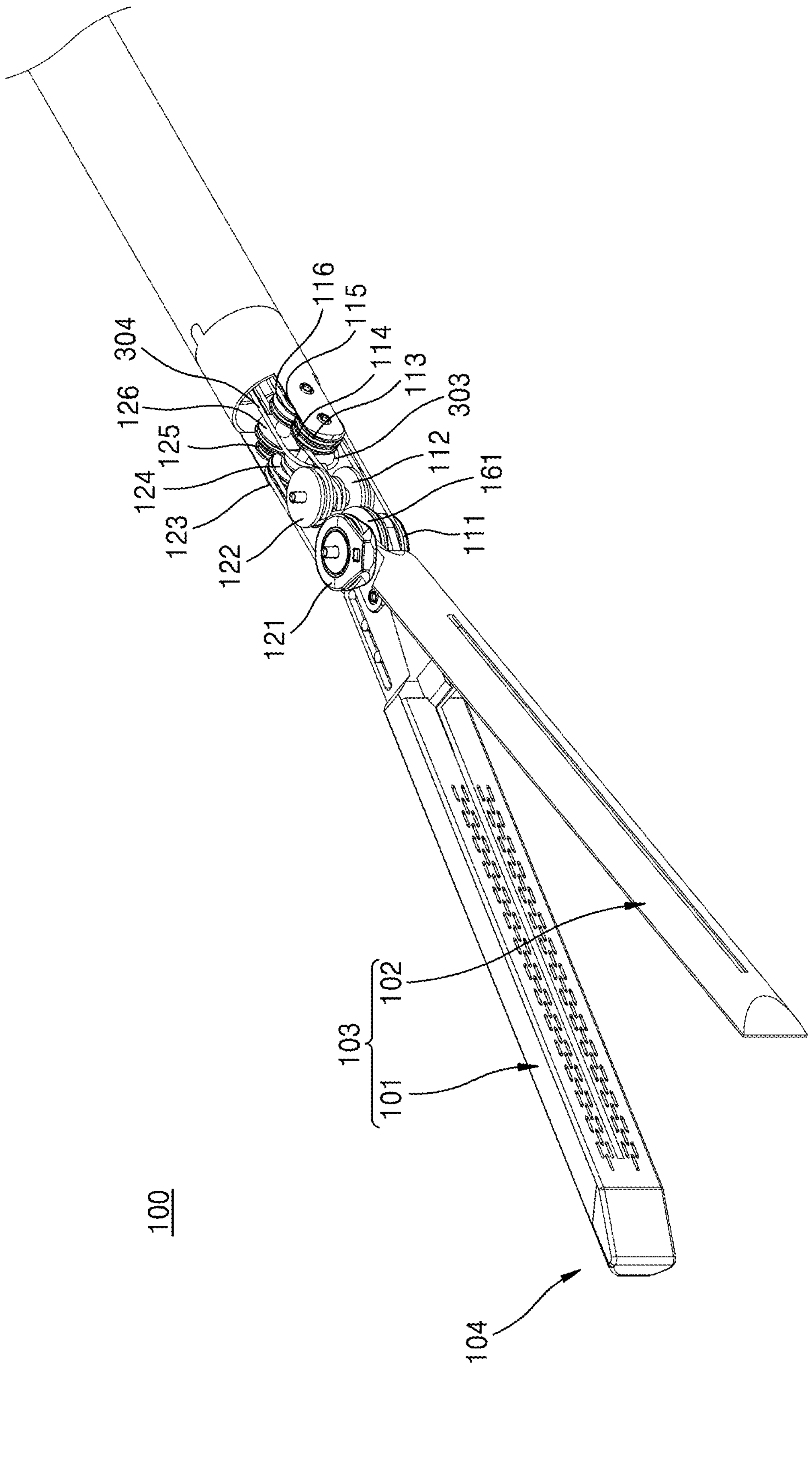
Figure 6:
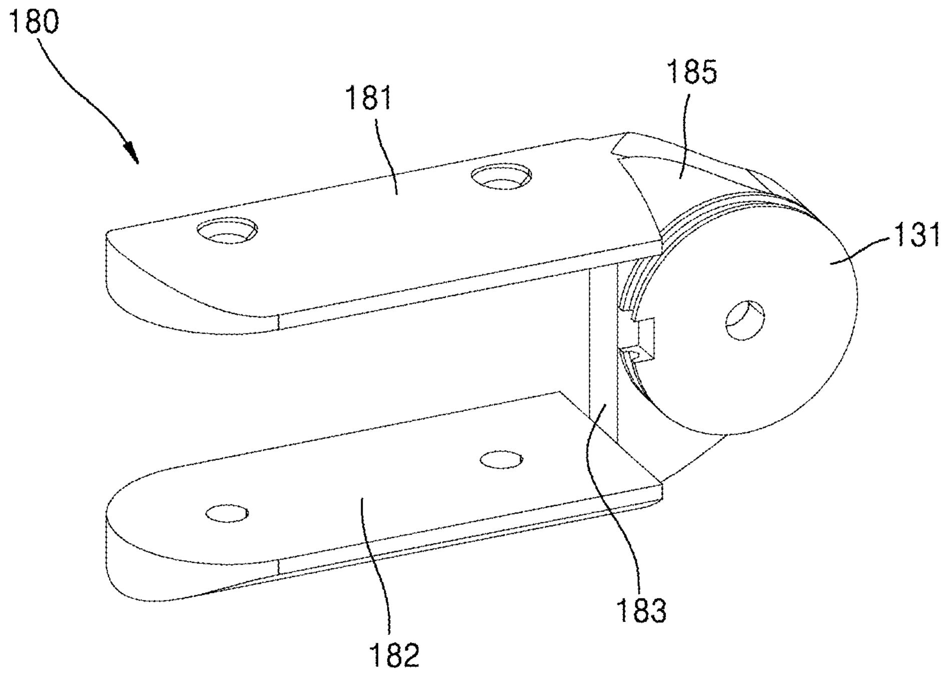
FIG. 6 is a perspective view illustrating an end tool hub of the end tool of the surgical instrument of FIG. 2.
Figure 7:
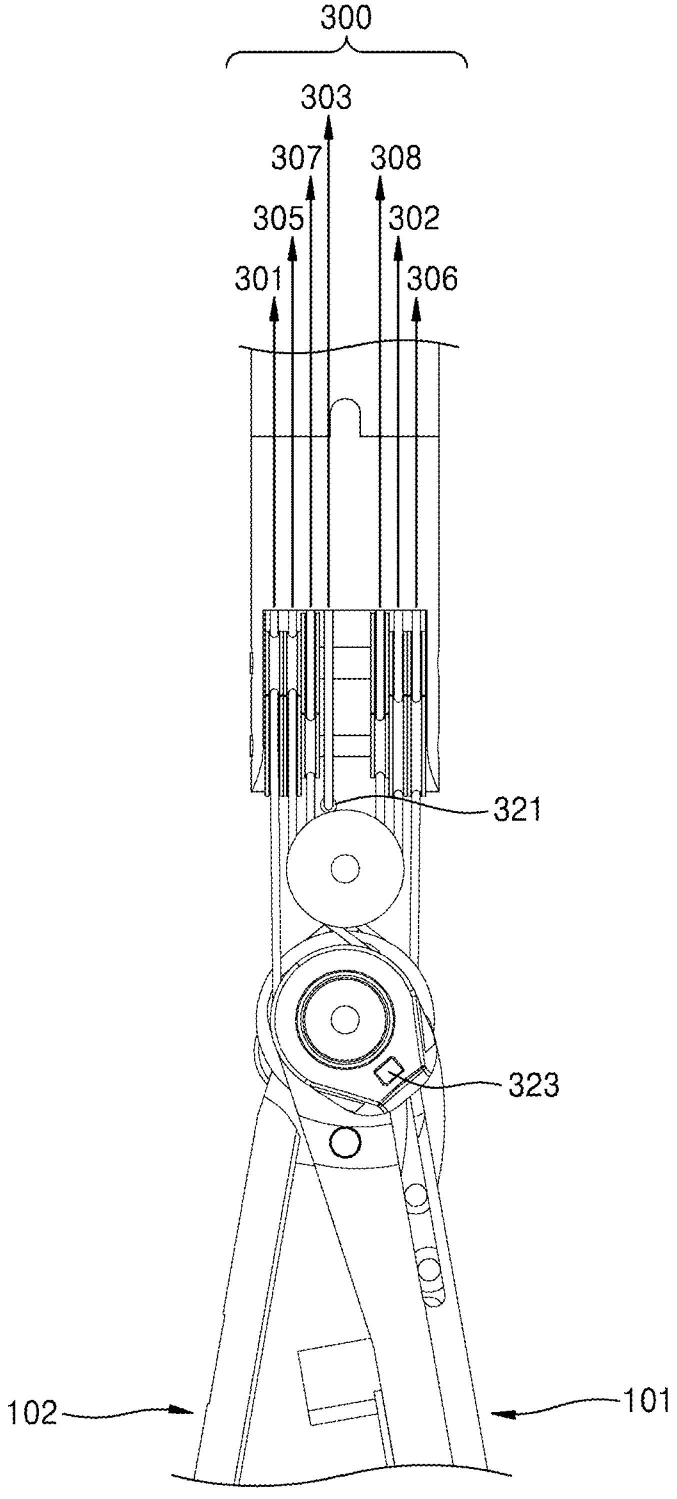
FIGS. 7 and 8 are plan views illustrating the end tool of the surgical instrument of FIG. 2.
Figure 8:
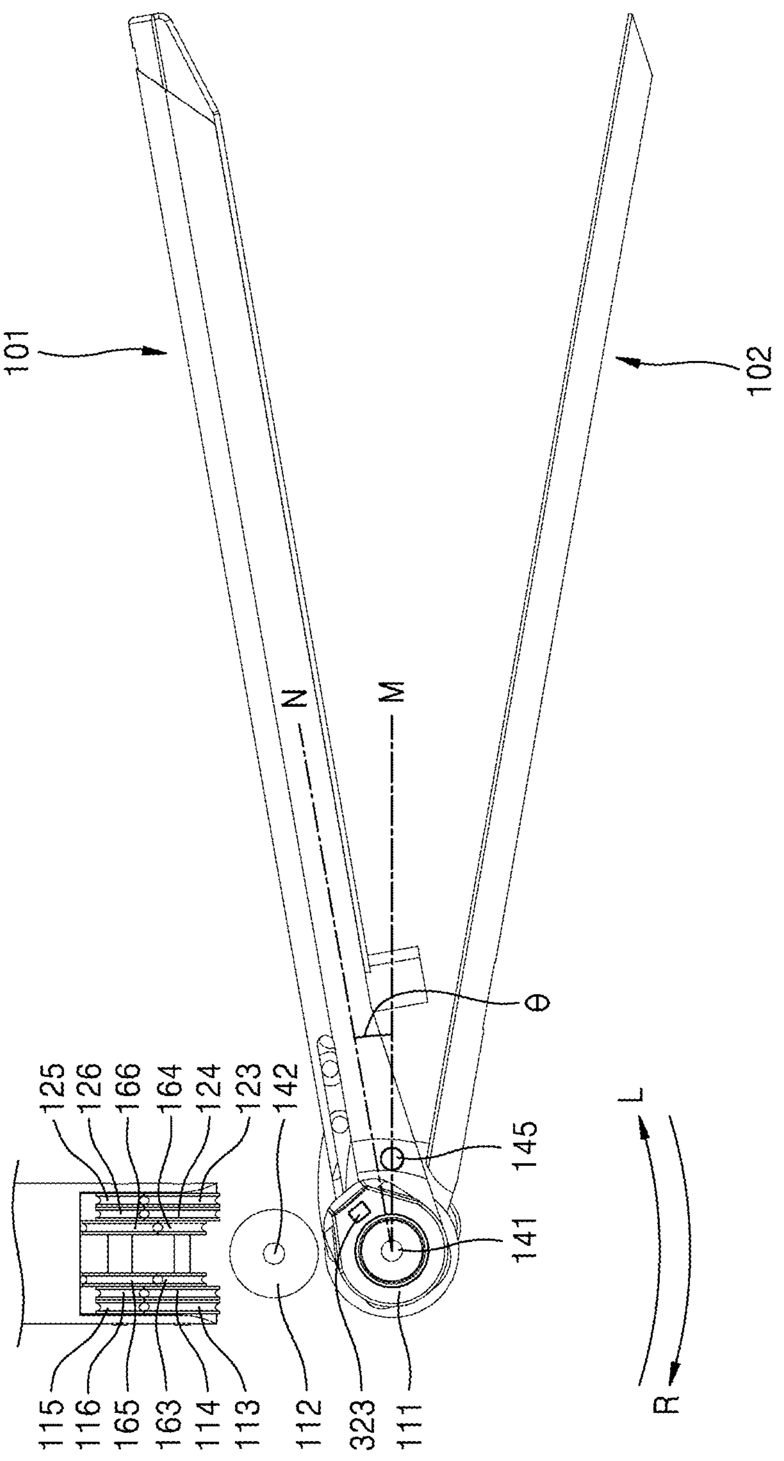
Figure 9:
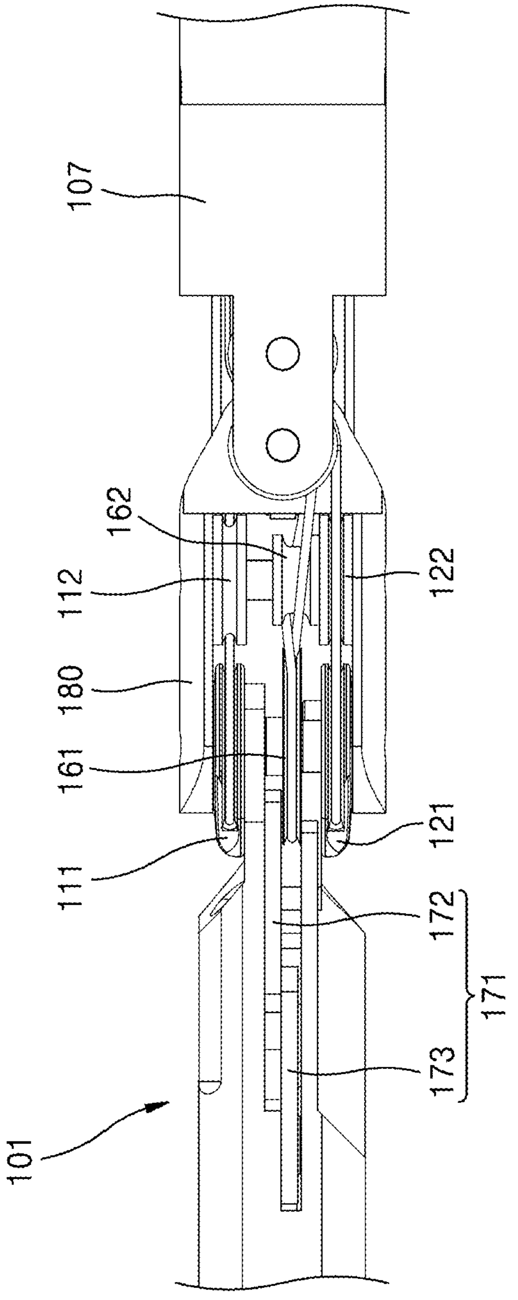
FIG. 9 is a side view illustrating the end tool of the surgical instrument of FIG. 2.
Figure 10:
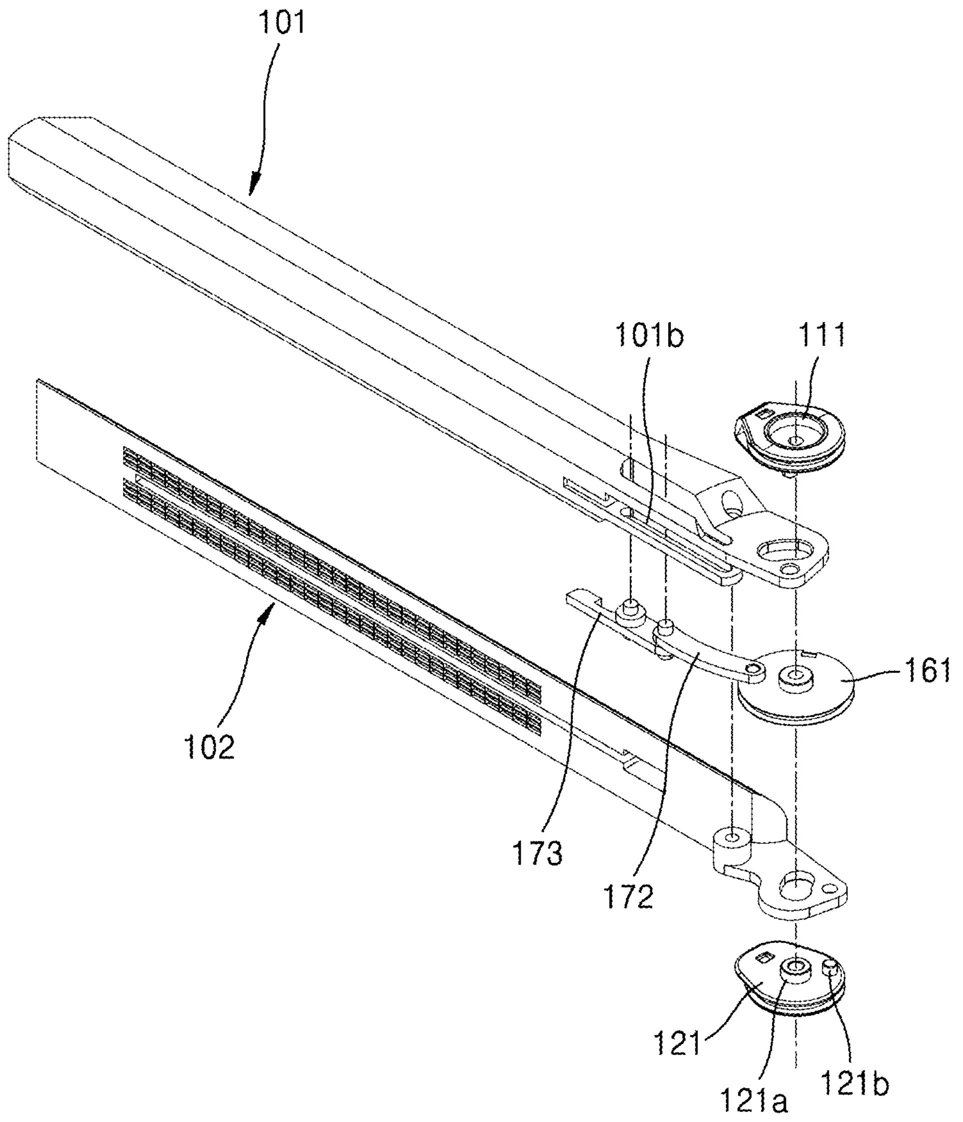
FIGS. 10 and 11 are exploded perspective views of the end tool of the surgical instrument of FIG. 2.
Figure 11:
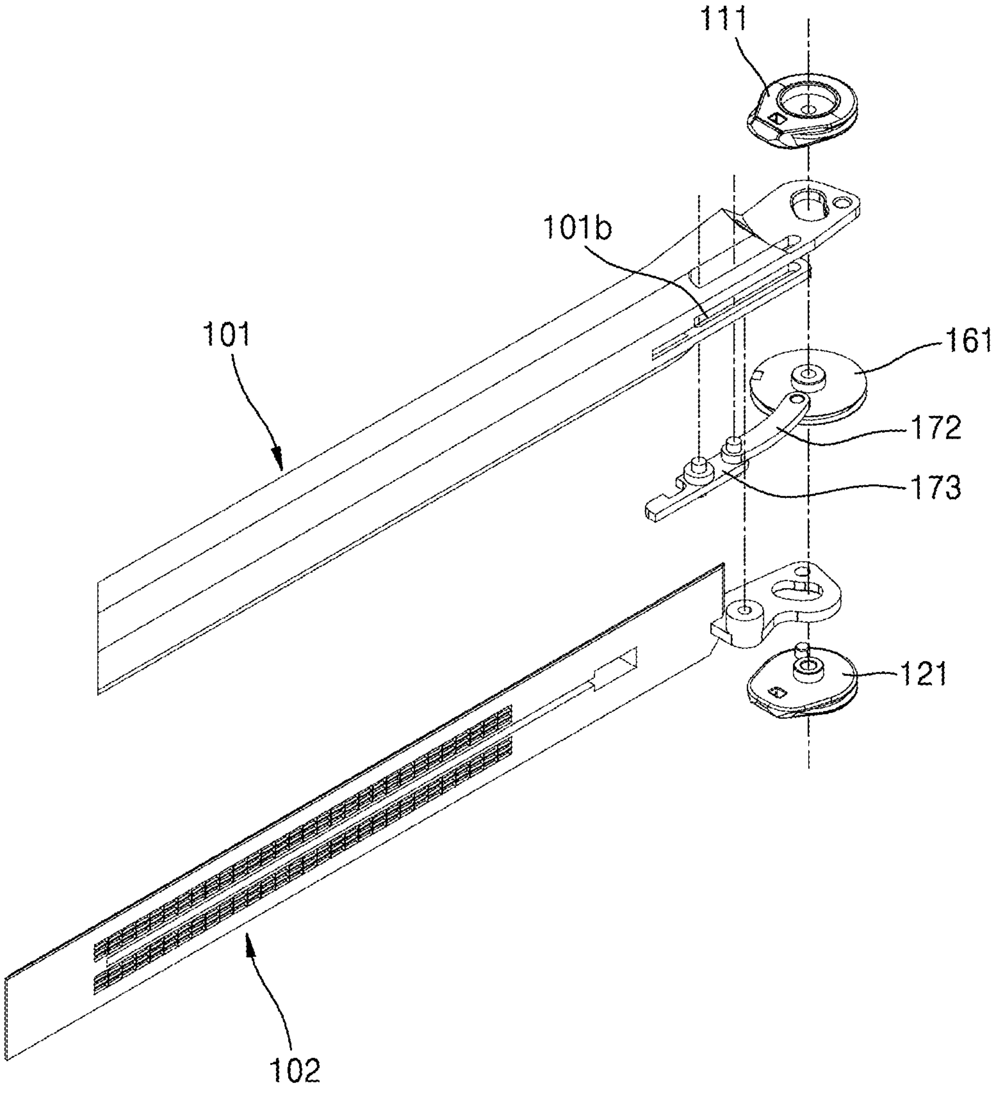
Figure 12:
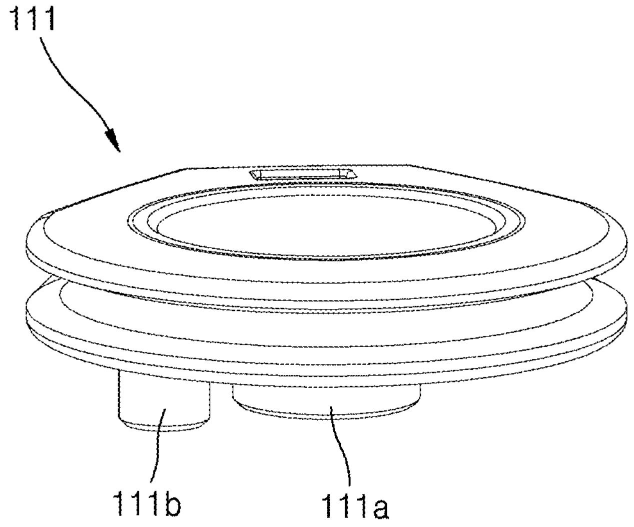
FIG. 12 is a perspective view illustrating a first jaw pulley of the surgical instrument of FIG. 2.
Figure 13:
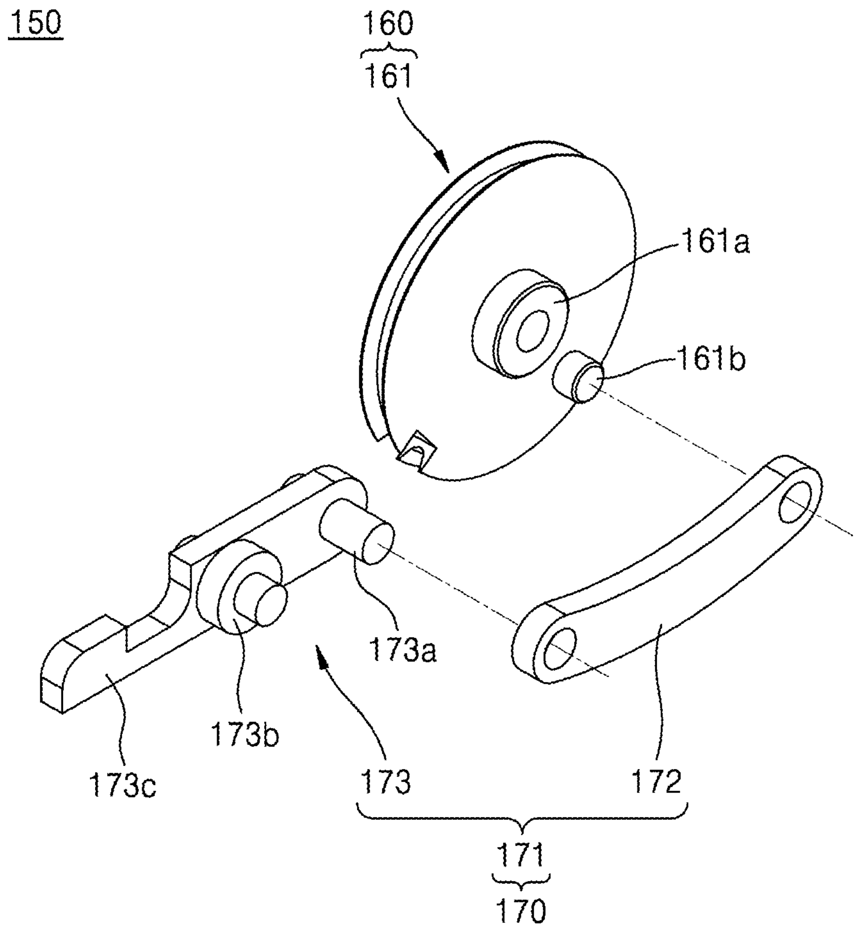
FIG. 13 is an exploded perspective view illustrating a staple pulley and a staple link of the surgical instrument of FIG. 2.
Figure 14:
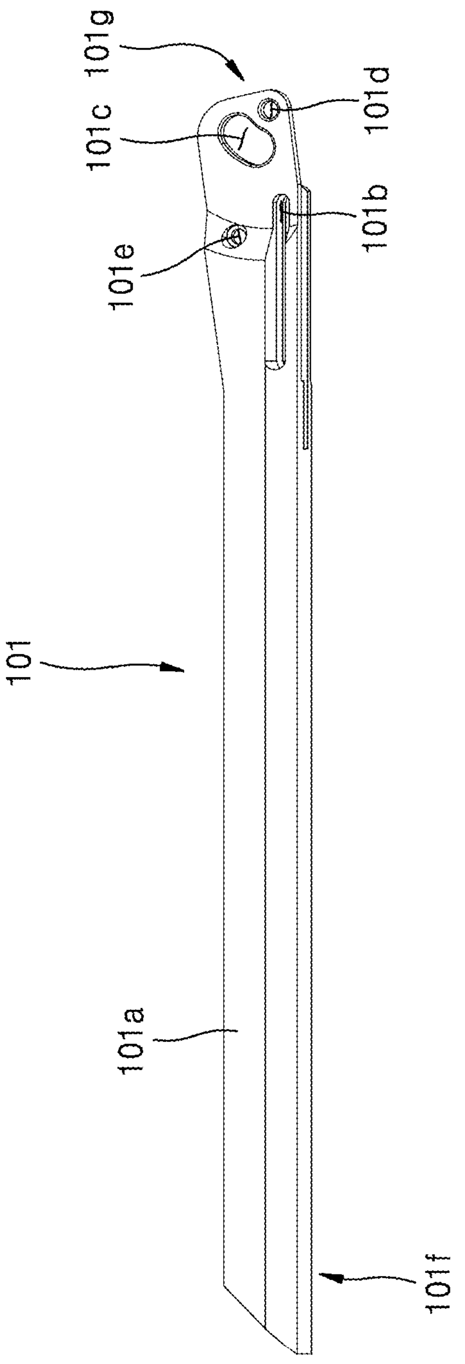
FIG. 14 is a plan view illustrating a first jaw of the surgical instrument of FIG. 2.
Figure 15:
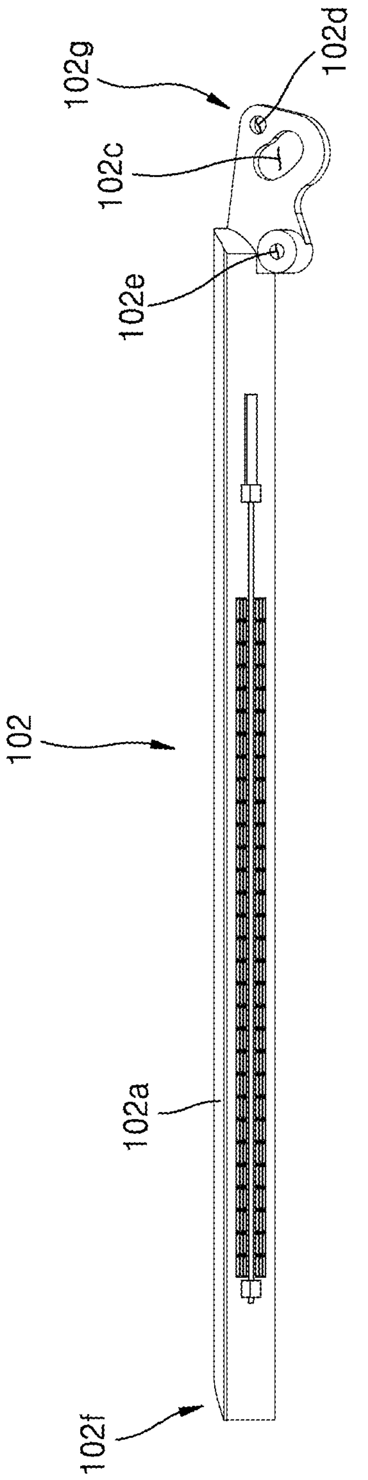
FIG. 15 is a plan view illustrating a second jaw of the surgical instrument of FIG. 2.
Figure 16:
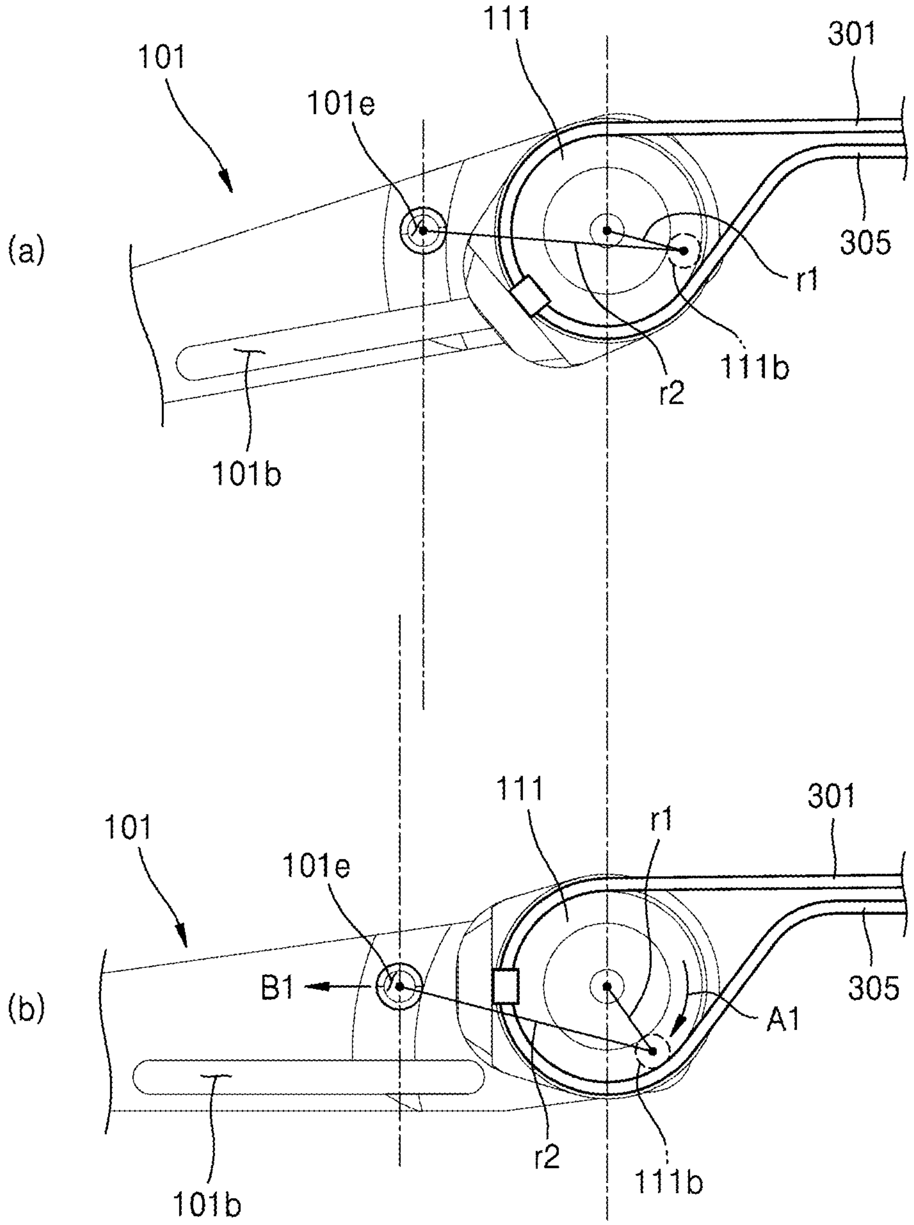
FIG. 16 is a plan view illustrating opening and closing motions of the first jaw of the surgical instrument of FIG. 2.
Figure 17:
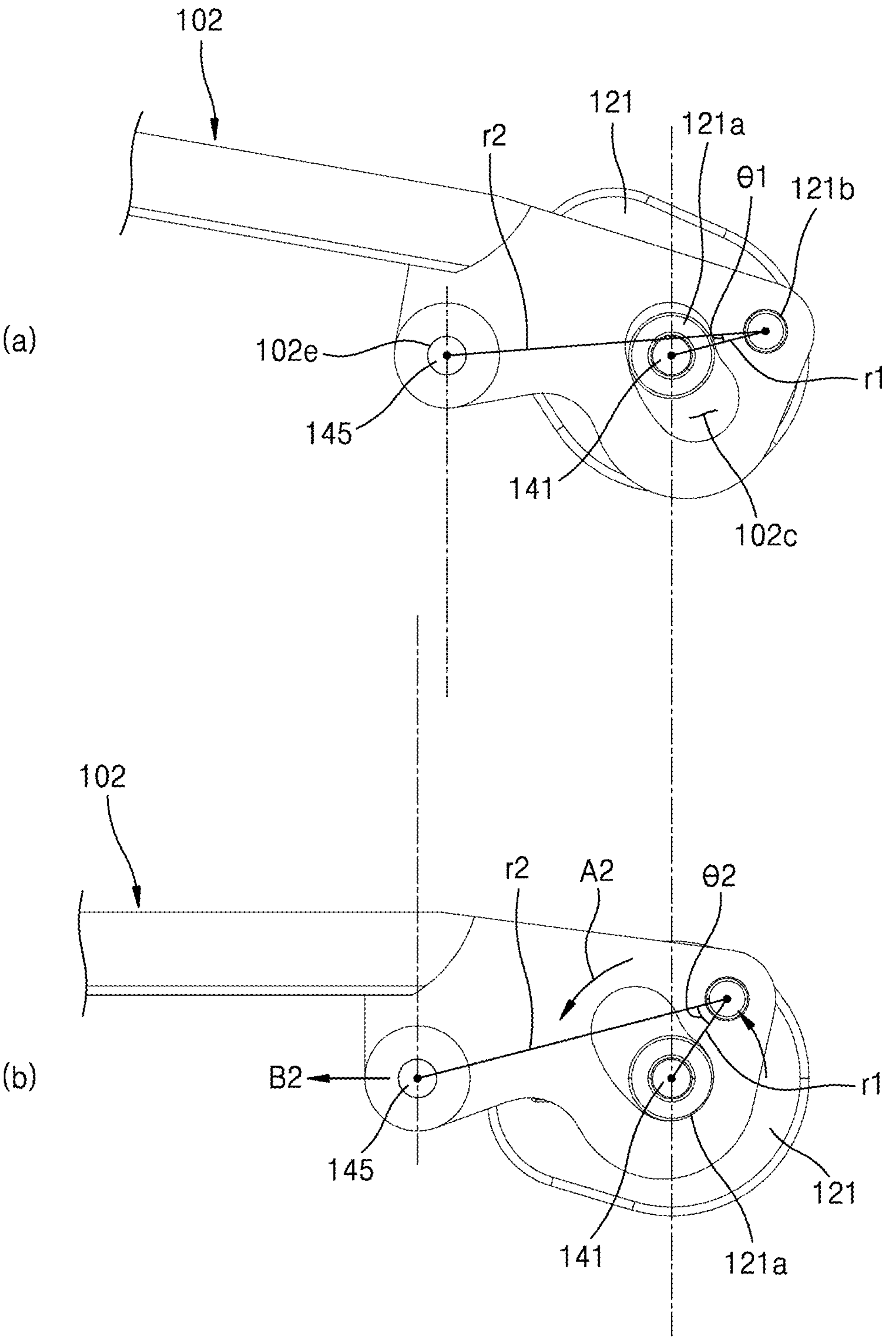
FIG. 17 is a plan view illustrating opening and closing motions of the second jaw of the surgical instrument of FIG. 2.
Figure 18:
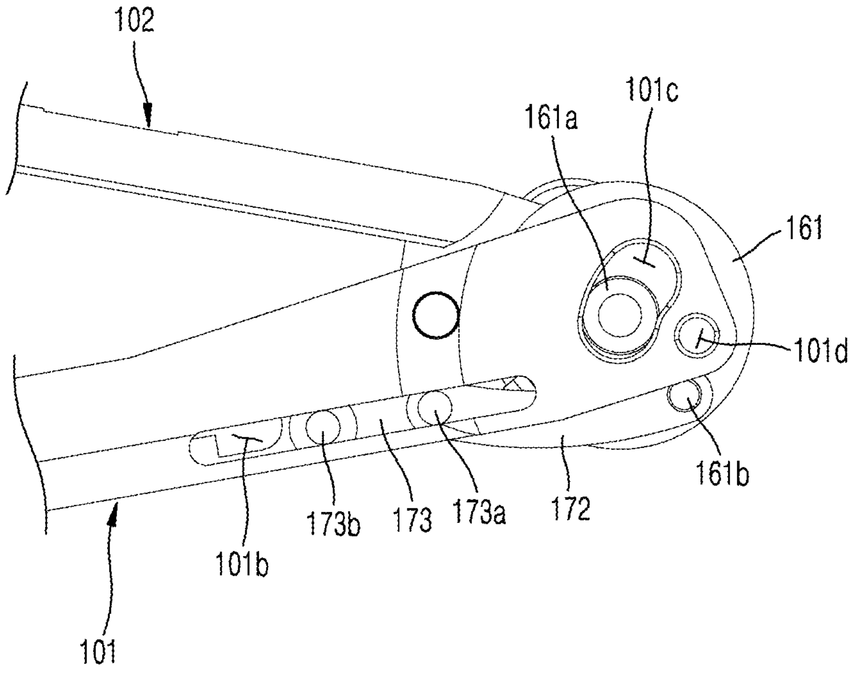
FIG. 18 is a plan view illustrating opening and closing motions of the first jaw and the second jaw of the surgical instrument of FIG. 2.
Figure 18:
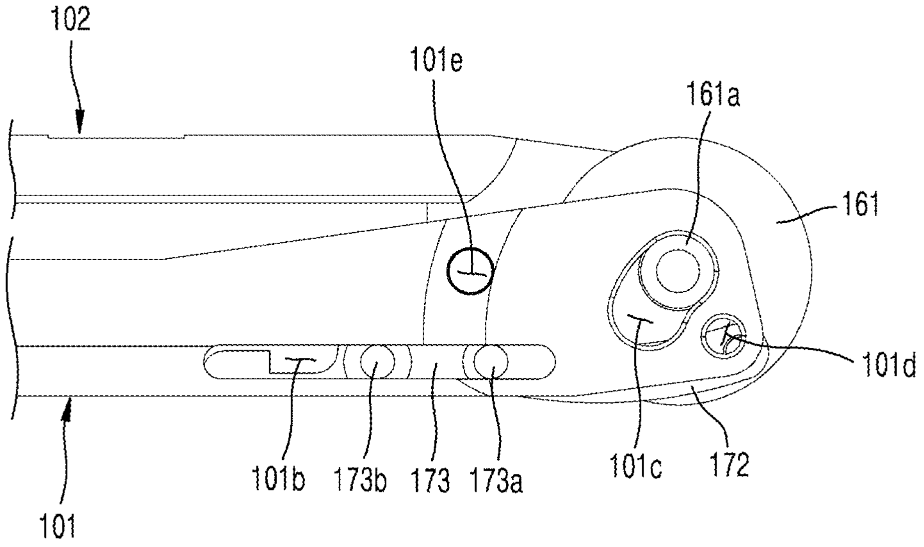
Figure 19:
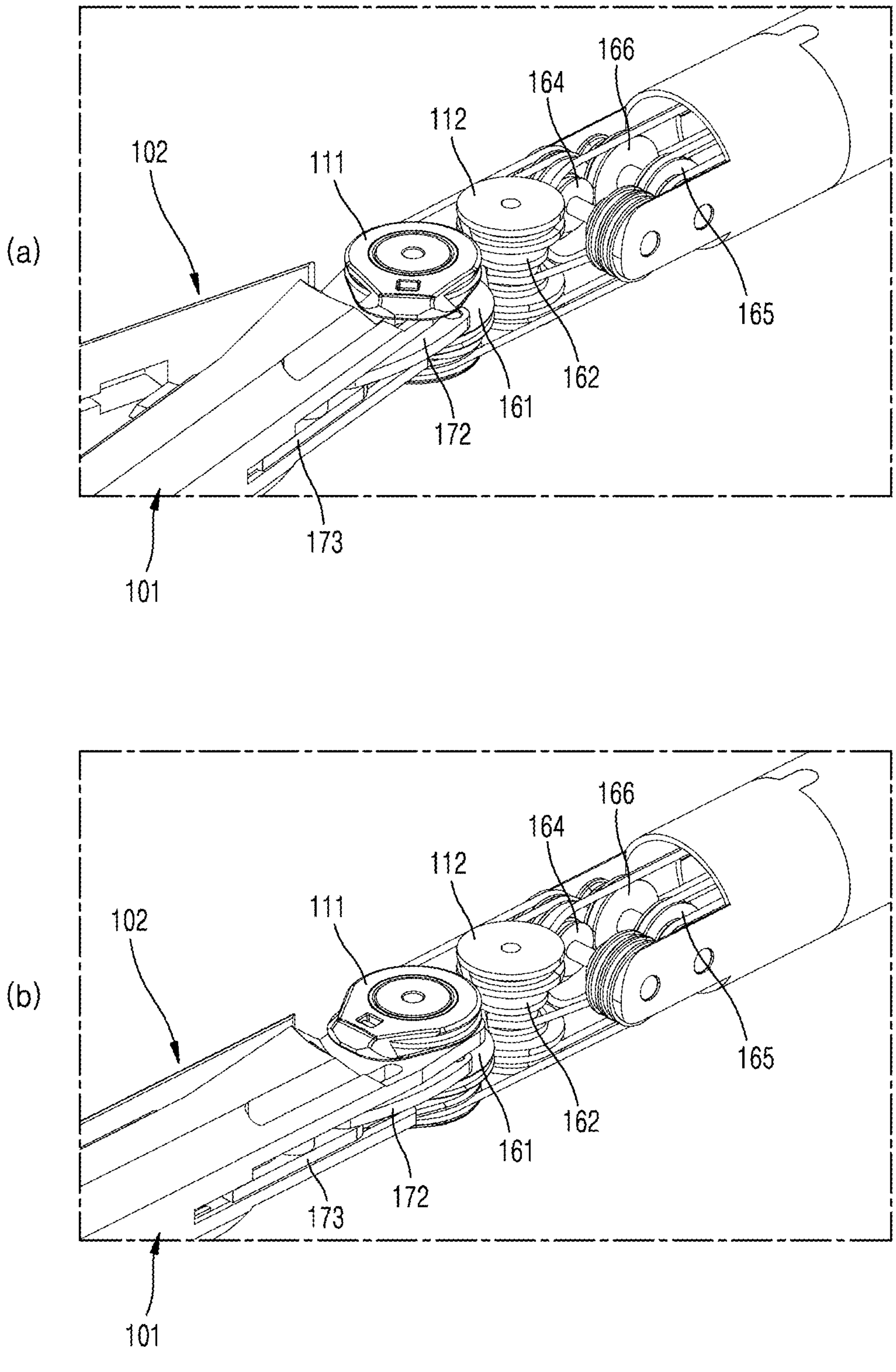
FIG. 19 is a perspective view illustrating opening and closing motions of the end tool of the surgical instrument of FIG. 2.
Figure 20:
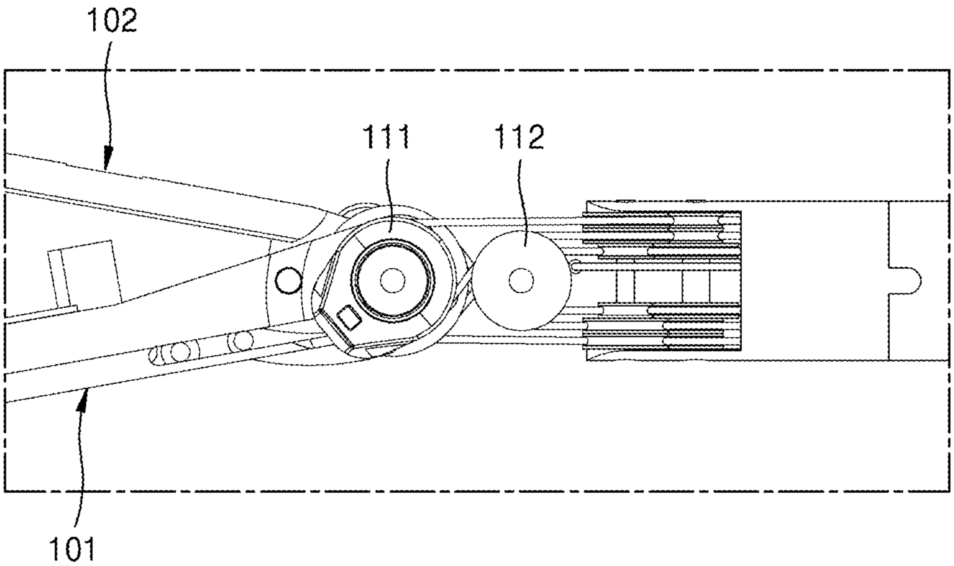
FIG. 20 is a plan view illustrating opening and closing motions of the end tool of the surgical instrument of FIG. 2.
Figure 20:
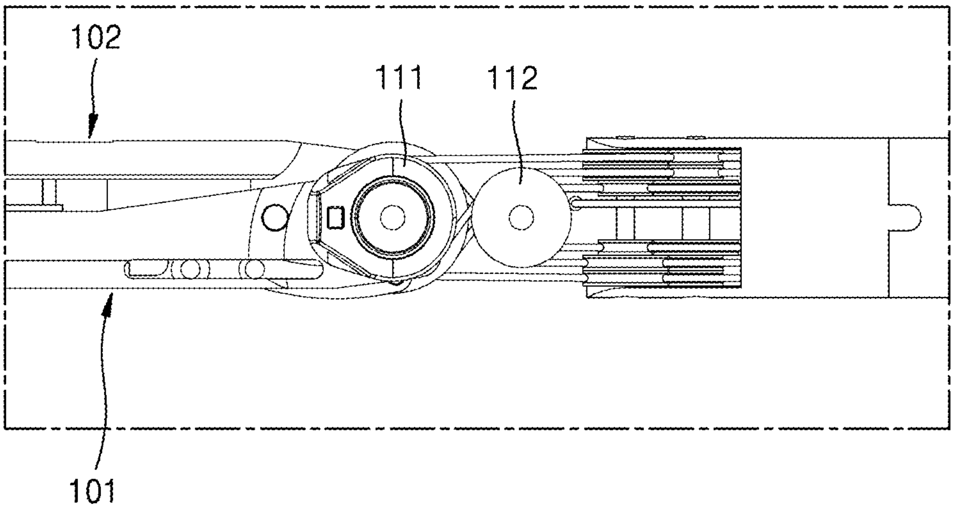

FIG. 2 is a perspective view illustrating a surgical instrument according to a first embodiment of the present disclosure, and FIG. 3 is a side view of the surgical instrument of FIG. 2. FIGS. 4 and 5 are perspective views illustrating an end tool of the surgical instrument of FIG. 2. FIG. 6 is a perspective view illustrating an end tool hub of the end tool of the surgical instrument of FIG. 2. FIGS. 7 and 8 are plan views illustrating the end tool of the surgical instrument of FIG. 2. FIG. 9 is a side view illustrating the end tool of the surgical instrument of FIG. 2. FIGS. 10 and 11 are exploded perspective views of the end tool of the surgical instrument of FIG. 2. FIG. 12 is a perspective view illustrating a first jaw pulley of the surgical instrument of FIG. 2. FIG. 13 is an exploded perspective view illustrating a staple pulley and a staple link of the surgical instrument of FIG. 2. FIG. 14 is a plan view illustrating a first jaw of the surgical instrument of FIG. 2, and FIG. 15 is a plan view illustrating a second jaw of the surgical instrument of FIG. 2. FIG. 16 is a plan view illustrating opening and closing motions of the first jaw of the surgical instrument of FIG. 2, FIG. 17 is a plan view illustrating opening and closing motions of the second jaw of the surgical instrument of FIG. 2, and FIG. 18 is a plan view illustrating opening and closing motions of the first jaw and the second jaw of the surgical instrument of FIG. 2. FIG. 19 is a perspective view illustrating opening and closing motions of the end tool of the surgical instrument of FIG. 2, and FIG. 20 is a plan view illustrating opening and closing motions of the end tool of the surgical instrument of FIG. 2.

First, referring to FIGS. 2 and 3, a surgical instrument 10 according to a first embodiment of the present disclosure includes an end tool 100, a manipulation part 200, a power transmission part 300, and a connection part 400.

Here, the connection part 400 is formed in the shape of a hollow shaft, and one or more wires and electric wires may be accommodated therein. The manipulation part 200 is coupled to one end portion of the connection part 400, the end tool 100 is coupled to the other end portion thereof, and the connection part 400 may serve to connect the manipulation part 200 and the end tool 100. Here, the connection part 400 of the surgical instrument 10 according to the first embodiment of the present disclosure includes a straight part 401 and a bent part 402, wherein the straight part 401 is formed at a side coupled to the end tool 100, and the bent part 402 is formed at a side to which the manipulation part 200 is coupled. As such, since the end portion of the connection part 400 at the side of the manipulation part 200 is formed to be bent, a pitch manipulation part 201, a yaw manipulation part 202, and an actuation manipulation part 203 may be formed along an extension line of the end tool 100 or adjacent to the extension line. From another perspective, it may be said that the pitch manipulation part 201 and the yaw manipulation part 202 are at least partially accommodated in a concave portion formed by the bent part 402. Due to the above-described shape of the bent part 402, the shapes and motions of the manipulation part 200 and the end tool 100 may be further intuitively matched with each other.

Meanwhile, a plane on which the bent part 402 is formed may be substantially the same plane as a pitch plane, that is, an XZ plane of FIG. 2. As such, as the bent part 402 is formed on substantially the same plane as the XZ plane, interference with the manipulation part may be reduced. Of course, for intuitive motions of the end tool and the manipulation part, any form other than the XZ plane may be possible.

Meanwhile, a connector 410 may be formed on the bent part 402. The connector 410 may be connected to an external power source (not shown), and the connector 410 may also be connected to the end tool 100 via an electric wire, and may transmit, to the end tool 100, electric energy supplied from the external power source (not shown). In addition, the electric energy transmitted to the end tool 100 as described above may produce a driving force for rotating a staple pulley (see 161 of FIG. 5) to be described later in the clockwise or counterclockwise direction.

The manipulation part 200 is formed at the one end portion of the connection part 400 and provided as an interface to be directly controlled by a medical doctor, for example, a tongs shape, a stick shape, a lever shape, or the like, and when the medical doctor controls the manipulation part 200, the end tool 100, which is connected to the interface and inserted into the body of a surgical patient, performs a certain motion, thereby performing surgery. Here, the manipulation part 200 is illustrated in FIG. 2 as being formed in a handle shape that is rotatable while the finger is inserted therein, the concept of the present disclosure is not limited thereto, and various types of manipulation parts that are connected to the end tool 100 and manipulate the end tool 100 may be possible.

The end tool 100 is formed on the other end portion of the connection part 400, and performs necessary motions for surgery by being inserted into a surgical site. In an example of the end tool 100, as illustrated in FIG. 2, a pair of jaws 103 for performing a grip motion may be used. However, the concept of the present disclosure is not limited thereto, and various devices for performing surgery may be used as the end tool 100. For example, a configuration of a cantilever cautery may also be used as the end tool. The end tool 100 is connected to the manipulation part 200 by the power transmission part 300, and receives a driving force of the manipulation part 200 through the power transmission part 300 to perform a motion necessary for surgery, such as gripping, cutting, suturing, or the like.

Here, the end tool 100 of the surgical instrument 10 according to the first embodiment of the present disclosure is formed to be rotatable in at least one direction, for example, the end tool 100 may perform a pitch motion around a Y-axis of FIG. 2 and simultaneously perform a yaw motion and an actuation motion around a Z-axis of FIG. 2.

Here, each of the pitch, yaw, and actuation motions used in the present disclosure are defined as follows.

First, the pitch motion means a motion of the end tool 100 rotating in a vertical direction with respect to an extension direction of the connection part 400 (an X-axis direction of FIG. 2), that is, a motion rotating around the Y-axis of FIG. 2. In other words, the pitch motion means a motion of the end tool 100, which is formed to extend from the connection part 400 in the extension direction of the connection part 400 (the X-axis direction of FIG. 2), rotating vertically around the Y-axis with respect to the connection part 400.

Next, the yaw motion means a motion of the end tool 100 rotating in the left and right directions, that is, a motion rotating around the Z-axis of FIG. 2, with respect to the extension direction of the connection part 400 (the X-axis direction of FIG. 2). In other words, the yaw motion means a motion of the end tool 100, which extends from the connection part 400 in the extension direction of the connection part 400 (the X-axis direction of FIG. 2), rotating horizontally around the Z-axis with respect to the connection part 400. That is, the yaw motion means a motion of the two jaws 103, which are formed on the end tool 100, rotating around the Z-axis in the same direction.

Meanwhile, the actuation motion may mean a motion of the end tool 100 rotating around the same shaft of rotation as that of the yaw motion, while the two jaws 103 rotating in the opposite directions so as to be closed or opened. That is, the actuation motion means rotating motions of the two jaws 103, which are formed on the end tool 100, in the opposite directions around the Z-axis.

The power transmission part 300 may connect the manipulation part 200 to the end tool 100, transmit the driving force of the manipulation part 200 to the end tool 100, and include a plurality of wires, pulleys, links, sections, gears, or the like.

The end tool 100, the manipulation part 200, and the power transmission part 300 of the surgical instrument 10 of FIG. 2 will be described in detail later.

(Intuitive Driving)

Hereinafter, intuitive driving of the surgical instrument 10 of the present disclosure will be described.

First, while holding a first handle 204 with the palm of the hand, the user may rotate a first handle 204 around the Y-axis (i.e., a rotation shaft 246 of FIG. 25) to perform a pitch motion, and rotate the first handle 204 around the Z-axis (i.e., a rotation shaft 243 of FIG. 43) to perform a yaw motion. In addition, the user may perform an actuation motion by manipulating the actuation manipulation part 203 while inserting the thumb and the index finger into a first actuation extension part 252 and/or a second actuation extension part 257 in the form of a hand ring formed at one end portion of the actuation manipulation part 203.

Here, in the surgical instrument 10 according to the first embodiment of the present disclosure, when the manipulation part 200 is rotated in one direction with respect to the connection part 400, the end tool 100 is rotated in a direction that is intuitively the same as a manipulation direction of the manipulation part 200. In other words, when the first handle 204 of the manipulation part 200 is rotated in one direction, the end tool 100 is also rotated in a direction intuitively the same as the one direction, so that a pitch motion or a yaw motion is performed. Here, the phrase "intuitively the same direction" may be further explained as meaning that a direction of movement of the user's finger gripping the manipulation part 200 and a direction of movement of a distal end of the end tool 100 form substantially the same direction. Of course, "the same direction" as used herein may not be a perfectly matching direction on a three-dimensional coordinate, and may be understood to be equivalent to the extent that, for example, when the user's finger moves to the left, the distal end of the end tool 100 is moved to the left, and when the user's finger moves down, the end portion of the end tool 100 is moved down.

In addition, to this end, in the surgical instrument 10 according to the first embodiment of the present disclosure, the manipulation part 200 and the end tool 100 are formed in the same direction with respect to a plane perpendicular to the extension axis (X-axis) of the connection part 400. That is, when viewed based on a YZ plane of FIG. 2, the manipulation part 200 is formed to extend in a positive (+) X-axis direction, and the end tool 100 is also formed to extend in the positive (+) X-axis direction. In other words, it may be said that a formation direction of the end tool 100 on one end portion of the connection part 400 is the same as a formation direction of the manipulation part 200 on the other end portion of the connection part 400 on the basis of the YZ plane. Further, in other words, it may be said that the manipulation part 200 may be formed in a direction away from the body of a user holding the manipulation part 200, that is, in a direction in which the end tool 100 is formed. That is, in the parts such as the first handle 204, a first actuation manipulation part 251, a second actuation manipulation part 256, and the like, which are moved by the user's grip for actuation motion, yaw motion, and pitch motions, a corresponding portion that is moved for the motion is formed to extend in the positive (+) X-axis direction from the rotation center of a corresponding joint for the motion. In this manner, the manipulation part 200 may be configured in the same manner as the end tool 100 in which each moving portion is formed to extend in the positive (+) X-axis direction from the rotation center of a corresponding joint for the motion, and as described with reference to FIG. 1, the manipulation direction of the user may be identical to the operation direction of the end tool from the viewpoint of the rotation directions and the left and right directions. As a result, intuitively the same manipulation may be achieved.

In detail, in the case of the conventional surgical instrument, a direction in which a user manipulates the manipulation part is different from a direction in which the end tool is actually operated, that is, intuitively different from the direction in which the end tool is actually operated, and thus, a surgical operator may not easily intuitively manipulate the surgical instrument and may spend a long time to learn a skill of operating the end tool in desired directions, and in some cases, malfunctions may occur, which may cause damage to patients.

In order to address such problems, the surgical instrument 10 according to the first embodiment of the present disclosure is configured such that the manipulation direction of the manipulation part 200 and the operation direction of the end tool 100 are intuitively identical to each other. To this end, the manipulation part 200 is configured like the end tool 100, that is, in the manipulation part 200, portions that are actually moved for actuation, yaw, and pitch motions extend respectively from rotation centers of corresponding joints in the positive (+) X-axis direction.

Hereinafter, the end tool 100, the manipulation part 200, the power transmission part 300, and the like of the surgical instrument 10 of FIG. 2 will be described in more detail.

(Power Transmission Part)

Hereinafter, the power transmission part 300 of the surgical instrument 10 of FIG. 2 will be described in more detail.

Referring to FIGS. 2 to 20, 43, and the like, the power transmission part 300 of the surgical instrument 10 according to an embodiment of the present disclosure may include a wire 301, a wire 302, a wire 303, a wire 304, a wire 305, a wire 306, a wire 307, and a wire 308.

Here, the wires 301 and 305 may be paired to serve as first jaw wires. The wires 302 and 306 may be paired to serve as second jaw wires. Here, the components encompassing the wires 301 and 305, which are first jaw wires, and the wires 302 and 306, which are second jaw wires, may be referred to as jaw wires. In addition, the wires 303 and 304 may be paired to serve as pitch wires. In addition, the wires 307 and 308, may be paired to serve as staple wires.

Further, the power transmission part 300 of the surgical instrument 10 according to an embodiment of the present disclosure may include a coupling member (see 321 of FIG. 7) a coupling member 323, a coupling member 324, a coupling member 326, a coupling member 327, and a coupling member (see 329 of FIG. 62) that are coupled to respective end portions of the wires to respectively couple the wires to the pulleys. Here, each of the coupling members may have various shapes as necessary, such as a ball shape, a tube shape, and the like.

Here, in the end tool 100 side, the coupling member (see 321 of FIG. 7) may serve as a pitch wire-end tool coupling member, the coupling member 323 may serve as a first jaw wire-end tool coupling member, the coupling member 326 may serve as a second jaw wire-end tool coupling member, and the coupling member (see 329 of FIG. 62) may serve as a staple wire-end tool coupling member.

Further, in the manipulation part 200 side, the coupling member 324 may serve as a first jaw wire-manipulation part coupling member, and the coupling member 327 may serve as a second jaw wire-manipulation part coupling member. In addition, although not shown in the drawings, a pitch wire-manipulation part coupling member and a staple wire-manipulation part coupling member may be further formed in the manipulation part 200 side.

The coupling relationship between the wires, the coupling members, and the respectively pulleys will be described in detail as follows.

First, the wires 301 and 305, which are first jaw wires, may be a single wire. The coupling member 323, which is a first jaw wire-end tool coupling member, is inserted at an intermediate point of the first jaw wire, which is a single wire, and the coupling member 323 is crimped and fixed, and then, both strands of the first jaw wire centered on the coupling member 323 may be referred to as the wire 301 and the wire 305, respectively.

Alternatively, the wires 301 and 305, which are first jaw wires, may also be formed as separate wires, and connected by the coupling member 323.

In addition, by coupling the coupling member 323 to a pulley 111, the wires 301 and 305 may be fixedly coupled to the pulley 111. This allows the pulley 111 to rotate as the wires 301 and 305 are pulled and released.

Meanwhile, the first jaw wire-manipulation part coupling member (see 324 of FIG. 43) may be coupled to end portions of the wires 301 and 305, which are opposite to one end portions to which the coupling member 323 is coupled.

In addition, by coupling the first jaw wire-manipulation part coupling member (see 324 of FIG. 43) to a pulley 210 as described above, the wires 301 and 305 may be fixedly coupled to the pulley 210 As a result, when the pulley 210 is rotated by a motor or a human force, the pulley 111 of the end tool 100 may be rotated as the wire 301 and the wire 305 are pulled and released.

Figure 43:
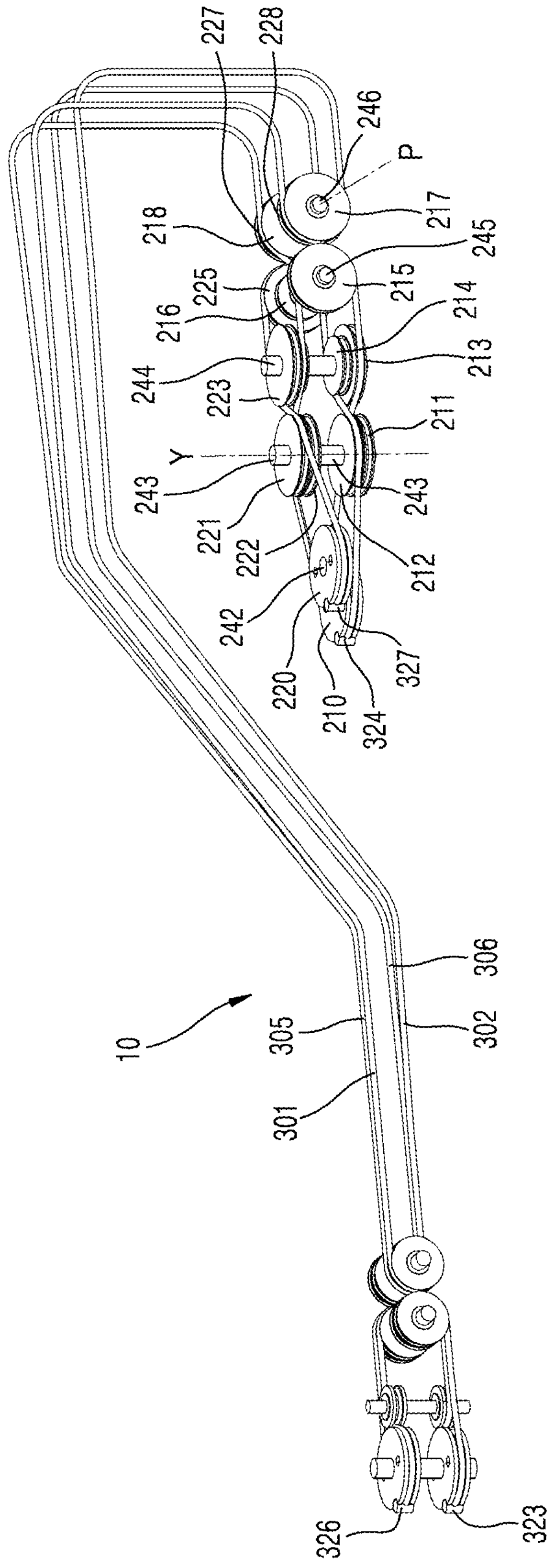
FIG. 43 is a view schematically illustrating only a configuration of pulleys and wires constituting joints of the surgical instrument illustrated in FIG. 2.

In the same manner, each of the wires 302 and 306, which are second jaw wires, is coupled to the coupling member (see 326 of FIG. 43), which is a second jaw wire-end tool coupling member, and the second jaw wire-manipulation part coupling member (see 327 of FIG. 43). In addition, the coupling member (see 326 of FIG. 43) is coupled to a pulley 121, and the second jaw wire-manipulation part coupling member (see 327 of FIG. 43) is coupled to a pulley 220. As a result, when the pulley 220 is rotated by a motor or a human force, the pulley 121 of the end tool 100 may be rotated as the wire 302 and the wire 306 are pulled and released.

In the same manner, the wires 303 and 304, which are pitch wires, are respectively coupled to the coupling member (see 321 of FIG. 7), which is a pitch wire-end tool coupling member, and the pitch wire-manipulation part coupling member (not shown). In addition, the coupling member (see 321 of FIG. 7) is coupled to a pulley 131, and the pitch wire-manipulation part coupling member (not shown) is coupled to a pulley 231. As a result, when the pulley 231 is rotated by a motor or a human force, the pulley 131 of the end tool 100 may be rotated as the wire 303 and the wire 304 are pulled and released.

In the same manner, the wires 307 and 308, which are staple wires, are respectively coupled to the coupling member (see 329 of FIG. 62), which is a staple wire-end tool coupling member, and the staple wire-manipulation part coupling member (not shown). In addition, the coupling member (see 329 of FIG. 62) is coupled to the staple pulley 161, and the staple wire-manipulation part coupling member (not shown) is coupled to a pulley (see 269 of FIG. 47). As a result, when the pulley 269 is rotated by a motor or a human force, the staple pulley 161 of the end tool 100 may be rotated as the wires 307 and 308 are pulled and released.

(End Tool)

Hereinafter, the end tool 100 of the surgical instrument 10 of FIG. 2 will be described in more detail.

FIGS. 4 and 5 are perspective views illustrating the end tool of the surgical instrument of FIG. 2, FIG. 6 is a perspective view illustrating an end tool hub of the end tool of the surgical instrument of FIG. 2, and FIGS. 7 and 8 are plan views illustrating the end tool of the surgical instrument of FIG. 2.

Here, FIG. 4 illustrates a state in which an end tool hub 180 and a pitch hub 107 are coupled, and FIG. 5 illustrates a state in which the end tool hub 180 is removed. Meanwhile, FIG. 7 is a view mainly illustrating the wires, and FIG. 8 is a view mainly illustrating the pulleys.

Referring to FIGS. 4 to 8 and the like, the end tool 100 of the first embodiment of the present disclosure includes a pair of jaws for performing a grip motion, that is, a first jaw 101 and a second jaw 102. Here, each of the first jaw 101 and the second jaw 102, or a component encompassing the first jaw 101 and the second jaw 102 may be referred to as the jaw 103.

Further, the end tool 100 may include the pulley 111, a pulley 112, a pulley 113, a pulley 114, a pulley 115, and a pulley 116 that are related to a rotational motion of the first jaw 101. In addition, the end tool 100 may include the pulley 121, a pulley 122, a pulley 123, a pulley 124, a pulley 125, and a pulley 126 that are related to a rotational motion of the second jaw 102.

Here, the pulleys facing each other are illustrated in the drawings as being formed parallel to each other, but the concept of the present disclosure is not limited thereto, and each of the pulleys may be variously formed with a position and a size suitable for the configuration of the end tool.

Further, the end tool 100 of the first embodiment of the present disclosure may include the end tool hub 180 and the pitch hub 107.

A rotation shaft 141 and a rotation shaft 142, which will be described later, may be inserted through the end tool hub 180, and the end tool hub 180 may internally accommodate at least some of the pulley 111 and the pulley 121, which are axially coupled to the rotation shaft 141. In addition, the end tool hub 180 may internally accommodate at least some of the pulley 112 and the pulley 122 that are axially coupled to the rotation shaft 142.

In detail, referring to FIG. 6, the end tool hub 180 includes a first jaw pulley coupling part 181, a second jaw pulley coupling part 182, a guide part 183, and a pitch pulley coupling part 185.

In detail, the first jaw pulley coupling part 181 and the second jaw pulley coupling part 182 are formed to face each other, and the pulley 111, the pulley 121, and the staple pulley 161 are accommodated inside the first jaw pulley coupling part 181 and the second jaw pulley coupling part 182. In addition, a through hole is formed in each of the first jaw pulley coupling part 181 and the second jaw pulley coupling part 182 such that the rotation shaft 141 passes through and axially couples the first jaw pulley coupling part 181, the pulley 111, the staple pulley 161, the pulley 121, and the second jaw pulley coupling part 182.

The first jaw pulley coupling part 181 and the second jaw pulley coupling part 182 are connected by the guide part 183. That is, the first jaw pulley coupling part 181 and the second jaw pulley coupling part 182 parallel to each other are coupled by the guide part 183 formed in a direction substantially perpendicular thereto, so that the first jaw pulley coupling part 181, the second jaw pulley coupling part 182, and the guide part 183 form a substantially "C-shape," in which the pulley 111, the pulley 121, and the staple pulley 161 are accommodated.

Here, the pulley 111, which is a first jaw pulley, is disposed adjacent to the first jaw pulley coupling part 181 of the end tool hub 180, and the pulley 121, which is a second jaw pulley, is disposed adjacent to the second jaw pulley coupling part 182 of the end tool hub 180, so that a staple assembly accommodation part may be formed between the first jaw pulley coupling part 181 and the second jaw pulley coupling part 182. In addition, at least some of a staple pulley assembly (see 160 of FIG. 13) and a staple link assembly (see 170 of FIG. 13), which will be described later, may be formed in the staple assembly accommodation part. In other words, it may be said that at least some of the staple pulley 161 and a link member 171 are disposed between the first jaw pulley coupling part 181 and the second jaw pulley coupling part 182. As such, according to the present disclosure, by disposing at least some of the staple pulley assembly (see 160 of FIG. 13) and the staple link assembly (see 170 of FIG. 13) between the pulley 111, which is a first jaw pulley, and the pulley 121, which is a second jaw pulley, the end tool 100 is allowed to perform pitch and yaw motions, as well as stapling and cutting motions using the staple pulley 161. This will be described in more detail later.

Meanwhile, the pulley 131 serving as an end tool pitch pulley may be formed at one end portion of the end tool hub 180. As shown in FIG. 6, the pulley 131 may be integrally formed with the end tool hub 180 as one body. That is, a disk-shaped pulley is formed at one end portion of the end tool hub 180, and a groove around which a wire may be wound may be formed on an outer circumferential surface of the pulley. Alternatively, the pulley 131 may be formed as a separate member from the end tool hub 180 to be coupled to the end tool hub 180. The wires 303 and 304 described above are coupled to the pulley 131 serving as an end tool pitch pulley, and a pitch motion is performed as the pulley 131 is rotated around a rotation shaft 143.

The rotation shaft 143 and a rotation shaft 144, which will be described later, are inserted through the pitch hub 107, and the pitch hub 107 may be axially coupled to the end tool hub 180 (and the pulley 131) by the rotation shaft 143. Thus, the end tool hub 180 and the pulley 131 may be formed to be rotatable around the rotation shaft 143 with respect to the pitch hub 107.

Further, the pitch hub 107 may internally accommodate at least some of the pulley 113, the pulley 114, the pulley 123, and the pulley 124 that are axially coupled to the rotation shaft 143. In addition, the pitch hub 107 may internally accommodate at least some of the pulley 115, the pulley 116, the pulley 125, and the pulley 126 that are axially coupled to the rotation shaft 144.

Further, the end tool 100 of the first embodiment of the present disclosure may include the rotation shaft 141, the rotation shaft 142, the rotation shaft 143, and the rotation shaft 144. As described above, the rotation shaft 141 and the rotation shaft 142 may be inserted through the end tool hub 180, and the rotation shaft 143 and the rotation shaft 144 may be inserted through the pitch hub 107.

The rotation shaft 141, the rotation shaft 142, the rotation shaft 143, and the rotation shaft 144 may be arranged sequentially from a distal end 104 of the end tool 100 toward a proximal end 105. Accordingly, starting from the distal end 104, the rotation shaft 141 may be referred to as a first pin, the rotation shaft 142 may be referred to as a second pin, the rotation shaft 143 may be referred to as a third pin, and the rotation shaft 144 may be referred to as a fourth pin.

Here, the rotation shaft 141 may function as an end tool jaw pulley rotation shaft, the rotation shaft 142 may function as an end tool jaw auxiliary pulley rotation shaft, the rotation shaft 143 may function as an end tool pitch rotating shaft, and the rotation shaft 144 may function as an end tool pitch auxiliary rotating shaft of the end tool 100.

Each of the rotation shafts 141, 142, 143, and 144 may be fitted into one or more pulleys, which will be described in detail below.

Meanwhile, a rotation shaft 145 may be further formed on one side of the rotation shaft 141, specifically, one side of the rotation shaft 141 at the distal end 104 side. The rotation shaft 145 is inserted through the first jaw 101 and the second jaw 102 to function as a jaw rotation shaft. This will be described in detail below.

The pulley 111 functions as an end tool first jaw pulley, and the pulley 121 functions as an end tool second jaw pulley. The pulley 111 may also be referred to as a first jaw pulley, and the pulley 121 may also be referred to as a second jaw pulley, and these two components may also be referred to collectively as an end tool jaw pulley or simply a jaw pulley.

The pulley 111 and the pulley 121, which are end tool jaw pulleys, are formed to face each other, and are formed to be rotatable independently of each other around the rotation shaft 141, which is an end tool jaw pulley rotation shaft. In this case, the pulley 111 and the pulley 121 are formed to be spaced apart from each other by a certain extent, and the staple assembly accommodation part may be formed therebetween. In addition, at least some of the staple pulley assembly 160 and the staple link assembly 170, which will be described later, may be disposed inside the staple assembly accommodation part.

Here, in the drawings, it is illustrated that the pulley 111 and the pulley 121 are formed to rotate around one rotation shaft 141, but it is of course possible that each end tool jaw pulley may be formed to be rotatable around a separate shaft. Here, the first jaw 101 is fixedly coupled to the pulley 111 and rotates together with the pulley 111, and the second jaw 102 is fixedly coupled to the pulley 121 and rotates together with the pulley 121. Yaw and actuation motions of the end tool 100 are performed according to the rotation of the pulley 111 and the pulley 121. That is, when the pulley 111 and the pulley 121 are rotated in the same direction around the rotation shaft 141, the yaw motion is performed, and when the pulley 111 and the pulley 121 are rotated in opposite directions around the rotation shaft 141, the actuation motion is performed.

Here, the first jaw 101 and the pulley 111 may be formed as separate members and coupled to each other, or the first jaw 101 and the pulley 111 may be integrally formed as one body. Similarly, the second jaw 102 and the pulley 121 may be formed as separate members and coupled to each other, or the second jaw 102 and the pulley 121 may be integrally formed as one body.

The pulley 112 functions as an end tool first jaw auxiliary pulley, and the pulley 122 functions as an end tool second jaw auxiliary pulley, and these two components may be collectively referred to as an end tool jaw auxiliary pulley or simply an auxiliary pulley.

In detail, the pulley 112 and the pulley 122, which are end tool jaw auxiliary pulleys, may be additionally provided on one sides of the pulley 111 and the pulley 121, respectively. In other words, the pulley 112, which is an auxiliary pulley, may be disposed between the pulley 111 and the pulley 113/pulley 114. In addition, the pulley 122, which is an auxiliary pulley, may be disposed between the pulley 121 and the pulley 123 or the pulley 124. The pulley 112 and the pulley 122 may be formed to be rotatable independently of each other around the rotation shaft 142. Here, in the drawings, it is illustrated that the pulley 112 and the pulley 122 are formed to rotate around one rotation shaft 142, but it is of course possible that each of the pulley 112 and the pulley 122 may be formed to be rotatable around a separate shaft. Such auxiliary pulleys will be described in more detail later.

The pulley 113 and the pulley 114 function as end tool first jaw pitch main pulleys, and the pulley 123 and the pulley 124 function as end tool second jaw pitch main pulleys, and these two components may be referred to collectively as an end tool jaw pitch main pulley.

The pulley 115 and the pulley 116 function as end tool first jaw pitch sub-pulleys, and the pulley 125 and the pulley 126 function as end tool second jaw pitch sub-pulleys, and these two components may be collectively referred to as an end tool jaw pitch sub-pulley.

Hereinafter, components related to the rotation of the pulley 111 will be described.

The pulley 113 and the pulley 114 function as end tool first jaw pitch main pulleys. That is, the pulley 113 and the pulley 114 function as main rotation pulleys for a pitch motion of the first jaw 101. Here, the wire 301, which is a first jaw wire, is wound around the pulley 113, and the wire 305, which is a first jaw wire, is wound around the pulley 114.

The pulley 115 and the pulley 116 function as end tool first jaw pitch sub-pulleys. That is, the pulley 115 and the pulley 116 function as sub rotation pulleys for a pitch motion of the first jaw 101. Here, the wire 301, which is a first jaw wire, is wound around the pulley 115, and the wire 305, which is a first jaw wire, is wound around the pulley 116.

Here, the pulley 113 and the pulley 114 are disposed on one side of the pulley 111 and the pulley 112 to face each other. Here, the pulley 113 and the pulley 114 are formed to be rotatable independently of each other around the rotation shaft 143 that is an end tool pitch rotating shaft. In addition, the pulley 115 and the pulley 116 are disposed on one sides of the pulley 113 and the pulley 114, respectively, to face each other. Here, the pulley 115 and the pulley 116 are formed to be rotatable independently of each other around the rotation shaft 144 that is an end tool pitch auxiliary rotating shaft. Here, in the drawings, it is illustrated that the pulley 113, the pulley 115, the pulley 114, and the pulley 116 are all formed to be rotatable around the Y-axis direction, but the concept of the present disclosure is not limited thereto, and the rotating axes of the respective pulleys may be formed in various directions according to configurations thereof.

The wire 301, which is a first jaw wire, is sequentially wound to make contact with at least portions of the pulley 115, the pulley 113, and the pulley 111. In addition, the wire 305 connected to the wire 301 by the coupling member 323 is sequentially wound to make contact with at least portions of the pulley 111, the pulley 112, the pulley 114, and the pulley 116 in turn.

In other words, the wires 301 and 305, which are first jaw wires, are sequentially wound to make contact with at least portions of the pulley 115, the pulley 113, the pulley 111, the pulley 112, the pulley 114, and the pulley 116 and are formed to move along the above pulleys while rotating the above pulleys.

Accordingly, when the wire 301 is pulled in the direction of an arrow 301 of FIG. 13, the coupling member 323 to which the wire 301 is coupled and the pulley 111 coupled to the coupling member 323 are rotated in an arrow L direction of FIG. 13. In contrast, when the wire 305 is pulled in the direction of an arrow 305 of FIG. 6, the coupling member 323 to which the wire 305 is coupled and the pulley 111 coupled to the coupling member 323 are rotated in an arrow R direction of FIG. 6.

Hereinafter, the pulley 112 and the pulley 122 serving as auxiliary pulleys will be described in more detail.

The pulley 112 and the pulley 122 may serve to enlarge rotation angles of the first jaw 101 and the second jaw 102, respectively, by coming into contact with the wire 305, which is a jaw wire, and the wire 302, which is a second jaw wire, to change the arrangement path of the wires 305 and 302 to a certain extent.

That is, when the auxiliary pulleys are not disposed, each of the first jaw and the second jaw may be rotated up to a right angle, but in an embodiment of the present disclosure, the pulley 112 and the pulley 122, which are auxiliary pulleys, are additionally provided, so that the maximum rotation angle may be increased by θ as shown in FIG. 8. This enables a motion of the two jaws of the end tool 100 being opened for an actuation motion while the two jaws are yaw-rotated by 90° in the L direction. This is because the second jaw 102 is rotated by the additional angle θ as shown in FIG. 8. Similarly, an actuation motion is possible even when the two jaws are yaw-rotated in the L direction. In other words, a feature of increasing the range of a yaw rotation in which an actuation motion is possible may be obtained through the pulley 112 and the pulley 122.

This will be described below in more detail.

When the auxiliary pulleys are not disposed, since the first jaw wire is fixedly coupled to the end tool first jaw pulley, and the second jaw wire is fixedly coupled to the end tool second jaw pulley, each of the end tool first jaw pulley and the end tool second jaw pulley may be rotated up to 90°. In this case, when the actuation motion is performed while the first jaw and the second jaw are located at a 90° line, the first jaw may be opened, but the second jaw may not be rotated beyond 90°. Accordingly, when the first jaw and the second jaw perform a yaw motion over a certain angle, there was a problem that the actuation motion is not smoothly performed.

In order to address such a problem, in the surgical instrument 10 of the present disclosure, the pulley 112 and the pulley 122, which are auxiliary pulleys, are additionally disposed at one sides of the pulley 111 and the pulley 121, respectively. As described above, as the arrangement path of the wire 305, which is a first jaw wire, and the wire 302, which is a second jaw wire, is changed to a certain extent by disposing the pulley 112 and the pulley 122, a tangential direction of the wires 305 and 302 is changed, and accordingly, the coupling member 323 for coupling the wire 301 and the pulley 111 may be rotated up to a line N of FIG. 8. That is, the coupling member 323, which is a coupling part of the wire 301 and the pulley 111, is rotatable until the coupling member 323 is located on a common internal tangent of the pulley 111 and the pulley 112. Similarly, the coupling member 326, which is a coupling part of the wire 302 and the pulley 121, is rotatable until the coupling member 326 is located on a common internal tangent of the pulley 121 and the pulley 122, so that the range of rotation in the L direction may be increased.

In other words, the wires 301 and 305, which are two strands of the first jaw wire wound around the pulley 111 by the pulley 112, are disposed at one side with respect to a plane perpendicular to the Y-axis and passing through the X-axis. Simultaneously, the wires 302 and 306, which are two strands of the second jaw wire wound around the pulley 121 by the pulley 122, are disposed at the other side with respect to a plane perpendicular to the Y-axis and passing through the X-axis.

In other words, the pulley 113 and the pulley 114 are disposed at one side with respect to the plane perpendicular to the Y-axis and passing through the X-axis, and the pulley 123 and the pulley 124 are disposed at the other side with respect to the plane perpendicular to the Y-axis and passing through the X-axis.

In other words, the wire 305 is located on the internal tangent of the pulley 111 and the pulley 112, and the rotation angle of the pulley 111 is increased by the pulley 112. In addition, the wire 302 is located on the internal tangent of the pulley 121 and the pulley 122, and the rotation angle of the pulley 121 is increased by the pulley 122.

According to the present disclosure, as the rotation radii of the jaw 101 and the jaw 102 increase, an effect of increasing a yaw motion range in which a normal opening/closing actuation motion is performed may be obtained.

Next, components related to the rotation of the pulley 121 will be described.

The pulley 123 and the pulley 124 function as end tool second jaw pitch main pulleys. That is, the second jaw 102 functions as a main rotation pulley for a pitch motion of the second jaw 102. Here, the wire 306, which is a second jaw wire, is wound around the pulley 123, and the wire 302, which is a second jaw wire, is wound around the pulley 124.

The pulley 125 and the pulley 126 function as end tool second jaw pitch sub-pulleys. That is, the pulley 125 and the pulley 126 function as sub rotation pulleys for a pitch motion of the second jaw 102. Here, the wire 306, which is a second jaw wire, is wound around the pulley 125, and the wire 302, which is a second jaw wire, is wound around the pulley 126.

On one side of the pulley 121, the pulley 123 and the pulley 124 are disposed to face each other. Here, the pulley 123 and the pulley 124 are formed to be rotatable independently of each other around the rotation shaft 143 which is an end tool pitch rotating shaft. In addition, the pulley 125 and the pulley 126 are disposed on one sides of the pulley 123 and the pulley 124, respectively, to face each other. Here, the pulley 125 and the J15 pulley 123J25 are formed to be rotatable independently of each other around the rotation shaft 144, which is an end tool pitch auxiliary rotating shaft. Here, in the drawings, it is illustrated that all of the pulley 123, the pulley 125, the pulley 124, and the pulley 126 are formed to be rotatable around the Y-axis direction, but the concept of the present disclosure is not limited thereto, and the rotating axes of the respective pulleys may be formed in various directions according to configurations thereof.

The wire 306, which is a second jaw wire, is sequentially wound to make contact with at least portions of the pulley 125, the pulley 123, and the pulley 121. In addition, the wire 302 connected to the wire 306 by the coupling member 326 is sequentially wound to make contact with at least portions of the pulley 121, the pulley 122, the pulley 124, and the pulley 126.

In other words, the wires 306 and 302, which are second jaw wires, are sequentially wound to make contact with at least portions of the pulley 125, the pulley 123, the pulley 121, the pulley 122, the pulley 124, and the pulley 126, and are formed to move along the above pulleys while rotating the above pulleys.

Accordingly, when the wire 306 is pulled in the direction of an arrow 306 of FIG. 13, the coupling member 322 to which the wire 306 is coupled and the pulley 121 coupled to the coupling member 322 are rotated in the arrow R direction of FIG. 13. In contrast, when the wire 302 is pulled in the direction of an arrow 302 of FIG. 13, the coupling member 326 to which the wire 302 is coupled and the pulley 121 coupled to the coupling member 326 are rotated in the arrow L direction of FIG. 13.

Hereinafter, a pitch motion of the present disclosure will be described in more detail.

Meanwhile, when the wire 301 is pulled toward the arrow 301 of FIG. 7, and simultaneously, the wire 305 is pulled toward the arrow 305 of FIG. 7 (that is, when both strands of the first jaw wire are pulled), as shown in FIG. 43, since the wires 301 and 305 are wound around lower portions of the pulley 113 and the pulley 114 rotatable around the rotation shaft 143, which is an end tool pitch rotating shaft, the pulley 111 to which the wires 301 and 305 are fixedly coupled and the end tool hub 180 to which the pulley 111 is coupled are rotated as a whole in the counterclockwise direction around the rotation shaft 143, so that the end tool 100 is rotated downward to perform a pitch motion. At this time, since the second jaw 102 and the wires 302 and 306 fixedly coupled thereto are wound around upper portions of the pulley 123 and the pulley 124 rotatable around the rotation shaft 143, the wires 302 and 306 are unwound in an opposite directions of the wires 302 and 306, respectively.

In contrast, when the wire 302 is pulled toward the arrow 302 of FIG. 7, and simultaneously, the wire 306 is pulled toward the arrow 306 of FIG. 7, as shown in FIG. 43, since the wires 302 and 306 are wound around the upper portions of the pulley 123 and the pulley 124 rotatable around the rotation shaft 143, which is an end tool pitch rotating shaft, the pulley 121 to which the wires 302 and 306 are fixedly coupled and the end tool hub 180 to which the pulley 121 is coupled are rotated as a whole in the clockwise direction around the rotation shaft 143, so that the end tool 100 is rotated upward to perform a pitch motion. At this time, since the first jaw 101 and the wires 301 and 305 fixedly coupled thereto are wound around lower portions of the pulley 113 and the pulley 114 rotatable around the rotation shaft 143, the wires 302 and 306 are moved in opposite directions of the wires 301 and 305, respectively.

Meanwhile, the end tool 100 of the surgical instrument 10 of the present disclosure may further include the pulley 131, which is an end tool pitch pulley, the manipulation part 200 may further include the pulley 231 and the pulley 232, which are manipulation part pitch pulleys, and the power transmission part 300 may further include the wires 303 and 304, which are pitch wires. In detail, the pulley 131 of the end tool 100 is rotatable around the rotation shaft 143, which is an end tool pitch rotating shaft, and may be integrally formed with the end tool hub 180 (or fixedly coupled to the end tool hub 180) as one body. In addition, the wires 303 and 304 may serve to connect the pulley 131 of the end tool 100 and the pulley 231 and the pulley 232 of the manipulation part 200.

Thus, when the pulley 231 and the pulley 232 of the manipulation part 200 are rotated, the rotation of the pulley 231 and the pulley 232 is transmitted to the pulley 131 of the end tool 100 through the wires 303 and 304 so that the pulley 131 is rotated together therewith, and as a result, the end tool 100 performs a pitch motion while rotating.

That is, in the surgical instrument 10 according to the first embodiment of the present disclosure, by providing the pulley 131 of the end tool 100, the pulley 231 and the pulley 232 of the manipulation part 200, and the wires 303 and 304 of the power transmission part 300 to transmit power for a pitch motion, the driving force for the pitch motion of the manipulation part 200 may be more completely transmitted to the end tool 100, thereby improving operation reliability.

Here, a diameter of each of the pulley 113, the pulley 114, the pulley 123, and the pulley 124, which are end tool jaw pitch main pulleys, and a diameter of the pulley 131, which is an end tool pitch pulley, may be the same as each other or different from each other. At this time, a ratio of the diameter of the end tool jaw pitch main pulley to the diameter of the end tool pitch pulley may be the same as a ratio of a diameter of the manipulation part pitch pulley of the manipulation part 200 to a diameter of a manipulation part pitch main pulley to be described later. This will be described in detail below.

(Components Related to Staple Pulley)

Hereinafter, the staple pulley 161 of the end tool 100 of the surgical instrument 10 of FIG. 2 will be described in more detail.

FIG. 9 is a side view illustrating the end tool of the surgical instrument of FIG. 2, and FIGS. 10 and 11 are perspective views illustrating the first jaw of the surgical instrument of FIG. 2. FIG. 12 is a perspective view illustrating the first jaw pulley of the surgical instrument of FIG. 2, and FIG. 13 is an exploded perspective view illustrating the staple pulley and the staple link of the surgical instrument of FIG. 2.

Referring to FIGS. 4 to 13 and the like, the end tool 100 of the first embodiment of the present disclosure may include the staple pulley 161, a staple auxiliary pulley 162, a pulley 163, a pulley 164, a pulley 165, and a pulley 166 that are related to a linear motion/rotational motion of respective pulleys and links for stapling and cutting.

The staple pulley 161 is formed to face each of the pulley 111 and the pulley 121, which are end tool jaw pulleys, and the staple pulley 161 and the pulley 111 and the pulley 121 are formed to be rotatable independently of each other around the rotation shaft 141, which is an end tool jaw pulley rotation shaft. Here, the staple pulley 161 is illustrated as being disposed between the pulley 111 and the pulley 121, but the concept of the present disclosure is not limited thereto, and the staple pulley 161 may be disposed at various positions adjacent to the pulley 111 or the pulley 121.

Here, in the present disclosure, the staple pulley 161, the pulley 111, and the pulley 121 are formed to rotate around substantially the same shaft. As the staple pulley 161, the pulley 111, and the pulley 121 are formed to rotate around the same shaft as described above, it is possible to perform a pitch motion/yaw motion/actuation motion as well as stapling and cutting motions. This will be described in more detail later. Here, although the staple pulley 161, the pulley 111, and the pulley 121 are illustrated in the drawing as being formed to rotate around one rotation shaft 141, it is of course possible that each jaw pulley may be formed to be rotatable around a separate shaft that is concentric therewith.

In other words, it may also be described as a structure in which the first jaw pulley, pulley 111, the staple pulley 161, and the pulley 121 that is a second jaw pulley are sequentially stacked along the rotation shaft 141. Alternatively, it may be also described as a structure in which the staple pulley 161 is disposed between the pulley 111 and the pulley 121 facing each other. Here, the first jaw pulley 111, the staple pulley 161, and the second jaw pulley 121 may be formed to be rotatable independently of each other.

The staple auxiliary pulley 162 may be further provided on one side of the staple pulley 161. In other words, the staple auxiliary pulley 162 may be disposed between the staple pulley 161 and the pulley 163/pulley 164. The staple auxiliary pulley 162 may be formed to be rotatable independently of the pulley 112 and the pulley 122 around the rotation shaft 142. Here, although the staple auxiliary pulley 162, the pulley 112, and the pulley 122 are illustrated in the drawing as being formed to rotate around one rotation shaft 142, it is of course possible that each of the staple auxiliary pulley 162, the pulley 112, and the pulley 122 may be formed to be rotatable around a separate shaft that is concentric therewith. Such a staple auxiliary pulley will be described in more detail below.

The pulley 163 and the pulley 164 may function as staple pitch main pulleys, and the pulley 165 and the pulley 166 may function as staple pitch sub-pulleys.

Hereinafter, components related to the rotation of the staple pulley 161 will be described.

The pulley 163 and the pulley 164 function as the staple pitch main pulleys. Here, the wire 307, which is a staple wire, is wound around the pulley 163, and the wire 308, which is the staple wire, is wound around the pulley 164.

The pulley 165 and the pulley 166 function as staple pitch sub-pulleys. Here, the wire 307, which is a staple wire, is wound around the pulley 165, and the wire 308, which is a staple wire, is wound around the pulley 166.

Here, the pulley 163 and the pulley 164 are disposed on one side of the staple pulley 161 and the staple auxiliary pulley 162 to face each other. Here, the pulley 163 and the pulley 164 are formed to be rotatable independently of each other around the rotation shaft 143 that is an end tool pitch rotating shaft. In addition, the pulley 165 and the pulley 166 are respectively disposed on one sides of the pulley 163 and the pulley 164 to face each other. Here, the pulley 165 and the pulley 166 are formed to be rotatable independently of each other around the rotation shaft 144 which is an end tool pitch auxiliary rotating shaft. Here, in the drawings, it is illustrated that all of the pulley 163, the pulley 165, the pulley 164, and the pulley 166 are formed to be rotatable around the Y-axis direction, but the concept of the present disclosure is not limited thereto, and the rotating axes of the respective pulleys may be formed in various directions according to configurations thereof.

As described above, the rotation shaft 141, the rotation shaft 142, the rotation shaft 143, and the rotation shaft 144 may be arranged sequentially from the distal end 104 of the end tool 100 toward the proximal end 105. Accordingly, the staple pulley 161, the staple auxiliary pulley 162, the pulley 163/pulley 164, the pulley 165/pulley 166 may be arranged sequentially from the distal end 104 of the end tool 100 toward the proximal end 105.

The wire 307, which is a staple wire, is sequentially wound to make contact with at least portions of the pulley 165, the pulley 163, the staple auxiliary pulley 162, and the staple pulley 161. In addition, the wire 308 connected to the wire 307 by the coupling member (see 329 of FIG. 62) is sequentially wound to make contact with at least portions of the staple pulley 161, the staple auxiliary pulley 162, the pulley 164, and the pulley 166.

In other words, the wires 307 and 308, which are the staple wires, are sequentially wound to make contact with at least portions of the pulley 165, the pulley 163, the staple auxiliary pulley 162, the staple pulley 161, the staple auxiliary pulley 162, the pulley 164, and the pulley 166, and the wires 307 and 308 are formed to move along the above pulleys while rotating the above pulleys.

Accordingly, when the wire 307 is pulled, the coupling member (see 329 of FIG. 62) to which the wire 307 is coupled and the staple pulley 161 coupled to the coupling member 329 are rotated in one direction. In contrast, when the wire 308 is pulled, the coupling member (see 329 of FIG. 62) to which the wire 308 is coupled and the staple pulley 161 coupled to the coupling member 329 are rotated in a direction opposite to the one direction.

Hereinafter, the staple auxiliary pulley 162 will be described in more detail.

The staple auxiliary pulley 162 may serve to increase the rotation angle of the staple pulley 161 by coming into contact with the wires 307 and 308, which are staple wires, to change the arrangement path of the wires 307 and 308 to a certain extent.

That is, when the staple auxiliary pulley is not disposed, the staple pulley may be rotated only up to a right angle, but in an embodiment of the present disclosure, by additionally providing the staple auxiliary pulley 162, which is an auxiliary pulley, the maximum rotation angle may be increased by θ in both directions. This allows the staple pulley 161 to rotate for the stapling and cutting motions while two jaws of the end tool 100 are yaw-rotated together by 90°, thus enabling a linear motion of an operation member 540 to be described later. In other words, a feature of increasing the range of yaw rotation in which stapling and cutting motions are possible may be obtained through the staple auxiliary pulley 162.

This will be described below in more detail.

In the case of the surgical instrument 10 of the present disclosure, the staple auxiliary pulley 162 is further disposed on one side of the staple pulley 161. By changing the arrangement path of the wires 307 and 308, which are staple wires, to a certain extent by disposing the staple auxiliary pulley 162 as described above, the tangential direction of the wires 307 and 308 is changed, and thus the rotation angle of the coupling member (see 329 of FIG. 62) that couple the wires 307 and 308 to the staple pulley 161 is increased. That is, the coupling member (see 329 of FIG. 62), which is a coupling part of the wires 307 and 308 and the staple pulley 161, is rotatable until the coupling member 329 is located on the common internal tangent of the staple pulley 161 and the staple auxiliary pulley 122.

In other words, the wires 307 and 308 are located on the internal tangent of the staple pulley 161 and the staple auxiliary pulley 162, and the rotation angle of the staple pulley 161 is increased by the staple auxiliary pulley 162.

According to the present disclosure, as the rotation radius of the staple pulley 161 increases, a yaw motion range in which normal stapling and cutting motions are performed may be increased.

(Staple Drive Assembly)

Hereinafter, a staple drive assembly 150 will be described in more detail.

Referring to FIG. 13 and the like, the staple drive assembly 150 may include the staple pulley assembly 160 and the staple link assembly 170. Here, the staple drive assembly 150 is connected to a reciprocating assembly 550 of a cartridge 500 to be described later, and converts a rotational motion of the staple pulley 161 into a linear motion of the reciprocating assembly 550. In other embodiments of the present disclosure, which will be described later, the staple drive assembly may be understood as a concept including the staple pulley assembly and the staple link assembly.

The staple pulley assembly 160 may include one or more staple pulleys 161. The staple pulley assembly 160 may be formed between the pulley 111 and the pulley 121 to be adjacent to each of the pulley 111 and the pulley 121. In the present embodiment, it is assumed that the staple pulley assembly 160 includes one staple pulley 161.

A shaft pass-through part **161*a* may be formed in the staple pulley 161. The shaft pass-through part 161*a* may be formed in the form of a hole, and the rotation shaft 141, which is an end tool jaw pulley rotation shaft, may be inserted through the shaft pass-through part 161*a*. In addition, a link coupling part 161*b* may be formed on the staple pulley 161. The staple link assembly 170 to be described later may be coupled to the link coupling part 161*b***. This will be described in more detail later.

Meanwhile, the end tool 100 of the first embodiment of the present disclosure may further include the staple link assembly 170 connected to the staple pulley assembly 160. The staple link assembly 170 may include one or more link members 171. The staple link assembly 170 may serve to connect the staple pulley assembly 160 to the reciprocating assembly 550 of the cartridge 500 to be described later. In the present embodiment, it is assumed that the staple link assembly 170 includes one link member 171, and the link member 171 includes a first link 172 and a second link 173.

The first link 172 is formed in the form of an elongated bar, which may have through holes formed at both end portions. The link coupling part **161*b* of the staple pulley 161 may be inserted through the through hole at one end portion of the first link 172. The second link 173 may be inserted through the through hole at the other end portion of the first link 172**.

The second link 173 is formed in the form of an elongated bar, and may be coupled to the first link 172. The second link 173 may include a first protrusion **173*a*, a second protrusion 173*b*, and a coupling part 173*c***.

In detail, the first protrusion **173*a* may be formed at one end portion of the second link 173. The first protrusion 173*a* is axially coupled to the first link 172 by being fitted into the through hole of the first link 172, so that the second link 173 may be coupled to the first link 172. In addition, the first protrusion 173*a* may be fitted into a guide groove 101*b* of the first jaw 101**, which will be described later.

Meanwhile, the second protrusion **173*b* may be formed in one region of a central portion of the second link 173. The second protrusion 173*b* may be fitted into the guide groove 101*b* of the first jaw 101**, which will be described later.

As described above, as the first protrusion **173*a* and the second protrusion 173*b* are moved along the guide groove 101*b* in a state in which the first protrusion 173*a* and the second protrusion 173*b* of the second link 173 formed in a protruding shape are fitted into the groove-shaped guide groove 101*b*, the staple link assembly 170 is moved with respect to the first jaw 101 (and the cartridge 500** therein). This will be described in more detail later.

Meanwhile, the coupling part **173*c* may be formed at the other end portion of the second link 173**. The coupling part

173*c* may be coupled to a coupling part 551*a* of the reciprocating assembly 550 of the cartridge 500, which will be described later.

In the state of FIG. 13, when the staple pulley 161 is rotated in the clockwise direction, the link member 171 connected to the staple pulley 161 may be moved as a whole toward the distal end (see 101*f* of FIG. 14) of the first jaw 101. In contrast, when the staple pulley 161 is rotated in the counterclockwise direction, the link member 171 connected to the staple pulley 161 may be moved as a whole toward the proximal end (see 101*g* of FIG. 14) of the first jaw 101.

Thus, a bidirectional rotational motion of the staple pulley assembly 160 causes a reciprocating linear motion of the reciprocating assembly 550 of the cartridge 500 through the staple link assembly 170. This will be described in more detail later.

(First and Second Jaws and Actuation Motion)

Hereinafter, the coupling structure of the first jaw 101 and the second jaw 102 of the end tool 100 of the surgical instrument 10 of FIG. 2 will be described in more detail.

FIG. 14 is a plan view illustrating the first jaw of the surgical instrument of FIG. 2, and FIG. 15 is a plan view illustrating the second jaw of the surgical instrument of FIG. 2. FIG. 16 is a plan view illustrating opening and closing motions of the first jaw of the surgical instrument of FIG. 2, FIG. 17 is a plan view illustrating opening and closing motions of the second jaw of the surgical instrument of FIG. 2, and FIG. 18 is a plan view illustrating opening and closing motions of the first jaw and the second jaw of the surgical instrument of FIG. 2. FIG. 19 is a perspective view illustrating opening and closing motions of the end tool of the surgical instrument of FIG. 2, and FIG. 20 is a plan view illustrating opening and closing motions of the end tool of the surgical instrument of FIG. 2.

Referring to FIGS. 9 to 20 and the like, the first jaw 101 includes a cartridge accommodation part 101*a*, the guide groove 101*b*, a movable-coupling-allowed hole 101*c*, a jaw pulley coupling hole 101*d*, and a shaft pass-through part 101*e*.

The first jaw 101 is formed entirely in the shape of an elongated bar, the cartridge 500 is accommodated in the distal end 101*f* side, and the pulley 111 is coupled to the proximal end 101*g*, so that the first jaw 101 is formed to be rotatable around the rotation shaft 141. In other words, the first jaw 101 may be formed entirely in the form of a hollow box with one surface (upper surface) thereof is removed, such that the cartridge accommodation part 101*a* capable of accommodating the cartridge 500 may be formed inside the first jaw 101. That is, the first jaw 101 may be formed in an approximately "U" shape in cross section.

The guide groove 101*b* configured to guide the movement of the staple link assembly 170, which will be described later, may be formed on one side of the cartridge accommodation part 101*a* of the first jaw 101, e.g., on the proximal end 101*g* side. The guide groove 101*b* may be formed in the shape of a groove formed along a moving path of the staple link assembly 170. In addition, as the first protrusion 173*a* and the second protrusion 173*b* are moved along the guide groove 101*b* in a state in which the first protrusion 173*a* and the second protrusion 173*b* of the second link 173 formed in a protruding shape are fitted into the groove-shaped guide groove 101*b*, the staple link assembly 170 is moved with respect to the first jaw 101 (and the cartridge 500 therein). That is, the staple link assembly 170 may be moved along the guide groove 101*b* of the first jaw 101.

Meanwhile, the movable-coupling-allowed hole 101*c*, the jaw pulley coupling hole 101*d*, and the shaft pass-through part 101*e* may be formed on the proximal end side of the first jaw 101.

Here, the movable-coupling-allowed hole 101*c* may be formed to have a predetermined curvature, and may be formed in an approximately elliptical shape. A shaft coupling part 111*a* of the pulley 111, which will be described later, may be fitted into the movable-coupling-allowed hole 101*c*. Here, a short radius of the movable-coupling-allowed hole 101*c* may be formed to be substantially the same as or slightly greater than a radius of the shaft coupling part 111*a*. Meanwhile, a long radius of the movable-coupling-allowed hole 101*c* may be formed to be greater than the radius of the shaft coupling part 111*a*. Thus, in a state in which the shaft coupling part 111*a* of the pulley 111 is fitted into the movable-coupling-allowed hole 101*c* of the first jaw 101, the shaft coupling part 111*a* is movable to a certain extent in the movable-coupling-allowed hole 101*c*. This will be described in more detail below.

Meanwhile, the jaw pulley coupling hole 101*d* is formed in the form of a cylindrical hole, and a jaw coupling part 111*b* of the pulley 111, which will be described later, may be fitted into the jaw pulley coupling hole 101*d*. Here, a radius of the jaw pulley coupling hole 101*d* may be formed to be substantially the same as or slightly greater than a radius of the jaw coupling part 111*b*. Thus, the jaw coupling part 111*b* of the pulley 111 may be formed to be rotatably coupled to the jaw pulley coupling hole 101*d* of the first jaw 101. This will be described in more detail below.

The shaft pass-through part 101*e* may be formed at the distal end 101*f* side of the first jaw 101 relative to the movable-coupling-allowed hole 101*c* and the jaw pulley coupling hole 101*d*. The shaft pass-through part 101*e* may be formed in the form of a hole, and the rotation shaft 145, which is a jaw rotation shaft, may be inserted through the shaft pass-through part 101*e*.

The second jaw 102 includes an anvil 102*a*, a movable-coupling-allowed hole 102*c*, a jaw pulley coupling hole 102*d*, and a shaft pass-through part 102*e*.

The second jaw 102 is formed entirely in the shape of an elongated bar, the anvil 102*a* is formed on a distal end 102*f* side, and the pulley 112 is coupled to a proximal end 102*g*, so that the second jaw 102 is formed to be rotatable around the rotation shaft 141.

In detail, the anvil 102*a* is formed in the form of a flat plane, on one surface of which shapes corresponding to the shapes of staples 530 to be described later may be formed. The above-described anvil 102*a* may serve as a support for supporting the staple 530 on the opposite side of the operation member 540 when the operation member 540 pushes and raises the staple 530 during a stapling motion, so that the staple 530 is bent.

Meanwhile, the movable-coupling-allowed hole 102*c*, the jaw pulley coupling hole 102*d*, and the shaft pass-through part 102*e* may be formed on the proximal end side of the second jaw 102.

Here, the movable-coupling-allowed hole 102*c* may be formed to have a predetermined curvature, and may be formed in an approximately elliptical shape. A shaft coupling part 121*a* of the pulley 121, which will be described later, may be fitted into the movable-coupling-allowed hole 102*c*. Here, a short radius of the movable-coupling-allowed hole 102*c* may be formed to be substantially the same as or slightly greater than a radius of the shaft coupling part 121*a*. Meanwhile, a long radius of the movable-coupling-allowed hole 102*c* may be formed to be greater than the radius of the shaft coupling part 121*a*. Thus, in a state in which the shaft coupling part 121*a* of the pulley 121 is fitted into the movable-coupling-allowed hole 102*c* of the second jaw 102, the shaft coupling part 121*a* is movable to a certain extent in the movable-coupling-allowed hole 102*c*. This will be described in more detail below.

Meanwhile, the jaw pulley coupling hole 102*d* is formed in the form of a cylindrical hole, and a jaw coupling part 121*b* of the pulley 121, which will be described later, may be fitted into the jaw pulley coupling hole 102*d*. Here, a radius of the jaw pulley coupling hole 102*d* may be formed to be substantially the same as or slightly greater than a radius of the jaw coupling part 121*b*. Thus, the jaw coupling part 121*b* of the pulley 121 may be formed to be rotatably coupled to the jaw pulley coupling hole 102*d* of the second jaw 102. This will be described in more detail below.

Meanwhile, the shaft pass-through part 102*e* may be formed at the distal end 102*g* side of the second jaw 102 relative to the movable-coupling-allowed hole 102*c* and the jaw pulley coupling hole 102*d*. The shaft pass-through part 102*e* may be formed in the form of a hole, and the rotation shaft 145, which is the jaw rotation shaft, may be inserted through the shaft pass-through part 102*e*.

The pulley 111, which is a first jaw pulley, may include the shaft coupling part 111*a* and the jaw coupling part 111*b*. The pulley 111 is formed entirely in the form of a rotatable disk, and the shaft coupling part 111*a* and the jaw coupling part 111*b* may be formed to protrude to a certain extent from one surface of the pulley 111. As described above, the shaft coupling part 111*a* of the pulley 111 may be fitted into the movable-coupling-allowed hole 101*c* of the first jaw 101, and the jaw coupling part 111*b* of the pulley 111 may be fitted into the jaw pulley coupling hole 101*d* of the first jaw 101. The pulley 111 may be formed to be rotatable around the center of the rotation shaft 141, which is an end tool jaw pulley rotation shaft.

Meanwhile, the pulley 121, which is a second jaw pulley, may include the shaft coupling part 121*a* and the jaw coupling part 121*b*. The pulley 121 is formed entirely in the form of a rotatable disk, and the shaft coupling part 121*a* and the jaw coupling part 121*b* may be formed to protrude to a certain extent from one surface of the pulley 121. As described above, the shaft coupling part 112*a* of the pulley 112 may be inserted into the movable-coupling-allowed hole 102*c* of the second jaw 102, and the jaw coupling part 112*b* of the pulley 112 may be inserted into the jaw pulley coupling hole 102*d* of the second jaw 102. The pulley 121 may be formed to be rotatable around the center of the rotation shaft 141, which is an end tool jaw pulley rotation shaft.

The coupling relationship between the components described above is as follows.

The rotation shaft 141, which is an end tool jaw pulley rotation shaft, is sequentially inserted through the shaft coupling part 111*a* of the pulley 111, the movable-coupling-allowed hole 101*c* of the first jaw 101, the shaft pass-through part 161*a* of the staple pulley 161, the movable-coupling-allowed hole 102*c* of the second jaw 102, and the shaft coupling part 121*a* of the pulley 121.

The rotation shaft 145, which is a jaw rotation shaft, is sequentially inserted through the shaft pass-through part 101*e* of the first jaw 101 and the shaft pass-through part 102*e* of the second jaw 102.

The shaft coupling part 111*a* of the pulley 111 is fitted into the movable-coupling-allowed hole 101*c* of the first jaw 101, and the jaw coupling part 111*b* of the pulley 111 is fitted into the jaw pulley coupling hole 101*d* of the first jaw 101.

At this time, the jaw pulley coupling hole 101*d* of the first jaw 101 and the jaw coupling part 111*b* of the pulley 111 are axially coupled to each other so as to be rotatable, and the movable-coupling-allowed hole 101*c* of the first jaw 101 and the shaft coupling part 111*a* of the pulley 111 are movably coupled to each other.

The shaft coupling part 121*a* of the pulley 121 is fitted into the movable-coupling-allowed hole 102*c* of the second jaw 102, and the jaw coupling part 121*b* of the pulley 121 is fitted into the jaw pulley coupling hole 102*d* of the second jaw 102.

At this time, the jaw pulley coupling hole 102*d* of the second jaw 101 and the jaw coupling part 121*b* of the pulley 121 are axially coupled to each other to be rotatable, and the movable-coupling-allowed hole 102*c* of the second jaw 102 and the shaft coupling part 121*a* of the pulley 121 are movably coupled to each other.

Here, the pulley 111 and the pulley 121 are rotated around the rotation shaft 141, which is an end tool jaw pulley rotation shaft. The first jaw 101 and the second jaw 102 are rotated around the rotation shaft 145, which is a jaw rotation shaft. That is, the pulley 111 and the first jaw 101 have different axes of rotation. Similarly, the pulley 121 and the second jaw 102 have different axes of rotation.

That is, the rotation angle of the first jaw 101 is limited to a certain extent by the movable-coupling-allowed hole 101*c*, but is essentially rotated around the rotation shaft 145, which is a jaw rotation shaft. Similarly, the rotation angle of the second jaw 102 is limited to a certain extent by the movable-coupling-allowed hole 102*c*, but is essentially rotated around the rotation shaft 145, which is a jaw rotation shaft.

Amplification of grip force due to the coupling relationship between the above-described components will be described.

In the surgical instrument 10 according to an embodiment of the present disclosure, the coupling structure of the first jaw 101 and the second jaw 102 forms an X-shaped structure, and thus, when the first jaw 101 and the second jaw 102 are rotated in directions close to each other (i.e., when the first jaw 101 and the second jaw 102 are closed), the grip force is greater in a direction in which the first jaw 101 and the second jaw 102 are closed. This will be described below in more detail.

As described above, in motions of the first jaw 101 and the second jaw 102 being opened and closed, there are two axes that become the center of rotation of the jaws. That is, the first jaw 101 and the second jaw 102 perform opening and closing motions around two axes of the rotation shaft 141 and the rotation shaft 145. In this case, the center of rotation of the first jaw 101 and the second jaw 102 is the rotation shaft 145, and the center of rotation of the pulley 111 and the pulley 121 is the rotation shaft 141. At this time, the rotation shaft 141 is a shaft whose position is relatively fixed, and the rotation shaft 145 is a shaft whose position is moved linearly. In other words, when the pulley 111 and the pulley 121 are rotated in a state in which the position of the rotation shaft 141 is fixed, the first jaw 101 and the second jaw 102 are opened/closed while the rotation shaft 145, which is a rotation shaft of the first jaw 101 and the second jaw 102, is moved backward and forward. This will be described below in more detail.

In FIG. 17, r1 is a distance from the jaw coupling part 121*b* of the pulley 121 to the shaft coupling part 121*a*, and a length thereof is constant. Thus, a distance from the rotation shaft 141 inserted into the shaft coupling part 121*a* to the jaw coupling part 121*b* is also constant as r1.

Meanwhile, r2 of FIG. 17 is a distance from the jaw pulley coupling hole 102*d* of the second jaw 102 to the shaft pass-through part 102*e*, and a length thereof is constant. Thus, a distance from the jaw coupling part 121*b* of the pulley 121 inserted into the jaw pulley coupling hole 102*d* to the rotation shaft 145 inserted into the shaft pass-through part 102*e* is also constant as r2.

That is, the lengths of r1 and r2 are kept constant. Accordingly, when the pulley 111 and the pulley 121 are rotated in the direction of an arrow A1 of FIG. 16 and the direction of an arrow A2 of FIG. 17, respectively, around the rotation shaft 141 to perform a closing motion, the first jaw 101 and the second jaw 102 are rotated around the rotation shaft 145 as the angle between r1 and r2 changes while the lengths of r1 and r2 remain constant, and at this time, the rotation shaft 145 itself is also linearly moved (i.e., is moved forward/backward) by as much as the arrow B1 of FIG. 16 and the arrow B2 of FIG. 17.

That is, when it is assumed that the position of the rotation shaft 141, which is an end tool jaw pulley rotation shaft, is fixed, when the first jaw 101 and the second jaw 102 are closed, a force is applied in the direction in which the rotation shaft 145, which is a jaw rotation shaft, is moved forward (i.e., toward the distal end), and thus the grip force in the direction in which the first jaw 101 and the second jaw 102 are closed becomes larger.

In other words, since the lengths of r1 and r2 remain constant when the second jaw 102 is rotated around the jaw rotation shaft 145, when the pulley 121 is rotated around the rotation shaft 141, the angle between r1 and r2 changes while the lengths of r1 and r2 remain constant. That is, 02, which is the angle between r1 and r2 when the second jaw 102 is closed as shown in FIG. 17A, is greater than θ1, which is the angle between r1 and r2 when the second jaw 102 is opened as shown in FIG. 17B.

Accordingly, when the second jaw 102 is rotated from the open state to the close state, the angle between r1 and r2 changes, and a force in a direction in which the rotation shaft 145 is moved forward is applied.

In this case, since the rotation shaft 141 is a shaft whose position is relatively fixed, the jaw rotation shaft 145 is moved forward in the direction of the arrow B1 of FIG. 16 and the direction of the arrow B2 of FIG. 17, and the grip force is further increased in a direction in which the second jaw 102 is closed.

In other words, when the pulley 111 and the pulley 121 are rotated around the rotation shaft 141, which is a shaft whose relative position is fixed, the angle θ between r1 and r2 changes while the distance between r1 and r2 remains constant. In addition, when the angle θ changes as described above, the first jaw 101 and the second jaw 102 push or pull the rotation shaft 145, and thus the rotation shaft 145 is moved forward or backward. In this case, when the first jaw 101 and the second jaw 102 are rotated in the direction of closing, the grip force is further increased as the rotation shaft 145 is moved forward in the direction of the arrow B1 of FIG. 16 and the direction of the arrow B2 of FIG. 17. In contrast, when the first jaw 101 and the second jaw 102 are rotated in the direction of opening, the rotation shaft 145 is moved backward in directions opposite to the arrow B1 of FIG. 16 and the direction of the arrow B2 of FIG. 17.

With this configuration, the grip force becomes stronger when the first jaw 101 and the second jaw 102 are closed, thereby enabling a surgical operator to perform the actuation motion powerfully even with a small force.

(Cartridge)

Hereinafter, the cartridge 500 of the surgical instrument 10 of FIG. 2 will be described in more detail.

Figure 21:
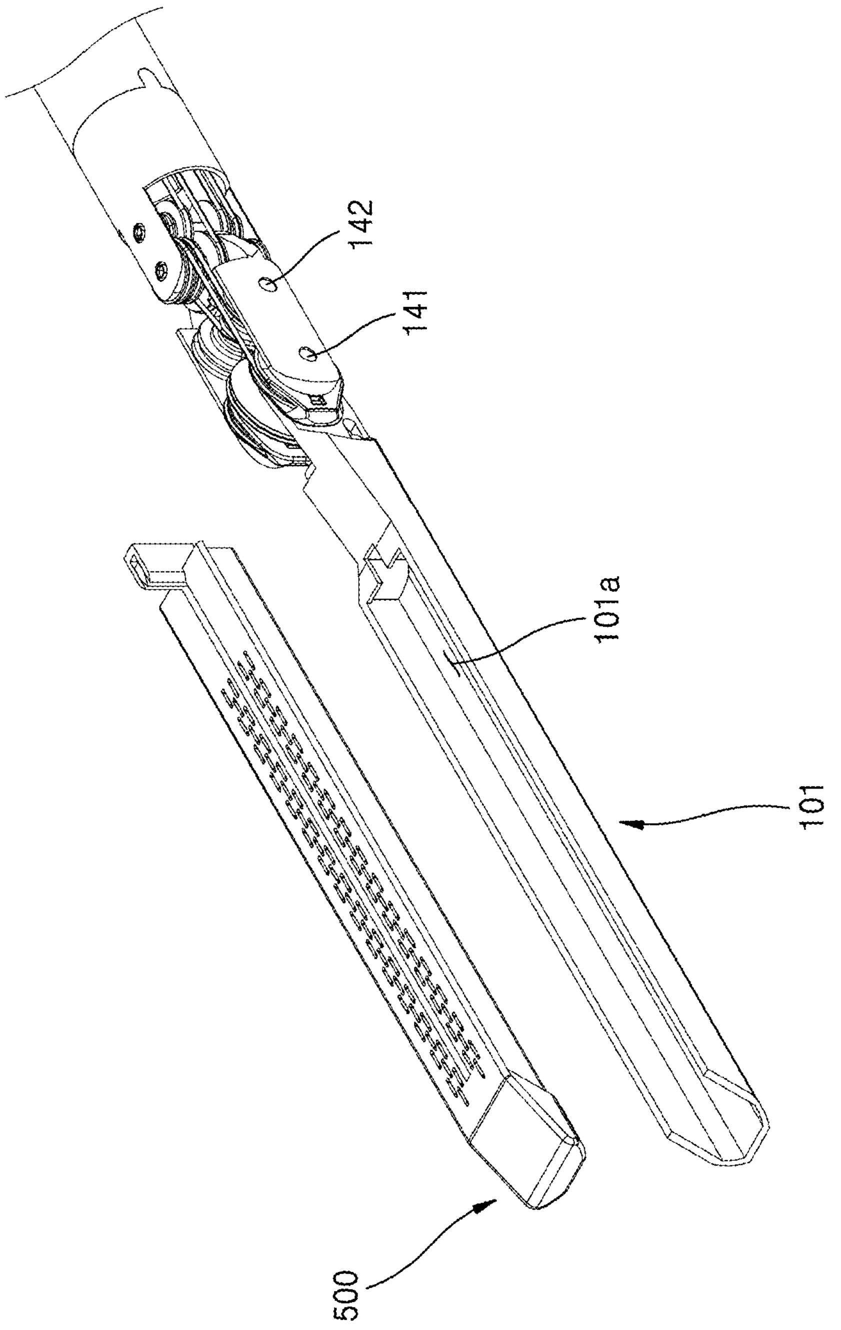
FIG. 21 is a perspective view illustrating the first jaw and a cartridge of the surgical instrument of FIG. 2.
Figure 22:
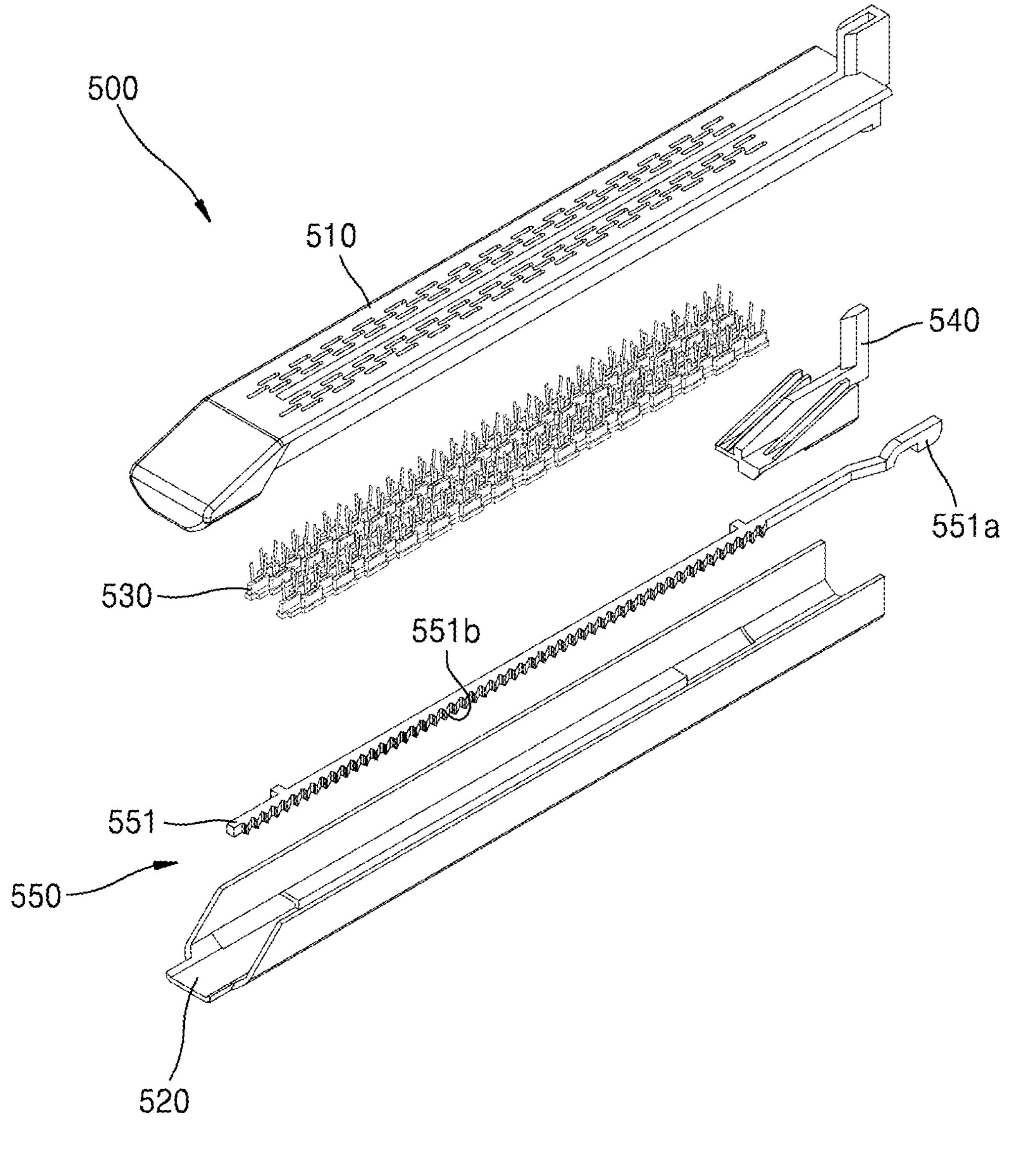
FIG. 22 is an exploded perspective view illustrating the cartridge of FIG. 21.
Figure 23:
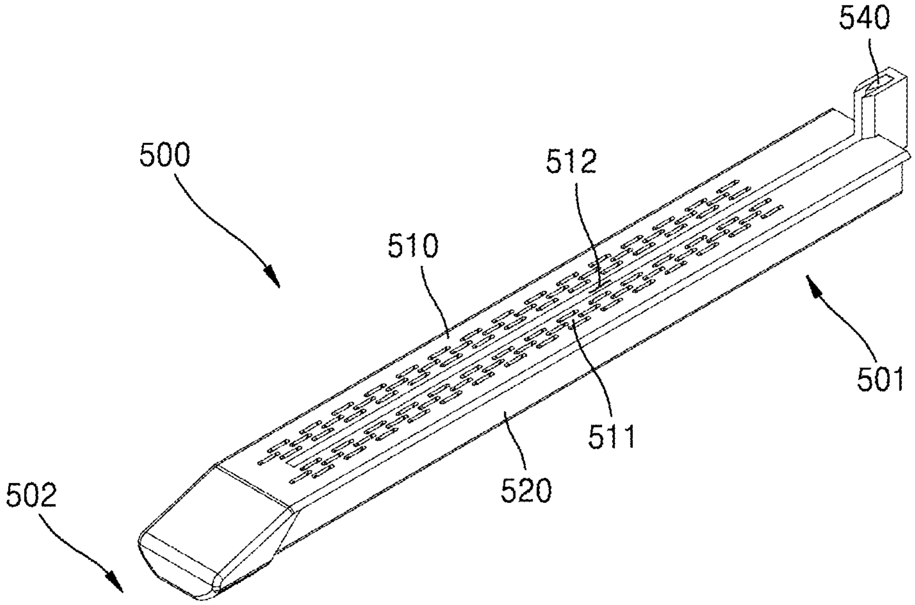
FIG. 23 is an assembled perspective view illustrating the cartridge of FIG. 21.
Figure 24:
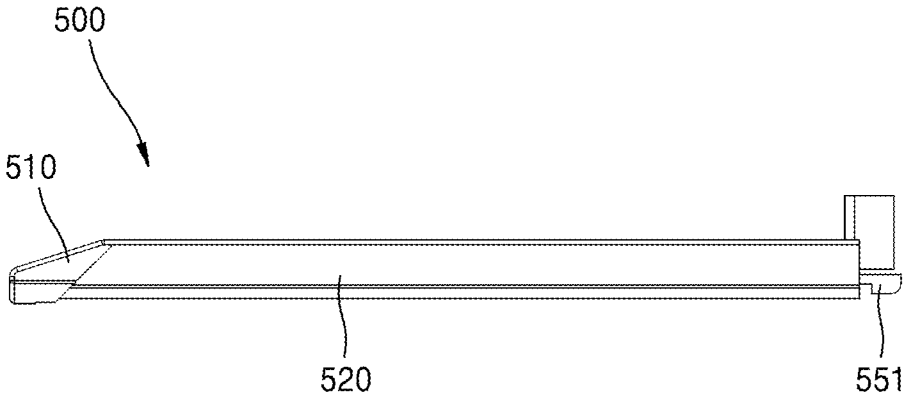
FIG. 24 is a side view illustrating the cartridge of FIG. 21.
Figure 25:
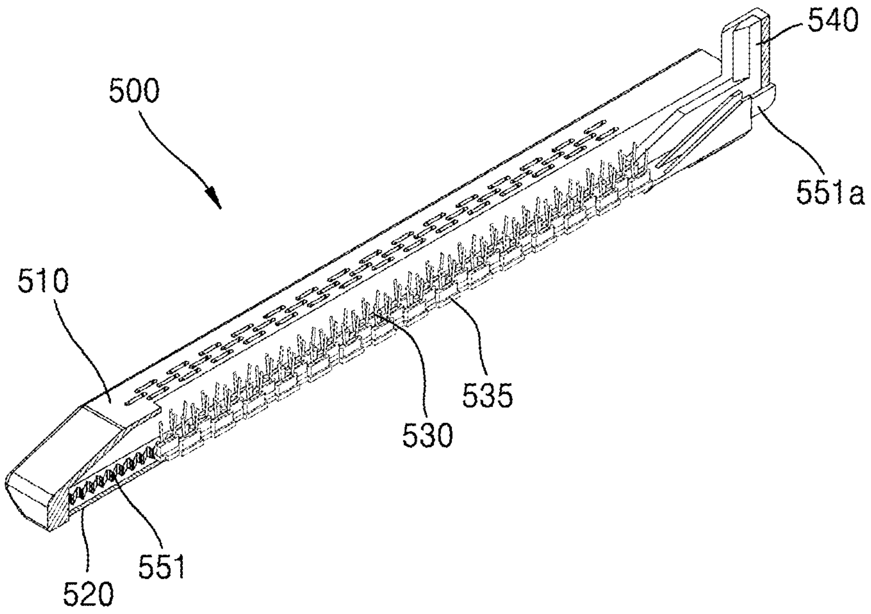
FIG. 25 is a perspective cross-sectional view illustrating the cartridge of FIG. 21.
Figure 26:
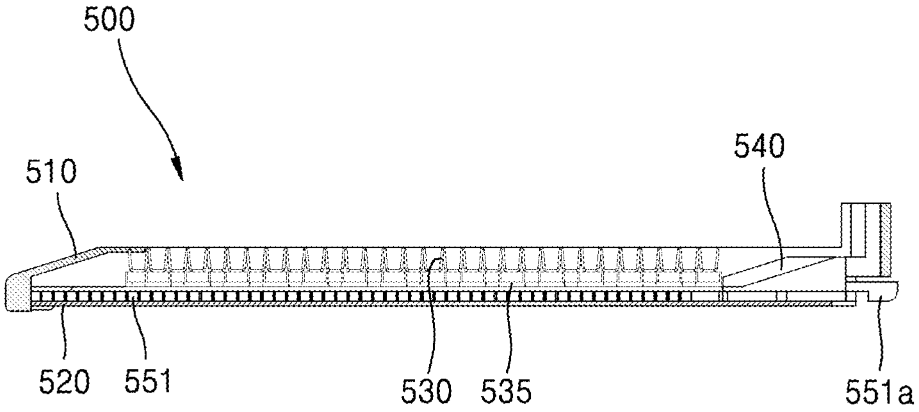
FIG. 26 is a side cross-sectional view illustrating the cartridge of FIG. 21.
Figure 27:
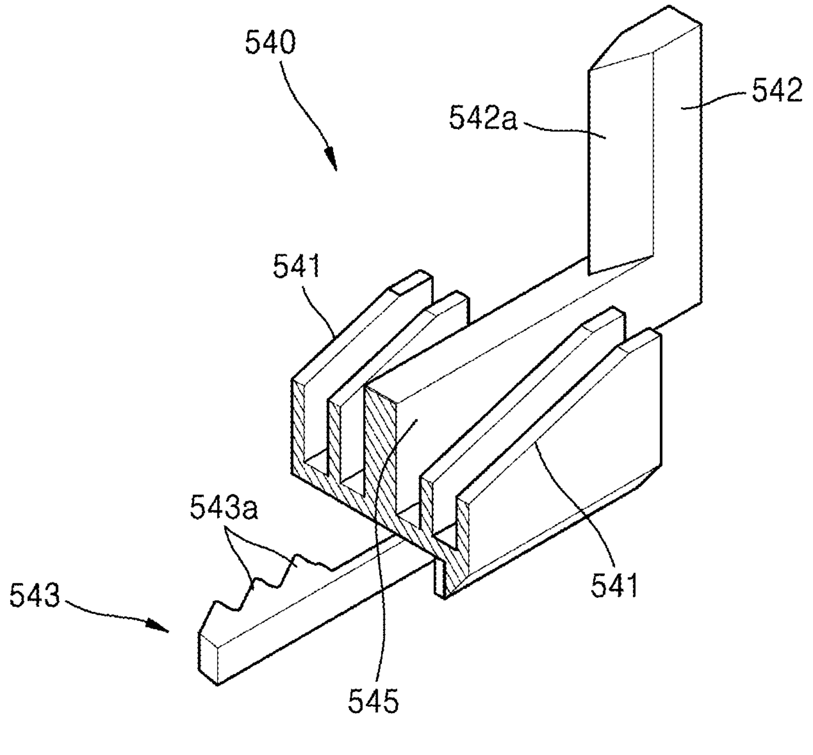
FIGS. 27 and 28 are perspective views illustrating an operation member of the cartridge of FIG. 21.
Figure 28:
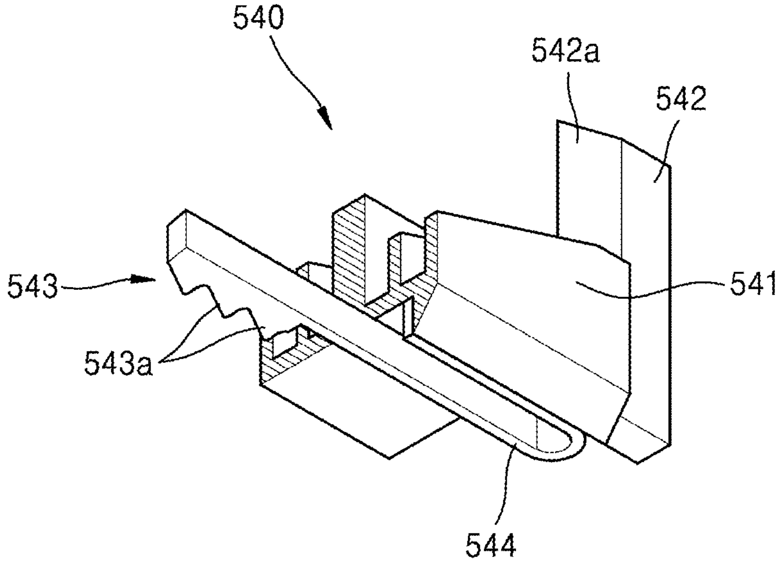
Figure 29:
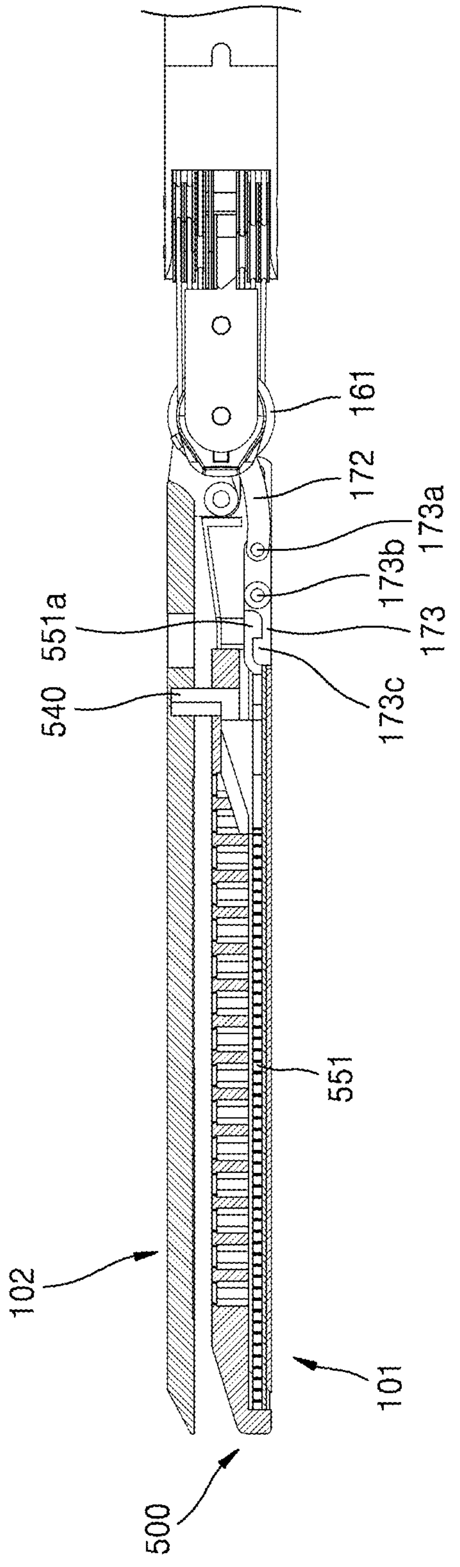
FIG. 29 is a side cross-sectional view illustrating a stapling-related structure of the end tool of the surgical instrument of FIG. 2.
Figure 30:
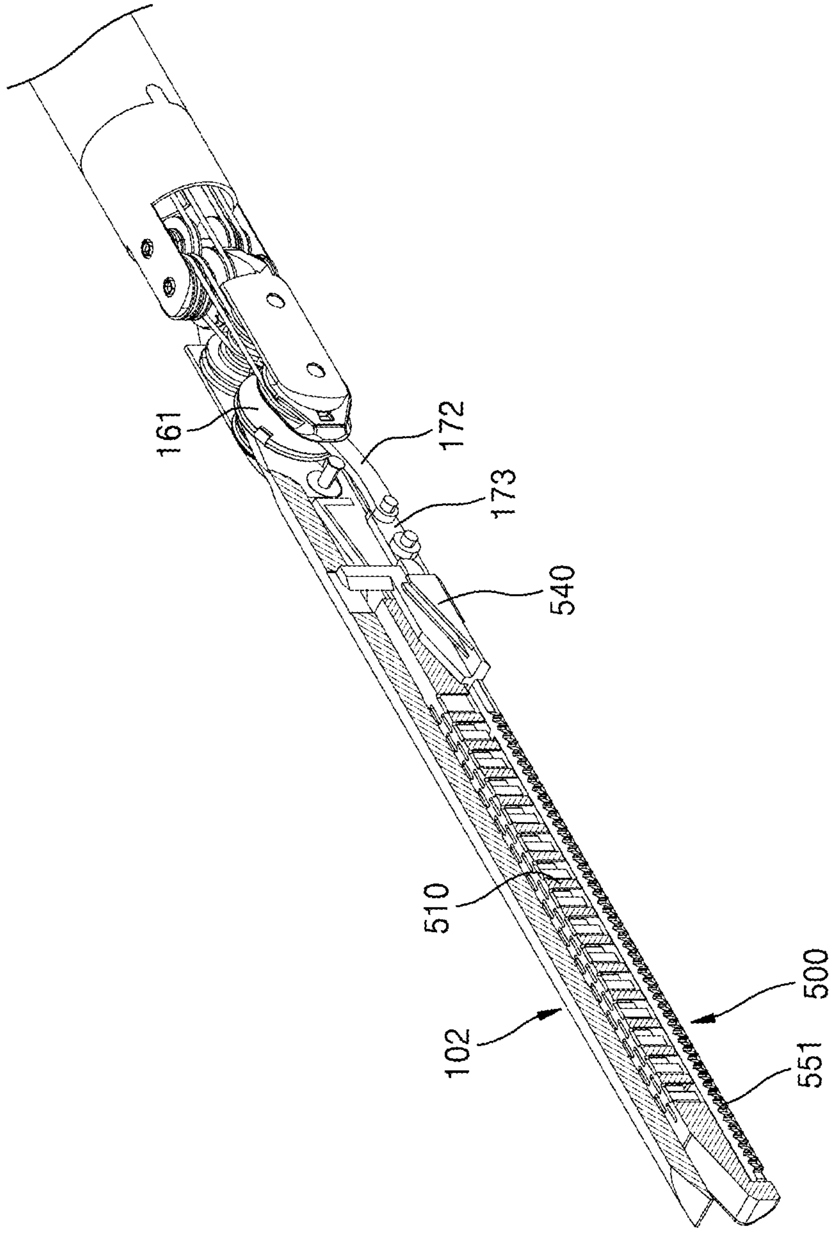
FIGS. 30 and 31 are perspective cross-sectional views illustrating a stapling structure of the end tool of the surgical instrument of FIG. 2.
Figure 31:
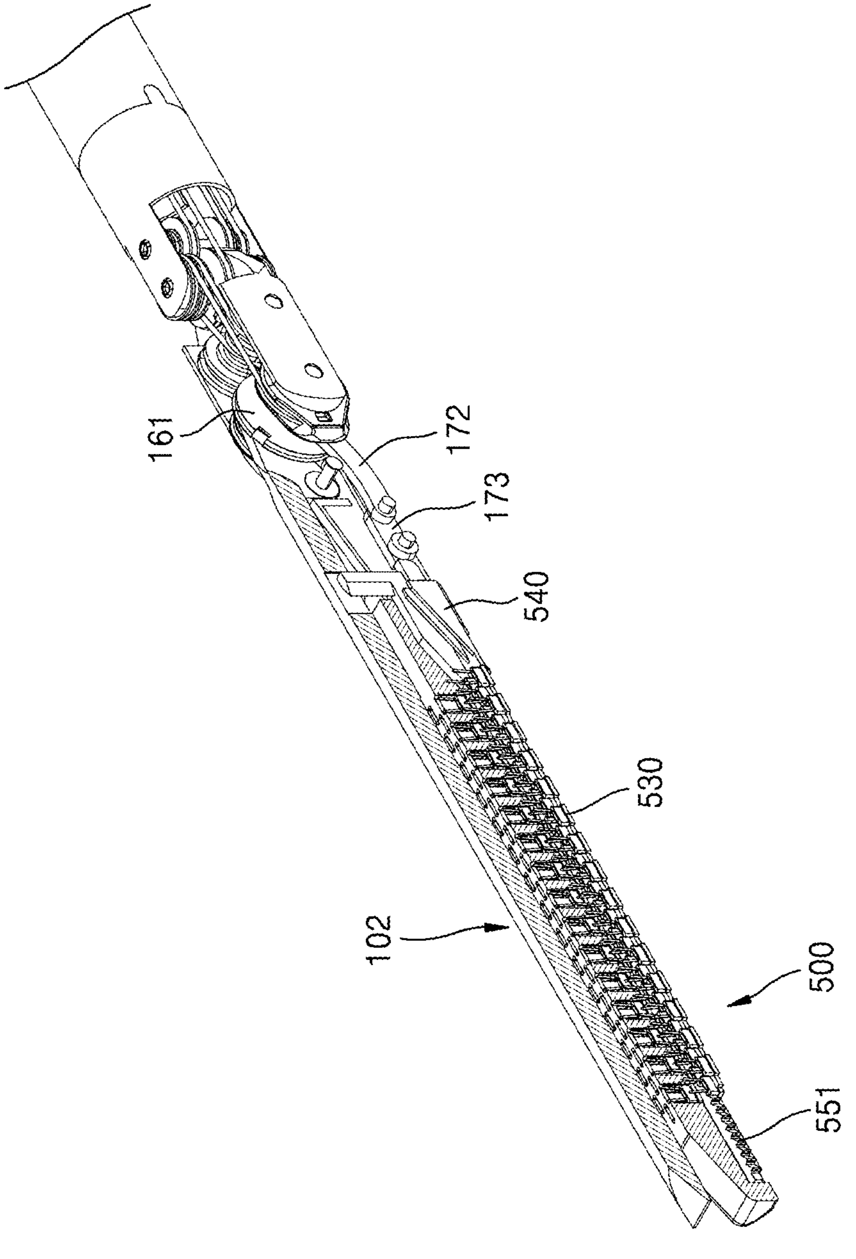
Figure 32:
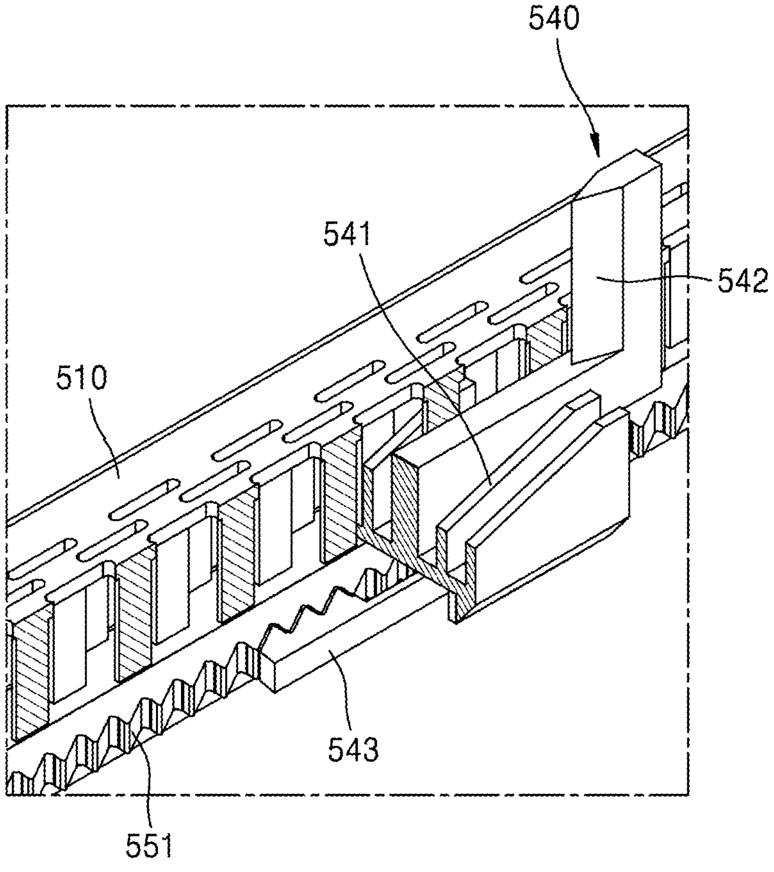
FIGS. 32 to 35 are perspective views illustrating a ratchet drive operation of the end tool of FIG. 30.
Figure 33:
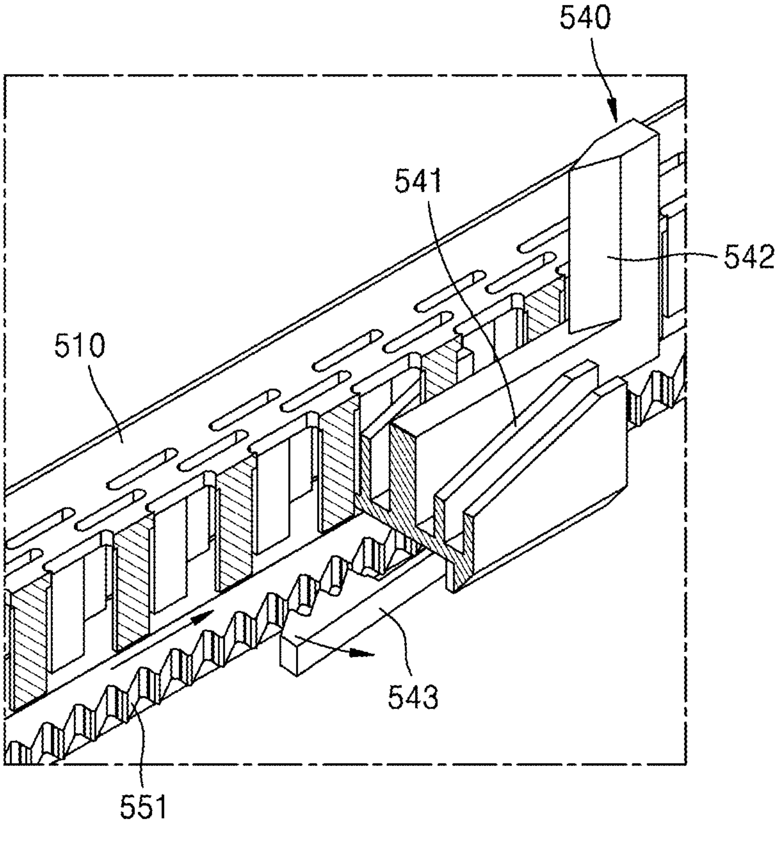
Figure 38:
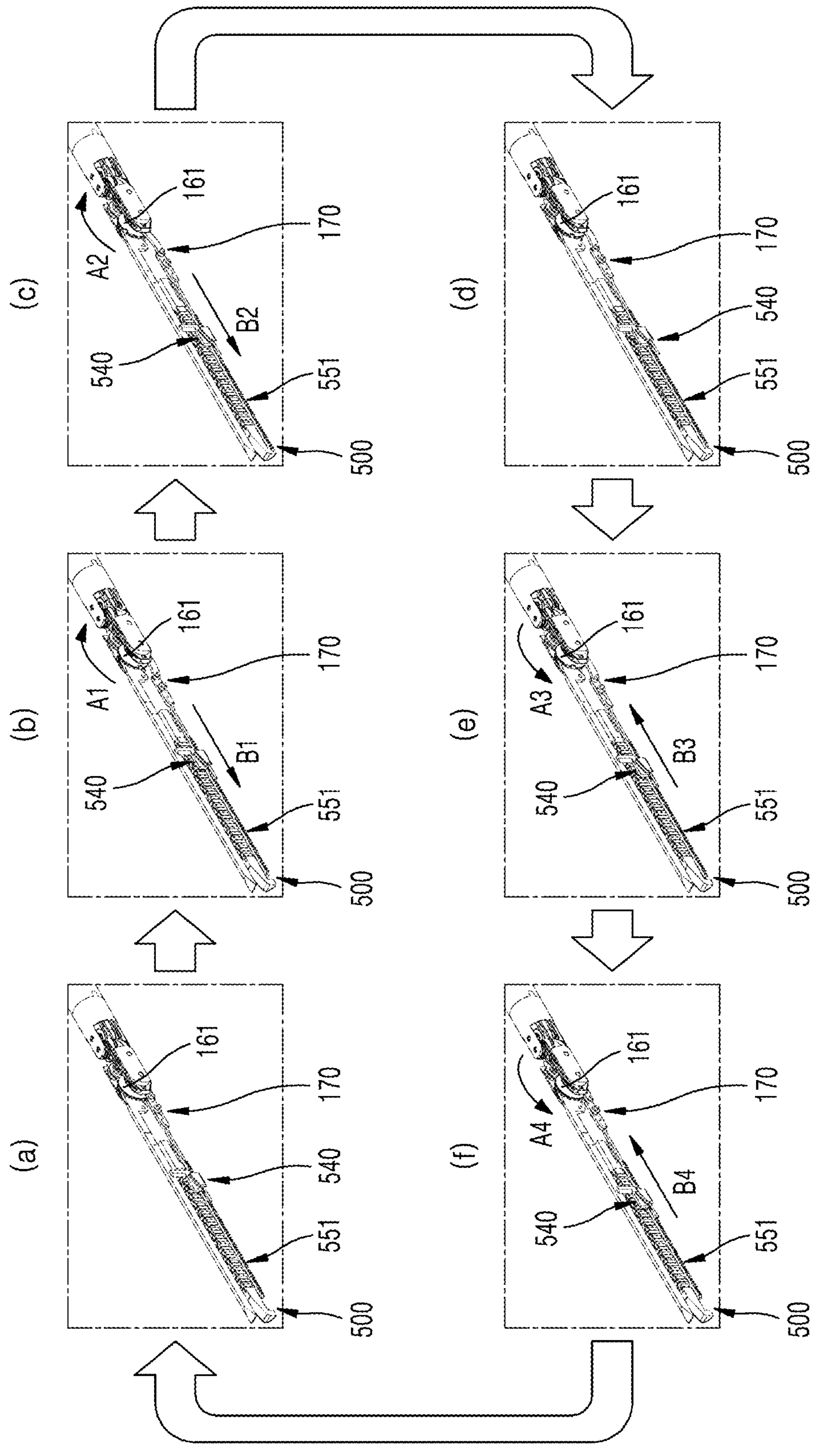
FIG. 38 is a perspective view illustrating an entire ratchet drive operation of the end tool of FIG. 30.
Figure 39:
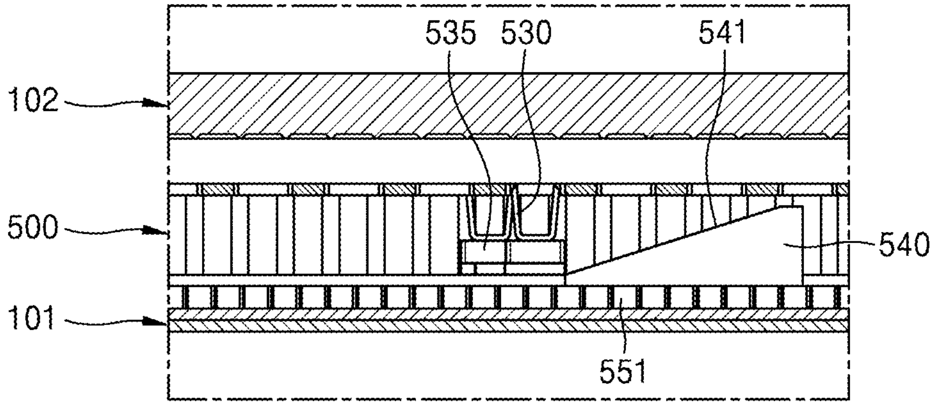
FIGS. 39 and 40 are perspective views illustrating an entire stapling motion of the end tool of FIG. 30.
Figure 39:
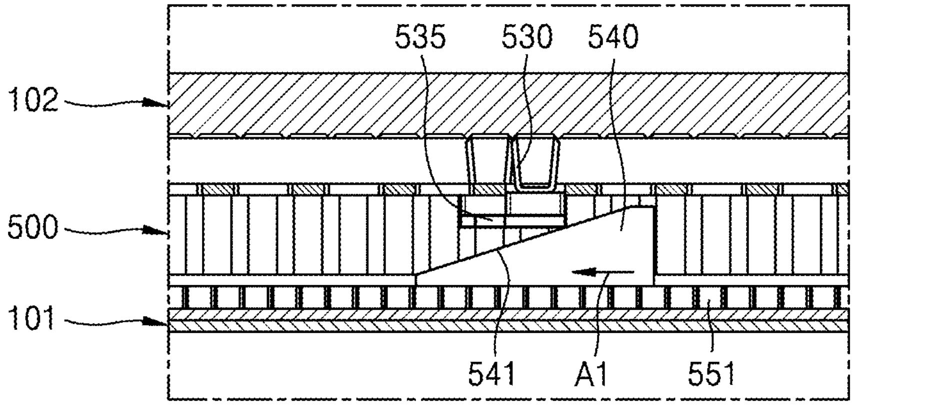
Figure 39:
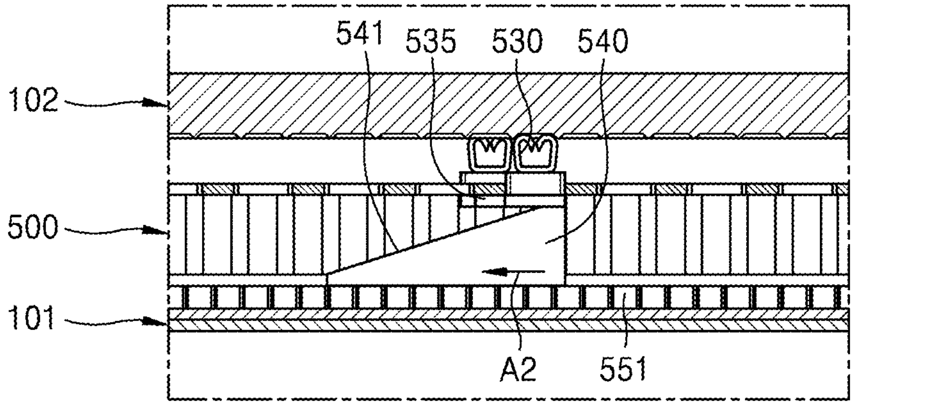
Figure 40:
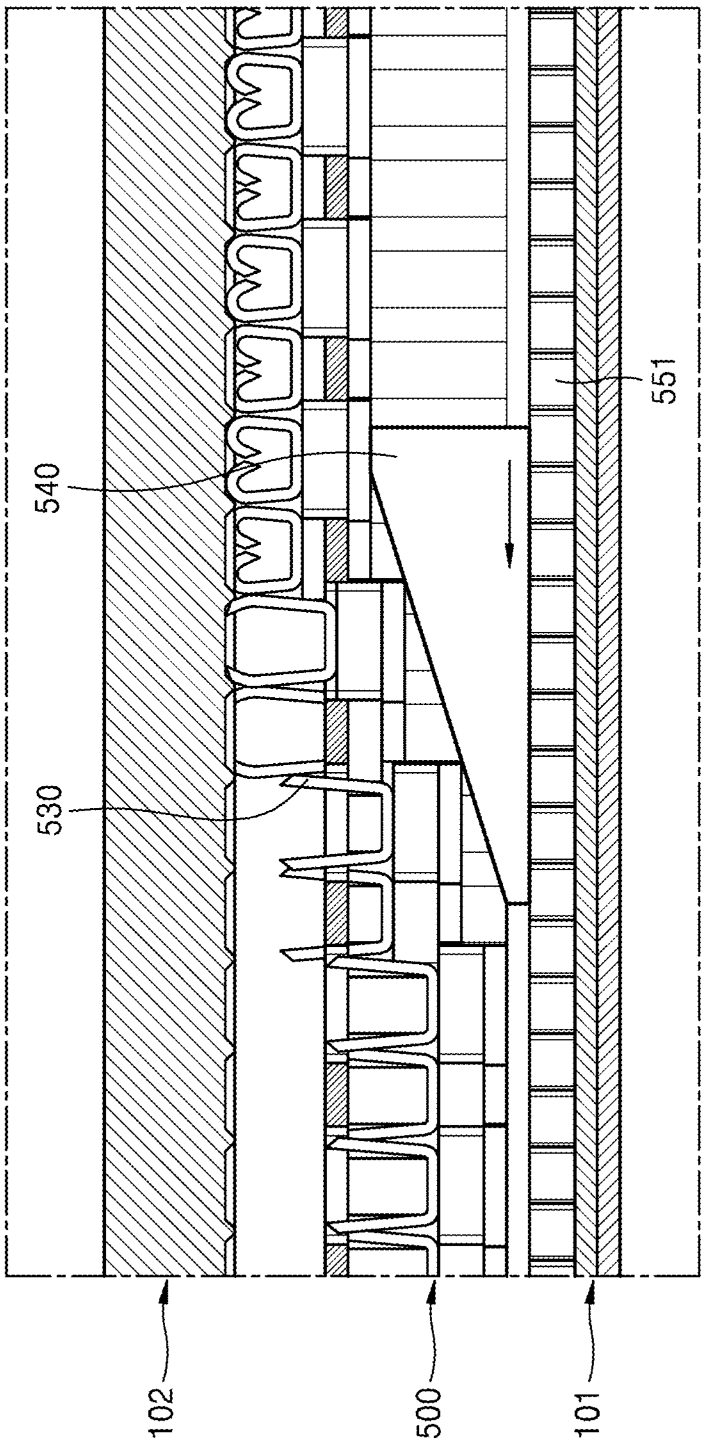

FIG. 21 is a perspective view illustrating the first jaw and the cartridge of the surgical instrument of FIG. 2. FIG. 22 is an exploded perspective view illustrating the cartridge of FIG. 21, FIG. 23 is a coupled perspective view illustrating the cartridge of FIG. 21, FIG. 24 is a side view illustrating the cartridge of FIG. 21, FIG. 25 is a perspective cross-sectional view illustrating the cartridge of FIG. 21, and FIG. 26 is a side cross-sectional view illustrating the cartridge of FIG. 21. FIGS. 27 and 28 are perspective views illustrating the operation member of the cartridge of FIG. 21. FIG. 29 is a side cross-sectional view illustrating a stapling-related structure of the end tool of the surgical instrument of FIG. 2, and FIGS. 30 and 31 are perspective cross-sectional views illustrating a stapling structure of the end tool of the surgical instrument of FIG. 2. FIGS. 32 to 35 are perspective views illustrating a ratchet drive operation of the end tool of FIG. 30, and FIGS. 36 and 37 are plan views illustrating a ratchet drive operation of the end tool of FIG. 30. FIG. 38 is a perspective view illustrating an entire ratchet drive operation of the end tool of FIG. 30. FIGS. 39 and 40 are perspective views illustrating an entire stapling motion of the end tool of FIG. 30.

Referring to FIGS. 21 to 40 and the like, the cartridge 500 is formed to be mountable to and dismountable from the first jaw 101, and includes a plurality of staples 530 and a blade 542 therein to perform suturing and cutting tissue. Here, the cartridge 500 may include a cover 510, a housing 520, the staples 530, withdrawal members 535, the operation member 540, and the reciprocating assembly 550.

The housing 520 forms an outer shape of the cartridge 500, and may be formed entirely in the form of a hollow box with one surface (upper surface) thereof removed to accommodate the reciprocating assembly 550, the operation member 540, and the staple 530 therein. Here, the housing 520 may be formed in an approximately "U" shape in cross section.

The cover 510 is formed to cover an upper portion of the housing 520. Staple holes 511 through which the plurality of staples 530 may be ejected to the outside may be formed in the cover 510. As the staples 530, which are accommodated inside the housing 520 before a stapling operation, are pushed and raised upward by the operation member 540 during a stapling motion, and pass through the staple holes 511 of the cover 510 to be withdrawn to the outside of the cartridge 500, stapling is performed.

Meanwhile, a slit 512 may be formed in the cover 510 along a length direction of the cover 510. The blade 542 of the operation member 540 may protrude out of the cartridge 500 through the slit 512. As the blade 542 of the operation member 540 passes along the slit 512, staple-completed tissue may be cut.

The plurality of staples 530 may be disposed inside the housing 520. As the operation member 540, which will be described later, is linearly moved in one direction, the plurality of staples 530 are sequentially pushed and raised from the inside of the housing 520 to the outside, thereby performing sealing, that is, stapling. Here, the staples 530 may be made of a material that may include titanium, stainless steel, or the like.

Meanwhile, the withdrawal member 535 may be further disposed between the housing 520 and the staple 530. In other words, it may be said that the staple 530 is disposed above the withdrawal member 535. In this case, the operation member 540 is linearly moved in one direction to push and raise the withdrawal member 535, and the withdrawal member 535 may push and raise the staple 530.

As such, the operation member 540 may be described as pushing and raising the staples 530 in both the case in which the operation member 540 directly pushes and raises the staples 530 and the case in which the operation member 540 pushes and raises the withdrawal members 535 and the withdrawal members 535 pushes and raises the staples 530 (i.e., the operation member 540 indirectly pushes and raises the staples 530).

The reciprocating assembly 550 may be disposed at an inner lower side of the housing 520. The reciprocating assembly 550 may include one or more reciprocating members 551. In the present embodiment, it is illustrated that one reciprocating member 551 is provided, but in embodiments to be described later, a plurality of reciprocating members 551 may be provided.

In the present embodiment, the reciprocating member 551 may be a rack. The reciprocating member 551 may include recesses 551*b* and the coupling part 551*a*. In detail, the reciprocating member 551 may be formed in the form of an elongated bar, and a plurality of recesses 551*b* having a sawtooth shape may be formed on one surface thereof. The recess 551*b* may be formed to be in contact with the operation member 540 to be described later, in particular, a ratchet member 543 of the operation member 540. In other words, the reciprocating member 551 may include the plurality of recesses 551*b* shaped to engage with ratchets 543*a* of the ratchet member 543.

Meanwhile, although not shown in the drawings, in addition to a rack shape, the reciprocating member 551 may be provided as various shapes of members, which are directly or indirectly connected to the staple pulley 161 and may perform a linear reciprocating motion according to a rotational motion of the staple pulley 161. For example, the reciprocating member 551 may be in the form of a clutch in which recesses are not present.

Here, the reciprocating member 551 is not fixedly coupled to the other components of the cartridge 500, and may be formed to be movable relatively to the other components of the cartridge 500. That is, the reciprocating member 551 may perform a reciprocating linear motion with respect to the housing 520 and the cover 510 coupled to the housing 520.

Meanwhile, in the reciprocating member 551, the coupling part 551*a* may be formed at the proximal end 501 side adjacent to the pulley 111, and the coupling part 551*a* may be fastened and coupled to the staple link assembly 170 of the end tool 100. Thus, when the staple link assembly 170 performs a reciprocating linear motion in the extension direction (i.e., the Y-axis direction) of the connection part 400, the reciprocating member 551 coupled thereto may also perform a reciprocating linear motion in the extension direction (i.e., the Y-axis direction) of the connection part 400. This will be described in more detail later.

The operation member 540 may be disposed inside the housing 520. The operation member 540 is formed to be in contact with the reciprocating member 551, and may be formed to linearly move in one direction according to the reciprocating linear motion of the reciprocating member 551. In other words, the operation member 540 interacts with the reciprocating member 551 to perform stapling and cutting motions while moving in the extension direction of the connection part 400.

The operation member 540 may include a wedge 541, the blade 542, the ratchet member 543, an elastic member 544, and a body 545.

The body 545 may be formed in the shape of an elongated square column, and forms a base of the operation member 540.

The wedge 541 is formed on at least one side of the body 545, and may be formed to have a predetermined inclined surface. That is, the wedge 541 may be formed to be inclined to a certain extent in the extension direction of the connection part 400. In other words, the wedge 541 may be formed to have a greater height at a proximal end 501 side of the cartridge 500 than a distal end 502 side of the cartridge 500. In the drawing, it is illustrated that two wedges 541 are formed on each side of the body 545, but the concept of the present disclosure is not limited thereto, and the wedge 541 may be formed in various numbers and shapes depending on the shape of the staple 530 or the withdrawal member 535 that is in contact with the wedge 541.

The wedge 541 may be formed to be in contact with the withdrawal members 535 or the plurality of staples 530 in turn and may serve to sequentially push and raise the staples 530. As shown in FIG. 40 to be described later and elsewhere herein, the operation member 540 may serve to withdraw the staples 530 to the outside of the cartridge 500 by sequentially pushing and raising the staples 530 while moving toward the distal end 502.

The blade 542 may be formed on one side of the wedge 541, more specifically, on one side of the wedge 541 at the proximal end 501 side. An edge 542*a* formed to be sharp to cut tissue is formed in one region of the blade 542. As at least a portion of the edge 542*a* is withdrawn to the outside of the first jaw 101 and the cartridge 500, tissue disposed between the first jaw 101 and the second jaw 102 may be cut. The edge 542*a* of the blade 542 may be always withdrawn to the outside of the first jaw 101. Alternatively, the edge 542*a* of the blade 542 may normally be accommodated inside the first jaw 101 or inside the cartridge 500, and may be withdrawn to the outside of the first jaw 101 only when the operation member 540 is moved in a length direction.

The ratchet member 543 is formed on one side of the wedge 541, more specifically, below wedge 541, and may be formed to face the reciprocating member 551 to be described later. The ratchet member 543 may be formed in the form of a bar and may include a plurality of ratchets 543*a* on one surface. The operation member 540 is moved only in one direction (i.e., toward the distal end) with respect to the reciprocating member 551 by the ratchet member 543. The ratchets 543*a* of the ratchet member 543 may be formed to be in contact with the recess 551*b* of the reciprocating member 551 described above.

The elastic member 544 is formed on one side of the body 545 or the wedge 541 and serves to apply a predetermined elastic force to the ratchet member 543. In an example, one region of the elastic member 544 may be connected to the wedge 541 or the body 545, and another region of the elastic member 544 may be connected to the ratchet member 543, so that the elastic member 544 may connect the wedge 541 or the body 545 to the ratchet member 543. Here, the elastic member 544 may apply an elastic force in a direction in which the ratchet member 543 comes into close contact with the reciprocating member 551. To this end, the elastic member 544 may be formed in the form of a leaf spring, and may be provided in various forms capable of providing a predetermined elastic force to the ratchet member 543, such as a coil spring, a dish spring, and the like.

Here, the ratchet 543*a* of the ratchet member 543 may be formed such that a first surface 543*a*1 (specifically, at the distal end 502 side) is formed to have a gentle slope with a predetermined angle, and a second surface 543*a*2 (specifically, at the proximal end 501 side) is formed to be vertical or near vertical.

In addition, in order to be engaged with the ratchet 543*a* of the ratchet member 543, the recess 551*b* of the reciprocating member 551 may also be formed such that a first surface 551*b*1 (specifically, at the distal end 502 side) is formed to have a gentle slope with a predetermined angle, and a second surface 551*b*2 (specifically, at the proximal end 501 side) is formed to be vertical or near vertical.

In a state in which the reciprocating member 551 and the ratchet member 543 are coupled to each other (or engaged or in close contact with each other), the inclined first surface 543*a*1 of the ratchet 543*a* and the inclined first surface 551*b*1 of the recess 551*b* may be formed to face each other (that is, in contact with each other). In addition, the vertically formed second surface 543*a*2 of the ratchet 543*a* and the vertically formed second surface 551*b*2 of the recess 551*b* may be disposed to face each other (i.e., in contact with each other).

With this configuration, in a state in which the ratchet 543*a* and the recess 551*b* are coupled to (or engaged with) each other, the ratchet 543*a* and the recess 551*b* may be allowed to move only in one direction, acting as a kind of ratchet.

In an example, when it is assumed that the reciprocating member 551 is in a fixed state, the operation member 540 is movable in a direction in which the second surface 543*a*2 and the second surface 551*b*2, which are vertically formed, are away from each other, but when the second surface 543*a*2 and the second surface 551*b*2 are in contact with each other, the operation member 540 is not movable in a direction in which the second surface 543*a*2 and the second surface 551*b*2 are closer to each other.

In other words, when the reciprocating member 551 is moved toward the distal end 502 in a state in which the reciprocating member 551 and the ratchet member 543 are coupled to each other (or engaged or in close contact with each other), the ratchet member 543 is moved together toward the distal end 502 by the reciprocating member 551. That is, the vertically formed second surface 551*b*2 of the reciprocating member 551 pushes the vertically formed second surface 543*a*2 of the operation member 540 such that the ratchet member 543 is moved together toward the distal end 502 by the reciprocating member 551.

In contrast, when the reciprocating member 551 is moved toward the proximal end 501 in a state in which the reciprocating member 551 and the ratchet member 543 are coupled to each other (or engaged or in close contact with each other), only the reciprocating member 551 is moved alone toward the proximal end 501 while the ratchet member 543 a fixed. That is, the inclined first surface 551*b*1 of the reciprocating member 551 is moved along the inclined first surface 543*a*1 of the operation member 540 in a state in which the operation member 540 is fixed, so that only the reciprocating member 551 is moved alone toward the proximal end 501.

Figure 34:
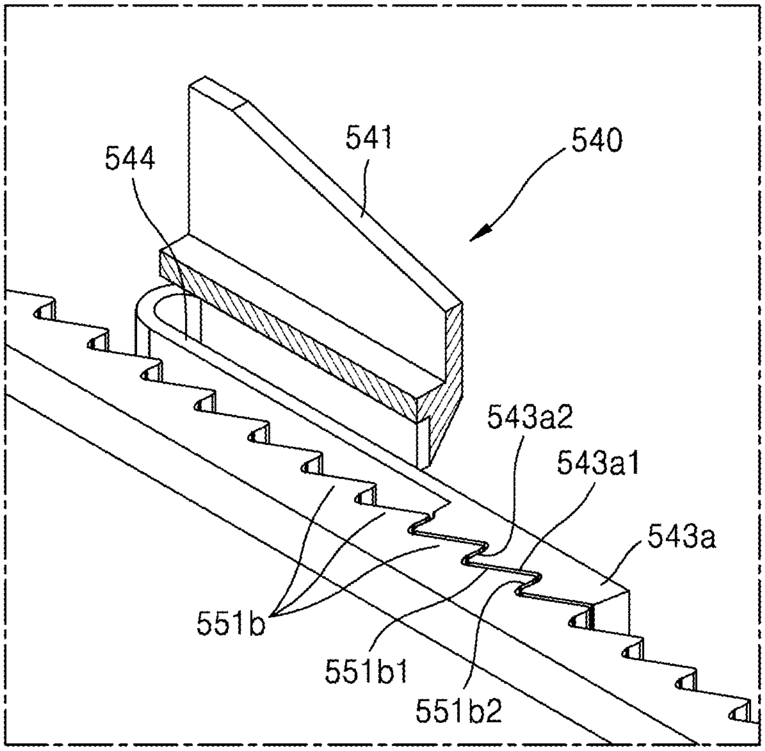
Figure 35:
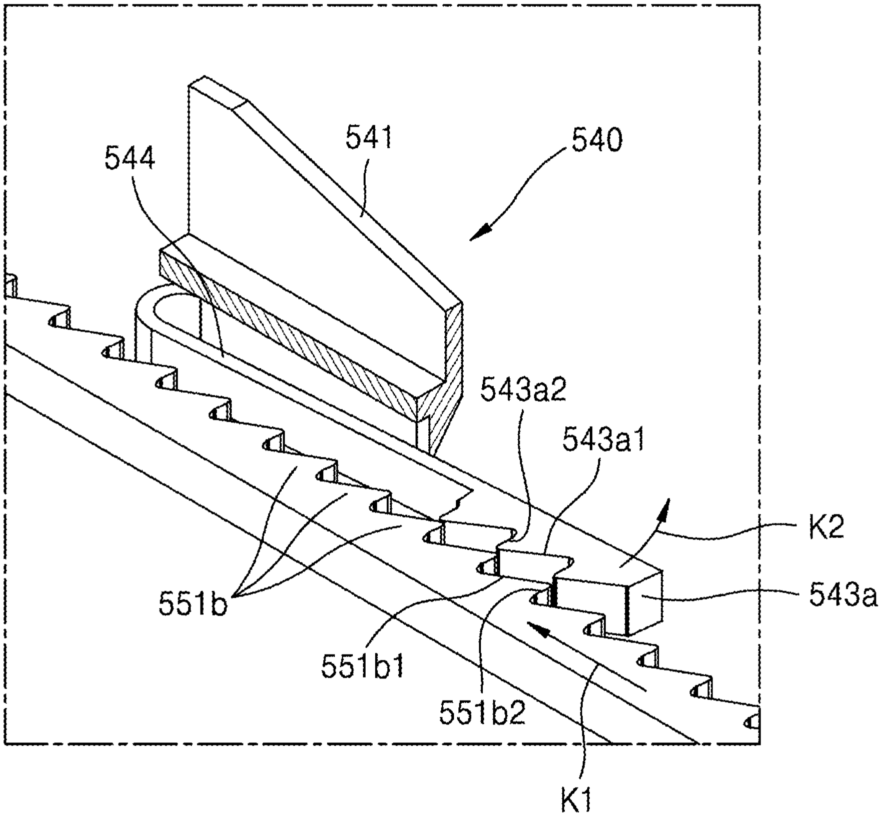
Figure 36:
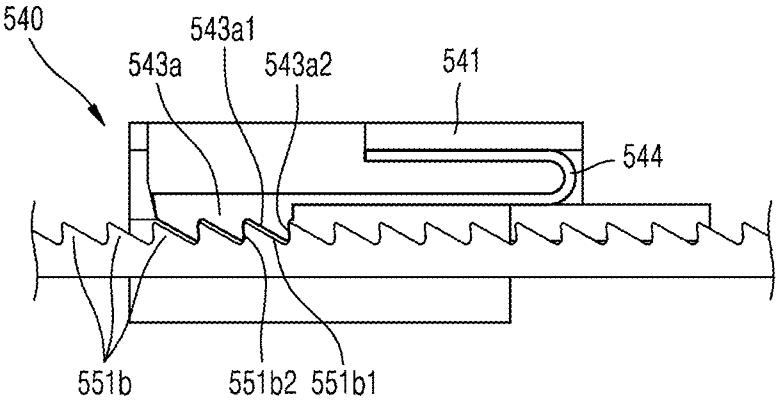
FIGS. 36 and 37 are plan views illustrating a ratchet drive operation of the end tool of FIG. 30.
Figure 37:
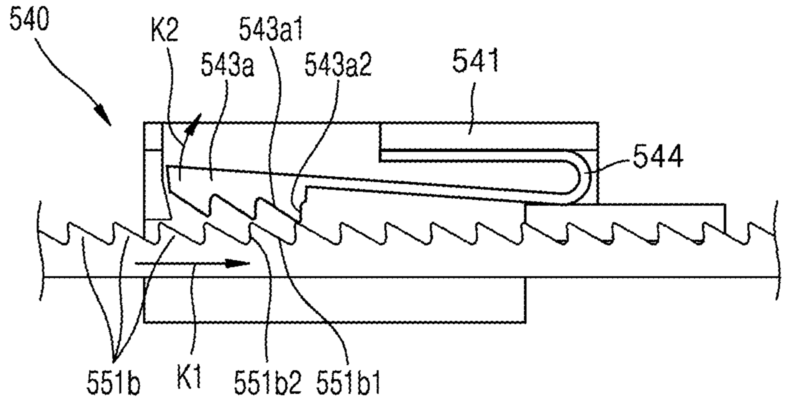

Referring to FIGS. 34 to 37, when the reciprocating member 551 is moved toward (in the direction of an arrow K1 of FIGS. 35 and 37) of the proximal end 501 in the state of FIGS. 34 and 36, as the inclined first surface 551*b*1 of the reciprocating member 551 is moved along the inclined first surface 543*a*1 of the operation member 540, the ratchet member 543 is pushed as a whole in the direction of an arrow K2 of FIG. 35. In addition, at this time, the elastic member 544 is elastically deformed to a certain extent.

In this state, when the reciprocating member 551 is further moved toward the proximal end 501, and the inclined first surface 551*b*1 of the reciprocating member 551 is moved beyond an end of the inclined first surface 543*a*1 of the operation member 540, the recess 551*b* of the reciprocating member 551 meets the next ratchet 543*a* of the ratchet member 543. In this case, since the elastic member 544 applies an elastic force in a direction in which the ratchet member 543 comes into close contact with the reciprocating member 551, front surfaces of the reciprocating member 551 and the ratchet member 543 are brought into close contact with each other again.

As a result, the cartridge 500 is accommodated in the cartridge accommodation part 101*a* of the first jaw 101, and in this case, the reciprocating member 551 of the cartridge 500 is coupled to the staple link assembly 170 of the end tool 100. Accordingly, the rotational motion of the staple pulley 161 of the end tool 100 is converted into a linear motion of the reciprocating member 551 through the staple link assembly 170.

In this case, when the coupling part 551*a* of the reciprocating member 551 is connected to the staple pulley 161 through the staple link assembly 170, and the staple pulley 161 is rotated alternately in the clockwise/counterclockwise directions, the reciprocating member 551 may be repeatedly moved forward and backward. In addition, when the reciprocating member 551 is moved forward, the operation member 540 may be moved forward together with the reciprocating member 551, and when the reciprocating member 551 is moved backward, only the reciprocating member 551 may be moved backward and the operation member 540 may remain stationary in place. As the operation member 540 is moved forward while repeating this process, the staple 530 may be stapled by the wedge 541 while the blade 542 cuts stapled tissue.

This will be described in more detail as follows.

(Stapling and Cutting Motions)

Referring to FIG. 38, a method of driving the surgical instrument according to an embodiment of the present disclosure is described as follows.

First, when the staple pulley 161 is rotated in one of the clockwise direction and the counterclockwise direction, the reciprocating assembly 550 of the staple link assembly 170 connected to the staple pulley 161 and the cartridge 500 connected to the staple link assembly 170 are moved toward the distal end 502 of the cartridge 500.

In addition, when the reciprocating assembly 550 is moved toward the distal end 502 of the cartridge 500, the operation member 540 in contact with the reciprocating assembly 550 is moved toward the distal end 502 of the cartridge 500 together with the reciprocating assembly 550.

In addition, as the operation member 540 is moved toward the distal end 502 of the cartridge 500, the blade 542 of the operation member 540 is moved toward the distal end 502 of the cartridge 500 while the operation member 540 ejects the staples 530 out of the cartridge 500.

Meanwhile, when the staple pulley 161 is rotated in the other one of the clockwise direction and the counterclockwise direction, the staple link assembly 170 connected to the staple pulley 161 and the reciprocating assembly 550 of the cartridge 500 connected to the staple link assembly 170 are moved toward the proximal end 501 of the cartridge 500, and in this case, the operation member 540 is stationary.

In addition, as the above operations are repeatedly performed, a stapling motion by the wedge 541 and a cutting motion by the blade 542 are simultaneously performed.

This will be described in more detail as follows.

First, in the state shown in FIG. 38A, when the staple pulley 161 is rotated in the direction of an arrow A1 (i.e., in the clockwise direction) as shown in FIG. 38B, the staple link assembly 170 connected to the staple pulley 161 and the reciprocating member 551 coupled to the staple link assembly 170 are moved in the direction of an arrow B1 (i.e., toward the distal end). In this state, since the reciprocating member 551 and the operation member 540 are in close contact with each other by the elastic member (see 544 of FIG. 37), when the reciprocating member 551 is moved in the direction of the arrow B1, the operation member 540 is also moved in the direction of the arrow B1 together with the reciprocating member 551.

Next, as shown in FIG. 38C, when the staple pulley 161 is further rotated in the direction of arrow A2, the staple link assembly 170 connected to the staple pulley 161, the reciprocating member 551, and the operation member 540 are further moved in the direction of the arrow B2.

In this state, when the staple pulley 161 stops rotating, as shown in FIG. 38D, the staple link assembly 170, the reciprocating member 551, and the operation member 540 also stop moving.

In this state, as shown in FIG. 38E, when the staple pulley 161 begins to rotate in the direction of an arrow A3 (i.e., in the counterclockwise direction), the staple link assembly 170 connected to the staple pulley 161 and the reciprocating member 551 coupled to the staple link assembly 170 are moved in the direction of an arrow B3 (i.e., toward the proximal end). In this state, due to the coupling structure of the ratchet member 543 and the reciprocating member 551, even when the reciprocating member 551 is moved in the direction of the arrow B3, only the ratchet member 543 is repeatedly spaced apart from and in contact with the reciprocating member 551 to a certain extent as the elastic member 544 is repeatedly elastically deformed and restored in a state in which the overall position of the operation member 540 remains unchanged. That is, (referring to FIGS. 35 and 37), when the reciprocating member 551 is moved in the direction of the arrow B3, the operation member 540 remains stationary in place when viewed in the X-axis direction.

As shown in FIG. 38F, when the staple pulley 161 is further rotated in the direction of an arrow A4, only the staple link assembly 170 connected to the staple pulley 161 and the reciprocating member 551 are further moved in the direction of an arrow B4.

In this state, when the staple pulley 161 stops rotating, as shown in FIG. 38A, the staple link assembly 170, the reciprocating member 551, and the operation member 540 also stop moving.

When the staple pulley 161 is alternately rotated in the clockwise/counterclockwise directions while repeating the above process, the reciprocating member 551 is repeatedly moved forward and backward, and the operation member 540 repeats moving forward and stopping, and as a result, the operation member 540 is moved toward the distal end 502. In addition, as the operation member 540 is moved toward the distal end 502, a stapling motion by the wedge 541 and a cutting motion by the blade 542 are simultaneously performed.

Hereinafter, a stapling motion of the surgical instrument according to an embodiment of the present disclosure will be described.

FIG. 39 is a perspective view illustrating a stapling motion of the end tool of FIG. 30 for each section, and FIG. 40 is a perspective view illustrating an entire stapling motion of the end tool of FIG. 30.

Referring to FIGS. 39 and 40, in the state as shown in FIG. 39A, as the operation member 540 is moved in the direction of an arrow A1 of FIG. 39B, the wedge 541 of the operation member 540 pushes and raises the withdrawal member 535, and the withdrawal member 535 pushes and raises one side of a lower portion of the staple 530. In addition, due thereto, the staple 530 is ejected to the outside of the first jaw 101 and the cartridge 500.

In this state, when the operation member 540 is further moved in the direction of an arrow A2 of FIG. 39C, the ejected staple 530 is continuously pushed and raised by the operation member 540 while in contact with the anvil 102*a* of the second jaw 102, so that stapling is performed while both end portions of the staple 530 are bent.

As such motions are continuously performed, stapling is sequentially performed from the staple 530 on the proximal end 501 side to the staple 530 on the distal end 502 side among the plurality of staples 530, as illustrated in FIG. 40.

(Manipulation Part)

Figure 41:
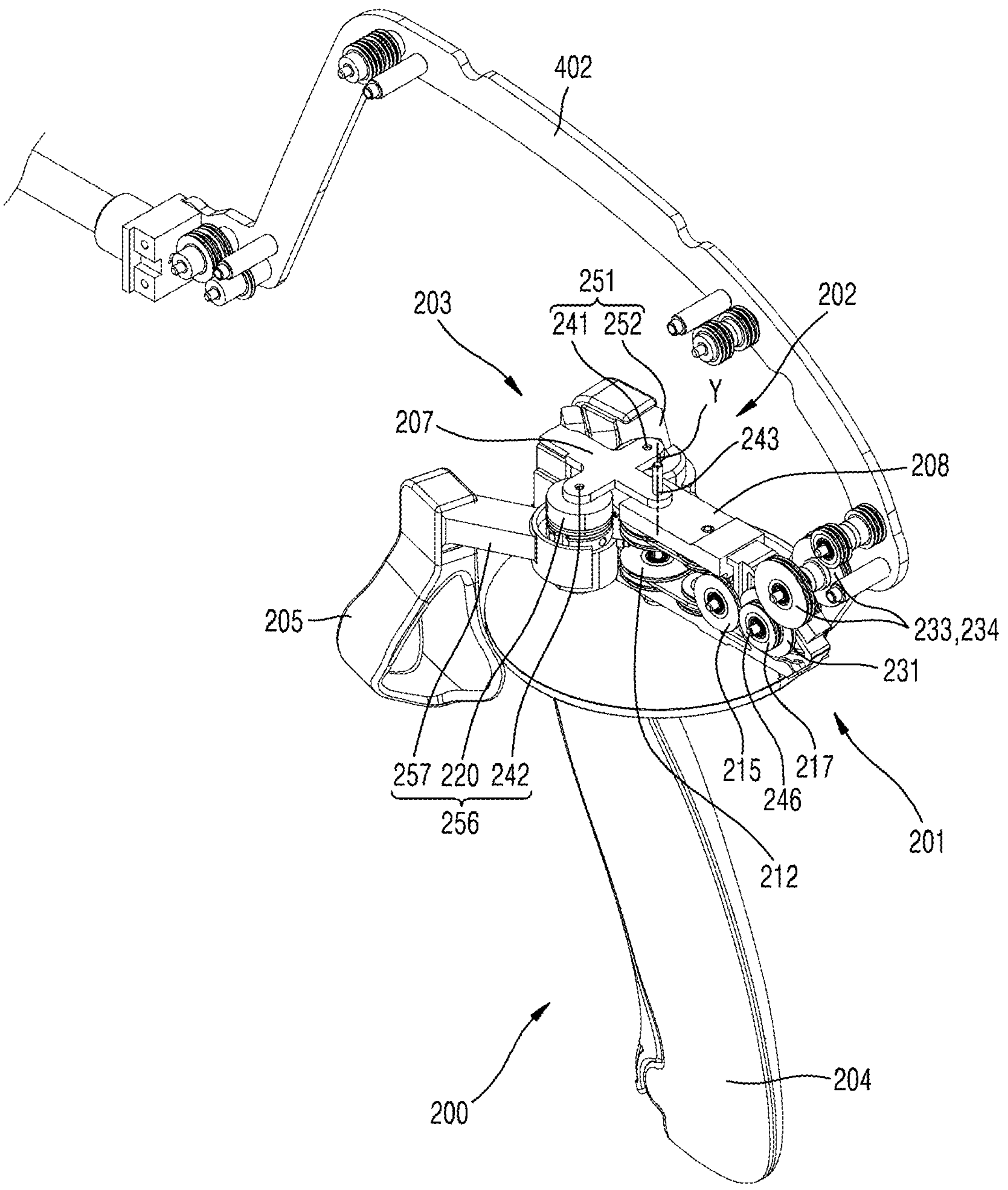
FIGS. 41 and 42 are perspective views illustrating a manipulation part of the surgical instrument of FIG. 2.
Figure 42:
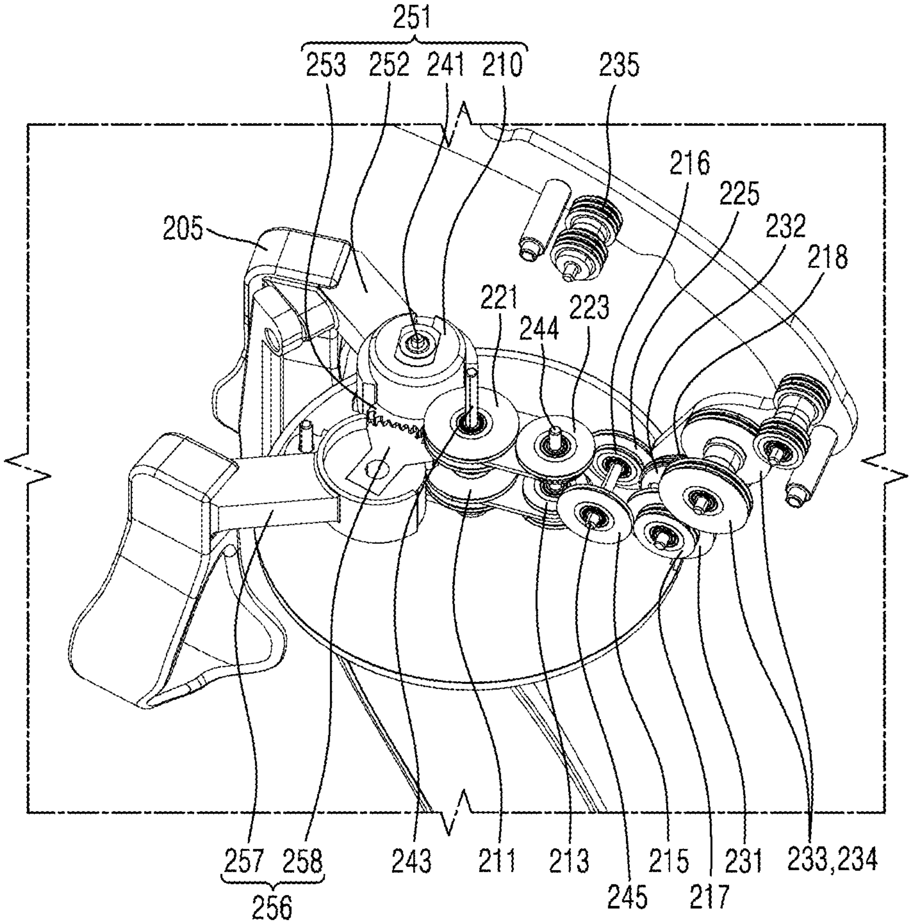

FIGS. 41 and 42 are perspective views illustrating the manipulation part of the surgical instrument of FIG. 2. FIG. 43 is a view schematically illustrating only a configuration of pulleys and wires constituting joints of the surgical instrument illustrated in FIG. 2.

Referring to FIGS. 2 to 42, the manipulation part 200 of the surgical instrument 10 according to the first embodiment of the present disclosure includes a first handle 204 that a user can grip, the actuation manipulation part 203 configured to control an actuation motion of the end tool 100, the yaw manipulation part 202 configured to control a yaw motion of the end tool 100, and the pitch manipulation part 201 configured to control a pitch motion of the end tool 100. Here, it is understood that only the components related to the pitch/yaw/actuation motions of the surgical instrument 10 are illustrated in FIGS. 41 and 42.

In addition, the manipulation part 200 of the surgical instrument 10 may further include a staple manipulation part 260 configured to control the motion of the staple pulley assembly 160 of the end tool 100 to perform stapling and cutting motions.

The manipulation part 200 may include the pulley 210, a pulley 211, a pulley 212, a pulley 213, a pulley 214, a pulley 215, a pulley 216, a pulley 217, and a pulley 218 that are related to a rotational motion of the first jaw 101. In addition, the manipulation part 200 may include the pulley 220, a pulley 221, a pulley 222, a pulley 223, a pulley 224, a pulley 225, a pulley 226, a pulley 227, and a pulley 228 that are related to a rotational motion of the second jaw 102. In addition, the manipulation part 200 may include the pulley 231, the pulley 232, a pulley 233, and a pulley 234 that are related to a pitch motion thereof. In addition, the manipulation part 200 may include a pulley 235, which is a relay pulley disposed at some places along the bent part 402 of the connection part 400.

Here, the pulleys facing each other are illustrated in the drawings as being formed parallel to each other, but the concept of the present disclosure is not limited thereto, and each of the pulleys may be variously formed with a position and a size suitable for the configuration of the manipulation part.

Further, the manipulation part 200 of the first embodiment of the present disclosure may include a rotation shaft 241, a rotation shaft 242, the rotation shaft 243, a rotation shaft 244, a rotation shaft 245, and the rotation shaft 246. Here, the rotation shaft 241 may function as a manipulation part first jaw actuation rotation shaft, and the rotation shaft 242 may function as a manipulation part second jaw actuation rotation shaft. In addition, the rotation shaft 243 may function as a manipulation part yaw main rotation shaft, and the rotation shaft 244 may function as a manipulation part yaw sub-rotation shaft. In addition, the rotation shaft 245 may function as a manipulation part pitch sub-rotation shaft, and the rotation shaft 246 may function as a manipulation part pitch main rotation shaft.

The rotation shaft 241/rotation shaft 242, the rotation shaft 243, the rotation shaft 244, the rotation shaft 245, and the rotation shaft 246 may be sequentially disposed from a distal end 205 of the manipulation part 200 toward a proximal end 206.

Each of the rotation shafts 241, 242, 243, 244, 245, and 246 may be fitted into one or more pulleys, which will be described in detail later.

The pulley 210 functions as a manipulation part first jaw actuation pulley, the pulley 220 functions as a manipulation part second jaw actuation pulley, and these components may also be collectively referred to as a manipulation part actuation pulley.

The pulley 211 and the pulley 212 function as manipulation part first jaw yaw main pulleys, the pulley 221 and the pulley 222 function as manipulation part second jaw yaw main pulleys, and these components may also be collectively referred to as a manipulation part yaw main pulley.

The pulley 213 and the pulley 214 function as manipulation part first jaw yaw sub-pulleys, the pulley 223 and the pulley 224 function as manipulation part second jaw yaw sub-pulleys, and these components may also be collectively referred to as a manipulation part yaw sub-pulley.

The pulley 215 and the pulley 216 function as manipulation part first jaw pitch sub-pulleys, the pulley 225 and the pulley 226 function as manipulation part second jaw pitch sub-pulleys, and these components may also be collectively referred to as a manipulation part pitch sub-pulley.

The pulley 217 and the pulley 218 function as manipulation part first jaw pitch main pulleys, and the pulley 227 and the pulley 228 function as manipulation part second jaw pitch main pulleys, and these components may also be collectively referred to as the manipulation part pitch main pulley.

The pulley 231 and the pulley 232 function as manipulation part pitch wire main pulleys, and the pulley 233 and the pulley 234 function as manipulation part pitch wire sub-pulleys.

The above components are categorized from the perspective of the manipulation part for each motion (pitch/yaw/actuation) as follows.

The pitch manipulation part 201 configured to control a pitch motion of the end tool 100 may include the pulley 215, the pulley 216, the pulley 217, the pulley 218, the pulley 225, the pulley 226, the pulley 227, the pulley 228, the pulley 231, the pulley 232, and the pulley 234. In addition, the pitch manipulation part 201 may include the rotation shaft 245 and the rotation shaft 246. In addition, the pitch manipulation part 201 may further include a pitch frame 208.

The yaw manipulation part 202 configured to control a yaw motion of the end tool 100 may include the pulley 211, the pulley 212, the pulley 213, the pulley 214, the pulley 221, the pulley 222, the pulley 223, and the pulley 224. In addition, the yaw manipulation part 202 may include the rotation shaft 243 and the rotation shaft 244. In addition, the yaw manipulation part 202 may further include a yaw frame 207.

The actuation manipulation part 203 configured to control an actuation motion of the end tool 100 may include the pulley 210, the pulley 220, the rotation shaft 241, and the rotation shaft 242. In addition, the actuation manipulation part 203 may further include the first actuation manipulation part 251 and the second actuation manipulation part 256.

Hereinafter, each component of the manipulation part 200 will be described in more detail.

The first handle 204 may be formed to be gripped by a user with the hand, and in particular, may be formed to be grasped by the user by wrapping the first handle 204 with his/her palm. In addition, the actuation manipulation part 203 and the yaw manipulation part 202 are formed on the first handle 204, and the pitch manipulation part 201 is formed on one side of the yaw manipulation part 202. In addition, the other end portion of the pitch manipulation part 201 is connected to the bent part 402 of the connection part 400.

The actuation manipulation part 203 includes the first actuation manipulation part 251 and the second actuation manipulation part 256. The first actuation manipulation part 251 includes the rotation shaft 241, the pulley 210, the first actuation extension part 252, and a first actuation gear 253. The second actuation manipulation part 256 includes the rotation shaft 242, the pulley 220, the second actuation extension part 257, and a second actuation gear 258. Here, end portions of the first actuation extension part 252 and the second actuation extension part 257 are formed in the shape of a hand ring, which may act as a second handle.

Here, the rotation shaft 241 and the rotation shaft 242, which are actuation rotation axes, may be formed to form a predetermined angle with an XY plane on which the connection part 400 is formed. For example, the rotation shaft 241 and the rotation shaft 242 may be formed in a direction parallel to the Z-axis, and in this state, when the pitch manipulation part 201 or the yaw manipulation part 202 is rotated, the coordinate system of the actuation manipulation part 203 may change relatively. Of course, the concept of the present disclosure is not limited thereto, and the rotation shaft 241 and the rotation shaft 242 may be formed in various directions so as to be suitable for a structure of the hand of the user gripping the actuation manipulation part 203 according to an ergonomic design.

Meanwhile, the pulley 210, the first actuation extension part 252, and the first actuation gear 253 are fixedly coupled to each other to be rotatable together around the rotation shaft 241. Here, the pulley 210 may be configured to be a single pulley or two pulleys fixedly coupled to each other.

Similarly, the pulley 220, the second actuation extension part 257, and the second actuation gear 258 are fixedly coupled to each other to be rotatable together around the rotation shaft 242. Here, the pulley 220 may be configured to be a single pulley or two pulleys fixedly coupled to each other.

Here, the first actuation gear 253 and the second actuation gear 258 are formed to be engaged with each other such that, when any one gear is rotated in one direction, the other gear is rotated together in a direction opposite to the one direction.

The yaw manipulation part 202 may include the rotation shaft 243, the pulleys 211 and 212, which are manipulation part first jaw yaw main pulleys, the pulleys 221 and 222, which are manipulation part second jaw yaw main pulleys, and the yaw frame 207. In addition, the yaw manipulation part 202 may further include the pulleys 213 and 214, which are manipulation part first jaw yaw sub-pulleys formed on one side of the pulleys 211 and 212, and the pulleys 223 and 224 that are manipulation part second jaw yaw sub-pulleys formed on one side of the pulleys 221 and 222. Here, the pulleys 213 and 214 and the pulleys 223 and 224 may be coupled to the pitch frame 208 to be described later.

Here, it is illustrated in the drawings that the yaw manipulation part 202 includes the pulleys 211 and 212 and the pulleys 221 and 222, wherein the pulleys 211 and 212 and the pulleys 221 and 222 are each provided with two pulleys formed to face each other and independently rotatable, but the concept of the present disclosure is not limited thereto. That is, one or more pulleys having the same diameter or different diameters may be provided according to the configuration of the yaw manipulation part 202.

In detail, the rotation shaft 243, which is a manipulation part yaw main rotation shaft, is formed on one side of the actuation manipulation part 203 on the first handle 204. At this time, the first handle 204 is formed to be rotatable around the rotation shaft 243.

Here, the rotation shaft 243 may be formed to form a predetermined angle with the XY plane on which the connection part 400 is formed. For example, the rotation shaft 243 may be formed in a direction parallel to the Z-axis, and in this state, when the pitch manipulation part 201 is rotated, the coordinate system of the rotation shaft 243 may change relatively as described above. Of course, the concept of the present disclosure is not limited thereto, and the rotation shaft 243 may be formed in various directions so as to be suitable for a structure of the hand of the user gripping the manipulation part 200 according to an ergonomic design.

Meanwhile, the pulleys 211 and 212 and the pulleys 221 and 222 are coupled to the rotation shaft 243 so as to be rotatable around the rotation shaft 243. In addition, the wire 301 or the wire 305, which is a first jaw wire, is wound around the pulleys 211 and 212, and the wire 302 or the wire 306, which is a second jaw wire, may be wound around the pulleys 221 and 222. In this case, the pulleys 211 and 212 and the pulleys 221 and 222 may each be configured as two pulleys formed to face each other and independently rotatable. Accordingly, a wire being wound and a wire being released may be wound around respective separate pulleys so that the wires may perform motions without interference with each other.

The yaw frame 207 rigidly connects the first handle 204, the rotation shaft 241, the rotation shaft 242, and the rotation shaft 243, so that the first handle 204, the yaw manipulation part 202, and the actuation manipulation part 203 are integrally yaw-rotated around the rotation shaft 243.

The pitch manipulation part 201 may include the rotation shaft 246, the pulley 217 and the pulley 218, which are manipulation part first jaw pitch main pulleys, the pulleys 227 and 228, which are manipulation part second jaw pitch main pulleys, and the pitch frame 208. In addition, the pitch manipulation part 201 may further include the rotation shaft 245, the pulleys 215 and 216, which are manipulation part first jaw pitch sub-pulleys formed on one side of the pulley 217 and the pulley 218, and the pulleys 225 and 226, which are manipulation part second jaw pitch sub-pulleys formed on one side of the pulley 227 and the pulley 228. The pitch manipulation part 201 may be connected to the bent part 402 of the connection part 400 through the rotation shaft 246.

In detail, the pitch frame 208 is a base frame of the pitch manipulation part 201, and the rotation shaft 243 is rotatably coupled to one end portion thereof. That is, the yaw frame 207 is formed to be rotatable around the rotation shaft 243 with respect to the pitch frame 208.

As described above, since the yaw frame 207 connects the first handle 204, the rotation shaft 243, the rotation shaft 241, and the rotation shaft 242, and the yaw frame 207 is also axially coupled to the pitch frame 208, when the pitch frame 208 is pitch-rotated around the rotation shaft 246, the yaw frame 207 connected to the pitch frame 208, the first handle 204, the rotation shaft 241, the rotation shaft 242, and the rotation shaft 243 are pitch-rotated together. That is, when the pitch manipulation part 201 is rotated around the rotation shaft 246, the actuation manipulation part 203 and the yaw manipulation part 202 are rotated together with the pitch manipulation part 201. In other words, when a user pitch-rotates the first handle 204 around the rotation shaft 246, the actuation manipulation part 203, the yaw manipulation part 202, and the pitch manipulation part 201 are moved together.

The pulleys 217 and 218 and the pulleys 227 and 228 are coupled to the rotation shaft 246 so as to be rotatable around the rotation shaft 246 of the pitch frame 208.

Here, the pulley 217 and the pulley 218 may be formed to face each other so as to be independently rotatable. Accordingly, a wire being wound and a wire being released may be wound around respective separate pulleys so that the wires may perform motions without interference with each other. Similarly, the pulley 227 and the pulley 228 may also be formed to face each other so as to be independently rotatable. Accordingly, a wire being wound and a wire being released may be wound around respective separate pulleys so that the wires may perform motions without interference with each other.

Next, a motion of each of the wires 303 and 304, which are pitch wires, is described as follows.

The pulley 131, which is an end tool pitch pulley, is fixedly coupled to the end tool hub 180 in the end tool 100, and the pulley 231 and the pulley 232, which are manipulation part pitch pulleys, are fixedly coupled to the pitch frame 208 in the manipulation part 200. In addition, these pulleys are connected to each other by the wires 303 and 304, which are pitch wires, so that a pitch motion of the end tool 100 may be performed more easily according to the pitch manipulation of the manipulation part 200. Here, the wire 303 is fixedly coupled to the pitch frame 208 via the pulley 231 and the pulley 233, and the wire 304 is fixedly coupled to the pitch frame 208 via the pulley 232 and the pulley 234. That is, the pitch frame 208 and the pulleys 231 and 232 are rotated together around the rotation shaft 246 by the pitch rotation of the manipulation part 200, and as a result, the wires 303 and 304 are also moved, and thus, a driving force of additional pitch rotation may be transmitted separately from the pitch motion of the end tool by the wire 301, the wire 302, the wire 305, and the wire 306, which are jaw wires.

A connection relationship of each of the first handle 204, the pitch manipulation part 201, the yaw manipulation part 202, and the actuation manipulation part 203 is summarized as follows. The rotation shafts 241 and 242, the rotation shaft 243, the rotation shaft 244, the rotation shaft 245, and the rotation shaft 246 may be formed on the first handle 204. In this case, since the rotation shafts 241 and 242 are directly formed on the first handle 204, the first handle 204 and the actuation manipulation part 203 may be directly connected to each other. Meanwhile, since the rotation shaft 243 is directly formed on the first handle 204, the first handle 204 and the yaw manipulation part 202 may be directly connected to each other. On the other hand, since the pitch manipulation part 201 is formed on one side of the yaw manipulation part 202 so as to be connected to the yaw manipulation part 202, the pitch manipulation part 201 is not directly connected to the first handle 204, and the pitch manipulation part 201 and the first handle 204 may be formed to be indirectly connected to each other via the yaw manipulation part 202.

Continuing to refer to the drawings, in the surgical instrument 10 according to the first embodiment of the present disclosure, the pitch manipulation part 201 and the end tool 100 may be formed on the same or parallel axis (X-axis). That is, the rotation shaft 246 of the pitch manipulation part 201 is formed at one end portion of the bent part 402 of the connection part 400, and the end tool 100 is formed at the other end portion of the connection part 400.

In addition, one or more relay pulleys 235 configured to change or guide paths of the wires may be disposed at some places along the connection part 400, particularly in the bent part 402. As at least some of the wires are wound around the relay pulleys 235 to guide the paths of the wires, these wires may be disposed along a bent shape of the bent part 402.

Here, in the drawings, it is illustrated that the connection part 400 is formed to be curved with a predetermined curvature by having the bent part 402, but the concept of the present disclosure is not limited thereto, and the connection part 400 may be formed linearly or to be bent one or more times as necessary, and even in this case, it may be said that the pitch manipulation part 201 and the end tool 100 are formed on substantially the same axis or parallel axes. In addition, although FIG. 3 illustrates that each of the pitch manipulation part 201 and the end tool 100 is formed on an axis parallel to the X-axis, the concept of the present disclosure is not limited thereto, and the pitch manipulation part 201 and the end tool 100 may be formed on different axes.

The staple manipulation part 260 is connected to the staple pulley 161 of the end tool 100 by the wires 307 and 308, which are staple wires, and serves to alternately rotate the staple pulley 161 in the clockwise or counterclockwise direction.

To this end, although not shown in the drawings, the staple manipulation part 260 may include a motor (not shown). That is, the motor (not shown) is driven while the user presses the staple manipulation part 260 formed in the form of a button to alternately rotate the manipulation part staple pulley (see 269 of FIG. 47) in the clockwise or counterclockwise direction. In addition, due thereto, the staple pulley 161 of the end tool 100 may be alternately rotated in the clockwise or counterclockwise direction.

(Actuation, Yaw, and Pitch Motions)

Actuation, yaw, and pitch motions in the present embodiment will be described as follows.

First, the actuation motion will be described below.

In a state in which a user inserts his/her index finger in the hand ring formed on the first actuation extension part 252 and his/her thumb in the hand ring formed on the second actuation extension part 257, when the user rotates the actuation rotation parts 252 and 257 using one or both of his/her index finger and thumb, the pulley 210 and the first actuation gear 253 fixedly coupled to the first actuation extension part 252 are rotated around the rotation shaft 241, and the pulley 220 and the second actuation gear 258 fixedly coupled to the second actuation extension part 257 are rotated around the rotation shaft 242. At this time, the pulley 210 and the pulley 220 are rotated in opposite directions, and thus the wires 301 and 305 fixedly coupled to the pulley 210 at one end portion thereof and the wires 302 and 306 fixedly coupled to the pulley 220 at one end portion thereof are also moved in opposite directions. In addition, a rotating force is transmitted to the end tool 100 through the power transmission part 300, and two jaws 103 of the end tool 100 perform an actuation motion.

Here, as described above, the actuation motion refers to a motion in which the two jaws 101 and 102 are splayed or closed while being rotated in opposite directions. That is, when the actuation rotation parts 252 and 257 of the actuation manipulation part 203 are rotated in directions close to each other, the first jaw 101 is rotated in the counterclockwise direction, and the second jaw 102 is rotated in the clockwise direction, thereby closing the end tool 100. That is, when the actuation rotation parts 252 and 257 of the actuation manipulation part 203 are rotated in directions away from each other, the first jaw 121 is rotated in the counterclockwise direction, and the second jaw 122 is rotated in the clockwise direction, thereby opening the end tool 100.

In the present embodiment, for the actuation manipulation described above, the first actuation extension part 252 and the second actuation extension part 257 are provided to configure the second handle and manipulated by gripping the second handle with two fingers. However, for the actuation manipulation in which the two jaws of the end tool 100 are opened or closed, the actuation manipulation part 203 may be configured in a manner different from the above-described manner, such as configuring the two actuation pulleys (the pulley 210 and the pulley 220) to act in opposition to each other with an actuation rotation part.

Next, the yaw motion will be described below.

When a user rotates the first handle 204 around the rotation shaft 243 while holding the first handle 204, the actuation manipulation part 203 and the yaw manipulation part 202 are yaw-rotated around the rotation shaft 243. That is, when the pulley 210 of the first actuation manipulation part 251 to which the wires 301 and 305 are fixedly coupled is rotated around the rotation shaft 243, the wires 301 and 305 wound around the pulleys 211 and 212 are moved. Similarly, when the pulley 220 of the second actuation manipulation part 256, to which the wires 302 and 306 are fixedly coupled, is rotated around the rotation shaft 243, the wires 302 and 306 wound around the pulleys 221 and 222 are moved. At this time, the wires 301 and 305 connected to the first jaw 101 and the wires 302 and 306 connected to the second jaw 102 are wound around the pulleys 211 and 212 and the pulleys 221 and 222, so that the first jaw 101 and the second jaw 102 are rotated in the same direction during yaw rotation. In addition, a rotating force is transmitted to the end tool 100 through the power transmission part 300, and thus a yaw motion in which two jaws 103 of the end tool 100 are rotated in the same direction is performed.

At this time, since the yaw frame 207 connects the first handle 204, the rotation shaft 241, the rotation shaft 242, and the rotation shaft 243, the first handle 204, the yaw manipulation part 202, and the actuation manipulation part 203 are rotated together around the rotation shaft 243.

Next, the pitch motion will be described below.

When a user rotates the first handle 204 around the rotation shaft 246 while holding the first handle 204, the actuation manipulation part 203, the yaw manipulation part 202, and the pitch manipulation part 201 are pitch-rotated around the rotation shaft 246. That is, when the pulley 210 of the first actuation manipulation part 251 to which the wires 301 and 305 are fixedly coupled is rotated around the rotation shaft 246, the wires 301 and 305 wound around the pulley 217 and the pulley 218 are moved. Similarly, when the pulley 220 of the second actuation manipulation part 256, to which the wires 302 and 306 are fixedly coupled, is rotated around the rotation shaft 246, the wires 302 and 306 wound around the pulley 227 and the pulley 228 are moved. At this time, as described with reference to FIG. 5, in order to allow the first jaw 101 and the second jaw 102 to pitch-rotate, the wires 301 and 305, which are first jaw wires, are moved in the same direction and respectively wound around the pulley 217 and the pulley 218, which are manipulation part pitch main pulleys, and the wires 302 and 306, which are second jaw wires, are moved in the same direction and respectively wound around the pulley 227 and the pulley 228, which are manipulation part pitch main pulleys. In addition, a rotating force is transmitted to the end tool 100 through the power transmission part 300, and two jaws 103 of the end tool 100 perform a pitch motion.

At this time, since the pitch frame 208 is connected to the yaw frame 207, and the yaw frame 207 connects the first handle 204, the rotation shaft 241, the rotation shaft 242, and the rotation shaft 243, when the pitch frame 208 is rotated around the rotation shaft 246, the yaw frame 207, the first handle 204, the rotation shaft 241, the rotation shaft 242, and the rotation shaft 243 connected to the pitch frame 208 are rotated together. That is, when the pitch manipulation part 201 is rotated around the rotation shaft 246, the actuation manipulation part 203 and the yaw manipulation part 202 are rotated together with the pitch manipulation part 201.

In summary, in the surgical instrument 10 according to an embodiment of the present disclosure, the pulleys are formed on respective joint points (an actuation joint, a yaw joint, and a pitch joint), the wires (the first jaw wire or the second jaw wire) are wound around the pulleys, the rotational manipulations (actuation rotation, yaw rotation, and pitch rotation) of the manipulation part cause the movement of each wire, which in turn induces the desired motion of the end tool 100. Furthermore, the auxiliary pulley may be formed on one side of each of the pulleys, and the wire may not be wound several times around one pulley due to the auxiliary pulley.

FIG. 43 is a view schematically illustrating only a configuration of pulleys and wires constituting joints of the surgical instrument 10 according to an embodiment of the present disclosure illustrated in FIG. 2. In FIG. 43, the relay pulleys for changing paths of the wires and not related to the operation of joints are omitted.

Referring to FIG. 43, the manipulation part 200 may include the pulley 210, the pulley 211, the pulley 212, the pulley 213, the pulley 214, the pulley 215, the pulley 216, the pulley 217, and the pulley 218 that are related to a rotational motion of the first jaw 101.

In addition, the manipulation part 200 may include the pulley 220, the pulley 221, the pulley 222, the pulley 223, the pulley 224, the pulley 225, the pulley 226, the pulley 227, and the pulley 228 that are related to a rotational motion of the second jaw 122 (the arrangement and structure of each of the pulleys of the manipulation part 200 are the same in principle as the arrangement and structure of each of the pulleys of the end tool 100, and thus specific designations of some reference numerals are omitted in the drawings).

The pulleys 211 and 212 and the pulleys 221 and 222 may be formed to be rotatable independently of each other around the same shaft, that is the rotation shaft 243. In this case, the pulleys 211 and 212 and the pulleys 221 and 222 may each be formed as two pulleys formed to face each other and formed to be independently rotatable.

The pulleys 213 and 214 and the pulleys 223 and 224 may be formed to be rotatable independently of each other around the same shaft, that is the rotation shaft 244. Here, the pulleys 213 and 214 may be formed as two pulleys formed to face each other and formed to be independently rotatable, and in this case, the two pulleys may be formed to have different diameters. Similarly, the pulleys 223 and 224 may be formed as two pulleys formed to face each other and formed to be independently rotatable, and in this case, the two pulleys may be formed to have different diameters.

The pulleys 215 and 216 and the pulleys 225 and 226 may be formed to be rotatable independently of each other around the same shaft, that is the rotation shaft 245. In this case, the pulleys 215 and 216 may be formed to have different diameters. In addition, the pulleys 225 and 226 may be formed to have different diameters.

The pulleys 217 and 218 and the pulleys 227 and 228 may be formed to be rotatable independently of each other around the same shaft, that is the rotation shaft 246.

The wire 301 is wound around the pulley 210 after sequentially passing through the pulley 217, the pulley 215, the pulley 213, and the pulley 211 of the manipulation part 200, and then is coupled to the pulley 210 by the coupling member 324. Meanwhile, the wire 305 sequentially passes through the pulley 218, the pulley 216, the pulley 214, and the pulley 212 of the manipulation part 200 and is coupled to the pulley 210 by the coupling member 324. Thus, when the pulley 210 is rotated, the wires 301 and 305 are wound around or released from the pulley 210, and accordingly, the first jaw 101 is rotated.

The wire 306 is wound around the pulley 220 after sequentially passing through the pulley 227, the pulley 225, the pulley 223, and the pulley 221 of the manipulation part 200, and then is coupled to the pulley 220 by the coupling member 327. Meanwhile, the wire 302 sequentially passes through the pulley 228, the pulley 226, the pulley 224, and the pulley 222 of the manipulation part 200 and is coupled to the pulley 220 by the coupling member 327. Thus, when the pulley 220 is rotated, the wire 302 and the wire 306 are wound around or released from the pulley 220, and accordingly, the second jaw 102 is rotated.

(Conceptual Diagram of Pulleys and Wires)

Figure 44:
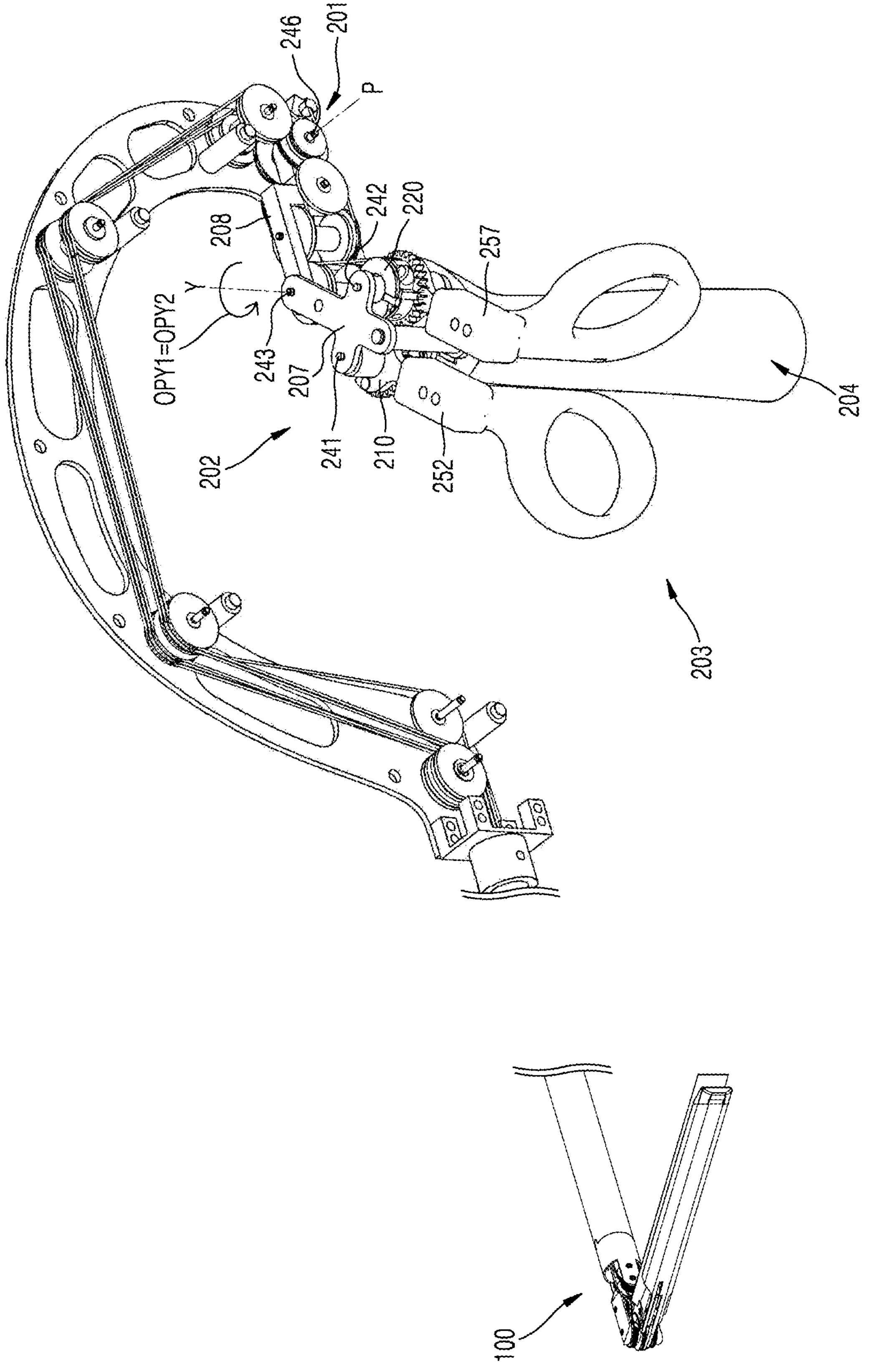
FIG. 44 is a perspective view illustrating a yaw motion of the surgical instrument of FIG. 2.
Figure 45:
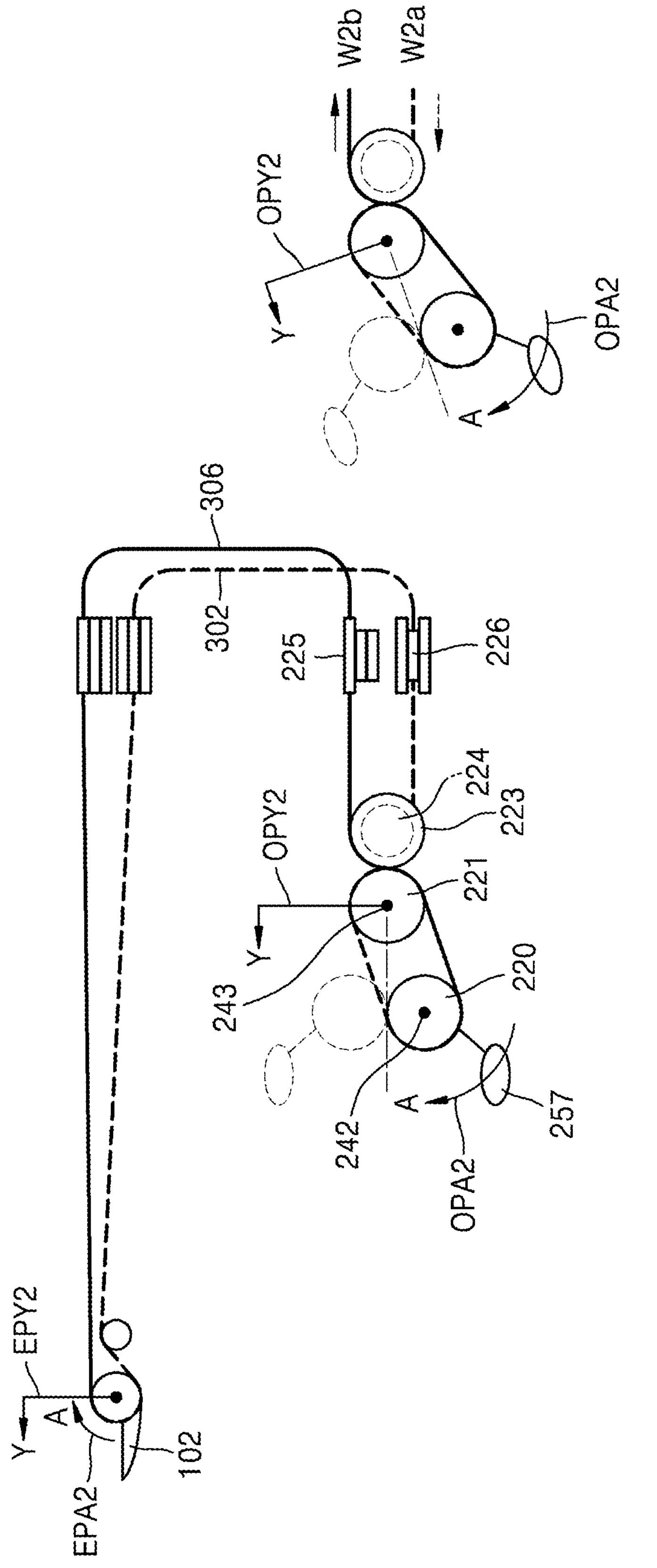
FIGS. 45 and 46 are diagrams illustrating a configuration of pulleys and wires, which are related to an actuation motion and a yaw motion of the surgical instrument illustrated in FIG. 2, in detail for each of the first jaw and the second jaw.
Figure 46:
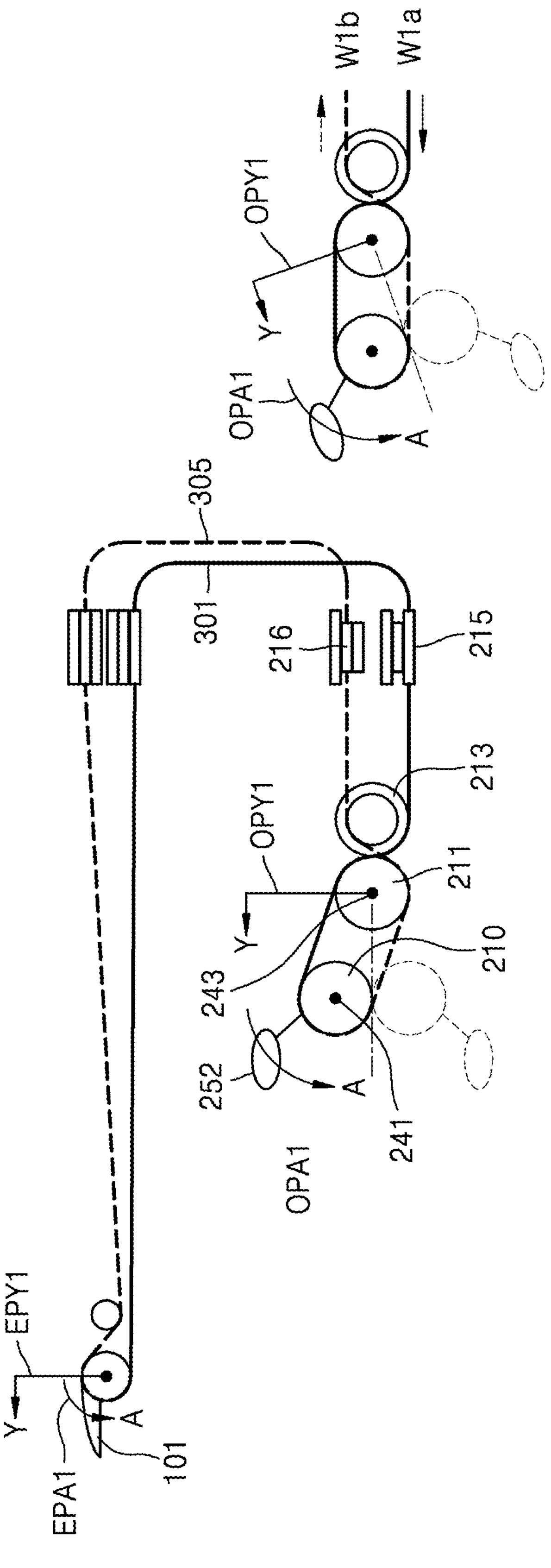

FIGS. 45 and 46 are diagrams illustrating a configuration of pulleys and wires, which are related to an actuation motion and a yaw motion of the surgical instrument 10 according to an embodiment of the present disclosure illustrated in FIG. 2, in detail for each of the first jaw and the second jaw. FIG. 45 is a diagram illustrating only pulleys and wires related to the second jaw, and FIG. 46 is a diagram illustrating only pulleys and wires related to the first jaw. In addition, FIG. 44 is a perspective view illustrating a yaw motion of the surgical instrument of FIG. 2. Here, in FIG. 44, components related to stapling and cutting motions are omitted.

First, a wire motion of the actuation motion will be described.

Referring to FIG. 46, when the first actuation extension part 252 is rotated around the rotation shaft 241 in the direction of an arrow OPA 1, the pulley 210 connected to the first actuation extension part 252 is rotated, and the wire 301 and the wire 305 wound around the pulley 210 are moved in directions W1*a* and W1*b*, respectively, and as a result, the first jaw 101 of the end tool 100 is rotated in the direction of an arrow EPA1.

Referring to FIG. 45, when the second actuation extension part 257 is rotated around the rotation shaft 242 in the direction of an arrow OPA 2, the pulley 220 connected to the second actuation extension part 257 is rotated, and thus both strands of the wires 302 and 306 wound around the pulley 220 are moved in directions W2*a* and W2*b*, respectively, and as a result, the second jaw 102 of the end tool 100 is rotated in the direction of an arrow EPA2. Accordingly, when a user manipulates the first actuation extension part 252 and the second actuation extension part 257 in directions close to each other, a motion of the first jaw 101 and the second jaw 102 of the end tool being close to each other is performed.

Next, a wire motion of the yaw motion will be described.

First, since the rotation shaft 243 is connected to the rotation shafts 241 and 242 by the yaw frame (see 207 of FIG. 30), the rotation shaft 243 and the rotation shafts 241 and 242 are integrally rotated together.

Referring to FIG. 46, when the first handle 204 is rotated around the rotation shaft 243 in the direction of an arrow OPY1, the pulley 210 and the pulleys 211 and 212 and the wires 301 and 305 wound therearound are rotated as a whole around the rotation shaft 243, and as a result, the wires 301 and 305 wound around the pulleys 211 and 212 are moved in the directions W1*a* and W1*b*, respectively, which in turn causes the first jaw 101 of the end tool 100 to rotate in the direction of an arrow EPY1.

Referring to FIG. 45, when the first handle 204 is rotated around the rotation shaft 243 in the direction of an arrow OPY2, the pulley 220 and the pulleys 221 and 222 and the wires 302 and 306 wound therearound are rotated as a whole around the rotation shaft 243, and as a result, the wires 302 and 306 wound around the pulleys 221 and 222 are respectively moved in a direction opposite to a direction W1*a* and a direction opposite to a direction W1*b*, which in turn causes the first jaw 101 of the end tool 100 to rotate in the direction of an arrow EPY2.

Figure 47:
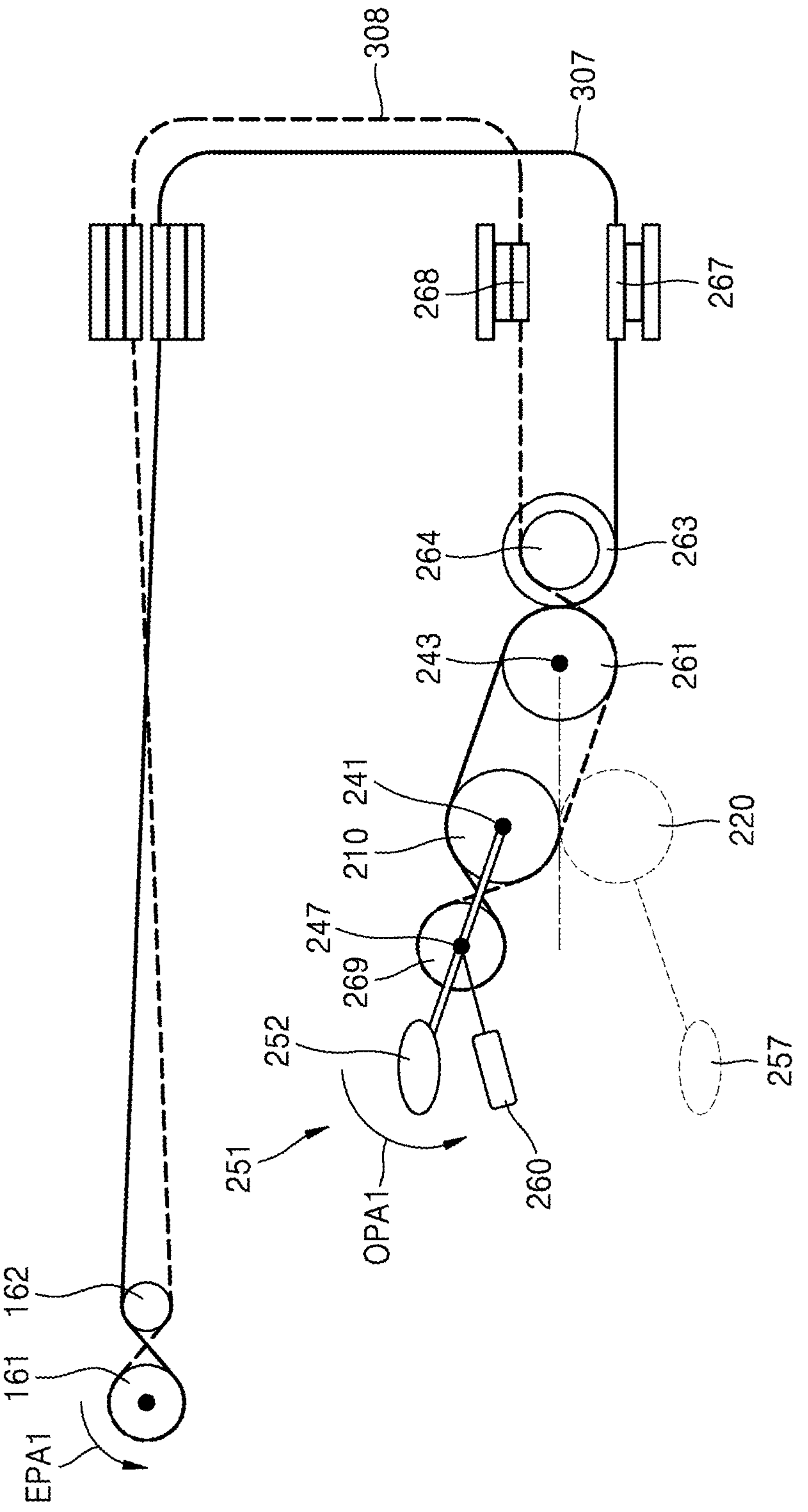
FIGS. 47 to 49 are diagrams illustrating a configuration of pulleys and wires, which are related to stapling and cutting motions of the surgical instrument illustrated in FIG. 2, in detail for each of the first jaw and the second jaw.
Figure 48:
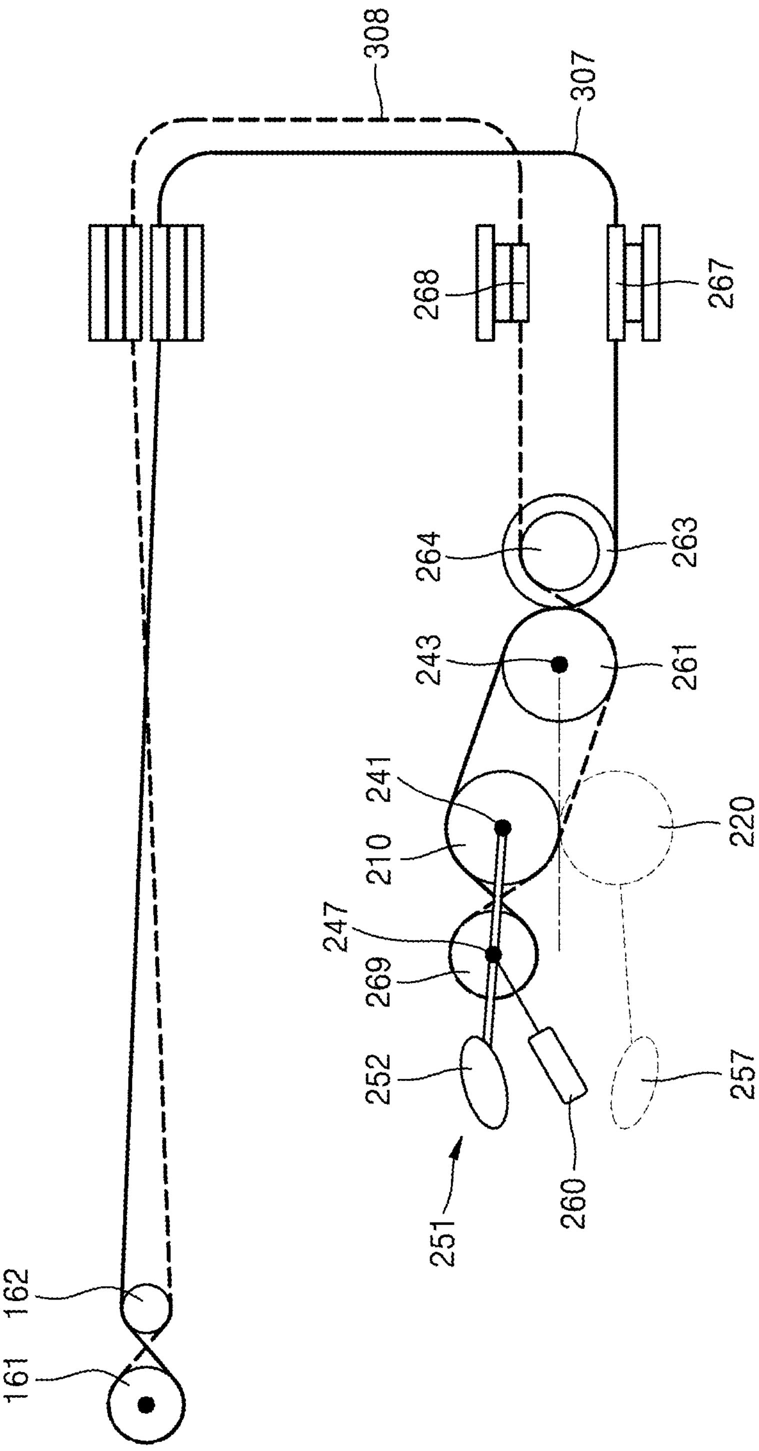
Figure 49:
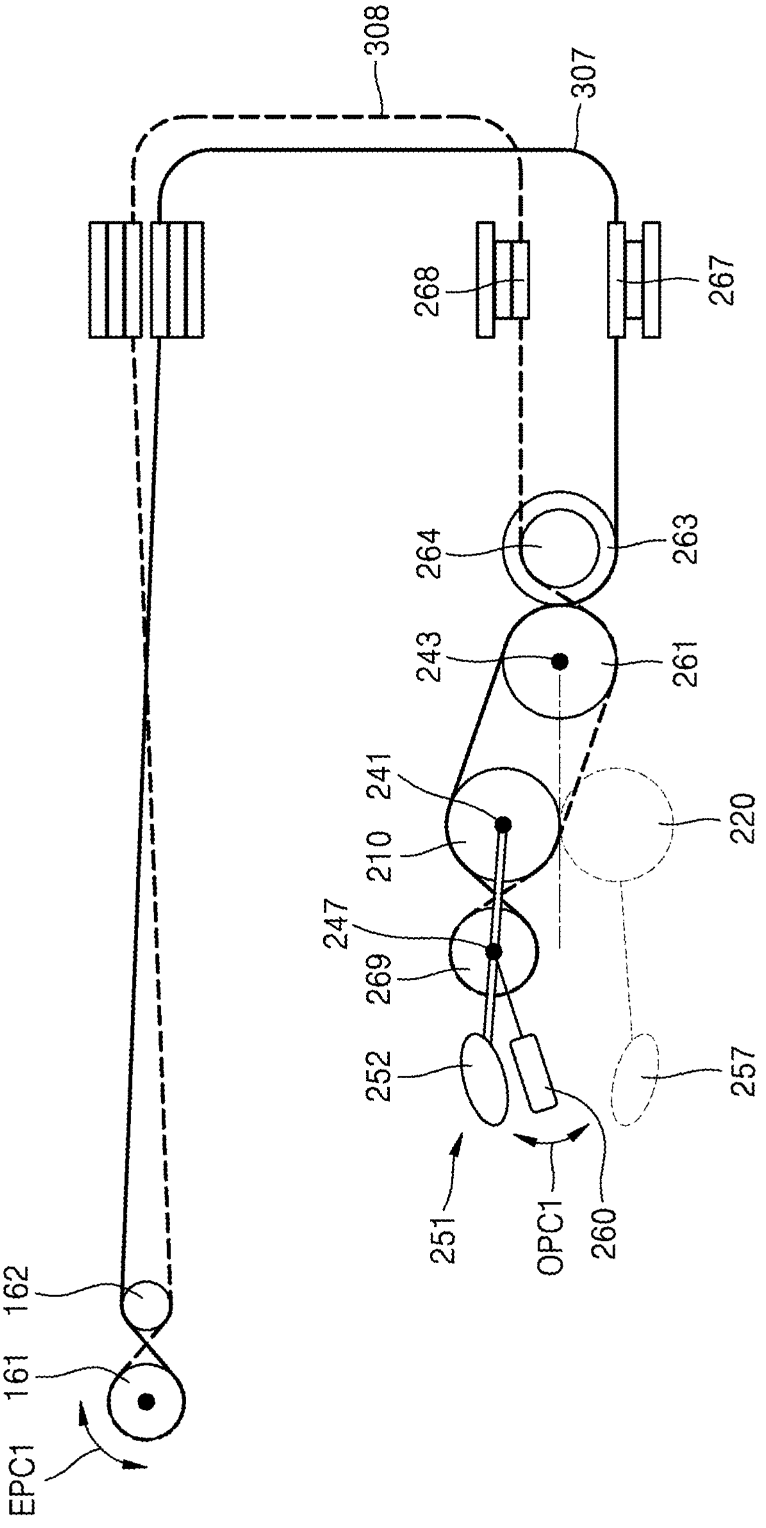

FIGS. 47 to 49 are diagrams illustrating a configuration of pulleys and wires, which are related to stapling and cutting motions of the surgical instrument 10 according to an embodiment of the present disclosure illustrated in FIG. 2, in detail for each of the first jaw and the second jaw. Here, FIGS. 47 to 49 are drawings mainly illustrating pulleys and wires related to the second jaw.

Here, FIGS. 47 and 48 illustrate the process of actuation motion of closing two jaws, and FIGS. 48 and 49 illustrate the process of motion of stapling and cutting of tissue interposed between two jaws.

First, a wire motion of the actuation motion will be described.

Referring to FIGS. 47 and 48, when the first actuation extension part 252 of the first actuation manipulation part 251 is rotated in the direction of an arrow OPA 1 around the rotation shaft 241, the pulley 210 connected to the first actuation extension part 252 is rotated, and each of the wire (see 301 of FIG. 43) and the wire (see 305 of FIG. 43) wound around the pulley 210 is moved, which in turn causes the first jaw 101 of the end tool 100 to rotate in the direction of an arrow EPA1.

At this time, the manipulation part staple pulley 269 of the staple manipulation part 260 is formed to be rotatable around the rotation shaft 241 together with the first actuation manipulation part 251. Thus, when the first actuation extension part 252 is rotated around the rotation shaft 241, the staple manipulation part 260 is also rotated around the rotation shaft 241 together with the first actuation manipulation part 251.

As a result, in the actuation motion, when the pulley 111 is rotated in the end tool 100, the staple pulley 161 is also rotated together with the pulley 111.

Next, a wire motion of the stapling and cutting motions will be described.

Referring to FIGS. 48 and 49, when the staple manipulation part 260 is rotated in the direction of an arrow OPC1 around a rotation shaft 247, which is a manipulation part cutting rotation shaft, the manipulation part staple pulley 269 and the wires 307 and 308 that are staple wires wound therearound are rotated around the rotation shaft 247, and as a result, each of the wires 307 and 308 wound around the manipulation part staple pulley 269 is moved, which in turn causes the staple pulley 161 of the end tool 100 to rotate in the direction of an arrow EPC1.

Meanwhile, when the staple manipulation part 260 is rotated, the manipulation part staple pulley 269 is rotated around the rotation shaft 247, and at this time, the rotation of the staple manipulation part 260 does not affect the first actuation manipulation part 251.

As a result, when the manipulation part staple pulley 269 is rotated, the staple pulley 161 of the end tool 100 is rotated alone independent of the first jaw 101. In addition, when the staple pulley 161 is alternately rotated in the clockwise/counterclockwise directions, the staple link assembly 170 connected to the staple pulley 161 and the reciprocating assembly 550 of the cartridge 500 connected to the staple link assembly 170 perform a reciprocating linear motion, and due to this, as the operation member 540 of the cartridge 500 is moved toward the distal end 502, the stapling and cutting motions are performed.

Here, it is illustrated in the drawings that the staple manipulation part 260 is formed in the form of a bar and a user manually rotates the staple manipulation part 260, but the concept of the present disclosure is not limited thereto. That is, as described above, the staple manipulation part 260 may include a motor (not shown), and while the user presses the staple manipulation part 260 formed in the form of a button, the motor (not shown) may be driven to alternately rotate the manipulation part staple pulley 269 in the clockwise or counterclockwise direction. In addition, due thereto, the staple pulley 161 of the end tool 100 may be alternately rotated in the clockwise or counterclockwise direction.

Figure 50:
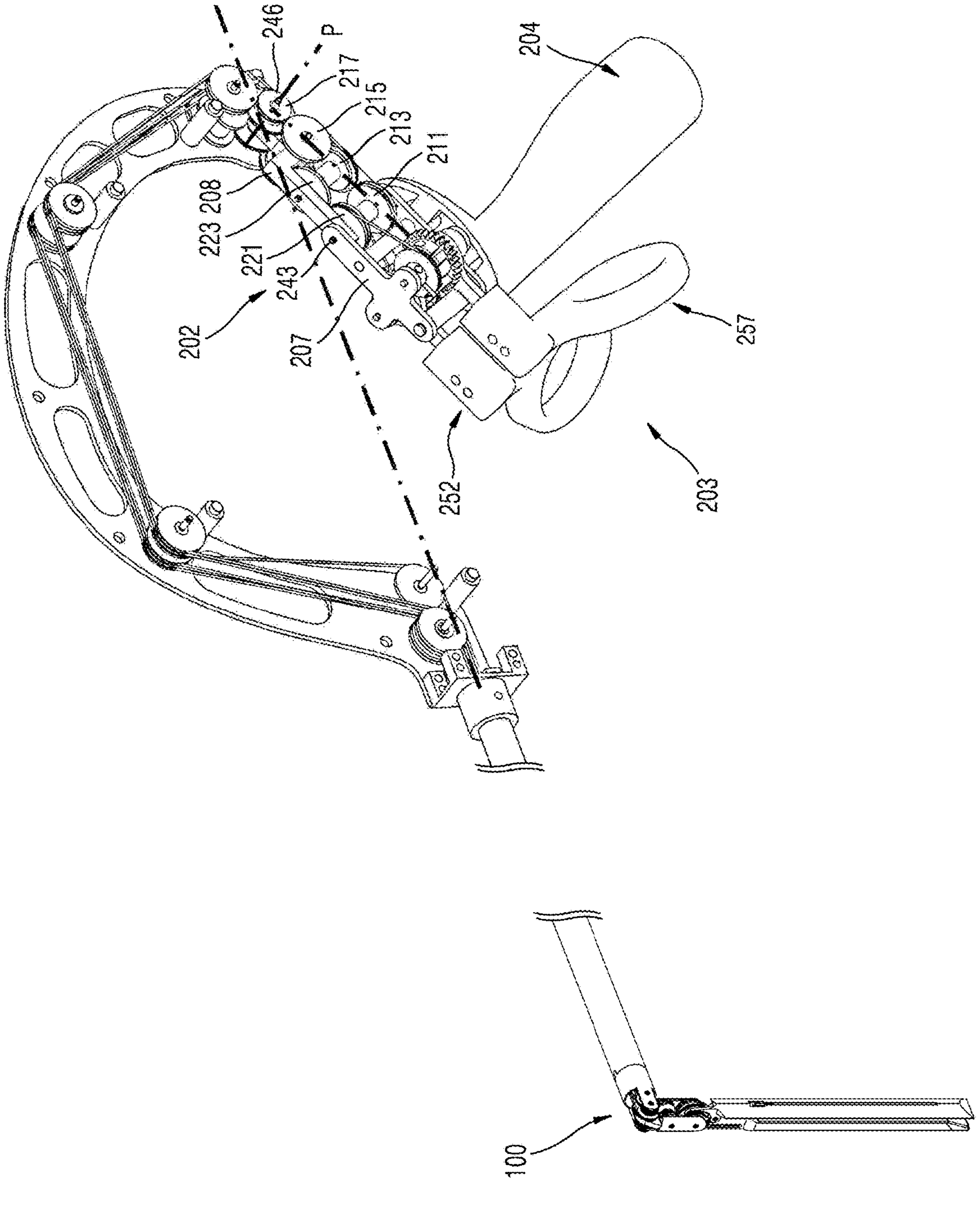
FIG. 50 is a perspective view illustrating a pitch motion of the surgical instrument of FIG. 2.
Figure 51:
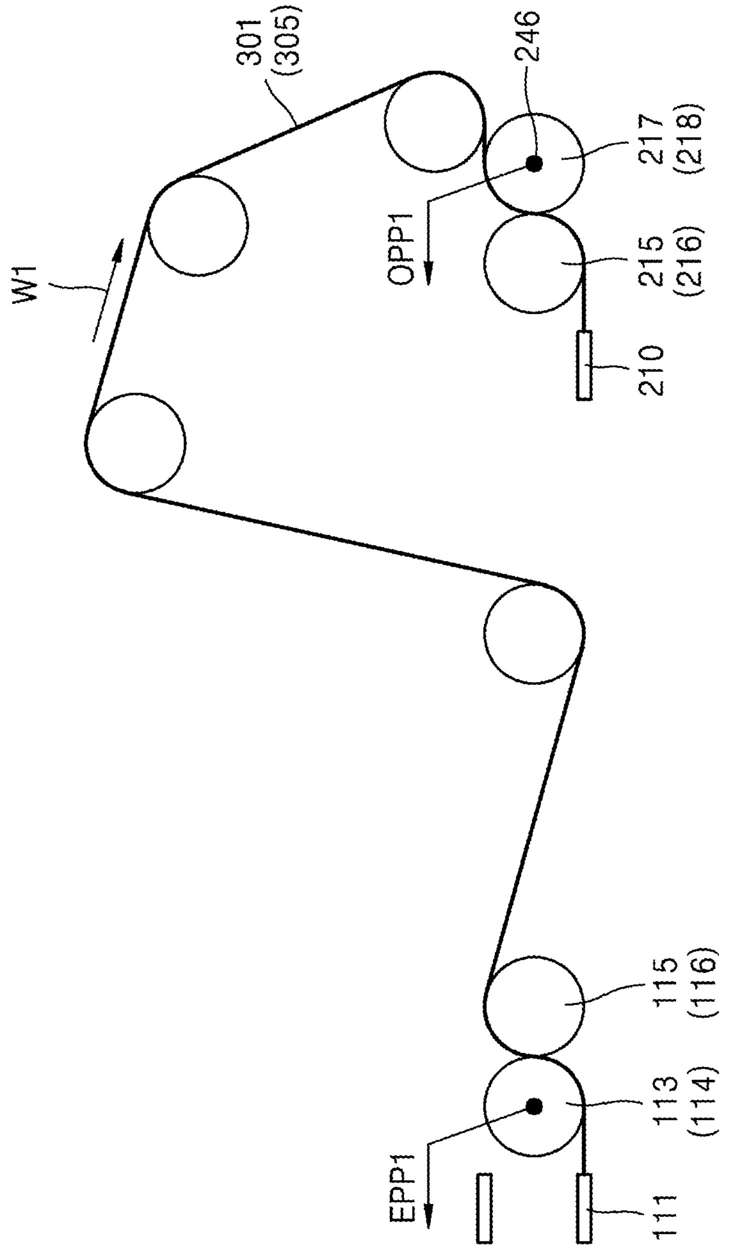
FIGS. 51 to 53 are diagrams illustrating a configuration of pulleys and wires, which are related to a pitch motion of the surgical instrument illustrated in FIG. 2, in detail for each of the first jaw and the second jaw.
Figure 52:
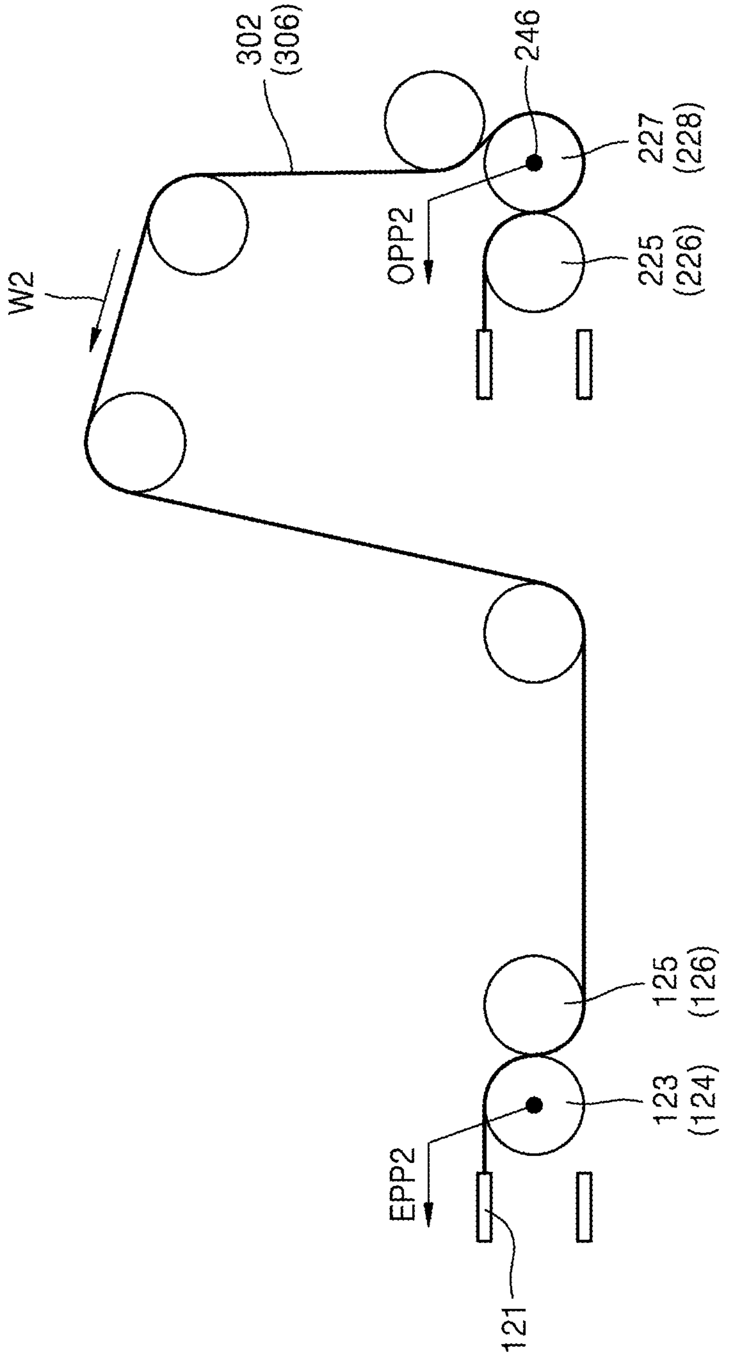
Figure 53:
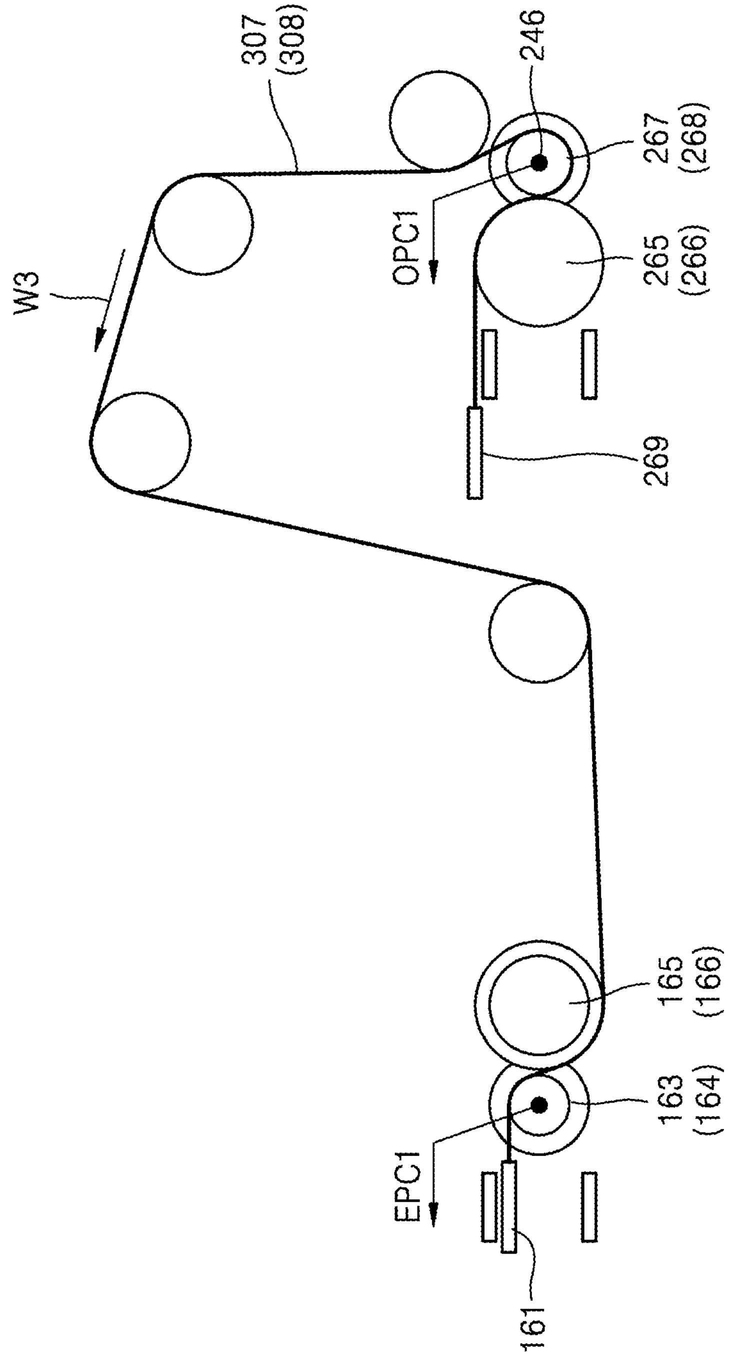

FIGS. 51 to 53 are diagrams illustrating a configuration of pulleys and wires, which are related to a pitch motion of the surgical instrument 10 according to an embodiment of the present disclosure illustrated in FIG. 2, in detail for each of the first jaw and the second jaw. FIG. 51 is a diagram illustrating only pulleys and wires related to the second jaw, and FIG. 52 is a diagram illustrating only pulleys and wires related to the first jaw. FIG. 53 is a diagram illustrating only pulleys and wires related to the staple pulley. As shown in FIG. 9 and elsewhere herein, there are two pulleys related to the pitch motion, and both strands of each wire are wound in the same path, which is illustrated with one line in FIGS. 51 and 53. In addition, FIG. 50 is a perspective view illustrating a pitch motion of the surgical instrument of FIG. 2. Here, in FIG. 50, components related to stapling and cutting motions are omitted.

Referring to FIG. 51, when the first handle 204 is rotated around the rotation shaft 246 in the direction of an arrow OPP1, the pulley 210, the pulley 215, the pulley 217, and the like, and the wire 301 and the like wound therearound are rotated as a whole around the rotation shaft 246. At this time, since the wires 301 and 305, which are first jaw wires, are wound around upper portions of the pulley 217 and the pulley 218 as shown in FIG. 51, the wires 301 and 305 are moved in the direction of an arrow W1. As a result, as described with reference to FIG. 5, the first jaw 101 of the end tool 100 is rotated in the direction of an arrow EPP1.

Referring to FIG. 52, when the first handle 204 is rotated around the rotation shaft 246 in the direction of an arrow OPP2, the pulley 220, the pulley 225, the pulley 227, and the like, and the wire 302 and the like wound therearound are rotated as a whole around the rotation shaft 246. At this time, since the wires 302 and 306, which are second jaw wires, are wound around lower portions of the pulley 227 and the pulley 228 as shown in FIG. 52, the wires 302 and 306 are moved in the direction of an arrow W2. As a result, as described with reference to FIG. 5, the second jaw 102 of the end tool 100 is rotated in the direction of an arrow EPP2.

Referring to FIG. 53, when the first handle 204 is rotated around the rotation shaft 246 in the direction of an arrow OPC1, the manipulation part staple pulley 269, a pulley 265, a pulley 267, and the like, and the wires 307 and 308 and the like wound therearound are rotated as a whole around the rotation shaft 246. At this time, since the wires 307 and 308, which are staple wires, are wound around lower portions of the pulley 267 and a pulley 268, the wires 307 and 308 are moved in the direction of an arrow W3. As a result, as described with reference to FIG. 5, the staple pulley 161 of the end tool 100 is rotated in the direction of an arrow EPC1.

As a result, in the pitch motion, when the pulley 111 is rotated around the rotation shaft 143 in the end tool 100, the staple pulley 161 is also rotated around the rotation shaft 143 together with the pulley 111.

Thus, the actuation, yaw, and pitch manipulations are manipulatable independent of each other.

As described with reference to FIG. 1, the actuation manipulation part 203, the yaw manipulation part 202, and the pitch manipulation part 201 are configured such that the respective rotation shafts are located at the rear thereof to be identical to the joint configuration of the end tool, so that a user may intuitively perform matching manipulations.

In particular, in the surgical instrument 10 according to an embodiment of the present disclosure, the pulleys are formed on respective joint points (an actuation joint, a yaw joint, and a pitch joint), the wires (the first jaw wire or the second jaw wire) are formed to be wound around the pulleys, the rotational manipulations (actuation rotation, yaw rotation, and pitch rotation) of the manipulation part cause the movement of each wire, which in turn induces the desired motion of the end tool 100. Furthermore, the auxiliary pulleys may be formed on one side of the respective pulleys, and these auxiliary pulleys may prevent the wire from being wound on one pulley multiple times, so that the wires wound on the pulley do not come into contact with each other, and paths of the wire being wound around the pulley and the wire being released from the pulley are safely formed, so that safety and efficiency in the transmission of driving force of a wire may be improved.

Meanwhile, as described above, the yaw manipulation part 202 and the actuation manipulation part 203 are directly formed on the first handle 204. Thus, when the first handle 204 is rotated around the rotation shaft 246, the yaw manipulation part 202 and the actuation manipulation part 203 are also rotated together with the first handle 204. Accordingly, the coordinate systems of the yaw manipulation part 202 and the actuation manipulation part 203 are not fixed, but are continuously changed relative to the rotation of the first handle 204. That is, in FIG. 2 or the like, the yaw manipulation part 202 and the actuation manipulation part 203 are illustrated as being parallel to the z-axis. However, when the first handle 204 is rotated, the yaw manipulation part 202 and the actuation manipulation part 203 are not parallel to the Z-axis any longer. That is, the coordinate systems of the yaw manipulation part 202 and the actuation manipulation part 203 are changed according to the rotation of the first handle 204. However, in the present specification, for convenience of description, unless described otherwise, the coordinate systems of the yaw manipulation part 202 and the actuation manipulation part 203 are described on the basis of a state in which the first handle 204 is located perpendicular to the connection part 400 as illustrated in FIG. 2.

(Correlation Between Stapling and Cutting Motions and Other Motions)

Hereinafter, a correlation between stapling and cutting motions and other motions (pitch, yaw, and actuation motions) will be described.

First, when the end tool 100 performs a pitch motion, the staple pulley 161 also performs a pitch motion. That is, when the pulley 111 and the pulley 121 perform pitch motions of being rotated in the same direction around the rotation shaft 143, the staple pulley 161 should also be rotated in the same direction as the pulley 111 and the pulley 121. If the staple pulley 161 is not rotated together with the pulley 111 and the pulley 121 when the pulley 111 and the pulley 121 are rotated around the rotation shaft 143, there is a risk that the cartridge 500 connected to the staple pulley 161 is moved relative to the first jaw 101 and is disconnected from the first jaw 101. Further, rotation of the staple pulley 161 that is not synchronized with that of the pulley 111 may cause the reciprocating member 551 to unintentionally move forward, which in turn may cause an unintended stapling motion.

Next, when the end tool 100 performs a yaw motion, the staple pulley 161 also performs a yaw motion. That is, when the pulley 111 and the pulley 121 perform yaw motions of being rotated in the same direction around the rotation shaft 141, the staple pulley 161 should also be rotated in the same direction as the pulley 111 and the pulley 121. If the staple pulley 161 is not rotated together with the pulley 111 and the pulley 121 when the pulley 111 and the pulley 121 are rotated around the rotation shaft 141, there is a risk that the cartridge 500 connected to the staple pulley 161 is moved relative to the first jaw 101 and is disconnected from the first jaw 101. Further, rotation of the staple pulley 161 that is not synchronized with that of the pulley 111 may cause the reciprocating member 551 to unintentionally move forward, which in turn may cause an unintended stapling motion.

Next, when the end tool 100 performs an actuation motion, the staple pulley 161 is rotated together with the pulley 111. That is, when the pulley 111 and the pulley 121 perform actuation motions of being rotated the opposite directions around the rotation shaft 141, the staple pulley 161 should be rotated in the same direction as the pulley 111. If the staple pulley 161 is not rotated together with the pulley 111 when the pulley 111 is rotated around the rotation shaft 143, there is a risk that the cartridge 500 connected to the staple pulley 161 is moved relative to the first jaw 101 and is disconnected from the first jaw 101. Further, rotation of the staple pulley 161 that is not synchronized with that of the pulley 111 may cause the reciprocating member 551 to unintentionally move forward, which in turn may cause an unintended stapling motion.

Meanwhile, when the end tool 100 performs stapling and cutting motions, the pulley 111 and the pulley 121 are not rotated. That is, when the staple pulley 161 is rotated around the rotation shaft 141 and the reciprocating member 551 of the link member 171 and the cartridge 500 connected thereto performs a linear reciprocating motion, the pulley 111 and the pulley 121 should not be rotated. Otherwise, the first jaw 101 or the second jaw 102 is rotated during the stapling and cutting motion, and the stapling and cutting motions will not be performed normally.

As a result, when the pulley 111, which is a first jaw pulley, is rotated, the staple pulley 161 accommodated in the first jaw 101 should be also rotated together with the pulley 111. On the other hand, when the staple pulley 161 is rotated for the stapling and cutting motions, the pulley 111 and the pulley 121 should be formed to maintain positions thereof without rotating. As such, the correlation between the stapling and cutting motions and other motions (the yaw and actuation motions) has been discussed above.

In other words, the pulley 111 and the pulley 121 may be said to be independent of the rotation of the staple pulley 161. That is, even when the staple pulley 161 is rotated by the staple wire, the pulley 111 and the pulley 121 may not be rotated. In contrast, the staple pulley 161 may be said to be dependent of the rotation of the pulley 111. That is, when the pulley 111 is rotated by the jaw wire, the staple pulley 161 may be formed to be rotated together with the pulley 111.

Figure 54:
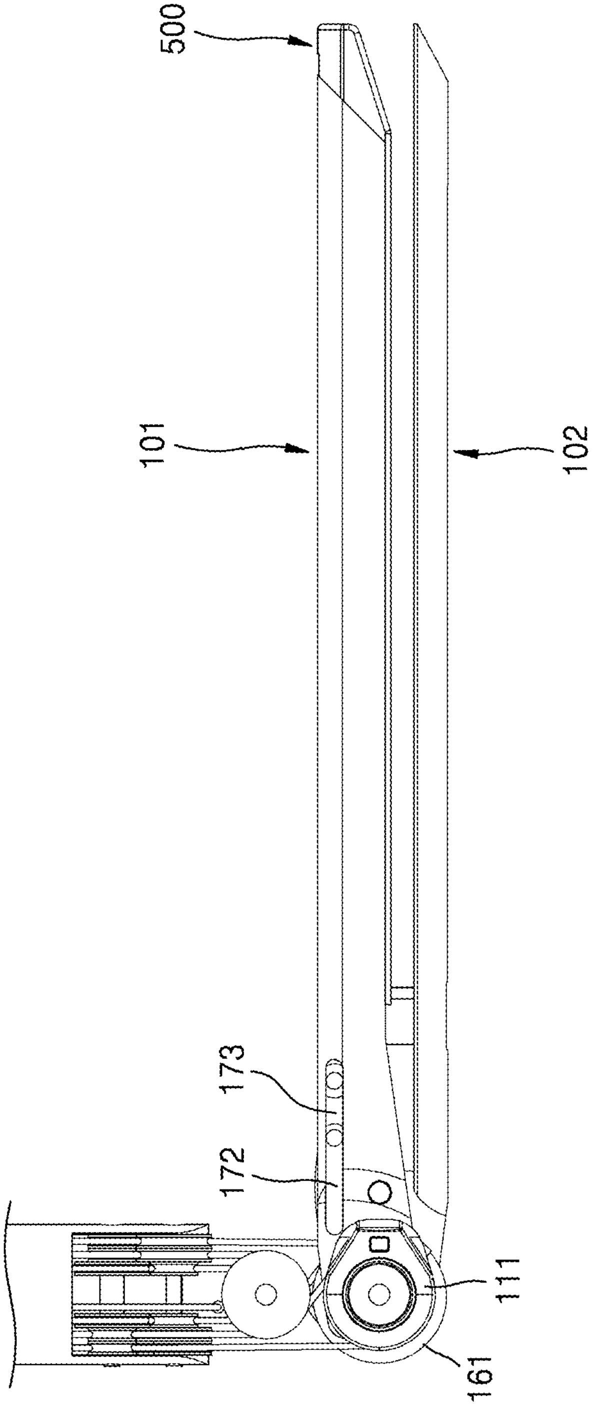
FIGS. 54 to 57 are plan views illustrating an actuation motion of the end tool of the surgical instrument of FIG. 2, and are views illustrating a process of performing an actuation motion in a state in which the jaws are yaw-rotated by −90°.
Figure 55:
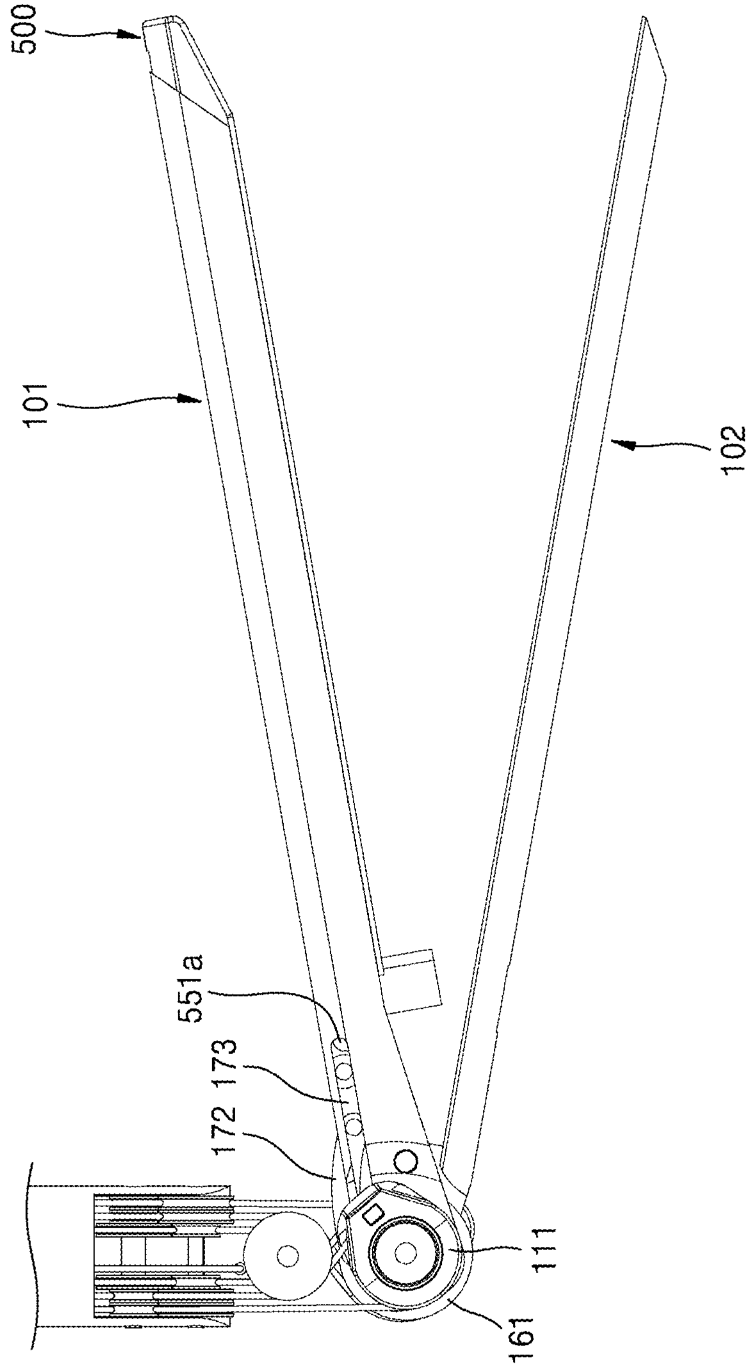
Figure 56:
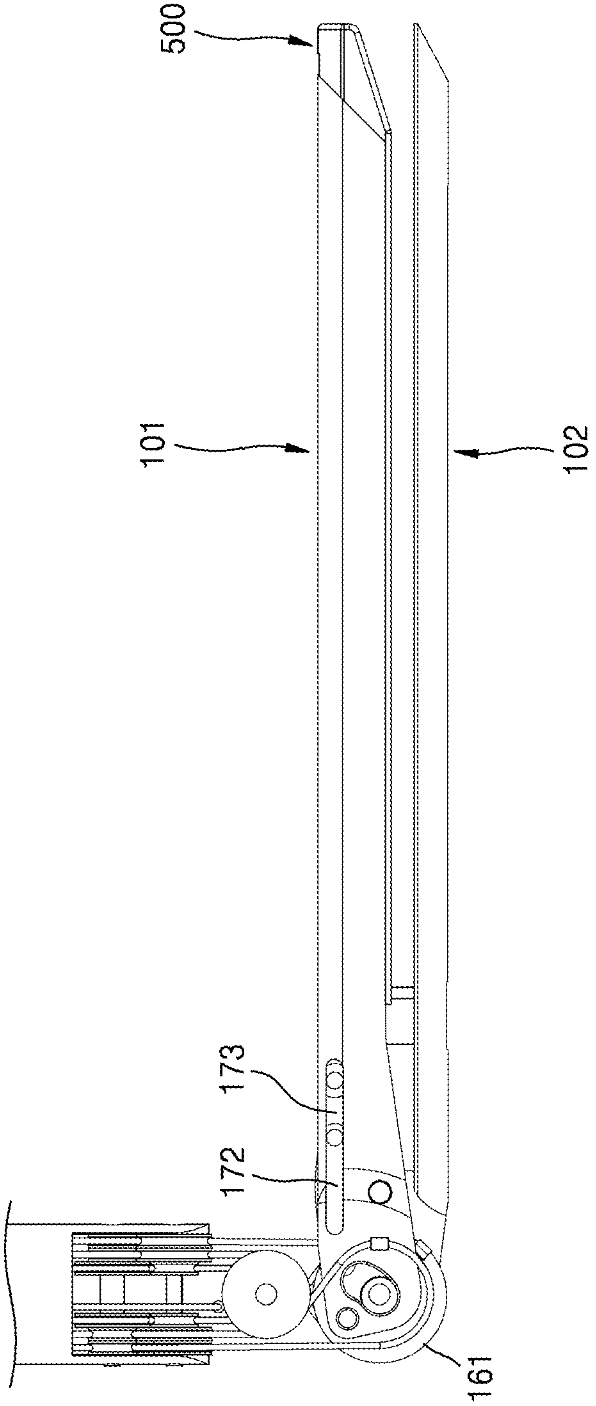
Figure 57:
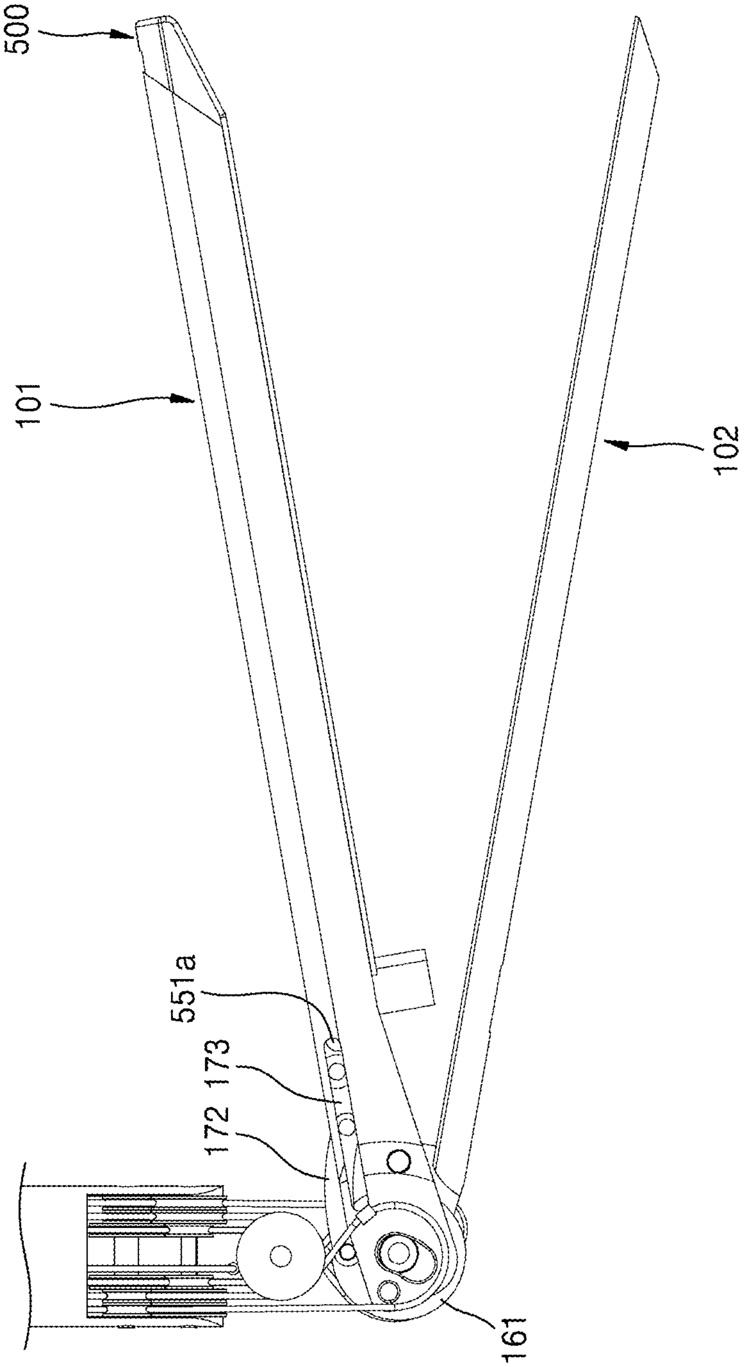

FIGS. 54 and 56 are views illustrating a state in which the jaws are yaw-rotated by −90°, and FIGS. 55 and 57 are views illustrating a process of performing an actuation motion in a state in which the jaws are yaw-rotated by −90°. Here, FIGS. 54 and 55 are views in which the pulley 111 is illustrated, and FIGS. 56 and 57 are views in which the pulley 111 is omitted.

Figure 58:
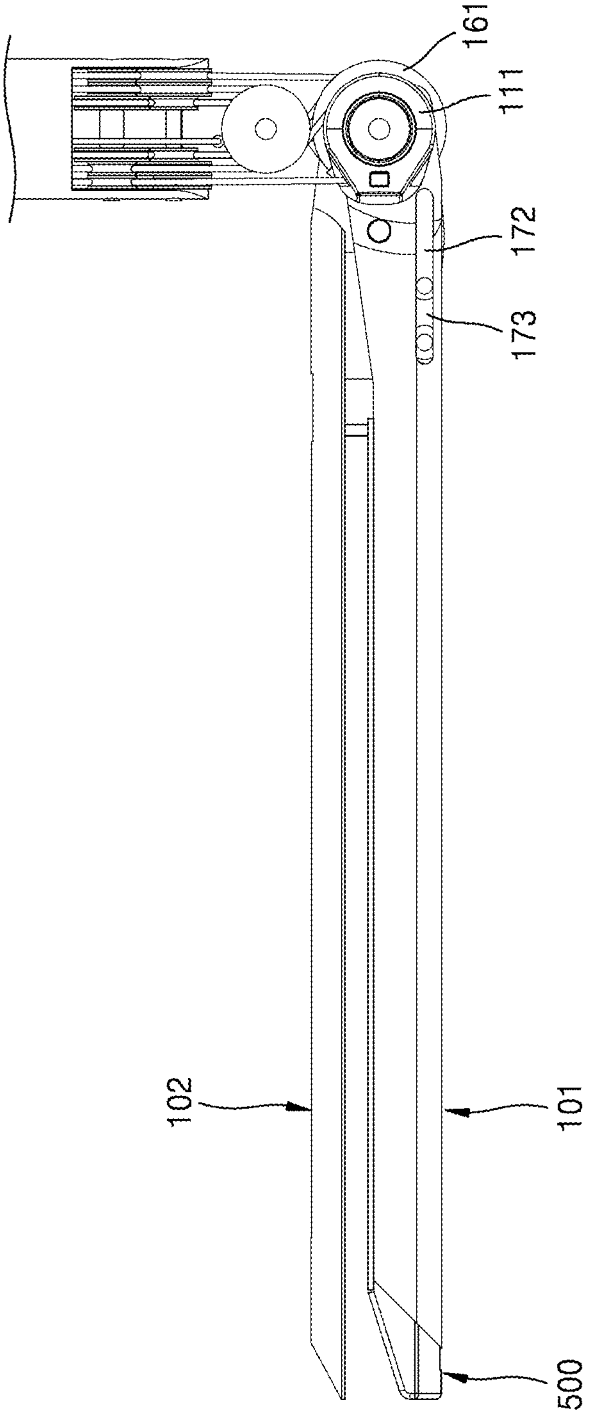
FIGS. 58 to 61 are plan views illustrating an actuation motion of the end tool of the surgical instrument of FIG. 2, and are views illustrating a process of performing an actuation motion in a state in which the jaws are yaw-rotated by +90°.
Figure 59:
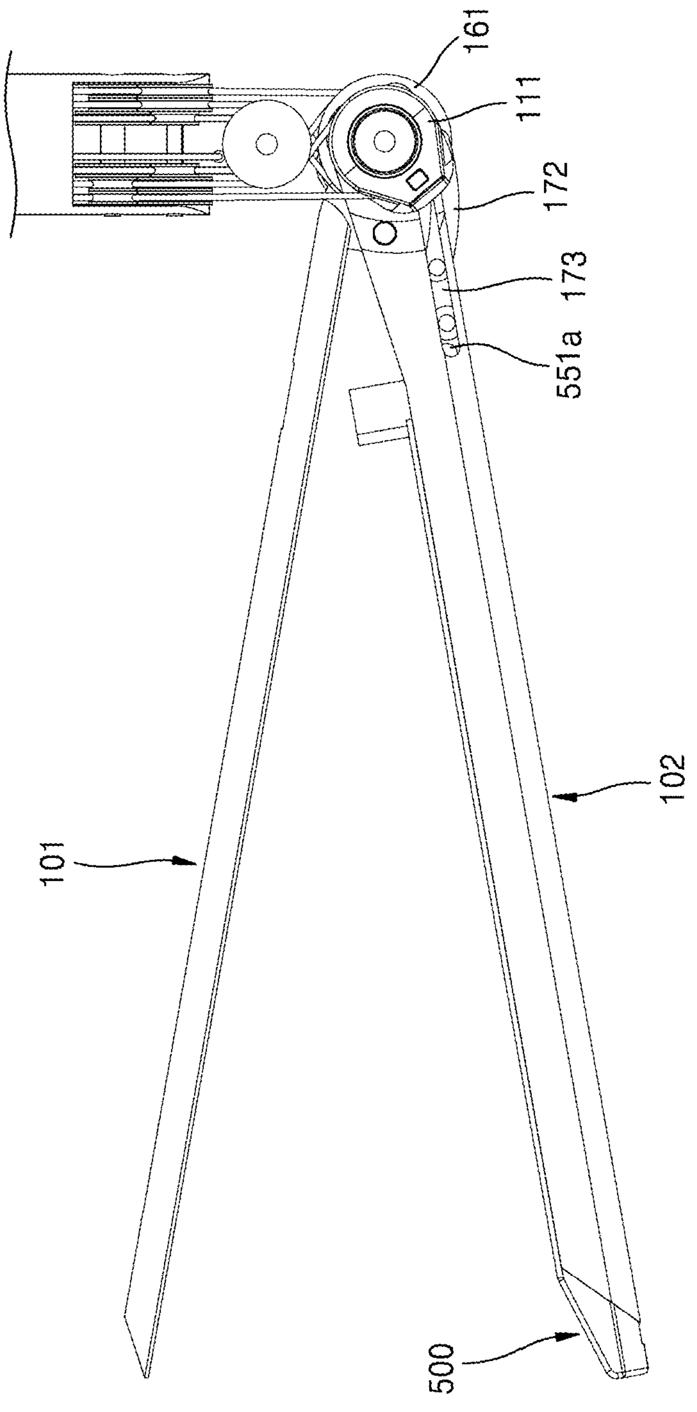
Figure 60:
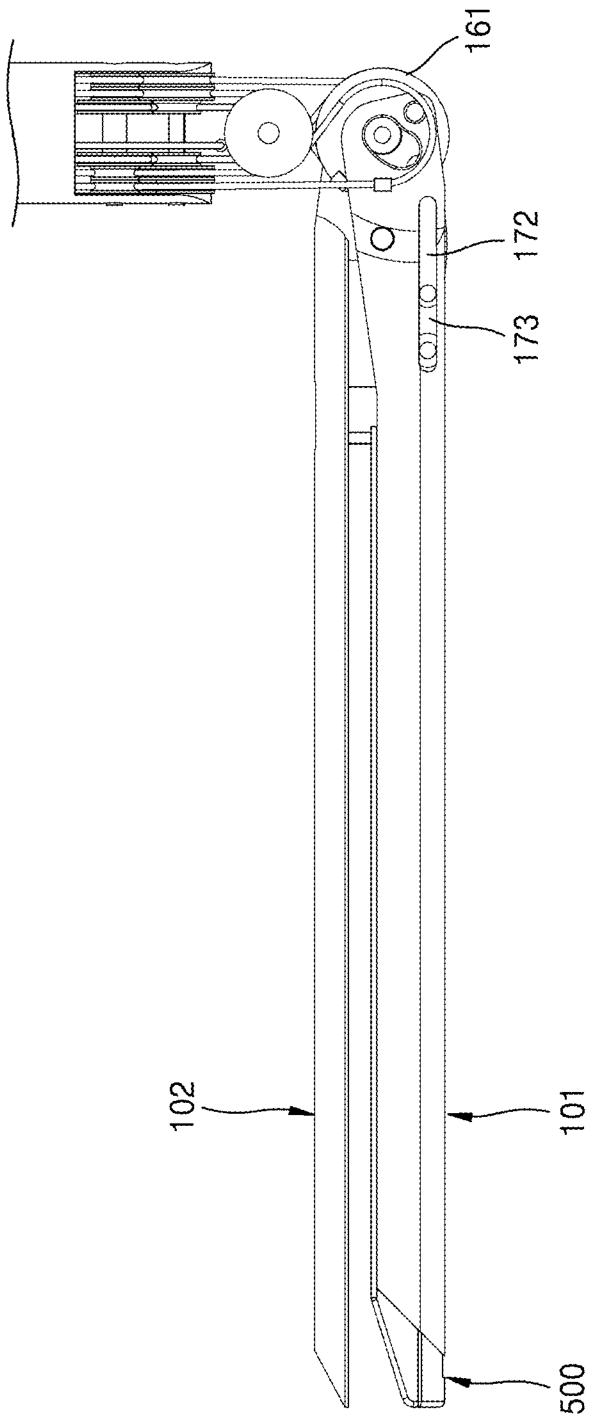
Figure 61:
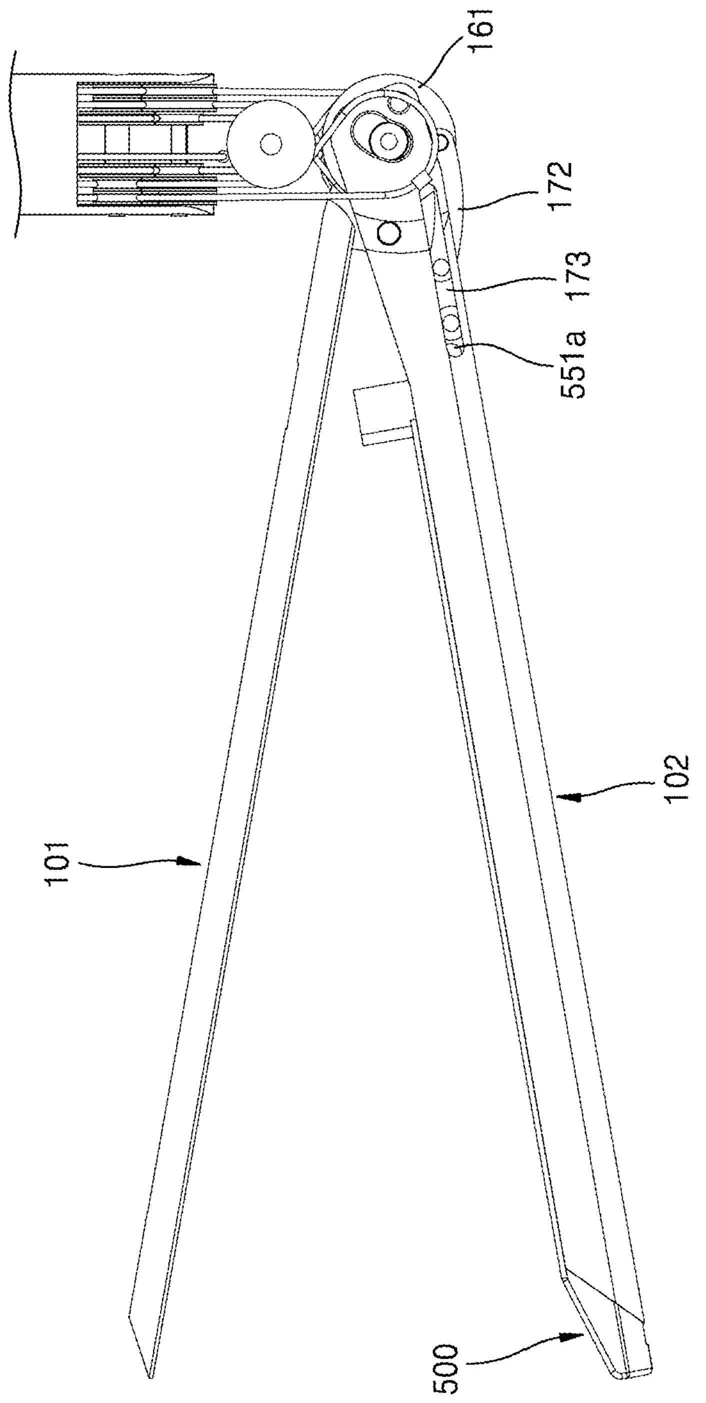

FIGS. 58 and 60 are views illustrating a state in which the jaws are yaw-rotated by +90°, and FIGS. 59 and 61 are views illustrating a process of performing an actuation motion in a state in which the jaws are yaw-rotated by +90°. Here, FIGS. 58 and 59 are views in which the pulley 111 is illustrated, and FIGS. 60 and 61 are views in which the pulley 111 is omitted.

As shown in FIGS. 54 to 61, the end tool of the surgical instrument according to the first embodiment of the present disclosure is formed to normally perform an actuation motion even when the jaws are yaw-rotated by +90° or −90°.

Figure 62:
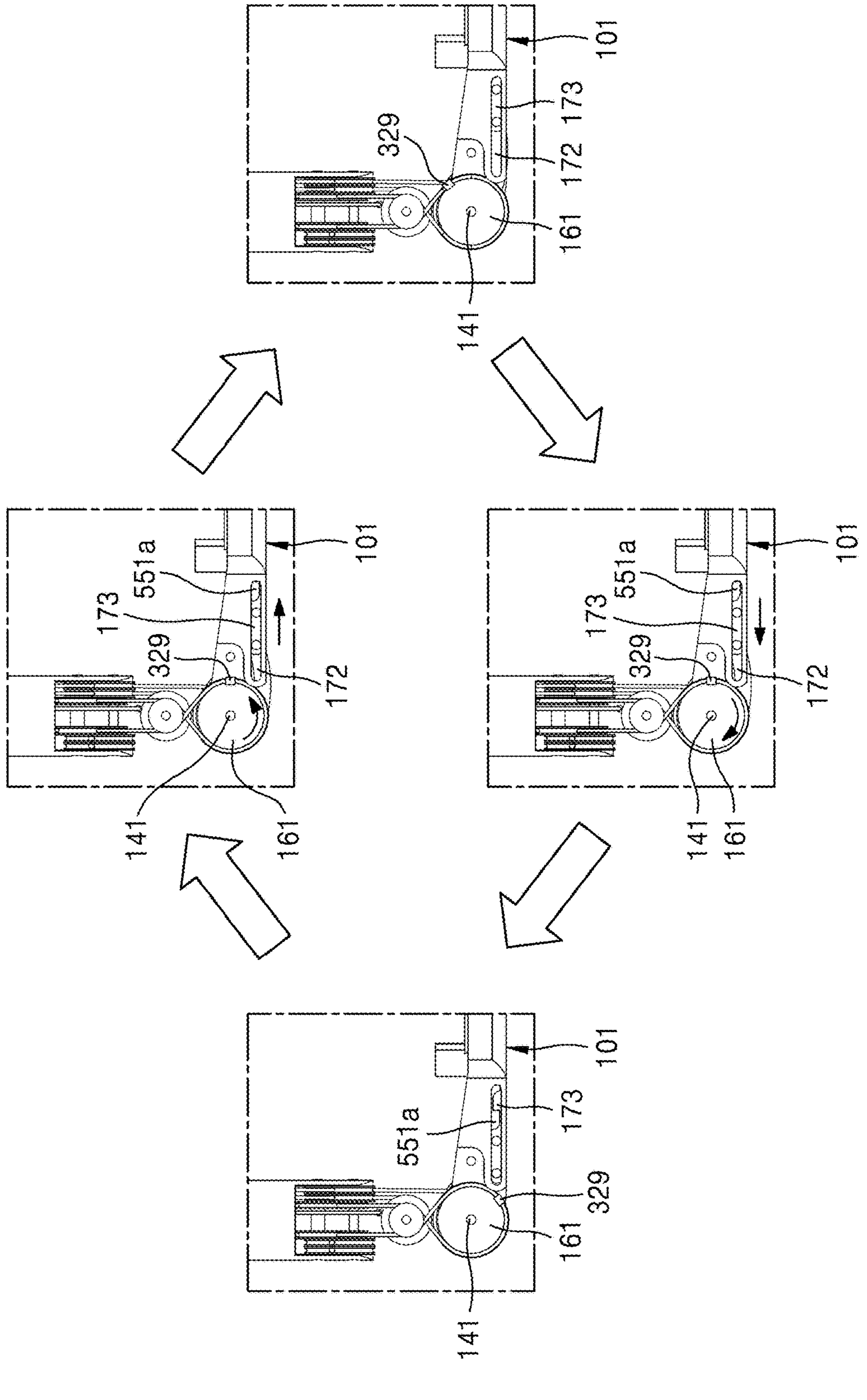
FIG. 62 is a plan view illustrating a stapling motion of the end tool of the surgical instrument of FIG. 2, and is a view illustrating a process of performing a stapling motion in a state in which the jaws are yaw-rotated by +90°.

FIG. 62 is a plan view illustrating stapling and cutting motions of the end tool of the surgical instrument of FIG. 2, and is a view illustrating a process of performing the stapling and cutting motions in a state in which the jaws are yaw-rotated by +90°. As shown in FIG. 62, the end tool of the surgical instrument according to the first embodiment of the present disclosure is formed to normally perform the stapling and cutting motions even when the jaws are yaw-rotated by +90°.

In detail, in a state in which the pulley 111, the pulley 121, and the staple pulley 161 are rotated by +90° around the rotation shaft 141, when the staple pulley 161 is alternately rotated in the clockwise/counterclockwise directions, the link member 171 and the reciprocating member 551 connected thereto are repeatedly moved forward and backward. In addition, when the reciprocating member 551 is moved forward, the operation member 540 may be moved forward together with the reciprocating member 551, and when the reciprocating member 551 is moved backward, only the reciprocating member 551 is moved backward and the operation member 540 remains stationary in place. By repeating this process, the stapling and cutting motions are performed while the operation member 540 is moved toward the distal end 502.

Figure 63:
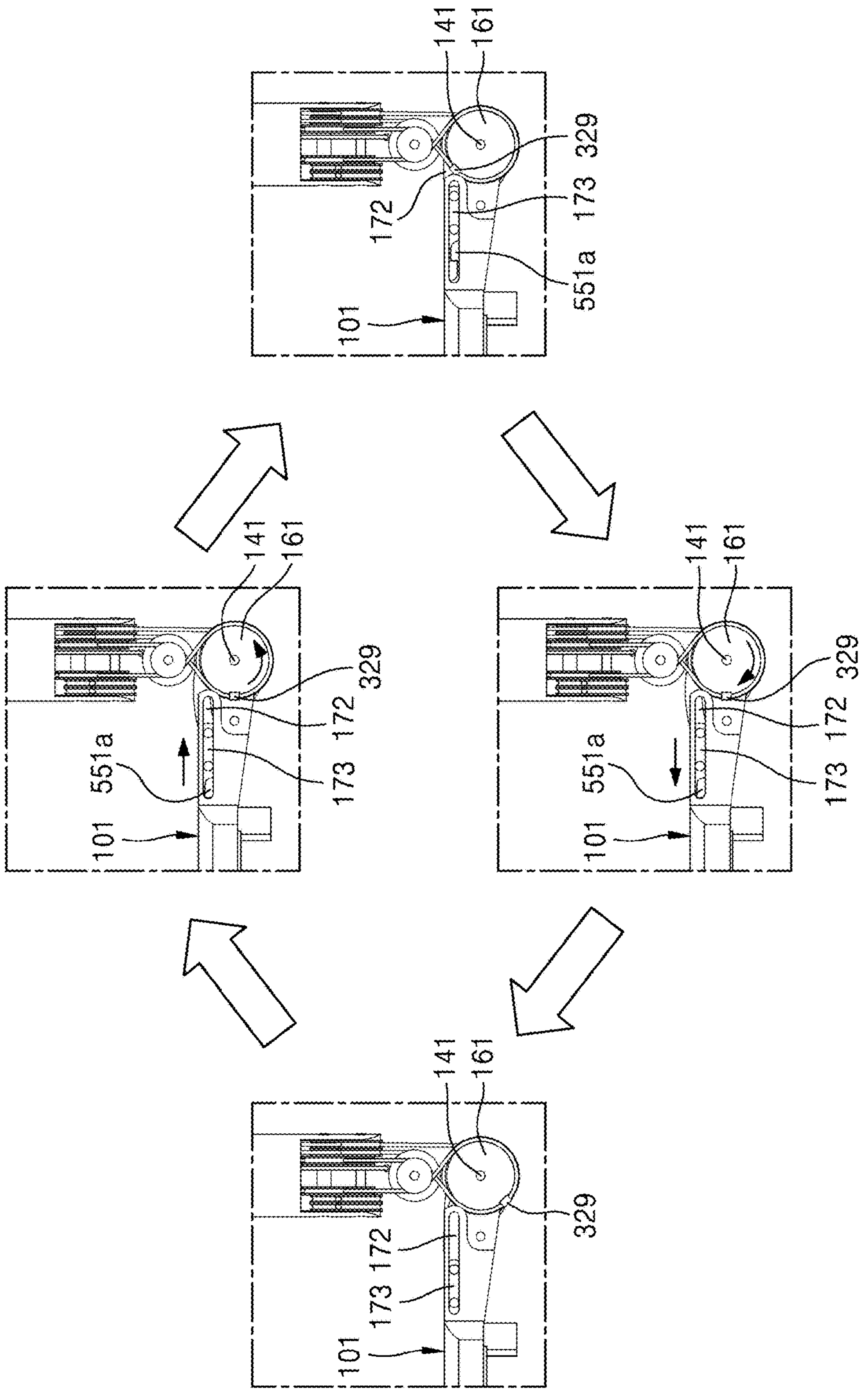
FIG. 63 is a plan view illustrating a stapling motion of the end tool of the surgical instrument of FIG. 2, and is a view illustrating a process of performing a stapling motion in a state in which the jaws are yaw-rotated by −90°.

FIG. 63 is a plan view illustrating stapling and cutting motions of the end tool of the surgical instrument of FIG. 2, and is a view illustrating a process of performing the stapling and cutting motions in a state in which the jaws are yaw-rotated by −90°. As shown in FIG. 63, the end tool of the surgical instrument according to the first embodiment of the present disclosure is formed to normally perform the stapling and cutting motions even when the jaws are yaw-rotated by −90°.

In detail, in a state in which the pulley 111, the pulley 121, and the staple pulley 161 are rotated by −90° around the rotation shaft 141, when the staple pulley 161 is alternately rotated in the clockwise/counterclockwise directions, the link member 171 and the reciprocating member 551 connected thereto are repeatedly moved forward and backward. In addition, when the reciprocating member 551 is moved forward, the operation member 540 may be moved forward together with the reciprocating member 551, and when the reciprocating member 551 is moved backward, only the reciprocating member 551 is moved backward and the operation member 540 remains stationary. By repeating this process, the stapling and cutting motions are performed while the operation member 540 is moved toward the distal end 502.

Figure 64:
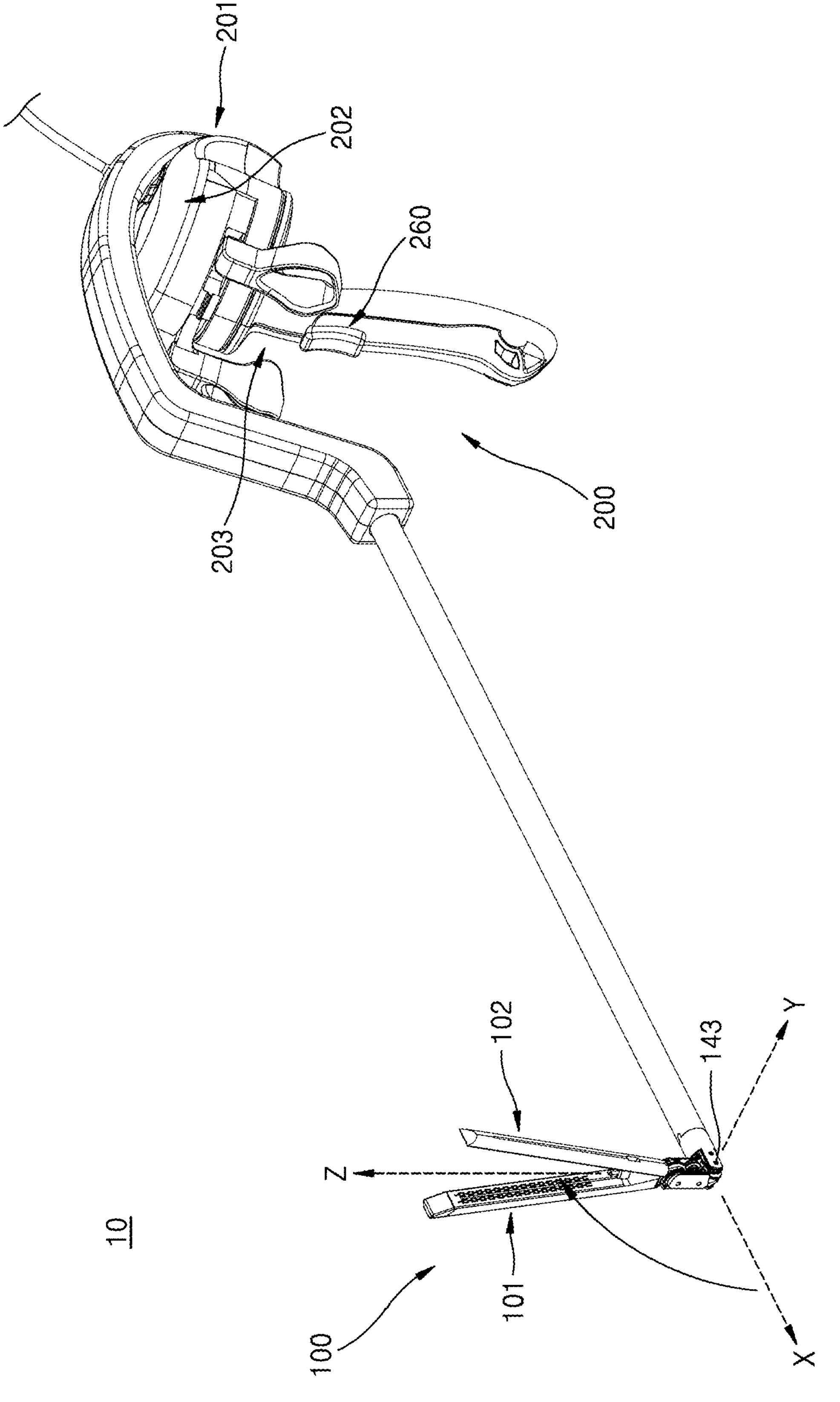
FIGS. 64 to 67 are perspective views illustrating a pitch motion of the surgical instrument of FIG. 2.
Figure 65:
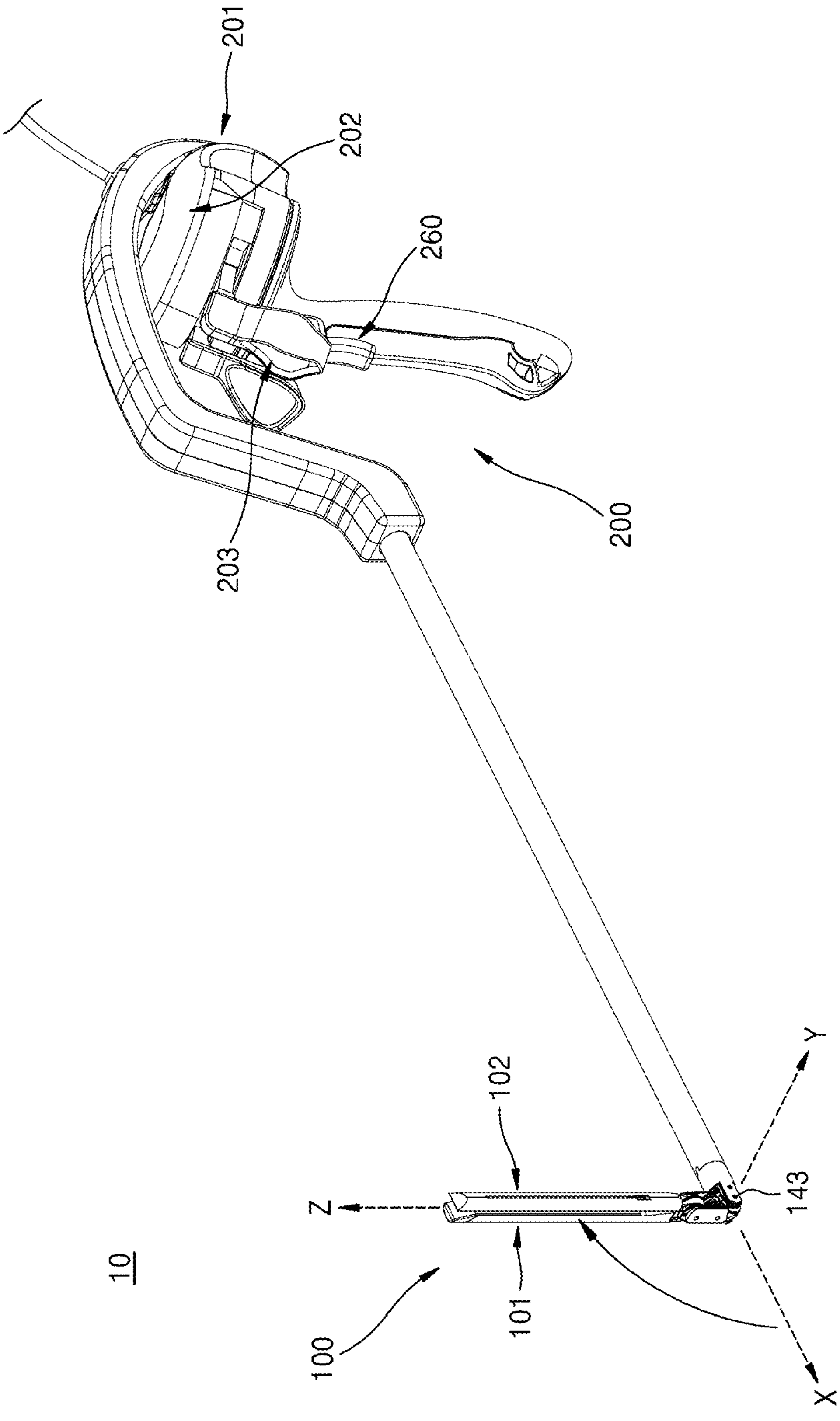
Figure 66:
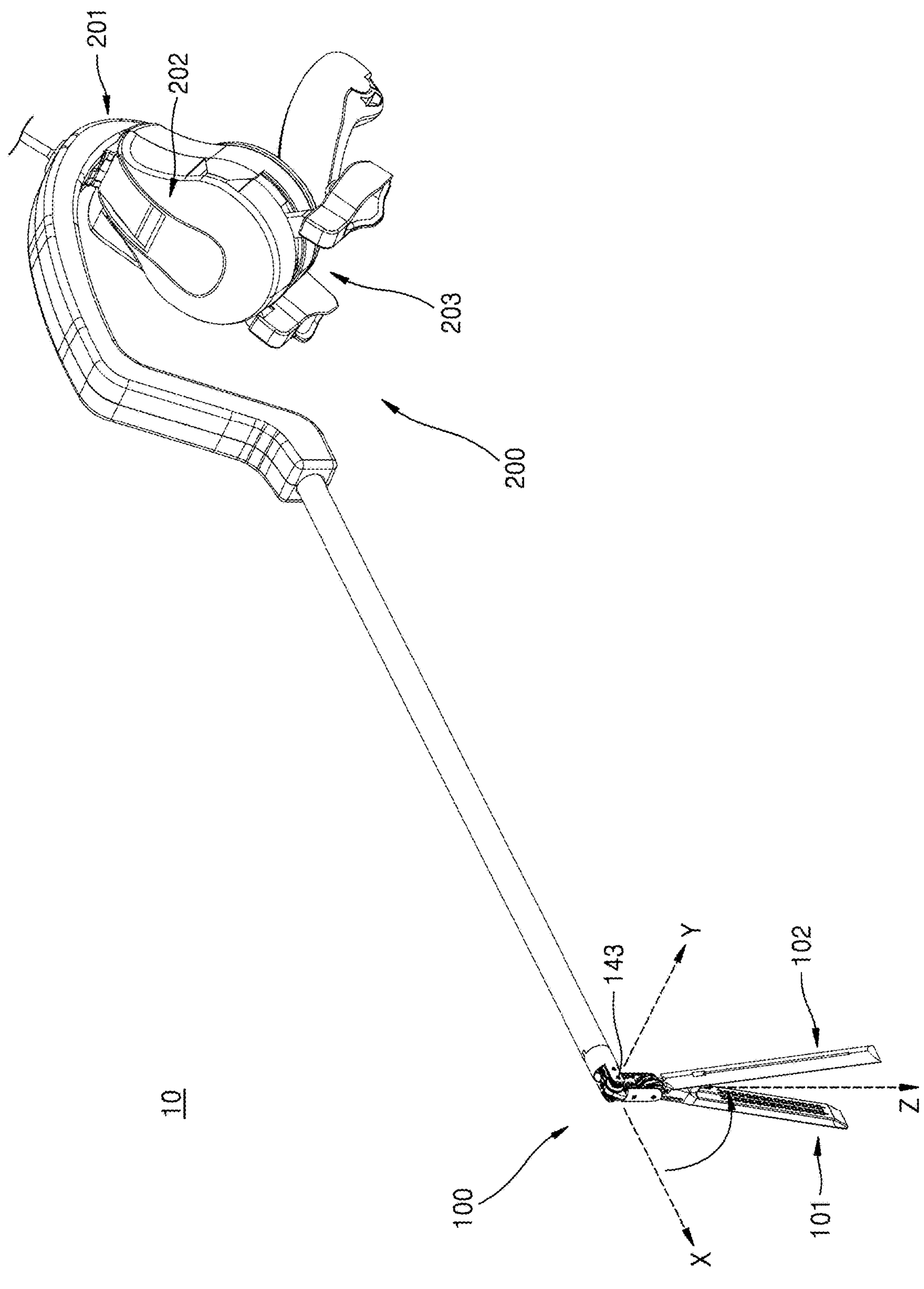
Figure 67:
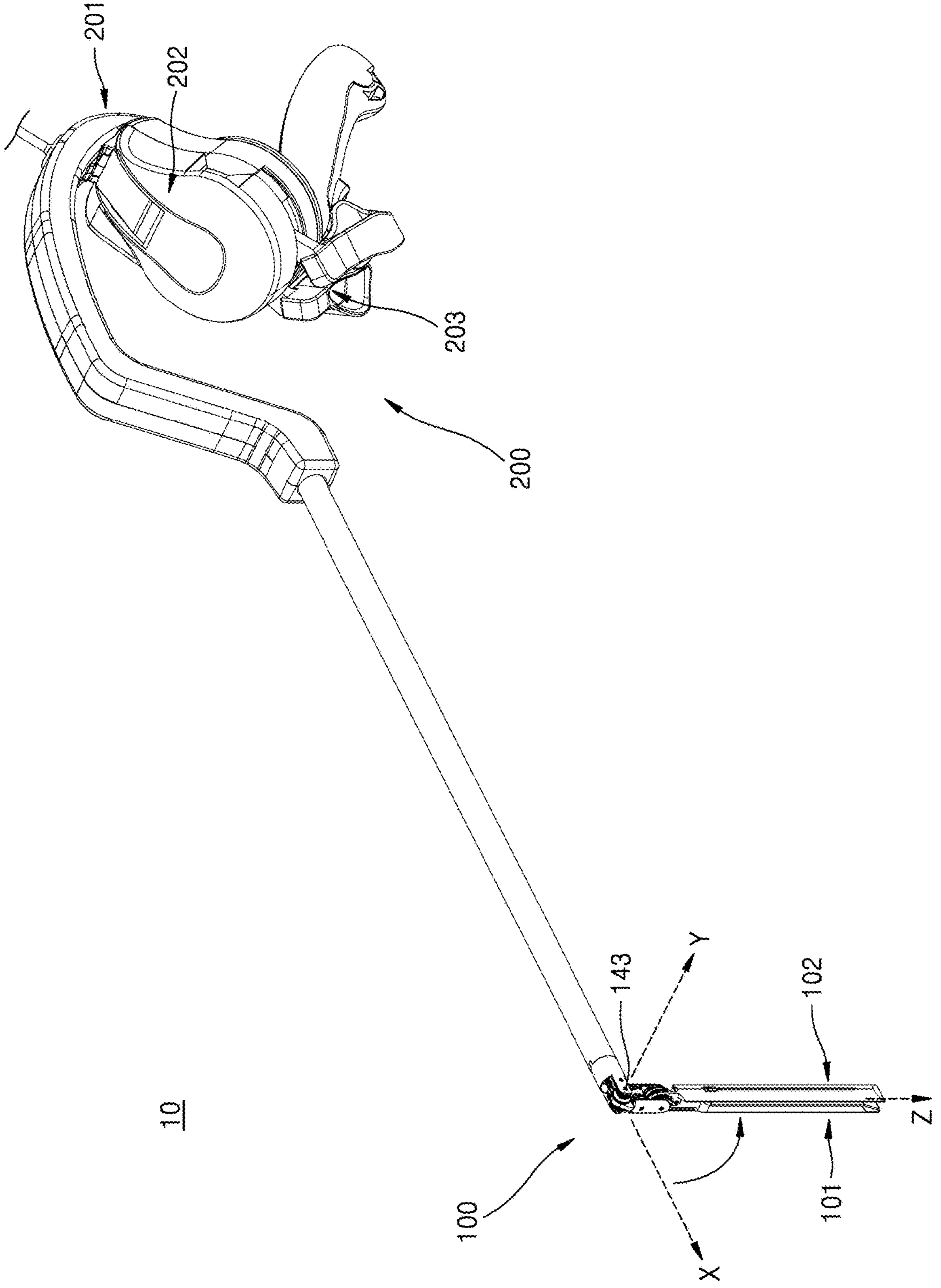

FIG. 64 is a view illustrating a state in which the jaws are pitch-rotated by −90°, and FIG. 65 is a view illustrating a process of performing an actuation motion in a state in which the jaws are pitch-rotated by −90°. FIG. 66 is a view illustrating a state in which the jaws are pitch-rotated by +90°, and FIG. 67 is a view illustrating a process of performing an actuation motion in a state in which the jaws are pitch-rotated by +90°.

Referring to FIGS. 64 to 67, it can be seen that, in performing a pitch motion, the motions of the manipulation part 200 and the end tool 100 are intuitively matched. That is, when the manipulation part 200 is rotated in a positive (+) direction with respect to the pitch rotation shaft (Y-axis), the end tool 100 is also rotated in the positive (+) direction with respect to the pitch rotation shaft (Y-axis). In addition, when the manipulation part 200 is rotated in a negative (−) direction with respect to the pitch rotation shaft (Y-axis), the end tool 100 is also rotated in the negative (−) direction with respect to the pitch rotation shaft (Y-axis). Here, the rotation angle of the manipulation part 200 and the rotation angle of the end tool 100 may be variously set according to the ratio of the pulleys.

Figure 68:
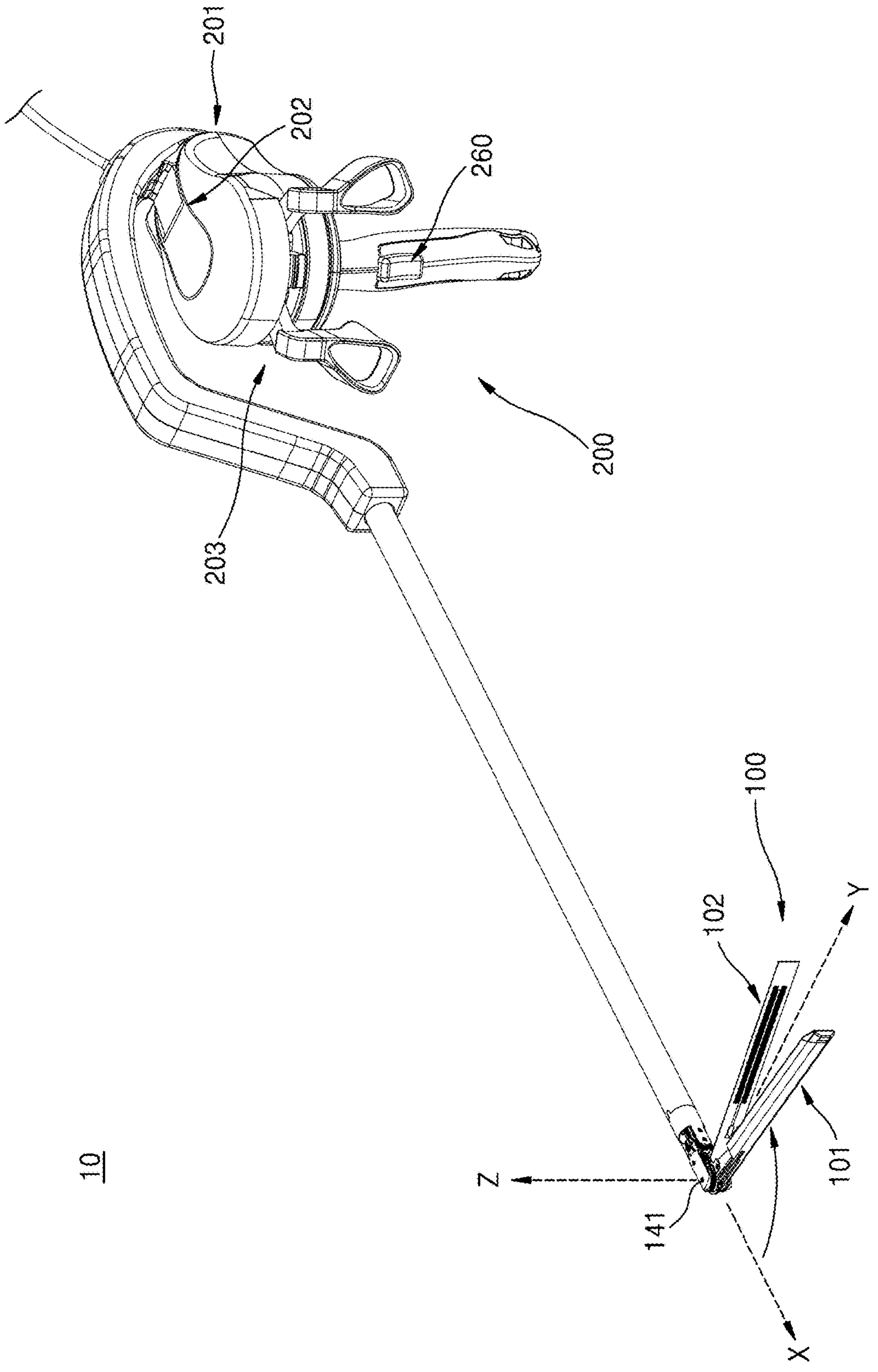
FIGS. 68 to 71 are perspective views illustrating a yaw motion of the surgical instrument of FIG. 2.
Figure 69:
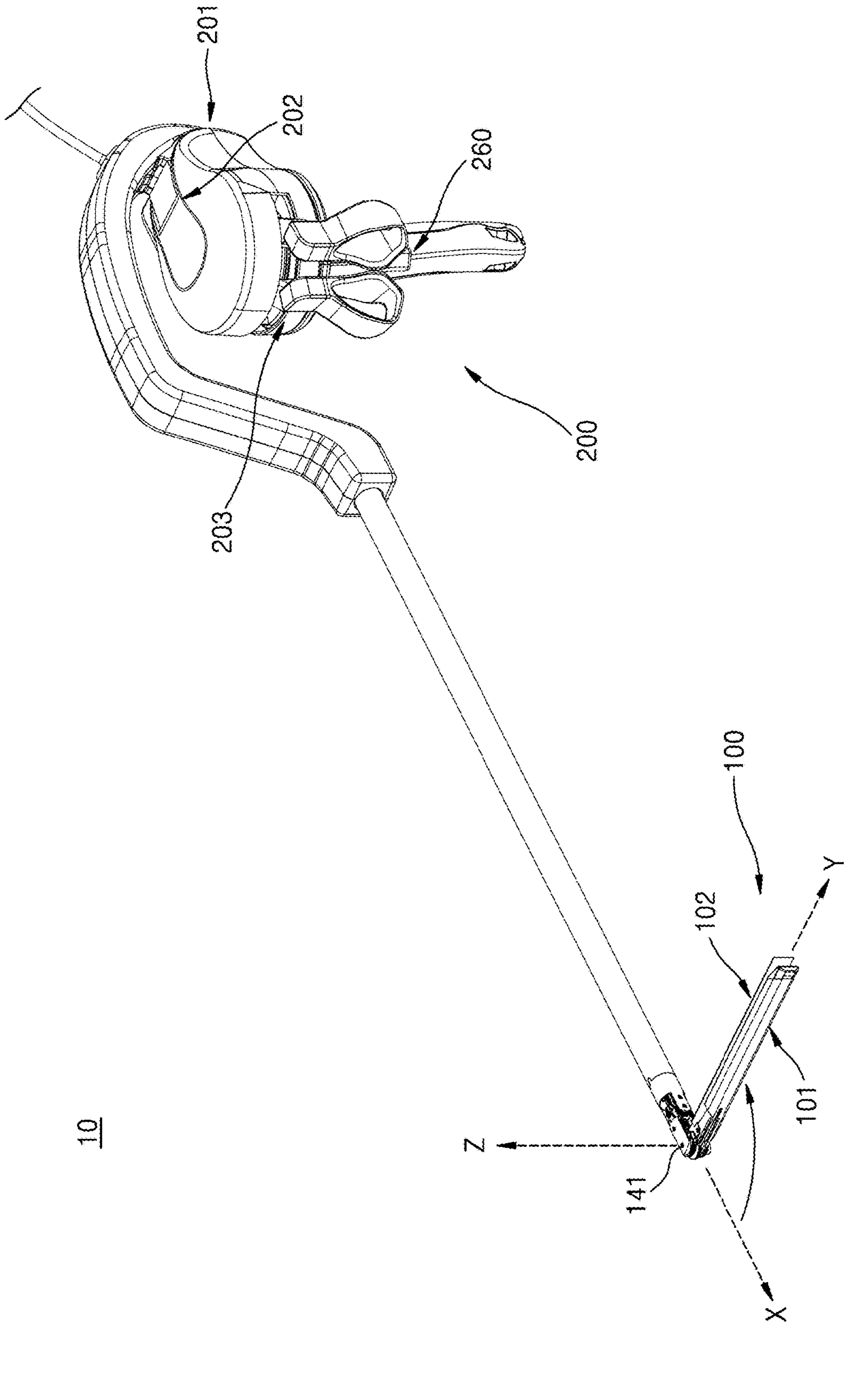
Figure 70:
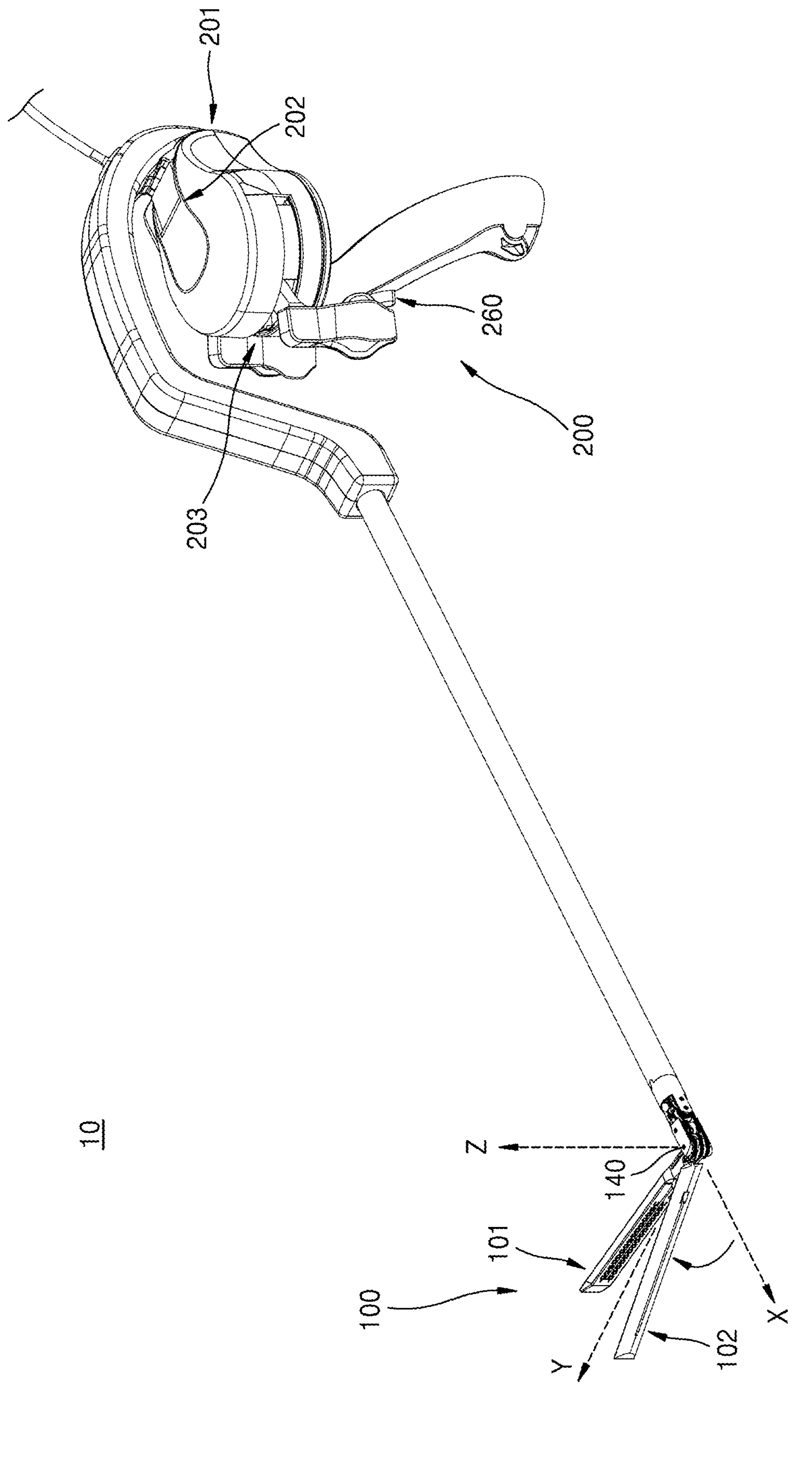
Figure 71:
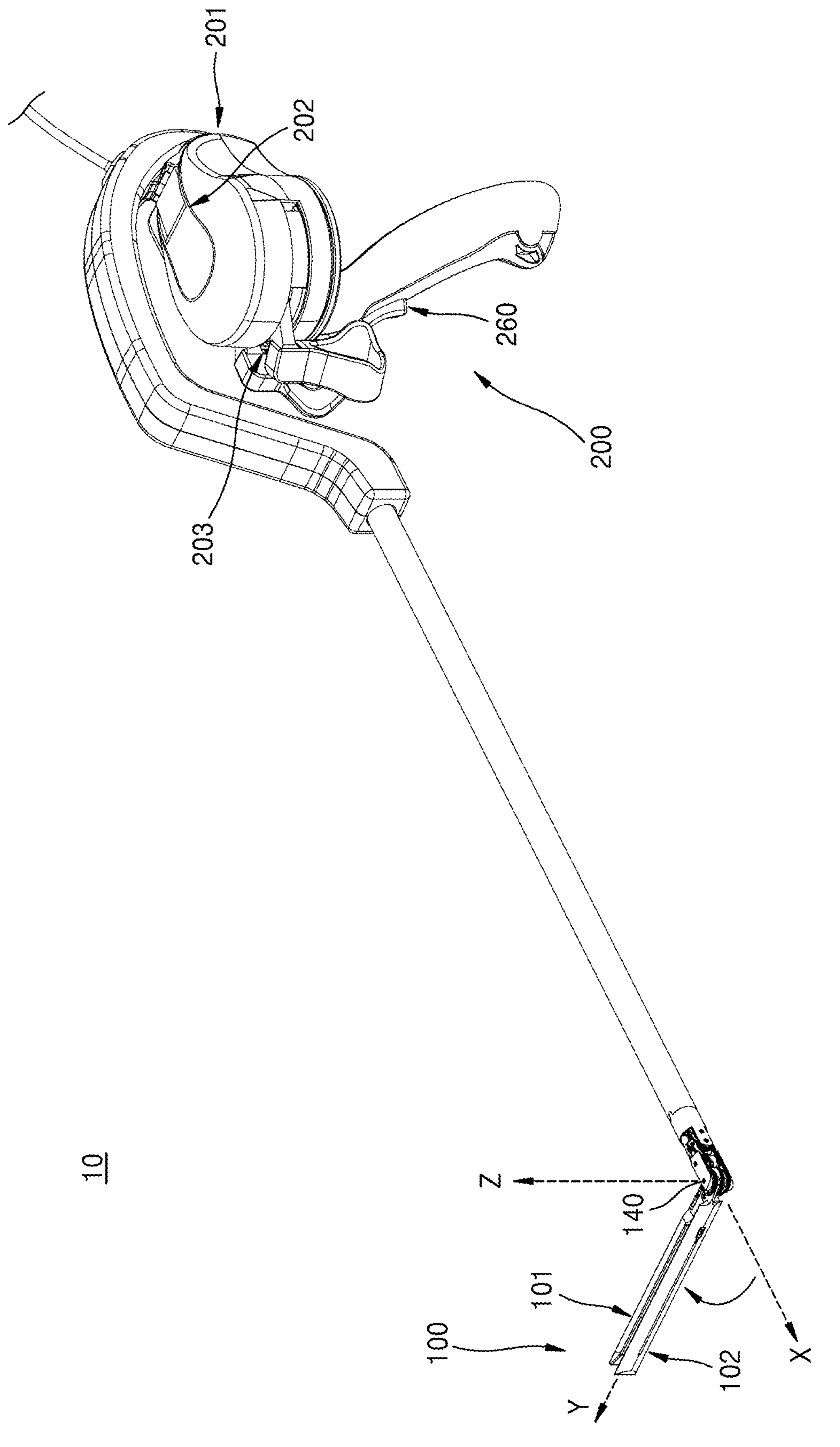

FIG. 68 is a view illustrating a state in which the jaws are yaw-rotated by +90°, and FIG. 69 is a view illustrating a process of performing an actuation motion in a state in which the jaws are yaw-rotated by +90°. FIG. 70 is a view illustrating a state in which the jaws are yaw-rotated by −90°, and FIG. 71 is a view illustrating a process of performing an actuation motion in a state in which the jaws are yaw-rotated by −90°.

Referring to FIGS. 68 to 71, it can be seen that, in performing a yaw motion, the motions of the manipulation part 200 and the end tool 100 are intuitively matched. That is, when the manipulation part 200 is rotated in a positive (+) direction with respect to the yaw rotation shaft (Z-axis), the end tool 100 is also rotated in the positive (+) direction with respect to the yaw rotation shaft (Z-axis). In addition, when the manipulation part 200 is rotated in a negative (−) direction with respect to the yaw rotation shaft (Z-axis), the end tool 100 is also rotated in the negative (−) direction with respect to the yaw rotation shaft (Z-axis). Here, the rotation angle of the manipulation part 200 and the rotation angle of the end tool 100 may be variously set according to the ratio of the pulleys.

Figure 72:
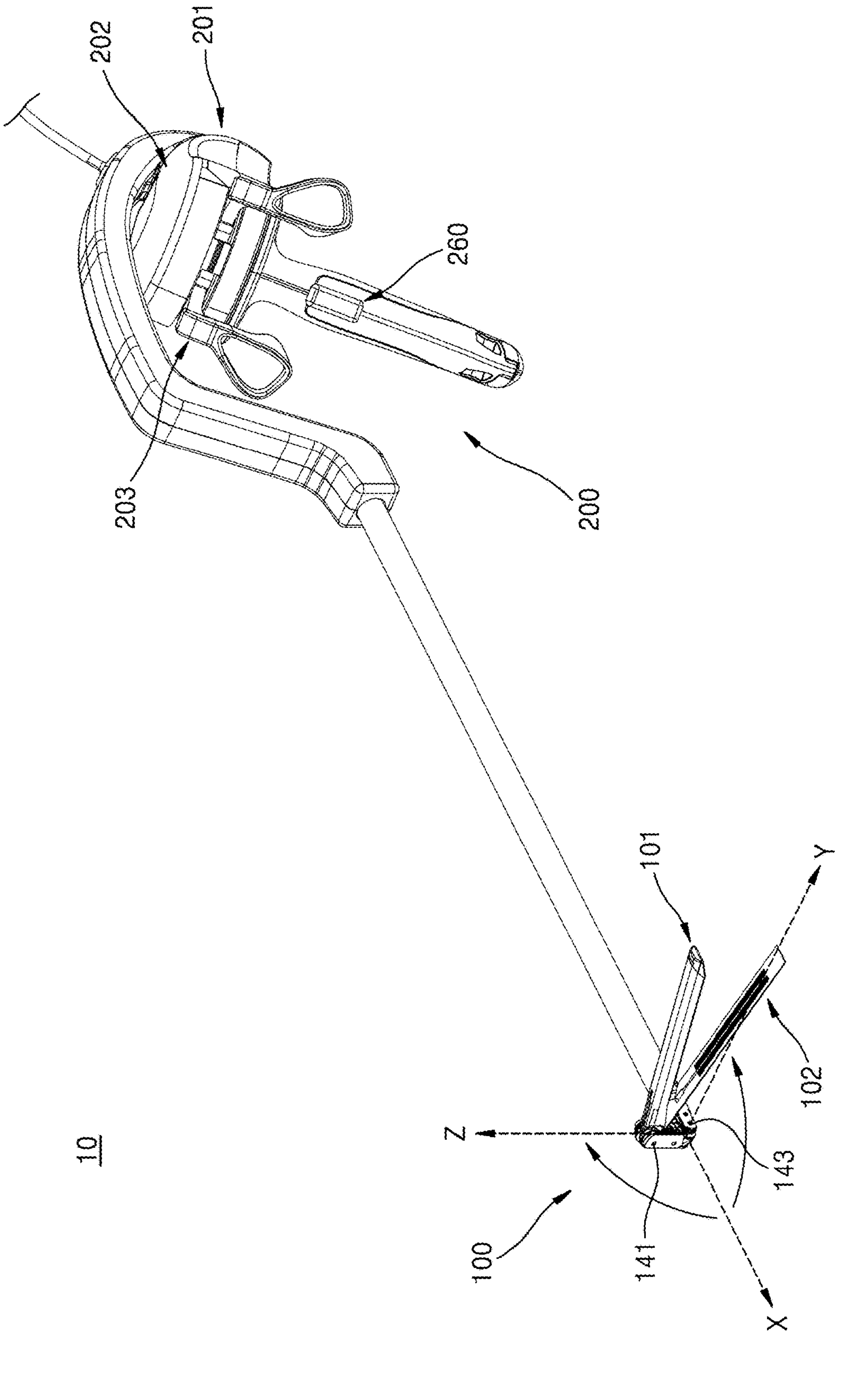
FIGS. 72 to 75 are plan views illustrating a state in which the end tool of the surgical instrument of FIG. 2 is pitch-rotated and yaw-rotated.
Figure 73:
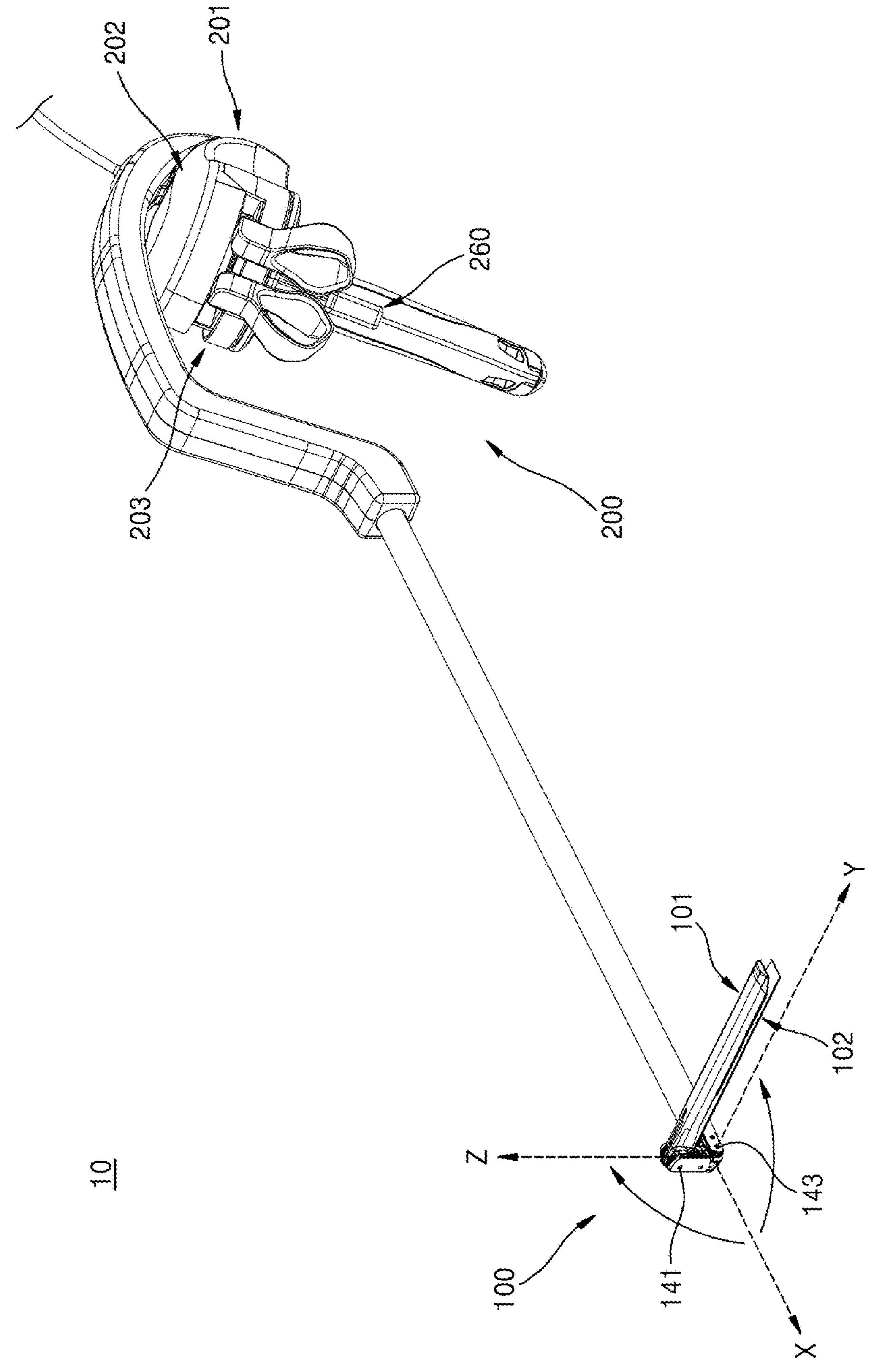
Figure 74:
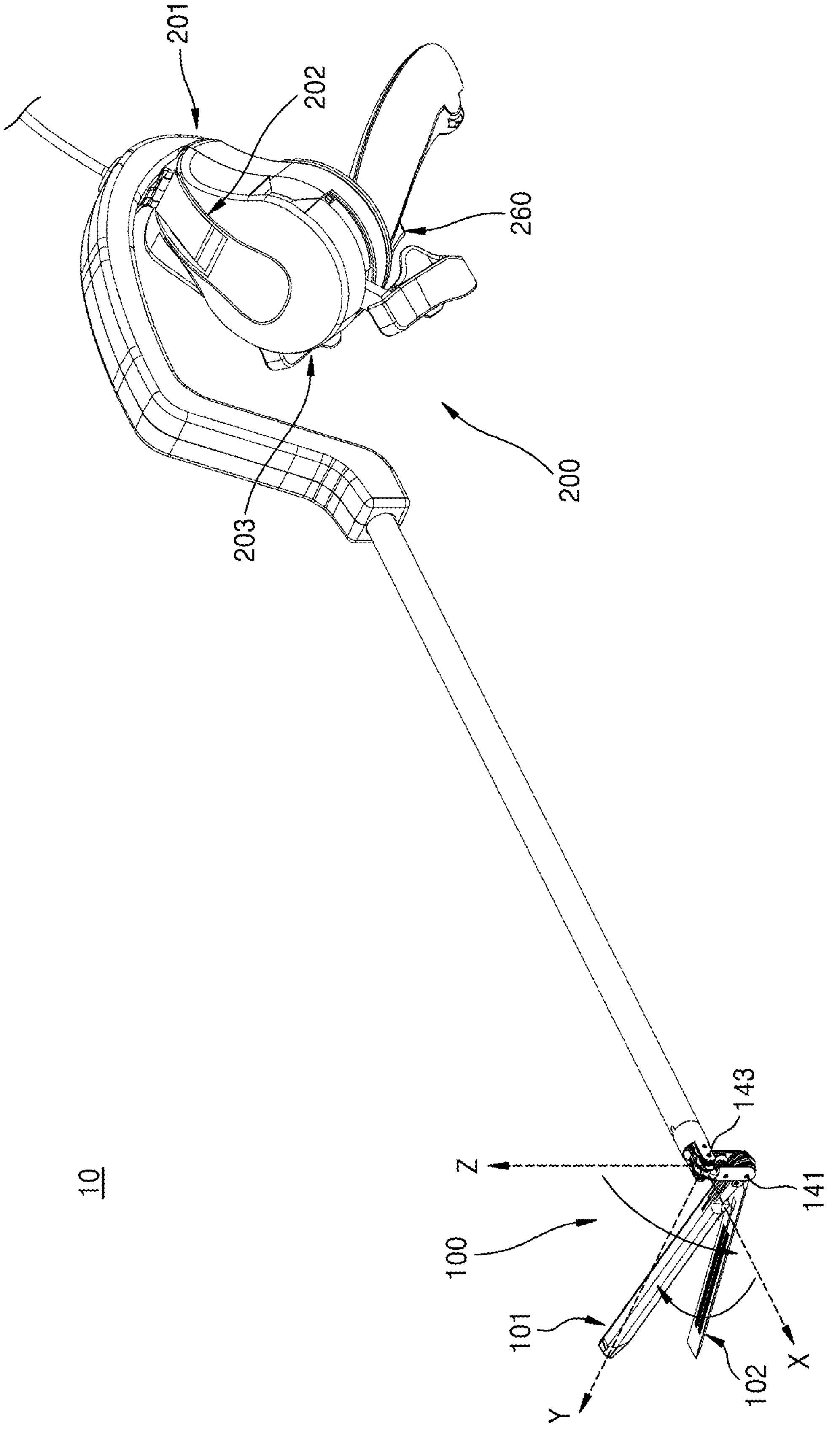
Figure 75:
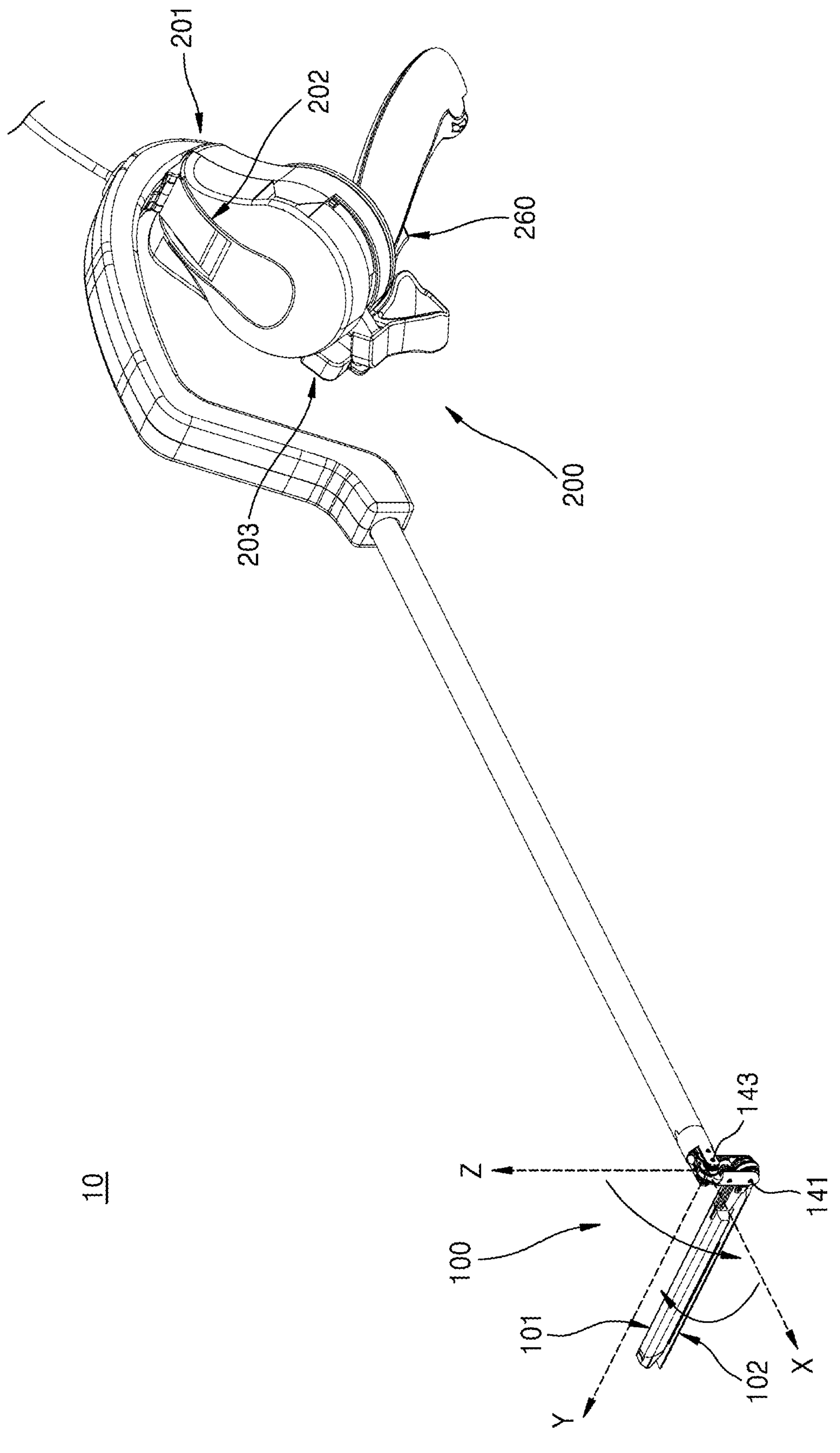

FIG. 72 is a view illustrating a state in which the jaws are pitch-rotated by −90° and at the same time yaw-rotated by +90°, and FIG. 73 is a view illustrating a process of performing an actuation motion in the state in which the jaws are pitch-rotated by −90° and at the same time yaw-rotated by +90°, FIG. 74 is a view illustrating a state in which the jaws are pitch-rotated by +90° and at the same time yaw-rotated by −90°, and FIG. 75 is a view illustrating a process of performing an actuation motion in the state in which the jaws are pitch-rotated by +90° and at the same time yaw-rotated by −90°, Referring to FIGS. 72 to 75, it can be seen that the motions of the manipulation part 200 and the end tool 100 are intuitively matched, even when performing the pitch and yaw motions simultaneously.

Second Embodiment—Engrave

Hereinafter, an end tool 700 of a surgical instrument according to a second embodiment of the present disclosure will be described. Here, the end tool 700 of the surgical instrument according to the second embodiment of the present disclosure is different from the end tool (see 100 of FIG. 2 or the like) of the surgical instrument according to the first embodiment of the present disclosure described above in that a configuration of an end tool hub 780 serving as an auxiliary pulley is different. The configuration changed from the first embodiment as described above will be described in detail later.

Figure 87:
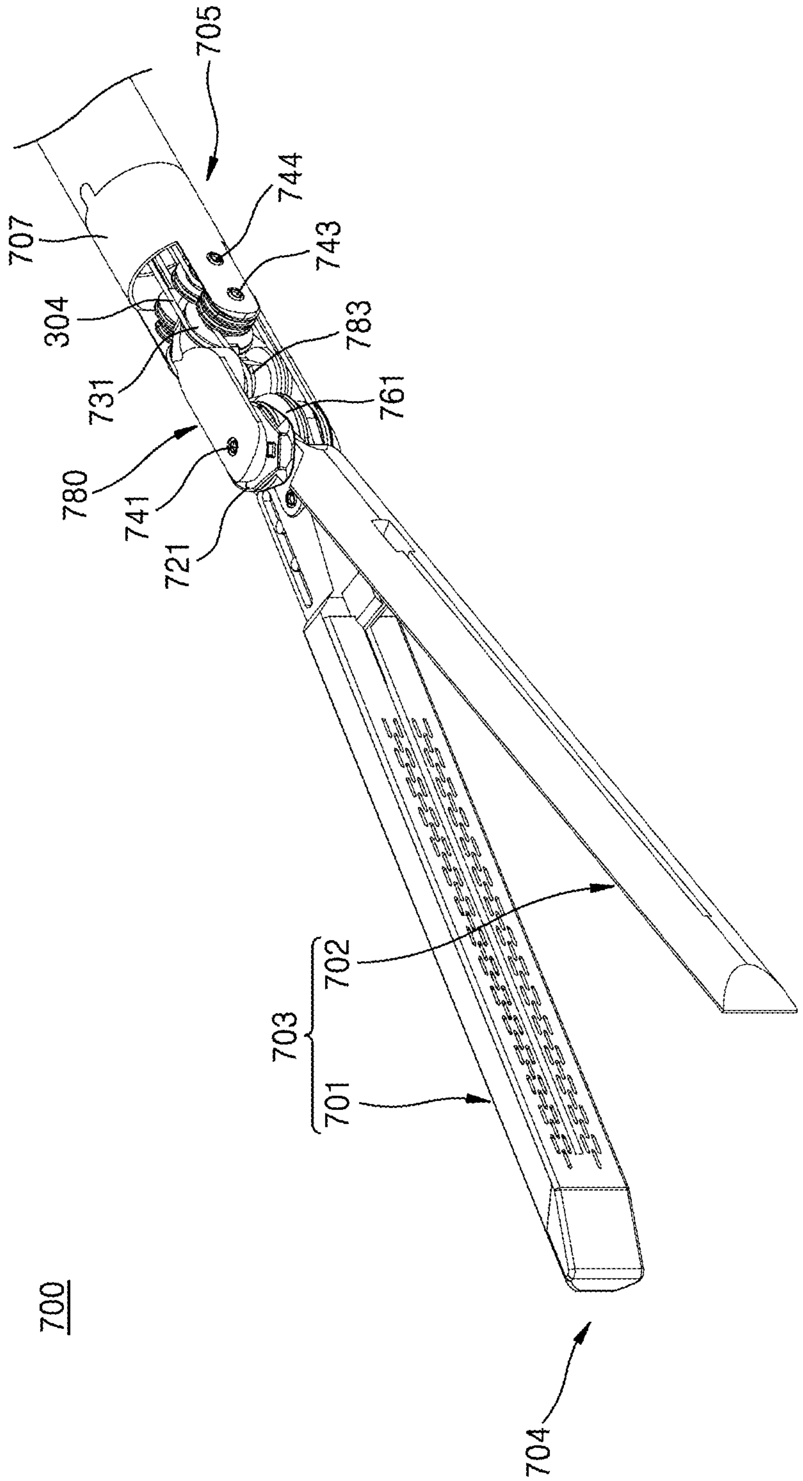
FIG. 87 is a perspective view illustrating an end tool of a surgical instrument according to a second embodiment of the present disclosure.
Figure 88:
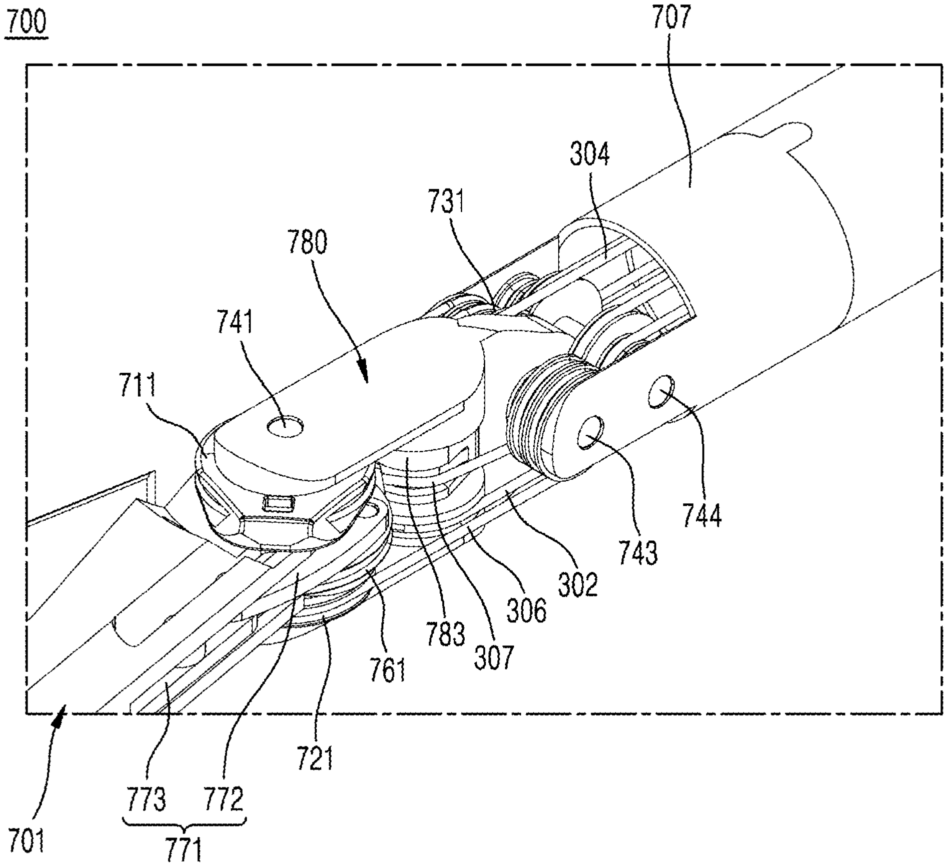
FIGS. 88 and 89 are magnified views of the end tool of the surgical instrument of FIG. 87.
Figure 89:
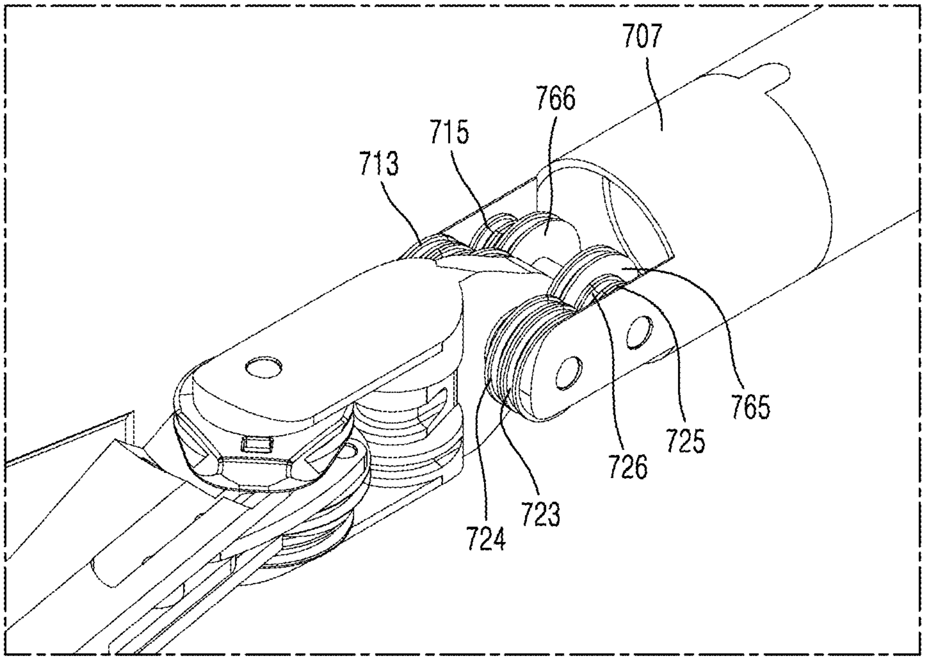
Figure 90:
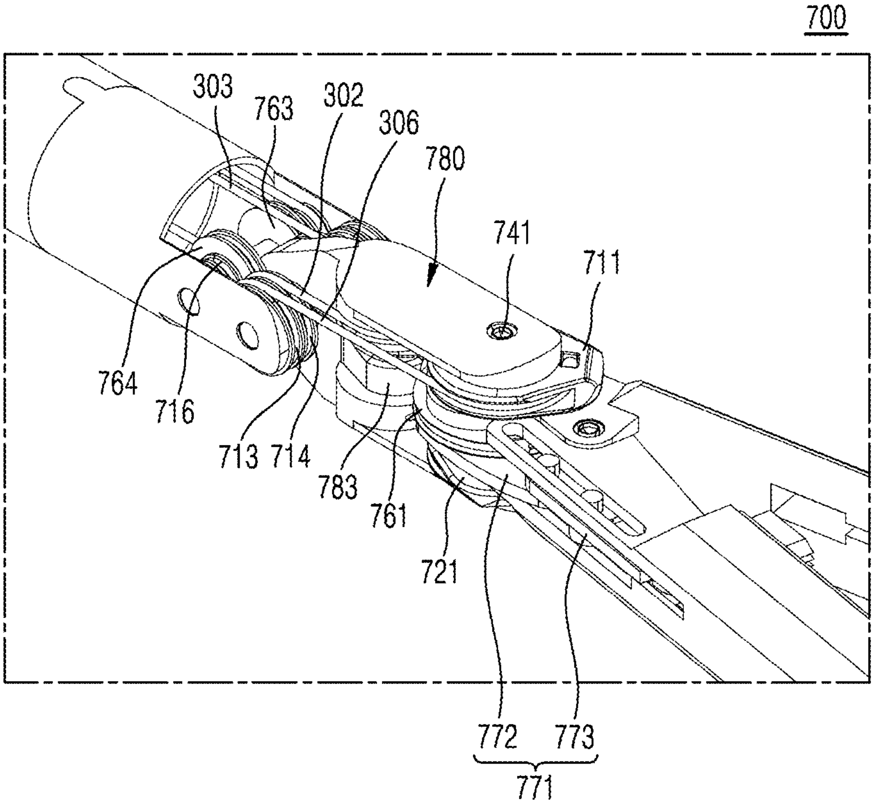
FIGS. 90 and 91 are magnified views illustrating the end tool of the surgical instrument of FIG. 87 from a different angle.
Figure 91:
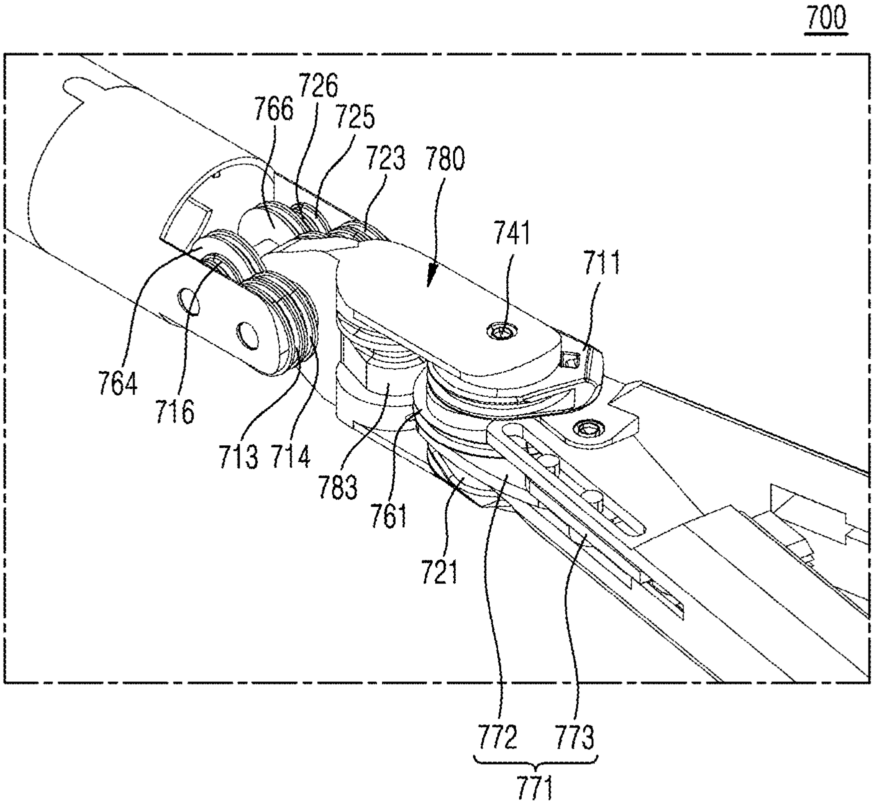
Figure 92:
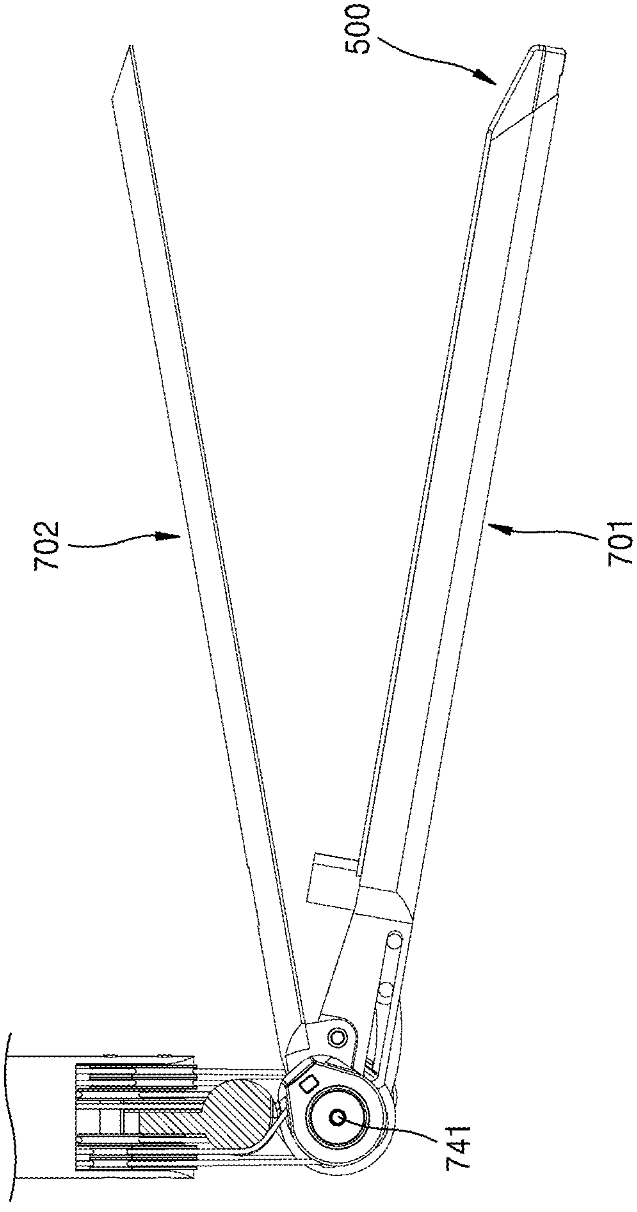
FIGS. 92 and 93 are views illustrating a state in which jaws of the end tool of the surgical instrument of FIG. 87 are yaw-rotated by 90° in a counterclockwise direction.
Figure 93:
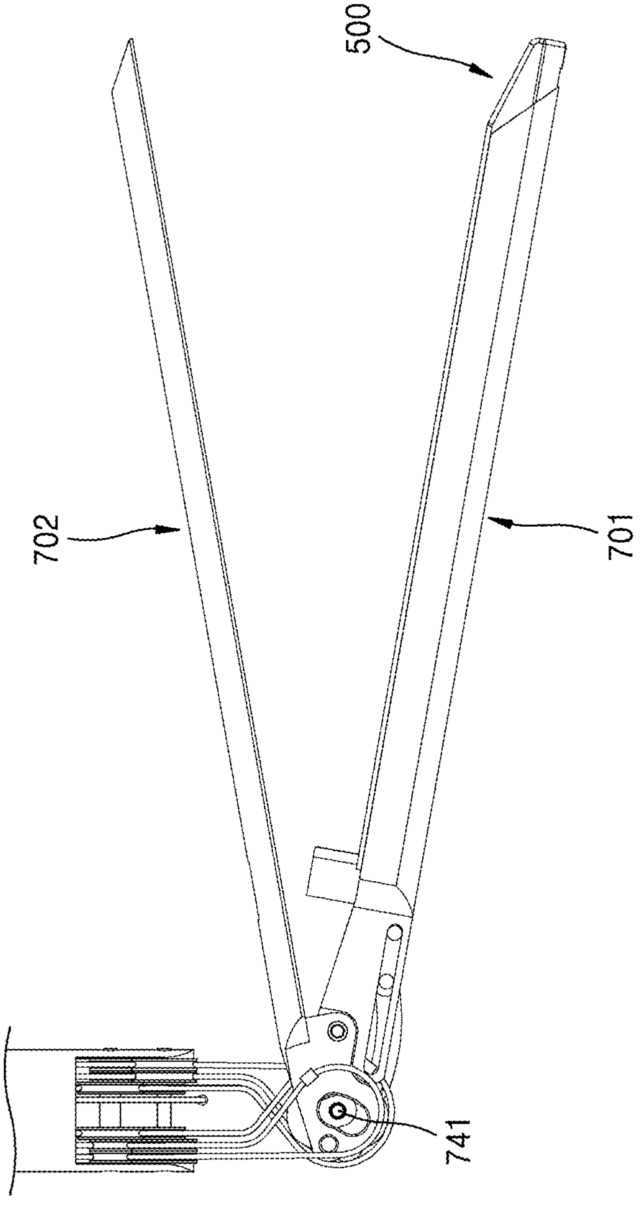
Figure 94:
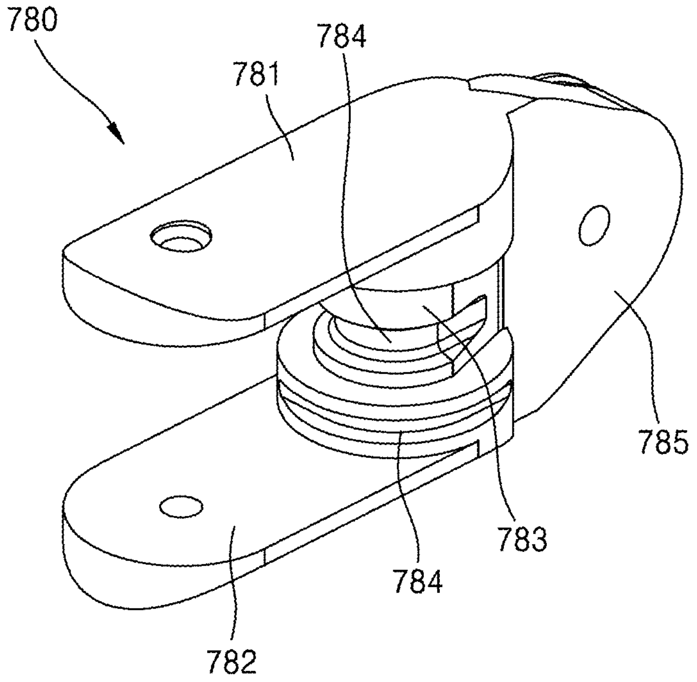
FIG. 94 is a magnified perspective view illustrating an end tool hub of the surgical instrument of FIG. 87.

FIG. 87 is a perspective view illustrating the end tool of the surgical instrument according to the second embodiment of the present disclosure, and FIGS. 88 and 89 are magnified views of the end tool of the surgical instrument of FIG. 87. FIGS. 90 and 91 are magnified views illustrating the end tool of the surgical instrument of FIG. 87 from a different angle. FIGS. 92 and 93 are views illustrating a state in which jaws of the end tool of the surgical instrument of FIG. 87 are yaw-rotated by 90° in a counterclockwise direction. FIG. 94 is a magnified perspective view illustrating the end tool hub of the surgical instrument of FIG. 87.

Here, FIGS. 89 and 91 illustrate a state in which wires are removed, and FIG. 93 illustrates a state in which jaw pulley coupling parts and jaw pulleys of the end tool hub are removed.

Referring to FIGS. 87 to 94, the end tool 700 of the second embodiment of the present disclosure includes a pair of jaws, that is, a first jaw 701 and a second jaw 702 for performing a grip motion, and here, each of the first jaw 701 and the second jaw 702 or a component encompassing the first jaw 701 and the second jaw 702 may be referred to as a jaw 703.

Meanwhile, the end tool 700 includes a plurality of pulleys including a pulley 711, a pulley 713, and a pulley 714 that are related to a rotational motion of the first jaw 701. The pulleys related to the rotational motion of the first jaw 701 described in the present embodiment are substantially the same as the pulley 113, the pulley 114, the pulley 115, and the pulley 116 described with reference to FIG. 8 or the like of the first embodiment, and thus, detailed descriptions thereof will be omitted herein.

Meanwhile, the end tool 700 includes a plurality of pulleys including a pulley 721 related to a rotational motion of the second jaw 702. The pulleys related to the rotational motion of the second jaw 702 described in the present embodiment are substantially the same as the pulley 123, the pulley 124, the pulley 125, and the pulley 126 described with reference to FIG. 8 or the like of the first embodiment, and thus, detailed descriptions thereof will be omitted herein.

In addition, the end tool 700 of the second embodiment of the present disclosure may include a rotation shaft 741, a rotation shaft 743, and a rotation shaft 744. Here, the rotation shaft 741 may be inserted through the end tool hub 780, and the rotation shaft 743 and the rotation shaft 744 may be inserted through a pitch hub 707. The rotation shaft 741, the rotation shaft 743, and the rotation shaft 744 may be arranged sequentially from a distal end 704 of the end tool 700 toward a proximal end 705.

In addition, the end tool 700 of the second embodiment of the present disclosure may include the end tool hub 780 and the pitch hub 707.

The rotation shaft 741, which will be described later, is inserted through the end tool hub 780, and the pulley 711 and the pulley 721, which are axially coupled to the rotation shaft 741, and at least some of the first jaw 701 and the second jaw 702 coupled to the pulley 711 and the pulley 721 may be accommodated inside the end tool hub 780. Here, in an embodiment of the present disclosure, a guide part 783 serving as an auxiliary pulley is formed in the end tool hub 780. That is, the guide part 783 configured to guide paths of the wires 305 and 302 may be formed in the end tool hub 780. The guide part 783 of the end tool hub 780 may serve as the auxiliary pulleys (see 112, 122, and 162 of FIG. 9) of the first embodiment and change the paths of the wires, and the guide part 783 of the end tool hub 780 serving as the auxiliary pulley will be described in more detail later.

Meanwhile, a pulley 731 serving as an end tool pitch pulley may be formed at one end portion of the end tool hub 780. The pulley 731 may be formed as a separate member from the end tool hub 780 to be coupled to the end tool hub 780. Alternatively, the pulley 731 may be integrally formed with the end tool hub 780 as one body. In addition, the wire (see 303 of FIG. 5) and the wire (see 304 of FIG. 5) are coupled to the pulley 731 serving as an end tool pitch pulley, and the pulley 731 is rotated around the rotation shaft 743 to perform a pitch motion.

The rotation shaft 743 and the rotation shaft 744 are inserted through the pitch hub 707, and the pitch hub 707 may be axially coupled to the end tool hub 780 and the pulley 731 by the rotation shaft 743. Accordingly, the end tool hub 780 and the pulley 731 may be formed to be pitch-rotatable around the rotation shaft 743 with respect to the pitch hub 707.

Meanwhile, the end tool 700 of the second embodiment of the present disclosure may further include components such as a staple drive assembly (see 150 of FIG. 13) including a staple pulley assembly (see 160 of FIG. 13) and a staple link assembly (see 170 of FIG. 13) to perform stapling and cutting motions.

The staple pulley assembly (see 160 of FIG. 13) may be formed between the pulley 711 and the pulley 721 to be adjacent to the pulley 711 and the pulley 721. In the present embodiment, it is assumed that the staple pulley assembly (see 160 of FIG. 13) includes one staple pulley 761.

The staple link assembly (see 170 of FIG. 13) may include one or more link members 771. The staple link assembly (see 170 of FIG. 13) may serve to connect the staple pulley assembly 760 to a reciprocating assembly (see 550 of FIG. 22) of a cartridge (see 500 of FIG. 22). In the present embodiment, it is assumed that the staple link assembly (see 170 of FIG. 13) includes one link member 771, and the link member 771 includes a first link 772 and a second link 773.

Meanwhile, in the second embodiment of the present disclosure, by disposing the staple pulley assembly (see 160 of FIG. 13) and the staple link assembly (see 170 of FIG. 13) between the pulley 711, which is a first jaw pulley, and the pulley 721, which is a second jaw pulley, the end tool 700 is allowed to perform pitch and yaw motions, as well as stapling and cutting motions using the cartridge (see 500 of FIG. 22). In the present embodiment, components for performing stapling and cutting motions are substantially the same as those described in the first embodiment, and thus detailed descriptions thereof will be omitted herein.

The surgical instrument according to the second embodiment of the present disclosure may include a wire 301, a wire 302, a wire 303, a wire 304, a wire 305, a wire 306, a wire 307, and a wire 308 as in the first embodiment of the present disclosure described with reference to FIG. 7 or the like.

In addition, the surgical instrument according to the second embodiment of the present disclosure may include a coupling member 321, a coupling member 323, a coupling member 324, a coupling member 326, a coupling member 327, and a coupling member 329, which are coupled to respective end portions of the wires to couple the wires and the pulleys, as in the first embodiment of the present disclosure described with reference to FIG. 7 or the like.

Hereinafter, the end tool hub 780 of the second embodiment of the present disclosure will be described in more detail, and in particular, the guide part 783 of the end tool hub 780 serving as an auxiliary pulley will be mainly described.

The end tool hub 780 includes a first jaw pulley coupling part 781, a second jaw pulley coupling part 782, a guide part 783, a guide groove 784, and a pitch pulley coupling part 785.

In detail, the first jaw pulley coupling part 781 and the second jaw pulley coupling part 782 are formed to face each other, and the pulley 711, the pulley 721, and the staple pulley 761 are accommodated inside the first jaw pulley coupling part 781 and the second jaw pulley coupling part 782. In addition, a through hole is formed in each of the jaw pulley coupling parts 781 and 782, and thus the rotation shaft 741 passes through the jaw pulley coupling parts 781 and 782, the pulley 711, the pulley 721, and the staple pulley 761 and axially couples them.

The first jaw pulley coupling part 781 and the second jaw pulley coupling part 782 are connected by the guide part 783. That is, the first jaw pulley coupling part 781 and the second jaw pulley coupling part 782 parallel to each other are coupled by the guide part 783 formed in a direction substantially perpendicular thereto, so that the first jaw pulley coupling part 781, the second jaw pulley coupling part 782, and the guide part 783 form a substantially "C-shape," in which the pulley 711, the pulley 721, and the staple pulley 761 are accommodated.

In other words, it may be said that the first jaw pulley coupling part 781 and the second jaw pulley coupling part 782 are formed to extend in an X-axis direction from both end portions of the guide part 783 that is formed long in a Z-axis direction.

Here, the guide part 783 may be formed in a cylindrical shape with a cross section that is approximately semi-circular. In addition, the semi-circular portion may protrude toward the pulley 711, the pulley 721, and the staple pulley 761. In other words, it may be said that the guide part 783 is formed to protrude toward a space formed by the first jaw pulley coupling part 781, the second jaw pulley coupling part 782, and the guide part 783. In other words, it may be said that a region of the guide part 783 adjacent to the jaw pulley coupling parts 781 and 782 is formed such that a cross section thereof is curved with a predetermined curvature.

Alternatively, in other words, it may be also said that the guide part 783 functions as a kind of pulley member around which the wire 305, the wire 302, the wire 307, and the wire 308 are wound to guide the paths of the wire 305, the wire 302, the wire 307, and the wire 308. However, here, the guide part 783 is not a member that is rotated around a certain axis like the original meaning pulley does, and it may be said that the guide part 783 is formed to be fixed as a portion of the end tool hub 780 and performs some similar functions of a pulley by winding a wire therearound.

Here, the guide part 783 is illustrated in the drawing as being formed in a cylindrical shape with a cross section that is approximately semi-circular. That is, at least a portion of the cross section of the guide part 783 on the XY plane is illustrated as having a certain arc shape. However, the concept of the present disclosure is not limited thereto, and the cross section may have a predetermined curvature like an oval or a parabola, or a corner of a polygonal column is rounded to a certain extent, so that the cross section may have various shapes and sizes suitable for guiding the paths of the wire 305, the wire 302, the wire 307, and the wire 308.

Here, in order to more effectively guide the paths of the wire 305, the wire 302, the wire 307, and the wire 308, the guide groove 784 may be further formed at a portion of the guide part 783 in contact with the wire 305, the wire 302, the wire 307, and the wire 308. The guide groove 784 may be formed in the form of a groove recessed to a certain extent from a protruding surface of the guide part 783.

Here, although the guide groove 784 is illustrated in the drawing as being formed in the entire arc surface of the guide part 783, the concept of the present disclosure is not limited thereto, and the guide groove 784 may be formed only in a portion of the arc surface of the guide part 783 as necessary.

By further forming the guide groove 784 in the guide part 783 as described above, the durability of the wire may be improved.

The pitch pulley coupling part 785 may be further formed in a direction opposite to a direction of formation of the jaw pulley coupling parts 781 and 782 in the guide part 783. The pitch pulley coupling part 785 may be formed in a direction parallel to the pulley 731 that is a pitch pulley, i.e., on the XZ plane. A through hole through which the rotation shaft 743 may be inserted may be formed in the pitch pulley coupling part 785, and the rotation shaft 743 may be inserted through the pitch pulley coupling part 785 and the pulley 731 to couple the pitch pulley coupling part 785 and the pulley 731. Here, the pitch pulley coupling part 785 is formed to be biased to a certain extent from the center to one side when viewed from the XY plane, thereby being balanced as a whole when coupled with the pulley 731.

Hereinafter, the role and function of the guide part 783 will be described in more detail.

The guide part 783 may be in contact with the wire 305 and the wire 302 and may change the arrangement path of the wires 305 and 302 to a certain extent to serve to increase a rotation radius of each of the first jaw 701 and the second jaw 702.

In addition, the guide part 783 may serve to increase the radius of rotation of the staple pulley 761 by coming into contact with the wires 307 and 308, which are blade wires, to change the arrangement path of the wires 307 and 308 to a certain extent.

That is, when the auxiliary pulley is not disposed, each of the first jaw pulley 711, the second jaw pulley 721, and the staple pulley 761 may be rotated up to a right angle, but in the second embodiment of the present disclosure, by additionally providing the guide part 783 in the end tool hub 780, the maximum rotation angle of each pulley may be increased.

This enables a motion that two jaws of the end tool 700 have to open for an actuation motion in a state in which the two jaws of the end tool 700 are yaw-rotated by 90°. In other words, a feature of increasing the range of a yaw rotation in which an actuation motion is possible may be obtained through the configuration of the guide part 783 of the end tool hub 780. In other words, a feature of increasing the range of a yaw rotation in which an actuation motion is possible may be obtained through the configuration of the guide part 783 of the end tool hub 780.

In addition, the guide part 783 of the end tool hub 780, which serves as an auxiliary pulley, allows a staple pulley 761 to further rotate for a cutting motion in a state in which the two jaws are yaw-rotated by 90°. In other words, a feature of increasing the range of a yaw rotation in which a cutting motion is possible may be obtained through the configuration of the guide part 783 of the end tool hub 780.

Furthermore, by forming the guide part 783 in the end tool hub 780, which already exists, without adding a separate structure such as an auxiliary pulley, the range of rotation may be increased without adding a component and a manufacturing process.

As described above, since there is no need to additionally dispose a separate structure for increasing the rotation angle, the number of components is decreased and the manufacturing process is simplified, and also a length of the end tool is shortened by as much as the size of the auxiliary pulley, so that the length of the end tool is shortened during a pitch motion. Accordingly, a surgical motion may be more easily performed in a narrow space.

This will be described below in more detail.

In the end tool 700 of the surgical instrument according to the second embodiment of the present disclosure, the arrangement path of the wires may be changed without a separate structure by forming the guide part 783 capable of changing the path of the wire on an inner side wall of the end tool hub 780. As described above, as the arrangement paths of the wires 305, 302, 307, and 308 are changed to a certain extent by forming the guide part 783 on the end tool hub 780, tangential directions of the wires 305, 302, 307, and 308 are changed, and accordingly, the rotation angles of the coupling members 323, 326, and 329, which respectively couple the wires and the pulleys, are increased.

That is, the coupling member 326 that couples the wire 302 and the pulley 721 is rotatable until being located on a common internal tangent of the pulley 721 and the guide part 783. Similarly, the coupling member (see 323 of FIG. 8) that couples the wire 305 and the pulley 711 is rotatable until being located on a common internal tangent of the pulley 711 and the guide part 783, so that a rotation angle of the coupling member (see 323 of FIG. 8) may be increased. Similarly, the coupling member 329 that couples the wires 307 and 308 and the pulley 761 is rotatable until being located on a common internal tangent of the pulley 761 and the guide part 783, so that a rotation angle of the coupling member 329 may be increased.

In other words, due to the guide part 783, the wire 301 and the wire 305 wound around the pulley 711 are disposed on one side with respect to a plane perpendicular to the Y-axis and passing through the X-axis. Simultaneously, due to the guide part 783, the wires 302 and 306 wound around the pulley 721 are disposed on the other side with respect to the plane perpendicular to the Y-axis and passing through the X-axis.

In other words, the pulley 713 and the pulley 714 are disposed at one side with respect to the plane perpendicular to the Y-axis and passing through the X-axis, and a pulley 723 and a pulley 724 are disposed at the other side with respect to the plane perpendicular to the Y-axis and passing through the X-axis.

In other words, the wire 305 is located on the internal tangent of the pulley 711 and the guide part 783, and the rotation angle of the pulley 711 is increased by the guide part 783. In addition, the wire 302 is located on the internal tangent of the pulley 721 and the guide part 783, and the rotation angle of the pulley 721 is increased by the guide part 783.

In the present modified example in which an auxiliary pulley is not formed and the guide part 783 capable of changing the path of the wire is formed on the inner side wall of the end tool hub 780, the length of the end tool of the surgical instrument may be shortened as compared to the surgical instrument of the first embodiment in which a separate auxiliary pulley is formed. Since the length of the end tool is shortened as described above, a surgical operator may easily manipulate a surgical instrument, and a side effect of surgery may be reduced when the surgery is performed in a narrow surgical space in the human body.

According to the present disclosure described above, as the rotation radii of the pulley 711, which is a first jaw pulley, the pulley 721, which is a second jaw pulley, and the staple pulley 761 increase, a yaw motion range in which a normal opening/closing actuation motion and a normal cutting motion may be performed may be increased.

Third Embodiment—Direct-Connection Type

Hereinafter, an end tool 800 of a surgical instrument according to a third embodiment of the present disclosure will be described. Here, the end tool 800 of the surgical instrument according to the third embodiment of the present disclosure is different from the end tool (see 100 of FIG. 2 or the like) of the surgical instrument according to the first embodiment of the present disclosure described above in that the configuration and coupling relationship of a first jaw 801 and a second jaw 802 are different. Hereinafter, the configuration that is different from that of the first embodiment will be described in detail.

Figure 95:
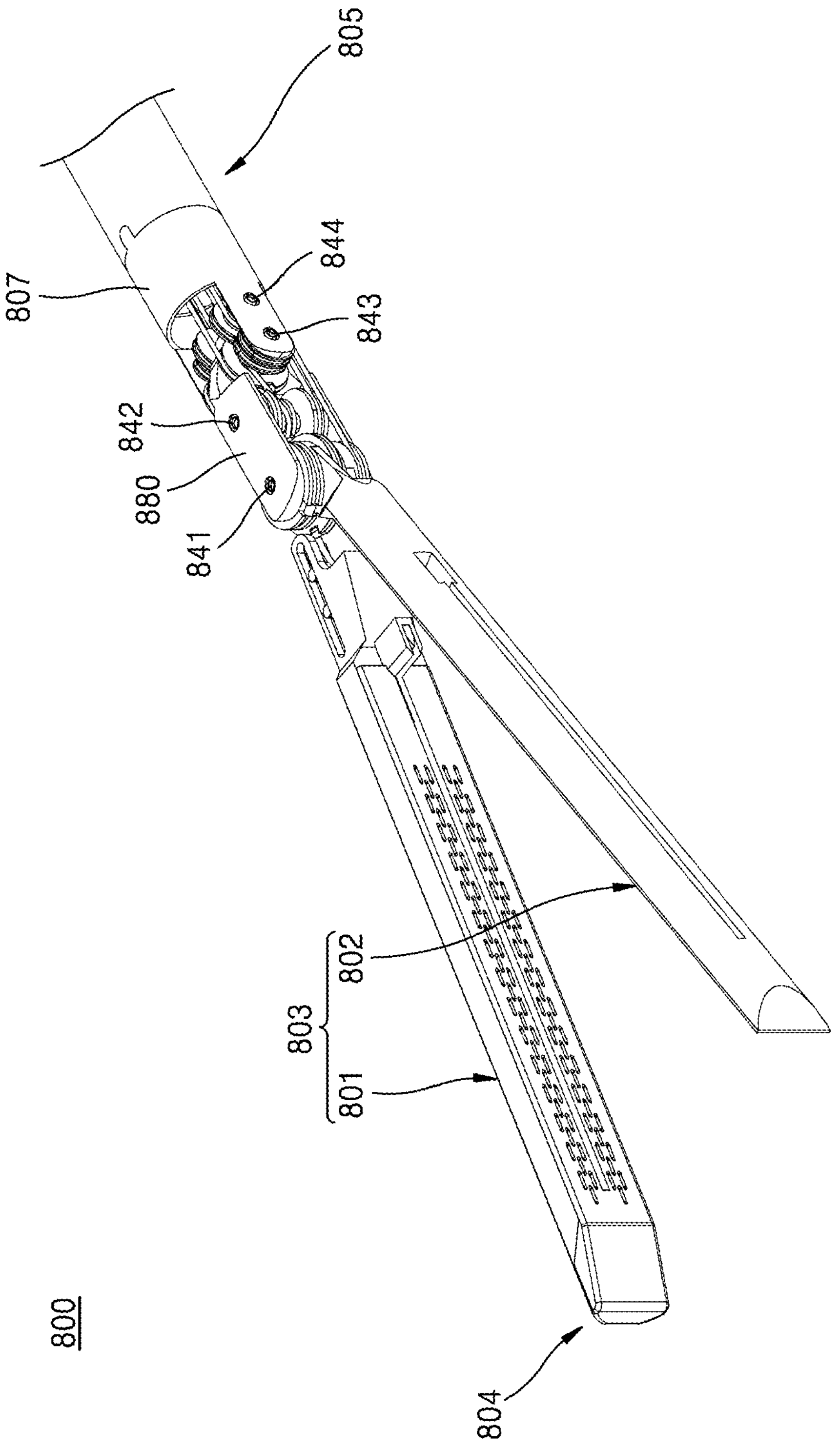
FIGS. 95 and 96 are perspective views illustrating an end tool of a surgical instrument according to a third embodiment of the present disclosure.
Figure 96:
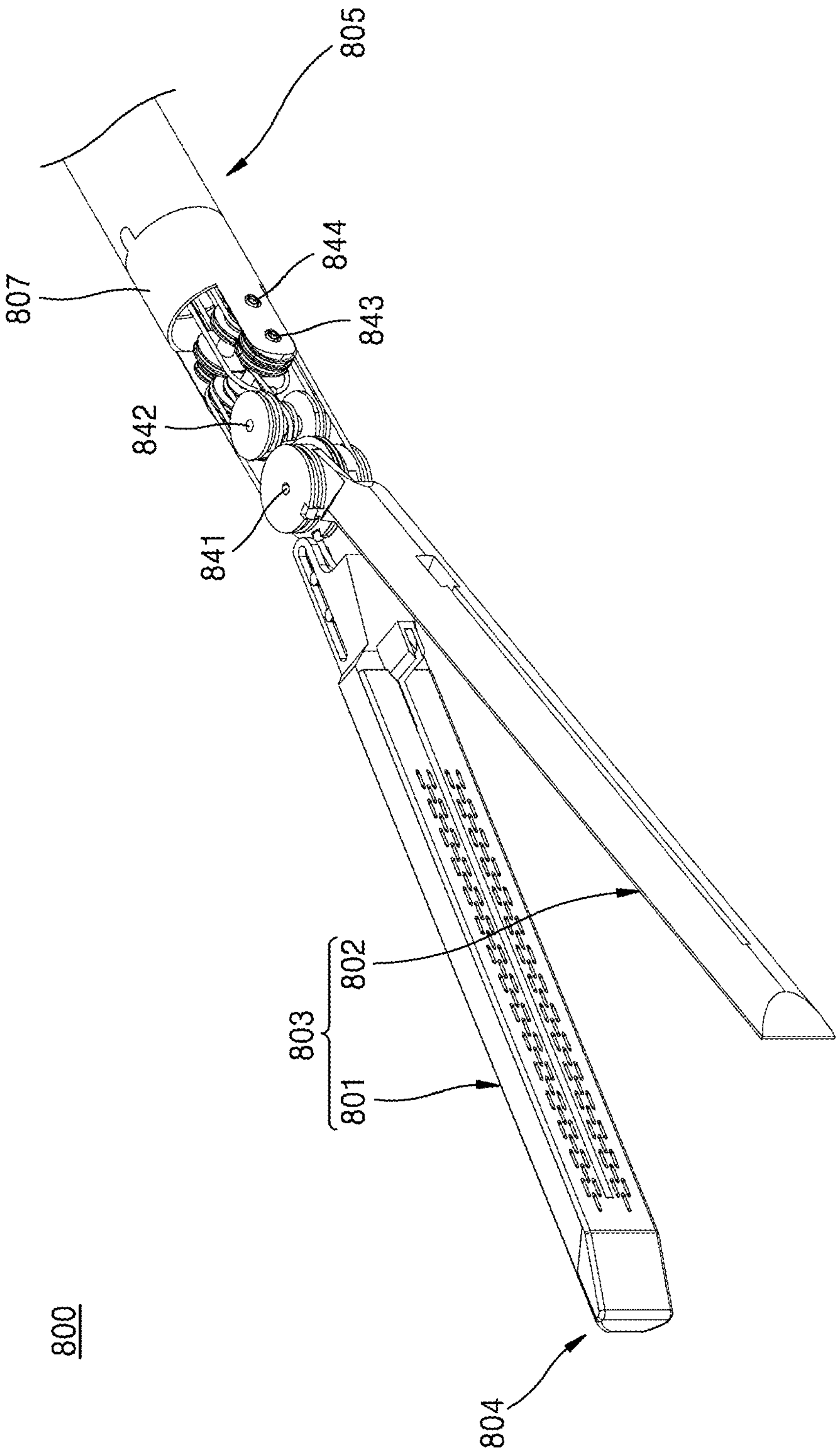
Figure 97:
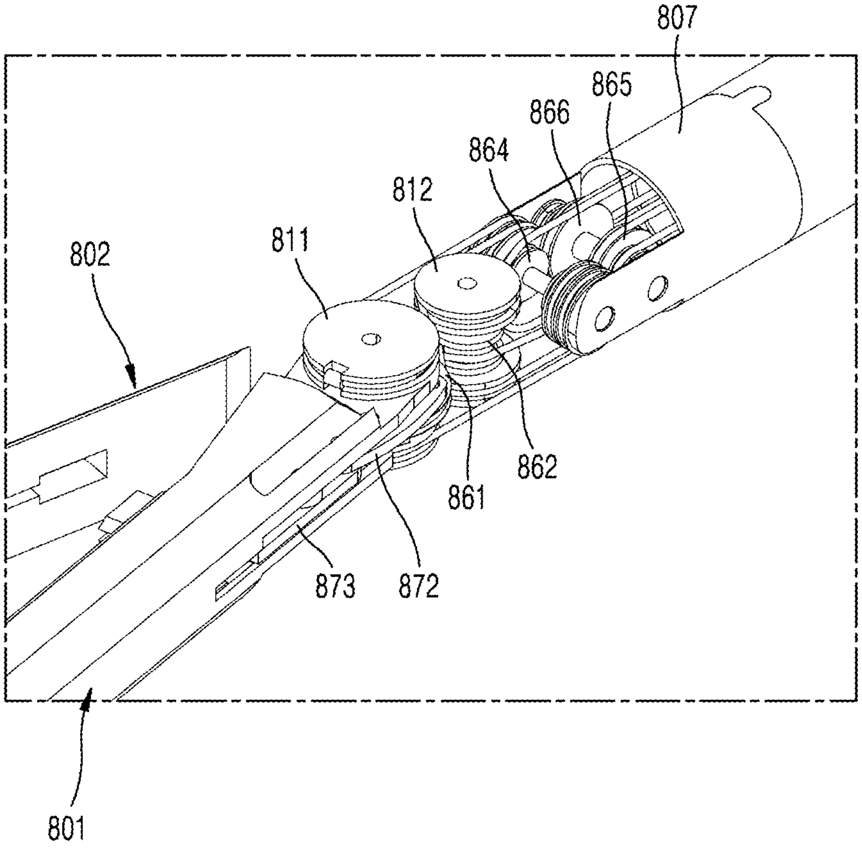
FIG. 97 is a perspective view illustrating a state in which the end tool of the surgical instrument of FIG. 96 is opened.
Figure 98:
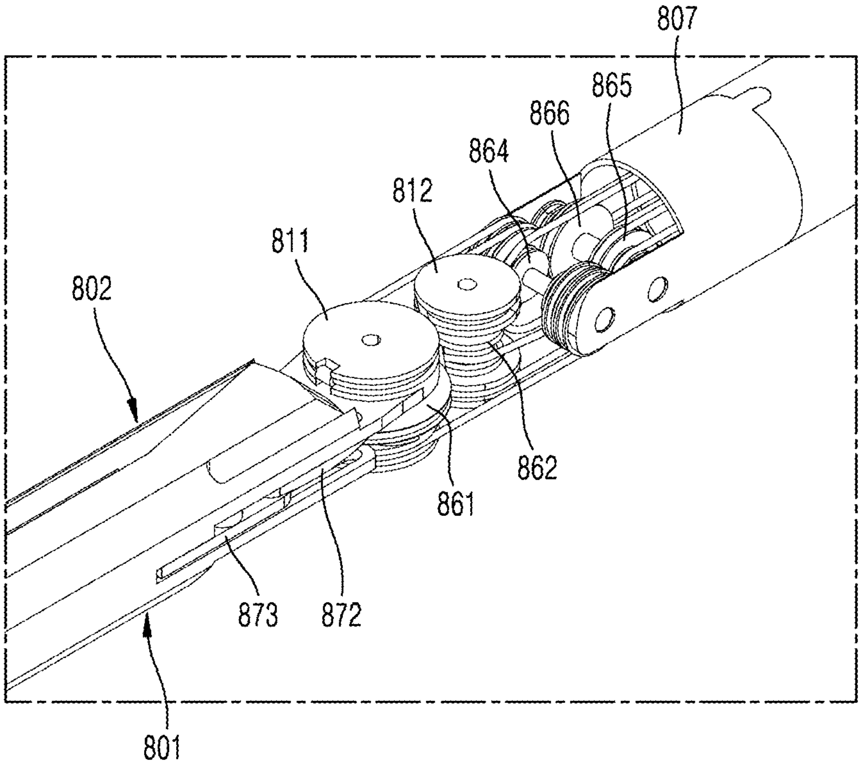
FIG. 98 is a perspective view illustrating a state in which the end tool of the surgical instrument of FIG. 96 is closed.
Figure 99:
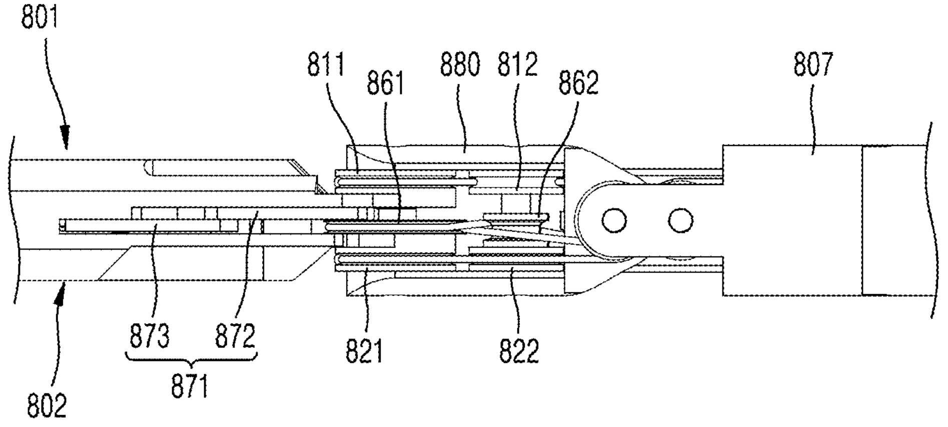
FIG. 99 is a side view illustrating the end tool of the surgical instrument of FIG. 96.
Figure 100:
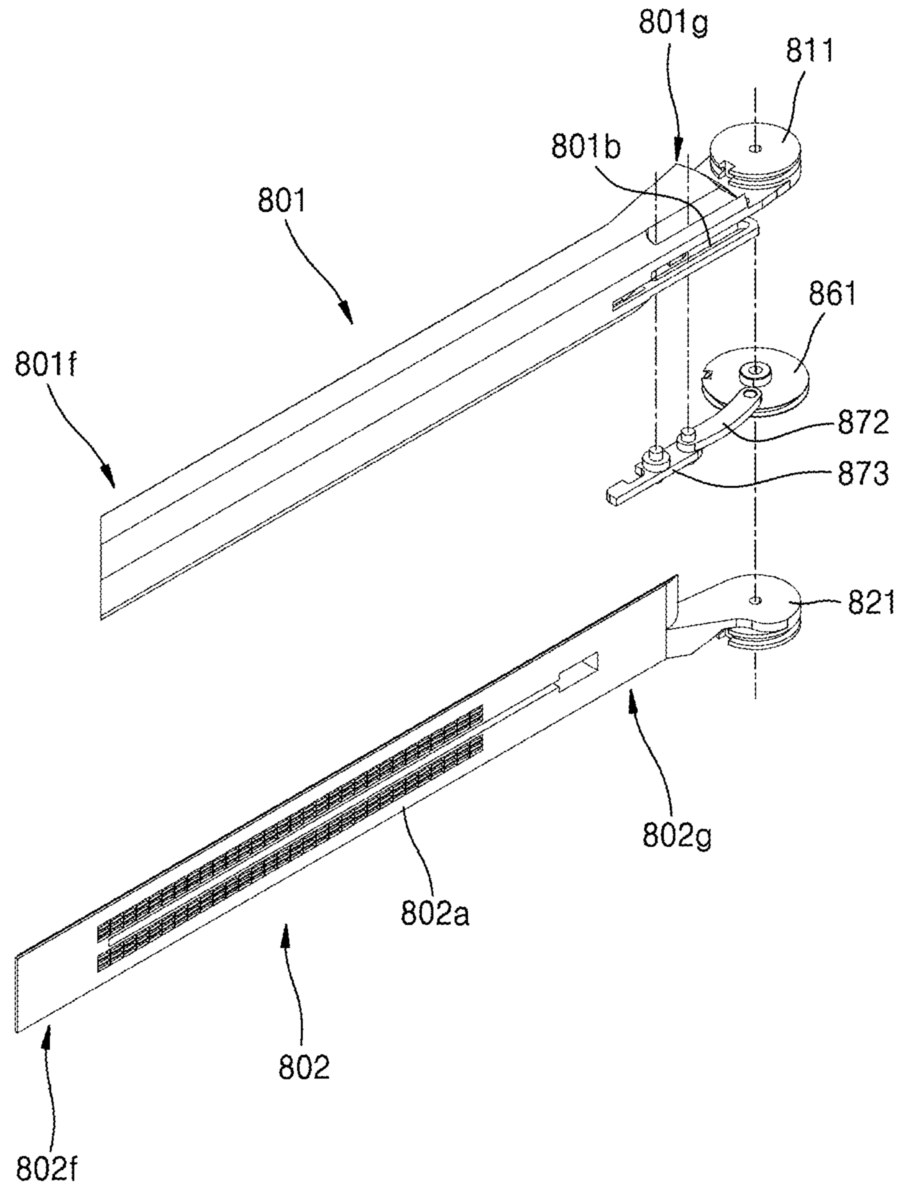
FIGS. 100 and 101 are exploded perspective views of the end tool of the surgical instrument of FIG. 96.
Figure 101:
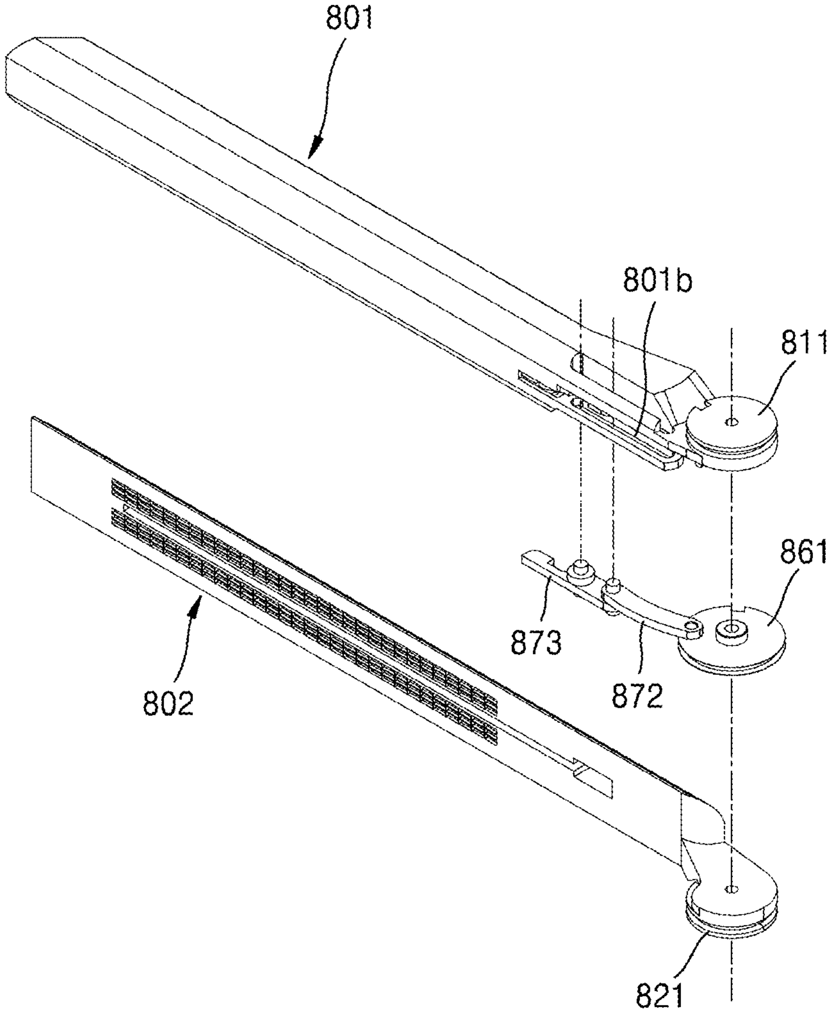
Figure 102:
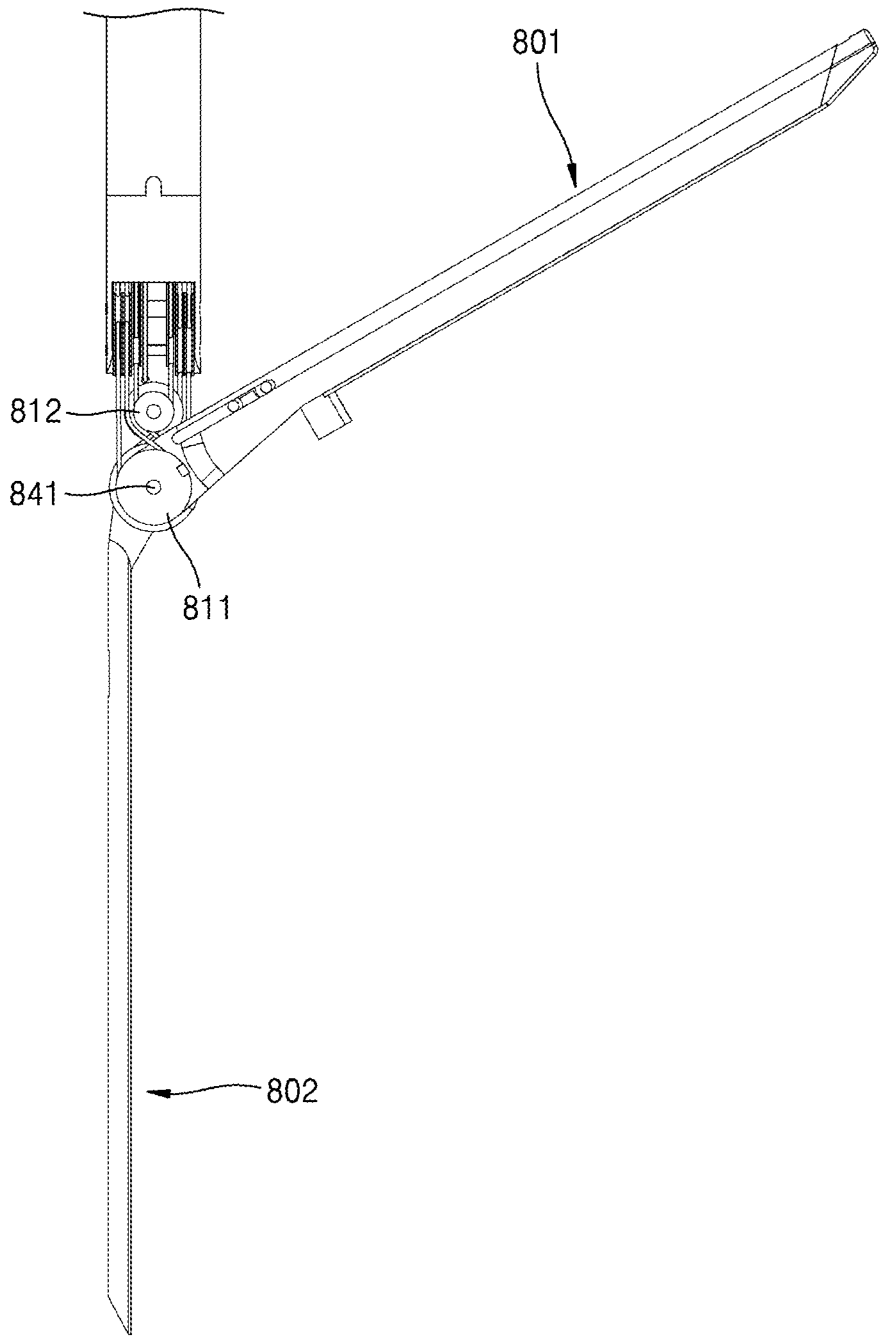
FIG. 102 is a plan view illustrating a state in which a first jaw of the end tool of the surgical instrument of FIG. 96 is fully opened.
Figure 103:
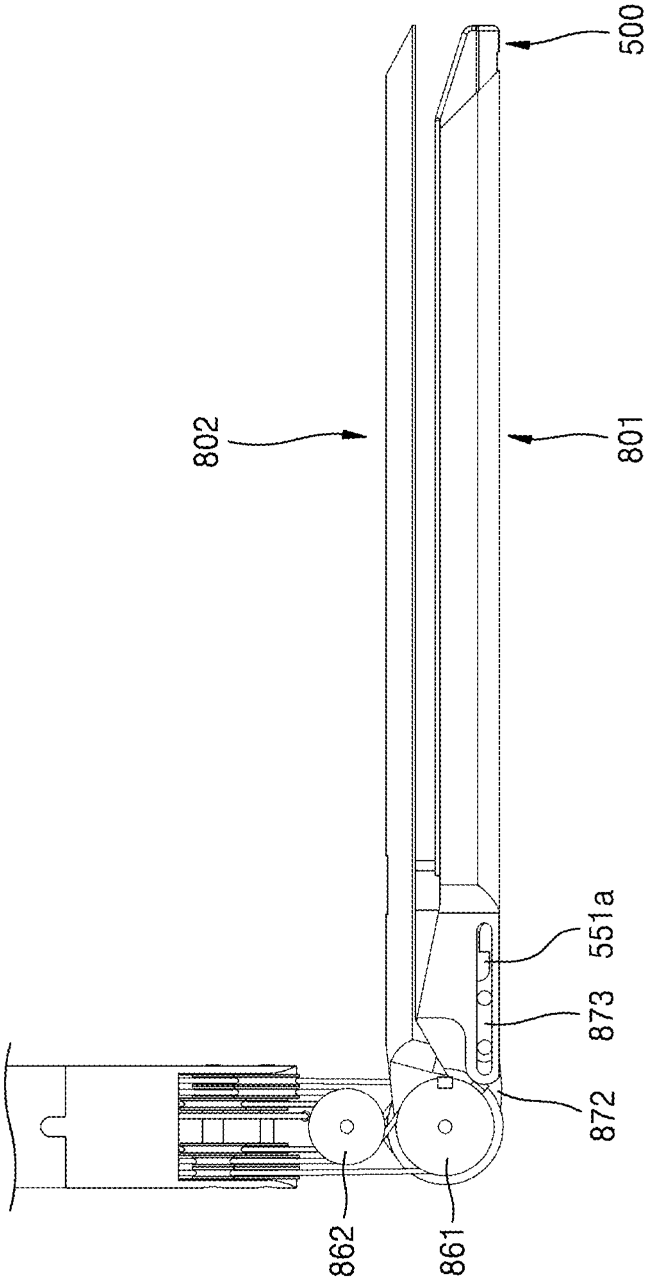
FIGS. 103 and 104 are plan views illustrating opening and closing motions of the end tool of the surgical instrument of FIG. 96.
Figure 104:
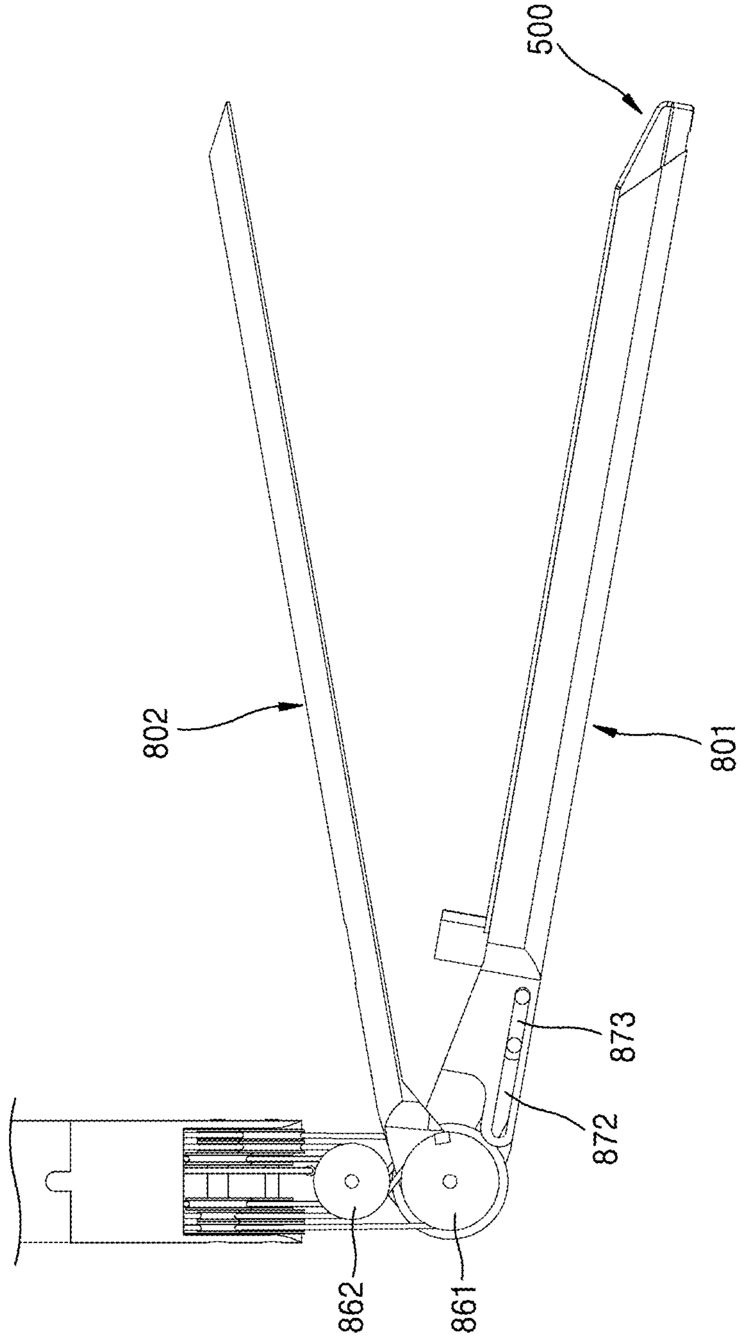

FIGS. 95 and 96 are perspective views illustrating the end tool of the surgical instrument according to the third embodiment of the present disclosure. Here, FIG. 96 illustrates a state in which an end tool hub is removed. FIG. 97 is a perspective view illustrating a state in which the end tool of the surgical instrument of FIG. 96 is opened, and FIG. 98 is a perspective view illustrating a state in which the end tool of the surgical instrument of FIG. 96 is closed. FIG. 99 is a side view illustrating the end tool of the surgical instrument of FIG. 96. FIGS. 100 and 101 are exploded perspective views of the end tool of the surgical instrument of FIG. 96. FIG. 102 is a plan view illustrating a state in which a first jaw of the end tool of the surgical instrument of FIG. 96 is fully opened. FIGS. 103 and 104 are plan views illustrating opening and closing motions of the end tool of the surgical instrument of FIG. 96.

Referring to FIGS. 95 to 104, the end tool 800 of the third embodiment of the present disclosure includes a pair of jaws 803 for performing a grip motion, that is, the first jaw 801 and the second jaw 802. Here, each of the first jaw 801 and the second jaw 802, or a component encompassing the first jaw 801 and the second jaw 802 may be referred to as the jaw 803.

Meanwhile, the end tool 800 includes a plurality of pulleys including a pulley 811 and a pulley 812 that are related to a rotational motion of the first jaw 801. The pulleys related to the rotational motion of the first jaw 801 described in the present embodiment are substantially the same as the pulley 111, the pulley 112, the pulley 113, the pulley 114, the pulley 115, and the pulley 116 described with reference to FIG. 8 or the like of the first embodiment, and thus, detailed descriptions thereof will be omitted herein.

Meanwhile, the end tool 800 includes a plurality of pulleys including a pulley 821 and a pulley 822 that are related to a rotational motion of the second jaw 802. The pulleys related to the rotational motion of the second jaw 802 described in the present embodiment are substantially the same as the pulley 121, the pulley 122, the pulley 123, the pulley 124, the pulley 125, and the pulley 126 described with reference to FIG. 8 or the like of the first embodiment, and thus, detailed descriptions thereof will be omitted herein.

In addition, the end tool 800 of the third embodiment of the present disclosure may include a rotation shaft 841, a rotation shaft 842, a rotation shaft 843, and a rotation shaft 844. Here, the rotation shaft 841 and the rotation shaft 842 may be inserted through an end tool hub 880, and the rotation shaft 843 and the rotation shaft 844 may be inserted through a pitch hub 807. The rotation shaft 841, the rotation shaft 842, the rotation shaft 843, and the rotation shaft 844 may be arranged sequentially from a distal end 804 of the end tool 800 toward a proximal end 805.

In addition, the end tool 800 of the third embodiment of the present disclosure may include the end tool hub 880 and the pitch hub 807.

The rotation shaft 841 and the rotation shaft 842, which will be described later, may be inserted through the end tool hub 880, and the pulley 811 and the pulley 821 axially coupled to the rotation shaft 841 and at least some of the first jaw 801 and the second jaw 802 coupled to the pulley 811 and the pulley 821 may be accommodated inside the end tool hub 880.

The rotation shaft 843 and the rotation shaft 844 may be inserted through the pitch hub 807, and the pitch hub 807 may be axially coupled to the end tool hub 880 by the rotation shaft 843.

Thus, the end tool hub 880 may be formed to be pitch-rotatable around the rotation shaft 843 with respect to the pitch hub 807.

Meanwhile, the end tool 800 of the third embodiment of the present disclosure may further include a component such as a staple pulley assembly (see 160 of FIG. 13) to perform stapling and cutting motions.

The staple pulley assembly (see 160 of FIG. 13) may be formed between the pulley 811 and the pulley 821 to be adjacent to the pulley 811 and the pulley 821. In the present embodiment, it is assumed that the staple pulley assembly (see 160 of FIG. 13) includes one staple pulley 861.

Meanwhile, in the third embodiment of the present disclosure, by disposing the staple pulley assembly (see 160 of FIG. 13) between the pulley 811, which is a first jaw pulley, and the pulley 821, which is a second jaw pulley, the end tool 800 is allowed to perform pitch and yaw motions as well as stapling and cutting motions using a cartridge (see 500 of FIG. 22). In the present embodiment, components for performing the stapling and cutting motions are substantially the same as those described in the first embodiment, and thus detailed descriptions thereof will be omitted herein.

Hereinafter, the first jaw 801 and the second jaw 802 of the end tool 800 of the surgical instrument according to the third embodiment of the present disclosure will be described in more detail.

The end tool 800 of the surgical instrument according to the third embodiment of the present disclosure includes one rotation shaft 841 that simultaneously performs the roles of a jaw pulley rotation shaft and a jaw rotation shaft, instead including the jaw pulley rotation shaft and the jaw rotation shaft separately. In other words, in the present embodiment, a direct connection structure is adopted for connecting the first jaw 801 and the second jaw 802 instead of the X-shaped structure of the first embodiment.

That is, in the first embodiment of the present disclosure, the rotation shaft (see 141 of FIG. 17), which is a jaw pulley rotation shaft, and the rotation shaft (see 145 of FIG. 17), which is a jaw rotation shaft, are separately provided, so that a stronger grip force may be provided when the jaws are closed. In contrast, in the third embodiment of the present disclosure, the rotation shaft 841 serves as both the jaw rotation shaft and the jaw pulley rotation shaft, allowing each jaw and each jaw pulley to rotate together as one body.

In detail, the first jaw 801 includes a cartridge accommodation part (see 101*a* of FIG. 14) and a guide groove 801*b*. The first jaw 801 is formed entirely in the shape of an elongated bar, the cartridge 500 is accommodated in a distal end 801*f* side, and the pulley 811 is coupled to a proximal end 801*g*, so that the first jaw 801 is formed to be rotatable around the rotation shaft 841.

Here, the first jaw 801 and the pulley 811 are illustrated in the drawings as being integrally formed, but a configuration in which the first jaw 801 and pulley 811 are formed as separate members and coupled together is also possible.

The second jaw 802 includes an anvil 802*a*. The second jaw 802 is formed entirely in the shape of an elongated bar, the anvil 802*a* is formed in a distal end 802*f* side, and the pulley 812 is coupled to a proximal end 802*g*, so that the second jaw 802 is formed to be rotatable around the rotation shaft 841.

Here, the second jaw 802 and the pulley 821 are illustrated in the drawings as being integrally formed, but a configuration in which the second jaw 802 and pulley 821 are formed as separate members and coupled together is also possible.

The rotation shaft 841, which is an end tool jaw pulley rotation shaft, is sequentially inserted through the pulley 811 coupled to (or integrally formed with) the first jaw 801, the staple pulley 861, and the pulley 821 coupled to (or integrally formed with) the second jaw 802.

Thus, the pulley 811 coupled to (or integrally formed with) the first jaw 801, the staple pulley 861, and the pulley 821 coupled to (or integrally formed with) the second jaw 802 are all rotated around the rotation shaft 841.

In addition, in the third embodiment of the present disclosure, the auxiliary pulley 812 is provided. The auxiliary pulley 812 may be in contact with the wire 305 and the wire 302 and may change the arrangement path of the wires 305 and 302 to a certain extent to serve to increase a rotation radius of each of the first jaw 801 and the second jaw 802.

As a result, unlike the first embodiment, in the present embodiment, since there is no separate jaw rotation shaft for restricting the first jaw 801 and the second jaw 802, a rotation angle between the first jaw 801 and the second jaw 802 is increased to approximately 120°. In addition, by coupling the first jaw 801 and the second jaw 802 by a single shaft without a separate connection structure for connecting the X-shaped structure between the first jaw 801 and the second jaw 802, the number of parts may be reduced and the manufacturing may be easily performed.

Fourth Embodiment—Dual Rack

Hereinafter, an end tool 900 of a surgical instrument according to a fourth embodiment of the present disclosure will be described. Here, the end tool 900 of the surgical instrument according to the fourth embodiment of the present disclosure is different from the end tool (see 100 of FIG. 2 or the like) of the surgical instrument according to the first embodiment of the present disclosure described above in that a reciprocating assembly 950 of a cartridge 910 and a staple link assembly 970 are different. Hereinafter, the configuration that is different from that of the first embodiment will be described in detail.

Figure 105:
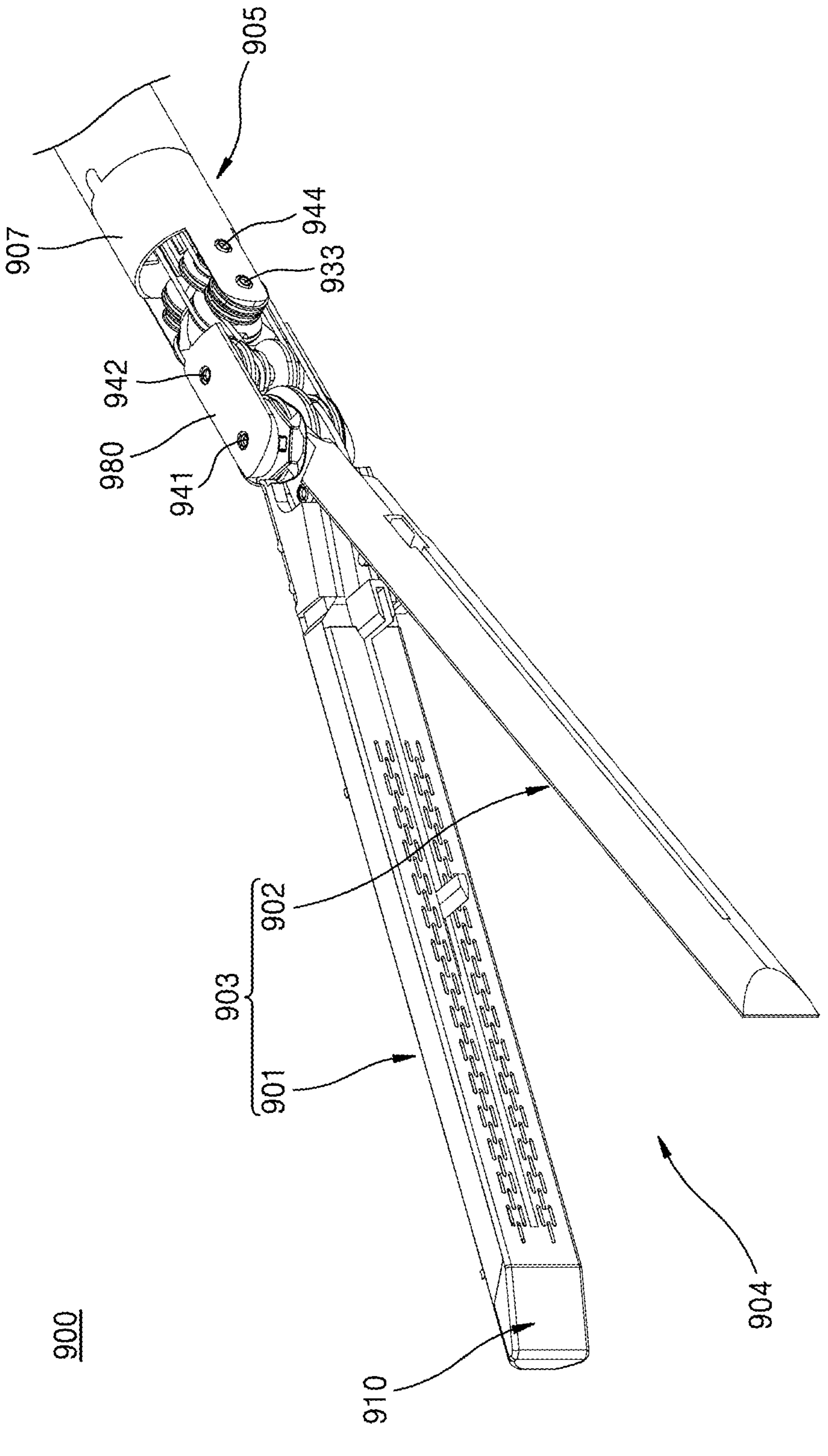
FIGS. 105 and 106 are perspective views illustrating an end tool of a surgical instrument according to a fourth embodiment of the present disclosure.
Figure 106:
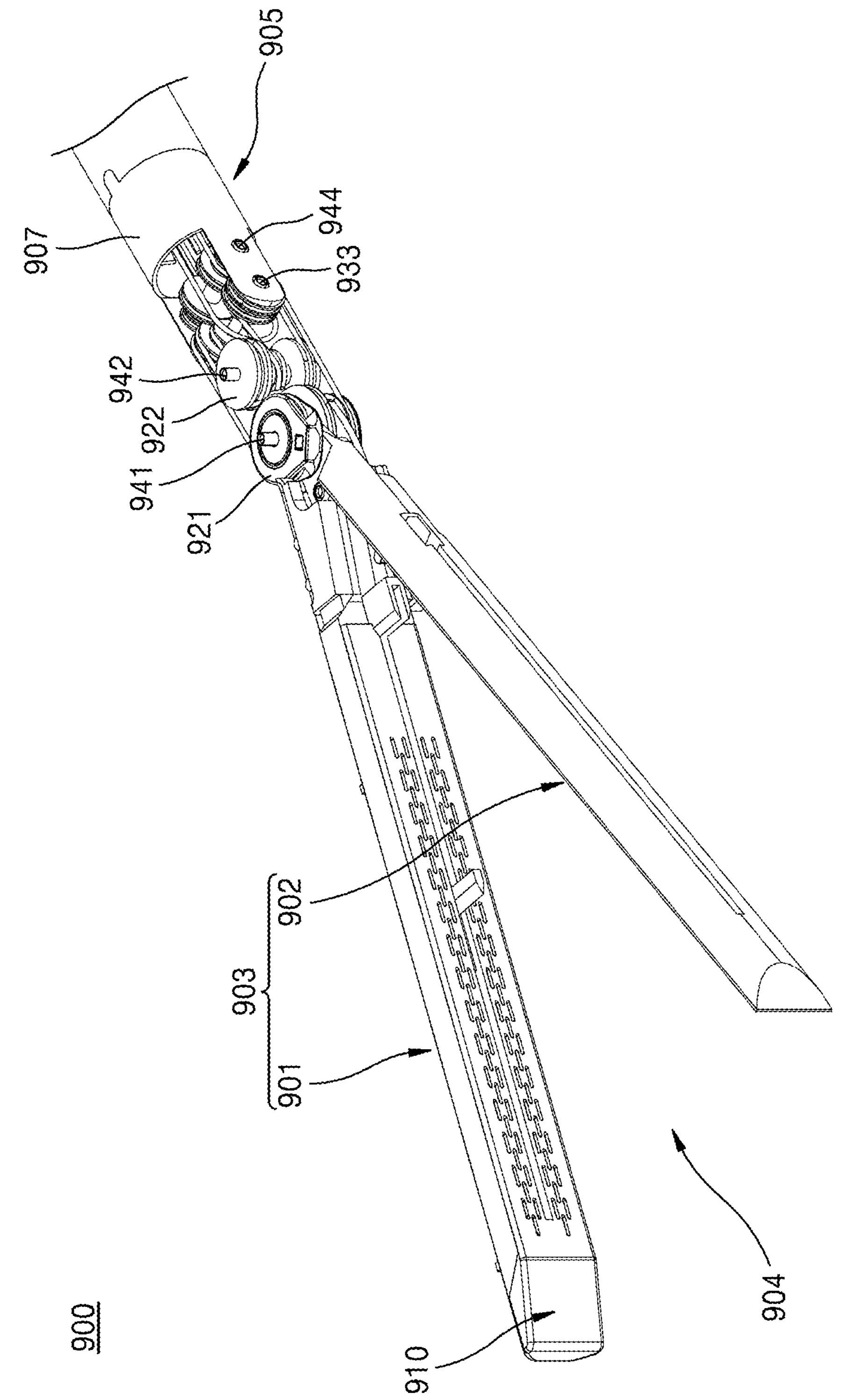
Figure 107:
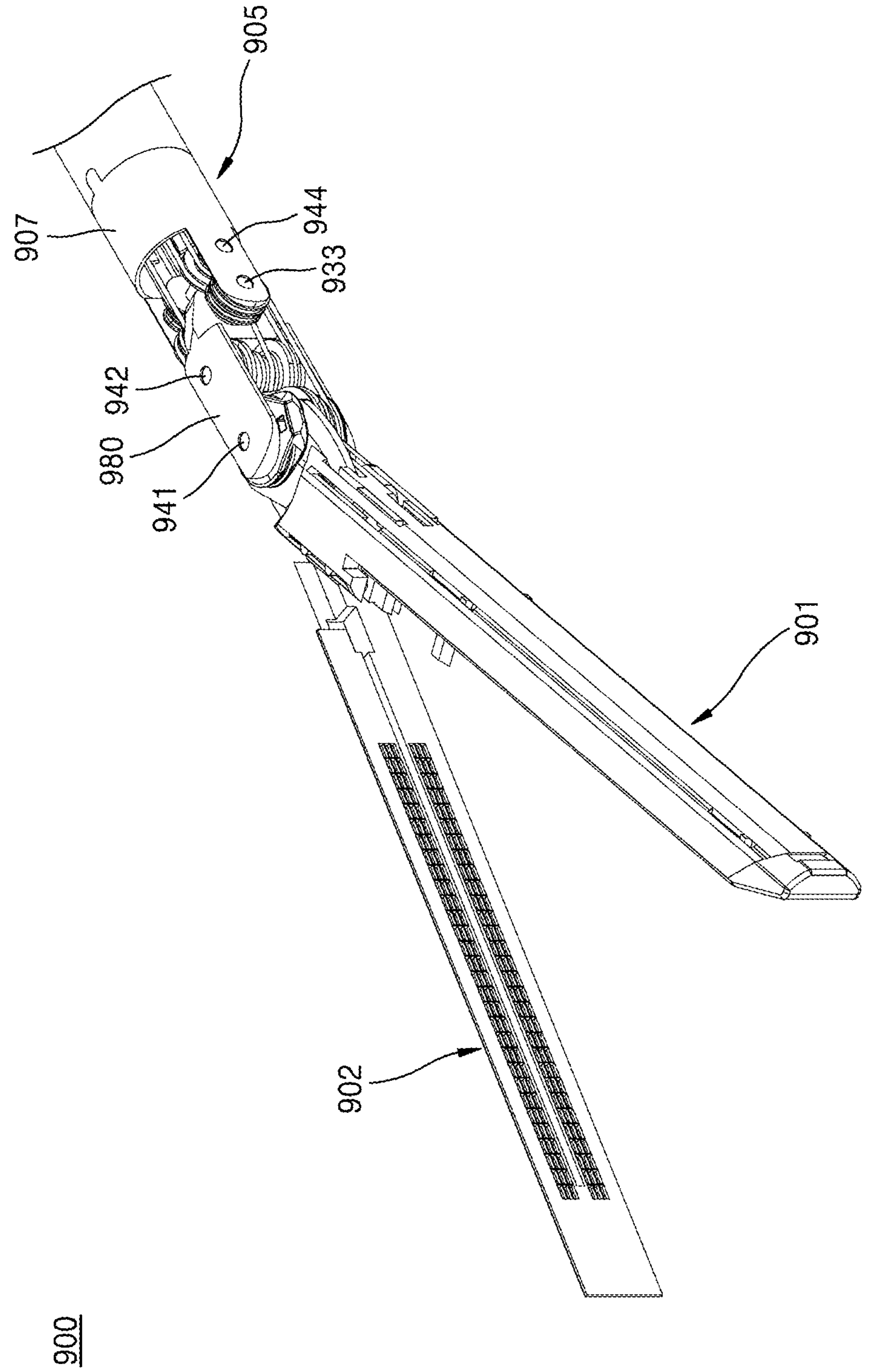
FIGS. 107 and 108 are perspective views of the end tool of the surgical instrument of FIG. 105 viewed from a different angle.
Figure 108:
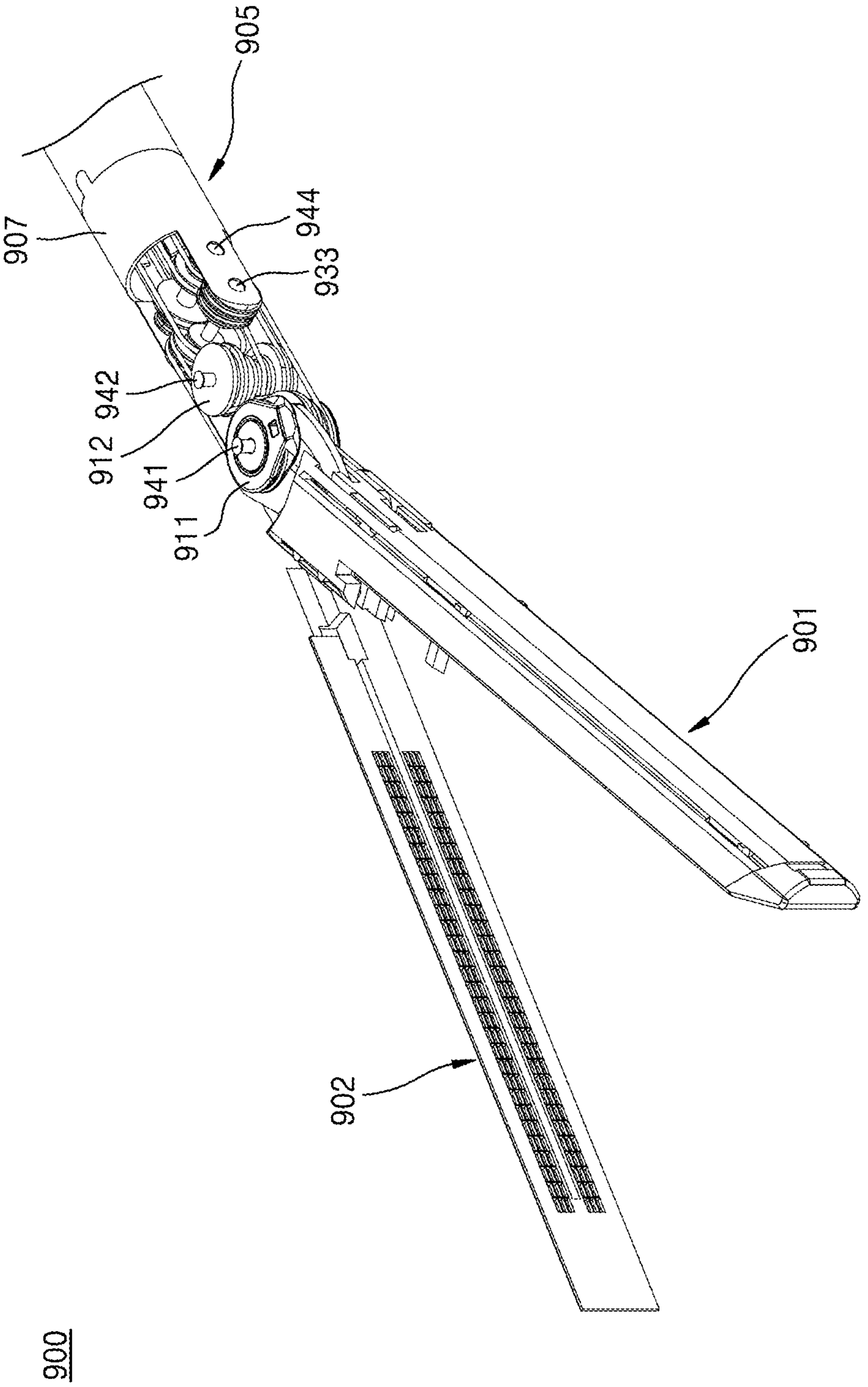
Figure 109:
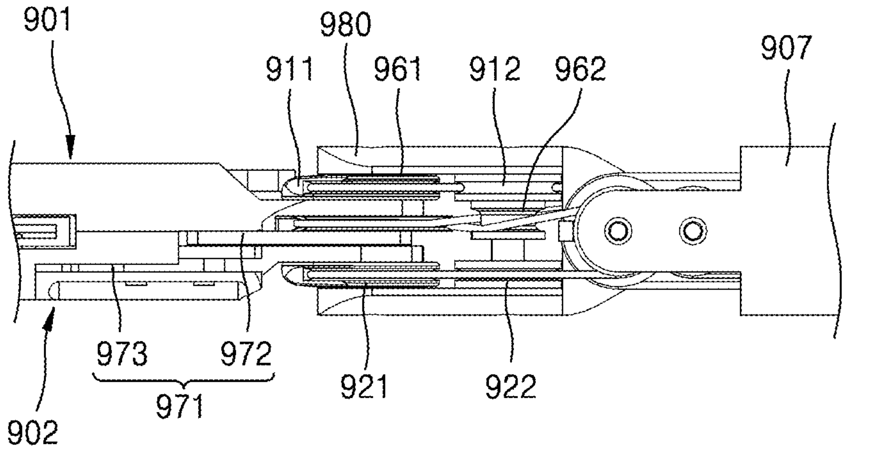
FIG. 109 is a side view illustrating the end tool of the surgical instrument of FIG. 105.
Figure 110:
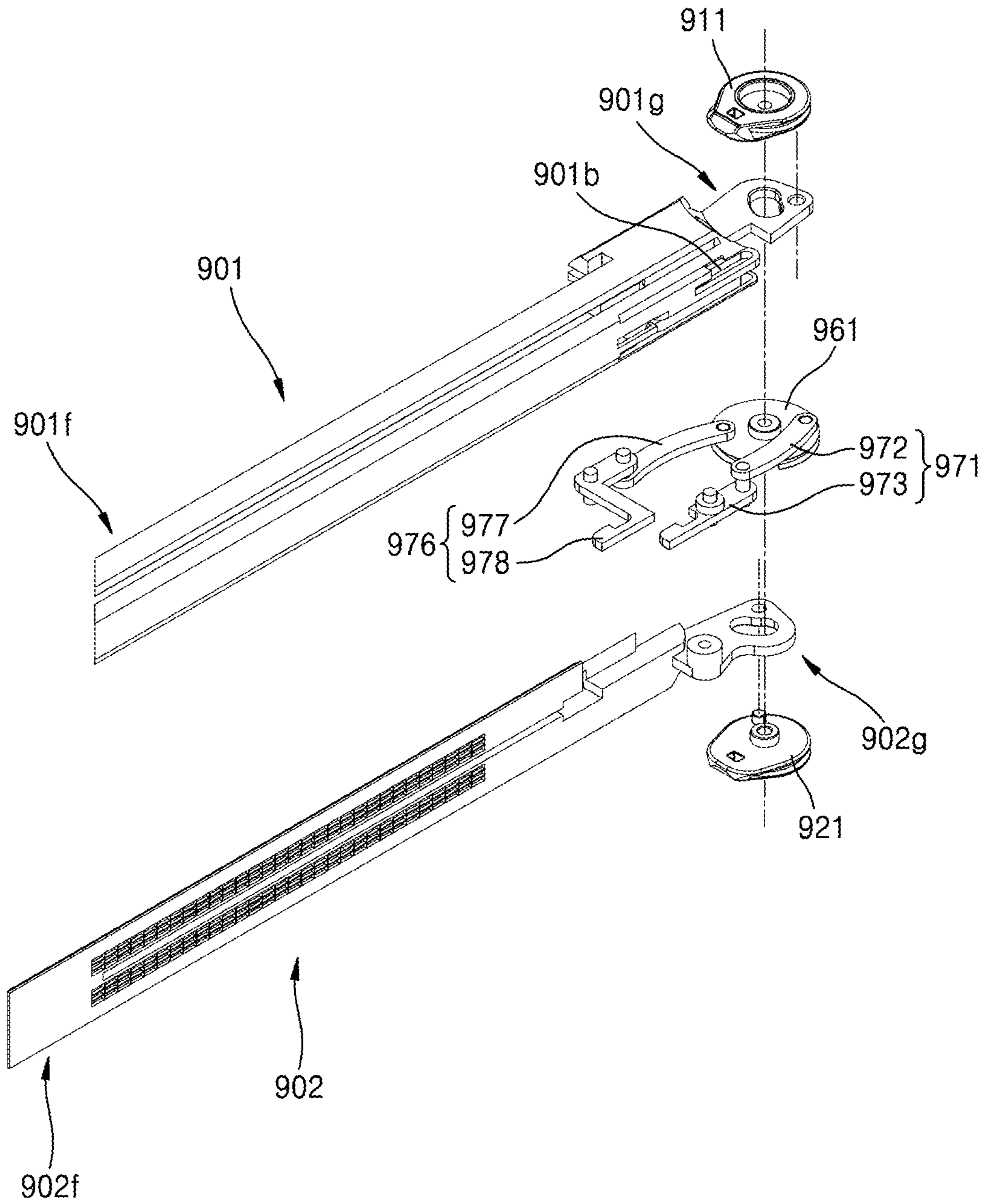
FIGS. 110 and 111 are exploded perspective views of the end tool of the surgical instrument of FIG. 105.
Figure 111:
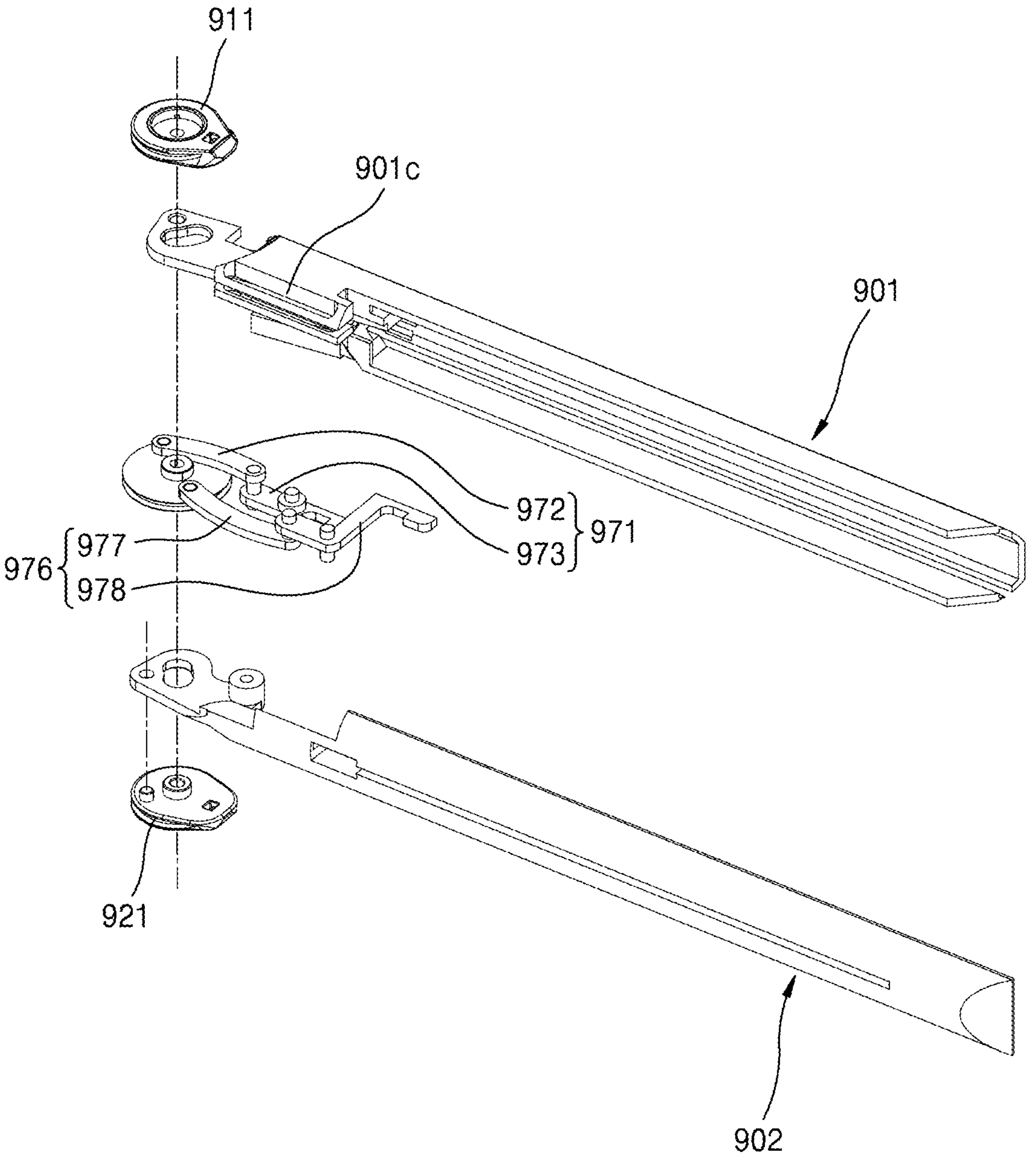
Figure 112:
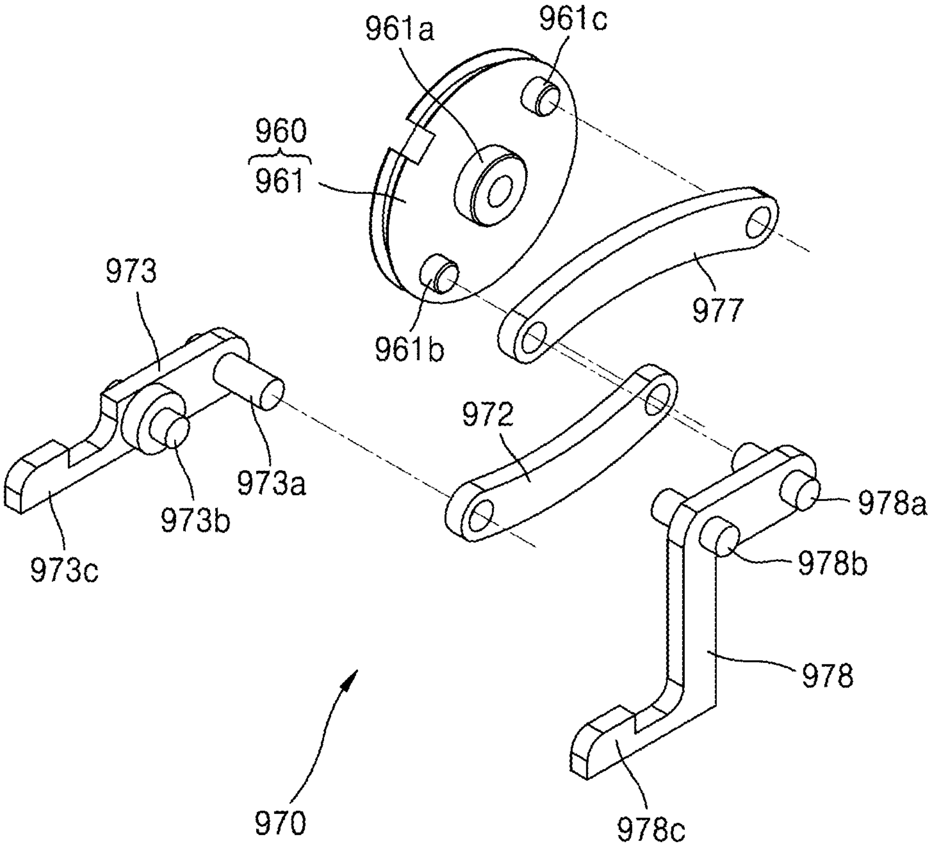
FIG. 112 is an exploded perspective view of a staple link assembly of the surgical instrument of FIG. 105.
Figure 113:
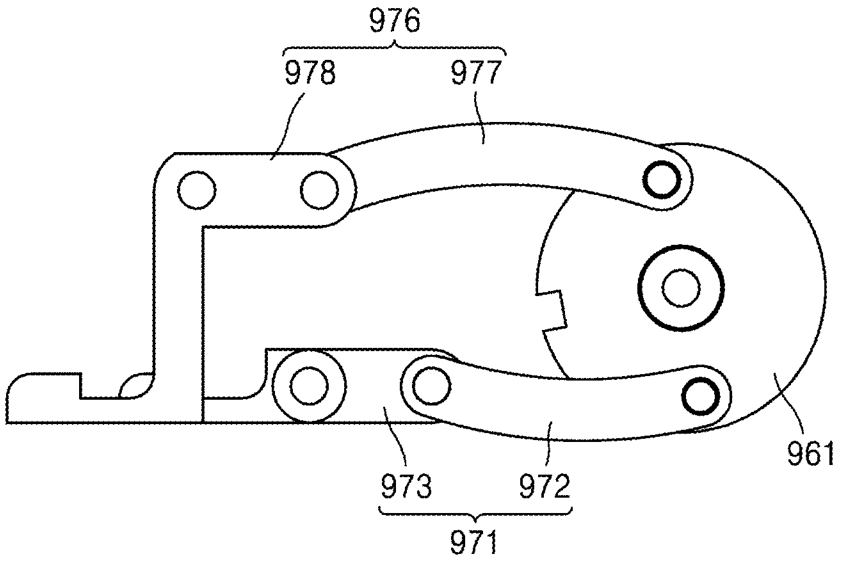
FIGS. 113 and 114 are a side view and a plan view illustrating respective operating states of the staple link assembly of FIG. 105.
Figure 113:
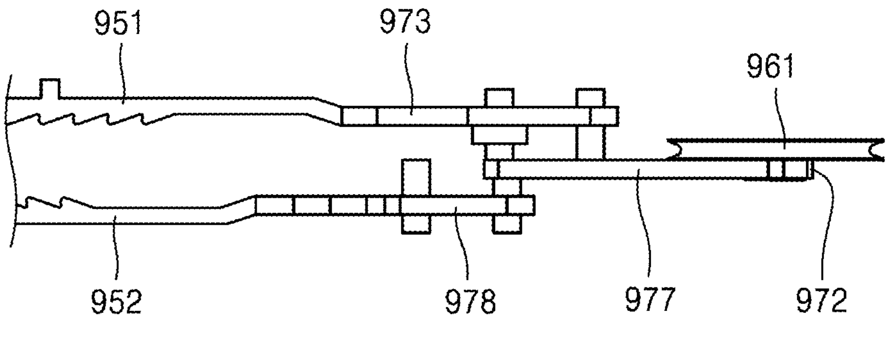
Figure 114:
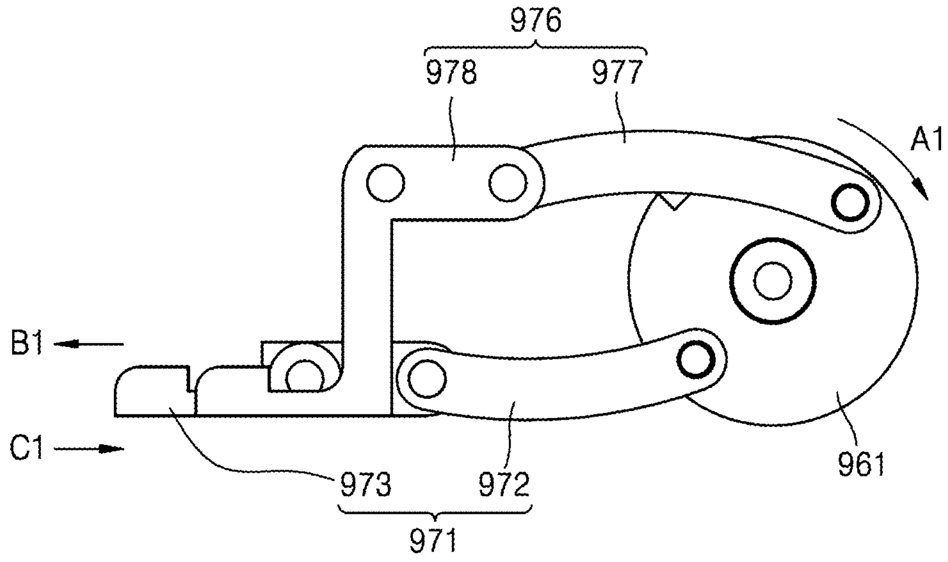
Figure 114:
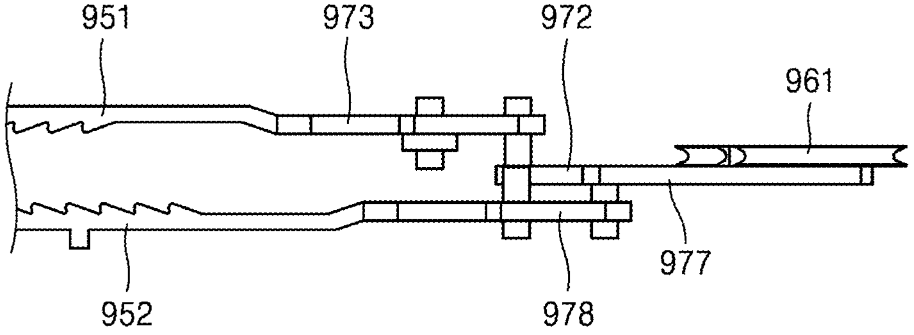
Figure 115:
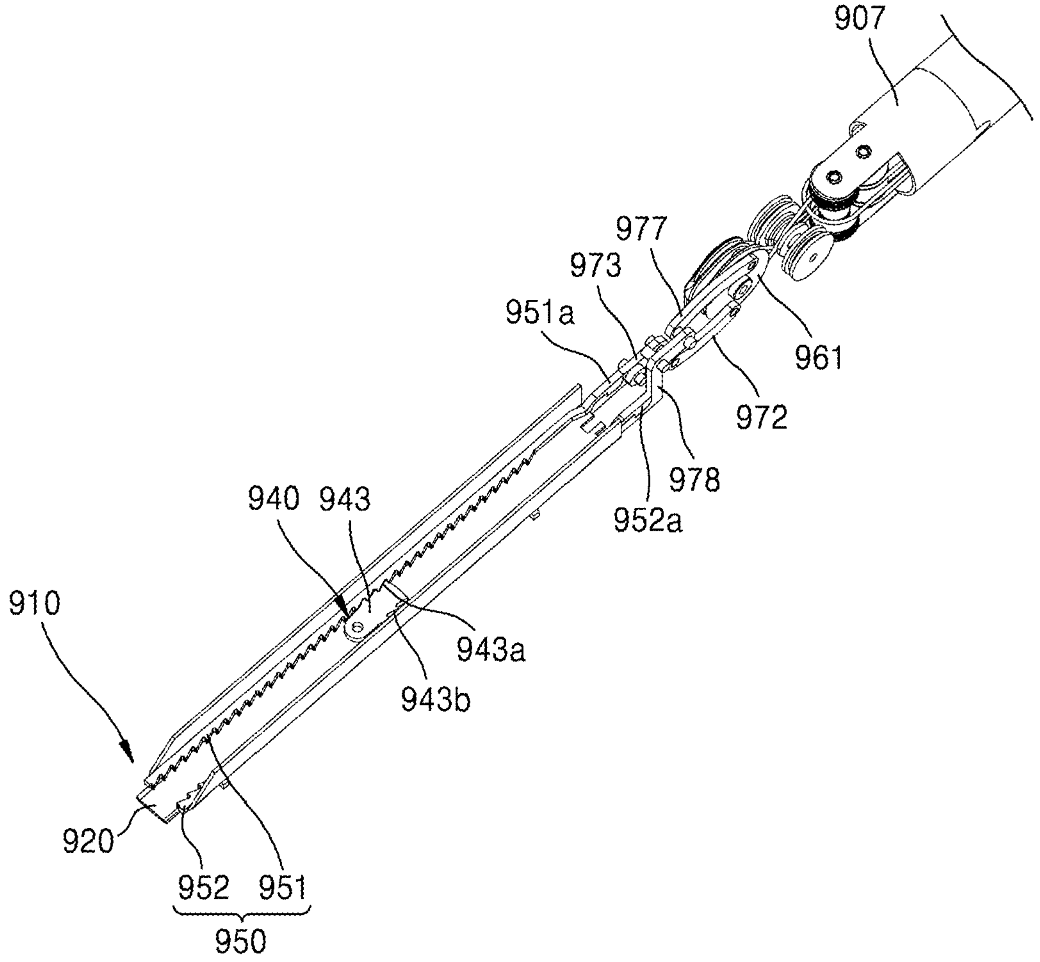
FIG. 115 is a perspective view illustrating an internal structure of the end tool of the surgical instrument of FIG. 105.
Figure 116:
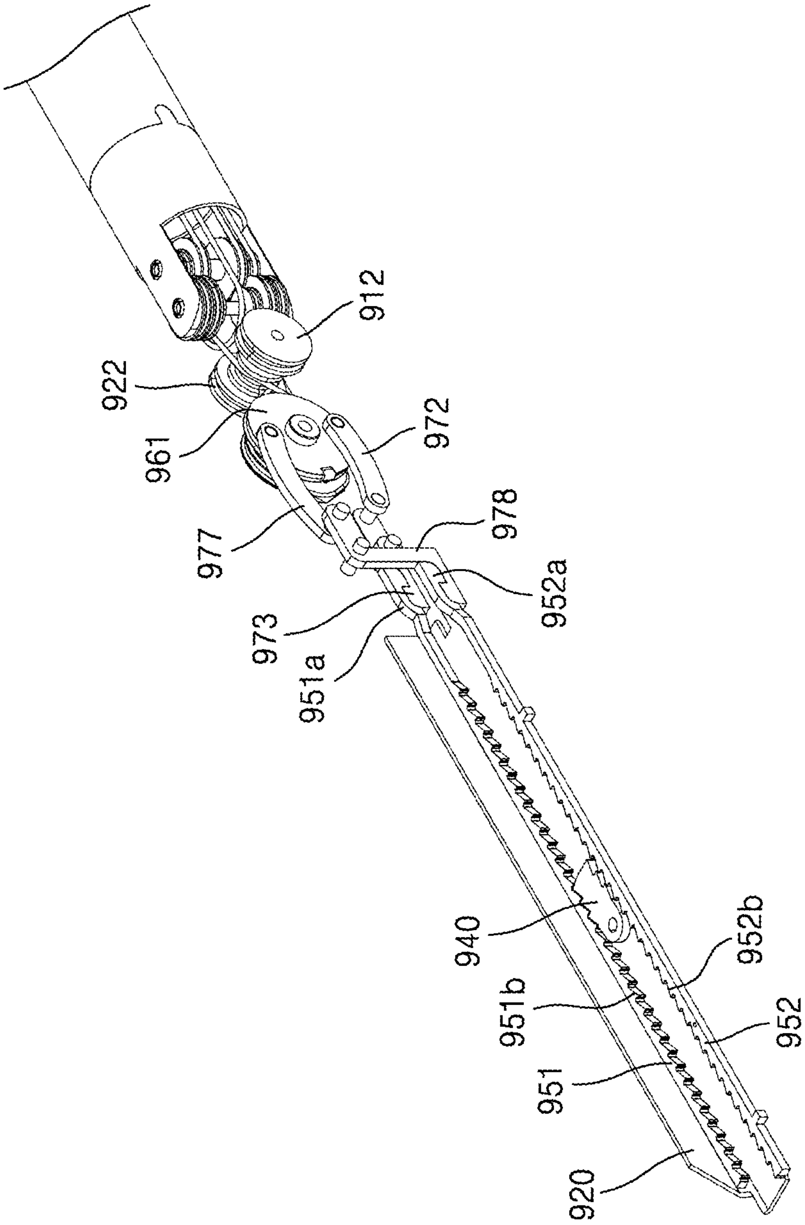
FIGS. 116 and 117 are perspective views illustrating respective operating states of the end tool of FIG. 115.
Figure 117:
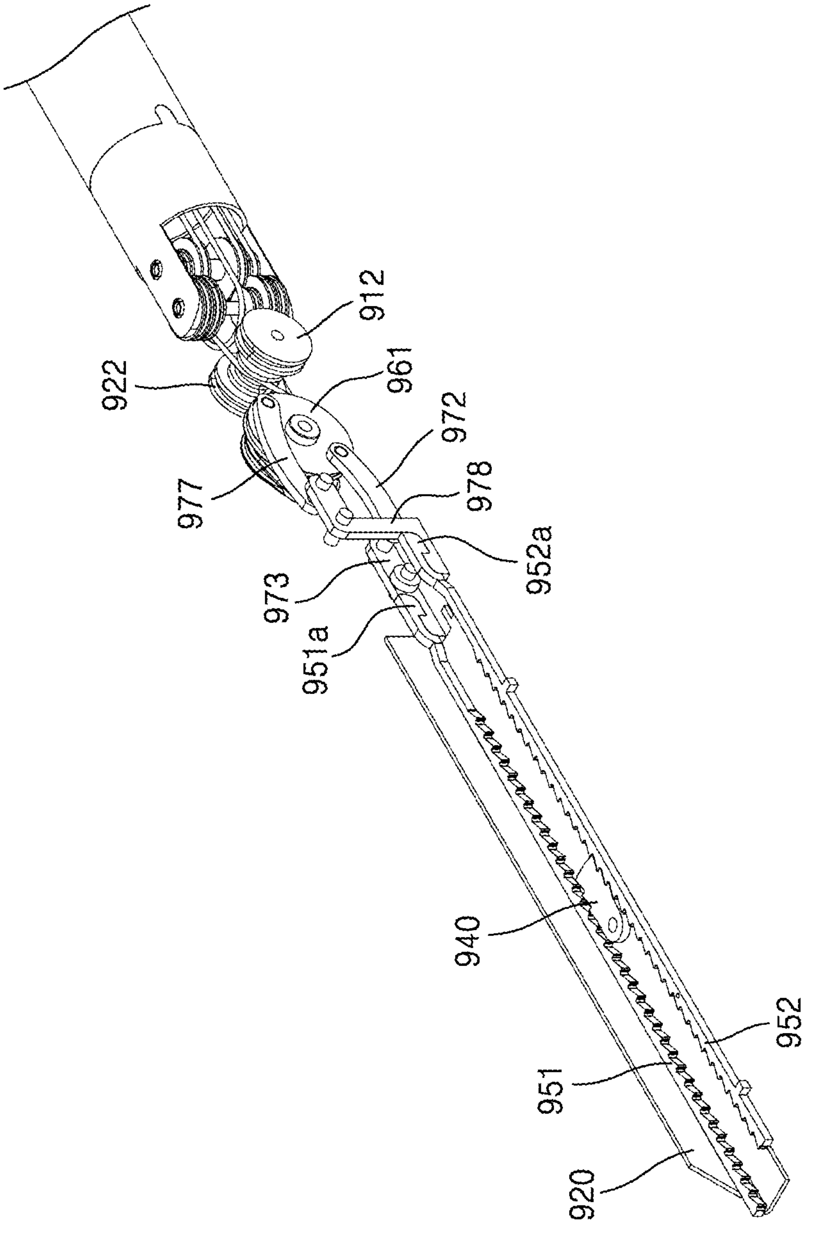
Figure 118:
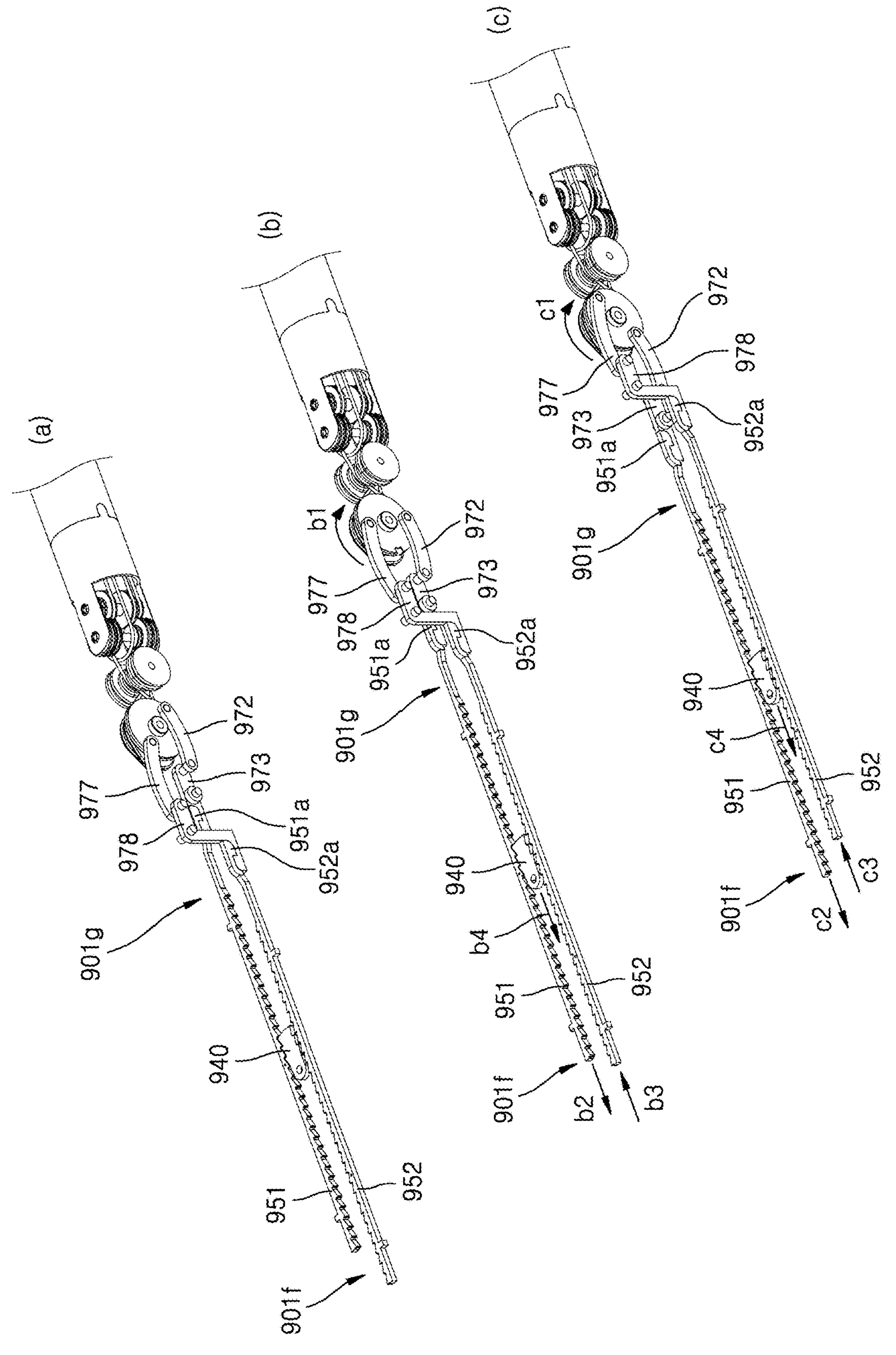
FIGS. 118 and 119 are perspective views illustrating respective operating states of the end tool of FIG. 115.
Figure 119:
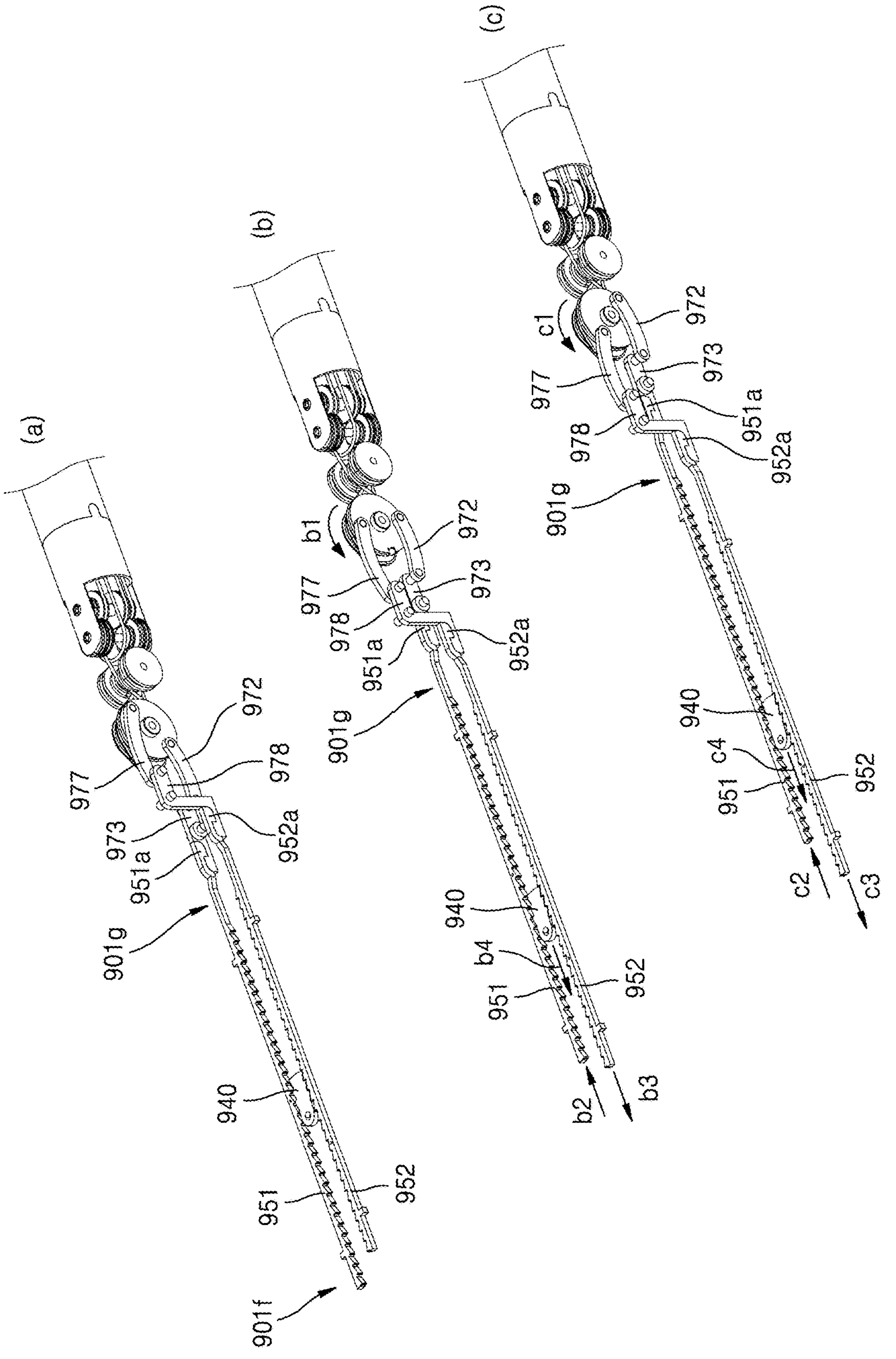
Figure 120:
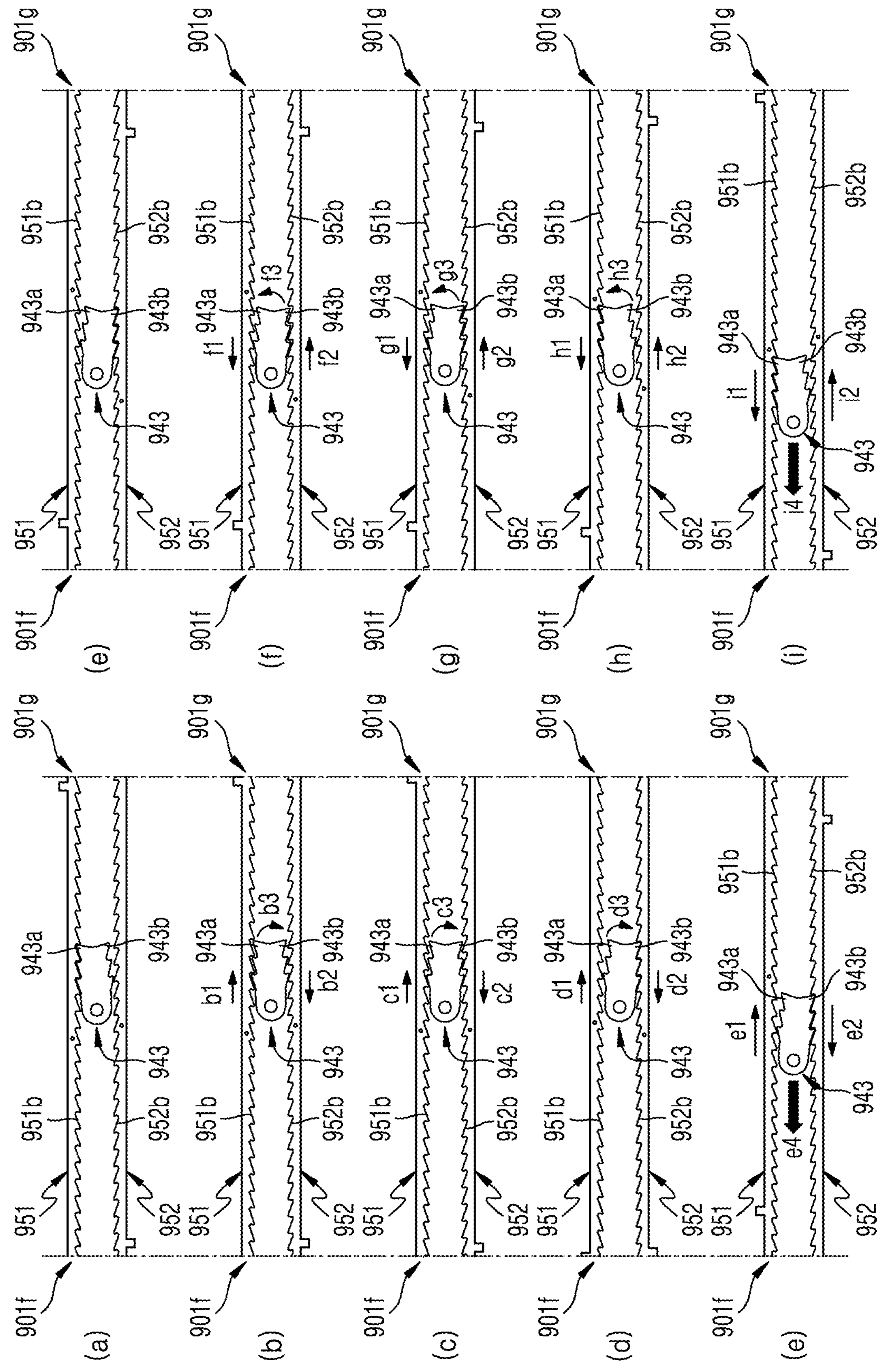
FIGS. 120 and 121 are perspective views illustrating respective operating states of the end tool of FIG. 115.
Figure 121:
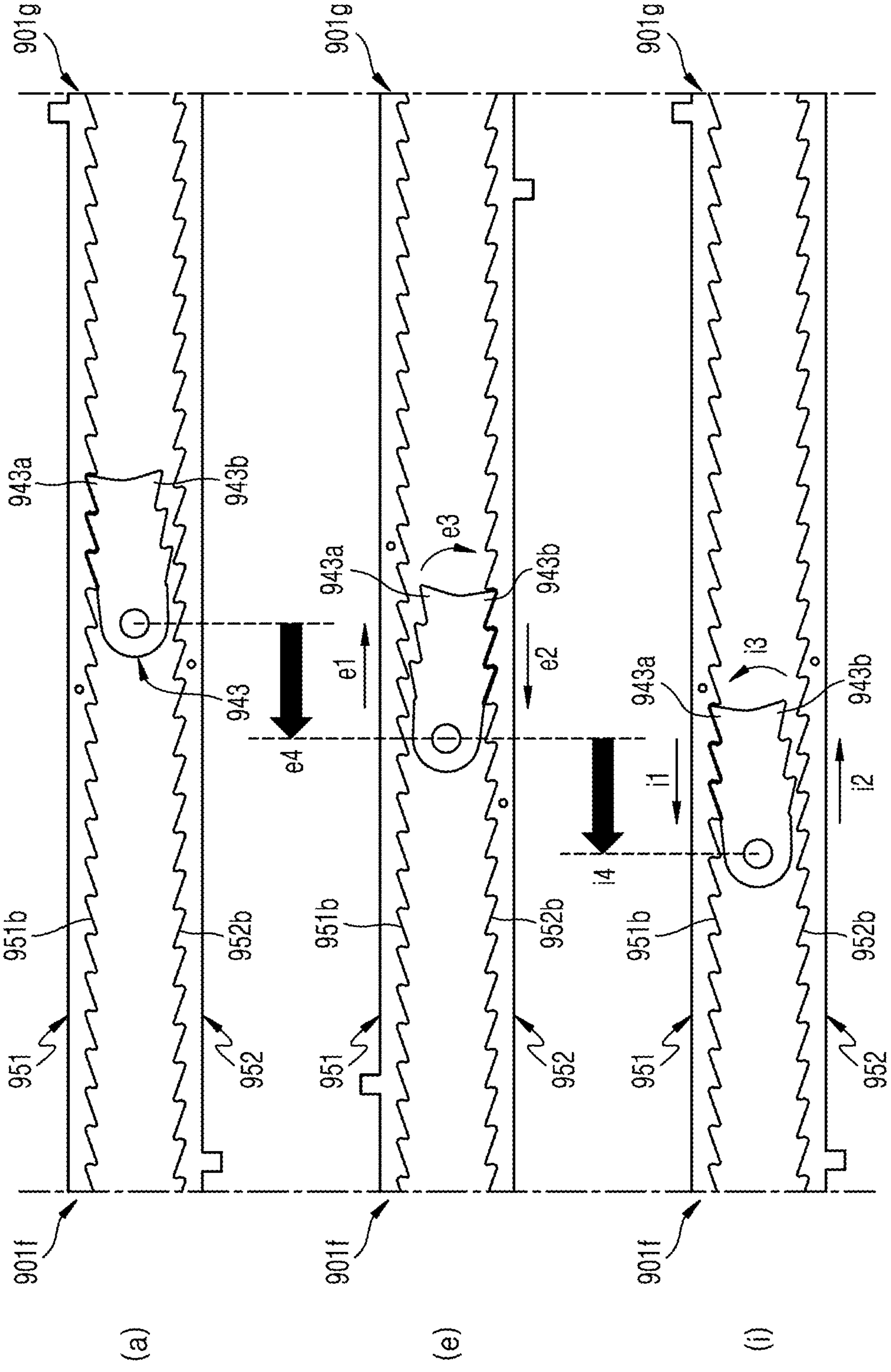

FIGS. 105 and 106 are perspective views illustrating the end tool of the surgical instrument according to the fourth embodiment of the present disclosure. Here, FIG. 106 illustrates a state in which an end tool hub is removed. FIGS. 107 and 108 are perspective views of the end tool of the surgical instrument of FIG. 105 viewed from a different angle. Here, FIG. 108 illustrates a state in which the end tool hub is removed. FIG. 109 is a side view illustrating the end tool of the surgical instrument of FIG. 105. FIGS. 110 and 111 are exploded perspective views of the end tool of the surgical instrument of FIG. 105. FIG. 112 is an exploded perspective view of the staple link assembly of the surgical instrument of FIG. 105. FIGS. 113 and 114 are a side view and a plan view illustrating respective operating states of the staple link assembly of FIG. 105. FIG. 115 is a perspective view illustrating an internal structure of the end tool of the surgical instrument of FIG. 105. FIGS. 116 and 117 are perspective views illustrating respective operating states of the end tool of FIG. 115. FIGS. 118 and 119 are perspective views illustrating respective operating states of the end tool of FIG. 115. Here, FIGS. 118 and 119 mainly illustrate operations of the reciprocating assembly and the staple link assembly. FIGS. 120 and 121 are perspective views illustrating respective operating states of the end tool of FIG. 115. Here, FIGS. 120 and 121 mainly illustrate operations of the reciprocating assembly and an operation member.

Referring to FIGS. 105 to 121, the end tool 900 of the fourth embodiment of the present disclosure includes a pair of jaws 903 for performing a grip motion, that is, a first jaw 901 and a second jaw 902. Here, each of the first jaw 901 and the second jaw 902, or a component encompassing the first jaw 901 and the second jaw 902 may be referred to as the jaw 903.

Meanwhile, the end tool 900 includes a plurality of pulleys including a pulley 911 and a pulley 912 that are related to a rotational motion of the first jaw 901. The pulleys related to the rotational motion of the first jaw 901 described in the present embodiment are substantially the same as the pulley 111, the pulley 112, the pulley 113, the pulley 114, the pulley 115, and the pulley 116 described with reference to FIG. 8 or the like of the first embodiment, and thus, detailed descriptions thereof will be omitted herein.

Meanwhile, the end tool 900 includes a plurality of pulleys including a pulley 921 and a pulley 922 that are related to a rotational motion of the second jaw 902. The pulleys related to the rotational motion of the second jaw 902 described in the present embodiment are substantially the same as the pulley 121, the pulley 122, the pulley 123, the pulley 124, the pulley 125, and the pulley 126 described with reference to FIG. 8 or the like of the first embodiment, and thus, detailed descriptions thereof will be omitted herein.

In addition, the end tool 900 of the fourth embodiment of the present disclosure may include a rotation shaft 941, a rotation shaft 942, a rotation shaft 933, and a rotation shaft 944. Here, the rotation shaft 941 and the rotation shaft 942 may be inserted through an end tool hub 980, and the rotation shaft 933 and the rotation shaft 944 may be inserted through a pitch hub 907. The rotation shaft 941, the rotation shaft 942, the rotation shaft 933, and the rotation shaft 944 may be arranged sequentially from a distal end 904 of the end tool 900 toward a proximal end 905.

In addition, the end tool 900 of the fourth embodiment of the present disclosure may include the end tool hub 980 and the pitch hub 907.

The rotation shaft 941 and the rotation shaft 942 may be inserted through the end tool hub 980, and the pulley 911 and the pulley 921 axially coupled to the rotation shaft 941 and at least some of the first jaw 901 and the second jaw 902 coupled to the pulley 911 and the pulley 921 may be accommodated inside the end tool hub 980.

The rotation shaft 933 and the rotation shaft 944 may be inserted through the pitch hub 907, and the pitch hub 907 may be axially coupled to the end tool hub 980 by the rotation shaft 933. Thus, the end tool hub 980 may be formed to be pitch-rotatable around the rotation shaft 933 with respect to the pitch hub 907.

Meanwhile, the end tool 900 of the fourth embodiment of the present disclosure may further include components, such as a staple drive assembly (see 150 of FIG. 13) including a staple pulley assembly 960 and the staple link assembly 970, to perform stapling and cutting motions.

The staple pulley assembly 960 may be formed between the pulley 911 and the pulley 921 to be adjacent to the pulley 911 and the pulley 921. In the present embodiment, it is assumed that the staple pulley assembly 960 includes one staple pulley 961.

In the fourth embodiment of the present disclosure, by disposing the staple pulley assembly 960 between the pulley 911, which is a first jaw pulley, and the pulley 921, which is a second jaw pulley, the end tool 900 is allowed to perform pitch and yaw motions as well as stapling and cutting motions using the cartridge 910.

Hereinafter, the staple pulley assembly 960, the staple link assembly 970, and the reciprocating assembly 950 of the cartridge 910 of the end tool 900 of the surgical instrument according to the fourth embodiment of the present disclosure will be described in more detail.

In the end tool 900 of the surgical instrument according to the fourth embodiment of the present disclosure, the staple link assembly 970 includes a first link member 971 and a second link member 976, and the reciprocating assembly 950 of the cartridge 910 includes a first reciprocating member 951 and a second reciprocating member 952, so that a kind of dual rack structure is formed in the end tool 900.

Referring to FIGS. 105 to 121 and the like, the staple pulley assembly 960 may include one or more staple pulleys 961.

A shaft pass-through part 961*a* may be formed in the staple pulley 961. The shaft pass-through part 961*a* may be formed in the form of a hole, and the rotation shaft 941, which is an end tool jaw pulley rotation shaft, may be inserted through the shaft pass-through part 961*a*.

In addition, a first link coupling part 961*b* and a second link coupling part 961*c* may be formed in the staple pulley 961. The first link member 971 of the staple link assembly 970 may be coupled to the first link coupling part 961*b*, and the second link member 976 of the staple link assembly 970 may be coupled to the second link coupling part 961*c*. Here, the first link coupling part 961*b* and the second link coupling part 961*c* may be disposed on opposite sides with respect to a central axis of the staple pulley 961.

Meanwhile, the end tool 900 of the fourth embodiment of the present disclosure may further include the staple link assembly 970 connected to the staple pulley assembly 960. Here, the staple link assembly 970 may serve to connect the staple pulley assembly 960 to the reciprocating assembly 950 of the cartridge 910 to be described later. In the end tool 900 of the fourth embodiment of the present disclosure, the staple link assembly 970 includes two pairs of link members in the first link member 971 and the second link member 976.

The first link member 971 may include a first link 972 and a second link 973.

The first link 972 is formed in the form of an elongated bar, which may have through holes formed at both end portions. The first link coupling part 961*b* of the staple pulley 961 may be inserted through the through hole at one end portion of the first link 972. The second link 973 may be inserted through the through hole at the other end portion of the first link 972.

The second link 973 is formed in the form of an elongated bar, and may be coupled to the first link 972. The second link 973 may include a first protrusion 973*a*, a second protrusion 973*b*, and a coupling part 973*c*.

In detail, the first protrusion 973*a* may be formed at one end portion of the second link 973. The first protrusion 973*a* is axially coupled to the first link 972 by being fitted into the through hole of the first link 972, so that the second link 973 may be coupled to the first link 972. In addition, the first protrusion 973*a* may be fitted into a first guide groove 901*b* of the first jaw 901, which will be described later.

Meanwhile, the second protrusion 973*b* may be formed in one region of a central portion of the second link 973. The second protrusion 973*b* may be fitted into the first guide groove 901*b* of the first jaw 901, which will be described later.

As described above, as the first protrusion 973*a* and the second protrusion 973*b* are moved along the first guide groove 901*b* in a state in which the first protrusion 973*a* and the second protrusion 973*b* of the second link 973 formed in a protruding shape are fitted into the groove-shaped first guide groove 901*b*, the first link member 971 is moved with respect to the first jaw 901 (and the cartridge 910 therein). This will be described in more detail later.

Meanwhile, the coupling part 973*c* may be formed at the other end portion of the second link 973. The coupling part 973*c* may be coupled to a coupling part 951*a* of the first reciprocating member 951 of the cartridge 910, which will be described later.

In the state of FIG. 113, when the staple pulley 961 is rotated in the direction of an arrow A1 of FIG. 114 (i.e., in the clockwise direction), the first link member 971 connected to the staple pulley 961 may be moved in the direction of an arrow B1 of FIG. 114, in other words, toward a distal end 901*f* of the first jaw 901. In contrast, when the staple pulley 961 is rotated in the counterclockwise direction, the first link member 971 connected to the staple pulley 961 may be moved in the direction of an arrow C1 of FIG. 114, in other words, toward a proximal end 901*g* of the first jaw 901.

Accordingly, a bidirectional rotational motion of the staple pulley assembly 960 may cause a reciprocating linear motion of the first reciprocating member 951 of the cartridge 910 through the first link member 971 of the staple link assembly 970. This will be described in more detail later.

The second link member 976 may include a third link 977 and a fourth link 978.

The third link 977 is formed in the form of an elongated bar, which may have through holes formed at both end portions. The second link coupling part 961*c* of the staple pulley 961 may be inserted through the through hole at one end portion of the third link 977. The fourth link 978 may be inserted through the through hole at the other end portion of the third link 977.

The fourth link 978 is formed in the form of a bar bent one or more times, and may be coupled to the third link 977. The fourth link 978 may include a first protrusion 978*a*, a second protrusion 978*b*, and a coupling part 978*c*.

In detail, the first protrusion 978*a* may be formed at one end portion of the fourth link 978. The first protrusion 978*a* is axially coupled to the third link 977 by being fitted into the through hole of the third link 977, so that the fourth link 978 may be coupled to the third link 977. In addition, the first protrusion 978*a* may be fitted into a second guide groove 901*c* of the first jaw 901, which will be described later.

Meanwhile, the second protrusion 978*b* may be formed in one region of a central portion of the fourth link 978. The second protrusion 978*b* may be fitted into the second guide groove 901*c* of the first jaw 901, which will be described later.

As described above, as the first protrusion 978*a* and the second protrusion 978*b* are moved along the second guide groove 901*c* in a state in which the first protrusion 978*a* and the second protrusion 978*b* of the fourth link 978 formed in a protruding shape are fitted into the groove-shaped second guide groove 901*c*, the second link member 976 is moved with respect to the first jaw 901 (and the cartridge 910 therein). This will be described in more detail later.

Meanwhile, the coupling part 978*c* may be formed at the other end portion of the fourth link 978. The coupling part 978*c* may be coupled to a coupling part 952*a* of the second reciprocating member 952 of the cartridge 910, which will be described later.

Here, the fourth link 978 may include two horizontal regions and one vertical region connecting the two horizontal regions.

In detail, since the first link coupling part 961*b* and the second link coupling part 961*c* are disposed on opposite sides with respect to the central axis of the staple pulley 961, a height difference (with respect to a z-axis direction) exists between the first link 972 coupled to the first link coupling part 961*b* and the third link 977 coupled to the second link coupling part 961*c*.

In contrast, it is structurally advantageous for the first reciprocating member 951 and the second reciprocating member 952 of the reciprocating assembly 950, which will be described later, to be located at the same height (with respect to the Z-axis direction) as each other.

Accordingly, in order to connect the third link 977 and the second reciprocating member 952, the fourth link 978 may be formed in the form of a bar that is bent one or more times.

Here, the first protrusion 978*a* and the second protrusion 978*b* are formed in a first horizontal region, and the coupling part 978*c* may be formed in a second horizontal region.

In the state of FIG. 113, when the staple pulley 961 is rotated in the direction of the arrow A1 of FIG. 114 (i.e., in the clockwise direction), the second link member 976 connected to the staple pulley 961 may be moved in the direction of the arrow C1 of FIG. 114, in other words, toward the proximal end 901*g* of the first jaw 901. In contrast, when the staple pulley 961 is rotated in the counterclockwise direction, the second link member 976 connected to the staple pulley 961 may be moved in the direction of the arrow B1 of FIG. 114, in other words, toward the distal end 901*f* of the first jaw 901.

Accordingly, a bidirectional rotational motion of the staple pulley assembly 960 may cause a reciprocating linear motion of the second reciprocating member 952 of the cartridge 910 through the second link member 976 of the staple link assembly 970. This will be described in more detail later.

As described above, the first link coupling part 961*b* and the second link coupling part 961*c* may be disposed on opposite sides with respect to the central axis of the staple pulley 961. In addition, the first link member 971 is coupled to the first link coupling part 961*b*, and the second link member 976 is coupled to the second link coupling part 961*c*.

Accordingly, when the staple pulley 961 is rotated in one direction (e.g., the clockwise direction), the first link member 971 is moved forward and the second link member 976 is moved backward. Meanwhile, when the staple pulley 961 is rotated in the other direction (e.g., the counterclockwise direction), the first link member 971 is moved backward and the second link member 976 is moved forward.

With this configuration, when the staple pulley 961 is alternately rotated in the clockwise and counterclockwise directions, the first link member 971 and the second link member 976 perform a linear reciprocating motion, and in this case, the first link member 971 and the second link member 976 are moved in opposite directions. That is, when the first link member 971 is moved forward (i.e., toward the distal end), the second link member 976 is moved backward (i.e., toward the proximal end). Conversely, when the first link member 971 is moved backward (i.e., toward the proximal end), the second link member 976 is moved forward (i.e., toward the distal end).

(Cartridge)

Hereinafter, the cartridge 910 of the end tool 900 of the surgical instrument according to the fourth embodiment of the present disclosure will be described in more detail.

In the cartridge 910 of the end tool 900 of the surgical instrument according to the fourth embodiment of the present disclosure, the reciprocating assembly 950 includes the first reciprocating member 951 and the second reciprocating member 952.

In detail, referring to FIGS. 115 to 117 and the like, the cartridge 910 is formed to be mountable to and dismountable from the first jaw 101 and includes a plurality of staples (see 530 of FIG. 22) and an operation member 940 therein to perform suturing and cutting tissue.

Here, the cartridge 910 may include a cover (see 510 of FIG. 22), a housing 920, a staple (see 530 of FIG. 22), the operation member 940, and the reciprocating assembly 950.

The housing 920 forms an outer shape of the cartridge 910, and may be formed entirely in the form of a hollow box with one surface (upper surface) removed to accommodate the reciprocating assembly 950, the operation member 940, and the staple (see 530 of FIG. 22) therein. Here, the housing 920 may be formed in an approximately "U" shape in cross section.

A plurality of staples (see 530 of FIG. 22) may be disposed inside the housing 920. As the operation member 940, which will be described later, is linearly moved in one direction, the plurality of staples (see 530 of FIG. 22) are sequentially pushed and raised from the inside of the housing 920 to the outside, thereby performing sealing, that is, stapling.

The reciprocating assembly 950 may be disposed at an inner lower side of the housing 920. In the present embodiment, the reciprocating assembly 950 includes the first reciprocating member 951 and the second reciprocating member 952.

In the present embodiment, the first reciprocating member 951 and the second reciprocating member 952 may form a rack. The first reciprocating member 951 may include a recess 951*b* and the coupling part 951*a*.

In detail, the first reciprocating member 951 may be formed in the form of an elongated bar, and a plurality of recesses 951*b* having a sawtooth shape may be formed on one surface thereof. The recess 951*b* may be formed to be in contact with an operation member 940 to be described later, in particular, a ratchet member 943 of the operation member 940. In other words, the first reciprocating member 951 may include the plurality of recesses 951*b* shaped to engage with first ratchets 943*a* of the ratchet member 943.

Similarly, the second reciprocating member 952 may include a recess 952*b* and the coupling part 952*a*. That is, the second reciprocating member 952 may include a plurality of recesses 952*b* shaped to engage with second ratchets 943*b* of the ratchet member 943.

Here, the first reciprocating member 951 and the second reciprocating member 952 are not fixedly coupled to other components of the cartridge 910, and may be formed to be movable relative to other components of the cartridge 910. That is, the first reciprocating member 951 and the second reciprocating member 952 may perform a reciprocating linear motion with respect to the cover 510 coupled to the housing 920 and the housing 920.

Meanwhile, in the first reciprocating member 951, the coupling part 951*a* may be formed at the proximal end side adjacent to the pulley 911 and the coupling part 951*a* may be fastened and coupled to the first link member 971 of the staple link assembly 970 of the end tool 900. Thus, when the first link member 971 performs a reciprocating linear motion in the extension direction (i.e., the Y-axis direction) of the connection part 400, the first reciprocating member 951 coupled thereto may also perform a reciprocating linear motion in the extension direction (i.e., the Y-axis direction) of the connection part 400.

Similarly, in the second reciprocating member 952, the coupling part 952*a* may be formed at the proximal end side adjacent to the pulley 911 and the coupling part 952*a* may be fastened and coupled to the second link member 976 of the staple link assembly 970 of the end tool 900. Thus, when the second link member 976 performs a reciprocating linear motion in the extension direction (i.e., the Y-axis direction) of the connection part 400, the second reciprocating member 952 coupled thereto may also perform a reciprocating linear motion in the extension direction (i.e., the Y-axis direction) of the connection part 400.

The operation member 940 may be disposed inside the housing 920. The operation member 940 is formed to be in contact with the first reciprocating member 951 and the second reciprocating member 952, and may be formed to linearly move in one direction according to the reciprocating linear motion of the first reciprocating member 951 and the second reciprocating member 952. In other words, the operation member 940 interacts with the first reciprocating member 951 and the second reciprocating member 952 to perform stapling and cutting while moving in the extension direction of the connection part 400.

The operation member 940 may include a wedge (see 541 of FIG. 22), a blade (see 542 of FIG. 22), the ratchet member 943, an elastic member (see 544 of FIG. 22), and the like. Here, in the drawings, components other than the ratchet member 943, that is, the wedge, the blade, and the like are omitted from the operation member 940, but it is of course possible that such components may be included in the operation member 940.

The ratchet member 943 may include the first ratchet 943*a* and the second ratchet 943*b*. Here, the first ratchet 943*a* may be formed to be engageable with the first reciprocating member 951, and the second ratchet 943*b* may be formed to be engageable with the second reciprocating member 952. That is, a motion, in which the first ratchet 943*a* is engaged with (or in close contact with) the first reciprocating member 951 and the operation member 940 is moved forward by the first reciprocating member 951, and a motion, in which the second ratchet 943*b* is engaged with (or in close contact with) the second reciprocating member 952 and the operation member 940 is moved forward by the second reciprocating member 952, are alternately performed.

Here, due to the structural shape of the ratchet member 943, even when a separate elastic member is not provided, the ratchet member 943 may alternately come into close contact with the first reciprocating member 951 and the second reciprocating member 952. This will be described in more detail below.

(Operations of Reciprocating Assembly and Operation Member)

Hereinafter, operations of the reciprocating assembly 950 and the operation member 940 will be described in more detail.

FIGS. 120 and 121 are views illustrating respective operating states of the reciprocating assembly 950 and the operation member 940. Here, FIG. 120A is a view illustrating a state in which the first ratchet 943*a* of the ratchet member 943 and the first reciprocating member 951 come into close contact with each other, and FIG. 120E is a view illustrating a state in which the second ratchet 943*b* of the ratchet member 943 and the second reciprocating member 952 come into close contact with each other, and FIG. 120I is a view illustrating a state in which the first ratchet 943*a* of the ratchet member 943 and the first reciprocating member 951 come into close contact with each other.

In addition, FIGS. 120A to 120E illustrate operating states in which the staple pulley 961 is rotated in the counterclockwise direction (in a direction opposite to the direction of the arrow A1 of FIG. 114) and thus the second reciprocating member 952 is moved forward, and FIGS. 120E to 1201 illustrate operating states in which the staple pulley 961 is rotated in the clockwise direction (in the direction of the arrow A1 of FIG. 114) and thus the first reciprocating member 951 is moved forward.

First, operations of FIGS. 120A to 120E will be described.

FIG. 120A illustrates a state in which the first ratchet 943*a* of the ratchet member 943 and the first reciprocating member 951 come into close contact with each other.

In this state, when the staple pulley 961 is rotated in the counterclockwise direction (in the opposite direction of the arrow A1 of FIG. 114), the first reciprocating member 951 is moved in the direction of an arrow b1 (i.e., is moved backward), and the second reciprocating member 952 is moved in the direction of an arrow b2 (i.e., is moved forward) as shown in FIG. 120B. Then, the recess 951*b* of the first reciprocating member 951 pushes the first ratchet 943*a* of the ratchet member 943 toward the second reciprocating member 952, which causes the entire ratchet member 943 to be rotationally moved in the direction of an arrow b3. In addition, when the ratchet member 943 is rotationally moved in the direction of the arrow b3, the first ratchet 943*a* of the ratchet member 943 starts to be spaced apart from the recess 951*b* of the first reciprocating member 951, and the second ratchet 943*b* of the ratchet member 943 starts to come into contact with the recess 952*b* of the second reciprocating member 952.

In this state, when the staple pulley 961 is further rotated in the counterclockwise direction (in the opposite direction of the arrow A1 of FIG. 114), the first reciprocating member 951 is further moved in the direction of an arrow c1 (i.e., is moved backward), and the second reciprocating member 952 is further moved in the direction of an arrow c2 (i.e., is moved forward) as shown in FIG. 120C. Then, the recess 951*b* of the first reciprocating member 951 further pushes the first ratchet 943*a* of the ratchet member 943 toward the second reciprocating member 952, so that the entire ratchet member 943 is further rotationally moved in the direction of an arrow c3. In addition, when the ratchet member 943 is rotationally moved in the direction of the arrow c3, the first ratchet 943*a* of the ratchet member 943 is further spaced apart from the recess 951*b* of the first reciprocating member 951, and the second ratchet 943*b* of the ratchet member 943 is further brought into contact with the recess 952*b* of the second reciprocating member 952.

In this state, when the staple pulley 961 is further rotated in the counterclockwise direction (in the opposite direction of the arrow A1 of FIG. 114), the first reciprocating member 951 is further moved in the direction of an arrow d1 (i.e., is moved backward), and the second reciprocating member 952 is further moved in the direction of an arrow d2 (i.e., is moved forward) as shown in FIG. 120D. Then, the recess 951*b* of the first reciprocating member 951 further pushes the first ratchet 943*a* of the ratchet member 943 toward the second reciprocating member 952, which causes the entire ratchet member 943 to be further rotationally moved in the direction of an arrow d3. In addition, when the ratchet member 943 is rotationally moved in the direction of the arrow d3, the first ratchet 943*a* of the ratchet member 943 is completely spaced apart from the recess 951*b* of the first reciprocating member 951, and the second ratchet 943*b* of the ratchet member 943 is brought into close contact with the recess 952*b* of the second reciprocating member 952.

In this state, when the staple pulley 961 is further rotated in the counterclockwise direction (in the opposite direction of the arrow A1 of FIG. 114), the first reciprocating member 951 is further moved in the direction of an arrow e1 (i.e., is moved backward), and the second reciprocating member 952 is further moved in the direction of an arrow e2 (i.e., is moved forward) as shown in FIG. 120E. Then, since the second ratchet 943*b* of the ratchet member 943 is in a state of being in close contact with the recess 952*b* of the second reciprocating member 952, the ratchet member 943 is linearly moved in the direction of an arrow e4 by the second reciprocating member 952.

Next, operations of FIGS. 120E to 1201 will be described.

FIG. 120E illustrates a state in which the second ratchet 943*b* of the ratchet member 943 and the second reciprocating member 952 come into close contact with each other.

In this state, when the staple pulley 961 is rotated in the clockwise direction (in the direction of the arrow A1 of FIG. 114), as shown in FIG. 120F, the first reciprocating member 951 is moved in the direction of an arrow f1 (i.e., is moved forward), and the second reciprocating member 952 is moved in the direction of an arrow f2 (i.e., is moved backward). Then, the recess 952*b* of the second reciprocating member 952 pushes the second ratchet 943*b* of the ratchet member 943 toward the first reciprocating member 951, which causes the entire ratchet member 943 to be rotationally moved in the direction of an arrow f3. In addition, when the ratchet member 943 is rotationally moved in the direction of the arrow f3, the second ratchet 943*b* of the ratchet member 943 starts to be spaced apart from the recess 952*b* of the second reciprocating member 952, and the first ratchet 943a of the ratchet member 943 starts come into contact with the recess 951b of the first reciprocating member 951.

In this state, when the staple pulley 961 is further rotated in the clockwise direction (in the direction of the arrow A1 of FIG. 114), as shown in FIG. 120G, the first reciprocating member 951 is further moved in the direction of an arrow g1 (i.e., is moved forward), and the second reciprocating member 952 is further moved in the direction of an arrow g2 (i.e., is moved backward). Then, the recess 952b of the second reciprocating member 952 further pushes the second ratchet 943b of the ratchet member 943 toward the first reciprocating member 951, which causes the entire ratchet member 943 to be further rotationally moved in the direction of an arrow g3. In addition, when the ratchet member 943 is rotationally moved in the direction of the arrow g3, the second ratchet 943b of the ratchet member 943 is further spaced apart from the recess 952b of the second reciprocating member 952, and the first ratchet 943a of the ratchet member 943 is further brought into contact with the recess 951b of the first reciprocating member 951.

In this state, when the staple pulley 961 is further rotated in the clockwise direction (in the direction of the arrow A1 of FIG. 114), as shown in FIG. 120H, the first reciprocating member 951 is further moved in the direction of an arrow h1 (i.e., is moved forward), and the second reciprocating member 952 is further moved in the direction of an arrow h2 (i.e., is moved backward). Then, the recess 952b of the second reciprocating member 952 further pushes the second ratchet 943b of the ratchet member 943 toward the first reciprocating member 951, which causes the entire ratchet member 943 to be further rotationally moved in the direction of an arrow h3. In addition, when the ratchet member 943 is rotationally moved in the direction of the arrow h3, the second ratchet 943b of the ratchet member 943 is completely spaced apart from the recess 952b of the second reciprocating member 952, and the first ratchet 943a of the ratchet member 943 is brought into close contact with the recess 951b of the first reciprocating member 951.

In this state, when the staple pulley 961 is further rotated in the clockwise direction (in the direction of the arrow A1 of FIG. 114), as shown in FIG. 120I, the first reciprocating member 951 is further moved in the direction of an arrow i1 (i.e., is moved forward), and the second reciprocating member 952 is further moved in the direction of an arrow i2 (i.e., is moved backward). Then, since the first ratchet 943a of the ratchet member 943 is in close contact with the recess 951b of the first reciprocating member 951, the ratchet member 943 is linearly moved in the direction of an arrow i4 by the first reciprocating member 951.

FIG. 121 is a view illustrating by extracting some operations of FIG. 120, and is a view in which the forward moving motion of the operation member 940 is mainly described.

FIG. 121A is a view illustrating the state in which the first ratchet 943a of the ratchet member 943 and the first reciprocating member 951 come into close contact with each other, and FIG. 121E is a view illustrating the state in which the second ratchet 943b of the ratchet member 943 and the second reciprocating member 952 come into close contact with each other, and FIG. 1211 is a view illustrating the state in which the first ratchet 943a of the ratchet member 943 and the first reciprocating member 951 come into close contact with each other.

In the state of FIG. 121A, when the staple pulley 961 is rotated in the counterclockwise direction (in the opposite direction of the arrow A1 of FIG. 114), the first reciprocating member 951 is moved in the direction of an arrow e1 (i.e., is moved backward), and the second reciprocating member 952 is moved in the direction of an arrow e2 (i.e., is moved forward) as shown in FIG. 121E.

Then, the recess 951b of the first reciprocating member 951 pushes the first ratchet 943a of the ratchet member 943 toward the second reciprocating member 952, which causes the entire ratchet member 943 to be rotationally moved in the direction of an arrow e3, so that the first ratchet 943a of the ratchet member 943 is spaced apart from the recess 951b of the first reciprocating member 951, and the second ratchet 943b of the ratchet member 943 comes into close contact with the recess 952b of the second reciprocating member 952.

In this state, when the staple pulley 961 is further rotated in the counterclockwise direction (in the opposite direction of the arrow A1 of FIG. 114), since the second ratchet 943b of the ratchet member 943 is in a state of being in close contact with the recess 952b of the second reciprocating member 952, the ratchet member 943 is linearly moved in the direction of an arrow e4 by the second reciprocating member 952.

Meanwhile, in the state of FIG. 121E, when the staple pulley 961 is rotated in the clockwise direction (in the direction of the arrow A1 of FIG. 114), as shown in FIG. 1211, the first reciprocating member 951 is moved in the direction of an arrow i1 (i.e., is moved forward), and the second reciprocating member 952 is moved in the direction of an arrow i2 (i.e., is moved backward).

Then, the recess 952b of the second reciprocating member 952 pushes the second ratchet 943b of the ratchet member 943 toward the first reciprocating member 951, which causes the entire ratchet member 943 to be rotationally moved in the direction of an arrow i3, so that the second ratchet 943b of the ratchet member 943 is spaced apart from the recess 952b of the second reciprocating member 952, and the first ratchet 943a of the ratchet member 943 is brought into close contact with the recess 951b of the first reciprocating member 951.

In this state, when the staple pulley 961 is further rotated in the clockwise direction (in the direction of the arrow A1 of FIG. 114), since the first ratchet 943a of the ratchet member 943 is in a state of being in close contact with the recess 951b of the first reciprocating member 951, the ratchet member 943 is linearly moved in the direction of an arrow i4 by the first reciprocating member 951.

Hereinafter, the overall operation of the present embodiment will be described.

FIGS. 118 and 119 are perspective views illustrating respective operating states of the end tool of FIG. 115. Here, FIG. 118 is a view illustrating when the staple pulley is rotated in the clockwise direction, and FIG. 119 is a view illustrating when the staple pulley is rotated in the counterclockwise direction.

FIG. 118A illustrates a state in which the first ratchet 943a of the ratchet member 943 and the first reciprocating member 951 come into close contact with each other. In this state, when the staple pulley 961 is continuously rotated in a direction b1 of FIG. 118B and a direction c1 of FIG. 118C, the first reciprocating member 951 is moved in a direction b2 of FIG. 118B and a direction c2 of FIG. 118C by the first link member 971 connected to the staple pulley 961. At the same time, the second reciprocating member 952 is moved in a direction b3 of FIG. 118B and a direction c3 of FIG. 118C by the second link member 976 connected to the staple pulley 961. In addition, since the first ratchet 943a of the ratchet member 943 is in close contact with the recess 951b of the first reciprocating member 951, the ratchet member

943 is linearly moved in a direction b4 of FIG. 118B and a direction c4 of FIG. 118C by the first reciprocating member 951.

FIG. 119A illustrates a state in which the second ratchet 943*b* of the ratchet member 943 and the second reciprocating member 952 come into close contact with each other. In this state, when the staple pulley 961 is continuously rotated in a direction b1 of FIG. 119B and a direction c1 of FIG. 118C, the first reciprocating member 951 is moved in a direction b2 of FIG. 119B and a direction c2 of FIG. 119C by the first link member 971 connected to the staple pulley 961. At the same time, the second reciprocating member 952 is moved in a direction b3 of FIG. 119B and a direction c3 of FIG. 119C by the second link member 976 connected to the staple pulley 961. In addition, since the second ratchet 943*b* of the ratchet member 943 is in close contact with the recess 952*b* of the second reciprocating member 952, the ratchet member 943 is linearly moved in a direction b4 of FIG. 119B and a direction c4 of FIG. 119C by the second reciprocating member 952.

In conclusion, when the staple pulley 961 is rotated in one direction, the first reciprocating member 951 is moved forward and the second reciprocating member 952 is moved backward, and in this case, the backward-moving second reciprocating member 952 pushes the operation member 940 toward the first reciprocating member 951 to bring the operation member 940 into close contact with the first reciprocating member 951, and the forward-moving first reciprocating member 951 moves the operation member 940, which is in close contact therewith, forward.

Meanwhile, when the staple pulley 961 is rotated in the other direction, the second reciprocating member 952 is moved forward and the first reciprocating member 951 is moved backward, and in this case, the backward-moving first reciprocating member 951 pushes the operation member 940 toward the second reciprocating member 952 to bring the operation member 940 into close contact with the second reciprocating member 952, and the forward-moving second reciprocating member 952 moves the operation member 940, which is in close contact therewith, forward.

As a result, when the staple pulley 961 is rotated in one direction, the first reciprocating member 951 moves the operation member 940 forward, and when the staple pulley 961 is rotated in the opposite direction, the second reciprocating member 952 moves the operation member 940 forward, and thus a forward-moving speed of the operation member 940 is approximately doubled as compared to the first embodiment, thereby reducing a stapling and cutting time.

Fifth Embodiment-Pin/Slot Type

Hereinafter, an end tool 1000 of a surgical instrument according to a fifth embodiment of the present disclosure will be described. Here, the end tool 1000 of the surgical instrument according to the fifth embodiment of the present disclosure is different from the end tool (see 100 of FIG. 2 or the like) of the surgical instrument according to the first embodiment of the present disclosure described above in that a configuration of a staple pulley assembly 1060 and a staple link assembly 1070 is different. Hereinafter, the configuration that is different from that of the first embodiment will be described in detail.

Figure 122:
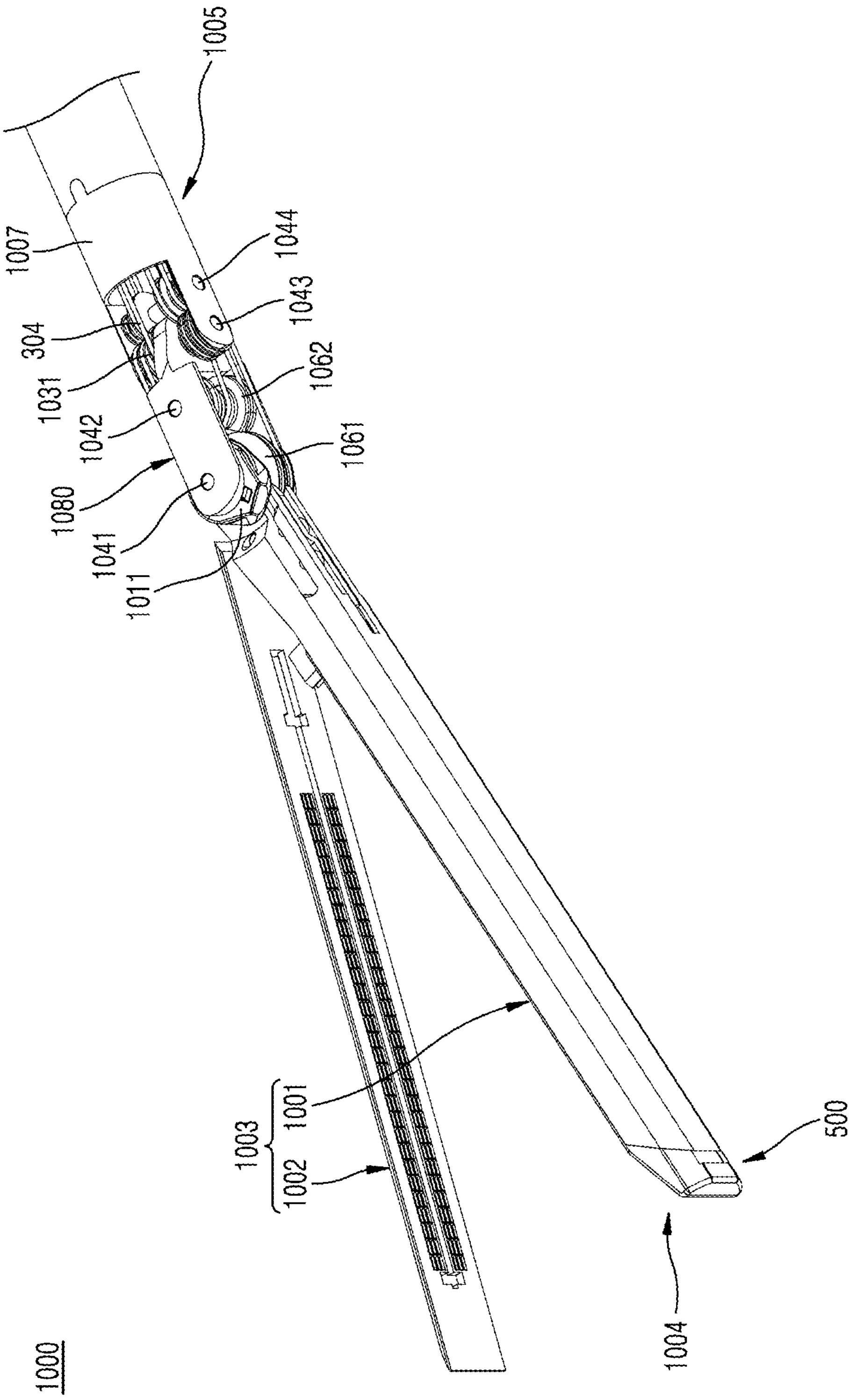
FIG. 122 is a perspective view illustrating an end tool of a surgical instrument according to a fifth embodiment of the present disclosure.
Figure 123:
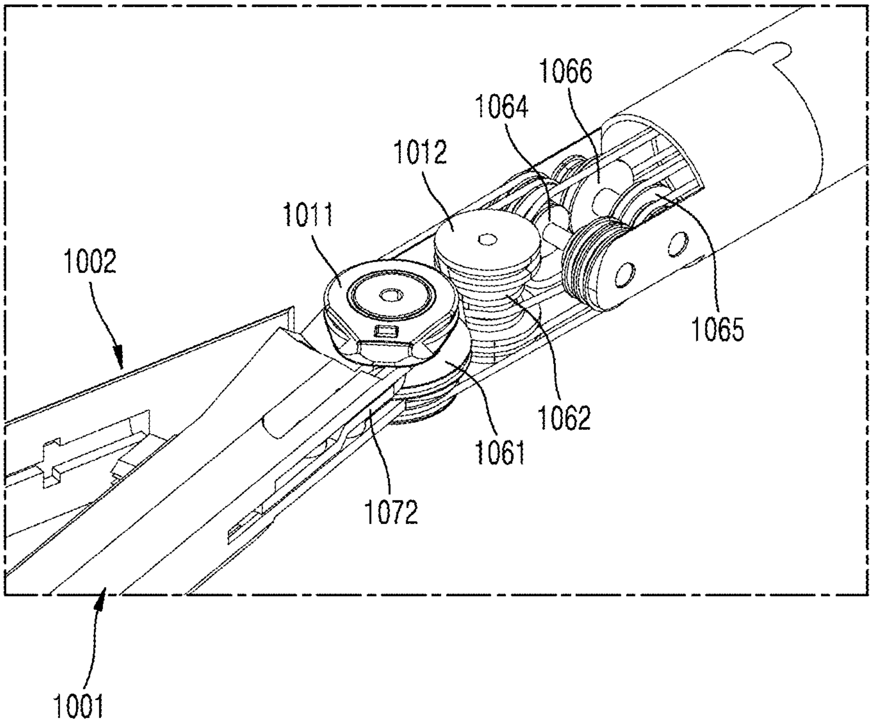
FIG. 123 is a magnified view of the end tool of the surgical instrument of FIG. 122.
Figure 124:
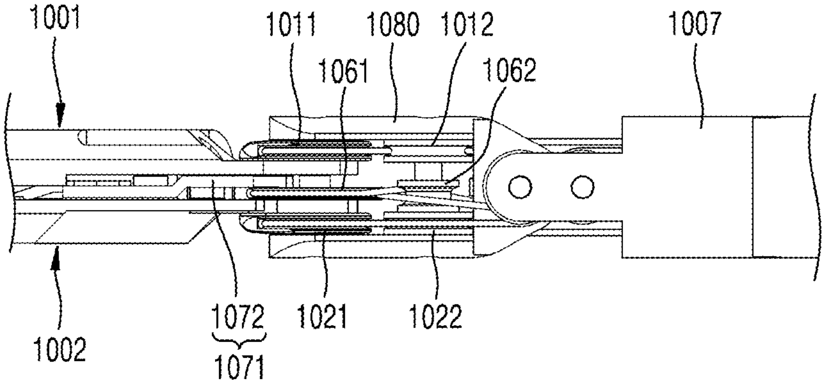
FIG. 124 is a side view illustrating the end tool of the surgical instrument of FIG. 122.
Figure 125:
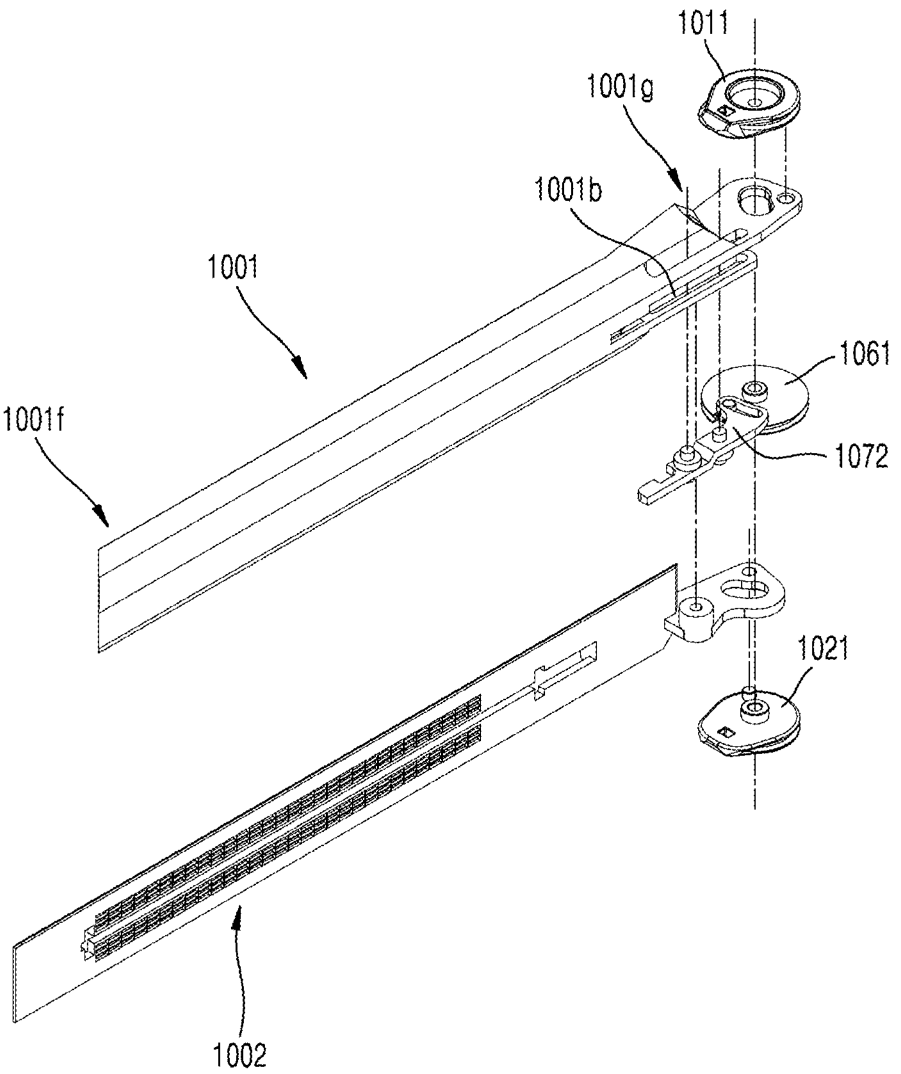
FIGS. 125 and 126 are exploded perspective views of the end tool of the surgical instrument of FIG. 122.
Figure 126:
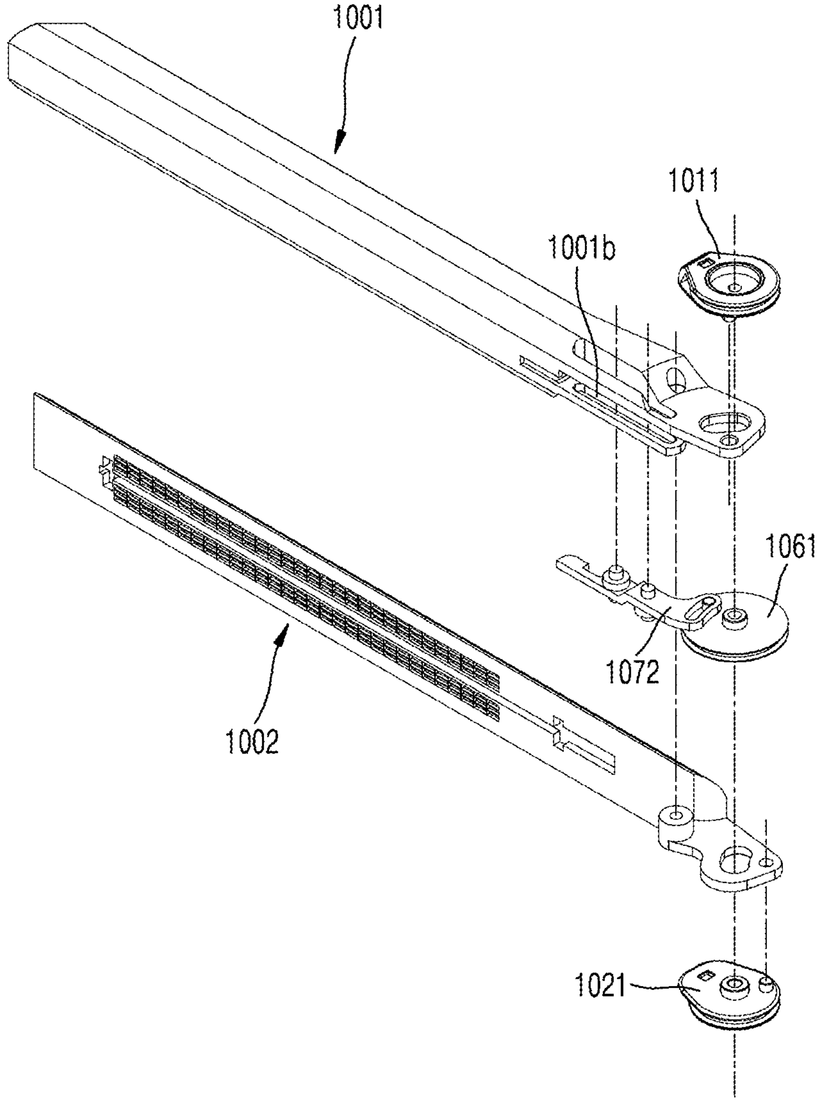
Figure 127:
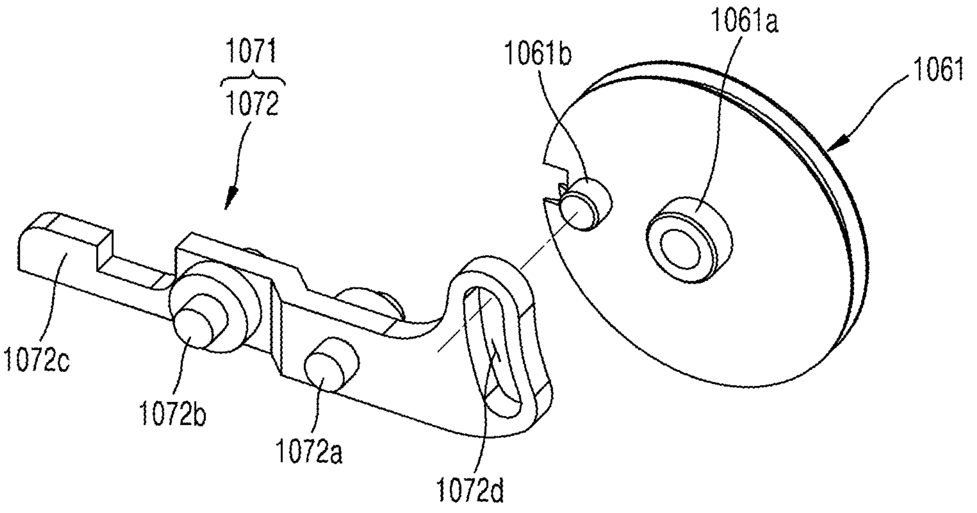
FIG. 127 is an exploded perspective view of a staple pulley assembly of the surgical instrument of FIG. 122.
Figure 128:
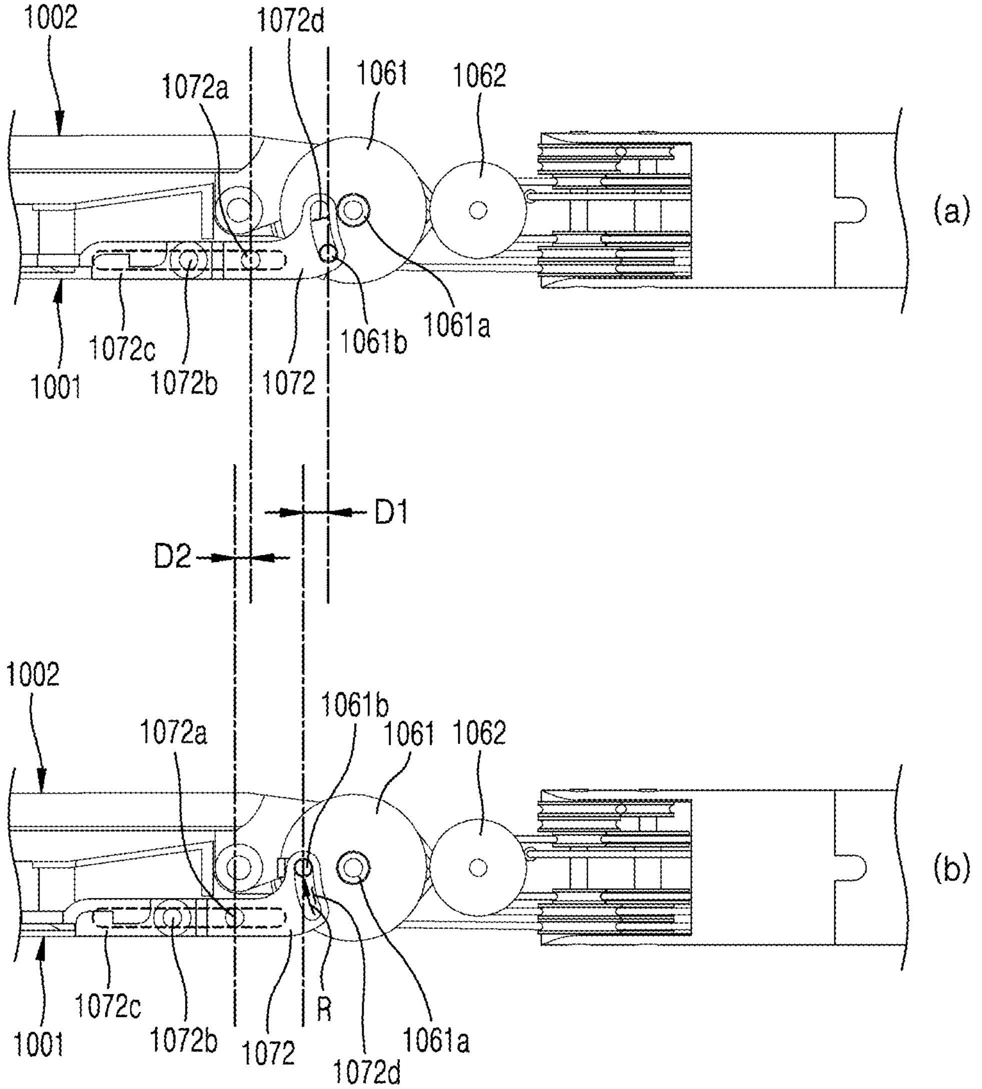
FIG. 128 is a plan view illustrating an operating states of a staple pulley in the end tool of FIG. 122.
Figure 129:
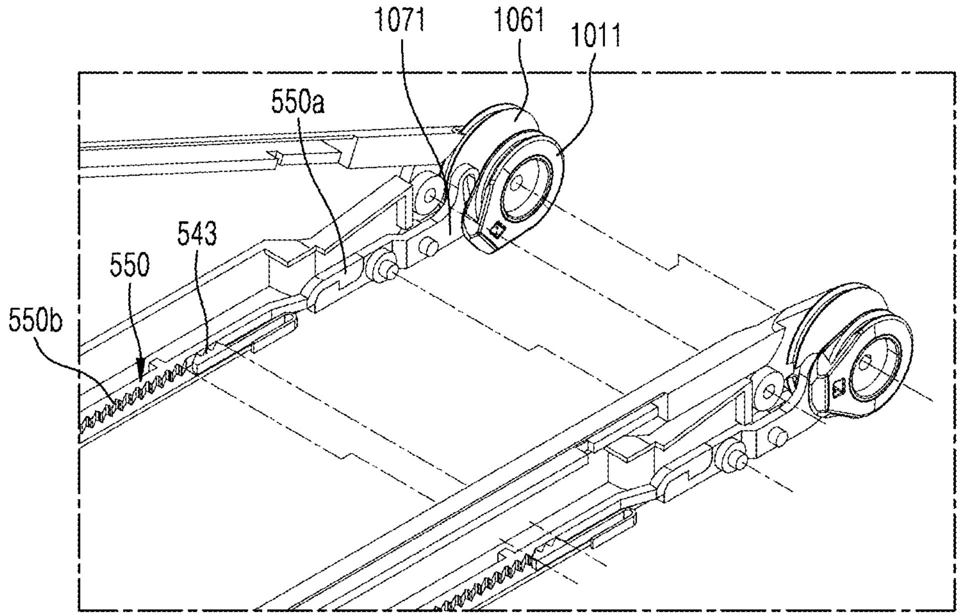
FIG. 129 is a perspective view illustrating opening and closing motions of the end tool of the surgical instrument of FIG. 122.
Figure 130:
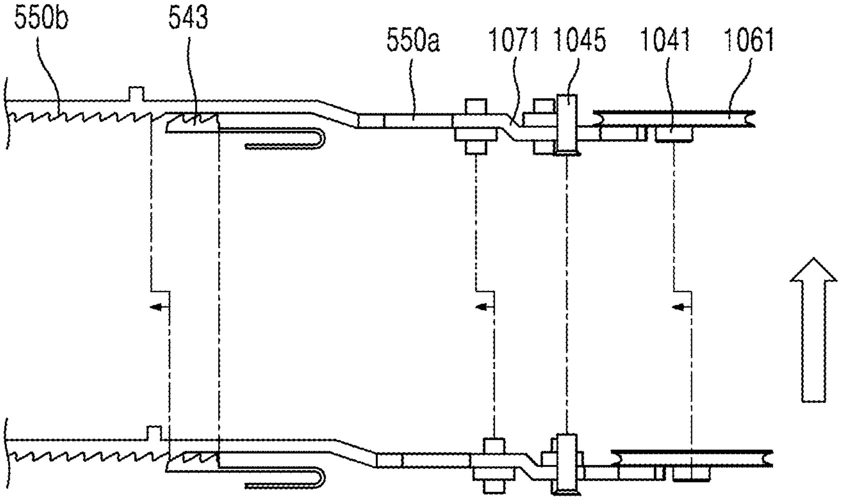
FIG. 130 is a plan view of FIG. 129.
Figure 131:
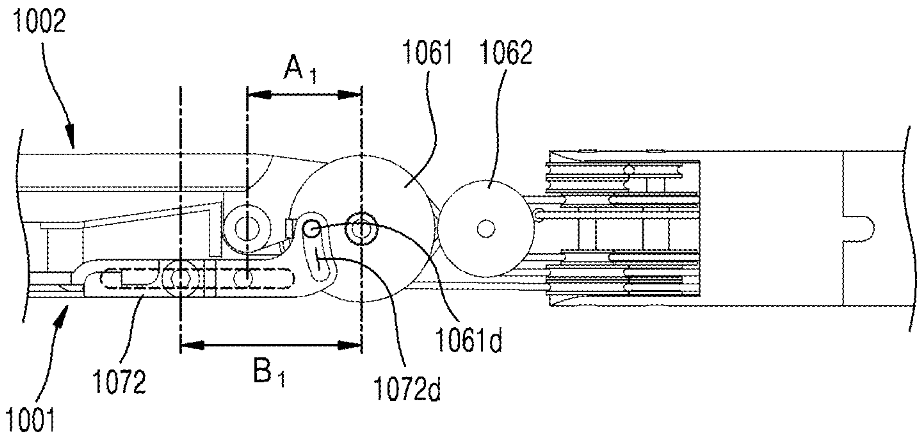
FIGS. 131 and 132 are plan views illustrating opening and closing motions of the end tool of the surgical instrument of FIG. 122.
Figure 131:
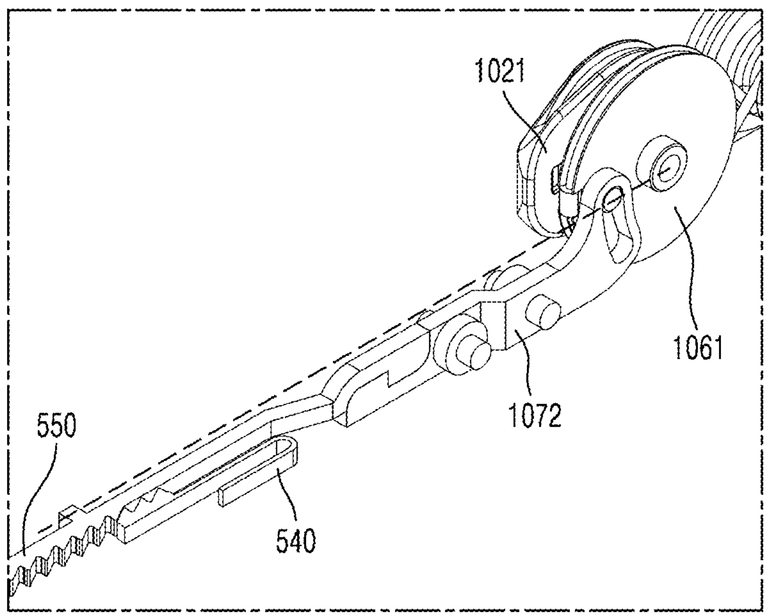
Figure 132:
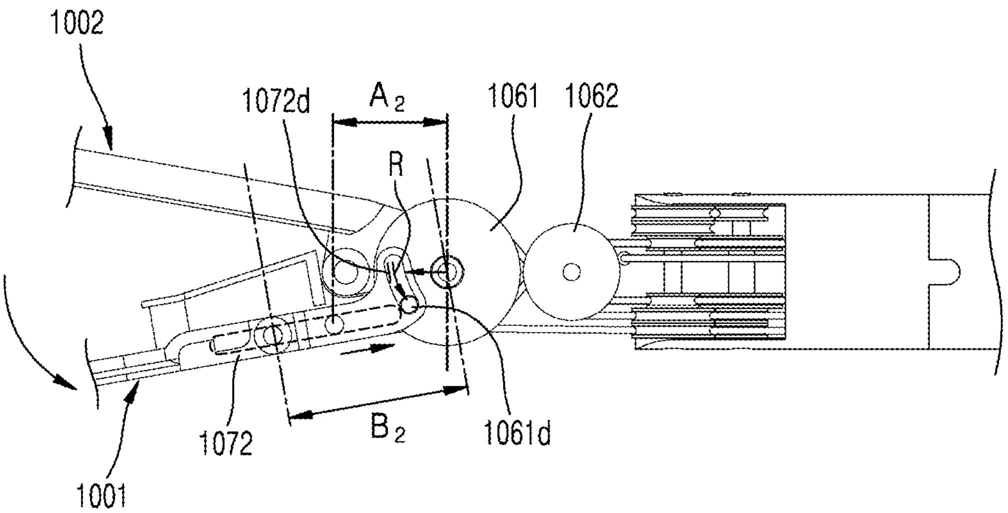
Figure 132:
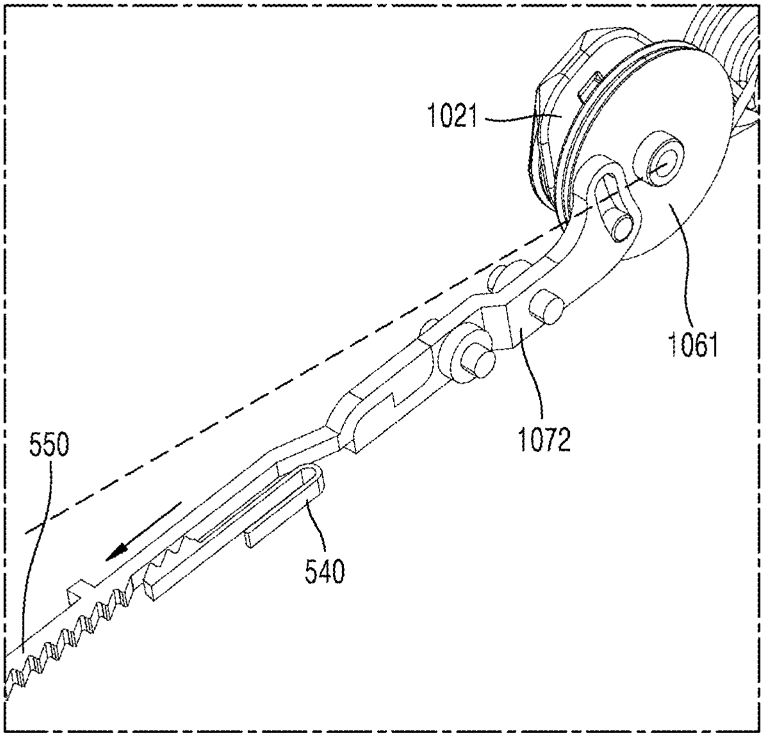
Figure 133:
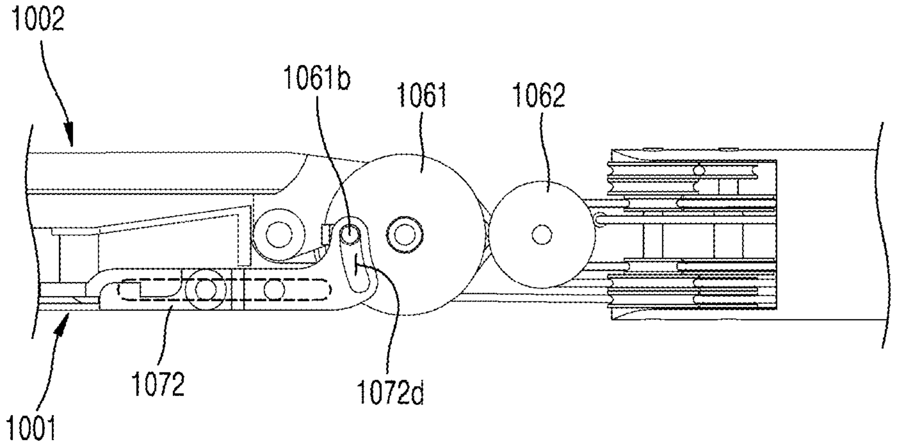
FIGS. 133 and 134 are views illustrating a process in which the end tool of the surgical instrument of FIG. 122 is switched from a deactivated state to an activated state.
Figure 133:
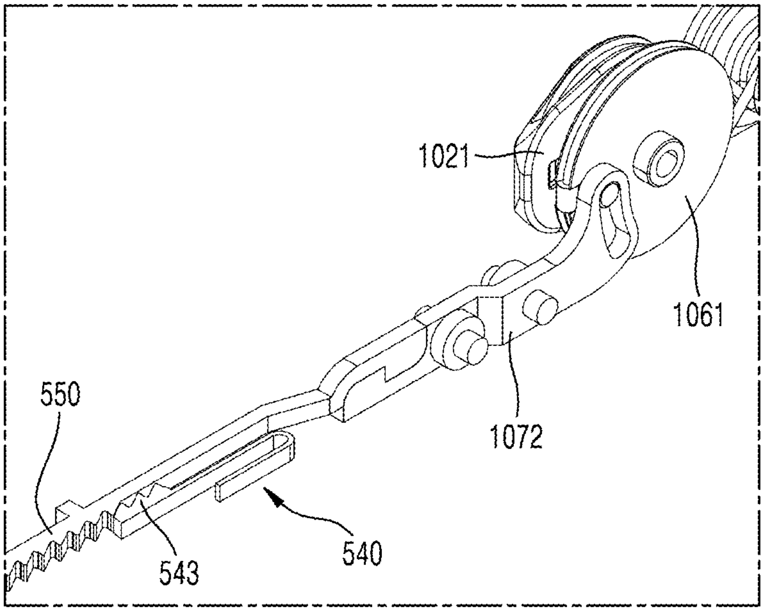
Figure 134:
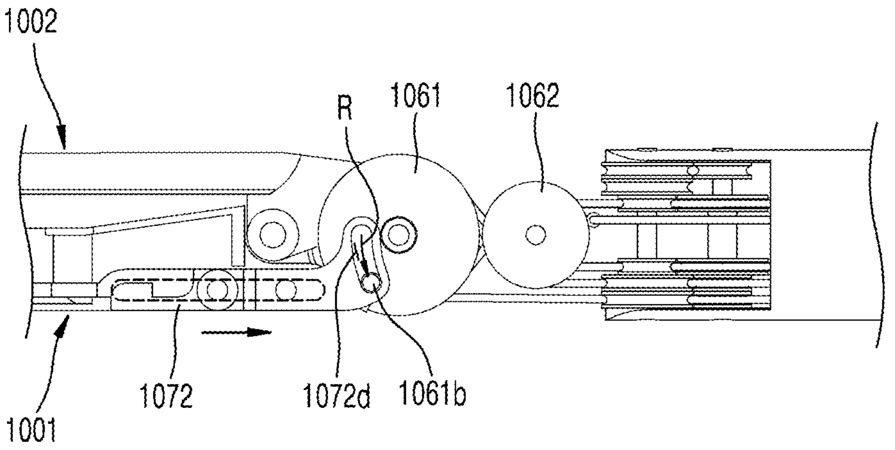
Figure 134:
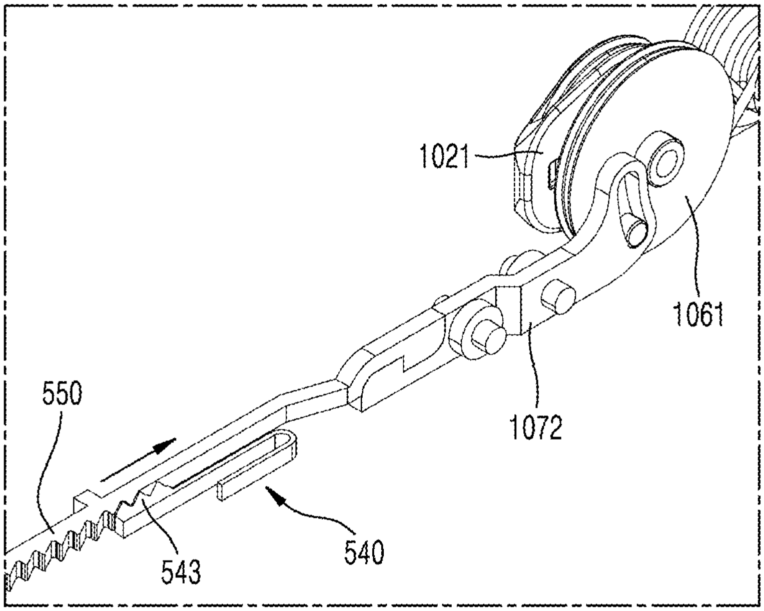

FIG. 122 is a perspective view illustrating the end tool of the surgical instrument according to the fifth embodiment of the present disclosure, and FIG. 123 is a magnified view of the end tool of the surgical instrument of FIG. 122. FIG. 124 is a side view illustrating the end tool of the surgical instrument of FIG. 122. FIGS. 125 and 126 are exploded perspective views of the end tool of the surgical instrument of FIG. 122. FIG. 127 is an exploded perspective view of a staple pulley assembly of the surgical instrument of FIG. 122. FIG. 128 is a plan view illustrating operating states of a staple pulley in the end tool of FIG. 122. FIG. 129 is a perspective view illustrating opening and closing motions of the end tool of the surgical instrument of FIG. 122, and FIG. 130 is a plan view of FIG. 129. FIGS. 131 and 132 are plan views illustrating opening and closing motions of the end tool of the surgical instrument of FIG. 122. FIGS. 133 and 134 are views illustrating a process in which the end tool of the surgical instrument of FIG. 122 is switched from a deactivated state to an activated state. FIGS. 135 to 139 are views illustrating a process of performing stapling and cutting motions as the end tool of the surgical instrument of FIG. 122 is switched from the deactivated state to the activated state.

Here, FIG. 123 illustrates a state in which an end tool hub is removed. FIGS. 128 and 129 illustrate a state in which the end tool hub and a jaw pulley are removed. FIGS. 131 to 134 mainly describe operations of the staple pulley assembly, the staple link assembly, and a reciprocating assembly. FIGS. 135 to 139 mainly describe a coupling relationship between the reciprocating member and an operation member.

Referring to FIGS. 122 to 139, the end tool 1000 of the fifth embodiment of the present disclosure includes a pair of jaws 1003 for performing a grip motion, that is, a first jaw 1001 and a second jaw 1002. Here, each of the first jaw 1001 and the second jaw 1002, or a component encompassing the first jaw 1001 and the second jaw 1002 may be referred to as the jaw.

Meanwhile, the end tool 1000 includes a plurality of pulleys including a pulley 1011 and a pulley 1012 that are related to a rotational motion of the first jaw 1001. The pulleys related to the rotational motion of the first jaw 1001 described in the present embodiment are substantially the same as the pulley 111, the pulley 112, the pulley 113, the pulley 114, the pulley 115, and the pulley 116 described with reference to FIG. 8 or the like of the first embodiment, and thus, detailed descriptions thereof will be omitted herein.

Meanwhile, the end tool 1000 includes a plurality of pulleys including a pulley 1021 and a pulley 1022 that are related to a rotational motion of the second jaw 1002. The pulleys related to the rotational motion of the second jaw 1002 described in the present embodiment are substantially the same as the pulley 121, the pulley 122, the pulley 123, the pulley 124, the pulley 125, and the pulley 126 described with reference to FIG. 8 or the like of the first embodiment, and thus, detailed descriptions thereof will be omitted herein.

In addition, the end tool 1000 of the fifth embodiment of the present disclosure may include a rotation shaft 1041, a rotation shaft 1042, a rotation shaft 1043, and a rotation shaft 1044. Here, the rotation shaft 1041 and the rotation shaft 1042 may be inserted through an end tool hub 1080, and the rotation shaft 1043 and the rotation shaft 1044 may be inserted through a pitch hub 1007. The rotation shaft 1041, the rotation shaft 1042, the rotation shaft 1043, and the rotation shaft 1044 may be arranged sequentially from a distal end 1004 of the end tool 1000 toward a proximal end 1005.

In addition, the end tool 1000 of the fifth embodiment of the present disclosure may include the end tool hub 1080 and the pitch hub 1007.

The rotation shaft 1041 and the rotation shaft 1042 may be inserted through the end tool hub 1080, and the pulley 1011 and the pulley 1021 axially coupled to the rotation shaft 1041 and at least some of the first jaw 1001 and the second jaw 1002 coupled to the pulley 1011 and the pulley 1021 may be accommodated inside the end tool hub 1080.

The rotation shaft 1043 and the rotation shaft 1044 may be inserted through the pitch hub 1007, and the pitch hub 1007 may be axially coupled to the end tool hub 1080 by the rotation shaft 1043. Accordingly, the end tool hub 1080 may be formed to be pitch-rotatable around the rotation shaft 1043 with respect to the pitch hub 1007.

Meanwhile, the end tool 1000 of the fifth embodiment of the present disclosure may further include components, such as a staple drive assembly (see 150 of FIG. 13) including the staple pulley assembly 1060 and the staple link assembly 1070, to perform stapling and cutting motions.

The staple pulley assembly 1060 may be formed between the pulley 1011 and the pulley 1021 to be adjacent to the pulley 1011 and the pulley 1021. In the present embodiment, it is assumed that the staple pulley assembly 1060 includes one staple pulley 1061.

In the fifth embodiment of the present disclosure, by disposing the staple pulley assembly 1060 between the pulley 1011, which is a first jaw pulley, and the pulley 1021, which is a second jaw pulley, the end tool 1000 is allowed to perform pitch and yaw motions, as well as stapling and cutting motions using a cartridge 1010.

Hereinafter, the staple pulley assembly 1060, the staple link assembly 1070, and a reciprocating assembly 1050 of the end tool 1000 of the surgical instrument according to the fifth embodiment of the present disclosure will be described in more detail.

In the end tool 1000 of the surgical instrument according to the fifth embodiment of the present disclosure, the staple pulley assembly 1060 and the staple link assembly 1070 form a pin-slot structure. In addition, with such a structure, a force for moving the reciprocating assembly 550 forward may be amplified. Furthermore, a deactivated state, in which the staple link assembly 1070 and the reciprocating assembly 1050 are separated from each other, may be switched to an activated state in which the staple link assembly 1070 and the reciprocating assembly 1050 are coupled to each other.

Referring to FIGS. 122 to 139 and the like, the staple pulley assembly 1060 may include one or more staple pulleys 1061.

A shaft pass-through part 1061*a* may be formed in the staple pulley 1061. The shaft pass-through part 1061*a* may be formed in the form of a hole, and the rotation shaft 1041, which is an end tool jaw pulley rotation shaft, may be inserted through the shaft pass-through part 1061*a*.

Further, a protruding member 1061*b* may be formed on the staple pulley 1061. A link member 1071 of the staple link assembly 1070 may be coupled to the protruding member 1061*b*. Here, the protruding member 1061*b* is formed in the form of a pin, and may be fitted into a slot 1072*d* of the link member 1071, which will be described later.

Meanwhile, the end tool 1000 of the fifth embodiment of the present disclosure may further include the staple link assembly 1070 connected to the staple pulley assembly 1060, and the staple link assembly 1070 may include the link member 1071. Here, the staple link assembly 1070 may serve to connect the staple pulley assembly 1060 to the reciprocating assembly 1050 of the cartridge 1010 to be described later.

In the present embodiment, the staple link assembly 1070 includes only one link. That is, by coupling the staple pulley assembly 1060 and the staple link assembly 1070 by a pin-slot structure, it is possible to convert a rotational motion of the staple pulley assembly 1060 into a linear motion of the staple link assembly 1070 even when the staple link assembly 1070 includes only one link.

In detail, the link member 1071 may be formed as a single link, which is a first link 1072. In other words, the first link 1072 may be formed as a single member.

The first link 1072 is formed in the form of an elongated bar, and may include a first protrusion 1072*a*, a second protrusion 1072*b*, a coupling part 1072*c*, and the slot 1072*d*.

The first protrusion 1072*a* and the second protrusion 1072*b* may be formed in one region of a central portion of the first link 1072. The first protrusion 1072*a* and the second protrusion 1072*b* may be fitted into a guide groove 1001*b* of the first jaw 1001.

As described above, as the first protrusion 1072*a* and the second protrusion 1072*b* are moved along the guide groove 1001*b* in a state in which the first protrusion 1072*a* and the second protrusion 1072*b* of the first link 1072 formed in a protruding shape are fitted into the groove-shaped guide groove 1001*b*, the link member 1071 is moved with respect to the first jaw 1001 (and the cartridge 500 therein). This will be described in more detail later.

Meanwhile, the coupling part 1072*c* may be formed at one end portion of the first link 1072. The coupling part 1072*c* may be coupled to a coupling part 551*a* of a reciprocating member 551 of the cartridge 500.

Meanwhile, the slot 1072*d* may be formed at one end portion of the first link 1072. Here, the slot 1072*d* may be formed in the form of an elongated hole, into which the protruding member 1061*b* in the form of a pin may be fitted. In detail, the slot 1072*d* may be formed to have a predetermined curvature, and may be formed in an approximately elliptical shape. Here, a short radius of the slot 1072*d* may be formed to be substantially the same as or slightly greater than a radius of the protruding member 1061*b*. Meanwhile, a long radius the slot 1072*d* may be formed to be greater than a radius of the protruding member 1061*b*. Accordingly, in a state in which the protruding member 1061*b* of the staple pulley 1061 is fitted into the slot 1072*d* of the first link 1072, the protruding member 1061*b* is moved to a certain extent in the slot 1072*d*.

Here, the slot 1072*d* may be formed obliquely without being concentric with the staple pulley 1061. Accordingly, when the staple pulley 1061 is rotated, the protruding member 1061*b*, while in contact with the slot 1072*d*, may push the slot 1072*d* to move the first link 1072. That is, when the staple pulley 1061 is rotated, the protruding member 1061*b* is moved in the slot 1072*d* while coming into contact with the slot 1072*d*, which causes the first link 1072 to be linearly moved along the guide groove 1001*b* of the first jaw 1001.

(Displacement of Staple Link Assembly According to Rotation of Staple Pulley)

Hereinafter, the displacement of the staple link assembly 1070 according to the rotation of the staple pulley 1061 will be described.

Referring to FIG. 129, in the fifth embodiment of the present disclosure, the staple pulley 1061 and the staple link assembly 1070 are coupled in the form of a pin-slot. That is, the protruding member 1061*b* formed in the form of a pin on the staple pulley 1061 is coupled to the slot 1072*d* formed in the staple link assembly 1070. Accordingly, when the staple pulley 1061 is rotated in the direction of an arrow R, the displacement of the protruding member 1061*b* of the staple pulley 1061 in the X-axis direction becomes D1. In addition, the displacement of the staple link assembly 1070 in the X-axis direction becomes D2.

Meanwhile, referring to FIG. 38 or the like, in the first embodiment of the present disclosure, the staple pulley 161 and the staple link assembly 170 are axially coupled to each other and thus the displacement of the protruding member 1061*b* of the staple pulley 1061 in the X-axis direction becomes much greater than that of the fourth embodiment.

In other words, as compared with the case in which the staple pulley and the staple link assembly are axially coupled as in the first embodiment of the present disclosure or the like, when the staple pulley and the staple link assembly are pin-slot coupled with each other as in the present embodiment, the displacement of the staple link assembly in the X-axis direction is reduced even when the staple pulley is rotated by the same distance.

Meanwhile, since work is the product of force and displacement, assuming that the work for rotating the staple pulley is the same, the displacement and the force are inversely proportional to each other. Accordingly, when the displacement is reduced, the force is increased in inverse proportion to the displacement.

As a result, in the fifth embodiment of the present disclosure, the staple pulley 1061 and the staple link assembly 1070 are coupled in the form of a pin-slot, and the displacement of the staple link assembly 1070 in the X-axis direction caused by the rotation of the staple pulley 1061 is relatively reduced compared to the other embodiments, and thus the force received by the staple link assembly 1070 in the X-axis direction is relatively increased compared to the other embodiments.

According to the fifth embodiment of the present disclosure described above, a force for moving the staple link assembly 1070 and the reciprocating assembly 550 connected thereto forward is amplified, and thus a stapling motion may be performed more robustly.

(Activated State and Deactivated State)

Hereinafter, the activated state and the deactivated state according to the present embodiment will be described.

In the first embodiment of the present disclosure or the like described above, the staple link assembly and the reciprocating assembly are always in the coupled state, and thus the reciprocating assembly is always linearly moved when the staple pulley is rotated. In addition, the staple pulley is dependent on the jaw pulley, and thus, when the jaw pulley is rotated, i.e., during a yaw or actuation motion, the staple pulley is also rotated As a result, the reciprocating assembly is also moved forward/backward during the yaw or actuation motion, and in this process, the operation member may be moved. Accordingly, when the yaw or actuation motion is repeated, an undesired stapling motion may be performed.

In order to address such a problem, in the fifth embodiment of the present disclosure, there are a deactivated state in which the reciprocating assembly 550 and the operation member 540 are not coupled to and separated from each other, and an activated state in which the reciprocating assembly 550 and the operation member 540 are coupled to each other. In addition, the deactivated state may be maintained in a jaw open state, and the deactivated state may be switched to the activated state in a jaw close state. In addition, after switching to the activated state, as the reciprocating assembly is repeatedly moved forward and backward according to an alternating rotational motion of the staple pulley, the operation member is moved forward.

This distinction between the activated and deactivated states may be made possible by the pin-slot structure described above. Hereinafter, this will be described in more detail.

Referring to FIGS. 130 to 132 and the like, in a state in which the jaw 1003 is closed as shown in FIG. 131, when the first jaw 1001 is rotated in the direction of an arrow R of FIG. 132 and the second jaw 1002 is rotated in the opposite direction of the arrow R, the jaw 1003 is in an opened state. Here, it is assumed that the position of a jaw rotation shaft 1045 in the X-axis direction is fixed, while the other components move.

When the jaw 1003 is in the opened state, the first jaw pulley 1011 and the staple pulley 1061 are rotated in the same direction.

When the first jaw pulley 1011 is rotated in the direction of the arrow R of FIG. 132, the pulley 1011, the staple pulley 1061, the staple link assembly 1070, and the reciprocating assembly 550 are moved together toward a distal end 1001*f* (i.e., are moved forward) in a state in which the jaw rotation shaft 1045 is fixed. Accordingly, A1 of FIG. 131, which is a distance between the rotation shaft 1041 and the jaw rotation shaft 1045 in a state in which the jaw 1003 is closed, is greater than A2 of FIG. 132, which is a distance between the rotation shaft 1041 and the jaw rotation shaft 1045 in a state in which the jaw 1003 is opened (i.e., A1>A2).

At the same time, when the staple pulley 1061 is rotated in the direction of the arrow R in FIG. 132, the staple link assembly 1070 connected to the staple pulley 1061 and the reciprocating assembly 550 connected the staple link assembly 1070 are moved as a whole (i.e., are moved backward) toward a proximal end 1001*g*. Accordingly, B1 of FIG. 131, which is a distance between the rotation shaft 1041 and the staple link assembly 1070 (the second protrusion 1072*b* thereof) in a state in which the jaw 1003 is closed, is greater than B2 of FIG. 132, which is a distance between the rotation shaft 1041 and the staple link assembly 1070 (the second protrusion 1072*b* thereof) in a state in which the jaw 1003 is opened (i.e., B1>B2).

However, here, due to the pin-slot structure as described above, the displacement of the staple link assembly 1070 in the x-axis direction when the staple pulley 1061 is rotated is relatively small (compared to other embodiments).

That is, in the fifth embodiment of the present disclosure, a relationship of (A1−A2)>(B1−B2) is established.

In other words, when the jaw 1003 is opened, the movement amount (A1−A2) of the pulley 1011, the staple pulley 1061, the staple link assembly 1070, and the reciprocating assembly 550 toward the distal end is greater than the movement amount (B1−B2) of the staple link assembly 1070 and the reciprocating assembly 550 connected thereto toward the proximal end.

As a result, when the two movement components of the reciprocating assembly 550 described above are synthesized, the reciprocating assembly 550 is moved toward the distal end 1001*f* when the jaw 1003 is opened. That is, the reciprocating assembly 550 is moved forward.

That is, in the first embodiment, the reciprocating member is moved backward when the moving-backward amount of the reciprocating assembly due to the rotation of the staple pulley is larger than the moving-forward amount of the reciprocating assembly due to the rotation of the jaw pulley, whereas in the present embodiment, the reciprocating member is moved forward when the moving-forward amount of the reciprocating assembly due to the rotation of the jaw pulley is larger than the moving-backward amount of the reciprocating assembly due to the rotation of the staple pulley.

In addition, when the reciprocating assembly 550 is moved forward as described above, the reciprocating assembly 550 and the operation member 540 are further spaced apart from each other, and thus, when the jaw is opened, the deactivated state in which the reciprocating assembly 550 and the operation member 540 are not coupled is maintained.

In contrast, in a state in which the jaw 1003 is opened as shown in FIG. 132, the first jaw 1001 is rotated in the opposite direction of the arrow R of FIG. 132, and when the second jaw 1002 is rotated in the direction of the arrow R, the jaw 1003 is in a closed state as shown in FIG. 131.

When the jaw 1003 is closed as described above, the reciprocating assembly 550 is moved toward the proximal end 1001*g*. That is, the reciprocating assembly 550 is moved backward.

In the closed state as shown in FIG. 131, a recess 550*b* of the reciprocating assembly 550 and a ratchet 543*a* of the ratchet member 543 of the operation member 540 are in contact with each other but are not coupled to each other.

Accordingly, the deactivated state in which the reciprocating assembly 550 and the operation member 540 are not coupled to and separated from each other is maintained between the state of FIG. 131, in which the jaw 1003 is fully opened, and the state of FIG. 132, in which the jaw 1003 is closed. That is, in this state, even when the staple pulley 1061 is rotated, the operation member 540 is not moved, and thus stapling and cutting motions are not performed.

Next, referring to FIGS. 133 and 134 and the like, in a state in which the jaw 1003 is closed as shown in FIG. 133, the staple pulley 1061 is rotated in the direction of an arrow R of FIG. 134 for stapling and cutting motions.

When the staple pulley 1061 is rotated in the direction of the arrow R, the staple link assembly 1070 connected to the staple pulley 1061 and the reciprocating assembly 550 connected to the staple link assembly 1070 are moved as a whole toward the proximal end 1001*g* (i.e., are moved backward). In addition, as shown in FIG. 134, when the reciprocating assembly 550 is moved toward the proximal end 1001*g* to be coupled to the ratchet member 543 of the operation member 540, the deactivated state is switched to the activated state.

After switching to the activated state as described above, as the staple pulley 1061 performs an alternating rotational motion, the reciprocating assembly 550 is repeatedly moved forward and backward, which causes the operation member 540 to move forward.

FIGS. 135 to 139 are views illustrating a process of performing stapling and cutting motions as the end tool of the surgical instrument of FIG. 122 is switched from the deactivated state to the activated state. Here, (a) of each drawing illustrates a state in which the jaw 1003 is opened, (b) of each drawing illustrates a state in which the jaw 1003 is closed, and (c) of each drawing illustrates a state in which the staple pulley 1061 is rotated in the state in which the jaw 1003 is closed.

Figure 135:
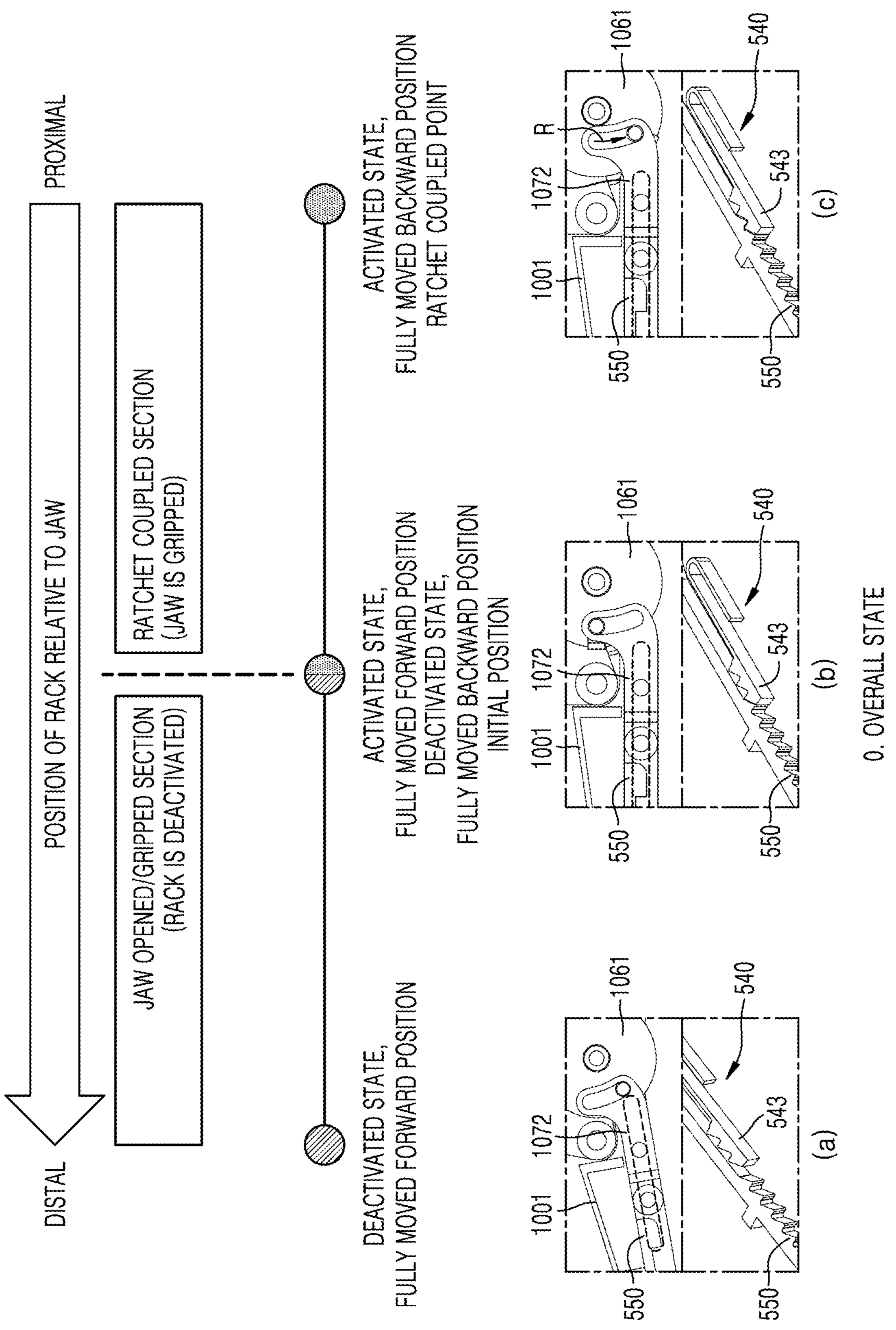
FIGS. 135 to 139 are views illustrating a process of performing stapling and cutting motions as the end tool of the surgical instrument of FIG. 122 is switched from the deactivated state to the activated state.

FIG. 135 is a view illustrating the entire process of performing the stapling and cutting motions as the end tool of the surgical instrument of FIG. 122 is switched from the deactivated state to the activated state.

In a state in which the jaw 1003 is opened as shown in FIG. 135A, the end tool is switched to the deactivated state in which the reciprocating assembly 550 and the operation member 540 are not coupled to and separated from each other. That is, as compared to the state of FIG. 135B in which the jaw 1003 is closed, in the state of FIG. 135A in which the jaw 1003 is opened, the reciprocating assembly 550 is moved forward toward the distal end 1001*f*. Accordingly, the reciprocating assembly 550 and the operation member 540 are in a state of being maximally spaced apart from each other.

Meanwhile, in the closed state as shown in FIG. 135B, the recess 550*b* of the reciprocating assembly 550 and the ratchet 543*a* of the ratchet member 543 of the operation member 540 are in contact with each other but are not coupled to each other. That is, even in this state, the end tool remains in the deactivated state in which the reciprocating assembly 550 and the operation member 540 are not coupled to and separated from each other.

Meanwhile, in a state in which the jaw 1003 is closed as shown in FIG. 135B, when the staple pulley 1061 is rotated in the direction of the arrow R as shown in FIG. 135C, the reciprocating assembly 550 is moved toward the proximal end 1001*g* to be coupled to the ratchet member 543 of the operation member 540, so that the deactivated state is switched to the activated state.

After switching to the activated state as described above, as the staple pulley 1061 performs an alternating rotational motion, the reciprocating assembly 550 is repeatedly moved forward and backward, which causes the operation member 540 to move forward.

Figure 136:
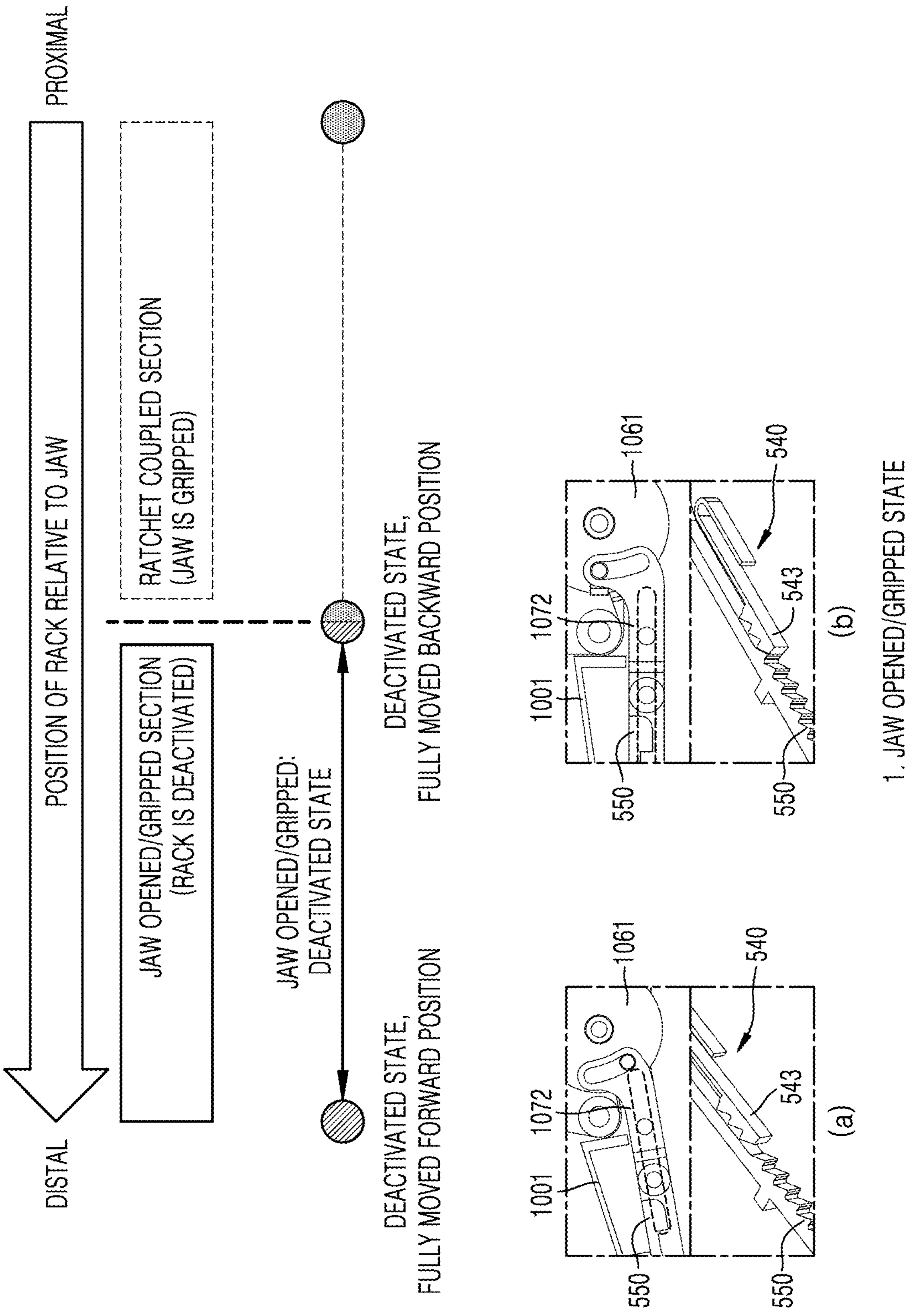

FIG. 136 is a view illustrating opened/closed states of the jaw 1003 in the end tool of the surgical instrument of FIG. 122.

In a state in which the jaw 1003 is opened as shown in FIG. 136A, the end tool is switched to the deactivated state in which the reciprocating assembly 550 and the operation member 540 are not coupled to and separated from each other. That is, as compared to the state of FIG. 136B in which the jaw 1003 is closed, in the state of FIG. 136A in which the jaw 1003 is opened, the reciprocating assembly 550 is moved forward toward the distal end 1001*f*. Accordingly, the reciprocating assembly 550 and the operation member 540 are in a state of being maximally spaced apart from each other.

Meanwhile, in the closed state as shown in FIG. 136B, the recess 550*b* of the reciprocating assembly 550 and the ratchet 543*a* of the ratchet member 543 of the operation member 540 are in contact with each other but are not coupled to each other. That is, even in this state, the end tool remains in the deactivated state in which the reciprocating assembly 550 and the operation member 540 are not coupled to and separated from each other.

Figure 137:
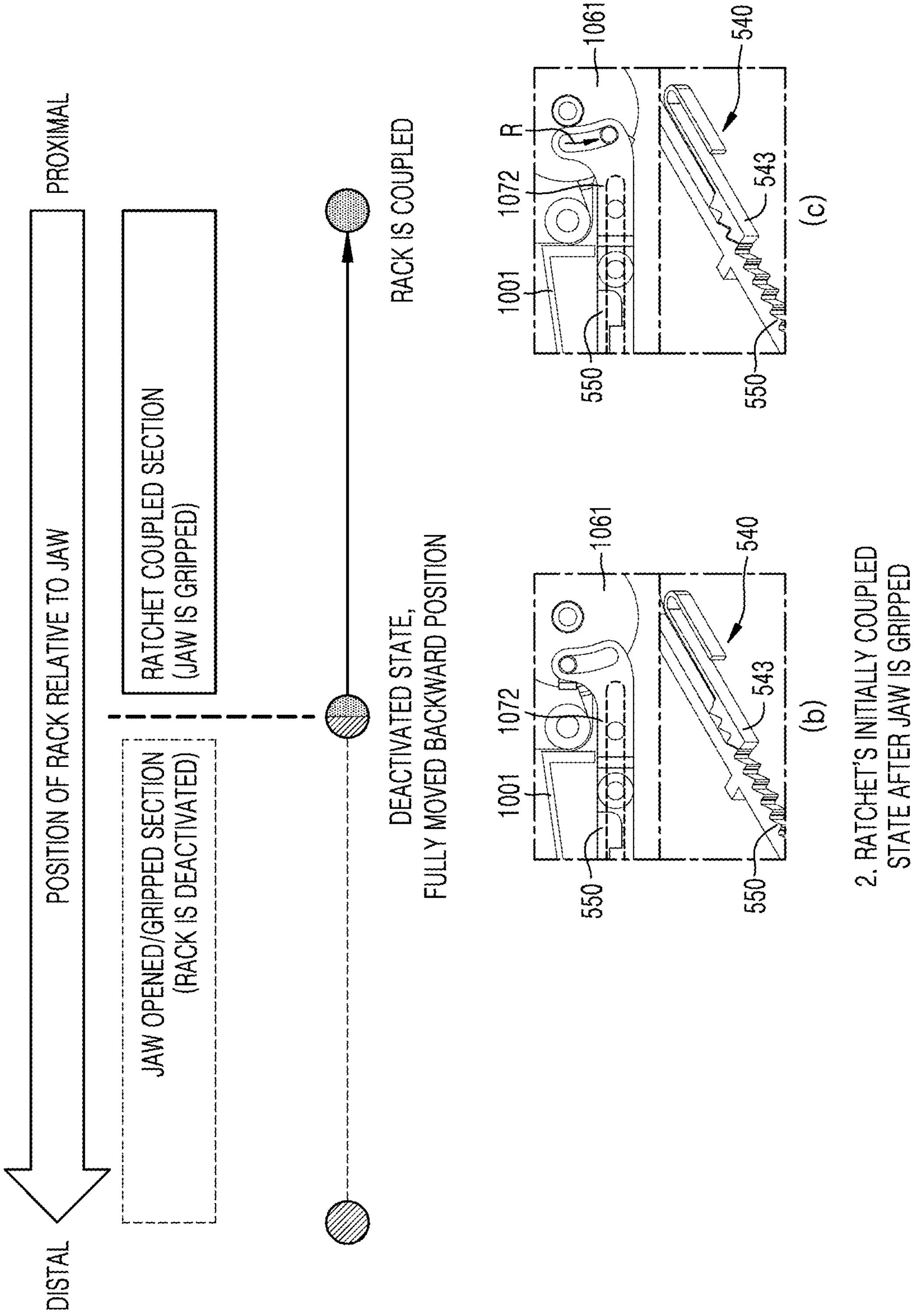

FIG. 137 is a view illustrating a state in which the reciprocating assembly 550 and the operation member 540 are coupled to each other as the staple pulley is rotated in a state in which the jaw 1003 is closed, in the end tool of the surgical instrument of FIG. 122.

In the state in which the jaw 1003 is closed as shown in FIG. 137B, when the staple pulley 1061 is rotated in the direction of the arrow R as shown in FIG. 137C, the reciprocating assembly 550 is moved toward the proximal end 1001*g* to be coupled to the ratchet member 543 of the operation member 540, so that the deactivated state is switched to the activated state.

Figure 138:
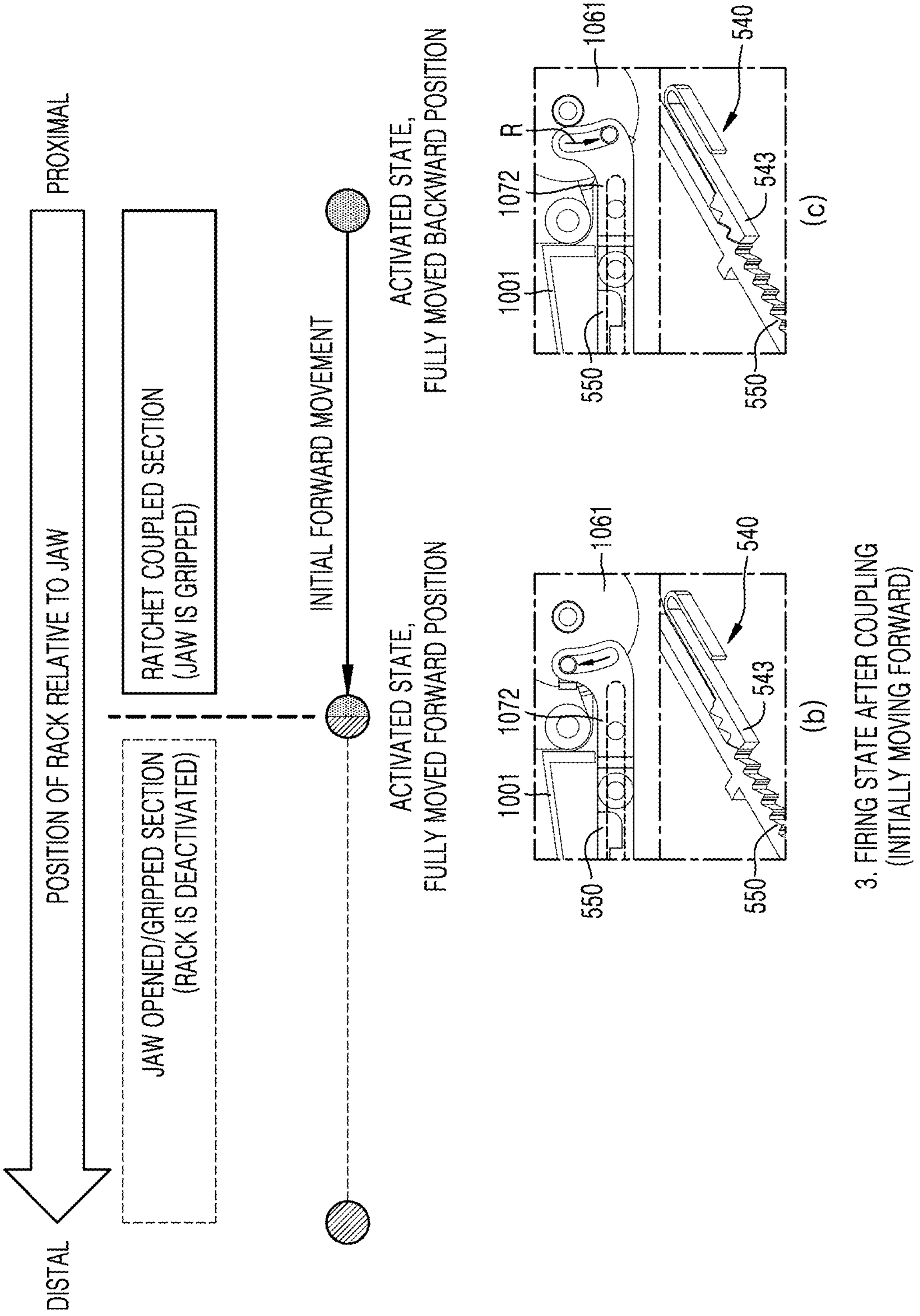
Figure 139:
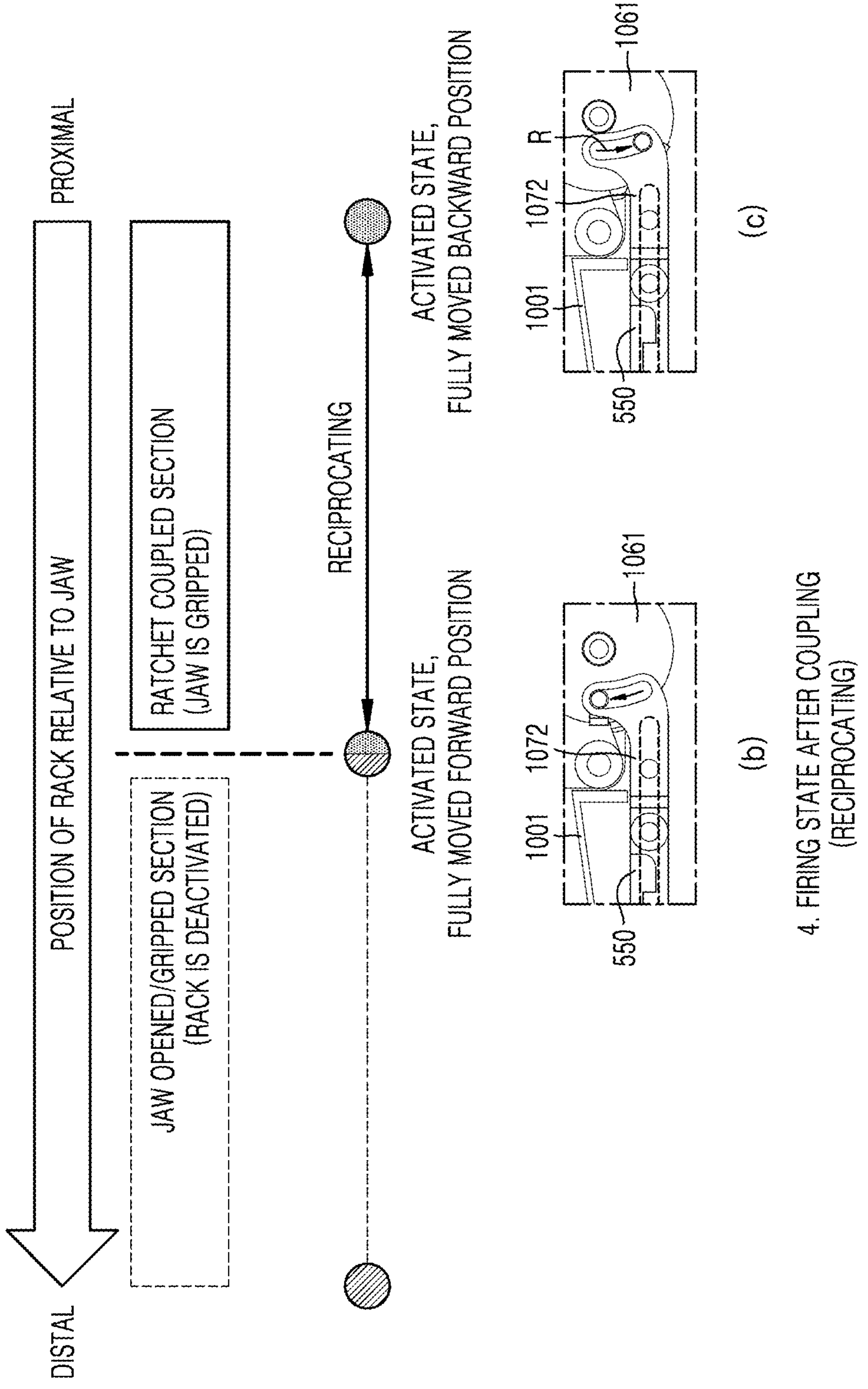

FIG. 138 is a view illustrating a motion in which the operation member 540 is initially moved forward after the end tool of the surgical instrument of FIG. 122 is switched to the activated state, and FIG. 139 is a view illustrating a motion in which the operation member 540 is gradually moved forward as the staple pulley 161 performs an alternating rotational motion in the end tool of the surgical instrument of FIG. 122.

After switching to the activated state as described above, as the staple pulley 1061 performs an alternating rotational motion, the reciprocating assembly 550 is repeatedly moved forward and backward, thereby performing stapling and cutting motions while the operation member 540 is moved forward.

Sixth Embodiment-Cam/Slot-Type

Hereinafter, an end tool 1100 of a surgical instrument according to a sixth embodiment of the present disclosure will be described. Here, the end tool 1100 of the surgical instrument according to the sixth embodiment of the present disclosure is different from the end tool (see 100 of FIG. 2 or the like) of the surgical instrument according to the fifth embodiment of the present disclosure described above in that a configuration of a staple pulley assembly 1160 and a staple link assembly 1170 is different. Hereinafter, the configuration that is different from that of the fifth embodiment will be described in detail.

Figure 140:
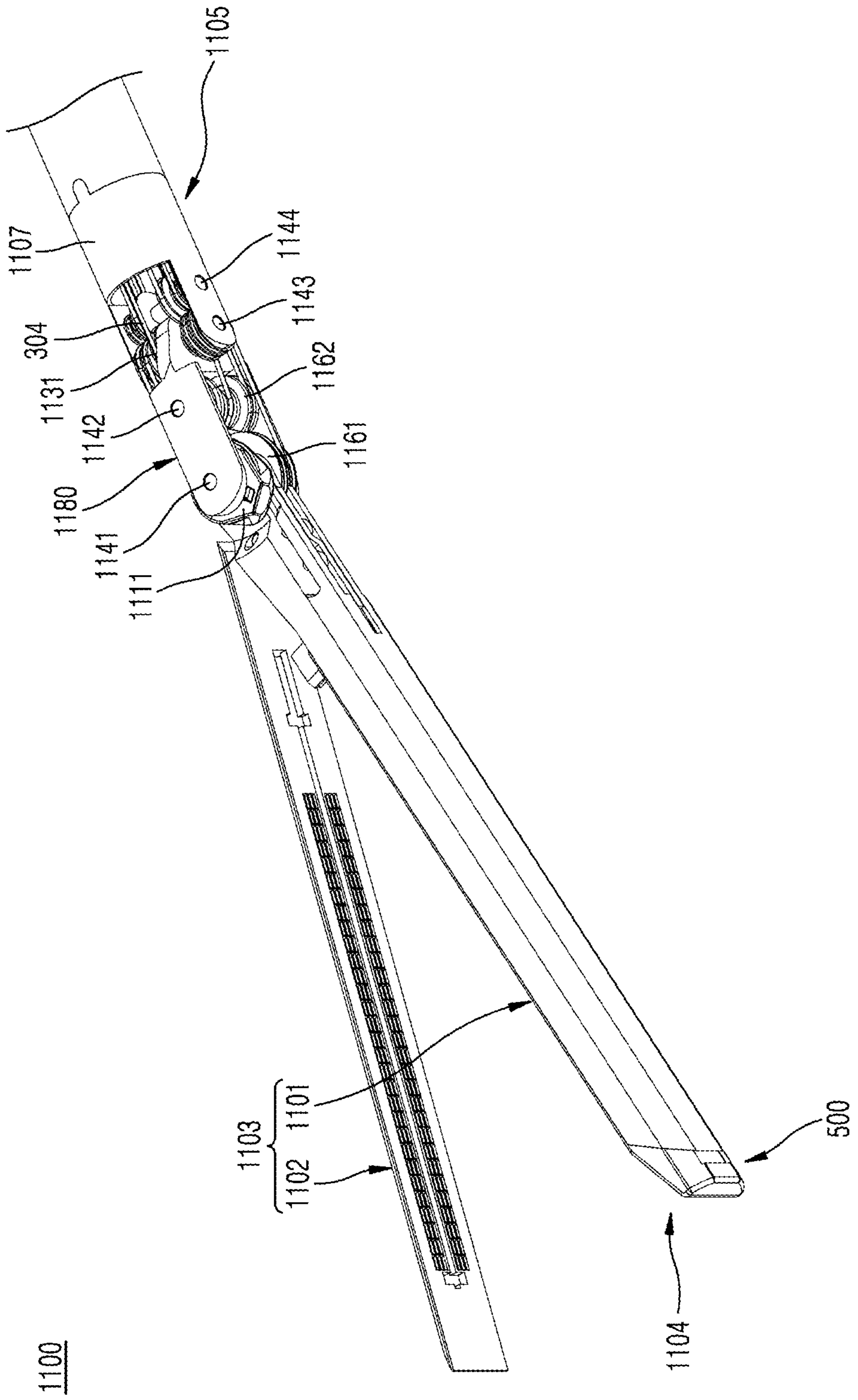
FIG. 140 is a perspective view illustrating an end tool of a surgical instrument according to a sixth embodiment of the present disclosure.
Figure 141:
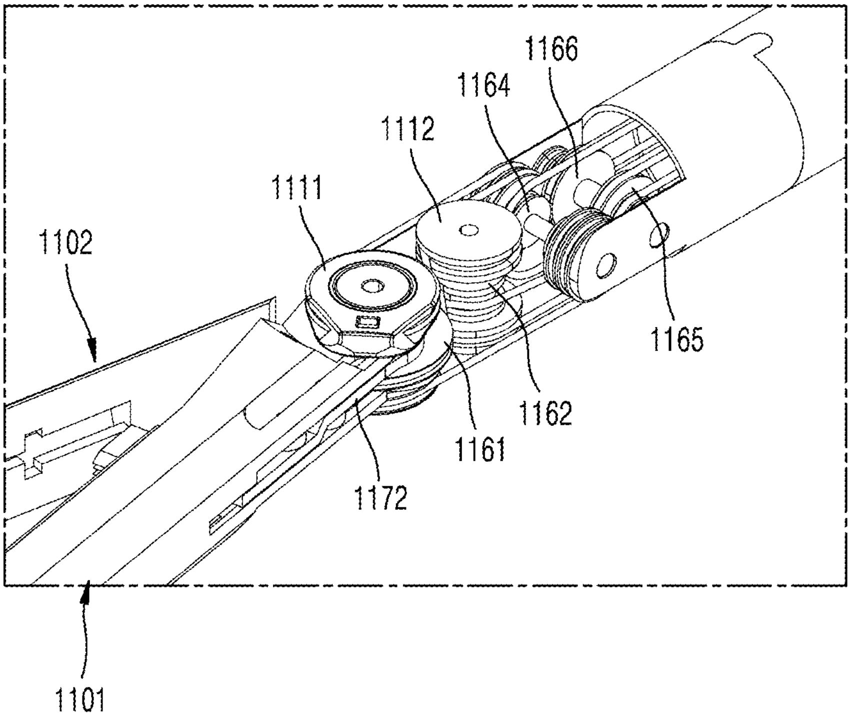
FIG. 141 is a magnified view of the end tool of the surgical instrument of FIG. 140.
Figure 142:
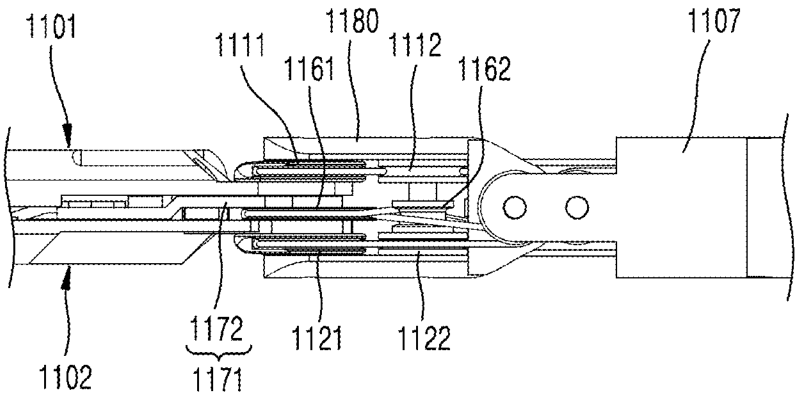
FIG. 142 is a side view illustrating the end tool of the surgical instrument of FIG. 140.
Figure 143:
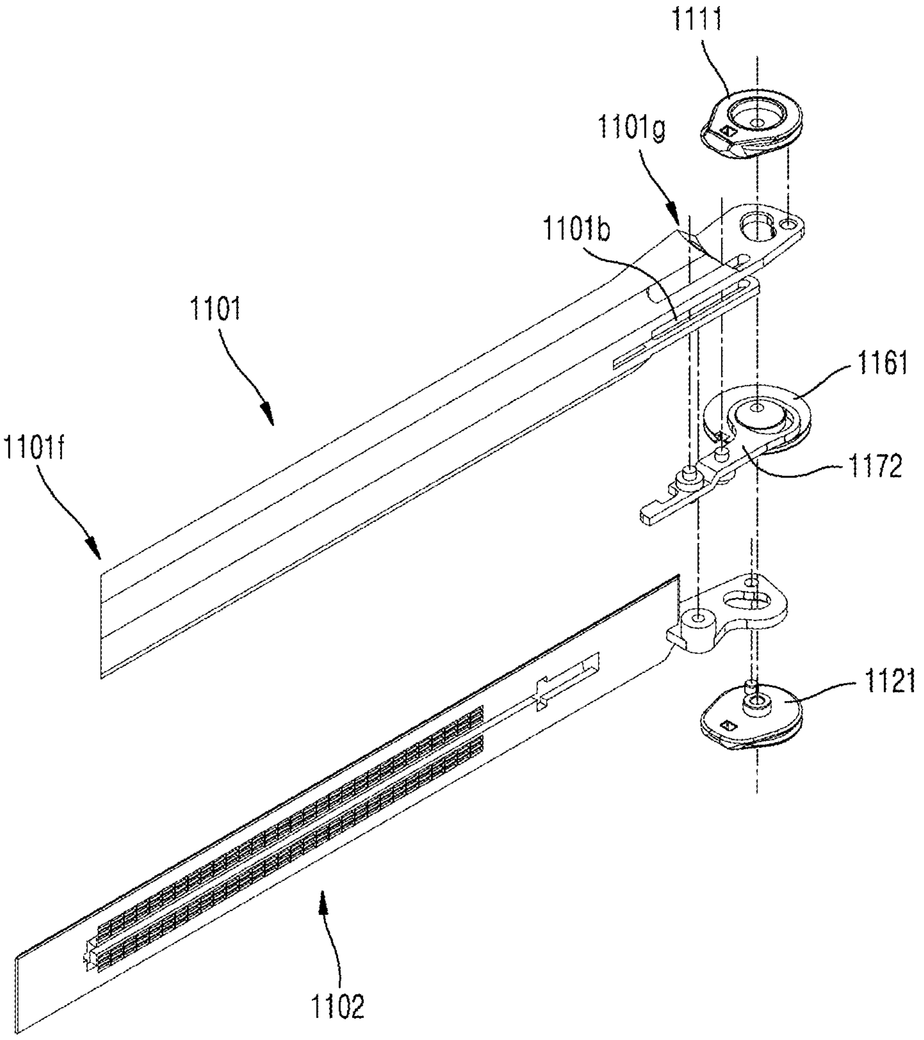
FIGS. 143 and 144 are exploded perspective views of the end tool of the surgical instrument of FIG. 140.
Figure 144:
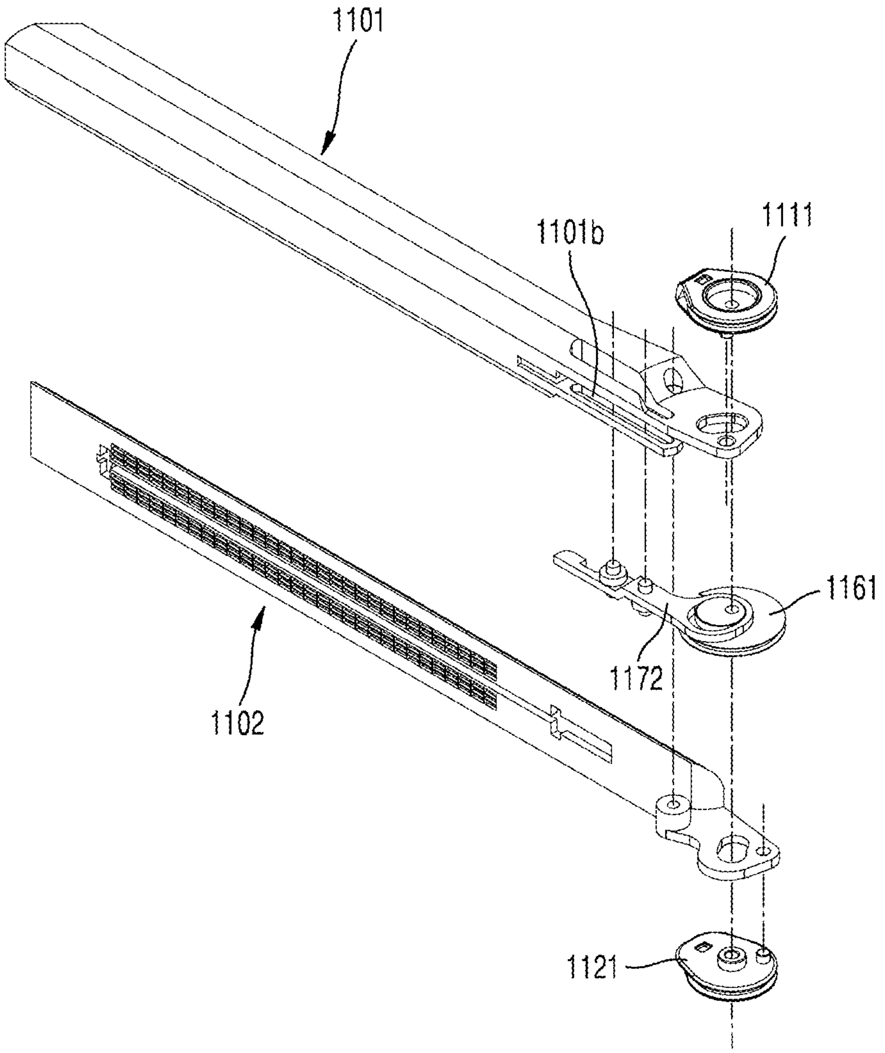
Figure 145:
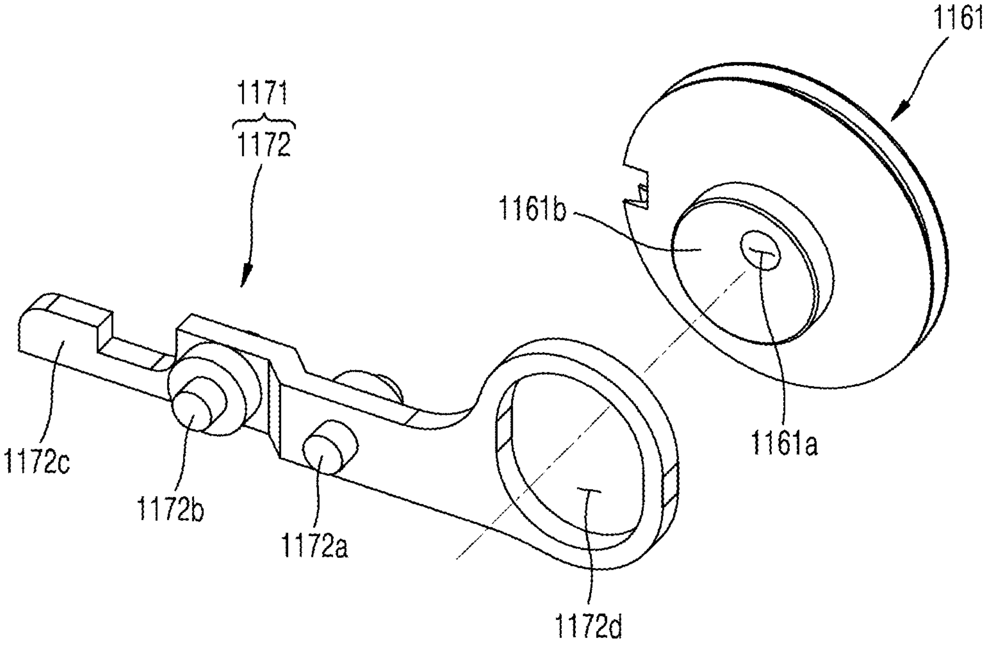
FIG. 145 is an exploded perspective view of a staple pulley assembly of the surgical instrument of FIG. 140.
Figure 146:
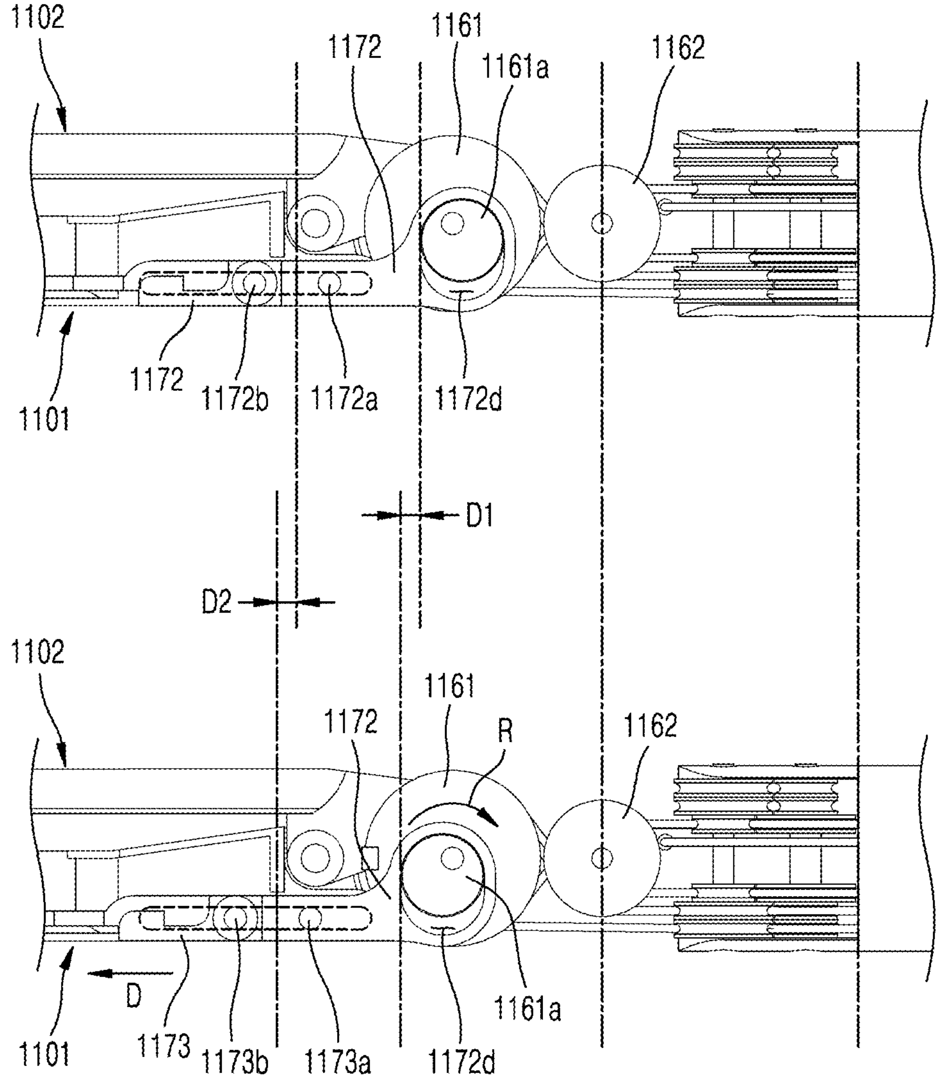
FIG. 146 is a side view illustrating operating states of a staple pulley in the end tool of FIG. 140.
Figure 147:
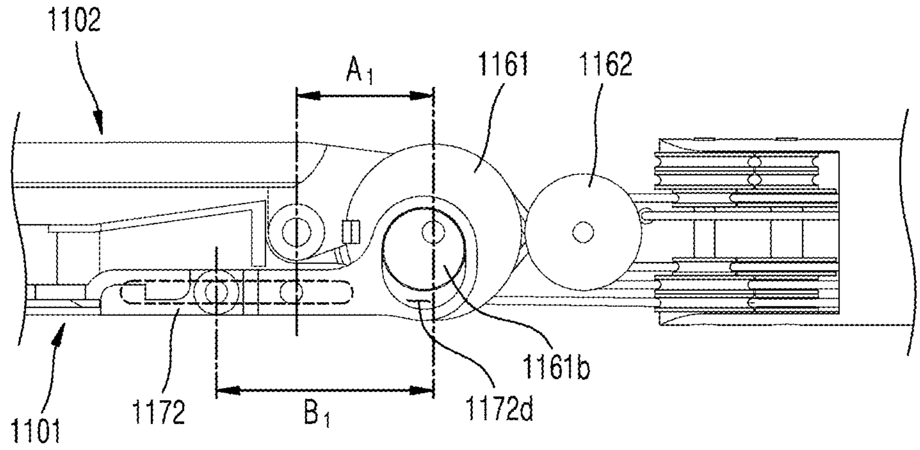
FIGS. 147 and 148 are plan views illustrating opening and closing motions of the end tool of the surgical instrument of FIG. 140.
Figure 148:
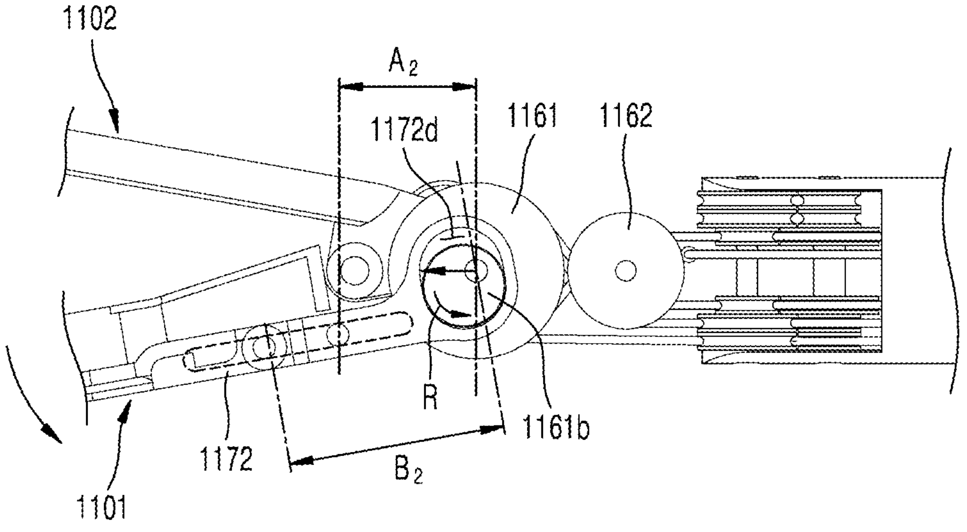
Figure 149:
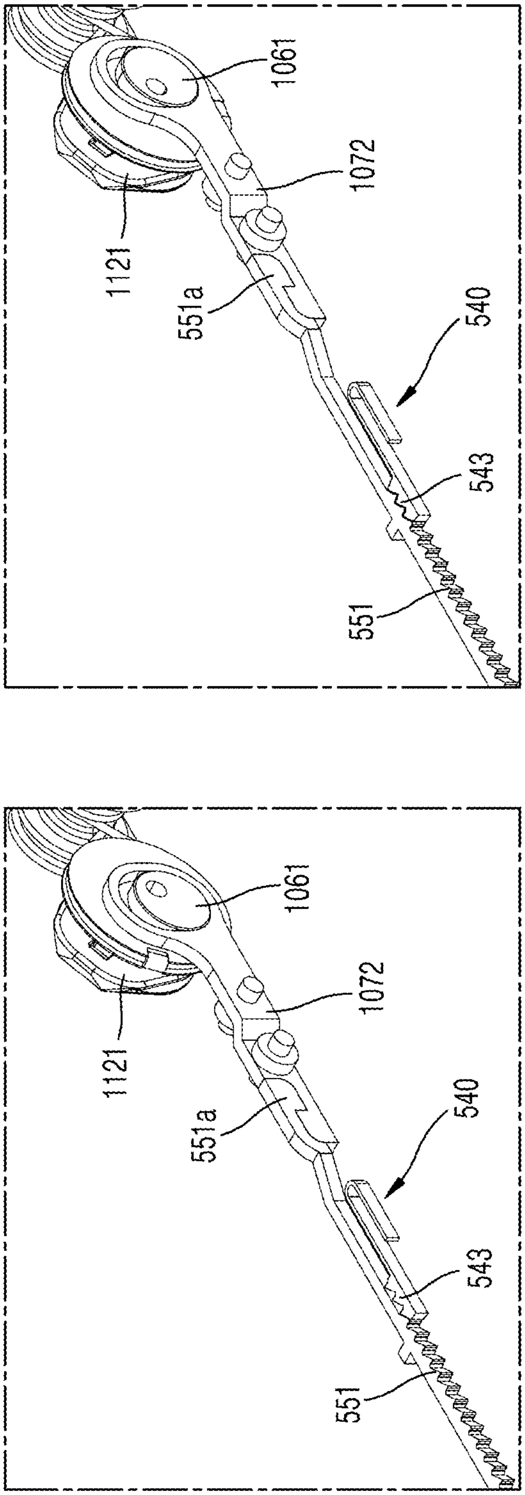
FIG. 149 is a perspective view illustrating a process in which the end tool of the surgical instrument of FIG. 140 is switched from a deactivated state to an activated state.

FIG. 140 is a perspective view illustrating the end tool of the surgical instrument according to the sixth embodiment of the present disclosure, and FIG. 141 is a magnified view of the end tool of the surgical instrument of FIG. 140. FIG. 142 is a side view illustrating the end tool of the surgical instrument of FIG. 140. FIGS. 143 and 144 are exploded perspective views of the end tool of the surgical instrument of FIG. 140. FIG. 145 is an exploded perspective view of a staple pulley assembly of the surgical instrument of FIG. 140. FIG. 146 is a side view illustrating operating states of a staple pulley in the end tool of FIG. 140. FIGS. 147 and 148 are plan views illustrating opening and closing motions of the end tool of the surgical instrument of FIG. 140. FIG. 149 is a perspective view illustrating a process in which the end tool of the surgical instrument of FIG. 140 is switched from a deactivated state to an activated state.

Here, FIG. 141 illustrates a state in which an end tool hub is removed. FIGS. 146 to 148 mainly describe operations of the staple pulley assembly, the staple link assembly, and a reciprocating assembly. FIG. 149 mainly describes a coupling relationship between the reciprocating member and an operation member.

Referring to FIGS. 140 to 149, the end tool 1100 of the sixth embodiment of the present disclosure includes a pair of jaws 1103 for performing a grip motion, that is, a first jaw 1101 and a second jaw 1102. Here, each of the first jaw 1101 and the second jaw 1102, or a component encompassing the first jaw 1101 and the second jaw 1102 may be referred to as the jaw.

Meanwhile, the end tool 1100 includes a plurality of pulleys including a pulley 1111 and a pulley 1112 that are related to a rotational motion of the first jaw 1101. The pulleys related to the rotational motion of the first jaw 1101 described in the present embodiment are substantially the same as the pulley 111, the pulley 112, the pulley 113, the pulley 114, the pulley 115, and the pulley 116 described with reference to FIG. 8 or the like of the first embodiment, and thus, detailed descriptions thereof will be omitted herein.

Meanwhile, the end tool 1100 includes a plurality of pulleys including a pulley 1121 and a pulley 1122 that are related to a rotational motion of the second jaw 1102. The pulleys related to the rotational motion of the second jaw 1102 described in the present embodiment are substantially the same as the pulley 121, the pulley 122, the pulley 123, the pulley 124, the pulley 125, and the pulley 126 described with reference to FIG. 8 or the like of the first embodiment, and thus, detailed descriptions thereof will be omitted herein.

In addition, the end tool 1100 of the sixth embodiment of the present disclosure may include a rotation shaft 1141, a rotation shaft 1142, a rotation shaft 1143, and a rotation shaft 1144. Here, the rotation shaft 1141 and the rotation shaft 1142 may be inserted through an end tool hub 1180, and the rotation shaft 1143 and the rotation shaft 1144 may be inserted through a pitch hub 1107. The rotation shaft 1141, the rotation shaft 1142, the rotation shaft 1143, and the rotation shaft 1144 may be arranged sequentially from a distal end 1104 of the end tool 1100 toward a proximal end 1105.

In addition, the end tool 1100 of the sixth embodiment of the present disclosure may include the end tool hub 1180 and the pitch hub 1107.

The rotation shaft 1141 and the rotation shaft 1142 may be inserted through the end tool hub 1180, and the pulley 1111 and the pulley 1121 axially coupled to the rotation shaft 1141 and at least some of the first jaw 1101 and the second jaw 1102 coupled to the pulley 1111 and the pulley 1121 may be accommodated inside the end tool hub 1180.

The rotation shaft 1143 and the rotation shaft 1144 may be inserted through the pitch hub 1107, and the pitch hub 1107 may be axially coupled to the end tool hub 1180 by the rotation shaft 1143.

Accordingly, the end tool hub 1180 may be formed to be pitch-rotatable around the rotation shaft 1143 with respect to the pitch hub 1107.

Meanwhile, the end tool 1100 of the sixth embodiment of the present disclosure may further include components, such as a staple drive assembly (see 150 of FIG. 13) including the staple pulley assembly 1160 and the staple link assembly 1170, to perform stapling and cutting motions.

The staple pulley assembly 1160 may be formed between the pulley 1111 and the pulley 1121 to be adjacent to the pulley 1111 and the pulley 1121. In the present embodiment, it is assumed that the staple pulley assembly 1160 includes one staple pulley 1161.

In the sixth embodiment of the present disclosure, by disposing the staple pulley assembly 1160 between the pulley 1111, which is a first jaw pulley, and the pulley 1121, which is a second jaw pulley, the end tool 1100 is allowed to perform pitch and yaw motions as well as stapling and cutting motions using a cartridge 1110.

Hereinafter, the staple pulley assembly 1160, the staple link assembly 1170, and a reciprocating assembly 1150 of the end tool 1100 of the surgical instrument according to the sixth embodiment of the present disclosure will be described in more detail.

In the end tool 1100 of the surgical instrument according to the sixth embodiment of the present disclosure, the staple pulley assembly 1160 and the staple link assembly 1170 form a cam-slot structure. In addition, with such a structure, a force for moving the reciprocating assembly 550 forward may be amplified. Furthermore, a deactivated state, in which the staple link assembly 1170 and the reciprocating assembly 1150 are separated from each other, may be switched to an activated state in which the staple link assembly 1170 and the reciprocating assembly 1150 are coupled to each other.

Referring to FIGS. 122 to 139 and the like, the staple pulley assembly 1160 may include one or more staple pulleys 1161.

A shaft pass-through part 1161*a* may be formed in the staple pulley 1161. The shaft pass-through part 1161*a* may be formed in the form of a hole, and the rotation shaft 1141, which is an end tool jaw pulley rotation shaft, may be inserted through the shaft pass-through part 1161*a*.

Further, a protruding member 1161*b* may be formed on the staple pulley 1161. A link member 1171 of the staple link assembly 1170 may be coupled to the protruding member 1161*b*. Here, the center of the protruding member 1161*b* does not coincide with the center of the staple pulley 1161, and the protruding member 1161*b* may be formed to be eccentric to a certain extent with respect to the staple pulley 1161. The protruding member 1161*b* may be fitted into a slot 1172*d* of the link member 1171 to be described later.

Meanwhile, the end tool 1100 of the sixth embodiment of the present disclosure may further include the staple link assembly 1170 connected to the staple pulley assembly 1160, and the staple link assembly 1170 may include the link member 1171. Here, the staple link assembly 1170 may serve to connect the staple pulley assembly 1160 to the reciprocating assembly 1150 of the cartridge 1110 to be described later.

In the present embodiment, the staple link assembly 1170 includes only one link. That is, by coupling the staple pulley assembly 1160 and the staple link assembly 1170 by a cam-slot structure, it is possible to convert a rotational motion of the staple pulley assembly 1160 into a linear motion of the staple link assembly 1170 even when the staple link assembly 1170 includes only one link.

In detail, the link member 1171 may be formed as a single link, which is a first link 1172. In other words, the first link 1172 may be formed as a single member.

The first link 1172 is formed in the form of an elongated bar, and may include a first protrusion 1172*a*, a second protrusion 1172*b*, a coupling part 1172*c*, and the slot 1172*d*.

The first protrusion 1172*a* and the second protrusion 1172*b* may be formed in one region of a central portion of the first link 1172. The first protrusion 1172*a* and the second protrusion 1172*b* may be fitted into a guide groove 1101*b* of the first jaw 1101.

As described above, as the first protrusion 1172*a* and the second protrusion 1172*b* are moved along the guide groove 1101*b* in a state in which the first protrusion 1172*a* and the second protrusion 1172*b* of the first link 1172 formed in a protruding shape are fitted into the groove-shaped guide groove 1101*b*, the link member 1171 is moved with respect to the first jaw 1101 (and the cartridge 500 therein). This will be described in more detail later.

Meanwhile, the coupling part 1172*c* may be formed at one end portion of the first link 1172. The coupling part 1172*c* may be coupled to a coupling part 551*a* of a reciprocating member 551 of the cartridge 500, which will be described later.

Meanwhile, the slot 1172*d* may be formed at one end portion of the first link 1172. Here, the slot 1172*d* may be formed in the form of an elongated hole, into which the protruding member 1161*b* may be fitted. In detail, the slot 1172*d* may be formed to have a predetermined curvature, and may be formed in an approximately elliptical shape. Here, the slot 1172*d* may be formed to be greater than the protruding member 1161*b* by a certain extent. Accordingly, in a state in which the protruding member 1161*b* of the staple pulley 1161 is fitted into the slot 1172*d* of the first link 1172, the protruding member 1161*b* is moved to a certain extent in the slot 1172*d*.

As described above, the protruding member 1161*b* may be formed to be eccentric with respect to the staple pulley 1161 by a certain extent. Accordingly, when the staple pulley 1161 is rotated, the protruding member 1161*b*, while in contact with the slot 1172*d*, may push the slot 1172*d* to move the first link 1172. That is, when the staple pulley 1161 is rotated, the protruding member 1161*b* is moved in the slot 1172*d* while coming into contact with the slot 1172*d*, which causes the first link 1172 to be linearly moved along the guide groove 1101*b* of the first jaw 1101.

(Displacement of Staple Link Assembly According to Rotation of Staple Pulley)

Hereinafter, the displacement of the staple link assembly 1170 according to the rotation of the staple pulley 1161 will be described.

Referring to FIG. 146, in the sixth embodiment of the present disclosure, the staple pulley 1161 and the staple link assembly 1170 are coupled in the form of a cam-slot. That is, the protruding member 1161*b* formed on the staple pulley 1161 is coupled to the slot 1172*d* formed in the form of a slot in the staple link assembly 1170. Accordingly, when the staple pulley 1161 is rotated in the direction of an arrow R, the displacement of the protruding member 1161*b* of the staple pulley 1161 in the X-axis direction becomes D1. In addition, the displacement of the staple link assembly 1170 in the X-axis direction becomes D2.

Meanwhile, referring to FIG. 38 or the like, in the first embodiment of the present disclosure, the staple pulley 161 and the staple link assembly 170 are axially coupled to each other and thus the displacement of the protruding member 1161*b* of the staple pulley 1161 in the X-axis direction becomes much greater than that of the fourth embodiment.

In other words, as compared with the case in which the staple pulley and the staple link assembly are axially coupled as in the first embodiment of the present disclosure or the like, when the staple pulley and the staple link assembly are cam-slot coupled with each other as in the present embodiment, the displacement of the staple link assembly in the X-axis direction is reduced even when the staple pulley is rotated by the same distance.

Meanwhile, since work is the product of force and displacement, assuming that the work for rotating the staple pulley is the same, the displacement and the force are inversely proportional to each other. Accordingly, when the displacement is reduced, the force is increased in inverse proportion to the displacement.

As a result, in the sixth embodiment of the present disclosure, the staple pulley 1161 and the staple link assembly 1170 are coupled in the form of a cam-slot, and the displacement of the staple link assembly 1170 in the X-axis direction caused by the rotation of the staple pulley 1161 is relatively reduced compared to the other embodiments, and thus the force received by the staple link assembly 1170 in the X-axis direction is relatively increased compared to the other embodiments.

According to the sixth embodiment of the present disclosure described above, a force for moving the staple link assembly 1170 and the reciprocating assembly 550 connected thereto forward is amplified, and thus a stapling motion may be performed more robustly.

(Activated State and Deactivated State)

Hereinafter, the activated state and the deactivated state according to the present embodiment will be described.

In the sixth embodiment of the present disclosure, there is a deactivated state in which the reciprocating assembly 550 and an operation member 540 are not coupled to and separated from each other, and an activated state in which the reciprocating assembly 550 and the operation member 540 are coupled. In addition, the deactivated state may be maintained in a jaw open state, and the deactivated state may be switched to the activated state in a jaw close state. In addition, after switching to the activated state, as the reciprocating assembly is repeatedly moved forward and backward according to an alternating rotational motion of the staple pulley, the operation member is moved forward.

This distinction between the activated and deactivated states may be made possible by the cam-slot structure described above. Hereinafter, this will be described in more detail.

Referring to FIGS. 147 to 149 and the like, in a state in which the jaw 1103 is closed as shown in FIG. 147, when the first jaw 1101 is rotated in the direction of an arrow R of FIG. 148 and the second jaw 1102 is rotated in the opposite direction of the arrow R, the jaw 1103 is in an opened state. Here, it is assumed that the position of a jaw rotation shaft 1145 in the X-axis direction is fixed, while the other components move.

When the jaw 1103 is in the opened state, the first jaw pulley 1111 and the staple pulley 1161 are rotated in the same direction.

When the first jaw pulley 1111 is rotated in the direction of the arrow R of FIG. 148, the pulley 1111, the staple pulley 1161, the staple link assembly 1170, and the reciprocating assembly 550 are moved together toward a distal end 1101*f* (i.e., are moved forward) in a state in which the jaw shaft 1145 is fixed. Accordingly, A1 of FIG. 147, which is a distance between the rotation shaft 1141 and the jaw rotation shaft 1145 in a state in which the jaw 1103 is closed, is greater than A2 of FIG. 148, which is a distance between the rotation shaft 1141 and the jaw rotation shaft 1145 in a state in which the jaw 1103 is opened (i.e., A1>A2).

At the same time, when the staple pulley 1161 is rotated in the direction of the arrow R of FIG. 148, the staple link assembly 1170 connected to the staple pulley 1161 and the reciprocating assembly 550 connected the staple link assembly 1170 are moved as a whole (i.e., are moved backward) toward a proximal end 1101g. Accordingly, B1 of FIG. 147, which is a distance between the rotation shaft 1141 and the staple link assembly 1170 (the second protrusion 1172*b* thereof) in a state in which the jaw 1103 is closed, is greater than B2 of FIG. 148, which is a distance between the rotation shaft 1141 and the staple link assembly 1170 (the second protrusion 1172*b* thereof) in a state in which the jaw 1103 is opened (i.e., B1>B2).

However, here, due to the cam-slot structure as described above, the displacement of the staple link assembly 1170 in the x-axis direction when the staple pulley 1161 is rotated is relatively small (compared to other embodiments).

That is, in the sixth embodiment of the present disclosure, a relationship of (A1−A2)>(B1−B2) is established.

In other words, when the jaw 1103 is opened, the movement amount (A1−A2) of the pulley 1111, the staple pulley 1161, the staple link assembly 1170, and the reciprocating assembly 550 toward the distal end is greater than the movement amount (B1−B2) of the staple link assembly 1170 and the reciprocating assembly 550 connected thereto toward the proximal end.

As a result, when the two movement components of the reciprocating assembly 550 described above are synthesized, the reciprocating assembly 550 is moved toward the distal end 1101*f* when the jaw 1103 is opened. That is, the reciprocating assembly 550 is moved forward.

That is, in the first embodiment, the reciprocating member is moved backward when the moving-backward amount of the reciprocating assembly due to the rotation of the staple pulley is larger than the moving-forward amount of the reciprocating assembly due to the rotation of the jaw pulley, whereas in the present embodiment, the reciprocating member is moved forward when the moving-forward amount of the reciprocating assembly due to the rotation of the jaw pulley is larger than the moving-backward amount of the reciprocating assembly due to the rotation of the staple pulley.

In addition, when the reciprocating assembly 550 is moved forward as described above, the reciprocating assembly 550 and the operation member 540 are further spaced apart from each other, and thus, when the jaw is opened, the deactivated state in which the reciprocating assembly 550 and the operation member 540 are not coupled is maintained.

In contrast, in a state in which the jaw 1103 is opened as shown in FIG. 148, the first jaw 1101 is rotated in the opposite direction of the arrow R of FIG. 148, and when the second jaw 1102 is rotated in the direction of the arrow R, the jaw 1103 is in a closed state as shown in FIG. 131.

When the jaw 1103 is closed as described above, the reciprocating assembly 550 is moved toward the proximal end 1101*g*. That is, the reciprocating assembly 550 is moved backward.

In the closed state as shown in FIG. 147, a recess 550*b* of the reciprocating assembly 550 and a ratchet 543*a* of a ratchet member 543 of the operation member 540 are in contact with each other, but are not coupled to each other.

Accordingly, the deactivated state in which the reciprocating assembly 550 and the operation member 540 are not coupled to and separated from each other is maintained between the state of FIG. 147, in which the jaw 1103 is fully opened, and the state of FIG. 148, in which the jaw 1103 is closed. That is, in this state, even when the staple pulley 1161 is rotated, the operation member 540 is not moved, and thus stapling and cutting motions are not performed.

Next, for stapling and cutting motions, the staple pulley 1161 is rotated in the direction of the arrow R of FIG. 149B in a state in which the jaw 1103 is closed as shown in FIG. 149A.

When the staple pulley 1161 is rotated in the direction of the arrow R, the staple link assembly 1170 connected to the staple pulley 1161 and the reciprocating assembly 550 connected to the staple link assembly 1170 are moved as a whole toward the proximal end 1101*g* (i.e., are moved backward). In addition, as shown in FIG. 149B, when the reciprocating assembly 550 is moved toward the proximal end 1101*g* to be coupled to the ratchet member 543 of the operation member 540, the deactivated state is switched to the activated state.

After switching to the activated state as described above, as the staple pulley 1161 performs an alternating rotational motion, the reciprocating assembly 550 is repeatedly moved forward and backward, thereby performing stapling and cutting motions while the operation member 540 is moved forward.

Seventh Embodiment—Adding Second Auxiliary Pulley for Staple Wire

Hereinafter, an end tool 1200 of a surgical instrument according to a seventh embodiment of the present disclosure will be described. Here, the end tool 1200 of the surgical instrument according to the seventh embodiment of the present disclosure is different from the end tool (see 100 of FIG. 2 or the like) of the surgical instrument according to the first embodiment of the present disclosure described above in that a staple second auxiliary pulley 967, which is a staple wire auxiliary pulley, is additionally provided. Hereinafter, the configuration that is different from that of the first embodiment will be described in detail.

Figure 150:
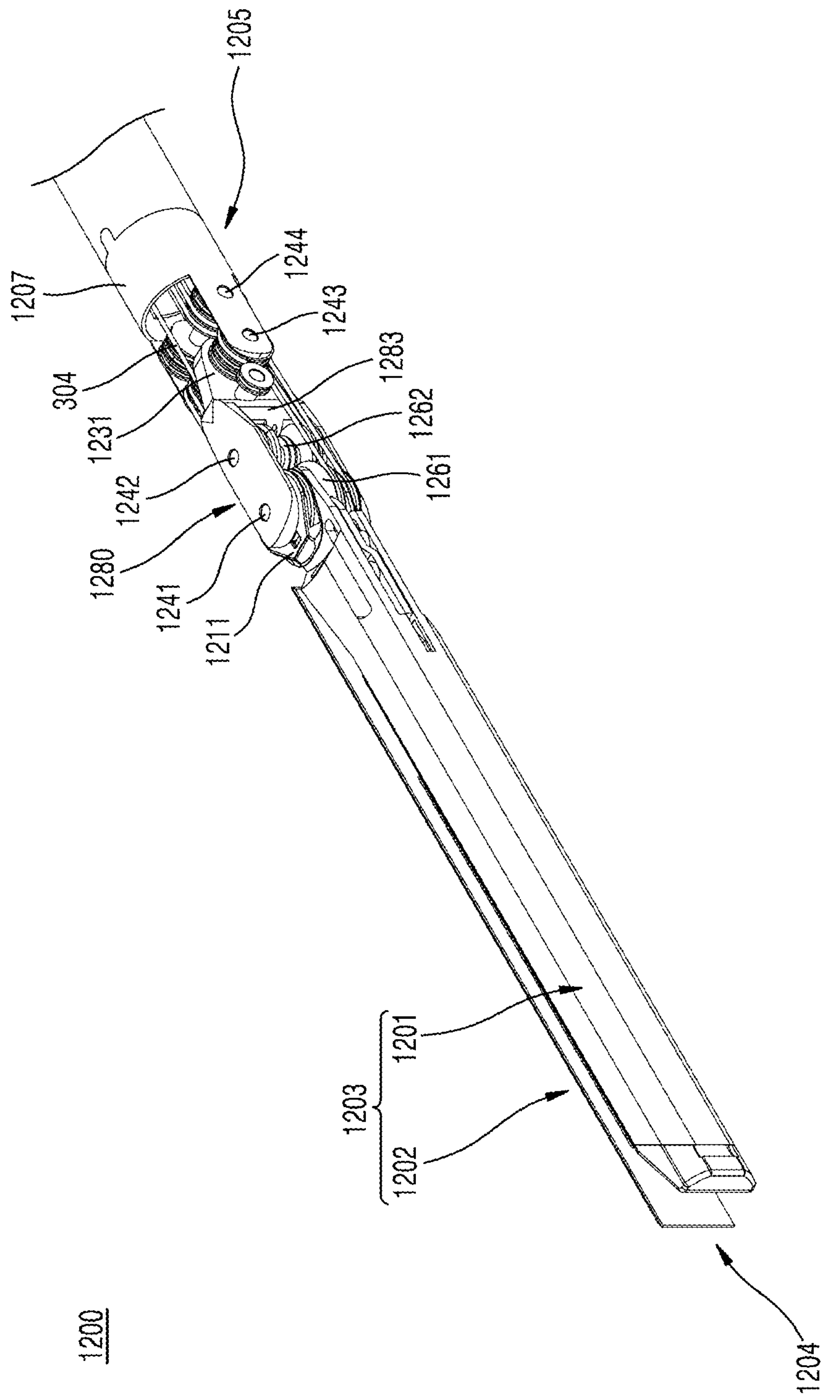
FIGS. 150 to 153 are perspective views illustrating an end tool of a surgical instrument according to a seventh embodiment of the present disclosure.
Figure 151:
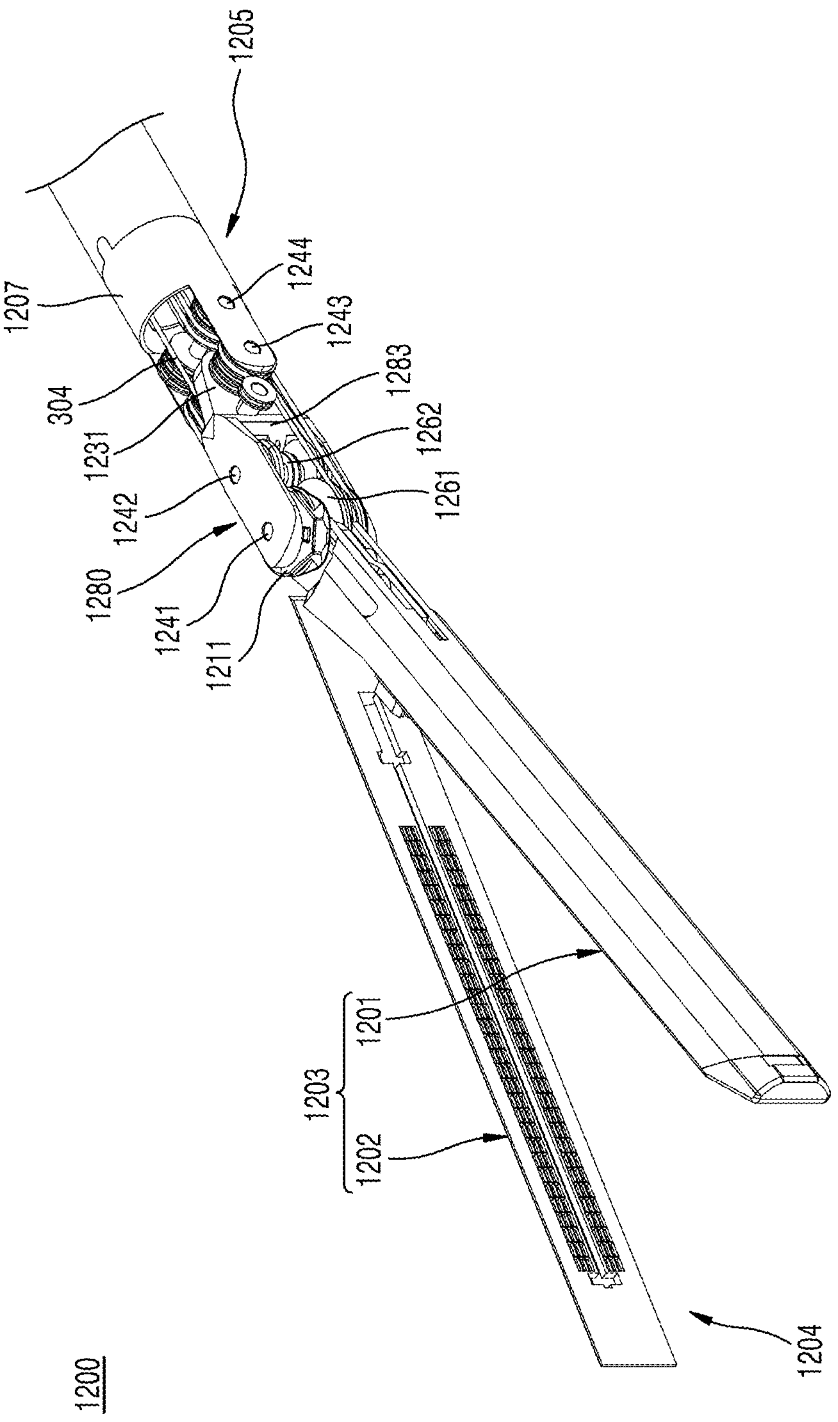
Figure 152:
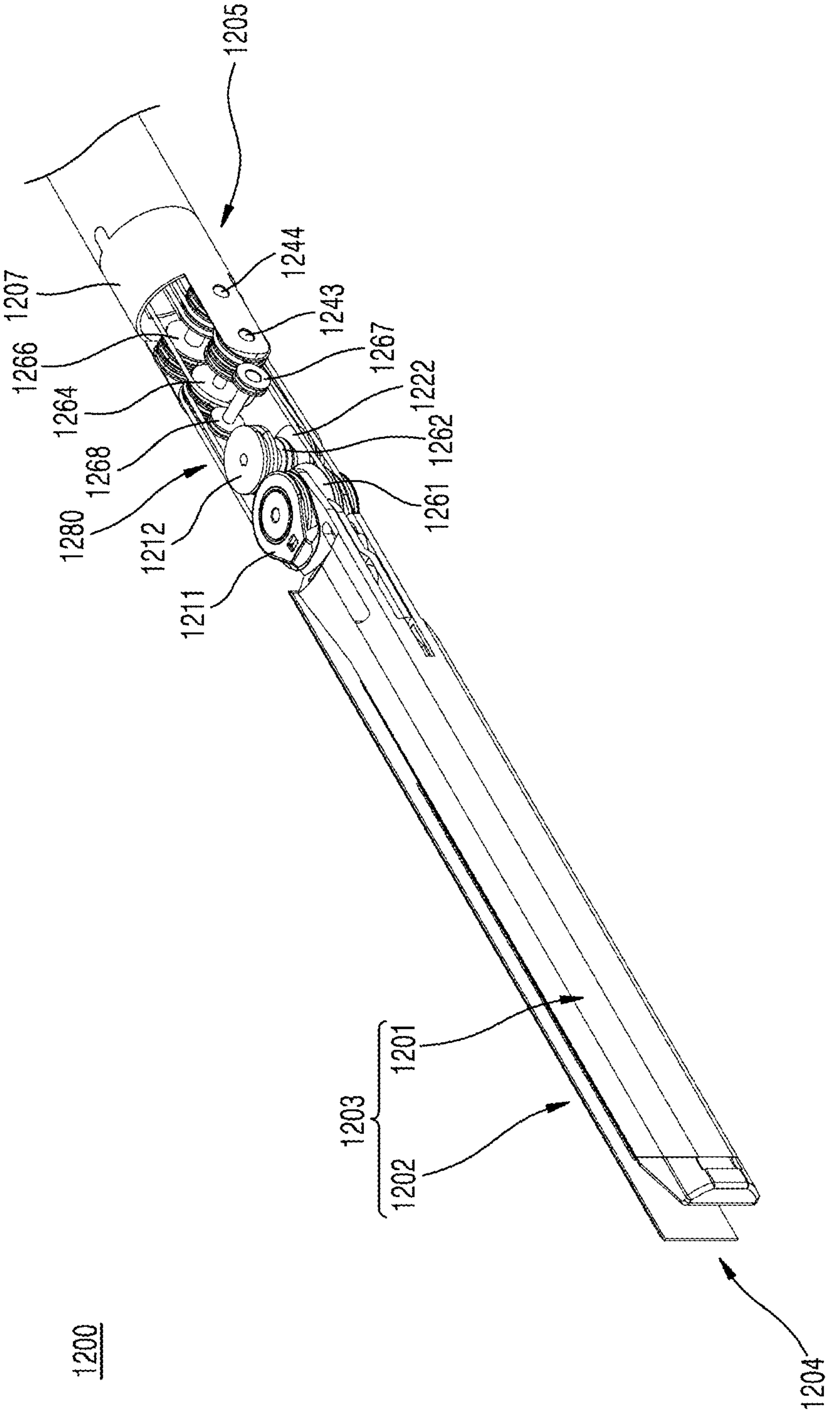
Figure 153:
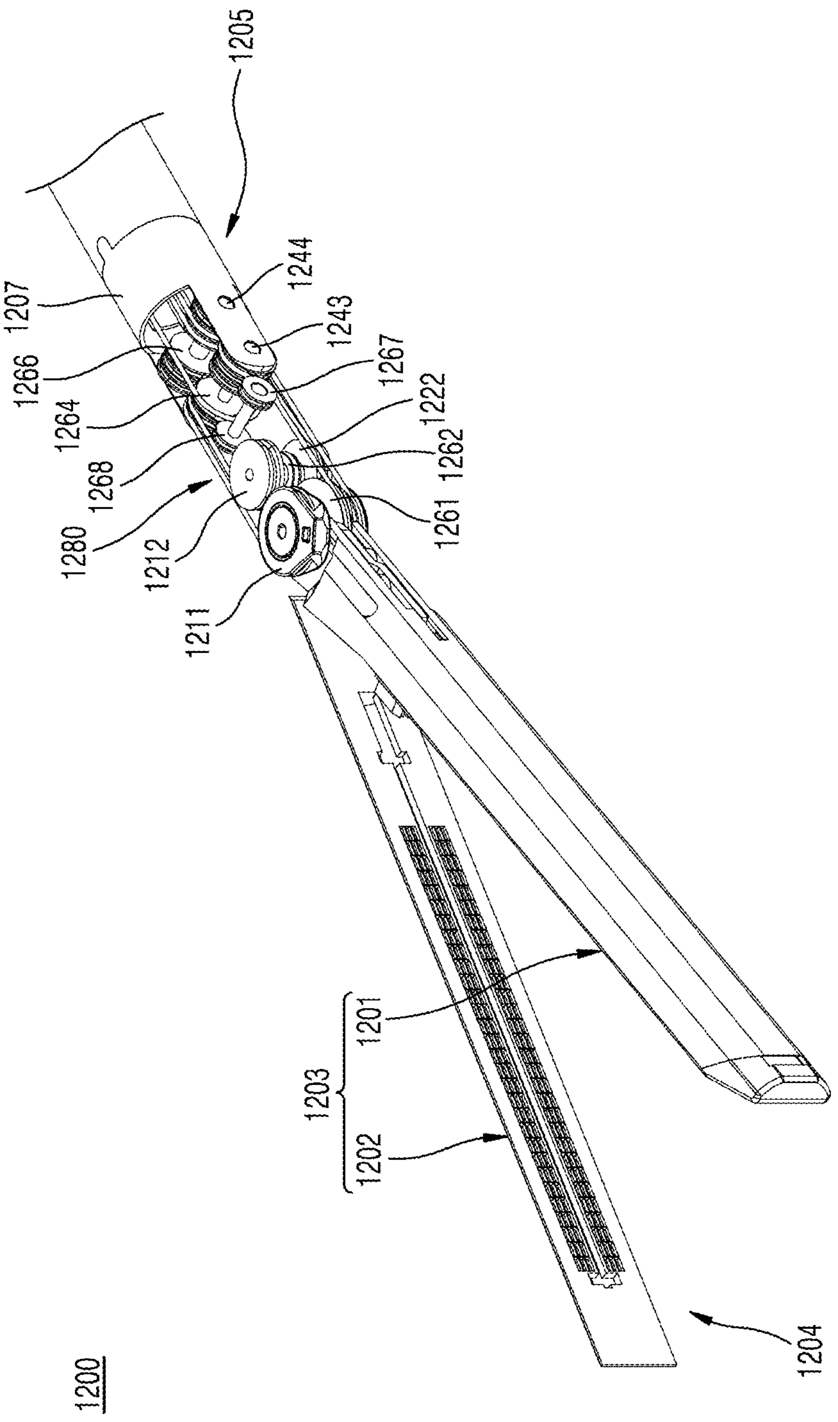
Figure 154:
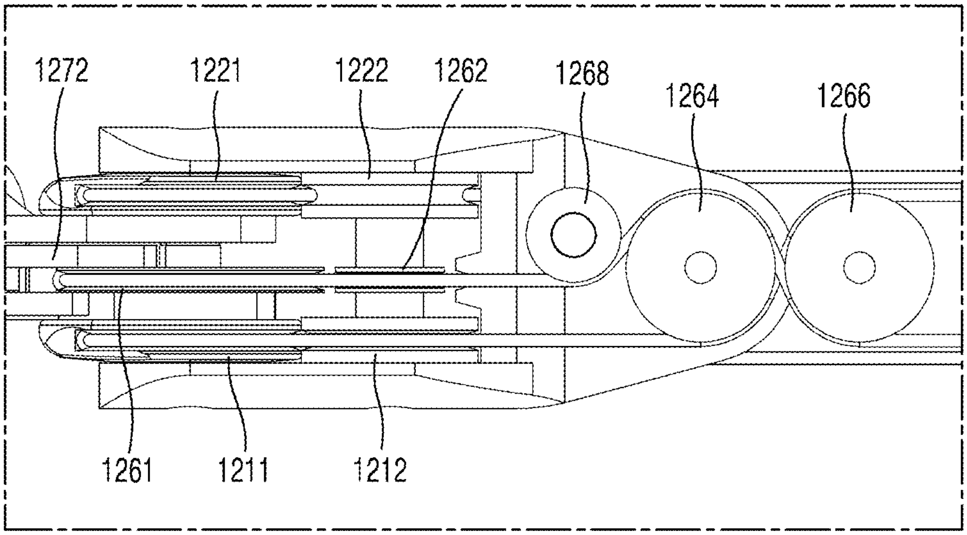
FIGS. 154 and 155 are side views illustrating the end tool of the surgical instrument of FIG. 150.
Figure 155:
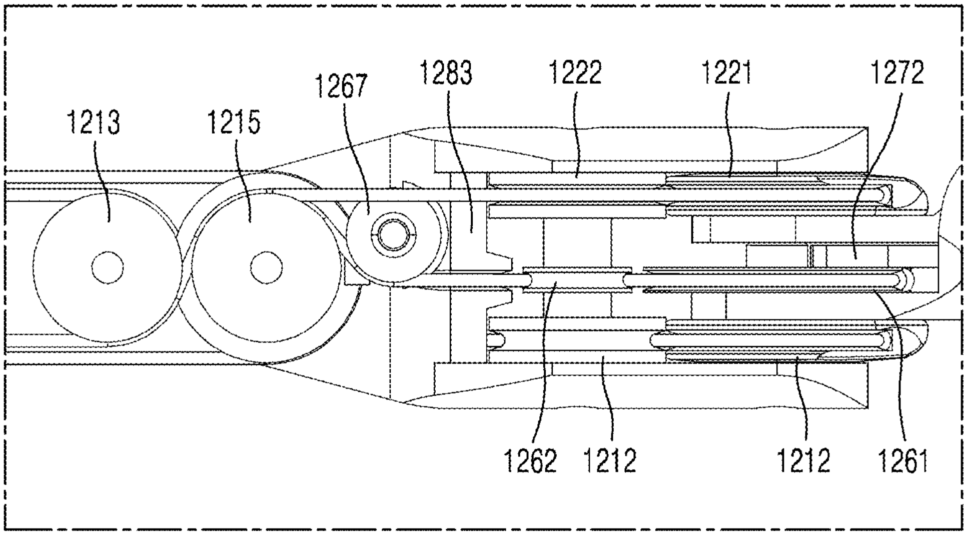
Figure 156:
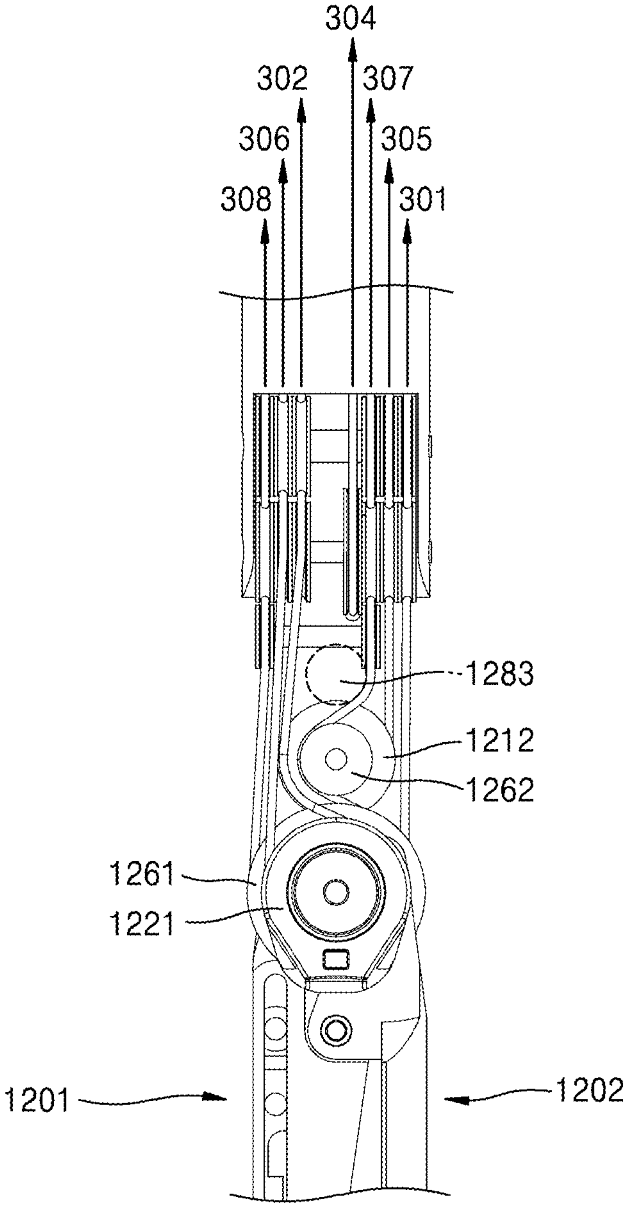
FIGS. 156 and 157 are plan views illustrating the end tool of the surgical instrument of FIG. 150.
Figure 157:
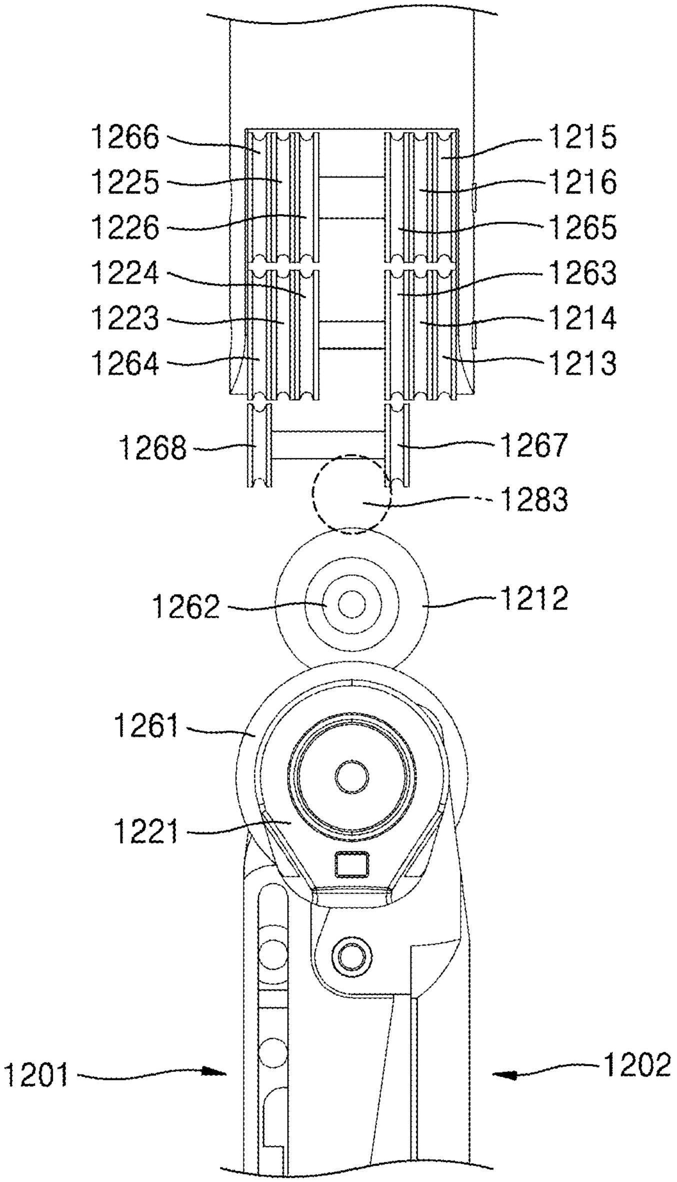
Figure 158:
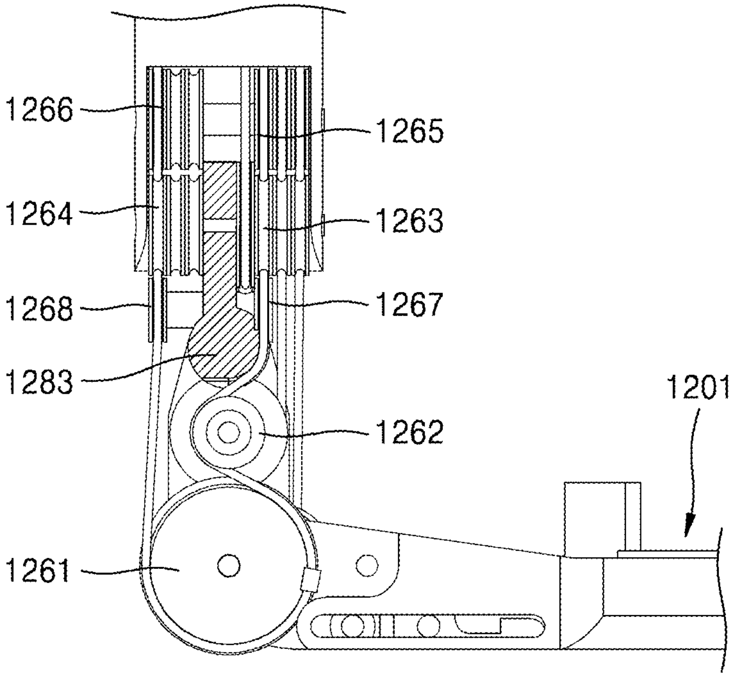
FIGS. 158 to 160 are plan views illustrating a stapling motion of the end tool of the surgical instrument of FIG. 150, and is a view illustrating a process of performing a stapling motion in a state in which jaws are yaw-rotated by +90°.
Figure 159:
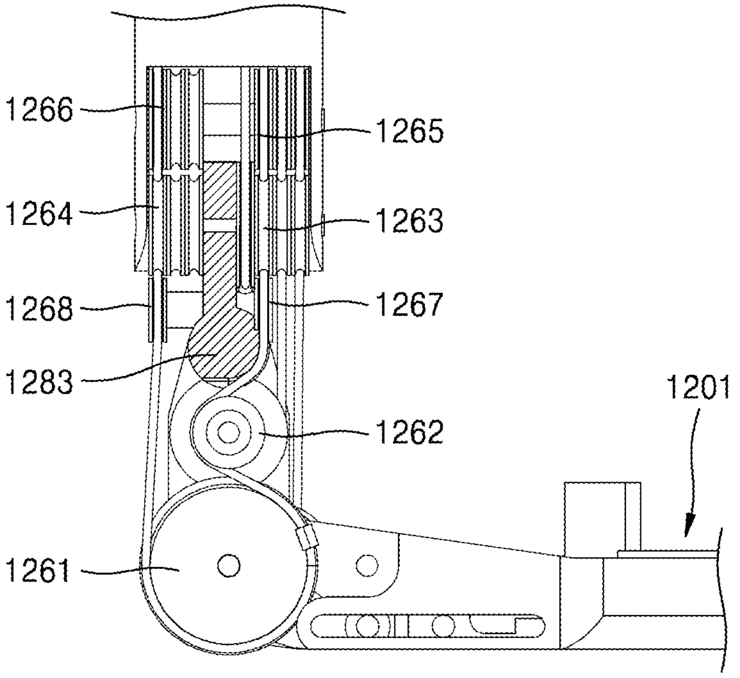
Figure 160:
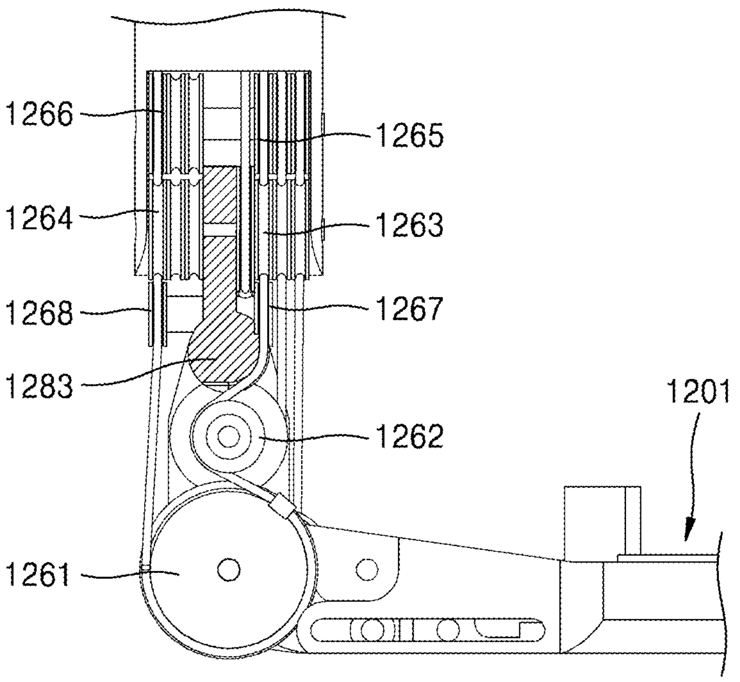
Figure 161:
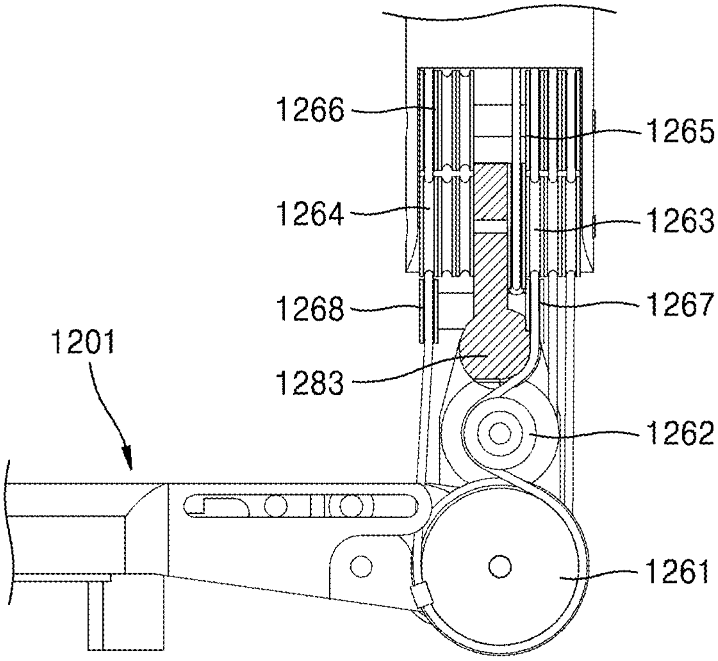
FIGS. 161 to 163 are plan views illustrating a stapling motion of the end tool of the surgical instrument of FIG. 150, and is a view illustrating a process of performing a stapling motion in a state in which the jaws are yaw-rotated by −90°.
Figure 162:
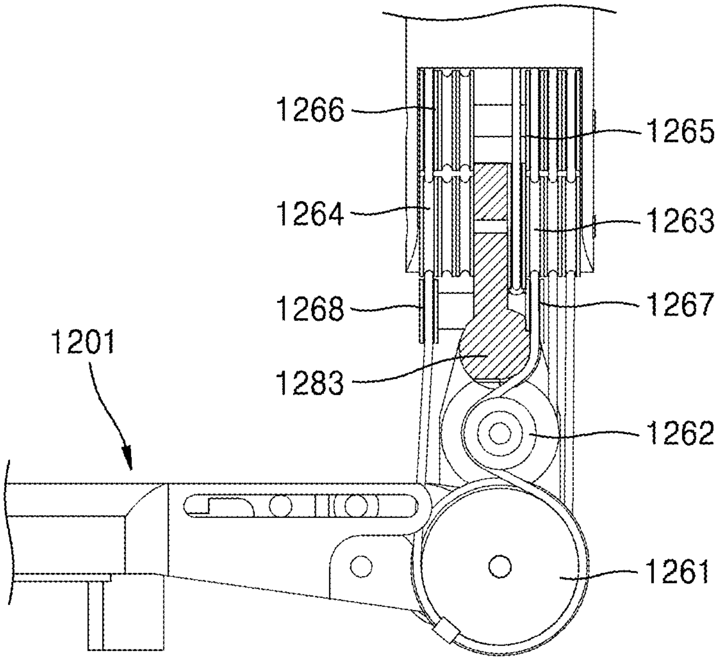
Figure 163:
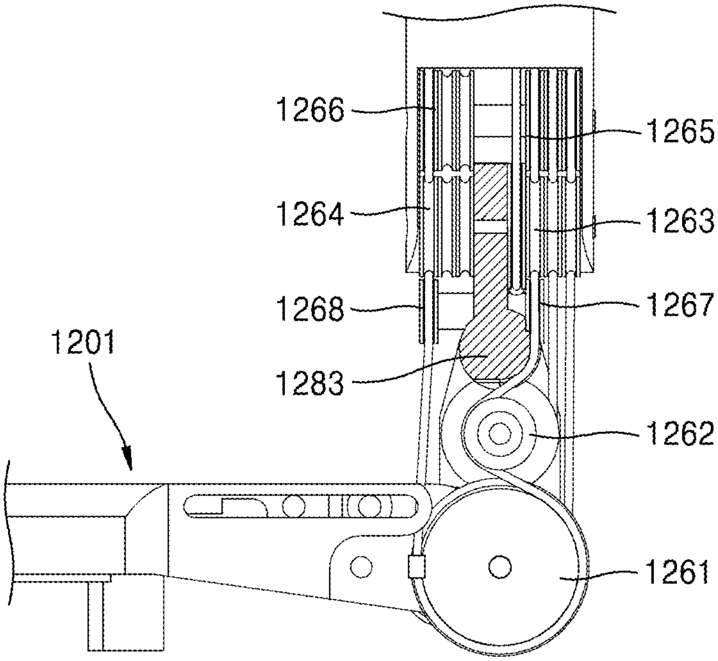

FIGS. 150 to 153 are perspective views illustrating the end tool of the surgical instrument according to the seventh embodiment of the present disclosure. Here, FIGS. 150 and 152 illustrate a state in which the end tool is closed, and FIGS. 151 and 153 illustrate a state in which the end tool is opened. Meanwhile, FIGS. 152 and 153 illustrate a state in which an end tool hub is removed. FIGS. 154 and 155 are side views illustrating the end tool of the surgical instrument of FIG. 150. FIGS. 156 and 157 are plan views illustrating the end tool of the surgical instrument of FIG. 150. FIGS. 158 to 160 are plan views illustrating a stapling motion of the end tool of the surgical instrument of FIG. 150, and is a view illustrating a process of performing a stapling motion in a state in which jaws are yaw-rotated by +90°. FIGS. 161 to 163 are plan views illustrating a stapling motion of the end tool of the surgical instrument of FIG. 150, and is a view illustrating a process of performing a stapling motion in a state in which the jaws are yaw-rotated by −90°.

Referring to FIGS. 150 to 163, the end tool 1200 of the seventh embodiment of the present disclosure includes a pair of jaws 1203 for performing a grip motion, that is, a first jaw 1201 and a second jaw 1202. Here, each of the first jaw 1201 and the second jaw 1202, or a component encompassing the first jaw 1201 and the second jaw 1202 may be referred to as the jaw.

Meanwhile, the end tool 1200 includes a plurality of pulleys including a pulley 1211 and a pulley 1212 that are related to a rotational motion of the first jaw 1201. The pulleys related to the rotational motion of the first jaw 1201 described in the present embodiment are substantially the same as the pulley 111, the pulley 112, the pulley 113, the pulley 114, the pulley 115, and the pulley 116 described with reference to FIG. 8 or the like of the first embodiment, and thus, detailed descriptions thereof will be omitted herein.

Meanwhile, the end tool 1200 includes a plurality of pulleys including a pulley 1221 and a pulley 1222 that are related to a rotational motion of the second jaw 1202. The pulleys related to the rotational motion of the second jaw 1202 described in the present embodiment are substantially the same as the pulley 121, the pulley 122, the pulley 123, the pulley 124, the pulley 125, and the pulley 126 described with reference to FIG. 8 or the like of the first embodiment, and thus, detailed descriptions thereof will be omitted herein.

In addition, the end tool 1200 of the seventh embodiment of the present disclosure may include a rotation shaft 1241, a rotation shaft 1242, a rotation shaft 1243, and a rotation shaft 1244. Here, the rotation shaft 1241 and the rotation shaft 1242 may be inserted through an end tool hub 1280, and the rotation shaft 1243 and the rotation shaft 1244 may be inserted through a pitch hub 1207. The rotation shaft 1241, the rotation shaft 1242, the rotation shaft 1243, and the rotation shaft 1244 may be arranged sequentially from a distal end 1204 of the end tool 1200 toward a proximal end 1205.

In addition, the end tool 1200 of the seventh embodiment of the present disclosure may include the end tool hub 1280 and the pitch hub 1207.

The rotation shaft 1241 and the rotation shaft 1242 may be inserted through the end tool hub 1280, and the pulley 1211 and the pulley 1221 axially coupled to the rotation shaft 1241 and at least some of the first jaw 1201 and the second jaw 1202 coupled to the pulley 1211 and the pulley 1221 may be accommodated inside the end tool hub 1280.

The rotation shaft 1243 and the rotation shaft 1244 may be inserted through the pitch hub 1207, and the pitch hub 1207 may be axially coupled to the end tool hub 1280 by the rotation shaft 1243. Accordingly, the end tool hub 1280 may be formed to be pitch-rotatable around the rotation shaft 1243 with respect to the pitch hub 1207.

Meanwhile, the end tool 1200 of the seventh embodiment of the present disclosure may further include components, such as a staple drive assembly (see 150 of FIG. 13) including a staple pulley assembly 1260 and a staple link assembly 1270, to perform stapling and cutting motions.

The staple pulley assembly 1260 may be formed between the pulley 1211 and the pulley 1221 to be adjacent to the pulley 1211 and the pulley 1221. In the present embodiment, it is assumed that the staple pulley assembly 1260 includes one staple pulley 1261.

In the seventh embodiment of the present disclosure, by disposing the staple pulley assembly 1260 between the pulley 1211, which is a first jaw pulley, and the pulley 1221, which is a second jaw pulley, the end tool 1200 is allowed to perform pitch and yaw motions as well as stapling and cutting motions using a cartridge 1210.

Hereinafter, a pulley configuration of the end tool 1200 of the surgical instrument according to the seventh embodiment of the present disclosure will be described in more detail.

The end tool 1200 of the seventh embodiment of the present disclosure may include the staple pulley 1261, a staple auxiliary pulley 1262, a pulley 1263, a pulley 1264, a pulley 1265, and a pulley 1266 that are related to a linear motion/rotational motion of the staples. In addition, the end tool 1200 of the seventh embodiment of the present disclosure may further include a pulley 1267 and a pulley 1268, which are staple second auxiliary pulleys.

The staple pulley 1261 is formed to face each of a pulley (see 111 of FIG. 6) and a pulley (see 121 of FIG. 6), which are end tool jaw pulleys, and are formed to be rotatable independently of each other around the rotation shaft 1241 that is an end tool jaw pulley rotation shaft.

Here, in the present disclosure, the staple pulley 1261, the pulley (see 111 of FIG. 6), and the pulley (see 121 of FIG. 6) are formed to rotate around the same shaft. As described above, as the staple pulley 1261, the pulley (see 111 of FIG. 6), and the pulley (see 121 of FIG. 6) are formed to rotate around the same shaft, it is possible to perform a pitch motion/yaw motion/actuation motion as well as a cutting motion using the staple.

The staple auxiliary pulley 1262 may be further provided on one side of the staple pulley 1261. In other words, the staple auxiliary pulley 1262 may be disposed between the pulley 1261 and the pulley 1263/the pulley 1264. The staple auxiliary pulley 1262 may be formed to be rotatable independently of each other around the rotation shaft 1242 together with the pulley (see 112 of FIG. 6) and the pulley (see 122 of FIG. 6).

The pulleys 1263 and 1264 function as staple pitch main pulleys, and the pulleys 1265 and 1266 function as staple pitch sub-pulleys.

The pulleys 1267 and 1268, which are staple second auxiliary pulleys, may be disposed between the staple auxiliary pulley 1262 and the pulley 1263/the pulley 1264. The staple auxiliary pulley 1262 may be formed to be rotatable around a predetermined axis parallel to the rotation shaft 1243 which is a central axis of the pulleys 1263 and 1264.

Hereinafter, components related to the rotation of the staple pulley 1261 will be described.

The pulleys 1263 and 1264 function as staple pitch main pulleys. Here, the wire 307, which is a staple wire, is wound around the pulley 1263, and the wire 308, which is a staple wire, is wound around the pulley 1264.

The pulleys 1265 and 1266 function as staple pitch sub-pulleys. Here, the wire 307, which is a staple wire, is wound around the pulley 1265, and the wire 308, which is a staple wire, is wound around the pulley 1266.

Here, the pulleys 1263 and 1264 are disposed on one side of the staple pulley 1261 and the staple auxiliary pulley 1262 to face each other. Here, the pulleys 1263 and 1264 are formed to be rotatable independently of each other around the rotation shaft 1243 that is an end tool pitch rotating shaft. In addition, the pulleys 1265 and 1266 are respectively disposed on one sides of the pulleys 1263 and 1264 to face each other. Here, the pulleys 1265 and 1266 are formed to be rotatable independently of each other around the rotation shaft 1244, which is an end tool pitch auxiliary rotating shaft. Here, in the drawings, it is illustrated that all of the pulley 1263, the pulley 1265, the pulley 1264, and the pulley 1266 are formed to be rotatable around the Y-axis direction, but the concept of the present disclosure is not limited thereto, and the rotating axes of the respective pulleys may be formed in various directions according to configurations thereof.

The wire 307, which is a staple wire, is sequentially wound to make contact with at least portions of the pulley 1265, the pulley 1263, the staple auxiliary pulley 1262, and the staple pulley 1261. In addition, the wire 308 connected to the wire 307 by the coupling member 329 is sequentially wound to make contact with at least portions of the staple pulley 1261, the staple auxiliary pulley 1262, the pulley 1268, the pulley 1264, and the pulley 1266.

In other words, the wires 307 and 308, which are staple wires, sequentially wound to make contact with at least portions of the pulley 1265, the pulley 1263, the pulley 1267, the staple auxiliary pulley 1262, the staple pulley 1261, the staple auxiliary pulley 1262, the pulley 1268, the pulley 1264, and the pulley 1266, and the wires 307 and 308 are formed to move along the above pulleys while rotating the above pulleys.

Accordingly, when the wire 307 is pulled, the coupling member 329, to which the wire 307 is coupled, and the staple pulley 1261 coupled to the coupling member 329 are rotated in one direction. In contrast, when the wire 308 is pulled, the coupling member 329, to which the wire 308 is coupled, and the staple pulley 1261 coupled to the coupling member 329 are rotated in a direction opposite to the one direction.

Here, in the end tool 1200 of the surgical instrument according to the seventh embodiment of the present disclosure, the pulleys 1267 and 1268, which are staple second auxiliary pulleys, are additionally provided to serve to prevent the wires 307 and 308, which are staple wires, from being separated.

That is, the staple second auxiliary pulley 1267 is disposed between the staple auxiliary pulley 1262 and the pulley 1263 to change the path of the wire 307 entering the end tool hub 1280 to a certain extent. In addition, the staple second auxiliary pulley 1268 is disposed between the staple auxiliary pulley 1262 and the pulley 1264 to change the path of the wire 308 entering the end tool hub 1280 to a certain extent.

In detail, a height of the wire 307 in the Z-axis direction coming from the staple auxiliary pulley 1262 and a height of the wire 307 in the Z-axis direction entering the pulley 1263 are different from each other. Here, when the pulley 1267, which is a staple second auxiliary pulley, is not present, the path of the wire 307 becomes oblique, and thus there is a risk that the wire 307 is removed from the pulley. Similarly, a height of the wire 308 in the Z-axis direction coming from the staple auxiliary pulley 1262 and a height of the wire 308 in the Z-axis direction entering the pulley 1264 are different from each other. Here, when the pulley 1268, which is a staple second auxiliary pulley, is not present, the path of the wire 308 becomes oblique, and thus there is a risk that the wire 308 is removed from the pulley.

Accordingly, in the present embodiment, the staple second auxiliary pulley 1267 is disposed between the staple auxiliary pulley 1262 and the pulley 1263 to change the path of the wire 307 to a certain extent so that the wire 307 coming out of the staple auxiliary pulley 1262 maintains a parallel path. Similarly, the staple second auxiliary pulley 1268 is disposed between the staple auxiliary pulley 1262 and the pulley 1264 to change the path of the wire 308 to a certain extent so that the wire 308 coming out of the staple auxiliary pulley 1262 maintains a parallel path.

According to the present disclosure, the wires 307 and 308, which are staple wires, are prevented from being separated from the pulleys, thereby more smoothly performing the cutting motion.

FIGS. 158 to 160 are plan views illustrating stapling and cutting motions of the end tool of the surgical instrument of FIG. 150, and is a view illustrating a process of performing the stapling and cutting motions in a state in which the jaws are yaw-rotated by +90°. As shown in FIGS. 158 to 160, the end tool of the surgical instrument according to the seventh embodiment of the present disclosure is formed to normally perform the stapling and cutting motions even when the jaws are yaw-rotated by +90°.

In detail, in a state in which the pulley 1211, the pulley 1221, and the staple pulley 1261 are rotated by +90° around the rotation shaft 1241, when the staple pulley 1261 is alternately rotated in the clockwise/counterclockwise directions, a link member 1271 and a reciprocating member 551 connected thereto are repeatedly moved forward and backward. In addition, when the reciprocating member 551 is moved forward, an operation member 540 may be moved forward together with the reciprocating member 551, and when the reciprocating member 551 is moved backward, only the reciprocating member 551 is moved backward and the operation member 540 remains stationary. By repeating this process, the stapling and cutting motions are performed while the operation member 540 is moved toward a distal end 502.

FIGS. 161 to 163 are plan views illustrating stapling and cutting motions of the end tool of the surgical instrument of FIG. 150, and are views illustrating a process of performing the stapling and cutting motions in a state in which the jaws are yaw-rotated by −90°. As shown in FIG. 63, the end tool of the surgical instrument according to the first embodiment of the present disclosure is formed to normally perform the stapling and cutting motions even when the jaws are yaw-rotated by −90°.

In detail, in a state in which the pulley 1211, the pulley 1221, and the staple pulley 1261 are rotated by −90° around the rotation shaft 1241, when the staple pulley 1261 is alternately rotated in the clockwise/counterclockwise directions, the link member 1271 and the reciprocating member 551 connected thereto are repeatedly moved forward and backward. In addition, when the reciprocating member 551 is moved forward, the operation member 540 may be moved forward together with the reciprocating member 551, and when the reciprocating member 551 is moved backward, only the reciprocating member 551 is moved backward and the operation member 540 remains stationary in place. By repeating this process, the stapling and cutting motions are performed while the operation member 540 is moved toward the distal end 502.

Eighth Embodiment—Dual Rack & Spring

Hereinafter, an end tool 1300 of a surgical instrument according to an eighth embodiment of the present disclosure will be described. Here, the end tool 1300 of the surgical instrument according to the eighth embodiment of the present disclosure is different from the end tool (see 900 of FIG. 105 or the like) of the surgical instrument according to the fourth embodiment of the present disclosure described above in that a staple link assembly 1370 and a reciprocating assembly 1350 of a cartridge 1310 are different. Hereinafter, the configuration that is different from that of the fourth embodiment will be described in detail.

Figure 164:
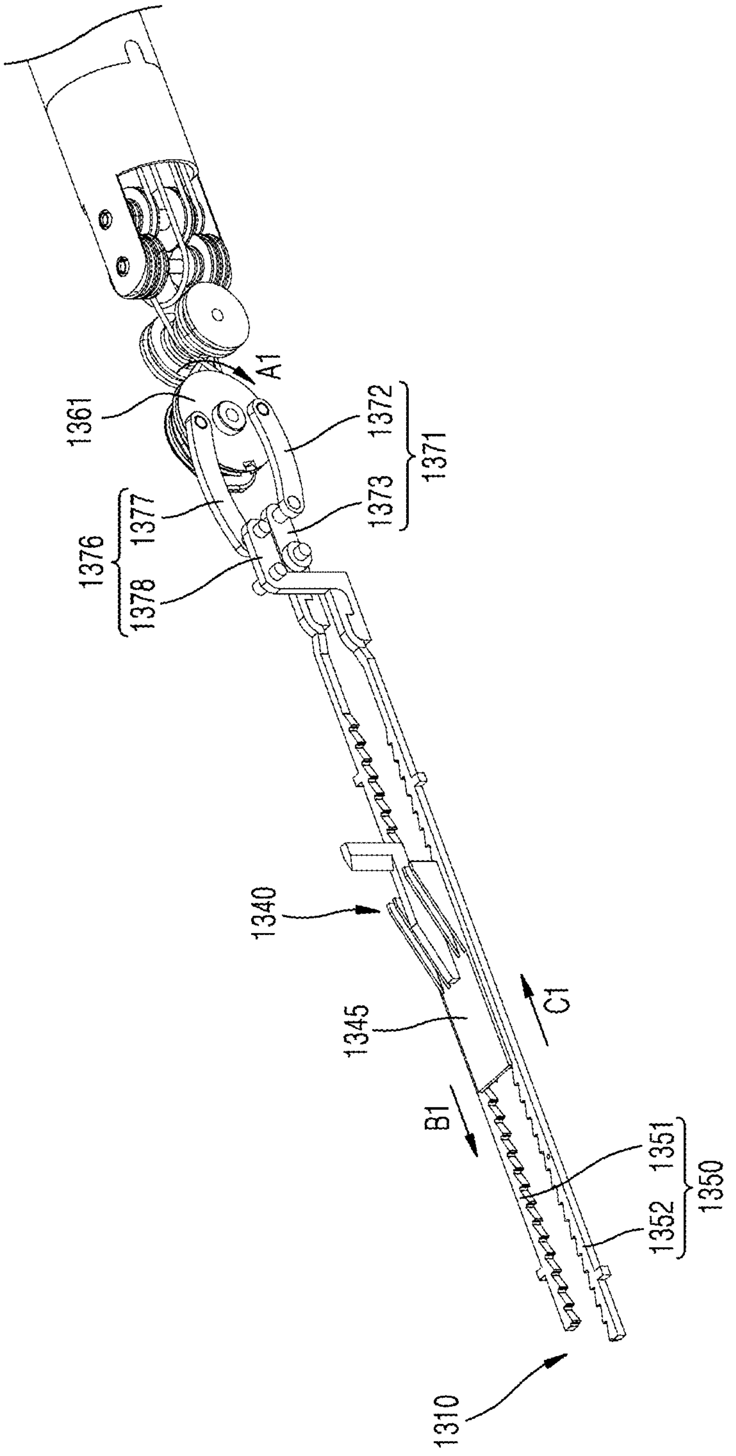
FIGS. 164 to 166 are perspective views illustrating an end tool of the surgical instrument according to an eighth embodiment of the present disclosure.
Figure 165:
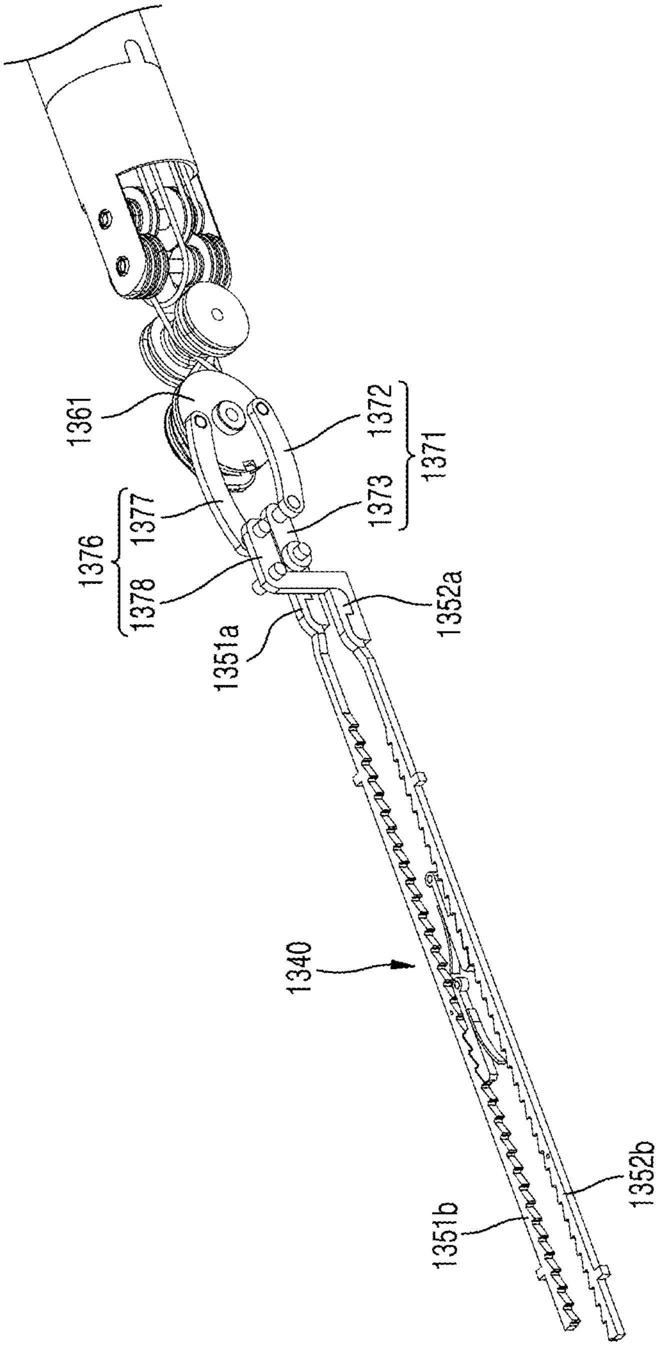
Figure 166:
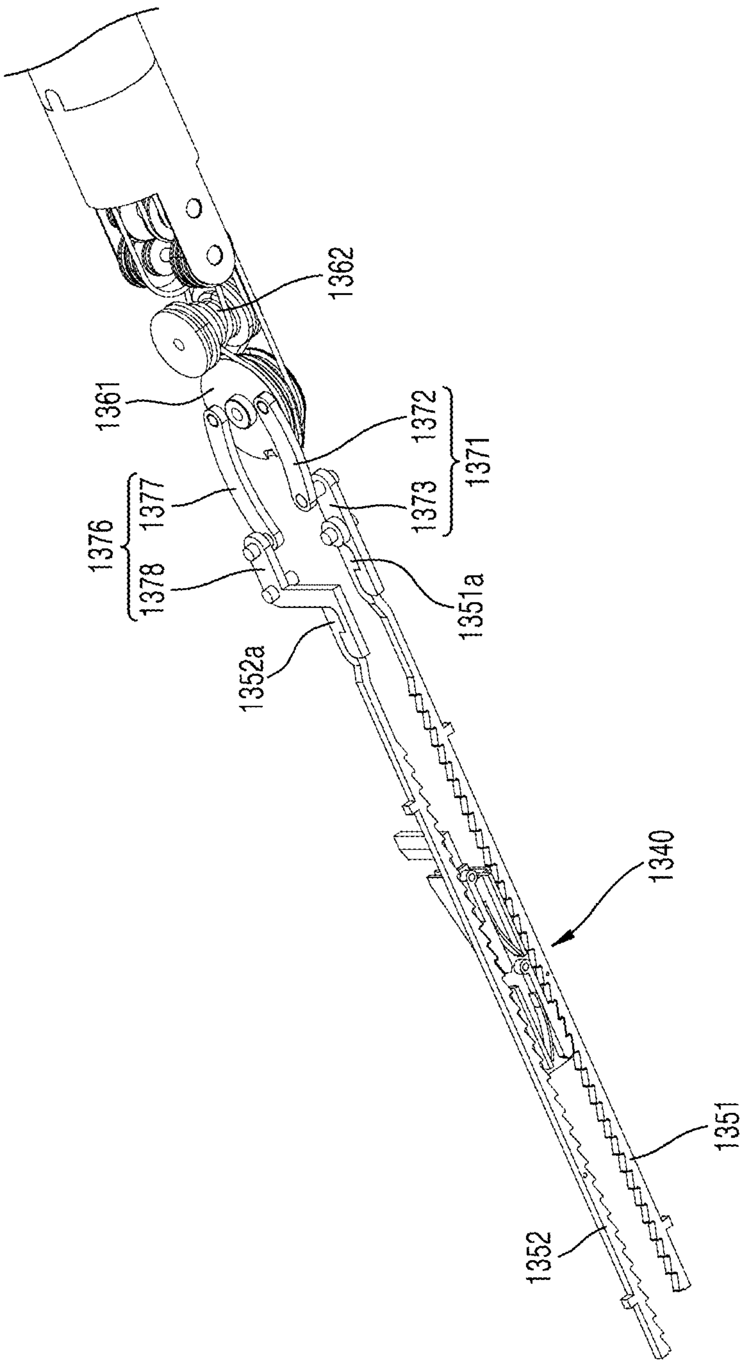
Figure 167:
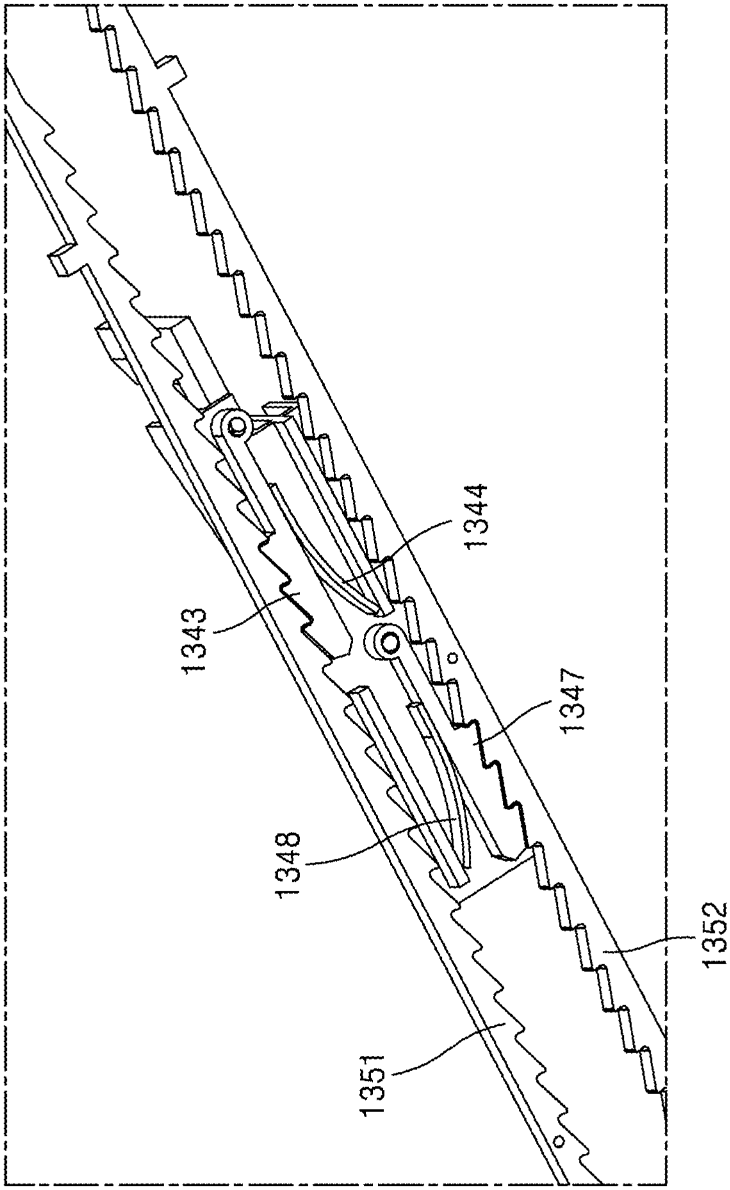
FIGS. 167 and 168 are perspective views illustrating a cartridge of the surgical instrument of FIG. 164.
Figure 168:
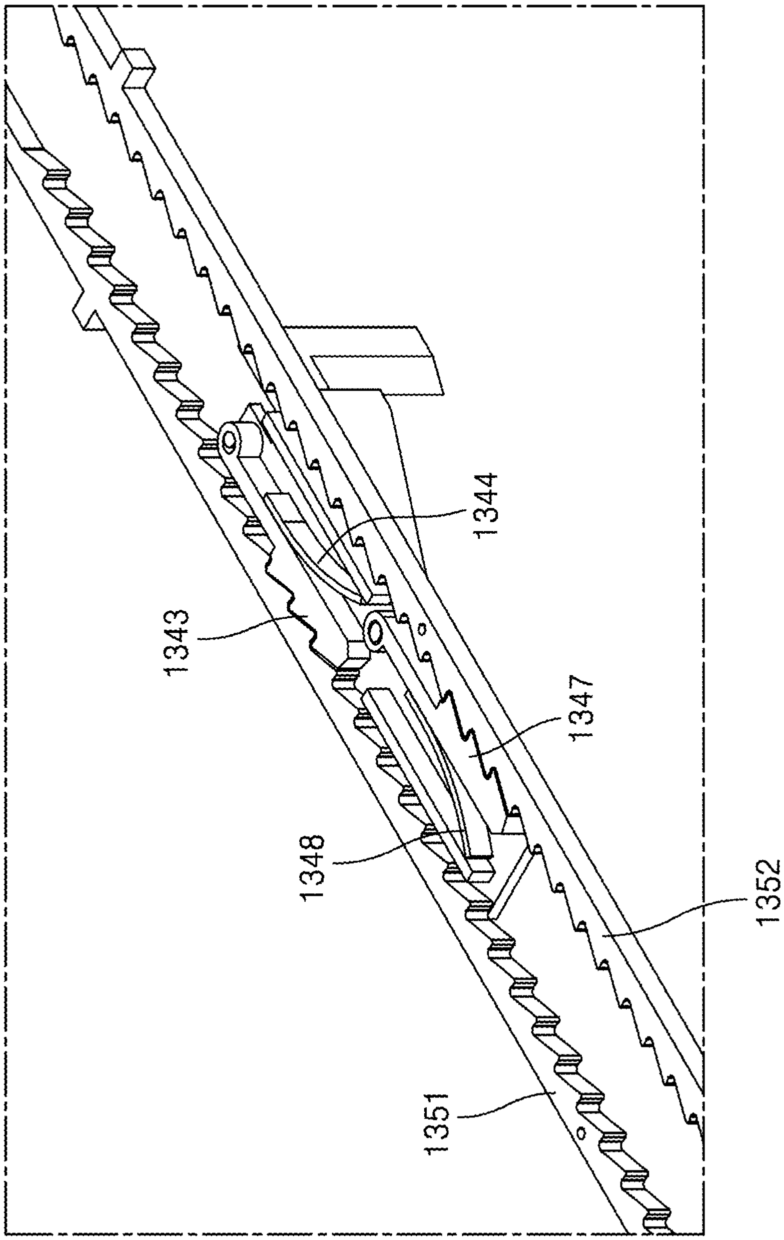
Figure 169:
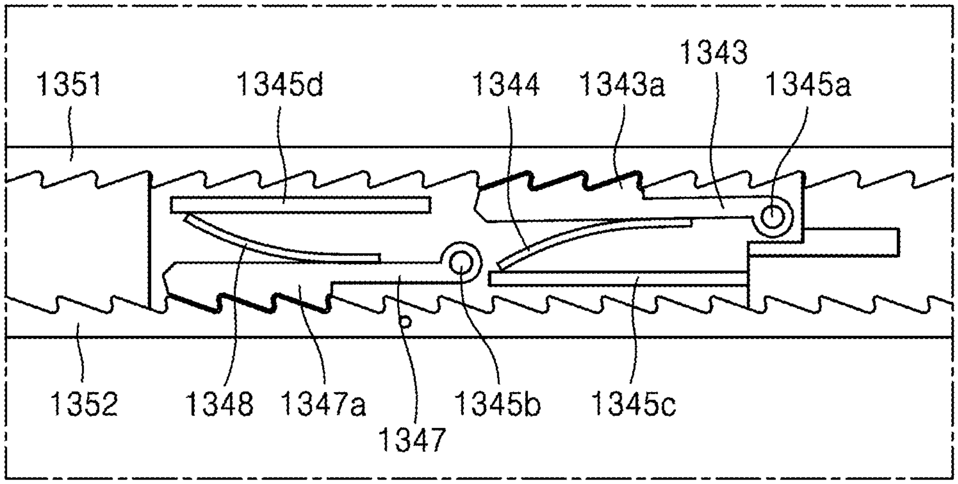
FIG. 169 is a bottom view of the cartridge of FIG. 167.
Figure 170:
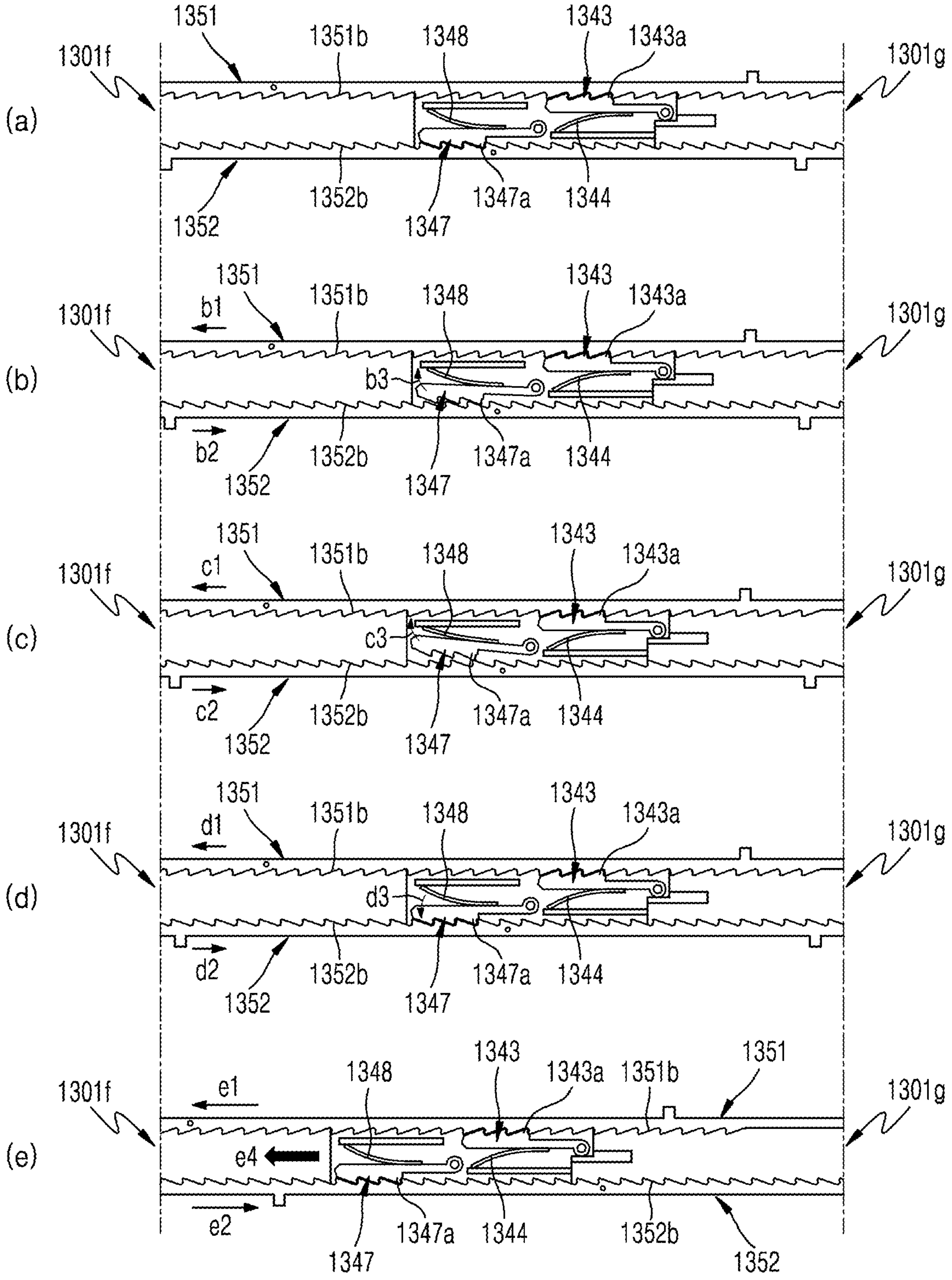
FIGS. 170 and 171 are perspective views illustrating respective operating states of the end tool of FIG. 164.
Figure 171:
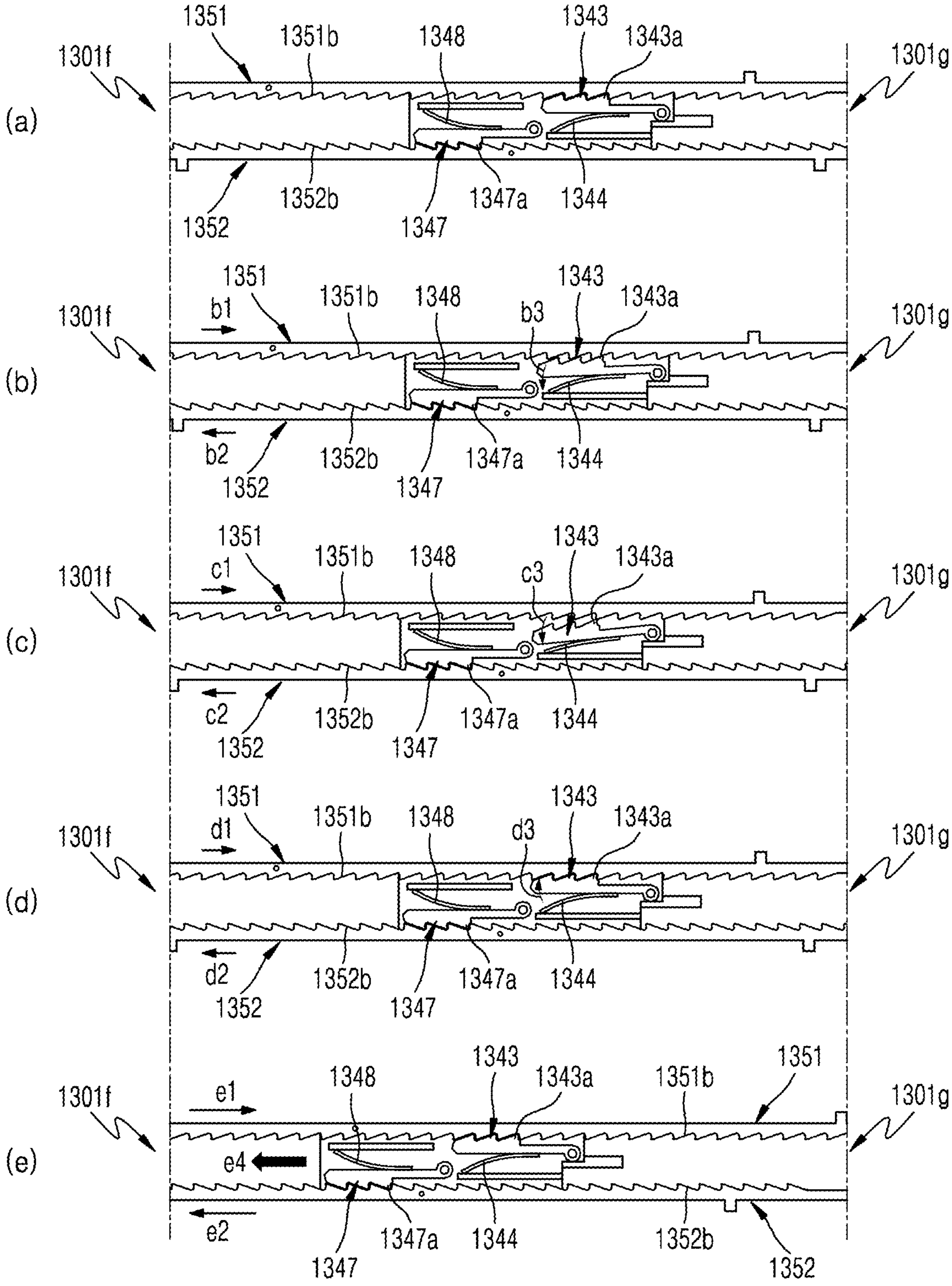

FIGS. 164 to 166 are perspective views illustrating the end tool of the surgical instrument according to the eighth embodiment of the present disclosure. Here, FIGS. 164 to 166 illustrate a state in which a first jaw, a second jaw, an end tool hub, and the like are removed. FIGS. 167 and 168 are perspective views illustrating the cartridge of the surgical instrument of FIG. 164. FIG. 169 is a bottom view of the cartridge of FIG. 167. FIGS. 170 and 171 are perspective views illustrating respective operating states of the end tool of FIG. 164. Here, FIGS. 170 and 171 mainly illustrate operations of the reciprocating assembly and an operation member.

Referring to FIGS. 164 to 171, the end tool 1300 of the eighth embodiment of the present disclosure includes a pair of jaws for performing a grip motion, that is, a first jaw (see 901 of FIG. 105) and a second jaw (see 902 in FIG. 105).

Meanwhile, the end tool 1300 includes a plurality of pulleys including a pulley 1311 and a pulley 1312 that are related to a rotational motion of the first jaw (see 901 of FIG. 105). The pulleys related to the rotational motion of the first jaw (see 901 of FIG. 105) described in the present embodiment are substantially the same as the pulley 111, the pulley 112, the pulley 113, the pulley 114, the pulley 115, and the pulley 116 described with reference to FIG. 105 or the like of the fourth embodiment, and thus, detailed descriptions thereof will be omitted herein.

Meanwhile, the end tool 1300 includes a plurality of pulleys including a pulley 1321 and a pulley 1322 that are related to a rotational motion of second jaw (see 902 in FIG. 105) The pulleys related to the rotational motion of the second jaw (see 902 in FIG. 105) described in the present embodiment are substantially the same as the pulley 121, the pulley 122, the pulley 123, the pulley 124, the pulley 125, and the pulley 126 described with reference to FIG. 105 or the like of the fourth embodiment, and thus, detailed descriptions thereof will be omitted herein.

Meanwhile, the end tool 1300 of the eighth embodiment of the present disclosure may further include components, such as a staple drive assembly (see 150 of FIG. 13) including a staple pulley assembly 1360 and the staple link assembly 1370, to perform stapling and cutting motions.

The staple pulley assembly 1360 may be formed between the pulley 1311 and the pulley 1321 to be adjacent to the pulley 1311 and the pulley 1321. In the present embodiment, it is assumed that the staple pulley assembly 1360 includes one staple pulley 1361.

In the eighth embodiment of the present disclosure, by disposing the staple pulley assembly 1360 between the pulley 1311, which is a first jaw pulley, and the pulley 1321, which is a second jaw pulley, the end tool 1300 is allowed to perform pitch and yaw motions as well as stapling and cutting motions using the cartridge 1310.

Hereinafter, the staple pulley assembly 1360, the staple link assembly 1370, and the reciprocating assembly 1350 of the cartridge 1310 of the end tool 1300 of the surgical instrument according to the eighth embodiment of the present disclosure will be described in more detail.

In the end tool 1300 of the surgical instrument according to the eighth embodiment of the present disclosure, the staple link assembly 1370 includes a first link member 1371 and a second link member 1376, and the reciprocating assembly 1350 of the cartridge 1310 includes a first reciprocating member 1351 and a second reciprocating member 1352, so that a kind of dual rack structure is formed in the end tool 1300.

Referring to FIGS. 105 to 121 and the like, the staple pulley assembly 1360 may include one or more staple pulleys 1361.

A shaft pass-through part 1361*a* may be formed in the staple pulley 1361. The shaft pass-through part 1361*a* may be formed in the form of a hole, and a rotation shaft 1341, which is an end tool jaw pulley rotation shaft, may be inserted through the shaft pass-through part 1361*a*.

In addition, a first link coupling part 1361*b* and a second link coupling part 1361*c* may be formed in the staple pulley 1361. The first link member 1371 of the staple link assembly 1370 may be coupled to the first link coupling part 1361*b*, and the second link member 1376 of the staple link assembly 1370 may be coupled to the second link coupling part 1361*c*. Here, the first link coupling part 1361*b* and the second link coupling part 1361*c* may be disposed on opposite sides with respect to a central axis of the staple pulley 1361.

Meanwhile, the end tool 1300 of the eighth embodiment of the present disclosure may further include the staple link assembly 1370 connected to the staple pulley assembly 1360. Here, the staple link assembly 1370 may serve to connect the staple pulley assembly 1360 to the reciprocating assembly 1350 of the cartridge 1310 to be described later. In the end tool 1300 of the eighth embodiment of the present disclosure, the staple link assembly 1370 includes two pairs of link members in the first link member 1371 and the second link member 1376.

The first link member 1371 may include a first link 1372 and a second link 1373.

The second link member 1376 may include a third link 1377 and a fourth link 1378.

The configuration of the first link member 1371 and the second link member 1376 is substantially the same as the configuration of the first link member (see 971 of FIG. 110) and the second link member (see 976 of FIG. 110) of the fourth embodiment illustrated in FIG. 105 or the like, and thus, detailed descriptions thereof will be omitted in the present embodiment.

In the state of FIG. 164, when the staple pulley 1361 is rotated in the direction of an arrow A1 of FIG. 164 (i.e., in the clockwise direction), the first link member 1376 connected to the staple pulley 1361 may be moved in the direction of an arrow B1 of FIG. 164, in other words, toward a distal end 1301*f* of the first jaw 1301. In contrast, when the staple pulley 1361 is rotated in the counterclockwise direction, the first link member 1376 connected to the staple pulley 1361 may be moved in the direction of an arrow C1 of FIG. 164, in other words, toward a proximal end 1301*g* of the first jaw 1301.

Meanwhile, when the staple pulley 1361 is rotated in the direction of the arrow A1 of FIG. 164 (i.e., in the clockwise direction), the second link member 1376 connected to the staple pulley 1361 may be moved in the direction of the arrow C1 of FIG. 164, in other words, toward the proximal end 1301*g* of the first jaw 1301. In contrast, when the staple pulley 1361 is rotated in the counterclockwise direction, the second link member 1376 connected to the staple pulley 1361 may be moved in the direction of the arrow B1 of FIG. 114, in other words, toward the distal end 1301*f* of the first jaw 1301.

That is, when the staple pulley 1361 is rotated in one direction (e.g., the clockwise direction), the first link member 1371 is moved forward and the second link member 1376 is moved backward. Meanwhile, when the staple pulley 1361 is rotated in the other direction (e.g., the counterclockwise direction), the first link member 1371 is moved backward and the second link member 1376 is moved forward.

With this configuration, when the staple pulley 1361 is alternately rotated in the clockwise and counterclockwise directions, the first link member 1371 and the second link member 1376 perform a linear reciprocating motion, and in this case, the first link member 1371 and the second link member 1376 are moved in opposite directions. That is, as the first link member 1371 is moved forward (i.e., toward the distal end), the second link member 1376 is moved backward (i.e., toward the proximal end). In contrast, as the first link member 1371 is moved backward (i.e., toward the proximal end), the second link member 1376 is moved forward (i.e., toward the distal end).

As a result, a bidirectional rotational motion of the staple pulley assembly 1360 may cause reciprocating linear motions of the first reciprocating member 1351 and the second reciprocating member 1352 of the cartridge 1310 through the first link member 1371 and the second link member 1376 of the staple link assembly 1370.

(Cartridge)

Hereinafter, the cartridge 1310 of the end tool 1300 of the surgical instrument according to the eighth embodiment of the present disclosure will be described in more detail.

In the cartridge 1310 of the end tool 1300 of the surgical instrument according to the eighth embodiment of the present disclosure, the reciprocating assembly 1350 includes the first reciprocating member 1351 and the second reciprocating member 1352.

In detail, referring to FIGS. 164 to 169 and the like, the cartridge 1310 is formed to be mountable to and dismountable from the first jaw 1301 and includes a plurality of staples (see 530 of FIG. 22) and an operation member 1340 therein to perform suturing and cutting tissue.

Here, the cartridge 1310 may include a cover (see 510 of FIG. 22), a housing (see 520 of FIG. 22), a staple (see 530 of FIG. 22), the operation member 1340, and the reciprocating assembly 1350.

The housing (see 520 of FIG. 22) forms an outer shape of the cartridge 1310, and may be formed entirely in the form of a hollow box with one surface (upper surface) removed to accommodate the reciprocating assembly 1350, the operation member 1340, and the staple (see 530 of FIG. 22) therein. Here, the housing (see 520 of FIG. 22) may be formed in an approximately "U" shape in cross section.

A plurality of staples (see 530 of FIG. 22) may be disposed inside the housing (see 520 of FIG. 22). As the operation member 1340, which will be described later, is linearly moved in one direction, the plurality of staples (see 530 of FIG. 22) are sequentially pushed and raised from the inside of the housing (see 520 of FIG. 22) to the outside, thereby performing sealing, that is, stapling.

The reciprocating assembly 1350 may be disposed at an inner lower side of the housing (see 520 of FIG. 22). In the present embodiment, the reciprocating assembly 1350 includes the first reciprocating member 1351 and the second reciprocating member 1352.

In the present embodiment, the first reciprocating member 1351 and the second reciprocating member 1352 may from a rack. The first reciprocating member 1351 may include a recess 1351*b* and a coupling part 1351*a*.

In detail, the first reciprocating member 1351 may be formed in the form of an elongated bar, and a plurality of recesses 1351*b* having a sawtooth shape may be formed on one surface thereof. The recess 1351*b* may be formed to be in contact with an operation member 1340 to be described later, in particular, a first ratchet member 1343 of the operation member 1340. In other words, the first reciprocating member 1351 may include the plurality of recesses 1351*b* shaped to engage with first ratchets 1343*a* of the first ratchet member 1343.

Similarly, the second reciprocating member 1352 may include a recess 1352*b* and a coupling part 1352*a*. That is, the second reciprocating member 1352 may include a plurality of recesses 1352*b* shaped to engage with recesses 1347*b* of a second ratchet member 1347.

Here, the first reciprocating member 1351 and the second reciprocating member 1352 are not fixedly coupled to other components of the cartridge 1310, and may be formed to be movable relative to other components of the cartridge 1310. That is, the first reciprocating member 1351 and the second reciprocating member 1352 may perform a reciprocating linear motion with respect to the housing (see 520 of FIG. 22) and the cover (see 510 of FIG. 22).

Meanwhile, in the first reciprocating member 1351, the coupling part 1351*a* may be formed at the proximal end side adjacent to the pulley 1311 and the coupling part 1351*a* may be fastened and coupled to the first link member 1371 of the staple link assembly 1370 of the end tool 1300. Thus, when the first link member 1371 performs a reciprocating linear motion in the extension direction (i.e., the Y-axis direction) of the connection part 400, the first reciprocating member 1351 coupled thereto may also perform a reciprocating linear motion in the extension direction (i.e., the Y-axis direction) of the connection part 400.

Similarly, in the second reciprocating member 1352, the coupling part 1352*a* may be formed at the proximal end side adjacent to the pulley 1311 and the coupling part 1352*a* may be fastened and coupled to the second link member 1376 of the staple link assembly 1370 of the end tool 1300. Thus, when the second link member 1376 performs a reciprocating linear motion in the extension direction (i.e., the Y-axis direction) of the connection part 400, the second reciprocating member 1352 coupled thereto may also perform a reciprocating linear motion in the extension direction (i.e., the Y-axis direction) of the connection part 400.

The operation member 1340 may be disposed inside the housing 1320. The operation member 1340 is formed to be in contact with the first reciprocating member 1351 and the second reciprocating member 1352, and may be formed to linearly move in one direction according to the reciprocating linear motion of the first reciprocating member 1351 and the second reciprocating member 1352. In other words, the operation member 1340 interacts with the first reciprocating member 1351 and the second reciprocating member 1352 to perform stapling and cutting while moving in the extension direction of the connection part 400.

The operation member 1340 may include a wedge (see 541 of FIG. 22), a blade (see 542 of FIG. 22), the first ratchet member 1343, a first elastic member 1344, the second ratchet member 1347, a second elastic member 1348, and the like. Here, in the drawings, components other than the ratchet member and the elastic member, that is, the wedge, the blade, and the like are omitted from the operation member 1340, but it is of course possible that such components may be included in the operation member 1340. Here, the first ratchet member 1343 and the second ratchet member 1437 may be collectively referred to as a ratchet member.

The first ratchet member 1343 may include the first ratchets 1343*a*, and the second ratchet member 1347 may include second ratchets 1347*a*. Here, the first ratchet 1343*a* of the first ratchet member 1343 may be formed to be engageable with the first reciprocating member 1351, and the second ratchet 1347*a* of the second ratchet member 1347 may be formed to be engageable with the second reciprocating member 1372. That is, the motion of the operation member 1340 being moved forward by the first reciprocating member 1351 as the first ratchet 1343*a* of the first ratchet member 1343 is engaged with (or brought into close contact with) the first reciprocating member 1351, and the motion of the operation member 1340 being moved forward by the second reciprocating member 1352 as the second ratchet 1347*a* of the second ratchet member 1347 is engaged with (or brought into close contact with) the second reciprocating member 1352 are alternately performed.

The first ratchet member 1343 may be formed to be rotatable around a rotation shaft 1345*a*. In an example, the rotation shaft 1345*a* is formed to protrude from a lower portion of a body 1345, and the first ratchet member 1343 may be fitted to the rotation shaft 1345*a*. Accordingly, when the first ratchet member 1343 is pressed by the first reciprocating member 1351 or is subjected to an elastic force by the first elastic member 1344, the first ratchet member 1343 may be rotated around the rotation shaft 1345*a*.

The first elastic member 1344 is formed on one side of the first ratchet member 1343, and serves to apply a predetermined elastic force to the first ratchet member 1343. In an example, one region of the elastic member 1344 may be in contact with a support 1345*c* formed to protrude from a lower portion of the body 1345, and another region of the elastic member 1344 may be in contact with the first ratchet member 1343. Here, the first elastic member 1344 may apply an elastic force in a direction in which the first ratchet member 1343 comes into close contact with the first reciprocating member 1351. To this end, the first elastic member 1344 may be formed in the form of a leaf spring, and may be provided in various forms capable of providing a predetermined elastic force to the first ratchet member 1343, such as a coil spring, a dish spring, and the like.

The second ratchet member 1347 may be formed to be rotatable around a rotation shaft 1345*b*. In an example, the rotation shaft 1345*b* is formed to protrude from the lower portion of the body 1345, and the second ratchet member 1347 may be fitted to the rotation shaft 1345*b*. Accordingly, when the second ratchet member 1347 is pressed by the second reciprocating member 1352 or is subjected to an elastic force by the second elastic member 1348, the second ratchet member 1347 may be rotated around the rotation shaft 1345*b*.

The second elastic member 1348 is formed on one side of the second ratchet member 1347, and serves to apply a predetermined elastic force to the second ratchet member 1347. In an example, one region of the elastic member 1344 may be in contact with a support 1345*d* formed to protrude from the lower portion of the body 1345, and another region of the elastic member 1344 may be in contact with the second ratchet member 1347. Here, the second elastic member 1348 may apply an elastic force in a direction in which the second ratchet member 1347 comes into close contact with the second reciprocating member 1352. To this end, the second elastic member 1348 may be formed in the form of a leaf spring, and may be provided in various forms capable of providing a predetermined elastic force to the second ratchet member 1347, such as a coil spring, a dish spring, and the like.

(Operations of Reciprocating Assembly and Operation Member)

Hereinafter, operations of the reciprocating assembly 1350 and the operation member 1340 will be described in more detail.

FIGS. 170 and 171 are views illustrating respective operating states of the reciprocating assembly 1350 and the operation member 1340. Here, FIG. 170 is a view illustrating when the first reciprocating member 1351 is moved forward and the second reciprocating member 1352 is moved backward, and FIG. 171 is a view illustrating when the first reciprocating member 1351 is moved backward and the second reciprocating member 1352 is moved forward.

Here, FIG. 170 is a view illustrating when the first reciprocating member 1351 is moved forward and the second reciprocating member 1352 is moved backward as the staple pulley 1361 is rotated in the clockwise direction (in the direction of the arrow A1 of FIG. 164).

In addition, FIG. 171 is a view illustrating when the first reciprocating member 1351 is moved backward and the second reciprocating member 1352 is moved forward as the staple pulley 1361 is rotated in the counterclockwise direction (in the opposite direction of the arrow A1 of FIG. 164).

First, operations of FIGS. 170A to 170E will be described.

FIG. 170A illustrates a state in which the first ratchet 1343*a* of the first ratchet member 1343 and the first reciprocating member 1351 are in close contact with each other, and the second ratchet 1347*a* of the second ratchet member 1347 and the second reciprocating member 1352 are in close contact with each other.

In this state, when the staple pulley 1361 is rotated in the clockwise direction (in the direction of the arrow A1 of FIG. 164), as shown in FIG. 170B, the first reciprocating member 1351 is moved in the direction of an arrow b1 (i.e., is moved forward), and the second reciprocating member 1352 is moved in the direction of an arrow b2 (i.e., is moved backward). Then, the recess 1352*b* of the second reciprocating member 1352 pushes the second ratchet 1347*a* of the second ratchet member 1347 toward the first reciprocating member 1351, which causes the second ratchet member 1347 to be rotated as a whole in the direction of an arrow b3 around the rotation shaft 1345*b*. In addition, as the second ratchet member 1347 is rotated, the second ratchet 1347*a* of the second ratchet member 1347 starts to be spaced apart from the recess 1352*b* of the second reciprocating member 1352.

In this state, when the staple pulley 1361 is further rotated in the clockwise direction (in the direction of the arrow A1 of FIG. 164), as shown in FIG. 170C, the first reciprocating member 1351 is further moved in the direction of an arrow c1 (i.e., is moved forward), and the second reciprocating member 1352 is further moved in the direction of an arrow c2 (i.e., is moved backward). Then, the recess 1352*b* of the second reciprocating member 1352 further pushes the second ratchet 1347*a* of the second ratchet member 1347 toward the first reciprocating member 1351, so that the entire second ratchet member 1347 is further rotationally moved in the direction of an arrow c3. In addition, as the second ratchet member 1347 is rotated, the second ratchet 1347*a* of the second ratchet member 1347 is further spaced apart from the recess 1352*b* of the second reciprocating member 1352.

In this state, when the staple pulley 1361 is further rotated in the clockwise direction (in the direction of the arrow A1 of FIG. 164), as shown in FIG. 170D, the first reciprocating member 1351 is further moved in the direction of an arrow d1 (i.e., is moved forward), and the second reciprocating member 1352 is further moved in the direction of an arrow d2 (i.e., is moved backward). Then, the recess 1352*b* of the second reciprocating member 1352 further pushes the second ratchet 1347*a* of the second ratchet member 1347 toward the first reciprocating member 1351, and meets the next second ratchet 1347*a* on the second ratchet member 1347 when an inclined first surface (see 551*b* of FIG. 36) of the second reciprocating member 1352 is moved beyond an end of an inclined first surface (see 543*a*1 of FIG. 36) of the second ratchet member 1347. In this case, since the second elastic member 1348 applies an elastic force in a direction in which the second ratchet member 1347 comes into close contact with the second reciprocating member 1352, front surfaces of the second reciprocating member 1352 and the second ratchet member 1347 are again brought into close contact with each other.

In this state, when the staple pulley 1361 is further rotated in the clockwise direction (in the direction of the arrow A1 of FIG. 164), as shown in FIG. 170E, the first reciprocating member 1351 is further moved in the direction of an arrow e1 (i.e., is moved forward), and the second reciprocating member 1352 is further moved in the direction of an arrow e2 (i.e., is moved backward). Then, the first ratchet member 1343 is linearly moved in the direction of an arrow e4 by the first reciprocating member 1351 while repeating the above-described operations.

Next, operations of FIGS. 171A to 171E will be described.

FIG. 171A illustrates a state in which the first ratchet 1343*a* of the first ratchet member 1343 and the first reciprocating member 1351 are in close contact with each other, and the second ratchet 1347*a* of the second ratchet member 1347 and the second reciprocating member 1352 are in close contact with each other.

In this state, when the staple pulley 1361 is rotated in the counterclockwise direction (in the opposite direction of the arrow A1 of FIG. 164, the first reciprocating member 1351 is moved in the direction of an arrow b1 (i.e., is moved backward), and the second reciprocating member 1352 is moved in the direction of an arrow b2 (i.e., is moved forward) as shown in FIG. 171B. Then, the recess 1351*b* of the first reciprocating member 1351 pushes the first ratchet 1343*a* of the first ratchet member 1343 toward the second reciprocating member 1352, so that the first ratchet member 1343 is entirely rotated in the direction of an arrow b3 around the rotation shaft 1345*a*. In addition, as the first ratchet member 1343 is rotated, the first ratchet 1343*a* of the first ratchet member 1343 starts to be spaced apart from the recess 1351*b* of the first reciprocating member 1351.

In this state, when the staple pulley 1361 is further rotated in the counterclockwise direction (in the opposite direction of the arrow A1 of FIG. 164), the first reciprocating member 1351 is further moved in the direction of an arrow c1 (i.e., is moved backward), and the second reciprocating member 1352 is further moved in the direction of an arrow c2 (i.e., is moved forward) as shown in FIG. 171C. Then, the recess 1351*b* of the first reciprocating member 1351 further pushes the first ratchet 1343*a* of the first ratchet member 1343 toward the second reciprocating member 1352, so that the entire first ratchet member 1343 is further rotationally moved in the direction of an arrow c3. In addition, as the first ratchet member 1343 is rotated, the first ratchet 1343*a* of the first ratchet member 1343 is further spaced apart from the recess 1351*b* of the first reciprocating member 1351.

In this state, when the staple pulley 1361 is further rotated in the counterclockwise direction (in the opposite direction of the arrow A1 of FIG. 164), the first reciprocating member 1351 is further moved in the direction of an arrow d1 (i.e., is moved backward), and the second reciprocating member 1352 is further moved in the direction of an arrow d2 (i.e., is moved forward) as shown in FIG. 171D. Then, the recess 1351*b* of the first reciprocating member 1351 further pushes the first ratchet 1343*a* of the first ratchet member 1343 toward the second reciprocating member 1352, and meets the next first ratchet 1343*a* on the first ratchet member 1343 when the inclined first surface (see 551*b* of FIG. 36) of the first reciprocating member 1351 is moved beyond an end of the inclined first surface (see 543*a*1 of FIG. 36) of the first ratchet member 1343. In this case, since the first elastic member 1344 applies an elastic force in a direction in which the first ratchet member 1343 comes into close contact with the first reciprocating member 1351, the first reciprocating member 1351 and the first ratchet member 1343 are brought into close contact with each other again.

In this state, when the staple pulley 1361 is further rotated in the counterclockwise direction (in the opposite direction of the arrow A1 of FIG. 164), the first reciprocating member 1351 is further moved in the direction of an arrow e1 (i.e., is moved backward), and the second reciprocating member 1352 is further moved in the direction of an arrow e2 (i.e., is moved forward) as shown in FIG. 171E. Then, the second ratchet member 1347 is linearly moved in the direction of an arrow e4 by the second reciprocating member 1352 while repeating the above-described operations.

In conclusion, when the staple pulley 1361 is rotated in one direction, the first reciprocating member 1351 is moved forward and the second reciprocating member 1352 is moved backward, and in this case, the backward-moving second reciprocating member 1352 pushes the operation member 1340 toward the first reciprocating member 1351 to bring the operation member 1340 into close contact with the first reciprocating member 1351, and the forward-moving first reciprocating member 1351 moves the operation member 1340, which is in close contact therewith, forward.

Meanwhile, when the staple pulley 1361 is rotated in the other direction, the second reciprocating member 1352 is moved forward and the first reciprocating member 1351 is moved backward, and in this case, the backward-moving first reciprocating member 1351 pushes the operation member 1340 toward the second reciprocating member 1352 to bring the operation member 1340 into close contact with the second reciprocating member 1352, and the forward-moving second reciprocating member 1352 moves the operation member 1340, which is in close contact therewith, forward.

As a result, when the staple pulley 1361 is rotated in one direction, the first reciprocating member 1351 moves the operation member 1340 forward, and when the staple pulley 1361 is rotated in the opposite direction, the second reciprocating member 1352 moves the operation member 1340 forward, and thus a forward-moving speed of the operation member 1340 is approximately doubled as compared to the first embodiment, thereby reducing a stapling and cutting time.

Ninth Embodiment—Anvil Clamp Structure

Hereinafter, an end tool 1500 of a surgical instrument according to a ninth embodiment of the present disclosure will be described. Here, the end tool 1500 of the surgical instrument according to the ninth embodiment of the present disclosure is different from the end tool (see 100 of FIG. 2 or the like) of the surgical instrument according to the first embodiment of the present disclosure described above in that a clamp 1545 is additionally formed on an operation member 1540 of a cartridge 1510. Hereinafter, the configuration that is different from that of the first embodiment will be described in detail.

Figure 172:
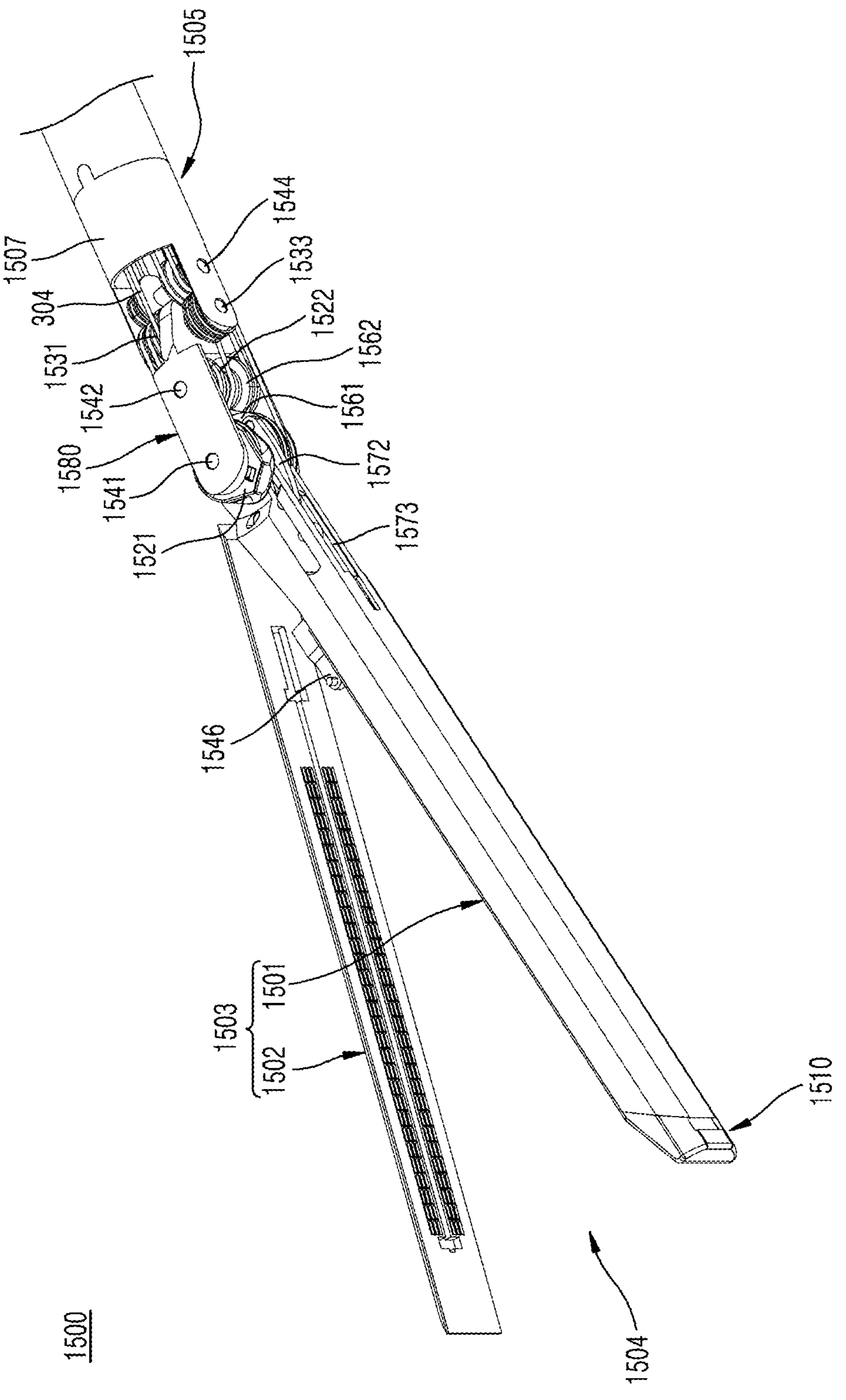
FIG. 172 is a perspective view illustrating an end tool of a surgical instrument according to an embodiment of the present disclosure.
Figure 173:
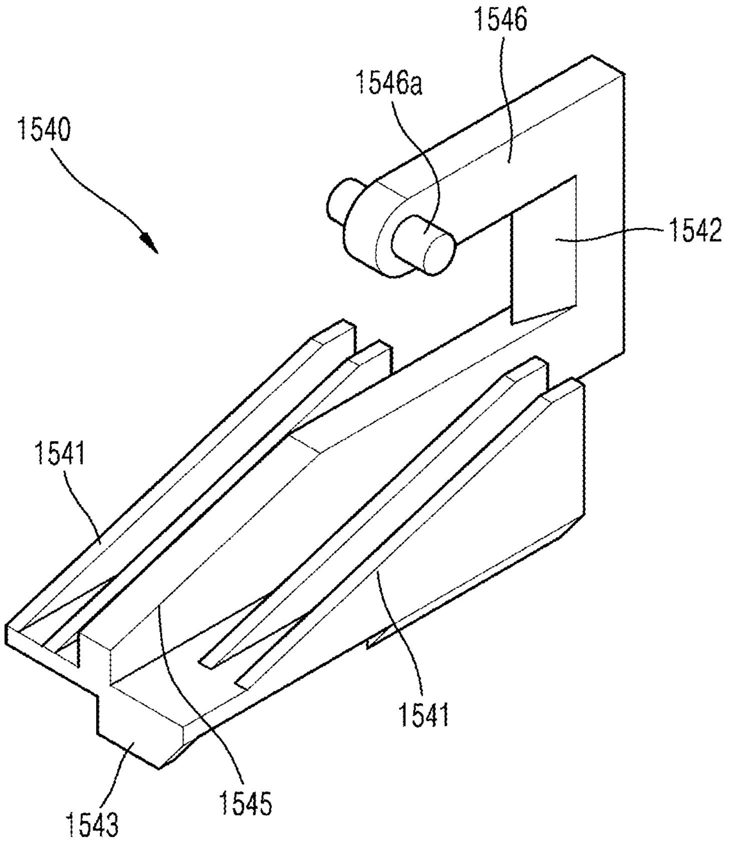
FIG. 173 is a side cross-sectional view illustrating a cartridge of the surgical instrument of FIG. 172.
Figure 174:
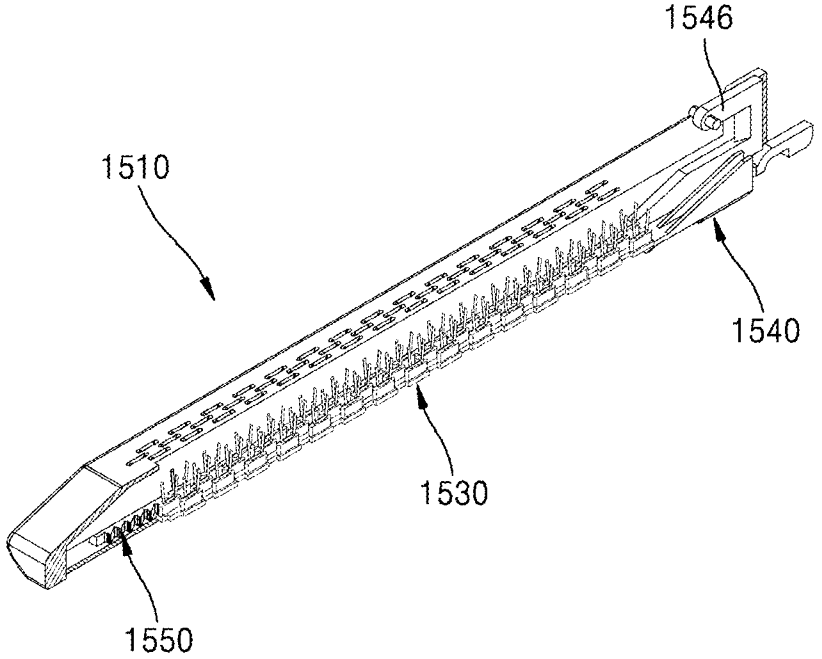
FIG. 174 is a perspective view illustrating an operation member of the cartridge of the surgical instrument of FIG. 172.
Figure 175:
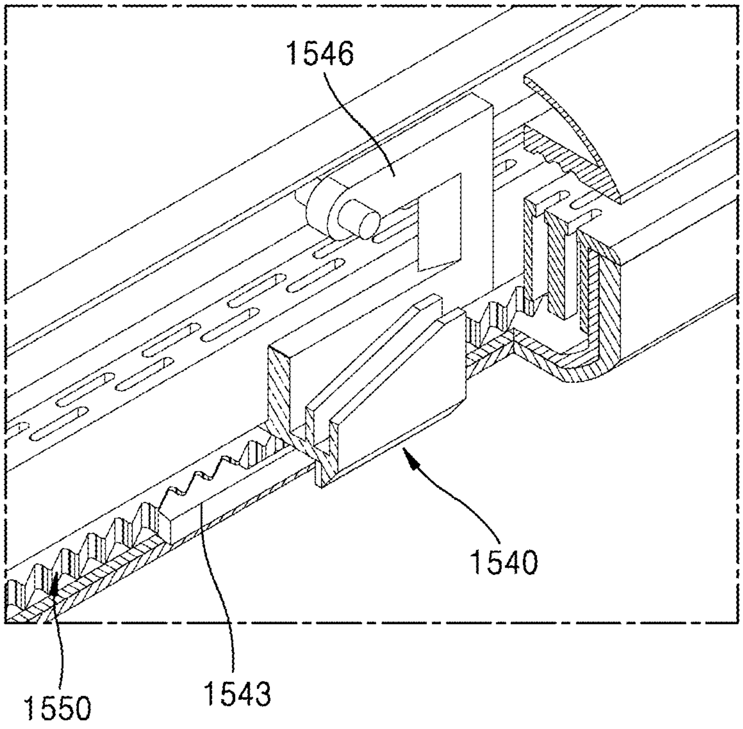
FIG. 175 is a magnified perspective view illustrating the cartridge of the surgical instrument of FIG. 172.
Figure 180:
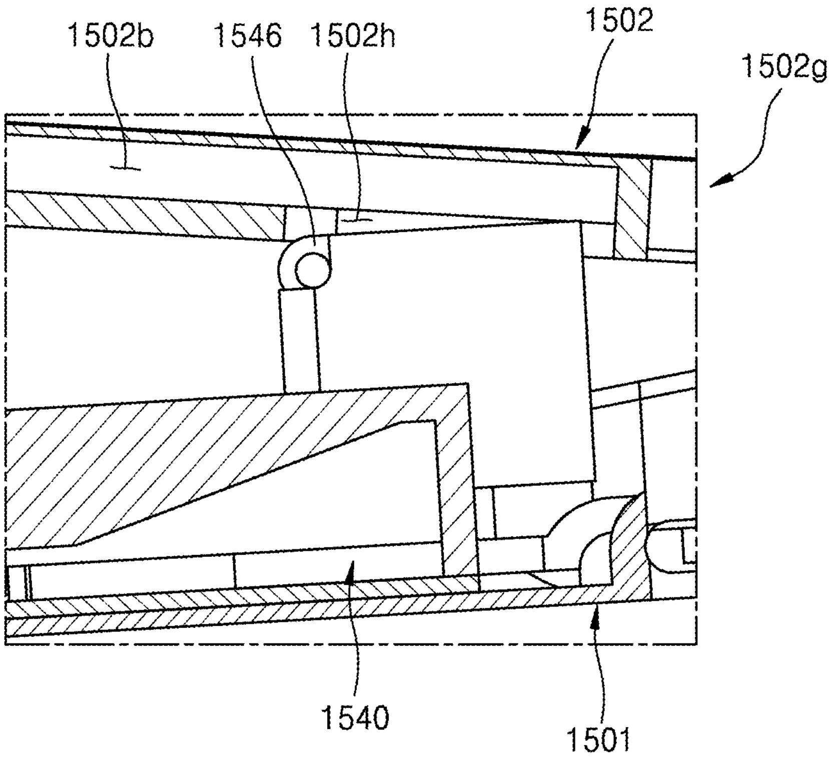
FIGS. 180 to 182 are views illustrating a process in which the operation member is coupled to a second jaw.
Figure 181:
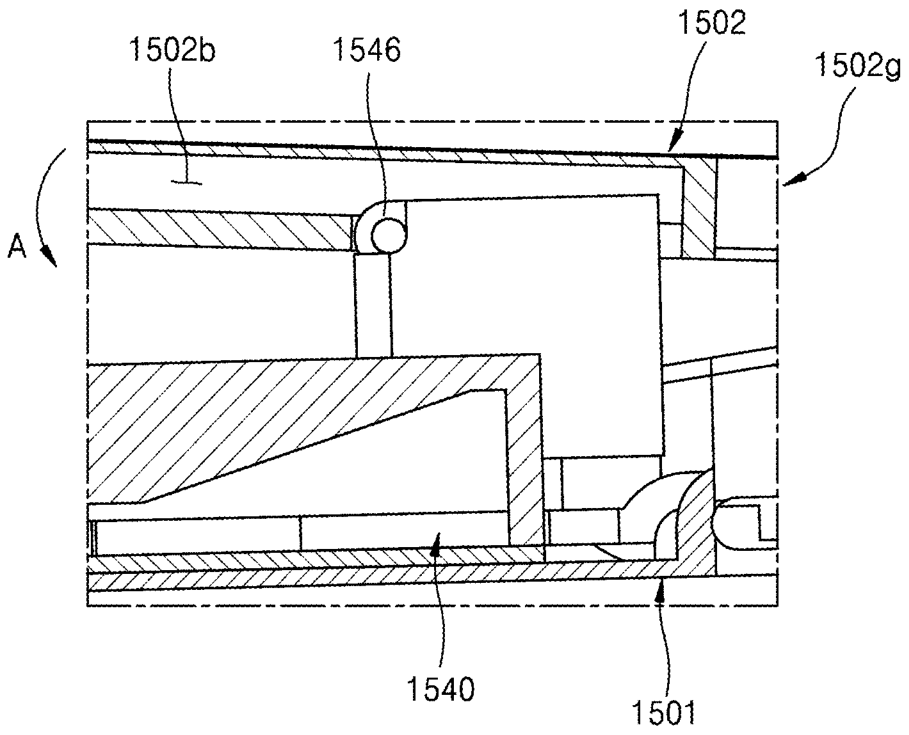
Figure 182:
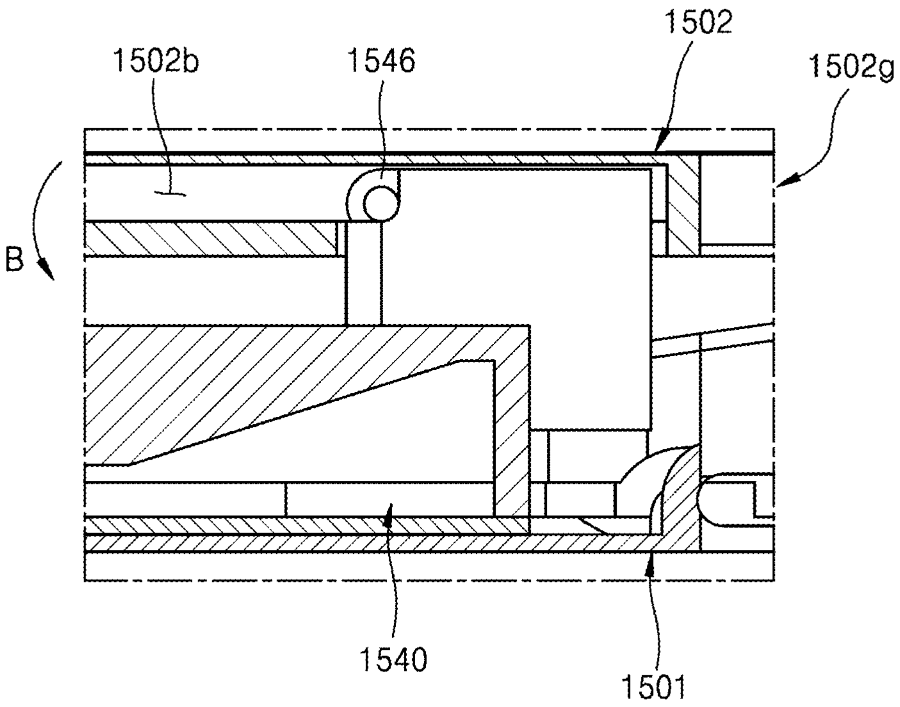
Figure 183:
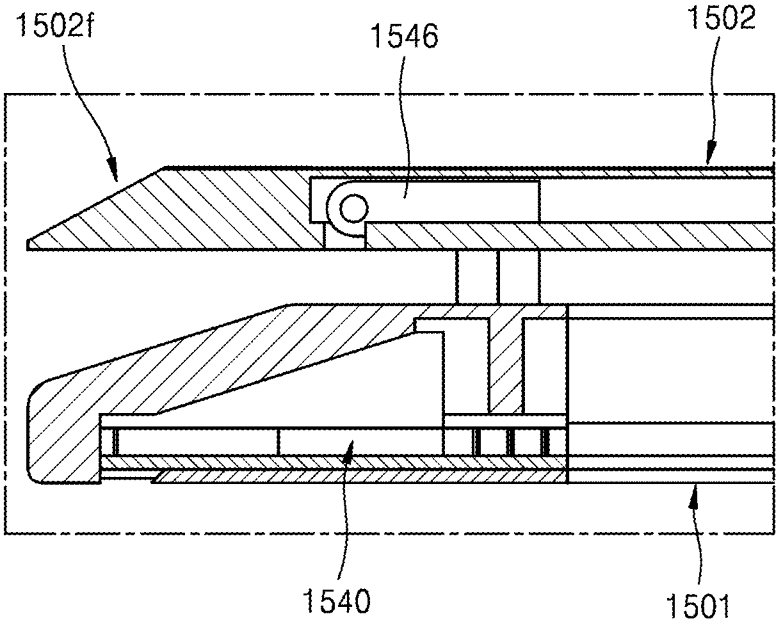
FIGS. 183 to 185 are views illustrating a process in which the operation member is separated from the second jaw.
Figure 184:
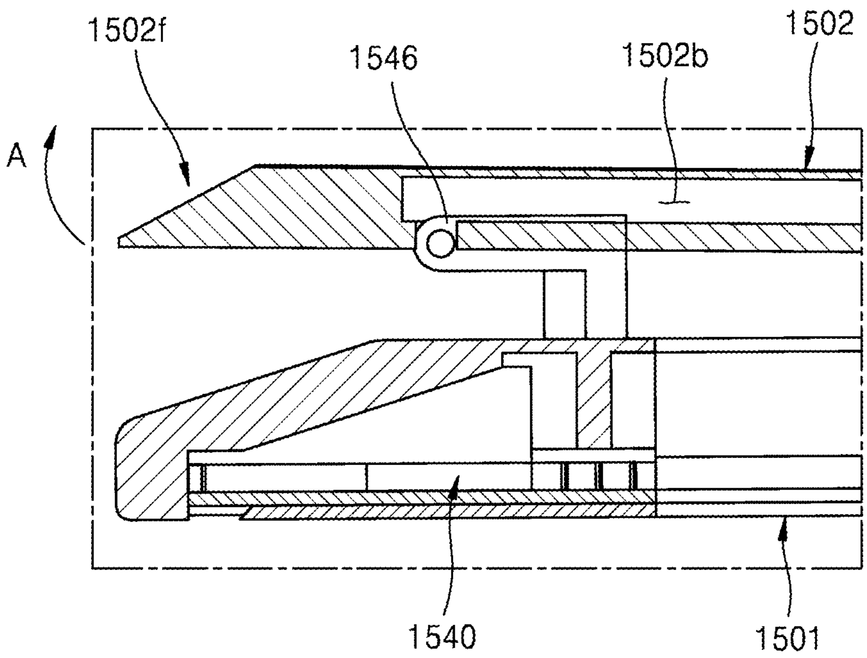
Figure 185:
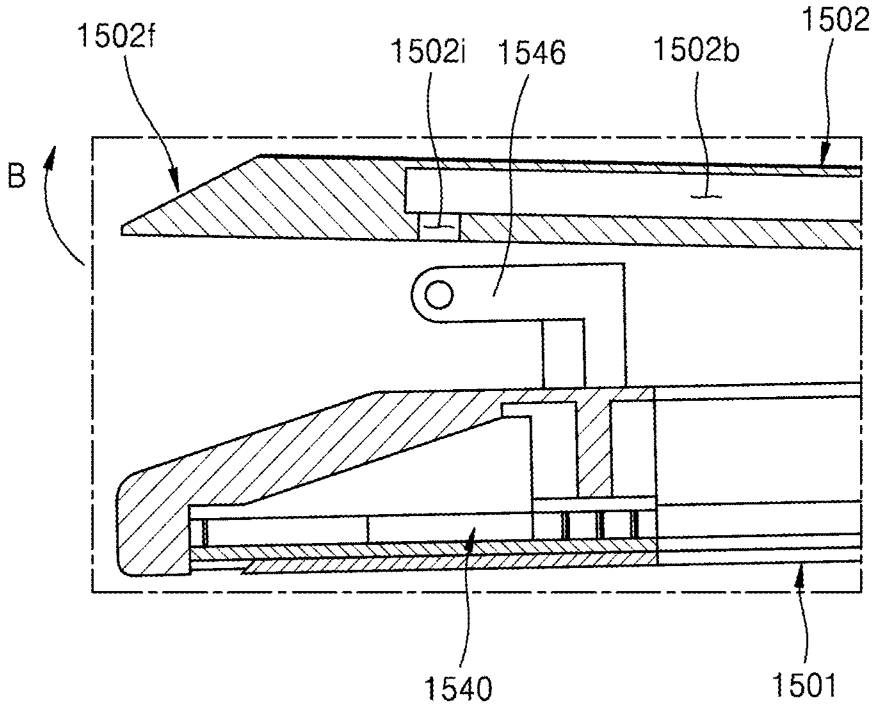

FIG. 172 is a perspective view illustrating the end tool of the surgical instrument according to the ninth embodiment of the present disclosure. FIG. 173 is a side cross-sectional view illustrating the cartridge of the surgical instrument of FIG. 172. FIG. 174 is a perspective view illustrating the operation member of the cartridge of the surgical instrument of FIG. 172. FIG. 175 is a magnified perspective view illustrating the cartridge of the surgical instrument of FIG. 172. FIGS. 176 to 179 are views illustrating a process in which the operation member is moved. FIGS. 180 to 182 are views illustrating a process in which the operation member is coupled to a second jaw. FIGS. 183 to 185 are views illustrating a process in which the operation member is separated from the second jaw.

Referring to FIGS. 172 to 185, the end tool 1500 of the ninth embodiment of the present disclosure includes a pair of jaws 1503 for performing a grip motion, that is, a first jaw 1501 and a second jaw 1502. Here, each of the first jaw 1501 and the second jaw 1502, or a component encompassing the first jaw 1501 and the second jaw 1502, may be referred to as the jaw 1503. This will be described in more detail later.

Meanwhile, the end tool 1500 includes a plurality of pulleys including a first jaw pulley (see 111 in FIG. 8) and a first jaw auxiliary pulley (see 121 of FIG. 8) that are related to the rotational motion of the first jaw 1501. The pulleys related to the rotational motion of the first jaw 1501 described in the present embodiment are substantially the same as the pulley 111, the pulley 112, the pulley 113, the pulley 114, the pulley 115, and the pulley 116 described with reference to FIG. 8 or the like of the first embodiment, and thus, detailed descriptions thereof will be omitted herein.

Meanwhile, the end tool 1500 includes a plurality of pulleys including a pulley 1521 and a pulley 1522 that are related to a rotational motion of the second jaw 1502. The pulleys related to the rotational motion of the second jaw 1502 described in the present embodiment are substantially the same as the pulley 151, the pulley 152, the pulley 153, the pulley 154, the pulley 155, and the pulley 156 described with reference to FIG. 8 or the like of the first embodiment, and thus, detailed descriptions thereof will be omitted herein.

Further, the end tool 1500 of the ninth embodiment of the present disclosure may include a rotation shaft 1541, a rotation shaft 1542, a rotation shaft 1543, and a rotation shaft 1544. Here, the rotation shaft 1541 and the rotation shaft 1542 may be inserted through an end tool hub 1580, and the rotation shaft 1543 and the rotation shaft 1544 may be inserted through a pitch hub 1507. The rotation shaft 1541, the rotation shaft 1542, the rotation shaft 1543, and the rotation shaft 1544 may be arranged sequentially from a distal end 1504 of the end tool 1500 toward a proximal end 1505.

In addition, the end tool 1500 of the ninth embodiment of the present disclosure may include the end tool hub 1580 and the pitch hub 1507.

The rotation shaft 1541 and the rotation shaft 1542 may be inserted through the end tool hub 1580, and a pulley 1511 and the pulley 1521 axially coupled to the rotation shaft 1541 and at least some of the first jaw 1501 and the second jaw 1502 coupled to the pulley 1511 and the pulley 1521 may be accommodated inside the end tool hub 1580.

The rotation shaft 1543 and the rotation shaft 1544 may be inserted through the pitch hub 1507, and the pitch hub 1507 may be axially coupled to the end tool hub 1580 by the rotation shaft 1543. Accordingly, the end tool hub 1580 may be formed to be pitch-rotatable around the rotation shaft 1543 with respect to the pitch hub 1507.

Meanwhile, the end tool 1500 of the ninth embodiment of the present disclosure may further include components such as a staple drive assembly (see 150 of FIG. 13) including a staple pulley assembly (see 160 of FIG. 13) and a staple link assembly (see 170 of FIG. 13) to perform stapling and cutting motions.

The staple pulley assembly (see 160 of FIG. 13) may be formed between the pulley 1511 and the pulley 1521 to be adjacent to the pulley 1511 and the pulley 1521. In the present embodiment, it is assumed that the staple pulley assembly (see 160 of FIG. 13) includes one staple pulley 1561.

The staple link assembly (see 170 of FIG. 13) may include one or more link members 1571. The staple link assembly (see 170 of FIG. 13) may serve to connect a staple pulley assembly 1560 and a reciprocating assembly 1550 of the cartridge 1510 In the present embodiment, it is assumed that the staple link assembly (see 170 of FIG. 13) includes one link member 1571, and the link member 1571 includes two links.

As described above, in the ninth embodiment of the present disclosure, by disposing the staple pulley assembly (see 160 of FIG. 13) and the staple link assembly (see 170 of FIG. 13) between the pulley 1511, which is a first jaw pulley, and the pulley 1521, which is a second jaw pulley, the end tool 1500 is allowed to perform pitch and yaw motions as well as stapling and cutting motions using the cartridge 1510. In the present embodiment, components for performing the stapling and cutting motions are substantially the same as those described in the first embodiment, and thus detailed descriptions thereof will be omitted herein.

Hereinafter, the second jaw 1502 and the cartridge 1510 of the ninth embodiment of the present disclosure will be described in more detail, and in particular, the clamp 1546 formed in the operation member 1540 of the cartridge 1510 will be mainly described.

The second jaw 1502 includes an anvil **1502*a*, a guide groove 1502*b*, a first coupling groove 1502*h*, and a second coupling groove 1502*h***.

The second jaw 1502 is formed entirely in the shape of an elongated bar, the anvil **1502*a* is formed in a distal end 1502*f* side, and a pulley 1512 is coupled to a proximal end 1502*g*, so that the second jaw 1502 is formed to be rotatable around the rotation shaft 1541**.

In detail, the anvil **1502*a* is formed in the form of a flat plane, on one surface of which shapes corresponding to the shapes of staples 1530 to be described later may be formed. The above-described anvil 1502*a* may serve as a support for supporting the staple 1530 on the opposite side of the operation member 1540 when the operation member 1540 pushes and raises the staple 1530 during a stapling motion, so that the staple 1530** is bent.

The guide groove 1502*b* for guiding the movement of the operation member 1540 of the cartridge 1510 may be formed inside the second jaw 1502. The guide groove 1502*b* may be formed in the shape of a groove formed along a moving path of the operation member 1540. In addition, the clamp 1546 is moved along the guide groove 1502*b* in a state in which the clamp 1546 of the operation member 1540 formed in a protruding shape is fitted into the groove-shaped guide groove 1502*b*, so that the operation member 1540 is moved with respect to the second jaw 1502. That is, the operation member 1540 may be moved along the guide groove 1502*b* of the second jaw 1502.

The first coupling groove 1502*h* may be formed in the proximal end 1502*g* of the second jaw 1502, and the second coupling groove 1502*i* may be formed in the distal end 1502*f*. Here, the first coupling groove 1502*h* and the second coupling groove 1502*i* may be formed at both end portions of the guide groove 1502*b*. Each of the first coupling groove 1502*h* and the second coupling groove 1502*i* is formed to be slightly larger than the clamp 1546 of the operation member 1540 so that the clamp 1546 may be inserted into or withdrawn from the second jaw 1502. That is, the clamp 1546 may be inserted into the second jaw 1502 through the first coupling groove 1502*h*, moved along the guide groove 1502*b*, and then withdrawn to the outside of the second jaw 1502 through the second coupling groove 1502*i*. This will be described in more detail below.

The cartridge 1510 may include a cover (see 510 of FIG. 22), a housing (see 520 of FIG. 22), the staple 1530, the operation member 1540, and the reciprocating assembly 1550. Here, the other components of the cartridge 1510 except for the operation member 1540 are substantially the same as those of the cartridge (see 500 of FIG. 22) described in the first embodiment, and thus detailed descriptions thereof will be omitted.

The operation member 1540 may include a wedge 1541, a blade 1542, a ratchet member 1543, an elastic member 1544, and a body 1545. Furthermore, the operation member 1540 of the ninth embodiment of the present disclosure further includes the clamp 1546.

The clamp 1546 may be formed on one side of the blade 1542 and may be formed in a shape that is approximately parallel to the body 1545 or the wedge 1541. In addition, a protrusion 1546*a* may be formed at one end portion of the clamp 1546, and the protrusion 1546*a* may be moved along the guide groove 1502*b*.

Here, the operation member 1540 according to the ninth embodiment of the present disclosure is formed as a whole in a "C" shape by further including the clamp 1546 parallel to the wedge 1541, and thus may better withstand a strong pressure applied to the wedge 1541 during a stapling motion.

FIGS. 176 to 179 are views illustrating a process in which the operation member is moved.

Figure 176:
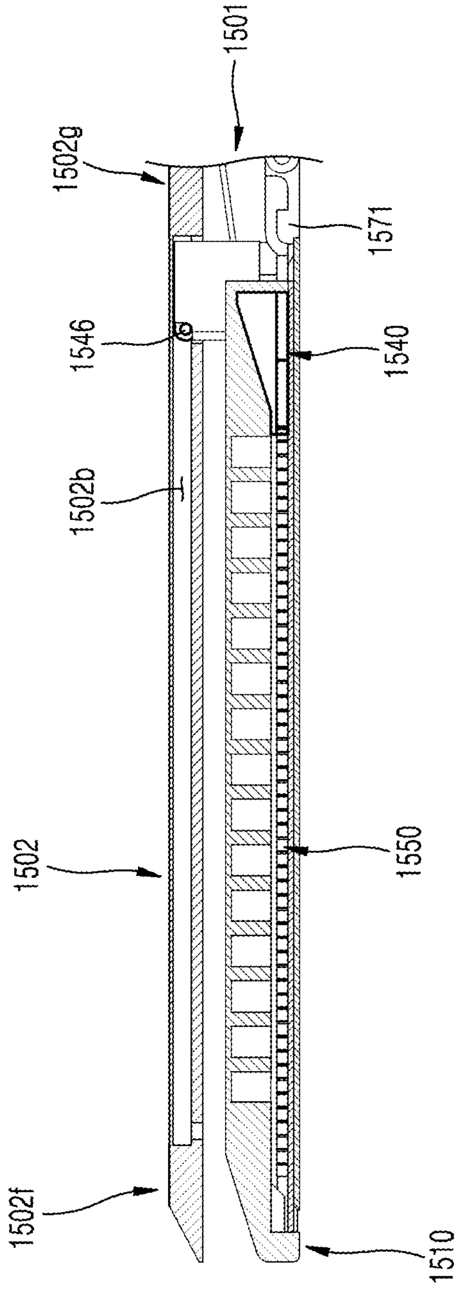
FIGS. 176 to 179 are views illustrating a process in which the operation member is moved.

As described above, in a state in which the first and second jaws 1501 and 1502 are closed, as shown in FIG. 176, the clamp 1546 may pass through the first coupling groove 1502*h* and be located in the guide groove 1502*b*.

Figure 177:
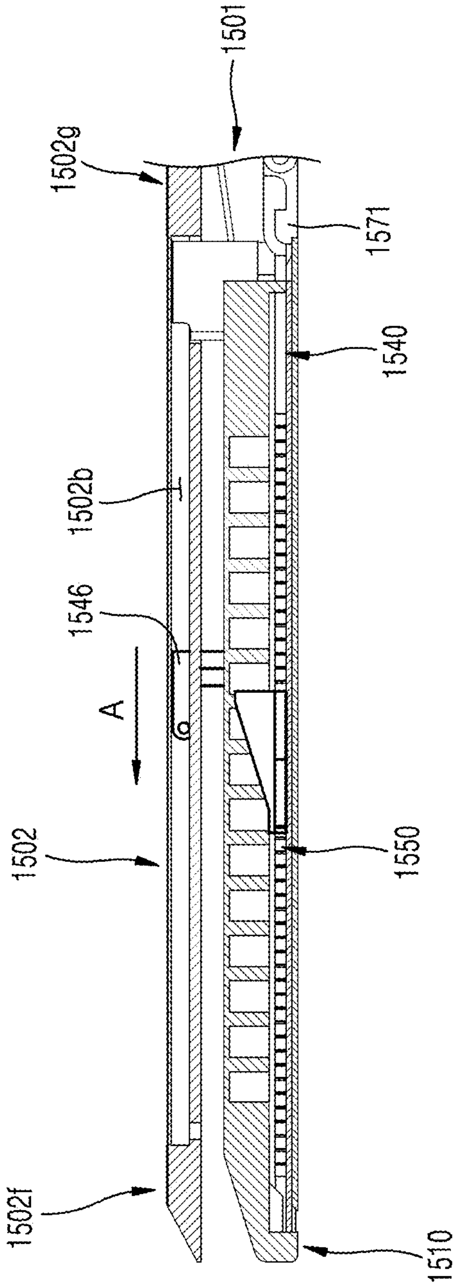

In this state, as shown in FIG. 177, when the operation member 1546 is moved in the direction of an arrow A, the clamp 1546 may also be moved along the guide groove 1502*b*.

Figure 178:
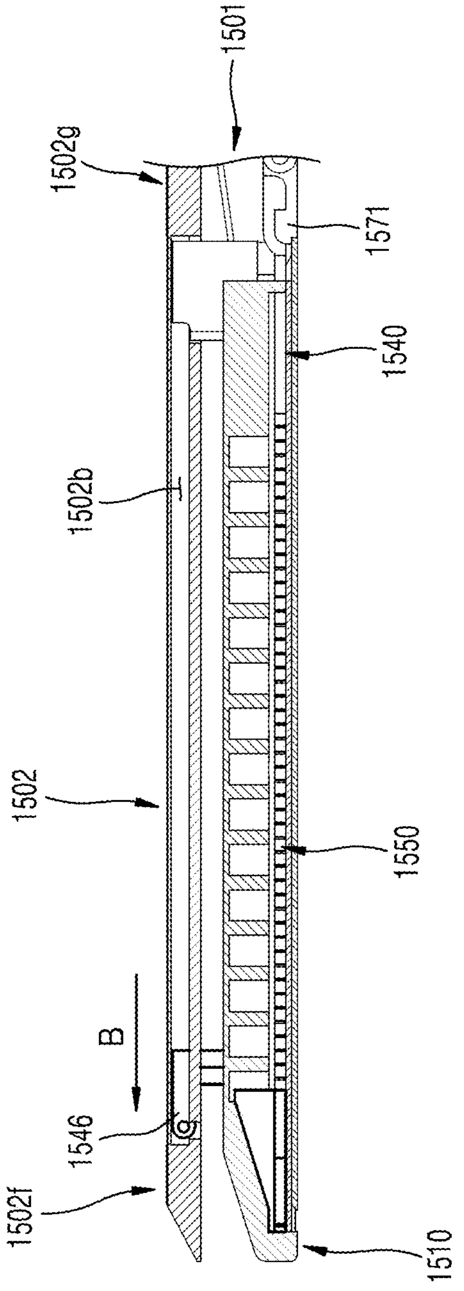
Figure 179:
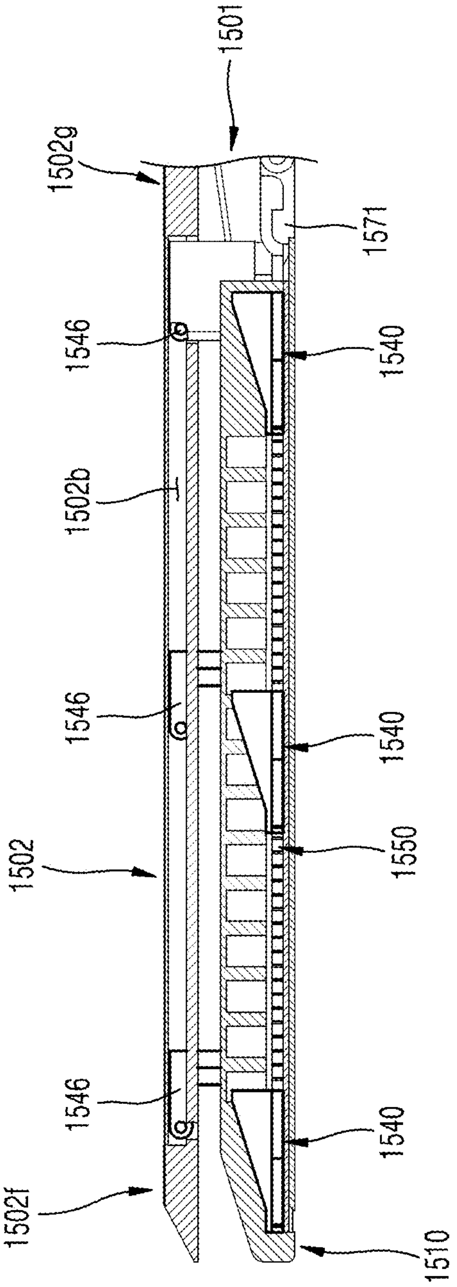

In this state, as shown in FIG. 178, when the operation member 1546 continues to move in the direction of an arrow B and reaches the distal end 1502*f* of the second jaw 1502, the clamp 1546 may pass through the second coupling groove 1502*i* and be withdrawn to the outside of the guide groove 1502*b*.

FIGS. 180 to 182 are views illustrating a process in which the operation member is coupled to the second jaw.

In the state as shown in FIG. 180, the second jaw 1502 is rotated in the direction of an arrow A on FIG. 181 and the direction of an arrow B of FIG. 182, so that the first and second jaws 1501 and 1502 are closed. Then, the clamp 1546 passes through the first coupling groove 1502*h* and is located in the guide groove 1502*b*.

FIGS. 183 to 185 are views illustrating a process in which the operation member is separated from the second jaw.

In the state as shown in FIG. 183, the second jaw 1502 is rotated in the direction of an arrow A of FIG. 184 and the direction of an arrow B of FIG. 185, so that the first and second jaws 1501 and 1502 are open. Then, the clamp 1546 passes through the second coupling groove 1502*i* and comes out of the guide groove 1502*b*.

As described above, the operation member 1540 according to the ninth embodiment of the present disclosure may better withstand a strong pressure applied to the wedge 1541 during a stapling motion by further including the clamp 1546 parallel to the wedge 1541.

First Modified Example of First Embodiment—Ratchet Modification: Hinge Type 1

Hereinafter, a surgical instrument according to a first modified example of the first embodiment of the present disclosure will be described. Here, the surgical instrument according to the first modified example of the first embodiment of the present disclosure is different from the surgical instrument (see 10 of FIG. 2 or the like) according to the first embodiment of the present disclosure in that the shape of an elastic member 564 of the cartridge is different.

Figure 76:
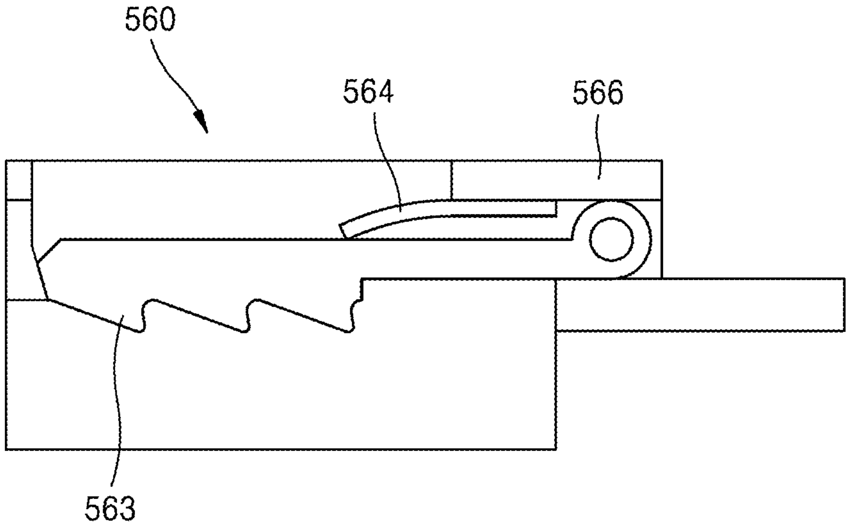
FIGS. 76 and 77 are views illustrating a cartridge of a surgical instrument according to a first modified example of the first embodiment of the present disclosure.
Figure 77:
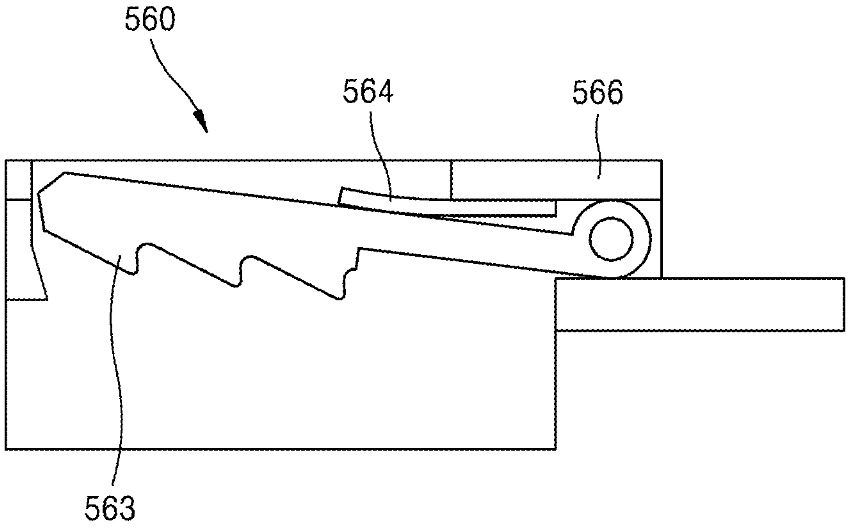

FIGS. 76 and 77 are views illustrating the cartridge of the surgical instrument according to the first modified example of the first embodiment of the present disclosure.

Referring to FIGS. 76 and 77, a support 566 may be formed to protrude from one surface of the body (see 545 of FIG. 27), for example, from a lower surface of the body (see 545 of FIG. 27). In addition, the elastic member 564 may be formed such that one end portion is coupled to the support 566 of the body (see 545 of FIG. 27) and the other end portion of the elastic member 564 is in contact with a ratchet member 563.

At this time, the elastic member 564 may apply an elastic force in a direction in which the ratchet member 563 comes into close contact with the reciprocating member (see 551 of FIG. 22). To this end, the elastic member 564 may be formed in the form of a leaf spring, and may be provided in various forms capable of providing a predetermined elastic force to the ratchet member 563, such as a coil spring, a dish spring, and the like.

Here, in the first modified example of the first embodiment of the present disclosure, the elastic member 564 is not integrally formed with an operation member 560 but is formed as a separate member and is disposed between the support 566 of the body (see 545 of FIG. 27) and the ratchet member 563.

In detail, in the first embodiment of the present disclosure, the elastic member (see 544 of FIG. 28) is integrally formed with the operation member (see 540 of FIG. 28), whereas in the present modified example, the elastic member 564 is formed as a separate member from the operation member

560 and is interposed between the support 566 and the ratchet member 563 of the body (see 545 of FIG. 27) of the operation member 560.

Second Modified Example of First Embodiment—Ratchet Modification: Hinge Type 2

Hereinafter, a surgical instrument according to a second modified example of the first embodiment of the present disclosure will be described. Here, the surgical instrument according to the second modified example of the first embodiment of the present disclosure is different from the surgical instrument (see 10 of FIG. 2 or the like) according to the first embodiment of the present disclosure in that the shape of an elastic member 574 of the cartridge is different.

Figure 78:
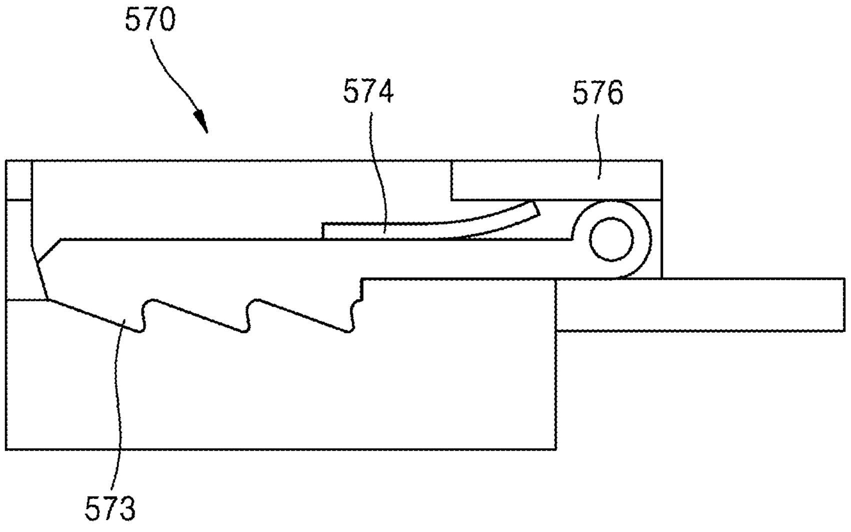
FIGS. 78 and 79 are views illustrating a cartridge of a surgical instrument according to a second modified example of the first embodiment of the present disclosure.
Figure 79:
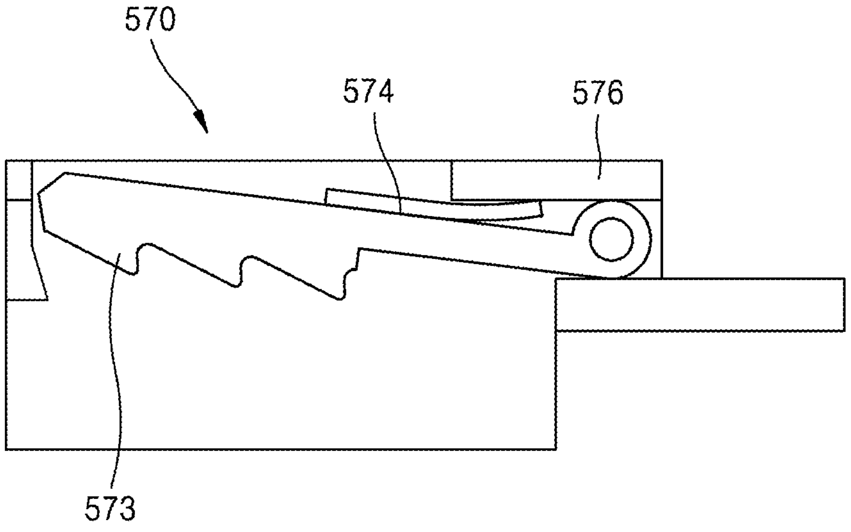

FIGS. 78 and 79 are views illustrating the cartridge of the surgical instrument according to the second modified example of the first embodiment of the present disclosure.

Referring to FIGS. 78 and 79, a support 576 may be formed to protrude from one surface of a body (see 545 of FIG. 27), for example, from a lower surface of the body (see 545 of FIG. 27). In addition, the elastic member 574 may be formed such that one end portion is in contact with the support 576 of the body (see 545 of FIG. 27) and the other end portion of the elastic member 574 is coupled to a ratchet member 573.

At this time, the elastic member 574 may apply an elastic force in a direction in which the ratchet member 573 comes into close contact with the reciprocating member (see 551 of FIG. 22). To this end, the elastic member 574 may be formed in the form of a leaf spring, and may be provided in various forms capable of providing a predetermined elastic force to the ratchet member 573, such as a coil spring, a dish spring, and the like.

Here, in the second modified example of the first embodiment of the present disclosure, the elastic member 574 is not integrally formed with an operation member 570 but is formed as a separate member, and is disposed between the support 576 of the body (see 545 of FIG. 27) and the ratchet member 573.

In detail, in the first embodiment of the present disclosure, the elastic member (see 544 of FIG. 28) is integrally formed with the operation member (see 540 of FIG. 28), whereas in the present modified example, the elastic member 574 is formed as a separate member from the operation member 570 and is interposed between the support 576 and the ratchet member 573 of the body (see 545 of FIG. 27) of the operation member 570.

Third Modified Example of First Embodiment—Ratchet Modification: Hinge Type 3

Hereinafter, a surgical instrument according to a third modified example of the first embodiment of the present disclosure will be described. Here, the surgical instrument according to the third modified example of the first embodiment of the present disclosure is different from the surgical instrument (see 10 of FIG. 2 or the like) according to the first embodiment of the present disclosure in that the shape of an elastic member 584 of the cartridge is different.

Figure 80:
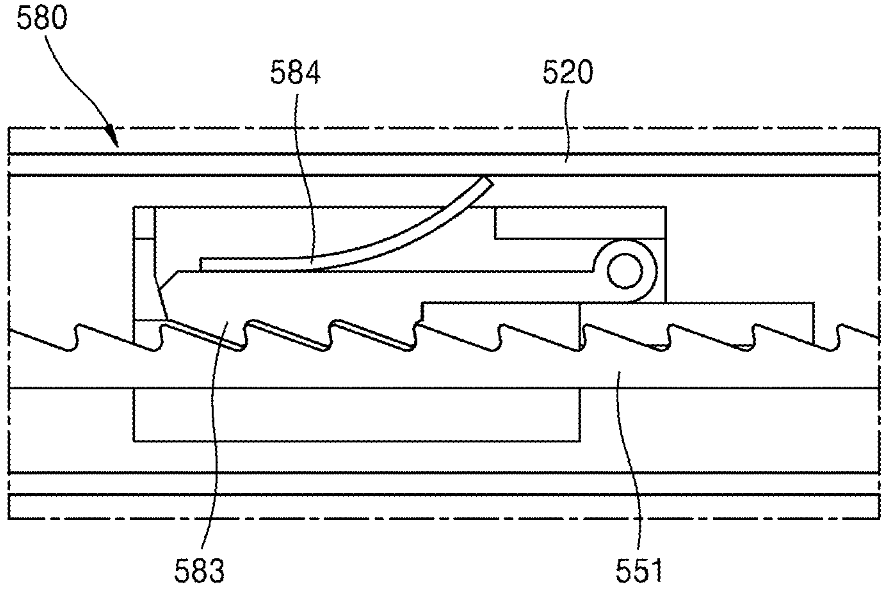
FIGS. 80 and 81 are views illustrating a cartridge of a surgical instrument according to a third modified example of the first embodiment of the present disclosure.
Figure 81:
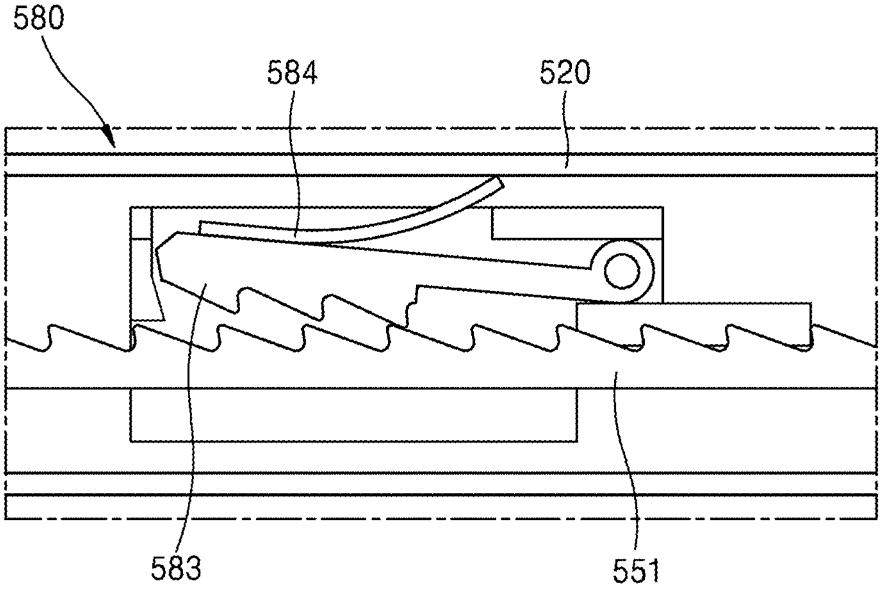

FIGS. 80 and 81 are views illustrating the cartridge of the surgical instrument according to the third modified example of the first embodiment of the present disclosure.

Referring to FIGS. 80 and 81, the elastic member 584 may be formed such that one end portion is in contact with an inner wall of the housing 520 and the other end portion of the elastic member 584 is coupled to a ratchet member 583.

Here, the elastic member 584 may apply an elastic force in a direction in which the ratchet member 583 comes into close contact with the reciprocating member 551. To this end, the elastic member 584 may be formed in the form of a leaf spring, and may be provided in various forms capable of providing a predetermined elastic force to the ratchet member 583, such as a coil spring, a dish spring, and the like.

Here, in the third modified example of the first embodiment of the present disclosure, the elastic member 584 is not integrally formed with an operation member 580 but is formed as a separate member, and is disposed between the housing 520 and the ratchet member 583.

In detail, in the first embodiment of the present disclosure, the elastic member (see 544 of FIG. 28) is integrally formed with the operation member (see 540 of FIG. 28), whereas in the present modified example, the elastic member 584 is formed as a separate member from the operation member 580 and is interposed between the housing 520 and the ratchet member 583.

Fourth Modified Example of First Embodiment—Ratchet Modification: Vertical Type

Hereinafter, a surgical instrument according to a fourth modified example of the first embodiment of the present disclosure will be described. Here, the surgical instrument according to the fourth modified example of the first embodiment of the present disclosure is different from the surgical instrument (see 10 of FIG. 2 or the like) according to the first embodiment of the present disclosure in that the shape of an elastic member 594 of the cartridge is different.

Figure 82:
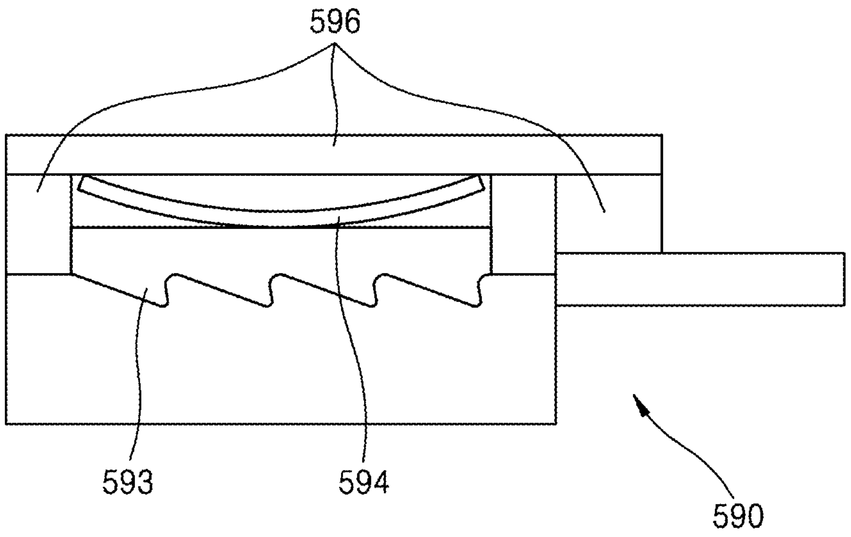
FIGS. 82 and 83 are views illustrating a cartridge of a surgical instrument according to a fourth modified example of the first embodiment of the present disclosure.
Figure 83:
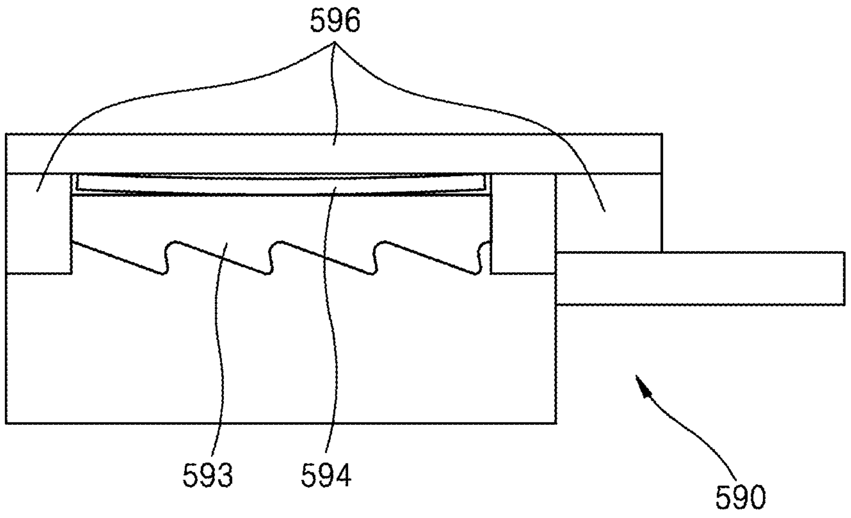

FIGS. 82 and 83 are views illustrating the cartridge of the surgical instrument according to the fourth modified example of the first embodiment of the present disclosure.

Referring to FIGS. 82 and 83, a support 596 may be formed to protrude from one surface of the body (see 545 of FIG. 27), for example, from a lower surface of the body (see 545 of FIG. 27). Here, the entire support 596 may be formed in a roughly "C" shape, in which the elastic member 594 may be accommodated. Accordingly, the elastic member 594 may be formed such that both end portions are in contact with the support 596 and a central portion is in contact with a ratchet member 593.

At this time, the elastic member 594 may apply an elastic force in a direction in which the ratchet member 593 comes into close contact with the reciprocating member (see 551 of FIG. 22). To this end, the elastic member 594 may be formed in the form of a leaf spring, and may be provided in various forms capable of providing a predetermined elastic force to the ratchet member 593, such as a coil spring, a dish spring, and the like.

Here, in the fourth modified example of the first embodiment of the present disclosure, the elastic member 594 is not integrally formed with an operation member 590 but is formed as a separate member, and is disposed between the support 596 of the body (see 545 of FIG. 27) and the ratchet member 593.

In detail, in the first embodiment of the present disclosure, the elastic member (see 544 of FIG. 28) is integrally formed with the operation member (see 540 of FIG. 28), whereas in the present modified example, the elastic member 594 is formed as a separate member from the operation member 590 and is interposed between the support 596 and the ratchet member 593 of the body (see 545 of FIG. 27) of the operation member 590.

Fifth Modified Example of First Embodiment—Moving-Backward Prevention Snap

Hereinafter, a surgical instrument according to a fifth modified example of the first embodiment of the present disclosure will be described. Here, the surgical instrument according to the fifth modified example of the first embodiment of the present disclosure is different from the surgical instrument (see 10 of FIG. 2 or the like) according to the first embodiment of the present disclosure in that a snap 646 for preventing a backward movement is further formed in a cartridge 600.

Figure 84:
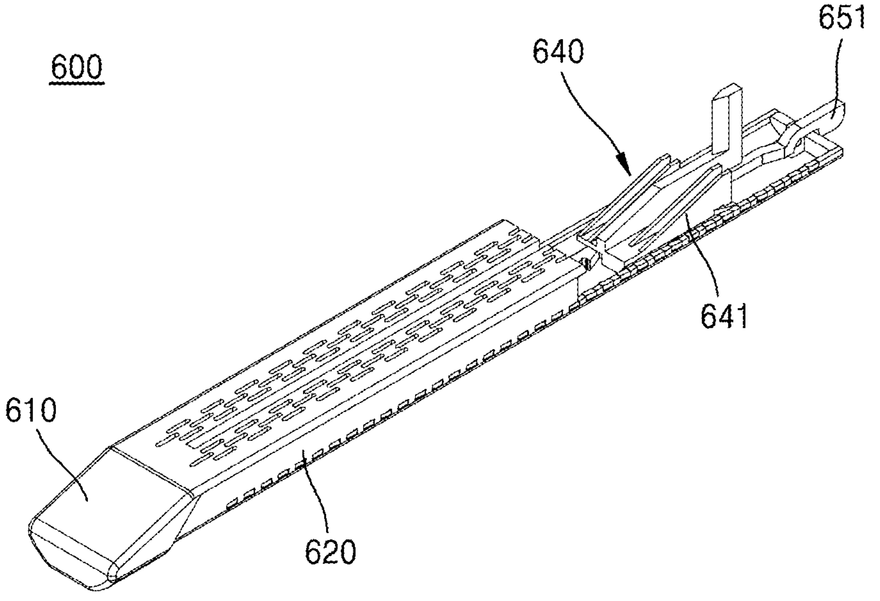
FIGS. 84 and 85 are views illustrating a cartridge of a surgical instrument according to a fifth modified example of the first embodiment of the present disclosure.
Figure 85:
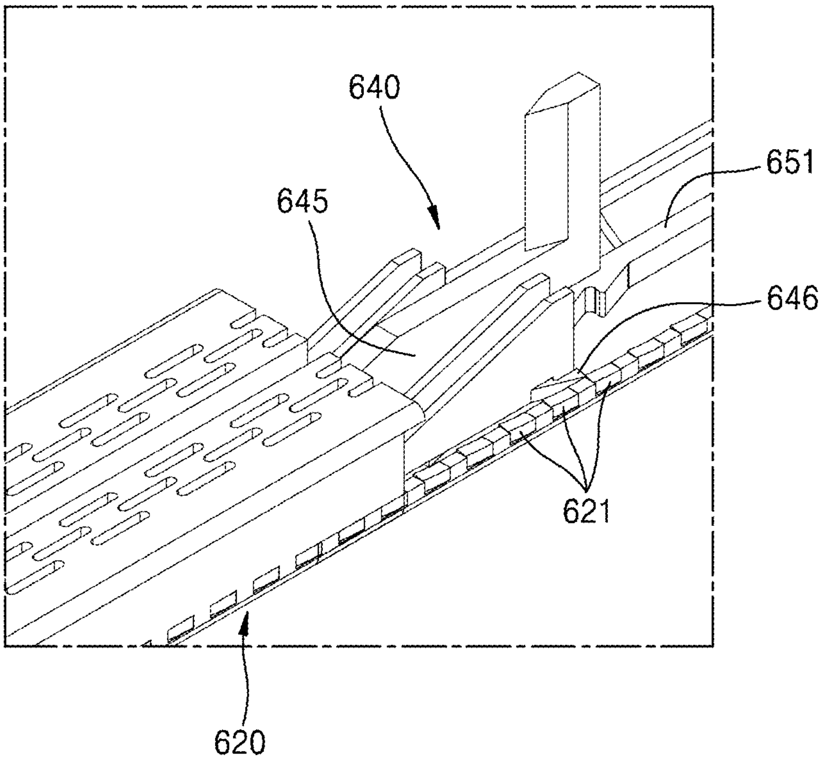
Figure 86:
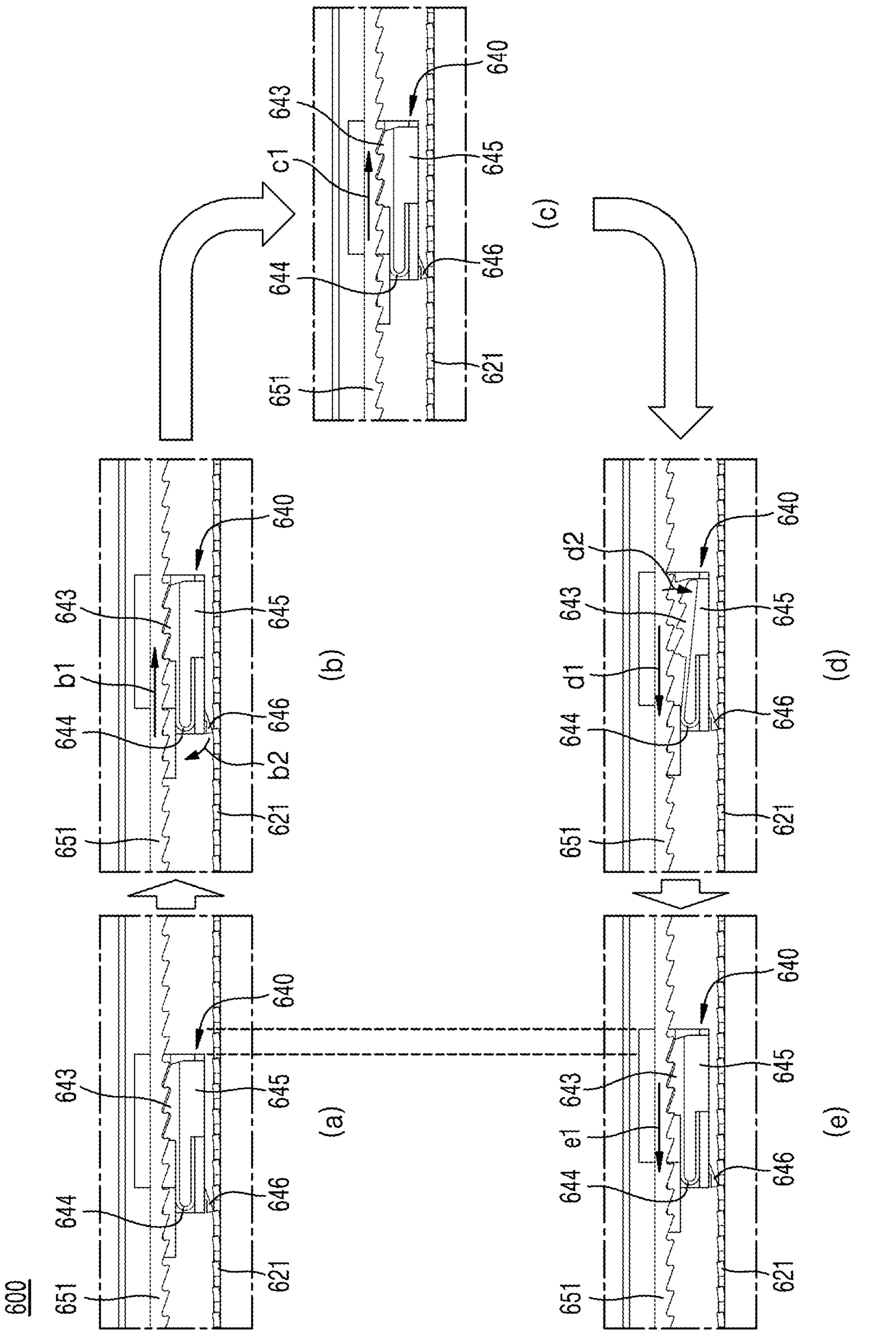
FIG. 86 is a view illustrating operating states of the cartridge of FIG. 84.

FIGS. 84 and 85 are views illustrating the cartridge of the surgical instrument according to the fifth modified example of the first embodiment of the present disclosure. FIG. 86 is a view illustrating operating states of the cartridge of FIG. 84.

Referring to FIGS. 84 to 86, the cartridge 600 is formed to be mountable to and dismountable from the first jaw (see 101 of FIG. 2), and includes a plurality of staples (see 530 of FIG. 25) and a blade (see 642 of FIG. 27) therein to perform suturing and cutting tissue. Here, the cartridge 600 may include a cover 610, a housing 620, the staples (see 530 of FIG. 25), a withdrawal member (see 535 of FIG. 25), an operation member 640, and a reciprocating assembly 650.

The housing 620 forms an outer shape of the cartridge 600, and may be formed entirely in the form of a hollow box with one surface (upper surface) removed to accommodate the reciprocating assembly 650, the operation member 640, and the staples (see 530 of FIG. 25) therein. Here, the housing 620 may be formed in an approximately "U" shape in cross section.

One or more protrusions 621 may be formed on an inner surface of the housing 620, more specifically, on the inner surface of the housing 620 facing the recess (see 551*b* of FIG. 22) of the reciprocating assembly 650. In other words, it may be said that one or more protrusions 621 are formed in a region of the inner surface of the housing 620, which is to be in contact with the operation member 640. The one or more protrusions 621 may be formed in a wedge shape. In other words, it may also be described that the one or more protrusions 621 include a slope formed to have a greater height at the distal end side of the cartridge 600 than the proximal end side. The protrusions 621 may be formed to be in contact with the snap 646 of the operation member 640 to prevent a backward movement of the operation member 640 (that is, the movement toward the proximal end). This will be described in more detail later.

The cover 610 is formed to cover an upper portion of the housing 620. Staple holes (see 511 of FIG. 23) through which the plurality of staples 630 may be ejected to the outside may be formed in the cover 610. Stapling is performed as the staples (see 530 of FIG. 25), which are accommodated in the housing 620 before a stapling operation, are pushed and raised upward by the operation member 640 during the stapling operation, and pass through the staple holes (see 511 of FIG. 23) of the cover 610 to be withdrawn to the outside of the cartridge 600.

The reciprocating assembly 650 may be disposed at an inner lower side of the housing 620. The reciprocating assembly 650 may include one or more reciprocating members 651. In this embodiment, the reciprocating member 651 may be a rack.

The operation member 640 may include a wedge 641, a blade 642, a ratchet member 643, the elastic member 644, the body 645, and the snap 646.

The snap 646 may be formed to protrude from any one side of the body 645 or the wedge 641. The snap 646 is formed in the shape of a wedge, and is formed to be in contact with the inner surface of the housing 620. Here, the snap 646 may be formed to engage with the protrusion 621 of the housing 620. When the snap 646 is engaged with the protrusion 621, the operation member 640 may be prevented from moving backward (i.e., moving toward the proximal end) due to the snap 646 and the protrusion 621.

Here, the snap 646 may be formed to be elastically deformable to a certain extent. That is, the snap 646 may serve as a kind of leaf spring. Accordingly, when the snap 646 is moved along an inclined surface of the protrusion 621, the snap 646 may be elastically deformed to a certain extent toward the body 645. In addition, when the snap 646 is brought into contact with the next protrusion 621 beyond the inclined surface of the protrusion 621, the snap 646 may be elastically restored toward the housing 620.

In summary, the cartridge 600 is accommodated in the cartridge accommodation part (see 101*a* of FIG. 2) of the first jaw (see 101 of FIG. 2), and in this case, the reciprocating member 651 of the cartridge 600 is coupled to the staple link assembly (see 170 of FIG. 13) of the end tool (see 100 of FIG. 2). Accordingly, a rotational motion of the staple pulley (see 161 of FIG. 13) of the end tool (see 100 of FIG. 2) is converted into a linear motion of the reciprocating member 651 through the staple link assembly (see 170 of FIG. 13).

In this case, when a coupling part 651*a* of the reciprocating member 651 is connected to the staple pulley 161 through the staple link assembly 170, and the staple pulley 161 is rotated alternately in the clockwise/counterclockwise directions, the reciprocating member 651 may be repeatedly moved forward and backward. In addition, when the reciprocating member 651 is moved forward, the operation member 640 is moved forward together with the reciprocating member 651, and when the reciprocating member 651 is moved backward, only the reciprocating member 651 may be moved backward and the operation member 640 may remain stationary in place. As the operation member 640 is moved forward while repeating this process, the staple 630 may be stapled by the wedge 641 while the blade 642 cuts the stapled tissue.

Here, when the reciprocating member 651 is moved backward, only the reciprocating member 651 may be moved backward and the operation member 640 may more securely remain stationary in place. That is, the operation member 640 may be more securely prevented from moving toward the proximal end (see 501 of FIG. 23) of the cartridge 600 by the snap 646 and the protrusion 621.

This will be described in more detail as follows.

First, in the state shown in FIG. 86A, when the staple pulley (see 161 of FIG. 13) is rotated in one direction as shown in FIG. 86B, the staple link assembly (see 170 of FIG. 13) connected to the staple pulley (see 161 of FIG. 13) and the reciprocating member 651 coupled to the staple link assembly (see 170 of FIG. 13) are moved in the direction of an arrow b1 (i.e., toward the distal end of the cartridge). In this state, since the reciprocating member 551 and the operation member 640 are in close contact with each other by the elastic member 644, when the reciprocating member 651 is moved in the direction of the arrow b1, the operation member 640 is also moved in the direction of the arrow b1 together with the reciprocating member 651. In addition, at this time, the snap 646 may be elastically deformed to a certain extent in the direction of an arrow b2 (i.e., toward the body 645) while moving along the inclined surface of the protrusion 621.

Next, as shown in FIG. 86C, when the staple pulley (see 161 of FIG. 13) is further rotated in the one direction, the staple link assembly (see 170 of FIG. 13) connected thereto, the reciprocating member 651, and the operation member 640 are further moved in the direction of an arrow c1. In addition, at this time, when the snap 646 is brought into contact with the next protrusion 621 beyond the inclined surface of the protrusion 621, the snap 646 may be elastically restored toward the housing 620.

Next, in the state shown in FIG. 86C, when the staple pulley (see 161 of FIG. 13) is rotated in the opposite direction as shown in FIG. 86D, the staple link assembly (see 170 of FIG. 13) connected to the staple pulley (see 161 of FIG. 13) and the reciprocating member 651 coupled to the staple link assembly (see 170 of FIG. 13) are moved in the direction of an arrow d1 (i.e., toward proximal end of the cartridge). In this state, due to the coupling structure of the ratchet member 643 and the reciprocating member 651, even when the reciprocating member 651 is moved in the direction of the arrow d1, the ratchet member 643 is repeatedly is spaced apart from the reciprocating member 651 to a certain extent as the elastic member 644 is repeatedly elastically deformed in the direction of an arrow d2, in a state in which the overall position (i.e., position in the X-axis direction) of the operation member 640 remains unchanged. That is, even when the reciprocating member 651 is moved in the direction of the arrow d1, the operation member 640 remains stationary when viewed in the X-axis direction.

At this time, since the snap 646 is engaged with the protrusion 621 of the housing 620, the movement of the operation member in the X-axis direction is more securely prevented.

Next, as shown in FIG. 86E, when the staple pulley (see 161 of FIG. 13) is further rotated in the opposite direction, only the staple link assembly (see 170 of FIG. 13) connected thereto, and the reciprocating member 651 are further moved in the direction of an arrow e1, and the operation member 640 remains stationary in place when viewed in the X-axis direction.

When the staple pulley (see 161 of FIG. 13) is alternately rotated in the clockwise/counterclockwise directions while repeating the above process, the reciprocating member 651 is repeatedly moved forward and backward, and the operation member 640 repeats moving forward and stopping, and as a result, the operation member 640 is moved toward the distal end (see 502 of FIG. 23). In addition, as the operation member 640 is moved toward the distal end (see 502 of FIG. 23), a stapling motion by the wedge 641 and a cutting motion by the blade 642 are simultaneously performed.

As such, the present disclosure has been described with reference to an embodiment shown in the drawings, but it will be understood that this is merely exemplary, and those of ordinary skill in the art will understand that various modifications and variations of the embodiments are possible therefrom. Accordingly, the true technical protection scope of the present disclosure should be defined by the technical spirit of the appended claims.

INDUSTRIAL USABILITY

The present disclosure relates to an end tool of a surgical instrument and a surgical instrument including the same, and more particularly, may be used to an end tool of a surgical instrument that may be mounted on a robotic arm or operable manually to be used in laparoscopic surgery or other various surgeries, wherein the end tool is rotatable in two or more directions and is moved in a way that intuitively matches a motion of a manipulation part, and a surgical instrument including the same.

The invention claimed is:

1. An end tool of a surgical instrument, the end tool comprising:
- a first jaw configured to accommodate a cartridge;
- a second jaw formed to face the first jaw;
- a first jaw pulley coupled to the first jaw and formed to be rotatable around a first shaft;
- a second jaw pulley coupled to the second jaw, formed to be rotatable around a shaft substantially the same as or parallel to the first shaft, and formed to be spaced apart from the first jaw pulley by a certain extent;
- a staple drive assembly including a staple pulley at least partially formed between the first jaw pulley and the second jaw pulley; and
- a staple wire at least partially in contact with the staple pulley and configured to transmit, to the staple pulley, a driving force necessary for rotating the staple pulley,
- wherein the staple drive assembly is configured to be connected to a reciprocating assembly of the cartridge and configured to convert a rotational motion of the staple pulley into a linear motion of the reciprocating assembly.

2. The end tool of claim 1, further comprising an end tool hub including a first jaw pulley coupling part and a second jaw pulley coupling part, which are formed to face each other, and a guide part configured to connect the first jaw pulley coupling part and the second jaw pulley coupling part,
- wherein the first jaw pulley is disposed adjacent to the first jaw pulley coupling part of the end tool hub,
- the second jaw pulley is disposed adjacent to the second jaw pulley coupling part of the end tool hub, and
- at least a portion of the staple drive assembly is formed between the first jaw pulley and the second jaw pulley.

3. The end tool of claim 2, wherein the first shaft is sequentially inserted through the first jaw pulley coupling part, the first jaw pulley, the staple pulley, the second jaw pulley, and the second jaw pulley coupling part.

4. The end tool of claim 2, wherein the first jaw pulley, the staple pulley, and the second jaw pulley are sequentially stacked in the end tool hub.

5. The end tool of claim 2, wherein the first jaw pulley, the staple pulley, and the second jaw pulley are formed to be rotatable independently of each other.

6. The end tool of claim 2, further comprising a staple auxiliary pulley disposed between the staple pulley and the guide part.

7. The end tool of claim 6, wherein
- the staple wire is located on a common internal tangent of the staple pulley and the staple auxiliary pulley, and
- a rotation angle of the staple pulley is increased by the staple auxiliary pulley.

8. The end tool of claim 2, wherein a region of the guide part adjacent to the first jaw pulley, the staple pulley, and the second jaw pulley is formed such that a cross section thereof is curved with a predetermined curvature.

9. The end tool of claim 8, wherein
- the staple wire is located on a common internal tangent of the staple pulley and the guide part, and
- a rotation angle of the staple pulley is increased by the guide part.

10. The end tool of claim 1, wherein the staple drive assembly includes a staple link assembly configured to connect the staple pulley and the reciprocating assembly.

11. The end tool of claim 10, wherein the staple link assembly includes a first link coupled to the staple pulley, and a second link coupled to each of the first link and the reciprocating assembly.

12. The end tool of claim 10, wherein when the staple pulley is alternately rotated in a clockwise direction and a counterclockwise direction, the staple link assembly connected to the staple pulley is alternately moved toward a distal end and a proximal end of the end tool.

13. The end tool of claim 10, wherein a bidirectional rotational motion of the staple pulley is converted into a reciprocating linear motion of the reciprocating assembly, which is connected to the staple link assembly, by the staple link assembly.

14. The end tool of claim 10, wherein a guide groove is formed in the first jaw in a length direction of the first jaw, and the staple link assembly is moved along the guide groove.

15. The end tool of claim 1, further comprising a jaw rotation shaft inserted through the first jaw and the second jaw and being a center of rotation of the first jaw and the second jaw, wherein the first shaft is a jaw pulley rotation shaft, which is inserted through the first jaw pulley and the second jaw pulley and being a center of rotation of the first jaw pulley and the second jaw pulley, and the jaw rotation shaft is moved relative to the jaw pulley rotation shaft when the first jaw pulley and the second jaw pulley are rotated around the jaw pulley rotation shaft.

16. The end tool of claim 15, wherein when the first jaw and the second jaw are closed, the jaw rotation shaft is moved toward a distal end of the end tool, and when the first jaw and the second jaw are opened, the jaw rotation shaft is moved toward a proximal end of the end tool.

17. The end tool of claim 1, further comprising:

a pair of end tool first jaw pitch main pulleys formed on one side of the first jaw pulley, and formed to be rotatable around a second shaft forming a predetermined angle with the first shaft; and a pair of end tool second jaw pitch main pulleys formed on one side of the second jaw pulley, and formed to be rotatable around a shaft that is substantially the same as or parallel to the second shaft.

18. The end tool of claim 17, wherein the end tool is formed to be yaw-rotatable around the first shaft and simultaneously pitch-rotatable around the second shaft.

19. The end tool of claim 17, further comprising:

a first jaw wire of which at least a portion is wound around the first jaw pulley and the pair of end tool first jaw pitch main pulleys; and a second jaw wire of which at least a portion is wound around the second jaw pulley and the pair of end tool second jaw pitch main pulleys.

* * * * *